United States Patent
Ochi et al.

(10) Patent No.: US 12,241,061 B2
(45) Date of Patent: Mar. 4, 2025

(54) CAR LIBRARY AND scFv MANUFACTURING METHOD

(71) Applicant: NATIONAL UNIVERSITY CORPORATION EHIME UNIVERSITY, Matsuyama (JP)

(72) Inventors: Toshiki Ochi, Ehime (JP); Masaki Yasukawa, Ehime (JP); Hiroshi Fujiwara, Ehime (JP); Katsuto Takenaka, Ehime (JP)

(73) Assignee: National University Corporation Ehime University, Ehime (JP)

( * ) Notice: Subject to any disclaimer, the term of this patent is extended or adjusted under 35 U.S.C. 154(b) by 702 days.

(21) Appl. No.: 17/428,214

(22) PCT Filed: Feb. 4, 2020

(86) PCT No.: PCT/JP2020/004123
§ 371 (c)(1),
(2) Date: Aug. 3, 2021

(87) PCT Pub. No.: WO2020/162452
PCT Pub. Date: Aug. 13, 2020

(65) Prior Publication Data
US 2022/0290128 A1    Sep. 15, 2022

(30) Foreign Application Priority Data

| Feb. 4, 2019 | (JP) | 2019-018269 |
| May 18, 2019 | (JP) | 2019-094188 |
| Jul. 30, 2019 | (JP) | 2019-140121 |
| Oct. 4, 2019 | (JP) | 2019-184071 |

(51) Int. Cl.
| C12N 15/10 | (2006.01) |
| A61K 39/00 | (2006.01) |
| C07K 14/47 | (2006.01) |
| C07K 14/705 | (2006.01) |
| C07K 14/725 | (2006.01) |
| C07K 16/28 | (2006.01) |
| C12N 5/0783 | (2010.01) |
| C12N 15/62 | (2006.01) |
| C40B 40/08 | (2006.01) |

(52) U.S. Cl.
CPC ...... *C12N 15/1068* (2013.01); *A61K 39/4611* (2023.05); *A61K 39/4631* (2023.05); *A61K 39/464412* (2023.05); *A61K 39/464488* (2023.05); *C07K 14/7051* (2013.01); *C07K 14/70521* (2013.01); *C07K 16/2803* (2013.01); *C12N 5/0636* (2013.01); *A61K 2239/31* (2023.05); *A61K 2239/38* (2023.05); *A61K 2239/48* (2023.05); *C07K 2317/14* (2013.01); *C07K 2317/565* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| 2015/0004162 A1 | 1/2015 | Kashyap et al. |
| 2016/0238613 A1 | 8/2016 | Wagner |
| 2017/0268056 A1 | 9/2017 | Vigneault et al. |
| 2017/0336393 A1 | 11/2017 | Wang et al. |
| 2020/0224191 A1* | 7/2020 | Lim .................. C07K 14/7051 |

FOREIGN PATENT DOCUMENTS

| JP | 2016-533507 | 10/2016 |
| JP | 2018-525992 | 9/2018 |
| JP | 2018-535652 | 12/2018 |
| WO | 2013/096828 | 6/2013 |
| WO | 2015/113140 | 8/2015 |
| WO | 2016/033570 | 3/2016 |
| WO | 2018/057051 | 3/2018 |
| WO | 2018/111763 | 6/2018 |
| WO | 2018/161017 | 9/2018 |
| WO | 2018/231759 | 12/2018 |

OTHER PUBLICATIONS

Beiboer et al., J. Mol. Biol. (2000), 296: 833-849.*
Davydov et al. (2018) Front Immunol 9:2309, 1-11.*
Griffiths et al. EMBO J. 13(14): 3245-3260.*
Alonso-Camino, et al., "CARbodies:Human Antibodies Against Cell Surface Tumor Antigens Selected From Repertoires Displayed on T Cell Chimeric Antigen Receptors", Molecular Therapy-Nucleic Acids, vol. 2, No. 5, p. e93, May 1, 2013 (May 1, 2013), pp. 1-11.
Alonso-Camino, et al. "Efficacy and toxicity management of CAR-T-cell immunotherapy: a matter of responsiveness control or tumour-specificity?", Biochemical Society Transaction S, vol. 44, No. 2, Apr. 15, 2016 (Apr. 15, 2016) , pp. 406-411.

(Continued)

*Primary Examiner* — Ilia I Ouspenski
(74) *Attorney, Agent, or Firm* — HSML P.C.

(57) ABSTRACT

Provided are a CAR library used to screen scFvs that can be functional in CAR-T cells, and an scFv manufacturing method in which the CAR library is used. A chimeric antigen receptor (CAR) library of the present invention includes nucleic acids coding for first CARs. Each of the first CARs includes a first antigen-binding domain, a first transmembrane domain, and a first intracellular signaling domain. The first antigen-binding domain includes a first single-chain antibody (scFv) to be screened for the ability to bind to a target antigen. The first scFv includes a first heavy-chain variable region and a first light-chain variable region. The first heavy-chain variable region and the first light-chain variable region meet a predetermined condition.

4 Claims, 37 Drawing Sheets
Specification includes a Sequence Listing.

(56) References Cited

OTHER PUBLICATIONS

Xu, et al., "Combinatorial surrobody libraries", Proceedings of the National Academy of Sciences, National Academy of Sciences, vol. 105, No. 31, Aug. 5, 2008 (Aug. 5, 2008), pp. 10756-10761.
Extended European Search Report issued in corresponding European Patent Application No. 20752298.8, Oct. 20, 2022, 12 pages.
Examination Report No. 1 issued in corresponding Australian Patent Application No. 2020218446, Nov. 4, 2022, 4 pages.
Ochi et al., "007-1 A novel scFv screening technology by exploiting T cells in combination with CAR-based scFv library", Program • Abstract Book of the 23rd Annual Meeting of Japanese Association of Cancer Immunology, Jul. 16, 2019, p. 172 [Methods].
A Klimka et al., "Human anti-CD30 recombinant antibodies by guided phage antibody selection using cell panning", British Journal of Cancer, 2000, 83(2), pp. 252-260.
Ochi et al., "Optimization of T-cell Reactivity by Exploiting TCR Chain Centricity for the Purpose of Safe and Effective Antitumor TCR Gene Therapy", Cancer Immunology Research, Res; 3(9), Sep. 2015, pp. 1070-1081.
Jespers et al., "Guiding the Selection of Human Antibodies from Phage Display Repertoires to a Single Epitope of an Antigen", Bio/Technology, vol. 12, Sep. 1994, pp. 899-903.
Suchanek et al., "Photo-leucine and photo-methionine allow identification of protein-protein interactions in living cells", Nature Methods, Published Online Mar. 23, 2005, pp. 1-7.
International Search Report issued in International Application No. PCT/JP2020/004123, Apr. 28, 2020, 8 pages w/translation.
Office Action issued in corresponding Australian Patent Application No. 2023204079, Aug. 21, 2024, 5 pages.
Office Action issued in Chinese Application Patent Application No. 202080012709.7, Oct. 16, 2024, 27 pages w/translation.

* cited by examiner

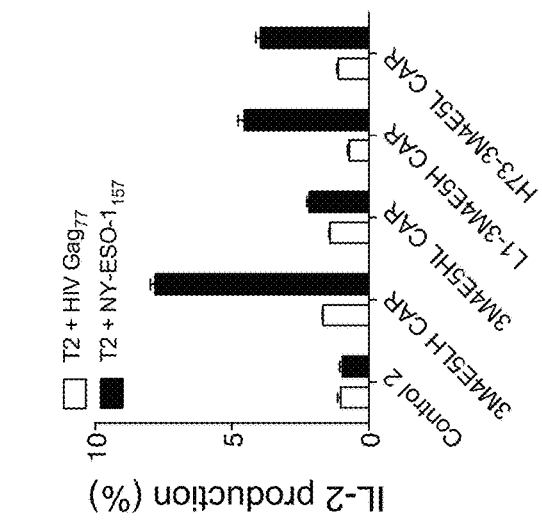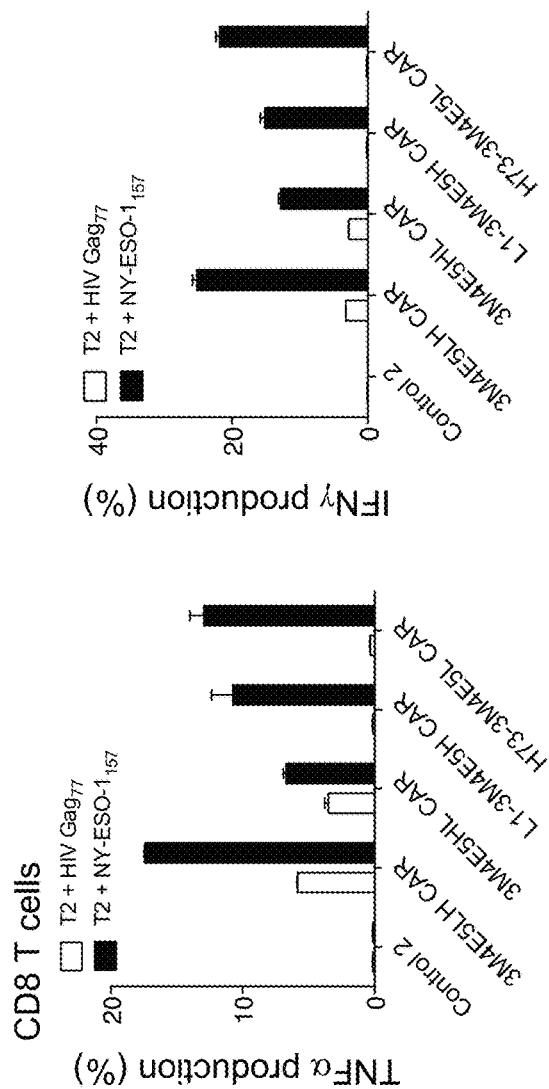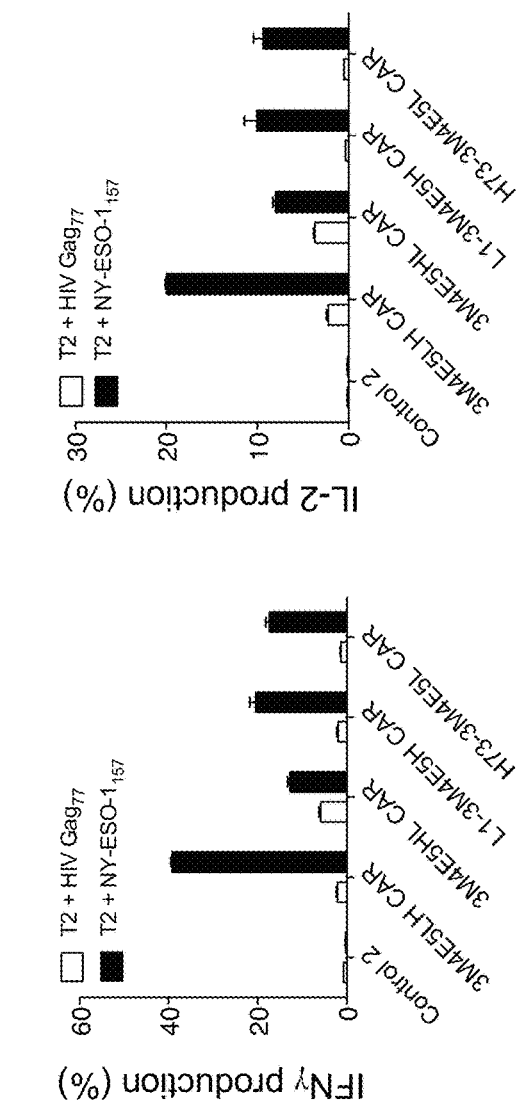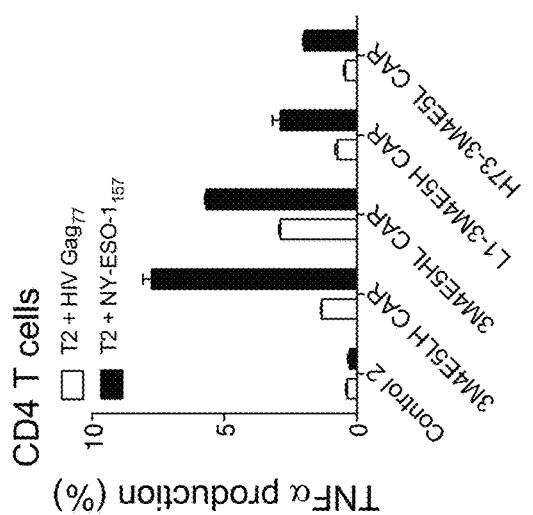
FIG. 15A
FIG. 15B

CAR LIBRARY AND scFv MANUFACTURING METHOD

TECHNICAL FIELD

The present invention relates to a CAR library and an scFv manufacturing method.

BACKGROUND ART

Attempts have been made to treat cancers using T cells (chimeric antigen receptor-expressing T cells, CAR-T cells) expressing single-chain antibodies (single-chain Fvs: scFvs) capable of binding to cancer-specific antigens or target antigens.

scFvs are screened using a technique in which hybridomas derived from B cells isolated from living organisms are used, or a phage display technique. Specifically, in the former technique, a hybridoma library is produced using B cells isolated from living organisms after antigen immunization. Then, a hybridoma that produces an antibody capable of binding to a target antigen is selected, and the sequence of the antigen-recognition site of the antibody produced by the hybridoma is determined.

In the latter technique, an scFv library that includes polynucleotides coding for scFvs is produced, and the scFvs are expressed in phages. Then, a phage capable of binding to a target antigen is selected, and the polynucleotide included in the phage is identified.

SUMMARY OF INVENTION

Technical Problem

With both of the techniques, an scFv capable of binding to a target antigen can be selected, but it is not clear whether this scFv is also functional in CAR-T cells. Accordingly, after the above-mentioned selection, it is necessary to express target antigen-binding scFvs in T cells and examine whether they are functional.

To address this, the present invention provides a CAR library used to screen scFvs that can be functional in CAR-T cells, for example, and an scFv manufacturing method in which the CAR library is used.

Solution to Problem

To achieve the above-mentioned object, a chimeric antigen receptor (CAR) library of the present invention includes nucleic acids coding for first chimeric antigen receptors (CARs),
wherein each of the first CARs includes a first antigen-binding domain, a first transmembrane domain, and a first intracellular signaling domain,
the first antigen-binding domain includes a first single-chain antibody (scFv) to be screened for the ability to bind to a target antigen,
the first scFv includes a first heavy-chain variable region and a first light-chain variable region,
the first heavy-chain variable region and the first light-chain variable region meet Condition 1 or Condition 2 below,
Condition 1 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of an antibody capable of binding to the target antigen or an antigen-binding fragment of the antibody, respectively, and
a light-chain complementarity determining region (CDRL) 1, a CDRL2, and a CDRL3 in the first light-chain variable region include a CDRL1, a CDRL2, and a CDRL3 in a light-chain variable region of a first B cell receptor, respectively, and
Condition 2 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of a first B cell receptor, respectively, and
a light-chain complementarity determining region (CDRL) 1, a CDRL2, and a CDRL3 in the first light-chain variable region include a CDRL1, a CDRL2, and a CDRL3 in a light-chain variable region of an antibody capable of binding to the target antigen or an antigen-binding fragment of the antibody, respectively.

An scFv manufacturing method of the present invention (also referred to as a "first screening method" hereinafter) includes
a first expression step of expressing the CAR library of the present invention in immune cells;
a first contact step of bringing the immune cells obtained in the first expression step into contact with the target antigen; and
a first selection step of selecting the first scFvs of the CARs expressed in the immune cells that have bound to the target antigen in the first contact step as first candidate scFvs capable of binding to the target antigen.

Advantageous Effects of Invention

With the present invention, it is possible to provide a CAR library used to screen scFvs that can be functional in CAR-T cells, for example, and an scFv manufacturing method in which the CAR library is used.

BRIEF DESCRIPTION OF DRAWINGS

FIG. 15 shows graphs indicating changes in a cytokine production amount in Example 4. FIG. 15(A) shows the results from CD8-positive T cells, and FIG. 15(B) shows the results from CD4-positive T cells.

FIG. 16 shows graphs indicating changes in a cytokine production amount in Example 5.

FIG. 18 shows graphs indicating changes in a cytokine production amount in Example 6.

FIG. 19 shows graphs indicating changes in a cytokine production amount in Example 6.

FIG. 20 shows graphs indicating changes in a cytokine production amount in Example 7.

FIG. 21 shows graphs indicating changes in a cytokine production amount in Example 7.

FIG. 23 shows graphs indicating changes in a cytokine production amount in Example 8.

FIG. 24 shows graphs indicating changes in a cytokine production amount in Example 8.

DESCRIPTION OF EMBODIMENTS

CAR Library

Figure 1:
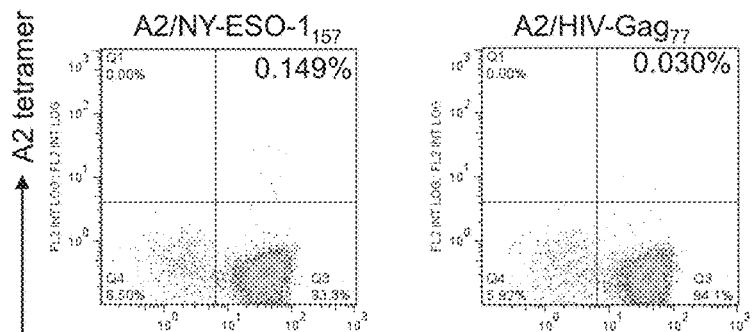
FIG. 1 shows dot plots showing the results of flow cytometry in Example 1.
Figure 1:
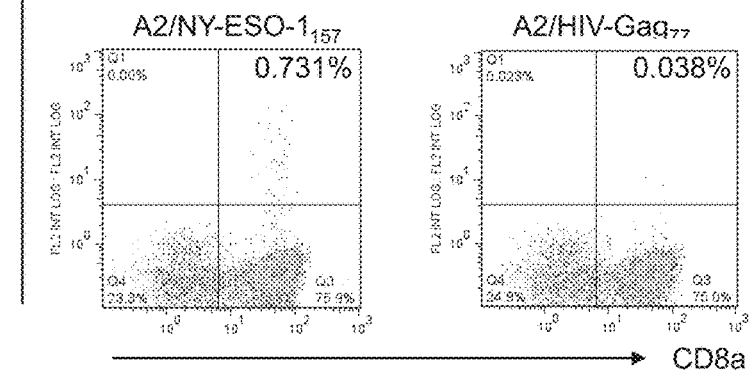
Figure 1:
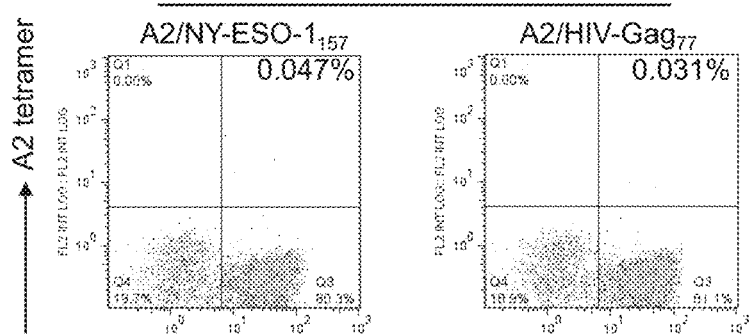
Figure 1:
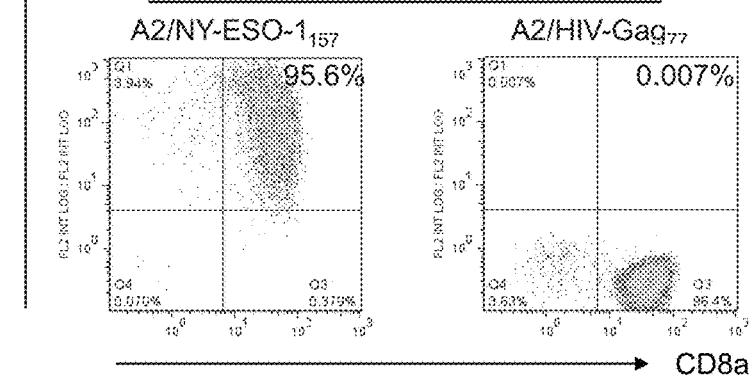

As described above, the chimeric antigen receptors (CAR) library of the present invention includes nucleic acids coding for first CARs, wherein each of the first CARs includes a first antigen-binding domain, a first transmembrane domain, and a first intracellular signaling domain, the first antigen-binding domain includes a first single-chain antibody (scFv) to be screened for the ability to bind to a target antigen, the first scFv includes a first heavy-chain variable region and a first light-chain variable region, and the first heavy-chain variable region and the first light-chain variable region meet Condition 1 or Condition 2 below. The CAR library of the present invention is characterized by meeting Condition 1 or Condition 2 below, and there is no particular limitation on other configurations and conditions.

Condition 1

The heavy-chain complementarity determining region (CDRH) 1, the CDRH2, and the CDRH3 in the first heavy-chain variable region include the CDRH1, the CDRH2, and the CDRH3 in the heavy-chain variable region of an antibody capable of binding to the target antigen or an antigen-binding fragment of the antibody (also referred to as an "antibody or the like" hereinafter), respectively, and the light-chain complementarity determining region (CDRL) 1, the CDRL2, and the CDRL3 in the first light-chain variable region include the CDRL1, the CDRL2, and the CDRL3 in the light-chain variable region of a first B cell receptor, respectively.

Condition 2

The heavy-chain complementarity determining region (CDRH) 1, the CDRH2, and the CDRH3 in the first heavy-chain variable region include the CDRH1, the CDRH2, and the CDRH3 in the heavy-chain variable region of a first B cell receptor, respectively, and the light-chain complementarity determining region (CDRL) 1, the CDRL2, and the CDRL3 in the first light-chain variable region include the CDRL1, the CDRL2, and the CDRL3 in the light-chain variable region of an antibody capable of binding to the target antigen or an antigen-binding fragment of the antibody, respectively.

The CAR library of the present invention is characterized in that each of the first CARs includes the first antigen-binding domain, the first transmembrane domain, and the first intracellular signaling domain, and the first heavy-chain variable region and the first light-chain variable region meet Condition 1 or Condition 2 above, and there is no particular limitation on other configurations and conditions.

In the CAR library of the present invention, each of the first CARs is a protein that includes the first antigen-binding domain, the first transmembrane domain, and the first intracellular signaling domain. The first CAR has a structure similar to that of a CAR that includes an extracellular domain capable of binding to an antigen, a transmembrane domain, and an intracellular signaling domain, for example, and the extracellular domain capable of binding to an antigen is changed to a first antigen-binding domain to be screened for the ability to bind to the target antigen. In the CAR library of the present invention, the first CAR has a structure similar to that of the CAR as mentioned above. Accordingly, a first CAR capable of binding to the target antigen can induce a signal via the first intracellular signaling domain in the expressing cell, for example. Thus, a first CAR capable of binding to the target antigen can activate the expressing cell (e.g., activating the cell proliferation, the expression of an activation marker, and the like), for example. That is, with the CAR library of the present invention, a first screening method, which will be described later, can be used to increase the ratio of cells expressing a first CAR capable of binding to the target antigen in a cell group expressing the CAR library, for example. Therefore, with the CAR library of the present invention, scFvs capable of binding to the target antigen can be screened using a smaller number of, or a smaller number of types of, nucleic acids compared with a phage display technique, for example. Moreover, a first CAR capable of binding to the target antigen can activate the expressing cell in the first screening method, which will be described later, for example, and thus it can be said that the first CAR includes an scFv that is functional in CAR-T cells. Therefore, with the CAR library of the present invention, scFvs that can be functional in CAR-T cells can be screened, for example.

Moreover, in the CAR library of the present invention, the first antigen-binding domain includes the first single-chain antibody (scFv) to be screened for the ability to bind to the target antigen. The first scFv has a structure similar to that of an scFv that is a single-chain polypeptide derived from an antibody capable of binding to an antigen and has an ability to bind to the antigen, for example. The scFv is a polypeptide obtained by coupling the fragments (Fvs) of variable regions of the heavy chain (H chain) and the light chain (L chain) of the antibody capable of binding to the antigen. On the other hand, in the first scFv, either the heavy-chain variable region or the light-chain variable region is a variable region of the antibody or the like capable of binding to the target antigen, and the other one is a variable region derived from a B cell receptor, namely a variable region that may or may not bind to the target antigen, as described later, for example. With the CAR library of the present invention in which the first scFv has such a configuration, heavy-chain variable regions or light-chain variable regions capable of binding to the target antigen can be screened, for example. Therefore, with the CAR library of the present invention, scFvs capable of binding to the target antigen can be screened using a smaller number of, or a smaller number of types of, nucleic acids compared with a phage display technique in which heavy-chain variable regions and light-chain variable regions capable of binding to the target antigen are screened at a time, for example.

In the CAR library of the present invention, the nucleic acids coding for first CARs are nucleic acids (polynucleotides) coding for the amino acid sequences of the first CARs, for example. The nucleic acids may be constituted by DNA, RNA, or both. The nucleic acids may be constituted by natural nucleic acids, modified nucleic acids obtained by modifying natural nucleic acids, artificial nucleic acids such as ENAs (2'-O,4'-C-Ethylene-bridged Nucleic Acids), LNAs (Locked nucleic acids), PNAs (Peptide Nucleic Acids), or morpholinos, or two or more of these compounds.

The term "domain" as used in the present invention means a region of a polypeptide specified based on the three-dimensional structure or functionality, for example. The polypeptide may be a peptide containing 10 or more amino acids, for example.

There is no particular limitation on the target antigen of the first scFv, and any antigen can be used. Examples of the target antigen include tumor antigens, viral antigens, bacterial antigens, parasitic antigens, antigens linked to autoimmune diseases, and sugar chain antigens. The tumor antigens are biomolecules having antigenicity such as antigens that are newly expressed or are expressed at an increased level due to cell canceration, for example. The tumor antigens may be tumor-specific antigens or tumor-related antigens, for example.

Examples of the tumor antigens include 5T4, α5β1-integrin, activated integrin β7, 707-AP, α-fetoprotein (AFP), lectin-reactive AFP, ART-4, AURKA (AURORAA), B7H4, BAGE, β-catenin, BCMA, Bcr-abl, BTAA, MN/CA IX antigens, CA125, CA19-9, CA72-4, CAMEL, CAP-1, CASP-8, CD4, CD19, CD20, CD22, CD25, CD27, CD30, CD33, CD47, CD52, CD56, CD80, CD96, CD123, CDK4, carcinoembryonic antigens (CEAs), CLL1, CT, cyclin A1, Cyp-B, DAM, EGFR, ErbB3, ELF2M, EMMPRIN, EpCam, ETV6-AML1, G250, GAGE (GAGE-1, GAGE-2, etc.), GD2 (ganglioside G2), GnT-V, Gp100, HAGE, 8-human chorionic gonadotropin (HCG), HER2/neu, HLA-A*0201-R170I, HPV-E7, HSP70-2M, HST-2, iCE, insulin growth factor (IGF)-1, IGF-2, IGF-1R, IL-2R, IL-5, KIAA0205, K-Ras, LAGE, LDLR/FUT, MAGE (MAGE-3, MAGE-4, MAGE-5, MAGE-6, etc.), MART-1/melan-A, MART-2/Ski, MC1R, mesothelin (MSLN), myosin, MUC1, MUM-1, MUM-2, MUM-3, NA88-A, prostatic acid phosphatase (PAP), proteinase-3, PRAME (melanoma antigen preferentially expressed in tumors), p53, p190 minor ber-abl, Pml/RARa, prostatic tumor antigen-1 (PCTA-1), PRAME, prostate-specific antigen (PSA), PSM, PSMA, RAGE, RAS, RHAMM (CD168), RU1, RU2, SAGE, SART-1, SART-3, thyroglobulin, survivin, telomerase reverse transcriptase (TERT or TRT), TEL/AML1, TGFβ, TIM3, TPI/m, TRP-1, TRP-2, TRP-2/INT2, VEGF, WT1, NY-Eso-1, and NY-Eso-B.

Examples of the viral antigens include antigens derived from viruses belonging to: the family Adenoviridae including adenoviruses; the family Coronaviridae including coronaviruses; the family Filoviridae including the genus Ebolavirus; the family Flaviviridae including hepatitis C virus (HCV), Dengue virus, Japanese encephalitis virus, west Nile virus, and yellow fever virus; the family Hepadnaviridae including hepatitis B virus (HVB); the family Herpesviridae including herpes simplex virus-1 (HSV-1), herpes simplex virus-2 (HSV-2), varicella zoster virus (VZV), human cytomegalovirus (HCMV), Epstein-Barr virus (EBV), and Kaposi's sarcoma-associated herpesvirus (KSHV); the family Orthomyxoviridae including the genus Influenzavirus A, the genus Influenzavirus B, and the genus Influenzavirus C; the family Paramyxoviridae including measles virus, Human parainfluenza viruses 1 to 4, Mumps virus, and Respiratory syncytial virus; the family Parvoviridae including Parvovirus B19; the family Picornaviridae including enteroviruses, poliovirus, human rhinoviruses A and B, hepatitis Avirus, coxsackievirus, and echo virus; the family Poxviridae including variola virus and Vaccinia virus; the family Retroviridae including human immunodeficiency viruses (HIVs)-1 and 2 and human T-lymphocytropic viruses (HTLV)-I and II; the family Rhabdoviridae including Rabies virus and Vesicular stomatitis virus; and the family Togaviridae including Rubella virus and Chikungunya virus.

Examples of the bacterial antigens include antigens derived from bacteria belonging to: the genus *Clostridium* including *Clostridium tetani*; the genus *Escherichia* including *Escherichia coli*, the genus *Helicobacter* including Helicobacterpyloris; the genus *Legionella* including *Legionella pneumophila*; the genus *Listeria* including *Listeria monocytogenes*; the genus *Mycobacterium* including *Mycobacterium tuberculosis*, *Mycobacterium leprae*, *Mycobacterium avium*, *Mycobacterium intracellulare*, *Mycobacterium kansasii*, and *Mycobacterium gordonae*; the genus *Neisseria* including *Neisseria gonorrhoeae* and *Neisseria meningitidis*; the genus *Pseudomonas* including *Pseudomonas aeruginosa*; the genus *Salmonella* including *Salmonella enterica* serovar *Typhi* and *Salmonella enterica* serovar Paratyphi A; the genus *Staphylococcus* including *Staphylococcus aureus*; and the genus *Streptococcus* including *Streptococcus pneumoniae* and *Streptococcus pyogenes*.

Examples of the parasitic antigens include antigens derived from parasites such as *Clonorchis sinensis, Schistosoma japonicum, Ascaris lumbricoides, Enterobius vermicularis, Cysticercus cellulosae, Diphyllobothrium latum, Echinococcus, Entamoeba histolytica*, and *Plasmodium*.

In the CAR library of the present invention, the first scFv includes the first heavy-chain variable region and the first light-chain variable region. The first heavy-chain variable region and the first light-chain variable region have structures similar to those of the heavy-chain variable region and the light-chain variable region in an antibody molecule, respectively. In general, the heavy-chain variable region and the light-chain variable region in an antibody molecule each include three complementarity determining regions (CDRs). The CDRs are also referred to as "hypervariable domains". The CDRs are regions in which the primary structure is particularly likely to be variable in the variable regions of the heavy chain and the light chain, and the primary structure generally includes three CDRs. In the present invention, the three CDRs in the heavy-chain variable region are referred to as a heavy-chain CDR 1 (CDRH1), a heavy-chain CDR 2 (CDRH2), and a heavy-chain CDR 3 (CDRH3), in this order from the amino terminus (N terminus) of the amino acid sequence of the heavy-chain variable region, and the three CDRs in the light-chain variable region are referred to as a light-chain CDR 1 (CDRL1), a light-chain CDR 2 (CDRL2), and a light-chain CDR 3 (CDRL3), in this order from the amino terminus of the amino acid sequence of the light-chain variable region. These sites are close to one another in the three-dimensional structure and determine the binding specificity for an antigen.

The first heavy-chain variable region includes the CDRH1, the CDRH2, and the CDRH3. The first light-chain variable region includes the CDRL1, the CDRL2, and the CDRL3. The first heavy-chain variable region and the first light-chain variable region meet Condition 1 or Condition 2 above.

In Condition 1 above, the CDRH1, the CDRH2, and the CDRH3 of an antibody or the like capable of binding to the target antigen are used as those in the first heavy-chain variable region, and the CDRL1, the CDRL2, and the CDRL3 in the first light-chain variable region are screened for the ability to bind to the target antigen. For example, the descriptions of an antibody and an antigen-binding fragment regarding the antibody of the present invention or the like, which will be described later, can be applied to specific examples of the antibody or the antigen-binding fragment thereof.

Known antibodies or the like can be used as the antibody or the like capable of binding to the target antigen in accordance with the target antigen, for example. As a specific example, a 3M4E5 antibody can be used as an antibody against a complex of HLA-A*02:01 and NY-ESO-$1_{157\text{-}165}$, for example. An FMC63 antibody can be used as an antibody against human CD19, for example. The antibody or the like capable of binding to the target antigen may be an scFv obtained using a first screening method of the present invention, which will be described later, or an antibody obtained through immunization with the target antigen, for example. The CDRH1, the CDRH2, and the CDRH3 in the first heavy-chain variable region may respectively be polypeptides that consist of the amino acid sequences of the CDRH1, the CDRH2, and the CDRH3 of the antibody or the like capable of binding to the target antigen, or polypeptides that include the amino acid sequences of the CDRH1, the CDRH2, and the CDRH3 of the antibody or the like capable of binding to the target antigen, for example.

Regions in the first heavy-chain variable region other than the CDRH1, the CDRH2, and the CDRH3, namely framework regions (FRs), may include the FRs in the heavy-chain variable region of the antibody or the like capable of binding to the target antigen, for example. The number of the FRs above in the primary structure is generally four. In the present invention, the four FRs in the heavy-chain variable region are referred to as a heavy-chain FR 1 (FRH1), a heavy-chain FR 2 (FRH2), a heavy-chain FR 3 (FRH3), and a heavy-chain FR 4 (FRH4), in this order from the N terminus of the amino acid sequence of the heavy-chain variable region. It should be noted that the CDRHs and the FRHs are arranged such that the FRH1, the CDRH1, the FRH2, the CDRH2, the FRH3, the CDRH3, and the FRH4 are lined up in this order from the N terminus of the amino acid sequence of the heavy-chain variable region, for example. The FRH1, the FRH2, the FRH3, and the FRH4 in the first heavy-chain variable region may respectively be polypeptides that consist of the amino acid sequences of the FRH1, the FRH2, the FRH3, and the FRH4 of the antibody or the like capable of binding to the target antigen, or polypeptides that include the amino acid sequences of the FRH1, the FRH2, the FRH3, and the FRH4 of the antibody or the like capable of binding to the target antigen, for example. It is preferable that "the antibody or the like capable of binding to the target antigen" in the descriptions of the CDRHs and "the antibody or the like capable of binding to the target antigen" in the descriptions of the FRHs are the same antibody or the like.

The first heavy-chain variable region may include the heavy-chain variable region of the antibody or the like capable of binding to the target antigen, for example. In this case, the first heavy-chain variable region may be a polypeptide that consist of the amino acid sequence of the heavy-chain variable region of the antibody or the like capable of binding to the target antigen, or a polypeptide that include the amino acid sequence of the heavy-chain variable region of the antibody or the like capable of binding to the target antigen, for example.

The first light-chain variable region is encoded by a VJ gene fragment formed through VJ gene recombination of a V gene fragment and a J gene fragment, for example. Therefore, the first B cell receptor may be a B cell receptor that includes a polypeptide encoded by an artificial VJ gene fragment designed as an artificial combination of a V gene fragment and a J gene fragment, for example. B cells in a living organism express a light-chain variable region encoded by a product formed through VJ gene recombination, for example. Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the CAR library of the present invention, the first B cell receptor is preferably the light-chain variable region of the B cell receptor derived from isolated B cells for the reason that the CAR library can be more easily prepared.

The CDRL1, the CDRL2, and the CDRL3 in the first light-chain variable region may respectively be polypeptides that consist of the amino acid sequences of the CDRL1, the CDRL2, and the CDRL3 of the first B cell receptor, or polypeptides that include the amino acid sequences of the CDRL1, the CDRL2, and the CDRL3 of the first B cell receptor, for example.

The FRs in the first light-chain variable region may include the FRs in the light-chain variable region of the first B cell receptor, for example. The number of the FRs above in the primary structure is generally four. In the present invention, the four FRs in the light-chain variable region are referred to as a light-chain FR 1 (FRL1), a light-chain FR 2 (FRL2), a light-chain FR 3 (FRL3), and a light-chain FR 4 (FRL4), in this order from the N terminus of the amino acid sequence of the light-chain variable region. It should be noted that the CDRLs and the FRLs are arranged such that the FRL1, the CDRL1, the FRL2, the CDRL2, the FRL3, the CDRL3, and the FRL4 are lined up in this order from the N terminus of the amino acid sequence of the light-chain variable region, for example. The FRL1, the FRL2, the FRL3, and the FRL4 in the first light-chain variable region may respectively be polypeptides that consist of the amino acid sequences of the FRL1, the FRL2, the FRL3, and the FRL4 of the first B cell receptor, or polypeptides that include the amino acid sequences of the FRL1, the FRL2, the FRL3, and the FRL4 of the first B cell receptor, for example. It is preferable that "the first B cell receptor" in the descriptions of the CDRLs and "the first B cell receptor" in the descriptions of the FRLs are the same B cell receptor.

The first light-chain variable region may include the light-chain variable region of the first B cell receptor, for example. In this case, the first light-chain variable region may be a polypeptide that consists of the amino acid sequence of the light-chain variable region of the first B cell receptor, or a polypeptide that includes the amino acid sequence of the light-chain variable region of the first B cell receptor, for example.

Next, in Condition 2 above, the CDRL1, the CDRL2, and the CDRL3 in the first light-chain variable region are derived from the antibody or the like capable of binding to the target antigen, and the CDRH1, the CDRH2, and the CDRH3 in the first heavy-chain variable region are screened for the ability to bind to the target antigen.

The first heavy-chain variable region is encoded by a VDJ gene fragment formed through VDJ gene recombination of a V gene fragment, a D gene fragment, and a J gene fragment, for example. Therefore, the first B cell receptor may be a B cell receptor that includes a polypeptide encoded by an artificial VDJ gene fragment designed as an artificial combination of a V gene fragment, a D gene fragment, and a J gene fragment, for example. A heavy-chain variable region is expressed in B cells in a living organism after VDJ gene recombination, for example. Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the CAR library of the present invention, the first B cell receptor is preferably the heavy-chain variable region of the B cell receptor derived from isolated B cells for the reason that the CAR library can be more easily prepared.

The CDRH1, the CDRH2, and the CDRH3 in the first heavy-chain variable region may respectively be polypeptides that consist of the amino acid sequences of the CDRH1, the CDRH2, and the CDRH3 of the first B cell receptor, or polypeptides that include the amino acid sequences of the CDRH1, the CDRH2, and the CDRH3 of the first B cell receptor, for example.

The FRH1, the FRH2, the FRH3, and the FRH4 in the first heavy-chain variable region may respectively be polypeptides that consist of the amino acid sequences of the FRH1, the FRH2, the FRH3, and the FRH4 of the first B cell receptor, or polypeptides that include the amino acid sequences of the FRH1, the FRH2, the FRH3, and the FRH4 of the first B cell receptor, for example. It is preferable that "the first B cell receptor" in the descriptions of the CDRHs and "the first B cell receptor" in the descriptions of the FRHs are the same B cell receptor.

The first heavy-chain variable region may include the heavy-chain variable region of the first B cell receptor, for example. In this case, the first heavy-chain variable region may be a polypeptide that consists of the amino acid sequence of the heavy-chain variable region of the first B cell receptor, or a polypeptide that includes the amino acid sequence of the heavy-chain variable region of the first B cell receptor, for example.

For example, regarding the first light-chain variable region, the descriptions of the antibody or the like capable of binding to the target antigen in Condition 1 above, and the like can be applied to the antibody or the like capable of binding to the target antigen. The CDRL1, the CDRL2, and the CDRL3 in the first light-chain variable region may respectively be polypeptides that consist of the amino acid sequences of the CDRL1, the CDRL2, and the CDRL3 of the antibody or the like capable of binding to the target antigen, or polypeptides that include the amino acid sequences of the CDRL1, the CDRL2, and the CDRL3 of the antibody or the like capable of binding to the target antigen, for example.

The FRs in the first light-chain variable region may include the FRs in the light-chain variable region of the antibody or the like capable of binding to the target antigen, for example. The FRL1, the FRL2, the FRL3, and the FRL4 in the first light-chain variable region may respectively be polypeptides that consist of the amino acid sequences of the FRL1, the FRL2, the FRL3, and the FRL4 of the antibody or the like capable of binding to the target antigen, or polypeptides that include the amino acid sequences of the FRL1, the FRL2, the FRL3, and the FRL4 of the antibody or the like capable of binding to the target antigen, for example. It is preferable that "the antibody or the like capable of binding to the target antigen" in the descriptions of the CDRLs and "the antibody or the like capable of binding to the target antigen" in the descriptions of the FRLs are the same antibody or the like.

The first light-chain variable region may include the light-chain variable region of the antibody or the like capable of binding to the target antigen, for example. In this case, the first light-chain variable region may be a polypeptide that consists of the amino acid sequence of the light-chain variable region of the antibody or the like capable of binding to the target antigen, or a polypeptide that includes the amino acid sequence of the light-chain variable region of the antibody or the like capable of binding to the target antigen, for example.

In the first scFv, the first heavy-chain variable region and the first light-chain variable region are coupled to each other via a linker peptide (Fv linker peptide), for example. It is preferable that the Fv linker peptide does not inhibit the first scFv from binding to the target antigen, for example. The Fv linker peptide is constituted by 1 to 40, 1 to 18, 1 to 15, 1 to 7, 1 to 3, or 1 or 2 amino acids, for example. The Fv linker peptide is constituted by amino acids such as glycine and serine, for example, and a specific example thereof is $(GGGGS)_n$. n in this formula is an integer from 1 to 6, for example. The amino acid sequence of the Fv linker peptide may be the amino acid sequence of the polypeptide represented by Sequence ID No. 1 or 2 below, for example.

```
Fv Linker Peptide 1
                                (Sequence ID No. 1)
GSTSGSGKPGSGEGSTKG Fv Linker Peptide 2
                                (Sequence ID No. 2)
GGGGSGGGGSGGGGS Base Sequence Coding for Fv Linker Peptide 1
                                (Sequence ID No. 3)
5'-GGCTCTACAAGCGGCTCTGGCAAGCCTGGATCTGGCGAGGGAAGCA
CCAAGGGC-3'

Base Sequence Coding for Fv Linker Peptide 2
                                (Sequence ID No. 4)
5'-GGTGGAGGAGGCTCAGGAGGAGGTGGCTCTGGTGGTGGAGGCTCG-3'
```

The first antigen-binding domain includes the first scFv, and the first binding domain may also include a structure other than the scFv that includes the heavy-chain variable region and the light-chain variable region. In a specific example, the first binding domain may be a Fab, Fab', F(ab')$_2$, variable region fragment (Fv), disulfide-bond Fv, or the like.

The first transmembrane domain is a domain that makes up the region that passes through the cell membrane when the first CAR is expressed in a cell, for example. The first transmembrane domain may be the transmembrane domain of a transmembrane protein or an artificial transmembrane domain that has been artificially designed, for example. In the former case, examples of the transmembrane protein include an α chain and a β chain of a T cell receptor, a CD3ζ chain, CD28, CD3ε, CD45, CD4, CD5, CD8 (CD8α or CD8β), CD9, CD16, CD22, CD27, CD33, CD37, CD64, CD80, CD86, CD134, CD137, CD154, ICOS, and GITR, and variants thereof having equivalent functions. The variants having equivalent functions are polypeptides that consist of amino acid sequences with deletion, substitution, insertion, and/or addition of one or several amino acids and function as a transmembrane domain, for example. The term "one or several" above refers to 1 to 15, 1 to 10, 1 to 5, or 1 or 2, for example. In the latter case, the artificial transmembrane domain is a polypeptide that is mainly constituted by hydrophobic amino acids such as leucine, isoleucine, and valine, for example. The artificial transmembrane domain may also include tripeptides constituted by phenylalanine, tryptophan, and valine at the two ends thereof, for example. When the first transmembrane domain is the transmembrane domain of the above-mentioned transmembrane protein, the first transmembrane domain may also include one or several amino acids continuous with the N terminus or C terminus of the transmembrane domain of the transmembrane protein, for example. The example as described above can be applied to the term "one or several" above, for example.

An example of the first transmembrane domain is the transmembrane domain of CD28. The transmembrane domain of CD28 may have an amino acid sequence listed below that corresponds to the amino acid sequence between position 153 and position 179 (Sequence ID No. 5) in the amino acid sequence registered as NCBI Accession No. NP_006130, for example. It should be noted that NCBI Accession No. above is a number assigned to the entire amino acid sequence of the precursor of the protein (the same applies hereinafter). A transmembrane unit that includes the transmembrane domain of CD28 as well as the extracellular region on the N-terminal side of the transmembrane domain and the intracellular region on the C-terminal side of the transmembrane domain may also be used as the transmembrane domain of the CD28, for example.

```
Transmembrane Domain of CD28
                                (Sequence ID No. 5)
FWVLVVVGGVLACYSLLVTVAFIIFWV Base Sequence Coding for Transmembrane Domain
of CD28
                                (Sequence ID No. 6)
5'-TTCTGGGTGCTGGTGGTCGTGGGCGGAGTGCTGGCCTGTTATAGCC
TGCTCGTGACCGTGGCCTTCATCATCTTTTGGGTG-3'

Transmembrane Unit of CD28
                                (Sequence ID No. 7)
IEVMYPPPYLDNEKSNGTIIHVKGKHLCPSPLFPGPSKPFWVLVVVGG
VLACYSLLVTVAFIIFWVRSKRSRLLHSDYMNMTPRRPGPTRKHYQPY
APPRDFAAYRS Base Sequence Coding for Transmembrane Unit of
CD28
                                (Sequence ID No. 8)
5'-ATCGAAGTGATGTACCCCCCTCCCTACCTGGACAACGAGAAGTCCA

ACGGCACCATTATCCACGTGAAGGGAAAGCACCTGTGCCCCAGCCCTCT

GTTCCCTGGCCCTAGCAAGCCTTTCTGGGTGCTGGTGGTCGTGGGCGGA

GTGCTGGCCTGTTATAGCCTGCTCGTGACCGTGGCCTTCATCATCTTTT
```

-continued

```
GGGTGCGCAGCAAGCGGAGCCGGCTGCTGCACAGCGACTACATGAACAT

GACCCCCAGACGGCCCGGACCCACCAGAAAGCACTACCAGCCTTACGCC

CCTCCCAGAGACTTCGCCGCCTACAGATCT-3'
```

The first intracellular signaling domain is a domain that can perform intracellular signaling when the first antigen-binding domain in the same protein binds to the target antigen, for example. The first signaling domain may be a domain having an amino acid sequence of a cytoplasmic region of a T cell receptor (TCR) complex or costimulatory molecule, or a variant thereof having functions equivalent to those of such an amino acid sequence, for example. The variant having equivalent functions is a polypeptide that consists of an amino acid sequence with deletion, substitution, insertion, and/or addition of one or several amino acids and functions as an intracellular signaling domain, for example. The descriptions above can be applied to the term "one or several" above, for example.

T cells are activated by an antigen-dependent cytoplasmic signal such as an intracellular signal transmitted via a TCR complex, for example (primary activation). This activation is increased by an antigen-non-specific cytoplasmic signal such as intracellular signal transmitted via a costimulatory molecule (secondary activation). Accordingly, T cells include a domain for activation via the TCR complex (primary-activation domain) and a domain for antigen-non-specific activation (secondary-activation domain), for example. Therefore, the first intracellular signaling domain includes at least either the primary-activation domain or the secondary-activation domain, and preferably both, for example.

The primary-activation domain can adjust primary activation by the TCR complex, for example. An example of a primary-activation domain that induces the primary activation is an intracellular signaling domain that includes an immunoreceptor tyrosine-based activation motif (ITAM). Meanwhile, an example of a primary-activation domain that suppresses the primary activation is an intracellular signaling domain that includes an immunoreceptor tyrosine-based inhibitory motif (ITIM).

Examples of the intracellular signaling domain that includes the ITAM include intracellular signaling domains of CD3ζ, FcRγ, FcRβ, CD3γ, CD3δ, CD3ε, CD5, CD22, CD79a, CD79b, and CD66d, and those of variants thereof having equivalent functions. The variants having equivalent functions are polypeptides that consist of amino acid sequences with deletion, substitution, insertion, and/or addition of one or several amino acids and function as an intracellular signaling domain that includes the ITAM. The descriptions above can be applied to the term "one or several" above, for example. The intracellular signaling domain that includes the ITAM of CD3ζ may have an amino acid sequence that corresponds to the amino acid sequence between position 52 and position 164 in the amino acid sequence registered as NCBI Accession No. NP_932170.1, or the amino acid sequence of Sequence ID No. 9 below, for example. The intracellular signaling domain that includes the ITAM of FcεRIγ may have an amino acid sequence that corresponds to the amino acid sequence between position 45 and position 86 in the amino acid sequence registered as NCBI Accession No. NP_004097.1, for example. The intracellular signaling domain that includes the ITAM of FcεRIβ may have an amino acid sequence that corresponds to the amino acid sequence between position 201 and position 244 in the amino acid sequence registered as NCBI Accession No. NP_000130.1, for example. The intracellular signaling domain that includes the ITAM of CD3γ may have an amino acid sequence that corresponds to the amino acid sequence between position 139 and position 182 in the amino acid sequence registered as NCBI Accession No. NP_000064.1, for example. The intracellular signaling domain that includes the ITAM of CD3δ may have an amino acid sequence that corresponds to the amino acid sequence between position 128 and position 171 in the amino acid sequence registered as NCBI Accession No. NP_000723.1, for example. The intracellular signaling domain that includes the ITAM of CD3ε may have an amino acid sequence that corresponds to the amino acid sequence between position 153 and position 207 in the amino acid sequence registered as NCBI Accession No. NP_000724.1, for example. The intracellular signaling domain that includes the ITAM of CD5 may have an amino acid sequence that corresponds to the amino acid sequence between position 402 and position 495 in the amino acid sequence registered as NCBI Accession No. NP_055022.2, for example. The intracellular signaling domain that includes the ITAM of CD22 may have an amino acid sequence that corresponds to the amino acid sequence between position 707 and position 847 in the amino acid sequence registered as NCBI Accession No. NP_001762.2, for example. The intracellular signaling domain that includes the ITAM of CD79a may have an amino acid sequence that corresponds to the amino acid sequence between position 166 and position 226 in the amino acid sequence registered as NCBI Accession No. NP_001774.1, for example. The intracellular signaling domain that includes the ITAM of CD79b may have an amino acid sequence that corresponds to the amino acid sequence between position 182 and position 229 in the amino acid sequence registered as NCBI Accession No. NP_000617.1, for example. The intracellular signaling domain that includes the ITAM of CD66d may have an amino acid sequence that corresponds to the amino acid sequence between position 177 and position 252 in the amino acid sequence registered as NCBI Accession No. NP_001806.2, for example.

```
Intracellular Signaling Domain That Includes ITAM
of CD3
                                  (Sequence ID No. 9)
RVKSRSADAPAYQQGQNQLYNELNLGRREEYDVLDKRRGRDPEMGGK
PRRKNPQEGLYNELQKDKNIAEAYSEIGMKGERRRGKGHDGLYQGLSTA
TKDTYDALHMQALPPR Base Sequence Coding for Intracellular Signaling
Domain That Includes ITAM of CD3
                                 (Sequence ID No. 10)
5'-CGAGTGAAGAGCAGAAGCGCCGACGCCCCTGCCTATCAGCAGGGCC

AGAACCAGCTGTACAACGAGCTGAACCTGGGCAGACGGGAAGAGTACGA

CGTGCTGGACAAGCGGAGAGGCAGGGACCCTGAGATGGGCGGCAAGCCC

AGAAGAAAGAACCCCCAGGAAGGCCTGTATAACGAACTGCAGAAAGACA

AGATGGCCGAGGCCTACAGCGAGATCGGCATGAAGGGCGAGCGGAGAAG

AGGCAAGGGCCACGATGGCCTGTACCAGGGCCTGAGCACCGCCACCAAG

GACACCTATGACGCCCTGCACATGCAGGCCCTGCCCCCCAGA-3'
```

Examples of the secondary-activation domain include intracellular signaling domains of CD2, CD4, CD5, CD8α, CD8β, CD27, CD28, CD134 (OX40), CD137 (4-1BB), CD154, GITR, and ICOS, and those of variants thereof having equivalent functions. The variants having equivalent functions are polypeptides that consist of amino acid sequences with deletion, substitution, insertion, and/or addition of one or several amino acids and function as an intracellular signaling domain. The descriptions above can be applied to the term "one or several" above, for example. Specifically, the intracellular signaling domain of CD2 may have an amino acid sequence that corresponds to the amino acid sequence between position 236 and position 351 in the amino acid sequence registered as NCBI Accession No. NP_001758.2, for example. The intracellular signaling domain of CD4 may have an amino acid sequence that corresponds to the amino acid sequence between position 421 and position 458 in the amino acid sequence registered as NCBI Accession No. NP_000607.1, for example. The intracellular signaling domain of CD5 may have an amino acid sequence that corresponds to the amino acid sequence between position 402 and position 495 in the amino acid sequence registered as NCBI Accession No. NP_055022.2, for example. The intracellular signaling domain of CD8α may have an amino acid sequence that corresponds to the amino acid sequence between position 207 and position 235 in the amino acid sequence registered as NCBI Accession No. NP_001759.3, for example. The intracellular signaling domain of CD88 may have an amino acid sequence that corresponds to the amino acid sequence between position 196 and position 210 in the amino acid sequence registered as NCBI Accession No. AAA35664.1, for example. The intracellular signaling domain of CD27 may have an amino acid sequence that corresponds to the amino acid sequence between position 213 and position 260 in the amino acid sequence registered as NCBI Accession No. M63928.1, for example. The intracellular signaling domain of CD28 may have an amino acid sequence that corresponds to the amino acid sequence between position 181 and position 220 (Sequence ID No. 11) in the amino acid sequence registered as NCBI Accession No. NP_006130.1, for example. The intracellular signaling domain of CD134 may have an amino acid sequence that corresponds to the amino acid sequence between position 241 and position 277 in the amino acid sequence registered as NCBI Accession No. NP_003318.1, for example. The intracellular signaling domain of CD137 may have an amino acid sequence that corresponds to the amino acid sequence between position 214 and position 255 in the amino acid sequence registered as NCBI Accession No. NP_001552.2, for example. The intracellular signaling domain of GITR may have an amino acid sequence that corresponds to the amino acid sequence between position 193 and position 241 in the amino acid sequence registered as NCBI Accession No. NP_004186.1, for example. The intracellular signaling domain of ICOS may have an amino acid sequence that corresponds to the amino acid sequence between position 166 and position 199 in the amino acid sequence registered as NCBI Accession No. NP_036224.1, for example.

```
Intracellular Signaling Domain of CD28
                            (Sequence ID No. 11)
RSKRSRLLHSDYMNMTPRRPGPTRKHYQPYAPPRDFAAYRS Base Sequence Coding for Intracellular Signaling
Domain of CD28
                            (Sequence ID No. 12)
5'-CGCAGCAAGCGGAGCCGGCTGCTGCACAGCGACTACATGAACATGA
CCCCCAGACGGCCCGGACCCACCAGAAAGCACTACCAGCCTTACGCCCC
TCCCAGAGACTTCGCCGCCTACAGATCT-3'
```

The first CAR includes one or more first intracellular signaling domains, for example. When the first CAR includes a plurality of first intracellular signaling domains, the first intracellular signaling domains may be the same or different. It is preferable that the first intracellular signaling domain includes the intracellular signaling domain that includes the ITAM of CD3ζ as the primary-activation domain, for example. Also, it is preferable that the first intracellular signaling domain includes at least one intracellular signaling domain selected from the group consisting of those of CD27, CD28, and CD137 as the secondary-activation domain, for example. In a specific example, the first intracellular signaling domain includes the intracellular signaling domain that includes the ITAM of CD3ζ and at least one intracellular signaling domain selected from the group consisting of those of CD27, CD28, and CD137, for example. Thus, with the CAR library of the present invention, scFvs capable of binding to the target antigen can be screened using a much smaller number of, or a much smaller number of types of, nucleic acids compared with a phage display technique, in the first screening method of the present invention, which will be described later, for example. When the first intracellular signaling domain includes the intracellular signaling domain that includes the ITAM of CD3ζ and the intracellular signaling domain of CD28, it is preferable that the intracellular signaling domain that includes the ITAM of CD3ζ is arranged on the C-terminal side of the intracellular signaling domain of CD28. When the first intracellular signaling domain includes the intracellular signaling domain that includes the ITAM of CD3ζ and the intracellular signaling domain of CD28, the first intracellular signaling domain may further include at least one of the intracellular signaling domain of CD134 and the intracellular signaling domain of CD137.

The first antigen-binding domain and the first transmembrane domain are directly or indirectly coupled to each other. When the first antigen-binding domain and the first transmembrane domain are indirectly coupled, it is preferable that they are coupled via a spacer peptide. The spacer peptide is constituted by 1 to 300, 1 to 100, 10 to 100, or 25 to 50 amino acids, for example. It is preferable that the spacer peptide includes amino acids (e.g., cysteine, serine, and threonine) that promote the binding of the first CAR to the target antigen and induce and/or increase signal transmission by the first intracellular signaling domain when the first CAR binds to the target antigen. In a specific example, the constant region of immunoglobulin such as the CH1 region or L region, a partial region of CD4, CD8α, CD8β, or CD28, or the like can be used as the spacer peptide, for example. The first spacer peptide has an amino acid sequence that has been artificially designed. An example of the partial region of CD8α is the hinge region of CD8α, and a specific example thereof may have an amino acid sequence that corresponds to the amino acid sequence between position 118 and position 178 in the amino acid sequence registered as NCBI Accession No. NP_001759.3. The partial region of CD88 may have an amino acid sequence that corresponds to the amino acid sequence between position 135 and position 195 in the amino acid sequence registered as NCBI Accession No. AAA35664.1, for example. The partial region of CD4 may have an amino acid sequence that corresponds to the amino acid sequence between position 315 and position 396 in the amino acid sequence registered as NCBI Accession No. NP_000607.1, for example. The partial region of CD28 may have an amino acid sequence that corresponds to the amino acid sequence between position 137 and position 152 (Sequence ID No. 13) in the amino acid sequence registered as NCBI Accession No. NP_006130.1, for example. The spacer peptide may have an amino acid sequence that corresponds to a part of the amino acid sequence of each example.

Partial Region of CD28 (Extracellular Region)
                                    (Sequence ID No. 13)
IEVMYPPPYLDNEKSNGTIIHVKGKHLCPSPLFPGPSKP Base Sequence Coding for Part of CD28
                                    (Sequence ID No. 14)
5'-ATCGAAGTGATGTACCCCCCTCCCTACCTGGACAACGAGAAGTCCAA
CGGCACCATTATCCACGTGAAGGGAAAGCACCTGTGCCCCAGCCCTCTGT
TCCCTGGCCCTAGCAAGCCT-3'

In the first CAR, the domains may be coupled to each other via a linker peptide (domain linker peptide), for example. The domain linker peptide is constituted by 1 to 40, 1 to 18, 1 to 15, 1 to 7, 1 to 3, or 1 or 2 amino acids, for example. The domain linker peptide is constituted by amino acids such as glycine and serine, for example, and a specific example thereof is $(GGGGS)_n$. n in this formula is an integer from 1 to 6, for example.

An example of the first CAR is a polypeptide that consists of the amino acid sequence (Sequence ID No. 15) represented by Formula (1) below. In Formula (1) below, $V_1$ and $V_2$ are the amino acid sequences of the heavy-chain variable region and the light-chain variable region, respectively, or the amino acid sequences of the light-chain variable region and the heavy-chain variable region, respectively. In Formula (1) below, the amino acid sequence between $V_1$ and $V_2$ is the amino acid sequence of the Fv linker peptide, and the amino acid sequence located on the C-terminal side of the $V_2$ includes the amino acid sequences of the spacer peptide, the transmembrane domain, and the intracellular signaling domain. In Formula (1) below, the Fv linker peptide is the Fv linker peptide 1, but may also be the Fv linker peptide 2.

(1)
[V₁]-[GSTSGSGKPGSGEGSTKG]-[V₂]-

[IEVMYPPPYLDNEKSNGTIIHVKGKHLCPSPLFPGPSKPFWVLVVVGG

VLACYSLLVTVAFIIFWVRSKRSRLLHSDYMNMTPRRPGPTRKHYQPYA

PPRDFAAYRS]-

[RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTAT

KDTYDALHMQALPPR]...

An example of the nucleic acid coding for the first CAR is a polynucleotide consisting of the base sequence (Sequence ID No. 16) represented by Formula (2) below. In Formula (2) below, $N_1$ and $N_2$ are the base sequences coding for the heavy-chain variable region and the light-chain variable region, respectively, or the base sequences coding for the light-chain variable region and the heavy-chain variable region, respectively. In Formula (2) below, the base sequence between $N_1$ and $N_2$ is the base sequence coding for the Fv linker peptide, and the base sequence located on the 3'-end side of the $N_2$ includes the base sequences coding for the spacer peptide, the transmembrane domain, and the intracellular signaling domain. In Formula (2) below, the base sequence coding for the Fv linker peptide is the base sequence coding for the Fv linker peptide 1, but may also be the base sequence coding for the Fv linker peptide 2.

(2)
5'-[N₁]-

[GGCTCTACAAGCGGCTCTGGCAAGCCTGGATCTGGCGAGGGAAGCACC

AAGGGC]-[N₂]-

[ATCGAAGTGATGTACCCCCCTCCCTACCTGGACAACGAGAAGTCCAAC

GGCACCATTATCCACGTGAAGGGAAAGCACCTGTGCCCCAGCCCTCTGT

TCCCTGGCCCTAGCAAGCCTTTCTGGGTGCTGGTGGTCGTGGGCGGAGT

GCTGGCCTGTTATAGCCTGCTCGTGACCGTGGCCTTCATCATCTTTTGG

GTGCGCAGCAAGCGGAGCCGGCTGCTGCACAGCGACTACATGAACATGA

CCCCCAGACGGCCCGGACCCACCAGAAAGCACTACCAGCCTTACGCCCC

TCCCAGAGACTTCGCCGCCTACAGATCT]-

[CGAGTGAAGTTCAGCAGAAGCGCCGACGCCCCTGCCTATCAGCAGGGC

CAGAACCAGCTGTACAACGAGCTGAACCTGGGCAGACGGGAAGAGTACG

ACGTGCTGGACAAGCGGAGAGGCAGGGACCCTGAGATGGGCGGCAAGCC

CAGAAGAAAGAACCCCCAGGAAGGCCTGTATAACGAACTGCAGAAAGAC

AAGATGGCCGAGGCCTACAGCGAGATCGGCATGAAGGGCGAGCGGAGAA

GAGGCAAGGGCCACGATGGCCTGTACCAGGGCCTGAGCACCGCCACCAA

GGACACCTATGACGCCCTGCACATGCAGGCCCTGCCCCCCAGA]-3'...

It is preferable that the CAR library of the present invention includes a plurality of types of nucleic acids, for example. In this case, the CAR library of the present invention is a mixture of a plurality of types of nucleic acids, for example. It is preferable that some or all of the plurality of types of nucleic acids code for different first CARs, and preferably code for different first antigen-binding domains, for example. When the plurality of types of nucleic acids code for different first antigen-binding domains, the regions other than the first antigen-binding domains in the first CARs have the same amino acid sequence or different amino acid sequences, for example. The number of types of nucleic acids included in the CAR library of the present invention is $1\times10^5$ to $1\times10^7$, $1\times10^5$ to $1\times10^6$, or $1\times10^6$ to $5\times10^6$, for example, and preferably about $2\times10^6$ (e.g., $1\times10^6$ to $3\times10^6$). In the phage display technique, the number of types of nucleic acids required to screen scFvs capable of binding to the target antigen is about $1\times10^8$. On the other hand, with the CAR library of the present invention, scFvs capable of binding to the target antigen can be screened using as few as about $1\times10^6$ types of nucleic acids, for example. Accordingly, with the CAR library of the present invention, scFvs capable of binding to the target antigen can be screened using a smaller number of, or a smaller number of types of, nucleic acids compared with the phage display technique, for example. The number of types of nucleic acids can also be referred to as the heterogeneity of the nucleic acids, for example. The heterogeneity can be measured through restriction enzyme mapping, sequencing of the CDRs and/or the FRHs using the Sanger's method etc., or the like, for example.

The first CAR may include a signal peptide at the N terminus, for example. An example of the signal peptide is a signal peptide serving as an endoplasmic reticulum transport signal. The first CAR may include a tag, for example. Examples of the tag include a peptide tag and a protein tag. Examples of the tag include a FLAG (registered trademark) tag, a HA tag, a His tag, a Myc tag, a V5 tag, and a truncated NGFR (nerve growth factor receptor). The tag peptide is added to at least either the N terminus or the C terminus of the first CAR, for example. When the truncated NGFR is used as the tag, the tag is arranged at the C-terminal side of the first CAR. Thus, with the CAR library of the present invention, the nucleic acid introduction efficiency can be adjusted such that one type of nucleic acid coding for a first CAR is introduced per cell, for example. The first CAR and the tag may be coupled to each other via a linker peptide.

In the present invention, the nucleic acids coding for the first CARs can be prepared based on the amino acid sequences of the first CARs using an ordinary method, for example. In a specific example, the nucleic acids coding for the first CARs can be prepared based on the base sequences coding for the amino acid sequences obtained from the database in which the amino acid sequences of the above-described domains are registered, using a molecular biological technique and/or a chemical synthesis method, for example. The base sequences of the nucleic acids may be subjected to codon optimization in accordance with the source of cells in which the CAR library of the present invention is to be expressed, for example.

The nucleic acids coding for the first CARs may be introduced into expression vectors, for example. The expression vectors can be prepared by coupling the nucleic acids coding for the first CARs to linking vectors, for example. There is no particular limitation on the types of linking vectors, and examples thereof include: retroviral vectors such as oncoretroviral vectors, lentiviral vectors, and pseudo type vectors; and viral vectors such as adenoviral vectors, adeno-associated viral (AAV) vectors, simian viral vectors, vaccinia viral vectors, Sendai viral vectors, Epstein-Barr viral (EBV) vectors, and HSV vectors. Specific examples of the linking vectors include pUC, pCMV, pMX, and pELP. The linking vectors can also be determined as appropriate in accordance with hosts into which the expression vectors are to be introduced, for example. There is no particular limitation on the hosts, and examples thereof include mammalian-derived cultured cells such as CHO cells, Jurkat cells, and Jurkat 76 cells, and immune cells. Examples of the immune cells include lymphocytes, granulocytes, and macrophages. Examples of the lymphocytes include T cells, NK cells, NKT cells, and B cells. The immune cells are cells isolated from a living organism, immune cells induced from stem cells such as multipotent stem cells, or cultured cells derived from immune cells, for example. The T cells may be T cell-like cells. Examples of the T cell-like cells include cultured cells derived from T cells, and specific examples thereof include Jurkat cells and Jurkat 76 cells.

It is preferable that each of the expression vectors includes a regulatory sequence for regulating at least either the expression of the nucleic acid coding for the first CAR or the expression of the first CAR encoded by the nucleic acid coding for the first CAR, for example. Examples of the regulatory sequence include a promoter, a terminator, an enhancer, a polyadenylation signal sequence, and a replication origin sequence (ori). There is no particular limitation on the arrangement of the regulatory sequence in the expression vector. It is sufficient that the regulatory sequence is arranged in the expression vector such that at least either the expression of the nucleic acid coding for the first CAR or the expression of the first CAR encoded by the nucleic acid can be functionally regulated, for example, and the regulatory sequence can be arranged using a known method. For example, a predetermined sequence included in the linking vector may be used as the regulatory sequence, or an additional regulatory sequence may be inserted into the linking vector, or a regulatory sequence included in the linking vector may be replaced with another regulatory sequence.

The expression vector may further include a sequence coding for a selective marker, for example. Examples of the selective marker include drug-resistant markers, fluorescent protein markers, enzymatic markers, and cell-surface receptor markers.

First scFv-Screening Method

A first screening method of the present invention includes: a first expression step of expressing the CAR library of the present invention (also referred to as a "first CAR library" hereinafter) in immune cells; a first contact step of bringing the immune cells obtained in the first expression step into contact with the target antigen; and a first selection step of selecting the first scFvs of the CARs expressed in the immune cells that have bound to the target antigen in the first contact step as first candidate scFvs capable of binding to the target antigen. The first screening method of the present invention is characterized by including the first expression step, the first contact step, and the first selection step, and using the CAR library of the present invention in the first expression step, and there is no particular limitation on the other configurations and conditions. With the first screening method of the present invention, scFvs that can be functional in CAR-T cells can be screened. Moreover, antibodies capable of binding to the target antigen or antigen-binding fragment thereof can be produced based on the amino acid sequences of the CDRs of the heavy-chain variable regions and the light-chain variable regions in the scFvs capable of binding to the target antigen, for example. Accordingly, the first screening method can also be referred to as a method for screening antibodies capable of binding to the target antigen or antigen-binding fragments thereof, for example. The descriptions of the CAR library of the present invention can be applied to the first screening method of the present invention. With the scFv manufacturing method of the present invention, novel scFvs can be screened. Accordingly, the scFv manufacturing method of the present invention can also be referred to as an "scFv screening method", for example.

When chimeric antigen receptors (CARs) and the like capable of binding to a target antigen are manufactured using a phage display technique or the like, an antibody library in which the number of types of antibodies is about $1 \times 10^{10}$ is produced, and antibodies capable of binding to the target antigen are obtained, followed by preparation of CARs and the like that include scFvs from the antibodies. Then, the effectiveness of the CARs and the like is examined using immune cells or the like. On the other hand, in the first screening method of the present invention, the CAR library of the present invention and the immune cells are used, thus making it possible to simultaneously perform screening of scFvs capable of binding to the target antigen and examination of the effectiveness of the scFvs in the immune cells, for example. Accordingly, with the first screening method of the present invention, scFvs capable of binding to a target antigen and being used for CARs that are functional in immune cells and the like can be more easily screened compared with a phage display technique and the like used to obtain antibodies capable of binding to a target antigen, for example.

In the first expression step, the CAR library of the present invention is expressed in immune cells. Specifically, in the first expression step, the first CAR library is introduced into the immune cells, for example. Then, in the first expression step, the first CAR library is expressed in the immune cells by culturing the immune cells into which the first CAR library has been introduced, for example. There is no particular limitation on a method for introducing the first CAR library, and a known method for introducing nucleic acids into cells can be used, for example. Specific examples of the method for introducing the first CAR library include a method in which a nucleic acid introducing reagent such as a liposome or a cationic lipid is used; and a method in which virus such as retrovirus or lentivirus is used. The immune cells are cultured for 6 hours to 30 days, 6 to 96 hours, or 1 to 30 days, for example, but there is no particular limitation thereto. The immune cells are cultured at a temperature of 28 to 37° C., for example.

The first CAR library may include nucleic acids coding for the first CARs, or expression vectors into which nucleic acids coding for the first CARs have been introduced, for example.

Examples of the immune cells include, but are not particularly limited to, T cells, NK cells, NKT cells, and B cells. Examples of the immune cells include immune cells isolated from a living organism, immune cells induced from stem cells such as multipotent stem cells, and cultured cells derived from immune cells. The isolated immune cells may be immune cell-like cultured cells, for example, and specific examples thereof include T cell-like cultured cells, NK cell-like cultured cells, NKT cell-like cultured cells, and B cell-like cultured cells. The immune cells are immune cells isolated from a living organism, for example, and specific examples thereof include immune cells derived from human peripheral blood. Examples of the T cell-like cultured cells include Jurkat cells and Jurkat 76 cells. The immune cells are preferably T cells, T cell-like cultured cells, NK cells, or NKT cells because scFvs that are more likely to be functional in CAR-T cells can be screened, and immune cells that express first CARs capable of binding to the target antigen can be enriched in the first contact step, which will be described later, for example.

In the first expression step, the number of the immune cells is not particularly limited, and is $1 \times 10^5$ to $1 \times 10^8$, $1 \times 10^5$ to $1 \times 10^7$, $1 \times 10^5$ to $1 \times 10^6$, $1 \times 10^6$ to $5 \times 10^6$, or $1 \times 10^6$ to $3 \times 10^6$, for example.

In the first expression step, it is preferable that the CAR library of the present invention is expressed in the immune cells such that the average number of expressed first CARs per immune cell is 1 or less. Accordingly, with the first screening method of the present invention, it is possible to suppress selection of non-specific first CARs incapable of binding to the target antigen, for example. The number of expressed first CARs per cell can be adjusted by changing the ratio between the number of cells and the amount of the nucleic acid or vector such as a viral vector to be introduced into the cells, for example. Specifically, in the first expression step, reducing the ratio of the amount of the vector to be introduced into the certain number of cells makes it possible to reduce the number of expressed first CARs per cell. On the other hand, in the first expression step, increasing the ratio of the amount of the vector to be introduced into the certain number of cells makes it possible to increase the number of expressed first CARs per cell. In the first expression step, the efficiency of introduction of the vector into the immune cells is not particularly limited, and can be set to 10 to 60%, 10 to 50%, 20 to 40%, or 25 to 35%, for example.

Next, in the first contact step, the immune cells (candidate immune cells) obtained in the first expression step are brought into contact with the target antigen. The candidate immune cells can be brought into contact with the target antigen by culturing the candidate immune cells together with the target antigen, for example. The candidate immune cells are cultured for 6 hours to 30 days, 6 to 96 hours, or 1 to 30 days, for example. The candidate immune cells are cultured at a temperature of 28 to 37° C., for example. Hereinafter, when the immune cells are T cells, the candidate immune cells can also be referred to as "candidate CAR-Ts", for example.

The candidate immune cells may express a single type of CAR or a plurality of types of CARs, for example. The former is preferable. It is preferable that the candidate immune cells are provided as a mixture of candidate immune cells that express CARs having different amino acid sequences, namely two or more types of candidate immune cells that express different CARs.

Examples of the target antigen to be brought into contact with the candidate immune cells include a target antigen monomer, a target antigen complex, and a target antigen-expressing cell, and a target antigen-expressing cell is preferable. An example of the target antigen complex is a target antigen multimer, and specific examples thereof include a target antigen dimer and a target antigen tetramer. The target antigen multimer can be prepared using a method in which tagged target antigens are cross-linked via an antibody, a method in which a complex of biotinylated target antigens is formed using avidin, or the like, for example. Examples of the target antigen-expressing cell include cells that intrinsically express the target antigen, and cells that express the target antigen due to the introduction of a nucleic acid coding for the target antigen. Examples of the target antigen-expressing cell include cultured cells such as 293 cells, 293 T cells, and K562 cells.

In the first contact step, the immune cells may be brought into contact with the target antigen together with a molecule for activating the immune cells, namely a costimulatory molecule. Examples of the costimulatory molecule include CD27, CD40, CD40L, CD80, CD83, CD86, OX40L, 4-1BBL, GITRL, and ICOS. Examples of the costimulatory molecule include a costimulatory molecule monomer, a costimulatory molecule complex, and a costimulatory molecule-expressing cell, and a costimulatory molecule-expressing cell is preferable. The costimulatory molecule complex can be prepared as in the case of the target antigen complex, for example.

When the target antigen-expressing cell is used as the target antigen, it is preferable that the target antigen-expressing cell also expresses a molecule for activating the immune cells, namely a costimulatory molecule. Examples of the costimulatory molecule include CD27, CD40, CD40L, CD80, CD83, CD86, OX40L, 4-1BBL, GITRL, and ICOS. The target antigen-expressing cell may express a single type of costimulatory molecule, or two or more types of costimulatory molecules. It is preferable that the target antigen-expressing cell expresses at least one selected from the group consisting of CD80, CD83, CD40, and 4-1BBL because the functions similar to those of antigen presenting cells in a living body can be exhibited and CARs that are functional in a living organism can be selected, for example.

In the first screening method of the present invention, the candidate immune cells are brought into contact with the target antigen in the first contact step. Accordingly, each of the candidate immune cells that express a CAR specific to the target antigen can continuously or intermittently form an immune synapse together with the target antigen in the same manner as in a living organism in accordance with the degree of avidity (binding ability) of the CAR for the target antigen, for example. Accordingly, the candidate immune cells that express a CAR specific to the target antigen can receive a survival signal, an activation signal, and/or a proliferation signal from the CAR in accordance with the degree of avidity (binding ability) of the CAR for the target antigen, for example. As a result, out of the candidate immune cells that have been subjected to the first contact step, candidate immune cells that express a CAR specific to the target antigen show a phenotype in which a survival or activation marker is expressed and/or the number of cells increases in accordance with the degree of avidity (binding ability) of the CAR for the target antigen, for example. Then, in the first selection step, which will be described later, the candidate immune cells showing such a phenotype are evaluated and selected, for example. Accordingly, in the first selection step, CARs can be screened based on the avidity of the CARs expressed in the candidate immune cells as well as the phenotype (functionality) shown when the CARs are activated, for example. Therefore, due to the first screening method of the present invention including the first contact step, scFvs capable of being used for CARs that are effectively functional in a living organism or immune cells can be favorably screened, for example.

The first contact step may be performed a plurality of times. The term "plurality of times" refers to 1 to 5 times or 2 or 3 times, for example, and preferably 2 or 3 times. When the first contact step is performed a plurality of times, the candidate immune cells are collected after the first contact step is performed for the first time, and then the first contact step is performed for the second time similarly to the case where the first contact step was performed for the first time. Then, the collection process and the contact process are repeated a desired number of times in the same manner. Since performing the first contact step a plurality of times makes it possible to proliferate and/or enrich candidate immune cells that express CARs capable of binding to the target antigen in the first contact step, for example, scFvs capable of binding to the target antigen can be more effectively screened. As shown in Examples, which will be described later, the CARs expressed in the candidate immune cells proliferated by performing the first contact step a plurality of times can favorably proliferate the CAR-expressing cells in a manner dependent on stimulation by the target antigen and induce the activation of target antigen-dependent cytotoxic activity and the like in the CAR-expressing cells even in the case (e.g., cancer) where the ratio of the target antigen-expressing cells to the CAR-expressing cells is high, for example. Accordingly, with the first screening method of the present invention, performing the first contact step a plurality of times makes it possible to favorably screen scFvs capable of being used for CARs that are functional more favorably in a living organism, for example.

It can also be said that, in the first contact step, out of the candidate immune cells, candidate immune cells that express CARs that recognize the target antigen are stimulated by the target antigen. Accordingly, the first contact step can also be referred to as an "antigen stimulation step", for example.

In the first contact step, the number of the candidate immune cells is not particularly limited, and is $1 \times 10^5$ to $1 \times 10^8$, $1 \times 10^5$ to $1 \times 10^7$, $1 \times 10^5$ to $1 \times 10^6$, $1 \times 10^6$ to $5 \times 10^6$, or $1 \times 10^6$ to $3 \times 10^6$, for example.

When a target antigen-expressing cell is used as the target antigen in the first contact step, the cell ratio (E:T) between the candidate immune cells (E) and the target antigen-expressing cells (T) in the first contact step is 2:1 to 50:1, 5:1 to 40:1, 10:1 to 30:1, or about 20:1, for example.

Then, in the first selection step, the first scFvs of the first CARs expressed in T cells that have bound to the target antigen in the first contact step are selected as first candidate scFvs capable of binding to the target antigen. The binding of the candidate immune cells to the target antigen can be evaluated directly or indirectly, for example. The binding of the candidate immune cells to the target antigen may be indirectly evaluated because scFvs capable of inducing the activation of T cells and exhibition of functionality of T cells when used as scFvs for chimeric antigen receptors can be obtained, for example.

The direct evaluation method can be performed using a technique for detecting the binding of an antibody to an antigen such as surface plasmon resonance (SPR) or flow cytometry, for example. In a specific example, the direct evaluation method can be performed using a labeled target antigen monomer or multimer, for example. In this case, in the first selection step, the candidate immune cells are brought into contact with the labeled target antigen, for example. When the candidate immune cells express CARs capable of binding to the target antigen, the labeled target antigen and the candidate immune cell form a complex. Accordingly, in the first selection step, the candidate immune cells forming the complex that includes the label can be determined to be T cells binding to the target antigen, for example.

In a specific example of the direct evaluation method, a fluorescence-labeled target antigen multimer is mixed with the candidate immune cells to form a complex of the candidate immune cells that express a CAR specific to the target antigen and the fluorescence-labeled target antigen. Next, the thus obtained mixture is analyzed by flow cytometry, and thus the candidate immune cells that form a complex with the fluorescence-labeled target antigen are detected, evaluated, and selected based on the signal from the fluorescent label.

The indirect evaluation method can be implemented as follows, for example. T cells that express CARs capable of binding to the target antigen bind to the target antigen and are thus activated, for example. Accordingly, in the indirect evaluation method, the activation of the candidate immune cells is used as an evaluation index, for example. In a specific example, when the candidate immune cells bind to the target antigen, the expression of activation markers is increased in the immune cells, the production amounts of cytokines and/or chemokines are increased in the immune cells, and the immune cells are proliferated, for example, compared with candidate immune cells that do not bind to the target antigen. In a specific example, when the immune cells are T cells, NK cells, NKT cells, or B cells, the expression of the following activation markers is increased in the cells, the production amounts of the following cytokines and/or chemokines are increased in the cells, and the cells are proliferated, for example. Accordingly, in the first selection step, when it is determined based on any one or more of the indices that the candidate immune cells are activated, the activated immune cells can be determined to be immune cells that bind to the target antigen. The increase in the production amounts of cytokines and/or chemokines may be evaluated using a reporter whose mRNA or protein expression level increases when the expression of the cytokines and/or chemokines is induced, for example. An example of the reporter is a fluorescent protein. The above-mentioned proliferation can be evaluated by using, as an index, the attenuation of fluorescence intensity of cells that have been stained using a cell staining fluorescent dye or the like such as carboxyfluorescein succinimidyl ester (CFSE), for example.

T cells
  Activation marker: CD69, CD107a, etc.
  Cytokine, chemokine: IFN-γ, IL-12, IL-2, TNFα, MIP-1β, etc.
NK cells
  Activation marker: CD69, CD107a, etc.
  Cytokine, chemokine: INF-γ, IL-12, etc.
NKT cells
  Activation marker: CD69, CD107a, CD25, etc.
  Cytokine, chemokine: INF-γ, IL-2, etc.
B cells
  Activation marker: CD28, CD69, CD80, CD138, B220, etc.
  Cytokine, chemokine: CXCR4, etc.

Then, the first scFvs of the first CARS expressed in the candidate immune cells that have bound to the target antigen are selected as first candidate scFvs capable of binding to the target antigen. The first candidate scFvs can be selected by selecting candidate immune cells that have bound to the target antigen and reading the base sequences coding for the scFvs or CARS in the selected candidate immune cells, for example. In the first selection step, the CDRH1, the CDRH2, and the CDRH3 in the heavy-chain variable region and the CDRL1, the CDRL2, and the CDRL3 in the light-chain variable region in each of the first candidate scFvs may also be identified, for example. The CDRs can be identified using a known method referring to the genome information (e.g., the website of IMGT (http://www.imgt.org/)), for example.

Accordingly, new scFvs capable of binding to the target antigen can be screened. If a first CAR of the first CAR library meets Condition 1 above, the first screening method of the present invention can be used to screen new light-chain variable regions capable of binding to the target antigen. If a first CAR of the first CAR library meets Condition 2 above, the first screening method of the present invention can be used to screen new heavy-chain variable regions capable of binding to the target antigen.

The first screening method of the present invention may be configured such that new heavy-chain variable regions or light-chain variable regions of the first candidate scFvs are considered as the heavy-chain variable regions or light-chain variable regions of antibody and the like capable of binding to the target antigen in the first CAR library, and then the other regions are screened, for example. In this case, the first screening method of the present invention further includes a preparation step of preparing a second CAR library based on the first candidate scFvs, for example.

The second CAR library includes nucleic acids coding for second CARs, for example. Each of the second CARs includes a second antigen-binding domain, a second transmembrane domain, and a second intracellular signaling domain, for example. The second antigen-binding domain includes a second scFv to be screened for the ability to bind to the target antigen, for example.

The nucleic acids coding for the second CARs are nucleic acids (polynucleotides) coding for the amino acid sequences of the second CARs, for example.

The target antigen of the second scFvs is the same as the target antigen of the first scFvs. The second scFvs have structures similar to those of the first scFvs, for example.

Each of the second scFvs includes a second heavy-chain variable region and a second light-chain variable region, for example. The second heavy-chain variable region includes a CDRH1, a CDRH2, and a CDRH3, for example. The second light-chain variable region includes a CDRL1, a CDRL2, and a CDRL3, for example. The second heavy-chain variable region and the second light-chain variable region meet Condition 3 or Condition 4 below, for example.

Condition 3

If the CAR library in the first expression step meets Condition 1 above,
  the CDRH1, the CDRH2, and the CDRH3 in the second heavy-chain variable region include the CDRH1, the CDRH2, and the CDRH3 in the heavy-chain variable region of a second B cell receptor, respectively, and
  the CDRL1, the CDRL2, and the CDRL3 in the second light-chain variable region include the CDRL1, the CDRL2, and the CDRL3 in the light-chain variable region of the first candidate scFv, respectively.

Condition 4

If the CAR library in the first expression step meets Condition 2 above,
  the CDRH1, the CDRH2, and the CDRH3 in the second heavy-chain variable region include the CDRH1, the CDRH2, and the CDRH3 in the heavy-chain variable region of the first candidate scFv, respectively, and
  the CDRL1, the CDRL2, and the CDRL3 in the second light-chain variable region include the CDRL1, the CDRL2, and the CDRL3 in the light-chain variable region of a second B cell receptor, respectively.

Condition 3 above is employed in the case where the second CAR library is prepared using the first candidate scFvs screened using the first CAR library that meets Condition 1 above, for example. In Condition 3 above, the CDRL1, the CDRL2, and the CDRL3 of the first candidate scFv are used as those in the second light-chain variable region, and the CDRH1, the CDRH2, and the CDRH3 in the second heavy-chain variable region are screened for the ability to bind to the target antigen, for example.

If the "first B cell receptor" is changed to the "second B cell receptor", and the "first heavy-chain variable region" is changed to the "second heavy-chain variable region", the descriptions of the first heavy-chain variable region in Condition 2 above can be applied to the second B cell receptor in the second heavy-chain variable region, for example.

The CDRH1, the CDRH2, and the CDRH3 in the second heavy-chain variable region may respectively be polypeptides that consist of the amino acid sequences of the CDRH1, the CDRH2, and the CDRH3 of the second B cell receptor, or polypeptides that include the amino acid sequences of the CDRH1, the CDRH2, and the CDRH3 of the second B cell receptor, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the second B cell receptor, or polypeptides that include the amino acid sequences of the FRH1, the FRH2, the FRH3, and the FRH4 of the second B cell receptor, for example. It is preferable that "the second B cell receptor" in the descriptions of the CDRHs and "the second B cell receptor" in the descriptions of the FRHs are the same B cell receptor.

The second heavy-chain variable region may include the heavy-chain variable region of the second B cell receptor, for example. In this case, the second heavy-chain variable region may be a polypeptide that consists of the amino acid sequence of the heavy-chain variable region of the second B cell receptor, or a polypeptide that includes the amino acid sequence of the heavy-chain variable region of the second B cell receptor, for example.

The CDRL1, the CDRL2, and the CDRL3 in the second light-chain variable region may respectively be polypeptides that consist of the amino acid sequences of the CDRL1, the CDRL2, and the CDRL3 of the first candidate scFv, or polypeptides that include the amino acid sequences of the CDRL1, the CDRL2, and the CDRL3 of the first candidate scFv, for example.

The FRs in the second light-chain variable region may include the FRs in the light-chain variable region of the first candidate scFv, for example. The FRL1, the FRL2, the FRL3, and the FRL4 in the second light-chain variable region may respectively be polypeptides that consist of the amino acid sequences of the FRL1, the FRL2, the FRL3, and the FRL4 of the first candidate scFv, or polypeptides that include the amino acid sequences of the FRL1, the FRL2, the FRL3, and the FRL4 of the first candidate scFv, for example. It is preferable that "the first candidate scFv" in the descriptions of the CDRLs and "the first candidate scFv" in the descriptions of the FRLs are the same scFv.

The second light-chain variable region may include the light-chain variable region of the first candidate scFv, for example. In this case, the second light-chain variable region may be a polypeptide that consists of the amino acid sequence of the light-chain variable region of the first candidate scFv, or a polypeptide that includes the amino acid sequence of the light-chain variable region of the first candidate scFv, for example.

Next, Condition 4 above is employed in the case where the second CAR library is prepared using the first candidate scFvs screened using the first CAR library that meets Condition 2 above, for example. In Condition 4 above, the CDRH1, the CDRH2, and the CDRH3 of the first candidate scFv are used as those in the second heavy-chain variable region, and the CDRL1, the CDRL2, and the CDRL3 in the second light-chain variable region are screened for the ability to bind to the target antigen, for example.

The CDRH1, the CDRH2, and the CDRH3 in the second heavy-chain variable region may respectively be polypeptides that consist of the amino acid sequences of the CDRH1, the CDRH2, and the CDRH3 of the first candidate scFv, or polypeptides that include the amino acid sequences of the CDRH1, the CDRH2, and the CDRH3 of the first candidate scFv, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the first candidate scFv, or polypeptides that include the amino acid sequences of the FRH1, the FRH2, the FRH3, and the FRH4 of the first candidate scFv, for example. It is preferable that "the first candidate scFv" in the descriptions of the CDRHs and "the first candidate scFv" in the descriptions of the FRHs are the same scFv.

The second heavy-chain variable region may include the heavy-chain variable region of the first candidate scFv, for example. In this case, the second heavy-chain variable region may be a polypeptide that consists of the amino acid sequence of the heavy-chain variable region of the first candidate scFv, or a polypeptide that includes the amino acid sequence of the heavy-chain variable region of the first candidate scFv, for example.

If the "first B cell receptor" is changed to the "second B cell receptor", and the "first light-chain variable region" is changed to the "second light-chain variable region", the descriptions of the first light-chain variable region in Condition 1 above can be applied to the second B cell receptor in the second light-chain variable region, for example.

The CDRL1, the CDRL2, and the CDRL3 in the second light-chain variable region may respectively be polypeptides that consist of the amino acid sequences of the CDRL1, the CDRL2, and the CDRL3 of the second B cell receptor, or polypeptides that include the amino acid sequences of the CDRL1, the CDRL2, and the CDRL3 of the second B cell receptor, for example.

The FRL1, the FRL2, the FRL3, and the FRL4 in the second light-chain variable region may respectively be polypeptides that consist of the amino acid sequences of the FRL1, the FRL2, the FRL3, and the FRL4 of the second B cell receptor, or polypeptides that include the amino acid sequences of the FRL1, the FRL2, the FRL3, and the FRL4 of the second B cell receptor, for example. It is preferable that "the second B cell receptor" in the descriptions of the CDRLs and "the second B cell receptor" in the descriptions of the FRLs are the same B cell receptor.

The second light-chain variable region may include the light-chain variable region of the second B cell receptor, for example. In this case, the second light-chain variable region may be a polypeptide that consists of the amino acid sequence of the light-chain variable region of the second B cell receptor, or a polypeptide that includes the amino acid sequence of the light-chain variable region of the second B cell receptor, for example.

In the second scFv, the second heavy-chain variable region and the second light-chain variable region are coupled to each other via the above-described linker peptide (Fv linker peptide), for example. The Fv linker peptide in the second scFv may be the same as or different from the Fv linker peptide in the first scFv, for example.

The second antigen-binding domain includes the second scFv, and the second binding domain may also include a structure other than the scFv that includes the heavy-chain variable region and the light-chain variable region. In a specific example, the second binding domain may be a Fab, Fab', F(ab')$_2$, variable region fragment (Fv), disulfide-bond Fv, or the like.

In the second CAR, the second transmembrane domain and the second intracellular signaling domain may be the same as or different from the first transmembrane domain and the first intracellular signaling domain in the first CAR library, respectively. The descriptions of the first transmembrane domain and the first intracellular signaling domain in the CAR library of the present invention can be applied to the second transmembrane domain and the second intracellular signaling domain in the second CAR library, respectively, for example.

In the second CAR, the domains may be coupled to each other via a linker peptide (domain linker peptide), for example. The domain linker peptide is constituted by 1 to 40, 1 to 18, 1 to 15, 1 to 7, 1 to 3, or 1 or 2 amino acids, for example. The domain linker peptide is constituted by amino acids such as glycine and serine, for example, and a specific example thereof is $(GGGGS)_n$. n in this formula is an integer from 1 to 6, for example.

An example of the second CAR is a polypeptide that consists of the amino acid sequence (Sequence ID No. 15) represented by Formula (1) above. In Formula (1) above, $V_1$ and $V_2$ are the amino acid sequences of the heavy-chain variable region and the light-chain variable region, respectively, or the amino acid sequences of the light-chain variable region and the heavy-chain variable region, respectively. It is preferable that the order of the heavy-chain variable region and the light-chain variable region in the second CAR is opposite to the order of the heavy-chain variable region and the light-chain variable region in the first CAR because the second CAR library can be prepared more easily, for example. In a specific example, if the heavy-chain variable region and the light-chain variable region are arranged in this order from the N terminus in the first CAR, the light-chain variable region and the heavy-chain variable region are arranged in this order from the N terminus in the second CAR, for example. If the light-chain variable region and the heavy-chain variable region are arranged in this order from the N terminus in the first CAR, the heavy-chain variable region and the light-chain variable region are arranged in this order from the N terminus in the second CAR, for example.

An example of the nucleic acid coding for the second CAR is a polynucleotide consisting of the base sequence (Sequence ID No. 16) represented by Formula (2) above. In Formula (2) above, $N_1$ and $N_2$ are the base sequences coding for the heavy-chain variable region and the light-chain variable region, respectively, or the base sequences coding for the light-chain variable region and the heavy-chain variable region, respectively.

It is preferable that the second CAR library includes a plurality of types of nucleic acids, for example. In this case, the second CAR library is a mixture of a plurality of types of nucleic acids, for example. It is preferable that some or all of the plurality of types of nucleic acids code for different second CARs, and preferably code for different second antigen-binding domains, for example. When the plurality of types of nucleic acids code for different second antigen-binding domains, the regions other than the second antigen-binding domains in the second CARs have the same amino acid sequence or different amino acid sequences, for example. The number of types of nucleic acids included in the second CAR library is $1 \times 10^5$ to $1 \times 10^7$, $1 \times 10^5$ to $1 \times 10^6$, or $1 \times 10^6$ to $5 \times 10^6$, for example, and preferably about $2 \times 10^6$ (e.g., $1 \times 10^6$ to $3 \times 10^6$).

The second CAR may include a signal peptide at the N terminus, for example. The second CAR may include a tag, for example. If the "first CAR" is changed to the "second CAR", the descriptions of the signal peptide and the tag in the first CAR can be applied to the above-mentioned signal peptide and the tag, for example.

In the present invention, the nucleic acids coding for the second CARs can be prepared based on the amino acid sequences of the second CARs using an ordinary method, for example. In a specific example, the nucleic acids coding for the second CARs can be prepared based on the base sequences coding for the amino acid sequences obtained from the database in which the amino acid sequences of the above-described domains are registered, using a molecular biological technique and/or a chemical synthesis method, for example. The base sequences of the nucleic acids may be subjected to codon optimization in accordance with the source of cells in which the second CAR library of the present invention is to be expressed, for example.

The nucleic acids coding for the second CARs may be introduced into expression vectors, for example. The descriptions of the expression vectors in the CAR library of the present invention can be applied to the above-mentioned expression vectors, for example.

Next, in the first screening method of the present invention, an expression step, a contact step, and a selection step are performed in the same manner, except that the second CAR library prepared in the preparation step is used instead of the first CAR library, for example. Specifically, the first screening method of the present invention further includes: a second expression step of expressing the second CAR library in immune cells; a second contact step of bringing the immune cells obtained in the second expression step into contact with the target antigen; and a second selection step of selecting the second scFvs of the CARs expressed in the immune cells that have bound to the target antigen in the second contact step as second candidate scFvs capable of binding to the target antigen, for example. The immune cells in the first expression step, the first contact step, and the first selection step and the immune cells in the second expression step, the second contact step, and the second selection step may be the same or different. The immune cells are preferably T cells or T cell-like cells.

If the "first expression step" is changed to the "second expression step", the "first CAR library" is changed to the "second CAR library", and the "first CAR" is changed to the "second CAR", the descriptions of the first expression step can be applied to the second expression step, for example.

If the "first expression step" is changed to the "second expression step", and the "first contact step" is changed to the "second contact step", the descriptions of the first contact step can be applied to the second contact step, for example.

If the "first contact step" is changed to the "second contact step", the "first selection step" is changed to the "second selection step", the "first scFv" is changed to the "second scFv", the "first candidate scFv" is changed to the "second candidate scFv", and the "first CAR" is changed to the "second CAR", the descriptions of the first selection step can be applied to the second selection step, for example.

Thus, with the first screening method of the present invention, scFvs that include new heavy-chain variable regions and light-chain variable regions capable of binding to the target antigen can be screened, for example.

The first screening method of the present invention may include a designing step of designing antibodies or antigen-binding fragments thereof based on the first candidate scFvs or the second candidate scFvs. The designing step can be performed by grafting the CDRH1, the CDRH2, and the CDRH3 into the heavy-chain variable region and the CDRL1, the CDRL2, and the CDRL3 in the light-chain variable region of the first candidate scFv or the second candidate scFv into a new antibody or an antigen-binding fragment thereof, for example. Specifically, the designing step can be performed by respectively using the amino acid sequences of the CDRH1, the CDRH2, and the CDRH3 of the first candidate scFv or the second candidate scFv and the amino acid sequences of the CDRL1, the CDRL2, and the CDRL3 in the light-chain variable region of the first candidate scFv or the second candidate scFv as the amino acid sequences of the CDRH1, the CDRH2, and the CDRH3 and the amino acid sequences of the CDRL1, the CDRL2, and the CDRL3 in the light-chain variable region of a new antibody or an antigen-binding fragment thereof, for example. The CDR grafting in the designing step may be performed on a single CDR or a plurality of CDRs of the first candidate scFv or the second candidate scFv, for example, and is preferably performed on all of the CDRs. The descriptions of the types of antibodies of the present invention or antigen-binding fragments thereof, which will be described later, can be applied to the type of the above-mentioned new antibody and the antigen-binding fragment thereof, for example.

In the designing step, the FRH1, the FRH2, the FRH3, and the FRH4 in the heavy-chain variable region and the FRL1, the FRL2, the FRL3, and the FRL4 in the light-chain variable region of the first candidate scFv or the second candidate scFv may be grafted into a new antibody or an antigen-binding fragment thereof. In this case, in the designing step, the amino acid sequences of the FRH1, the FRH2, the FRH3, and the FRH4 of the first candidate scFv or the second candidate scFv and the amino acid sequences of the FRL1, the FRL2, the FRL3, and the FRL4 in the light-chain variable region of the first candidate scFv or the second candidate scFv can be respectively used as the amino acid sequences of the FRH1, the FRH2, the FRH3, and the FRH4 and the amino acid sequences of the FRL1, the FRL2, the FRL3, and the FRL4 in the light-chain variable region of the new antibody or the antigen-binding fragment thereof, for example. The FR grafting in the designing step may be performed on a single FR or a plurality of FRs of the first candidate scFv or the second candidate scFv, for example, and is preferably performed on all of the FRs.

The first screening method of the present invention includes the first expression step, but is not limited thereto in the present invention. The first screening method may have a configuration in which the first expression step is not included. In this case, the first screening method of the present invention can be started from the first contact step by using immune cells (CAR library cells) that are prepared in advance and express the CAR library of the present invention, for example.

CAR Library Cells

The chimeric antigen receptor (CAR) library cells of the present invention include cells that express the CAR library of the present invention. The CAR library cells of the present invention are characterized by including cells that express the CAR library of the present invention, and there is no particular limitation on the other configurations and conditions. With the CAR library cell of the present invention, the first screening method of the present invention can be favorably implemented. The descriptions of the CAR library and the first screening method of the present invention can be applied to the CAR library cells of the present invention.

The number of the CAR library cells of the present invention is $1\times10^5$ to $1\times10^8$, $1\times10^5$ to $1\times10^7$, $1\times10^5$ to $1\times10^6$, $1\times10^6$ to $5\times10^6$, or $1\times10^6$ to $3\times10^6$, for example. It is preferable that CARs expressed in the CAR library cells are different CARs that are included in the CAR library of the present invention, for example. The CAR library cells may include cells that do not express the CAR library of the present invention, namely cells into which the CAR library is not introduced, for example.

When the number of the CAR library cells of the present invention used is $1\times10^6$, the number of types of expressed CARs is $1\times10^4$ to $1\times10^7$, $1\times10^5$ to $1\times10^6$, $1\times10^6$ to $5\times10^6$, or $1\times10^5$ to $1\times10^6$, for example.

The CAR library cells of the present invention can be manufactured in the same manner as in the first expression step of the first screening method of the present invention, for example. The CAR library cells of the present invention are preferably cells derived from immune cells, for example, and are preferably cells derived from T cells, NK cells, or NKT cells.

First Antibody and Antigen-Binding Fragment Thereof

As described above, the antibody of the present invention against the complex of HLA-A*02:01 and NY-ESO-$1_{157-165}$ (also referred to as "A2/NY-ESO-$1_{157}$" hereinafter) or the antigen-binding fragment thereof includes the heavy-chain variable region of (H) below and the light-chain variable region of (L) below. The antibody of the present invention or the like is characterized by including the heavy-chain variable region of (H) below and the light-chain variable region of (L) below, and there is no particular limitation on the other configurations and conditions. The antibody of the present invention or the like is capable of binding to A2/NY-ESO-$1_{157}$. It is known that A2/NY-ESO-$1_{157}$ is expressed in specific cancer cells derived from lung cancer, malignant melanoma, synovial sarcoma, myeloma, and the like, for example. Accordingly, the antibody of the present invention or the like can be favorably used as a bispecific antibody against A2/NY-ESO-$1_{157}$-expressing cancer cells, the antigen-binding domain of a CAR in CAR-T cells, and the like, for example. The descriptions of the CAR library, the first screening method, and the like of the present invention can be applied.

(H) A heavy-chain variable region that includes
a heavy-chain complementarity determining region (CDRH) 1, a CDRH2, and a CDRH3,
wherein the CDRH1 is a polypeptide that includes an amino acid sequence of (H1),
the CDRH2 is a polypeptide that includes an amino acid sequence of (H2),
the CDRH3 is a polypeptide that includes an amino acid sequence of (H3), and
the amino acid sequences of (H1), (H2), and (H3) are as follows:
(H1) an amino acid sequence of (H1-1), (H1-2), or (H1-3) below:
(H1-1) any one of amino acid sequences of CDRH1 shown in Table 1A below,
(H1-2) an amino acid sequence having 80% or more identity to the amino acid sequence of (H1-1), and
(H1-3) an amino acid sequence consisting of the amino acid sequence of (H1-1) with deletion, substitution, insertion, and/or addition of one or several amino acids,
(H2) an amino acid sequence of (H2-1), (H2-2), or (H2-3) below:
(H2-1) any one of amino acid sequences of CDRH2 shown in Table 1A below,
(H2-2) an amino acid sequence having 80% or more identity to the amino acid sequence of (H2-1), and
(H2-3) an amino acid sequence consisting of the amino acid sequence of (H2-1) with deletion, substitution, insertion, and/or addition of one or several amino acids; and
(H3) an amino acid sequence of (H3-1), (H3-2), or (H3-3) below:
(H3-1) any one of amino acid sequences of CDRH3 shown in Table 1A below,
(H3-2) an amino acid sequence having 80% or more identity to the amino acid sequence of (H3-1), and
(H3-3) an amino acid sequence consisting of the amino acid sequence of (H3-1) with deletion, substitution, insertion, and/or addition of one or several amino acids.
(L) A light-chain variable region that includes
a light-chain complementarity determining region (CDRL) 1, a CDRL2, and a CDRL3,
wherein the CDRL1 is a polypeptide that includes an amino acid sequence of (L1),
the CDRL2 is a polypeptide that includes an amino acid sequence of (L2),
the CDRL3 is a polypeptide that includes an amino acid sequence of (L3), and
the amino acid sequences of (L1), (L2), and (L3) are as follows:
(L1) an amino acid sequence of (L1-1), (L1-2), or (L1-3) below:
(L1-1) any one of amino acid sequences of CDRL1 shown in Table 1B below, (L1-2) an amino acid sequence having 80% or more identity to the amino acid sequence of (L1-1), and
(L1-3) an amino acid sequence consisting of the amino acid sequence of (L1-1) with deletion, substitution, insertion, and/or addition of one or several amino acids;
(L2) an amino acid sequence of (L2-1), (L2-2), or (L2-3) below:
(L2-1) any one of amino acid sequences of CDRL2 shown in Table 1B below,
(L2-2) an amino acid sequence having 80% or more identity to the amino acid sequence of (L2-1), and
(L2-3) an amino acid sequence consisting of the amino acid sequence of (L2-1) with deletion, substitution, insertion, and/or addition of one or several amino acids; and
(L3) an amino acid sequence of (L3-1), (L3-2), or (L3-3) below:
(L3-1) any one of amino acid sequences of CDRL3 shown in Table 1B below,
(L3-2) an amino acid sequence having 80% or more identity to the amino acid sequence of (L3-1), and
(L3-3) an amino acid sequence consisting of the amino acid sequence of (L3-1) with deletion, substitution, insertion, and/or addition of one or several amino acids.

TABLE 1A

| Heavy-chain variable region | CDRH1 | CDRH2 | CDRH3 | |
|---|---|---|---|---|
| (HA) | GGSISSNY (Sequence ID No. 17) | VSYSGST (Sequence ID No. 18) | ARESYYYYGMDV (Sequence ID No. 19) | H1 |
| (HB) | GFTFSTYQ (Sequence ID No. 21) | IVSSGGST (Sequence ID No. 22) | AGELLPYYGMDV (Sequence ID No. 23) | 3M4E5H |
| (HC) | GGSISSYY (Sequence ID No. 25) | INHSGST (Sequence ID No. 26) | ARCPTYYYGMDV (Sequence ID No. 27) | H73 |

TABLE 1B

| Light-chain variable region | CDRL1 | CDRL2 | CDRL3 | |
|---|---|---|---|---|
| (LA) | SRDVGGYNY (Sequence ID No. 29) | DVI (Sequence ID No. 30) | WSFAGSYYV (Sequence ID No. 31) | 3M4E5L |
| (LB) | QSISSY (Sequence ID No. 33) | AAS (Sequence ID No. 34) | QQYYSTPQT (Sequence ID No. 35) | K52 |
| (LC) | QSISSY (Sequence ID No. 37) | AAS (Sequence ID No. 38) | QQYESYRRS (Sequence ID No. 39) | K73 |
| (LD) | QSISSY (Sequence ID No. 41) | AAS (Sequence ID No. 42) | QQYNSYSRT (Sequence ID No. 43) | K124 |
| (LE) | QSISSY (Sequence ID No. 46) | AAS (Sequence ID No. 47) | QQYNSYSPCT (Sequence ID No. 48) | K125 |
| (LF) | QDISRY (Sequence ID No. 50) | AAS (Sequence ID No. Si) | QQYDNLIT (Sequence ID No. 52) | K131 |
| (LG) | QDISRY (Sequence ID No. 54) | AAS (Sequence ID No. 55) | QQYNSYSRT (Sequence ID No. 56) | K145 |
| (LH) | QSISSY (Sequence ID No. 58) | AAS (Sequence ID No. 59) | QQYDNLIT (Sequence ID No. 60) | K151 |
| (LI) | QSVSSN (Sequence ID No. 62) | GAS (Sequence ID No. 63) | QQYNSYSRT (Sequence ID No. 64) | K160 |
| (LJ) | QSISSY (Sequence ID No. 66) | AAS (Sequence ID No. 67) | QQYESYSRT (Sequence ID No. 68) | K173 |
| (LK) | SSDVGGYDF (Sequence ID No. 70) | DVN (Sequence ID No. 71) | SSYAGSNSV (Sequence ID No. 72) | L1 |
| (LL) | SSDVGGYEF (Sequence ID No. 74) | DVI (Sequence ID No. 75) | SSYTSSSTYV (Sequence ID No. 76) | L66 |
| (LM) | GSDVGAYDY (Sequence ID No. 78) | DVS (Sequence ID No. 79) | SSYSGSSTWV (Sequence ID No. 80) | L73 |
| (LN) | SSDVGSYNL (Sequence ID No. 82) | DVS (Sequence ID No. 83) | SSYTSSSTFAV (Sequence ID No. 84) | L80 |
| (LO) | SSDVGGYNY (Sequence ID No. 86) | DVS (Sequence ID No. 87) | CSYAGGYYV (Sequence ID No. 88) | L88 |

TABLE 1B-continued

| Light-chain variable region | CDRL1 | CDRL2 | CDRL3 | |
|---|---|---|---|---|
| (LP) | SSDVGGYNY (Sequence ID No. 90) | DVS (Sequence ID No. 91) | SSYAGSGSTPFV (Sequence ID No. 92) | L102 |
| (LQ) | SSDVGGYNY (Sequence ID No. 94) | DVS (Sequence ID No. 95) | CSYAGRRYV (Sequence ID No. 96) | L124 |

In the present invention, the term "HLA-A*02:01" means a class-I antigen derived from the A*02:01 allele of a human major histocompatibility complex (MHC), for example. HLA-A*02:01 forms a complex with human β2-microglobulin, for example. An example of the amino acid sequence of HLA-A*02:01 is the amino acid sequence registered as NCBI Accession No. HG794376. An example of the amino acid sequence of human β2-microglobulin is the amino acid sequence registered as NCBI Accession No. NM_004048.2.

In the present invention, the term "NY-ESO-$1_{157-165}$" means a peptide constituted by amino acids between position 157 and position 165 (SLLMWITQC (Sequence ID No. 206)) of the amino acid sequence of the NY-ESO-1 protein, for example. NY-ESO-1 is a cancer antigen expressed in cancers such as human lung cancer, malignant melanoma, synovial sarcoma, and myeloma, for example. An example of the amino acid sequence of the NY-ESO-1 protein is the amino acid sequence registered as NCBI Accession No. NM_001327.2.

In the present invention, the term "A2/NY-ESO-$1_{157}$" means a complex formed by HLA-A*02:01 and NY-ESO-$1_{157-165}$, for example, and specifically a complex in which NY-ESO-$1_{157-165}$ binds to the peptide-binding groove of HLA-A*02:01. A2/NY-ESO-$1_{157}$ is preferably a complex in which NY-ESO-$1_{157-165}$ binds to the peptide-binding groove of the complex of HLA-A*02:01 and human 82-microglobulin.

The antibody of the present invention may be a so-called "antibody" having an immunoglobulin molecular structure, or an antigen-binding fragment thereof, for example. The antibody of the present invention or the like need only include the heavy-chain variable region and the light-chain variable region described above. If the present invention is directed to an antibody, there is no particular limitation on the immunoglobulin class and isotype thereof, for example. Examples of the immunoglobulin class include IgG, IgM, IgA, IgD, and IgE. Examples of the IgG include IgG1, IgG2, IgG3, and IgG4.

The antibody may be a monoclonal antibody, a polyclonal antibody, a recombinant antibody, a human antibody (e.g., fully human antibody), a humanized antibody, a chimeric antibody, or a multispecific antibody, for example.

The term "antigen-binding fragment" as used in the present invention means a part (e.g., a partial fragment) of the antibody that recognizes (is capable of binding to) A2/NY-ESO-$1_{157}$ above. Examples of the antigen-binding fragment include Fabs, Fab's, F(ab')$_2$s, variable region fragments (Fvs), disulfide-bond Fvs, single-chain Fvs (scFvs), bispecific antibodies, and polymers thereof. In each of the scFvs, the heavy-chain variable region and the light-chain variable region are coupled to each other via a linker, for example. The heavy-chain variable region, the linker, and the light-chain variable region may be arranged in the stated order from the N terminus, or in the inverse order from the N terminus.

The antibody of the present invention or the like may include a constant region in addition to the heavy-chain variable region and the light-chain variable region described above, and the constant region is a human constant region or a mouse constant region, for example. In the case of an antibody (immunoglobulin), the constant region of the heavy chain includes the CH1 region, the CH2 region, and the CH3 region, for example, and the constant region of the light chain includes the CL region, for example. If the antibody of the present invention or the like includes the constant region, the heavy-chain variable region binds to at least one of the CH1, the CH2, and the CH3, and the light-chain variable region binds to the CL, for example. In such a case, the heavy-chain variable region directly binds to the CH1, for example.

In general, the heavy chain and the light chain in an antibody molecule each include three complementarity determining regions (CDRs). The CDRs are also referred to as "hypervariable domains". The CDRs are regions in which the primary structure is particularly likely to be variable in the variable regions of the heavy chain and the light chain, and the primary structure generally includes three CDRs. In the present invention, the three CDRs in the heavy chain are referred to as a heavy-chain CDR 1 (CDRH1), a heavy-chain CDR 2 (CDRH2), and a heavy-chain CDR 3 (CDRH3), in this order from the amino terminus of the amino acid sequence of the heavy chain, and the three CDRs in the light-chain are referred to as a light-chain CDR 1 (CDRL1), a light-chain CDR 2 (CDRL2), and a light-chain CDR 3 (CDRL3), in this order from the amino terminus of the amino acid sequence of the light chain. These sites are close to one another in the three-dimensional structure and determine the binding specificity for an antigen.

In the heavy-chain variable region of (H) above, the CDRH1 is the CDRH1 of (HA), (HB), or (HC) above. The CDRH2 is the CDRH2 of (HA), (HB), or (HC) above. The CDRH3 is the CDRH3 of (HA), (HB), or (HC) above.

In the light-chain variable region of (L) above, the CDRL1 is the CDRL1 of any one of (LA) to (LQ) above. The CDRL2 is the CDRL2 of any one of (LA) to (LQ) above. The CDRL3 is the CDRL3 of any one of (LA) to (LQ) above.

The term "identity" as used for the CDRs refers to the degree of identity when appropriately aligning sequences to be compared, for example, and means the ratio (%) of exactly the same amino acids in these sequences. The "identity" in each case refers to 80% or more, 85% or more, 90% or more, 95% or more, 96% or more, 97% or more, 98% or more, or 99% or more identity, for example. The identity can be calculated with default parameters using analysis software such as BLAST or FASTA (the same applies hereinafter).

The term "one or several" as used for the CDRs regarding substitution and the like refers to 1 to 5, 1 to 4, 1 to 3, 1 or 2, or 1, for example.

The amino acid substitution may be conservative substitution, for example (the same applies hereinafter). The term "conservative substitution" means that one or several amino acids are substituted by other amino acids and/or amino acid derivatives such that the functions of a protein are not substantially modified. It is preferable that a "substituting amino acid" and an "amino acid to be substituted" have similar properties and/or functions, for example. Specifically, it is preferable that they are similar in chemical properties such as a hydrophobicity/hydrophilicity index (hydropathy), a polarity, and an electric charge, physical properties such as a secondary structure, and the like, for example. Amino acids or amino acid derivatives having similar properties and/or functions are known in the art, for example. Specific examples of nonpolar amino acids (hydrophobic amino acids) include alanine, valine, isoleucine, leucine, proline, tryptophan, phenylalanine, and methionine; specific examples of polar amino acids (neutral amino acids) include glycine, serine, threonine, tyrosine, glutamine, asparagine, and cysteine; specific examples of positively charged amino acids (basic amino acids) include arginine, histidine, and lysine; and specific examples of negatively charged amino acids (acidic amino acids) include aspartic acid and glutamic acid.

In the heavy-chain variable region of (H) above, there is no particular limitation on the combination of (H1-1), (H2-1), and (H3-1) above, and the CDRH1 of (HA), (HB), or (HC) above, the CDRH2 of (HA), (HB), or (HC) above, and the CDRH3 of (HA) or (HB) above can be combined as desired, for example. The combination of (H1-1), (H2-1), and (H3-1) above is preferably a combination of the CDRH1, the CDRH2, and the CDRH3 of (HA), (HB), or (HC) above.

In the light-chain variable region of (L) above, there is no particular limitation on the combination of (L1-1), (L2-1), and (L3-1) above, and the CDRL1 of any one of (LA) to (LQ) above, the CDRL2 of any one of (LA) to (LQ) above, and the CDRL3 of any one of (LA) to (LQ) above can be combined as desired, for example. The combination of (L1-1), (L2-1), and (L3-1) above is preferably a combination of the CDRL1, the CDRL2, and the CDRL3 of any one of (LA) to (LQ) above. There is no particular limitation on the combination of (H1-1), (H2-1), and (H3-1) above and (L1-1), (L2-1), and (L3-1) above, and the CDRH1 of (HA), (HB), or (HC) above, the CDRH2 of (HA), (HB), or (HC) above, and the CDRH3 of (HA), (HB), or (HC) above, and the CDRL1 of any one of (LA) to (LQ) above, the CDRL2 of any one of (LA) to (LQ) above, and the CDRL3 of any one of (LA) to (LQ) above can be combined as desired, for example. The combination of (H1-1), (H2-1), and (H3-1) above and (L1-1), (L2-1), and (L3-1) above is preferably a combination of the CDRH1, the CDRH2, and the CDRH3 of (HA), (HB), or (HC) above and the CDRL1, the CDRL2, and the CDRL3 of any one of (LA) to (LQ) above, and more preferably a combination shown in Table 2 below.

TABLE 2

| Combination | Heavy-chain variable region | Light-chain variable region |
| --- | --- | --- |
| (1) | (HA) | (LA) |
| (2) | (HA) | (LB) |
| (3) | (HA) | (LC) |

TABLE 2-continued

| Combination | Heavy-chain variable region | Light-chain variable region |
| --- | --- | --- |
| (4) | (HA) | (LD) |
| (5) | (HA) | (LE) |
| (6) | (HA) | (LF) |
| (7) | (HA) | (LG) |
| (8) | (HA) | (LH) |
| (9) | (HA) | (LI) |
| (10) | (HA) | (LJ) |
| (11) | (HB) | (LK) |
| (12) | (HB) | (LL) |
| (13) | (HB) | (LM) |
| (14) | (HB) | (LN) |
| (15) | (HB) | (LO) |
| (16) | (HB) | (LP) |
| (17) | (HB) | (LQ) |
| (18) | (HC) | (LA) |

Hereinafter, the combination of the heavy-chain variable region or heavy chain and the light-chain variable region or light chain in the antibody of the present invention or the like will be described more specifically. In this combination, the descriptions of the heavy-chain variable region can be applied to the heavy chain, and vice versa. Also, in this combination, the descriptions of the light-chain variable region can be applied to the light chain, and vice versa. In the amino acid sequences and the base sequences shown below, underlined amino acid sequences and base sequences are amino acid sequences that correspond to the CDRs and base sequences coding for the amino acid sequences that correspond to the CDRs, respectively, unless otherwise stated.

As described above, the combination of the heavy-chain variable region and the light-chain variable region in the antibody of the present invention or the like is one of the combinations of (1) to (18) above, for example.

Combination (1)

The antibodies or the like of Combination (1) are also referred to as an antibody H1-3M4E5L group, for example. In Combination (1) above, the heavy-chain variable region of (HA) above includes the CDRH1, the CDRH2, and the CDRH3, the CDRH1 is a polypeptide that includes the amino acid sequence of (H1-A) below, the CDRH2 is a polypeptide that includes the amino acid sequence of (H2-A) below, and the CDRH3 is a polypeptide that includes the amino acid sequence of (H3-A) below. The light-chain variable region of (LA) above includes the CDRL1, the CDRL2, and the CDRL3, the CDRL1 is a polypeptide that includes the amino acid sequence of (L1-A) below, the CDRL2 is a polypeptide that includes the amino acid sequence of (L2-A) below, and the CDRL3 is a polypeptide that includes the amino acid sequence of (L3-A) below.

(H1-A) An amino acid sequence of (H1-A1), (H1-A2), or (H1-A3) below:

(H1-A1) an amino acid sequence of Sequence ID No. 17 (GGSISSNY), (H1-A2) an amino acid sequence having 80% or more identity to the amino acid sequence of Sequence ID No. 17, and (H1-A3) an amino acid sequence consisting of the amino acid sequence of Sequence ID No. 17 with deletion, substitution, insertion, and/or addition of one or several amino acids.

(H2-A) An amino acid sequence of (H2-A1), (H2-A2), or (H2-A3) below:
  (H2-A1) an amino acid sequence of Sequence ID No. 18 (VSYSGST),
  (H2-A2) an amino acid sequence having 80% or more identity to the amino acid sequence of Sequence ID No. 18, and
  (H2-A3) an amino acid sequence consisting of the amino acid sequence of Sequence ID No. 18 with deletion, substitution, insertion, and/or addition of one or several amino acids.
(H3-A) An amino acid sequence of (H3-A1), (H3-A2), or (H3-A3) below:
  (H3-A1) an amino acid sequence of Sequence ID No. 19 (ARESYYYYGMDV),
  (H3-A2) an amino acid sequence having 80% or more identity to the amino acid sequence of Sequence ID No. 19, and
  (H3-A3) an amino acid sequence consisting of the amino acid sequence of Sequence ID No. 19 with deletion, substitution, insertion, and/or addition of one or several amino acids.
(L1-A) An amino acid sequence of (L1-A1), (L1-A2), or (L1-A3) below:
  (L1-A1) an amino acid sequence of Sequence ID No. 29 (SRDVGGYNY),
  (L1-A2) an amino acid sequence having 80% or more identity to the amino acid sequence of Sequence ID No. 29, and
  (L1-A3) an amino acid sequence consisting of the amino acid sequence of Sequence ID No. 29 with deletion, substitution, insertion, and/or addition of one or several amino acids.
(L2-A) An amino acid sequence of (L2-A1), (L2-A2), or (L2-A3) below:
  (L2-A1) an amino acid sequence of Sequence ID No. 30 (DVI),
  (L2-A2) an amino acid sequence having 80% or more identity to the amino acid sequence of Sequence ID No. 30, and
  (L2-A3) an amino acid sequence consisting of the amino acid sequence of Sequence ID No. 30 with deletion, substitution, insertion, and/or addition of one or several amino acids.
(L3-A) An amino acid sequence of (L3-A1), (L3-A2), or (L3-A3) below:
  (L3-A1) an amino acid sequence of Sequence ID No. 31 (WSFAGSYYV),
  (L3-A2) an amino acid sequence having 80% or more identity to the amino acid sequence of Sequence ID No. 31, and
  (L3-A3) an amino acid sequence consisting of the amino acid sequence of Sequence ID No. 31 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (1) above, the heavy-chain variable region of (HA) above includes a polypeptide consisting of the amino acid sequence of (H-A) below, for example. The light-chain variable region of (LA) above includes a polypeptide consisting of the amino acid sequence of (L-A) below, for example.
(H-A) An amino acid sequence of (H-A1), (H-A2), or (H-A3) below:
  (H-A1) an amino acid sequence of Sequence ID No. 20:

```
Sequence ID No. 20:
QVQLQESGPGLVKPSDTLSLTCLVSGGSISSNYWSWIRQAPGKGLEWIG
HVSYSGSTNYNPSLKSRVTISVDTSKNQFSLKLSSVTAADTAVYYCARE
SYYYYGMDVWGQGTTVTVSS,
```

(H-A2) an amino acid sequence having 80% or more identity to the amino acid sequence of Sequence ID No. 20, and
  (H-A3) an amino acid sequence consisting of the amino acid sequence of Sequence ID No. 20 with deletion, substitution, insertion, and/or addition of one or several amino acids.
(L-A) An amino acid sequence of (L-A1), (L-A2), or (L-A3) below:
  (L-A1) an amino acid sequence of Sequence ID No. 32:

```
Sequence ID No. 32:
QSELTQPRSVSGSPGQSVTISCTGTSRDVGGYNYVSWYQQHPGKAPKLI
IHDVIERSSGVPDRFSGSKSGNTASLTISGLQAEDEADYYCWSFAGSYY
VFGTGTDVTVL,
```

(L-A2) an amino acid sequence having 80% or more identity to the amino acid sequence of Sequence ID No. 32, and
  (L-A3) an amino acid sequence consisting of the amino acid sequence of Sequence ID No. 32 with deletion, substitution, insertion, and/or addition of one or several amino acids.

The amino acid sequence of (H-A) above is a sequence that includes the amino acid sequences of (H1-A1) of the CDRH1, (H2-A1) of the CDRH2, and (H3-A1) of the CDRH3, for example. The amino acid sequence of (H-A2) above may be an amino acid sequence that includes the amino acid sequences of (H1-A1) of the CDRH1, (H2-A1) of the CDRH2, and (H3-A1) of the CDRH3 and that has 80% or more identity to the amino acid sequence of Sequence ID No. 20, for example. The amino acid sequence of (H-A3) above may be an amino acid sequence that includes the amino acid sequences of (H1-A1) of the CDRH1, (H2-A1) of the CDRH2, and (H3-A1) of the CDRH3 and that consists of the amino acid sequence of Sequence ID No. 20 with deletion, substitution, insertion, and/or addition of one or several amino acids, for example.

The amino acid sequence of (L-A1) above is a sequence that includes the amino acid sequences of (L1-A1) of the CDRL1, (L2-A1) of the CDRL2, and (L3-A1) of the CDRL3, for example. The amino acid sequence of (L-A2) above may be an amino acid sequence that includes the amino acid sequences of (L1-A1) of the CDRL1, (L2-A1) of the CDRL2, and (L3-A1) of the CDRL3 and that has 80% or more identity to the amino acid sequence of Sequence ID No. 32, for example. The amino acid sequence of (L-A3) above may be an amino acid sequence that includes the amino acid sequences of (L1-A1) of the CDRL1, (L2-A1) of the CDRL2, and (L3-A1) of the CDRL3 and that consists of the amino acid sequence of Sequence ID No. 32 with deletion, substitution, insertion, and/or addition of one or several amino acids, for example.

In the antibody of the present invention, the heavy-chain variable region is (H-A1) above, and the light-chain variable region is (L-A1) above, for example. The antibody that includes this combination is also referred to as an "antibody H1-3M4E5L" hereinafter.

The "identity" as used for the polypeptide of the heavy-chain variable region and the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the heavy-chain variable region and the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (2)

The antibodies or the like of Combination (2) are also referred to as an antibody H1-K52 group, for example. In Combination (2) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LB) above includes the CDRL1, the CDRL2, and the CDRL3, the CDRL1 is a polypeptide that includes the amino acid sequence of (L1-B) below, the CDRL2 is a polypeptide that includes the amino acid sequence of (L2-B) below, and the CDRL3 is a polypeptide that includes the amino acid sequence of (L3-B) below.

(L1-B) An amino acid sequence of (L1-B1), (L1-B2), or (L1-B3) below:
- (L1-B1) an amino acid sequence of Sequence ID No. 33 (QSISSY),
- (L1-B2) an amino acid sequence having 80% or more identity to the amino acid sequence of Sequence ID No. 33, and
- (L1-B3) an amino acid sequence consisting of the amino acid sequence of Sequence ID No. 33 with deletion, substitution, insertion, and/or addition of one or several amino acids.

(L2-B) An amino acid sequence of (L2-B1), (L2-B2), or (L2-B3) below:
- (L2-B1) an amino acid sequence of Sequence ID No. 34 (AAS),
- (L2-B2) an amino acid sequence having 80% or more identity to the amino acid sequence of Sequence ID No. 34, and
- (L2-B3) an amino acid sequence consisting of the amino acid sequence of Sequence ID No. 34 with deletion, substitution, insertion, and/or addition of one or several amino acids.

(L3-B) An amino acid sequence of (L3-B1), (L3-B2), or (L3-B3) below:
- (L3-B1) an amino acid sequence of Sequence ID No. 35 (QQYYSTPQT),
- (L3-B2) an amino acid sequence having 80% or more identity to the amino acid sequence of Sequence ID No. 35, and
- (L3-B3) an amino acid sequence consisting of the amino acid sequence of Sequence ID No. 35 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (2) above, the heavy-chain variable region of (HA) above includes a polypeptide consisting of the amino acid sequence of (H-A) above, for example. The light-chain variable region of (LB) above includes a polypeptide consisting of the amino acid sequence of (L-B) below, for example.

(L-B) An amino acid sequence of (L-B1), (L-B2), or (L-B3) below:
- (L-B1) an amino acid sequence of Sequence ID No. 36:

```
Sequence ID No. 36:
DIQMTQSPSAMSASVGDRVTITCRASQSISSYLNWYQQKPGKAPKLLIY
AASSLQSGVPSRFSGSGSGTDFTLTISSLQPEDFATYYCQQYYSTPQTF
GPGTKVDIK,
```

- (L-B2) an amino acid sequence having 80% or more identity to the amino acid sequence of Sequence ID No. 36, and
- (L-B3) an amino acid sequence consisting of the amino acid sequence of Sequence ID No. 36 with deletion, substitution, insertion, and/or addition of one or several amino acids.

The amino acid sequence of (L-B1) above is a sequence that includes the amino acid sequences of (L1-B1) of the CDRL1, (L2-B1) of the CDRL2, and (L3-B1) of the CDRL3, for example. The amino acid sequence of (L-B2) above may be an amino acid sequence that includes the amino acid sequences of (L-B1) of the CDRL1, (L2-B1) of the CDRL2, and (L3-B1) of the CDRL3, and having 80% or more identity to the amino acid sequence of Sequence ID No. 36, for example. The amino acid sequence of (L-B3) above may be an amino acid sequence that includes the amino acid sequences of (L1-B1) of the CDRL1, (L2-B1) of the CDRL2, and (L3-B1) of the CDRL3, and consisting of the amino acid sequence of Sequence ID No. 36 with deletion, substitution, insertion, and/or addition of one or several amino acids, for example.

In the antibody of the present invention, the heavy-chain variable region is (H-A1) above, and the light-chain variable region is (L-B1) above, for example. The antibody that includes this combination is also referred to as an "antibody H1-K52" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (3)

The antibodies or the like of Combination (3) are also referred to as an antibody H1-K73 group, for example. In Combination (3) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A)

above, and the CDRH3 is a polypeptide that includes the amino acid sequence of (H3-A) above. The light-chain variable region of (LC) above includes the CDRL1, the CDRL2, and the CDRL3, the CDRL1 is a polypeptide that includes the amino acid sequence of (L1-C) below, the CDRL2 is a polypeptide that includes the amino acid sequence of (L2-C) below, and the CDRL3 is a polypeptide that includes the amino acid sequence of (L3-C) below.

(L1-C) An amino acid sequence of (L1-C1), (L1-C2), or (L1-C3) below:
  (L1-C1) an amino acid sequence of Sequence ID No. 37 (QSISSY),
  (L1-C2) an amino acid sequence having 80% or more identity to the amino acid sequence of Sequence ID No. 37, and
  (L1-C3) an amino acid sequence consisting of the amino acid sequence of Sequence ID No. 37 with deletion, substitution, insertion, and/or addition of one or several amino acids.

(L2-C) An amino acid sequence of (L2-C1), (L2-C2), or (L2-C3) below:
  (L2-C1) an amino acid sequence of Sequence ID No. 38 (AAS),
  (L2-C2) an amino acid sequence having 80% or more identity to the amino acid sequence of Sequence ID No. 38, and
  (L2-C3) an amino acid sequence consisting of the amino acid sequence of Sequence ID No. 38 with deletion, substitution, insertion, and/or addition of one or several amino acids.

(L3-C) An amino acid sequence of (L3-C1), (L3-C2), or (L3-C3) below:
  (L3-C1) an amino acid sequence of Sequence ID No. 39 (QQYESYRRS),
  (L3-C2) an amino acid sequence having 80% or more identity to the amino acid sequence of Sequence ID No. 39, and
  (L3-C3) an amino acid sequence consisting of the amino acid sequence of Sequence ID No. 39 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (3) above, the heavy-chain variable region of (HA) above includes a polypeptide consisting of the amino acid sequence of (H-A) above, for example. The light-chain variable region of (LC) above includes a polypeptide consisting of the amino acid sequence of (L-C) below, for example.

(L-C) An amino acid sequence of (L-C1), (L-C2), or (L-C3) below:
  (L-C1) an amino acid sequence of Sequence ID No. 40:

```
Sequence ID No. 40:
DIQMTQSPSSLSASVGDRVTITCRASQSISSYLNWYQQKAGKAPKLLIY
AASSLQSGVPSRFSGSGSGTDFTLTISCLQSEDVATYYCQQYESYRRSF
GQGTKVEIK,
```

(L-C2) an amino acid sequence having 80% or more identity to the amino acid sequence of Sequence ID No. 40, and
  (L-C3) an amino acid sequence consisting of the amino acid sequence of Sequence ID No. 40 with deletion, substitution, insertion, and/or addition of one or several amino acids.

The amino acid sequence of (L-C1) above is a sequence that includes the amino acid sequences of (L1-C1) of the CDRL1, (L2-C1) of the CDRL2, and (L3-C1) of the CDRL3, for example. The amino acid sequence of (L-C2) above may be an amino acid sequence that includes the amino acid sequences of (L1-C1) of the CDRL1, (L2-C1) of the CDRL2, and (L3-C1) of the CDRL3 and that has 80% or more identity to the amino acid sequence of Sequence ID No. 40, for example. The amino acid sequence of (L-C3) above may be an amino acid sequence that includes the amino acid sequences of (L1-C1) of the CDRL1, (L2-C1) of the CDRL2, and (L3-C1) of the CDRL3 and that consists of the amino acid sequence of Sequence ID No. 40 with deletion, substitution, insertion, and/or addition of one or several amino acids, for example.

In the antibody of the present invention, the heavy-chain variable region is (H-A1) above, and the light-chain variable region is (L-C1) above, for example. The antibody that includes this combination is also referred to as an "antibody H1-K73" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (4)

The antibodies or the like of Combination (4) are also referred to as an antibody H1-K121-K124 group, for example. In Combination (4) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LD) above includes the CDRL1, the CDRL2, and the CDRL3, the CDRL1 is a polypeptide that includes the amino acid sequence of (L1-D) below, the CDRL2 is a polypeptide that includes the amino acid sequence of (L2-D) below, and the CDRL3 is a polypeptide that includes the amino acid sequence of (L3-D) below.

(L1-D) An amino acid sequence of (L1-D1), (L1-D2), or (L1-D3) below:
  (L1-D1) an amino acid sequence of Sequence ID No. 41 (QSISSY),
  (L1-D2) an amino acid sequence having 80% or more identity to the amino acid sequence of Sequence ID No. 41, and
  (L1-D3) an amino acid sequence consisting of the amino acid sequence of Sequence ID No. 41 with deletion, substitution, insertion, and/or addition of one or several amino acids.

(L2-D) An amino acid sequence of (L2-D1), (L2-D2), or (L2-D3) below:
  (L2-D1) an amino acid sequence of Sequence ID No. 42 (AAS), (L2-D2) an amino acid sequence having 80% or more identity to the amino acid sequence of Sequence ID No. 42, and
(L2-D3) an amino acid sequence consisting of the amino acid sequence of Sequence ID No. 42 with deletion, substitution, insertion, and/or addition of one or several amino acids.
(L3-D) An amino acid sequence of (L3-D1), (L3-D2), or (L3-D3) below:
(L3-D1) an amino acid sequence of Sequence ID No. 43 (QQYNSYSRT),
(L3-D2) an amino acid sequence having 80% or more identity to the amino acid sequence of Sequence ID No. 43, and
(L3-D3) an amino acid sequence consisting of the amino acid sequence of Sequence ID No. 43 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (4) above, the heavy-chain variable region of (HA) above includes a polypeptide consisting of the amino acid sequence of (H-A) above, for example. The light-chain variable region of (LD) above includes a polypeptide consisting of the amino acid sequence of (L-DA) or (L-DB) below, for example.
(L-DA) An amino acid sequence of (L-DA1), (L-DA2), or (L-DA3) below:
(L-DA1) an amino acid sequence of Sequence ID No. 44:

```
Sequence ID No. 44:
DIQMTQSPSSLSASVGDRVTITCRASQSISSYLNWYQQKPGKAPKLLIY
AASSLQSGVPSRFSGSGSGTDFTLTISCLQSEDFATYYCQQYNSYSRTF
GQGTKVEIK,
```

(L-DA2) an amino acid sequence having 80% or more identity to the amino acid sequence of Sequence ID No. 44, and
(L-DA3) an amino acid sequence consisting of the amino acid sequence of Sequence ID No. 44 with deletion, substitution, insertion, and/or addition of one or several amino acids.
(L-DB) An amino acid sequence of (L-DB1), (L-DB2), or (L-DB3) below:
(L-DB1) an amino acid sequence of Sequence ID No. 45:

```
Sequence ID No. 45:
DIQMTQSPSSLSASVGDRVTITCRASQSISSYLNWYQQKPGKAPKLLIY
AASRLESGVPSRFSGSGSGTDFTLTISCLQSEDFATYYCQQYNSYSRTF
GQGTKVEIK,
```

(L-DB2) an amino acid sequence having 80% or more identity to the amino acid sequence of Sequence ID No. 45, and
(L-DB3) an amino acid sequence consisting of the amino acid sequence of Sequence ID No. 45 with deletion, substitution, insertion, and/or addition of one or several amino acids.

The amino acid sequence of (L-DA1) above is a sequence that includes the amino acid sequences of (L1-D1) of the CDRL1, (L2-D1) of the CDRL2, and (L3-D1) of the CDRL3, for example. The amino acid sequence of (L-DA2) above may be an amino acid sequence that includes the amino acid sequences of (L1-D1) of the CDRL1, (L2-D1) of the CDRL2, and (L3-D1) of the CDRL3 and that has 80% or more identity to the amino acid sequence of Sequence ID No. 44, for example. The amino acid sequence of (L-DA3) above may be an amino acid sequence that includes the amino acid sequences of (L1-D1) of the CDRL1, (L2-D1) of the CDRL2, and (L3-D1) of the CDRL3 and that consists of the amino acid sequence of Sequence ID No. 44 with deletion, substitution, insertion, and/or addition of one or several amino acids, for example.

The amino acid sequence of (L-DB1) above is a sequence that includes the amino acid sequences of (L1-D1) of the CDRL1, (L2-D1) of the CDRL2, and (L3-D1) of the CDRL3, for example. The amino acid sequence of (L-DB2) above may be an amino acid sequence that includes the amino acid sequences of (L1-D1) of the CDRL1, (L2-D1) of the CDRL2, and (L3-D1) of the CDRL3 and that has 80% or more identity to the amino acid sequence of Sequence ID No. 45, for example. The amino acid sequence of (L-DB3) above may be an amino acid sequence that includes the amino acid sequences of (L1-D1) of the CDRL1, (L2-D1) of the CDRL2, and (L3-D1) of the CDRL3 and that consists of the amino acid sequence of Sequence ID No. 45 with deletion, substitution, insertion, and/or addition of one or several amino acids, for example.

In the antibody of the present invention, the heavy-chain variable region is (H-A1) above, and the light-chain variable region is (L-DA1) above, for example. The antibody that includes this combination is also referred to as an "antibody H1-K121" hereinafter. In the antibody of the present invention, the heavy-chain variable region is (H-A1) above, and the light-chain variable region is (L-DB1) above, for example. The antibody that includes this combination is also referred to as an "antibody H1-K124" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (5)

The antibodies or the like of Combination (5) are also referred to as an antibody H1-K125 group, for example. In Combination (5) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LE) above includes the CDRL1, the CDRL2, and the CDRL3, the CDRL1 is a polypeptide that includes the amino acid sequence of (L1-E) below, the CDRL2 is a polypeptide that includes the amino acid sequence of (L2-E) below, and the CDRL3 is a polypeptide that includes the amino acid sequence of (L3-E) below.
(L1-E) An amino acid sequence of (L1-E1), (L1-E2), or (L1-E3) below:
(L1-E1) an amino acid sequence of Sequence ID No. 46 (QSISSY), (L1-E2) an amino acid sequence having 80% or more identity to the amino acid sequence of Sequence ID No. 46, and
(L1-E3) an amino acid sequence consisting of the amino acid sequence of Sequence ID No. 46 with deletion, substitution, insertion, and/or addition of one or several amino acids.
(L2-E) An amino acid sequence of (L2-E1), (L2-E2), or (L2-E3) below:
(L2-E1) an amino acid sequence of Sequence ID No. 47 (AAS),
(L2-E2) an amino acid sequence having 80% or more identity to the amino acid sequence of Sequence ID No. 47, and
(L2-E3) an amino acid sequence consisting of the amino acid sequence of Sequence ID No. 47 with deletion, substitution, insertion, and/or addition of one or several amino acids.
(L3-E) An amino acid sequence of (L3-E1), (L3-E2), or (L3-E3) below:
(L3-E1) an amino acid sequence of Sequence ID No. 48 (QQYNSYSPCT),
(L3-E2) an amino acid sequence having 80% or more identity to the amino acid sequence of Sequence ID No. 48, and
(L3-E3) an amino acid sequence consisting of the amino acid sequence of Sequence ID No. 48 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (5) above, the heavy-chain variable region of (HA) above includes a polypeptide consisting of the amino acid sequence of (H-A) above, for example. The light-chain variable region of (LE) above includes a polypeptide consisting of the amino acid sequence of (L-E) below, for example.
(L-E) An amino acid sequence of (L-E1), (L-E2), or (L-E3) below:
(L-E1) an amino acid sequence of Sequence ID No. 49:

```
Sequence ID No. 49:
DIQMTQSPSSLSASVGDRVTITCRASQSISSYLNWYQQKPGKAPKLLLY
AASRLESGVPSRFSGSGSGTEFTLTISSLQPDDFATYYCQQYNSYSPCT
FGPGTKVDIK,
```

(L-E2) an amino acid sequence having 80% or more identity to the amino acid sequence of Sequence ID No. 49, and
(L-E3) an amino acid sequence consisting of the amino acid sequence of Sequence ID No. 49 with deletion, substitution, insertion, and/or addition of one or several amino acids.

The amino acid sequence of (L-E1) above is a sequence that includes the amino acid sequences of (L1-E1) of the CDRL1, (L2-E1) of the CDRL2, and (L3-E1) of the CDRL3, for example. The amino acid sequence of (L-E2) above may be an amino acid sequence that includes the amino acid sequences of (L1-E1) of the CDRL1, (L2-E1) of the CDRL2, and (L3-E1) of the CDRL3, and that has 80% or more identity to the amino acid sequence of Sequence ID No. 49, for example. The amino acid sequence of (L-E3) above may be an amino acid sequence that includes the amino acid sequences of (L1-E1) of the CDRL1, (L2-E1) of the CDRL2, and (L3-E1) of the CDRL3 and that consists of the amino acid sequence of Sequence ID No. 49 with deletion, substitution, insertion, and/or addition of one or several amino acids, for example.

In the antibody of the present invention, the heavy-chain variable region is (H-A1) above, and the light-chain variable region is (L-E1) above, for example. The antibody that includes this combination is also referred to as an "antibody H1-K125" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (6)

The antibodies or the like of Combination (6) are also referred to as an antibody H1-K131 group, for example. In Combination (6) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LF) above includes the CDRL1, the CDRL2, and the CDRL3, the CDRL1 is a polypeptide that includes the amino acid sequence of (L1-F) below, the CDRL2 is a polypeptide that includes the amino acid sequence of (L2-F) below, and the CDRL3 is a polypeptide that includes the amino acid sequence of (L3-F) below.
(L1-F) An amino acid sequence of (L1-F1), (L1-F2), or (L1-F3) below:
(L1-F1) an amino acid sequence of Sequence ID No. 50 (QDISRY),
(L1-F2) an amino acid sequence having 80% or more identity to the amino acid sequence of Sequence ID No. 50, and
(L1-F3) an amino acid sequence consisting of the amino acid sequence of Sequence ID No. 50 with deletion, substitution, insertion, and/or addition of one or several amino acids.
(L2-F) An amino acid sequence of (L2-F1), (L2-F2), or (L2-F3) below:
(L2-F1) an amino acid sequence of Sequence ID No. 51 (AAS),
(L2-F2) an amino acid sequence having 80% or more identity to the amino acid sequence of Sequence ID No. 51, and
(L2-F3) an amino acid sequence consisting of the amino acid sequence of Sequence ID No. 51 with deletion, substitution, insertion, and/or addition of one or several amino acids.
(L3-F) An amino acid sequence of (L3-F1), (L3-F2), or (L3-F3) below:
(L3-F1) an amino acid sequence of Sequence ID No. 52 (QQYDNLIT),
(L3-F2) an amino acid sequence having 80% or more identity to the amino acid sequence of Sequence ID No. 52, and (L3-F3) an amino acid sequence consisting of the amino acid sequence of Sequence ID No. 52 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (6) above, the heavy-chain variable region of (HA) above includes a polypeptide consisting of the amino acid sequence of (H-A) above, for example. The light-chain variable region of (LF) above includes a polypeptide consisting of the amino acid sequence of (L-F) below, for example.

(L-F) An amino acid sequence of (L-F1), (L-F2), or (L-F3) below:

(L-F1) an amino acid sequence of Sequence ID No. 53:

```
Sequence ID No. 53:
DIQMTQSPSSLSASVGDRVSITCRASQDISRYLNWYQQKPGKAPKLLLY
AASRLESGVPSRFSGSGSGTDFTLTITSLQPDDFATYYCQQYDNLITFG
QGTRLEIK,
```

(L-F2) an amino acid sequence having 80% or more identity to the amino acid sequence of Sequence ID No. 53, and (L-F3) an amino acid sequence consisting of the amino acid sequence of Sequence ID No. 53 with deletion, substitution, insertion, and/or addition of one or several amino acids.

The amino acid sequence of (L-F1) above is a sequence that includes the amino acid sequences of (L1-F1) of the CDRL1, (L2-F1) of the CDRL2, and (L3-F1) of the CDRL3, for example. The amino acid sequence of (L-F2) above may be an amino acid sequence that includes the amino acid sequences of (L1-F1) of the CDRL1, (L2-F1) of the CDRL2, and (L3-F1) of the CDRL3 and that has 80% or more identity to the amino acid sequence of Sequence ID No. 53, for example. The amino acid sequence of (L-F3) above may be an amino acid sequence that includes the amino acid sequences of (L1-F1) of the CDRL1, (L2-F1) of the CDRL2, and (L3-F1) of the CDRL3 and that consists of the amino acid sequence of Sequence ID No. 53 with deletion, substitution, insertion, and/or addition of one or several amino acids, for example.

In the antibody of the present invention, the heavy-chain variable region is (H-A1) above, and the light-chain variable region is (L-F1) above, for example. The antibody that includes this combination is also referred to as an "antibody H1-K131" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (7)

The antibodies or the like of Combination (7) are also referred to as an antibody H1-K145 group, for example. In Combination (7) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LG) above includes the CDRL1, the CDRL2, and the CDRL3, the CDRL1 is a polypeptide that includes the amino acid sequence of (L1-G) below, the CDRL2 is a polypeptide that includes the amino acid sequence of (L2-G) below, and the CDRL3 is a polypeptide that includes the amino acid sequence of (L3-G) below.

(L1-G) An amino acid sequence of (L1-G1), (L1-G2), or (L1-G3) below:

(L1-G1) an amino acid sequence of Sequence ID No. 54 (QDISRY), (L1-G2) an amino acid sequence having 80% or more identity to the amino acid sequence of Sequence ID No. 54, and (L1-G3) an amino acid sequence consisting of the amino acid sequence of Sequence ID No. 54 with deletion, substitution, insertion, and/or addition of one or several amino acids.

(L2-G) An amino acid sequence of (L2-G1), (L2-G2), or (L2-G3) below:

(L2-G1) an amino acid sequence of Sequence ID No. 55 (AAS), (L2-G2) an amino acid sequence having 80% or more identity to the amino acid sequence of Sequence ID No. 55, and (L2-G3) an amino acid sequence consisting of the amino acid sequence of Sequence ID No. 55 with deletion, substitution, insertion, and/or addition of one or several amino acids.

(L3-G) An amino acid sequence of (L3-G1), (L3-G2), or (L3-G3) below:

(L3-G1) an amino acid sequence of Sequence ID No. 56 (QQYNSYSRT), (L3-G2) an amino acid sequence having 80% or more identity to the amino acid sequence of Sequence ID No. 56, and (L3-G3) an amino acid sequence consisting of the amino acid sequence of Sequence ID No. 56 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (7) above, the heavy-chain variable region of (HA) above includes a polypeptide consisting of the amino acid sequence of (H-A) above, for example. The light-chain variable region of (LG) above includes a polypeptide consisting of the amino acid sequence of (L-G) below, for example.

(L-G) An amino acid sequence of (L-G1), (L-G2), or (L-G3) below:
(L-G1) an amino acid sequence of Sequence ID No. 57:

```
Sequence ID No. 57:
DIQMTQSPSSLSASVGDRVSITCRASQDISRYLNWYQQKPGKAPKLLLY
AASRLESGVPSRFSGSGSGTDFTLTITSLQPDDFATYYCQQYNSYSRTF
GQGTKVEIK,
```

(L-G2) an amino acid sequence having 80% or more identity to the amino acid sequence of Sequence ID No. 57, and (L-G3) an amino acid sequence consisting of the amino acid sequence of Sequence ID No. 57 with deletion, substitution, insertion, and/or addition of one or several amino acids.

The amino acid sequence of (L-G1) above is a sequence that includes the amino acid sequences of (L1-G1) of the CDRL1, (L2-G1) of the CDRL2, and (L3-G1) of the CDRL3, for example. The amino acid sequence of (L-G2) above may be an amino acid sequence that includes the amino acid sequences of (L1-G1) of the CDRL1, (L2-G1) of the CDRL2, and (L3-G1) of the CDRL3 and that has 80% or more identity to the amino acid sequence of Sequence ID No. 57, for example. The amino acid sequence of (L-G3) above may be an amino acid sequence that includes the amino acid sequences of (L1-G1) of the CDRL1, (L2-G1) of the CDRL2, and (L3-G1) of the CDRL3 and that consists of the amino acid sequence of Sequence ID No. 57 with deletion, substitution, insertion, and/or addition of one or several amino acids, for example.

In the antibody of the present invention, the heavy-chain variable region is (H-A1) above, and the light-chain variable region is (L-G1) above, for example. The antibody that includes this combination is also referred to as an "antibody H1-K145" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (8)

The antibodies or the like of Combination (8) are also referred to as an antibody H1-K151 group, for example. In Combination (8) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LH) above includes the CDRL1, the CDRL2, and the CDRL3, the CDRL1 is a polypeptide that includes the amino acid sequence of (L1-H) below, the CDRL2 is a polypeptide that includes the amino acid sequence of (L2-H) below, and the CDRL3 is a polypeptide that includes the amino acid sequence of (L3-H) below.

(L1-H) An amino acid sequence of (L1-H1), (L1-H2), or (L1-H3) below:
(L1-H1) an amino acid sequence of Sequence ID No. 58 (QSISSY), (L1-H2) an amino acid sequence having 80% or more identity to the amino acid sequence of Sequence ID No. 58, and (L1-H3) an amino acid sequence consisting of the amino acid sequence of Sequence ID No. 58 with deletion, substitution, insertion, and/or addition of one or several amino acids.

(L2-H) An amino acid sequence of (L2-H1), (L2-H2), or (L2-H3) below:
(L2-H1) an amino acid sequence of Sequence ID No. 59 (AAS),
(L2-H2) an amino acid sequence having 80% or more identity to the amino acid sequence of Sequence ID No. 59, and
(L2-H3) an amino acid sequence consisting of the amino acid sequence of Sequence ID No. 59 with deletion, substitution, insertion, and/or addition of one or several amino acids.

(L3-H) An amino acid sequence of (L3-H1), (L3-H2), or (L3-H3) below:
(L3-H1) an amino acid sequence of Sequence ID No. 60 (QQYDNLIT),
(L3-H2) an amino acid sequence having 80% or more identity to the amino acid sequence of Sequence ID No. 60, and
(L3-H3) an amino acid sequence consisting of the amino acid sequence of Sequence ID No. 60 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (8) above, the heavy-chain variable region of (HA) above includes a polypeptide consisting of the amino acid sequence of (H-A) above, for example. The light-chain variable region of (LH) above includes a polypeptide consisting of the amino acid sequence of (L-H) below, for example.

(L-H) An amino acid sequence of (L-H1), (L-H2), or (L-H3) below:
(L-H1) an amino acid sequence of Sequence ID No. 61:

```
Sequence ID No. 61:
DIQMTQSPSSLSASVGDRVTITCRASQSISSYLNWYQQKPGKAPKLLIY
AASSLQSGVPSRFSGSGSGTDFTLTITSLQPDDFATYYCQQYDNLITFG
QGTRLEIK,
```

(L-H2) an amino acid sequence having 80% or more identity to the amino acid sequence of Sequence ID No. 61, and (L-H3) an amino acid sequence consisting of the amino acid sequence of Sequence ID No. 61 with deletion, substitution, insertion, and/or addition of one or several amino acids.

The amino acid sequence of (L-H1) above is a sequence that includes the amino acid sequences of (L1-H1) of the CDRL1, (L2-H1) of the CDRL2, and (L3-H1) of the CDRL3, for example. The amino acid sequence of (L-H2) above may be an amino acid sequence that includes the amino acid sequences of (L1-H1) of the CDRL1, (L2-H1) of the CDRL2, and (L3-H1) of the CDRL3 and that has 80% or more identity to the amino acid sequence of Sequence ID No. 61, for example. The amino acid sequence of (L-H3)

above may be an amino acid sequence that includes the amino acid sequences of (L1-H1) of the CDRL1, (L2-H1) of the CDRL2, and (L3-H1) of the CDRL3 and that consists of the amino acid sequence of Sequence ID No. 61 with deletion, substitution, insertion, and/or addition of one or several amino acids, for example.

In the antibody of the present invention, the heavy-chain variable region is (H-A1) above, and the light-chain variable region is (L-H1) above, for example. The antibody that includes this combination is also referred to as an "antibody H1-K151" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (9)

The antibodies or the like of Combination (9) are also referred to as an antibody H1-K160 group, for example. In Combination (9) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LI) above includes the CDRL1, the CDRL2, and the CDRL3, the CDRL1 is a polypeptide that includes the amino acid sequence of (L1-I) below, the CDRL2 is a polypeptide that includes the amino acid sequence of (L2-I) below, and the CDRL3 is a polypeptide that includes the amino acid sequence of (L3-I) below.

(L1-I) An amino acid sequence of (L1-I1), (L1-I2), or (L1I3) below:
 (L1-I1) an amino acid sequence of Sequence ID No. 62 (QSVSSN),
 (L1-I2) an amino acid sequence having 80% or more identity to the amino acid sequence of Sequence ID No. 62, and
 (L1-I3) an amino acid sequence consisting of the amino acid sequence of Sequence ID No. 62 with deletion, substitution, insertion, and/or addition of one or several amino acids.

(L2-I) An amino acid sequence of (L2-I1), (L2-I2), or (L2-I3) below:
 (L2-I1) an amino acid sequence of Sequence ID No. 63 (GAS),
 (L2-I2) an amino acid sequence having 80% or more identity to the amino acid sequence of Sequence ID No. 63, and
 (L2-I3) an amino acid sequence consisting of the amino acid sequence of Sequence ID No. 63 with deletion, substitution, insertion, and/or addition of one or several amino acids.

(L3-I) An amino acid sequence of (L3-I1), (L3-I2), or (L3-I3) below:
 (L3-I1) an amino acid sequence of Sequence ID No. 64 (QQYNSYSRT),
 (L3-I2) an amino acid sequence having 80% or more identity to the amino acid sequence of Sequence ID No. 64, and
 (L3-I3) an amino acid sequence consisting of the amino acid sequence of Sequence ID No. 64 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (9) above, the heavy-chain variable region of (HA) above includes a polypeptide consisting of the amino acid sequence of (H-A) above, for example. The light-chain variable region of (LI) above includes a polypeptide consisting of the amino acid sequence of (L-I) below, for example.

(L-I) An amino acid sequence of (L-I1), (L-I2), or (L-I3) below:
 (L-I1) an amino acid sequence of Sequence ID No. 65:

```
Sequence ID No. 65:
EIVLTQSPATLSVSPGERATLSCRASQSVSSNLAWYQQKPGQAPRLLIY
GASTRATGIPARFSGSGSGTEFTLTISRLEPEDFATYYCQQYNSYSRTF
GQGTKVEIK,
```

(L-I2) an amino acid sequence having 80% or more identity to the amino acid sequence of Sequence ID No. 65, and
 (L-I3) an amino acid sequence consisting of the amino acid sequence of Sequence ID No. 65 with deletion, substitution, insertion, and/or addition of one or several amino acids.

The amino acid sequence of (L-I1) above is a sequence that includes the amino acid sequences of (L1-I1) of the CDRL1, (L2-I1) of the CDRL2, and (L3-I1) of the CDRL3, for example. The amino acid sequence of (L-I2) above may be an amino acid sequence that includes the amino acid sequences of (L1-I1) of the CDRL1, (L2-I1) of the CDRL2, and (L3-I1) of the CDRL3 and that has 80% or more identity to the amino acid sequence of Sequence ID No. 65, for example. The amino acid sequence of (L-I3) above may be an amino acid sequence that includes the amino acid sequences of (L1-I1) of the CDRL1, (L2-I1) of the CDRL2, and (L3-I1) of the CDRL3 and that consists of the amino acid sequence of Sequence ID No. 65 with deletion, substitution, insertion, and/or addition of one or several amino acids, for example.

In the antibody of the present invention, the heavy-chain variable region is (H-A1) above, and the light-chain variable region is (L-I1) above, for example. The antibody that includes this combination is also referred to as an "antibody H1-K160" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (10)

The antibodies or the like of Combination (10) are also referred to as an antibody H1-K173 group, for example. In Combination (10) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LJ) above includes the CDRL1, the CDRL2, and the CDRL3, the CDRL1 is a polypeptide that includes the amino acid sequence of (L1-J) below, the CDRL2 is a polypeptide that includes the amino acid sequence of (L2-J) below, and the CDRL3 is a polypeptide that includes the amino acid sequence of (L3-J) below.

(L1-J) An amino acid sequence of (L1-J1), (L1-J2), or (L1-J3) below:
- (L1-J1) an amino acid sequence of Sequence ID No. 66 (QSISSY),
- (L1-J2) an amino acid sequence having 80% or more identity to the amino acid sequence of Sequence ID No. 66, and
- (L1-J3) an amino acid sequence consisting of the amino acid sequence of Sequence ID No. 66 with deletion, substitution, insertion, and/or addition of one or several amino acids.

(L2-J) An amino acid sequence of (L2-J1), (L2-J2), or (L2-J3) below:
- (L2-J1) an amino acid sequence of Sequence ID No. 67 (AAS),
- (L2-J2) an amino acid sequence having 80% or more identity to the amino acid sequence of Sequence ID No. 67, and
- (L2-J3) an amino acid sequence consisting of the amino acid sequence of Sequence ID No. 67 with deletion, substitution, insertion, and/or addition of one or several amino acids.

(L3-J) An amino acid sequence of (L3-J1), (L3-J2), or (L3-J3) below:
- (L3-J1) an amino acid sequence of Sequence ID No. 68 (QQYESYSRT),
- (L3-J2) an amino acid sequence having 80% or more identity to the amino acid sequence of Sequence ID No. 68, and
- (L3-J3) an amino acid sequence consisting of the amino acid sequence of Sequence ID No. 68 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (10) above, the heavy-chain variable region of (HA) above includes a polypeptide consisting of the amino acid sequence of (H-A) above, for example. The light-chain variable region of (LJ) above includes a polypeptide consisting of the amino acid sequence of (L-J) below, for example.

(L-J) An amino acid sequence of (L-J1), (L-J2), or (L-J3) below:
- (L-J1) an amino acid sequence of Sequence ID No. 69:

```
Sequence ID No. 69:
DIQMTQSPSSLSASVGDRVTITCRASQSISSYLNWYQQKAGKAPKLLIY
AASSLQSGVPSRFSGSGSGTDFTLTISCLQSEDVATYYCQQYESYSRTF
GQGTKVEIK,
```

- (L-J2) an amino acid sequence having 80% or more identity to the amino acid sequence of Sequence ID No. 69, and
- (L-J3) an amino acid sequence consisting of the amino acid sequence of Sequence ID No. 69 with deletion, substitution, insertion, and/or addition of one or several amino acids.

The amino acid sequence of (L-J1) above is a sequence that includes the amino acid sequences of (L1-J1) of the CDRL1, (L2-J1) of the CDRL2, and (L3-J1) of the CDRL3, for example. The amino acid sequence of (L-J2) above may be an amino acid sequence that includes the amino acid sequences of (L1-J1) of the CDRL1, (L2-J1) of the CDRL2, and (L3-J1) of the CDRL3 and that has 80% or more identity to the amino acid sequence of Sequence ID No. 69, for example. The amino acid sequence of (L-J3) above may be an amino acid sequence that includes the amino acid sequences of (L1-J1) of the CDRL1, (L2-J1) of the CDRL2, and (L3-J1) of the CDRL3 and that consists of the amino acid sequence of Sequence ID No. 69 with deletion, substitution, insertion, and/or addition of one or several amino acids, for example.

In the antibody of the present invention, the heavy-chain variable region is (H-A1) above, and the light-chain variable region is (L-J1) above, for example. The antibody that includes this combination is also referred to as an "antibody H1-K173" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (11)

The antibodies or the like of Combination (11) are also referred to as an antibody 3M4E5H-L1 group, for example. In Combination (11) above, the heavy-chain variable region of (HB) above includes the CDRH1, the CDRH2, and the CDRH3, the CDRH1 is a polypeptide that includes the amino acid sequence of (H1-B) below, the CDRH2 is a polypeptide that includes the amino acid sequence of (H2-B) below, and the CDRH3 is a polypeptide that includes the amino acid sequence of (H3-B) below. The light-chain variable region of (LK) above includes the CDRL1, the CDRL2, and the CDRL3, the CDRL1 is a polypeptide that includes the amino acid sequence of (L1-K) below, the CDRL2 is a polypeptide that includes the amino acid sequence of (L2-K) below, and the CDRL3 is a polypeptide that includes the amino acid sequence of (L3-K) below.

(H1-B) An amino acid sequence of (H1-B1), (H1-B2), or (H1-B3) below:
- (H1-B1) an amino acid sequence of Sequence ID No. 21 (GFTFSTYQ),
- (H1-B2) an amino acid sequence having 80% or more identity to the amino acid sequence of Sequence ID No. 21, and
- (H1-B3) an amino acid sequence consisting of the amino acid sequence of Sequence ID No. 21 with deletion, substitution, insertion, and/or addition of one or several amino acids.

(H2-B) An amino acid sequence of (H2-B1), (H2-B2), or (H2-B3) below:
 (H2-B1) an amino acid sequence of Sequence ID No. 22 (IVSSGGST),
 (H2-B2) an amino acid sequence having 80% or more identity to the amino acid sequence of Sequence ID No. 22, and
 (H2-B3) an amino acid sequence consisting of the amino acid sequence of Sequence ID No. 22 with deletion, substitution, insertion, and/or addition of one or several amino acids.

(H3-B) An amino acid sequence of (H3-B1), (H3-B2), or (H3-B3) below:
 (H3-B1) an amino acid sequence of Sequence ID No. 23 (AGELLPYYGMDV),
 (H3-B2) an amino acid sequence having 80% or more identity to the amino acid sequence of Sequence ID No. 23, and
 (H3-B3) an amino acid sequence consisting of the amino acid sequence of Sequence ID No. 23 with deletion, substitution, insertion, and/or addition of one or several amino acids.

(L1-K) An amino acid sequence of (L1-K1), (L1-K2), or (L1-K3) below:
 (L1-K1) an amino acid sequence of Sequence ID No. 70 (SSDVGGYDF),
 (L1-K2) an amino acid sequence having 80% or more identity to the amino acid sequence of Sequence ID No. 70, and
 (L1-K3) an amino acid sequence consisting of the amino acid sequence of Sequence ID No. 70 with deletion, substitution, insertion, and/or addition of one or several amino acids.

(L2-K) An amino acid sequence of (L2-K1), (L2-K2), or (L2-K3) below:
 (L2-K1) an amino acid sequence of Sequence ID No. 71 (DVN),
 (L2-K2) an amino acid sequence having 80% or more identity to the amino acid sequence of Sequence ID No. 71, and
 (L2-K3) an amino acid sequence consisting of the amino acid sequence of Sequence ID No. 71 with deletion, substitution, insertion, and/or addition of one or several amino acids.

(L3-K) An amino acid sequence of (L3-K1), (L3-K2), or (L3-K3) below:
 (L3-K1) an amino acid sequence of Sequence ID No. 72 (SSYAGSNSV),
 (L3-K2) an amino acid sequence having 80% or more identity to the amino acid sequence of Sequence ID No. 72, and
 (L3-K3) an amino acid sequence consisting of the amino acid sequence of Sequence ID No. 72 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (11) above, the heavy-chain variable region of (HB) above includes a polypeptide consisting of the amino acid sequence of (H-B) below, for example. The light-chain variable region of (LK) above includes a polypeptide consisting of the amino acid sequence of (L-K) below, for example.

(H-B) An amino acid sequence of (H-B1), (H-B2), or (H-B3) below:
 (H-B1) an amino acid sequence of Sequence ID No. 24:

```
Sequence ID No. 24:
EVQLLESGGGLVQPGGSLRLSCAASGFTFSTYQMSWVRQAPGKGLEWVS
GIVSSGGSTAYADSVKGRFTISRDNSKNTLYLQMNSLRAEDTAVYYCAG
ELLPYYGMDVWGQGTTVTVSS,
```

(H-B2) an amino acid sequence having 80% or more identity to the amino acid sequence of Sequence ID No. 24, and
 (H-B3) an amino acid sequence consisting of the amino acid sequence of Sequence ID No. 24 with deletion, substitution, insertion, and/or addition of one or several amino acids.

(L-K) An amino acid sequence of (L-K1), (L-K2), or (L-K3) below:
 (L-K1) an amino acid sequence of Sequence ID No. 73:

```
Sequence ID No. 73:
QSALTQPPSASGSPGQSVTISCTGTSSDVGGYDFVSWYQQHPGEAPKLL
VYDVNNRPSGVSNRFSGSKSGNTASLTISGLQAEDEGDYYCSSYAGSNS
VFGTGTKVTVL,
```

(L-K2) an amino acid sequence having 80% or more identity to the amino acid sequence of Sequence ID No. 73, and
 (L-K3) an amino acid sequence consisting of the amino acid sequence of Sequence ID No. 73 with deletion, substitution, insertion, and/or addition of one or several amino acids.

The amino acid sequence of (H-B1) above is a sequence that includes the amino acid sequences of (H1-B1) of the CDRH1, (H2-B1) of the CDRH2, and (H3-B1) of the CDRH3, for example. The amino acid sequence of (H-B2) above may be an amino acid sequence that includes the amino acid sequences of (H1-B1) of the CDRH1, (H2-B1) of the CDRH2, and (H3-B1) of the CDRH3 and that has 80% or more identity to the amino acid sequence of Sequence ID No. 24, for example. The amino acid sequence of (H-B3) above may be an amino acid sequence that includes the amino acid sequences of (H1-B1) of the CDRH1, (H2-B1) of the CDRH2, and (H3-B1) of the CDRH3 and that consists of the amino acid sequence of Sequence ID No. 24 with deletion, substitution, insertion, and/or addition of one or several amino acids, for example.

The amino acid sequence of (L-K1) above is a sequence that includes the amino acid sequences of (L1-K1) of the CDRL1, (L2-K1) of the CDRL2, and (L3-K1) of the CDRL3, for example. The amino acid sequence of (L-K2) above may be an amino acid sequence that includes the amino acid sequences of (L1-K1) of the CDRL1, (L2-K1) of the CDRL2, and (L3-K1) of the CDRL3 and that has 80% or more identity to the amino acid sequence of Sequence ID No. 73, for example. The amino acid sequence of (L-K3) above may be an amino acid sequence that includes the amino acid sequences of (L1-K1) of the CDRL1, (L2-K1) of the CDRL2, and (L3-K1) of the CDRL3 and that consists of the amino acid sequence of Sequence ID No. 73 with deletion, substitution, insertion, and/or addition of one or several amino acids, for example.

In the antibody of the present invention, the heavy-chain variable region is (H-B1) above, and the light-chain variable region is (L-K1) above, for example. The antibody that includes this combination is also referred to as an "antibody 3M4E5H-L1" hereinafter.

The "identity" as used for the polypeptide of the heavy-chain variable region and the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the heavy-chain variable region and the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (12)

The antibodies or the like of Combination (12) are also referred to as an antibody 3M4E5H-L66 group, for example. In Combination (12) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B) above, and the CDRH3 is a polypeptide that includes the amino acid sequence of (H3-B) above. The light-chain variable region of (LL) above includes the CDRL1, the CDRL2, and the CDRL3, the CDRL1 is a polypeptide that includes the amino acid sequence of (L1-L) below, the CDRL2 is a polypeptide that includes the amino acid sequence of (L2-L) below, and the CDRL3 is a polypeptide that includes the amino acid sequence of (L3-L) below.

(L1-L) An amino acid sequence of (L1-L1), (L1-L2), or (L1-L3) below:
  (L1-L1) an amino acid sequence of Sequence ID No. 74 (SSDVGGYEF),
  (L1-L2) an amino acid sequence having 80% or more identity to the amino acid sequence of Sequence ID No. 74, and
  (L1-L3) an amino acid sequence consisting of the amino acid sequence of Sequence ID No. 74 with deletion, substitution, insertion, and/or addition of one or several amino acids.
(L2-L) An amino acid sequence of (L2-L1), (L2-L2), or (L2-L3) below:
  (L2-L1) an amino acid sequence of Sequence ID No. 75 (DVI),
  (L2-L2) an amino acid sequence having 80% or more identity to the amino acid sequence of Sequence ID No. 75, and
  (L2-L3) an amino acid sequence consisting of the amino acid sequence of Sequence ID No. 75 with deletion, substitution, insertion, and/or addition of one or several amino acids.
(L3-L) An amino acid sequence of (L3-L1), (L3-L2), or (L3-L3) below:
  (L3-L1) an amino acid sequence of Sequence ID No. 76 (SSYTSSSTYV),
  (L3-L2) an amino acid sequence having 80% or more identity to the amino acid sequence of Sequence ID No. 76, and
  (L3-L3) an amino acid sequence consisting of the amino acid sequence of Sequence ID No. 76 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (12) above, the heavy-chain variable region of (HB) above includes a polypeptide consisting of the amino acid sequence of (H-B) above, for example. The light-chain variable region of (LL) above includes a polypeptide consisting of the amino acid sequence of (L-L) below, for example.

(L-L) An amino acid sequence of (L-L1), (L-L2), or (L-L3) below:
  (L-L1) an amino acid sequence of Sequence ID No. 77:

```
Sequence ID No. 77:
QSALTQPASVSGSPGQSITISCTGTSSDVGGYEFVSWYQQHPGSAPKLI
TYDVIERPFGVSYRFSASKSGNTASLTISGLQGEDEADYFCSSYTSSST
YVFGTGTKVTVL,
```

(L-L2) an amino acid sequence having 80% or more identity to the amino acid sequence of Sequence ID No. 77, and
  (L-L3) an amino acid sequence consisting of the amino acid sequence of Sequence ID No. 77 with deletion, substitution, insertion, and/or addition of one or several amino acids.

The amino acid sequence of (L-L1) above is a sequence that includes the amino acid sequences of (L1-L1) of the CDRL1, (L2-L1) of the CDRL2, and (L3-L1) of the CDRL3, for example. The amino acid sequence of (L-L2) above may be an amino acid sequence that includes the amino acid sequences of (L1-L1) of the CDRL1, (L2-L1) of the CDRL2, and (L3-L1) of the CDRL3 and that has 80% or more identity to the amino acid sequence of Sequence ID No. 77, for example. The amino acid sequence of (L-L3) above may be an amino acid sequence that includes the amino acid sequences of (L1-L1) of the CDRL1, (L2-L1) of the CDRL2, and (L3-L1) of the CDRL3 and that consists of the amino acid sequence of Sequence ID No. 77 with deletion, substitution, insertion, and/or addition of one or several amino acids, for example.

In the antibody of the present invention, the heavy-chain variable region is (H-B1) above, and the light-chain variable region is (L-L1) above, for example. The antibody that includes this combination is also referred to as an "antibody 3M4E5H-L66" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (13)

The antibodies or the like of Combination (13) are also referred to as an antibody 3M4E5H-L73 group, for example. In Combination (13) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B)

above, and the CDRH3 is a polypeptide that includes the amino acid sequence of (H3-B) above. The light-chain variable region of (LM) above includes the CDRL1, the CDRL2, and the CDRL3, the CDRL1 is a polypeptide that includes the amino acid sequence of (L1-M) below, the CDRL2 is a polypeptide that includes the amino acid sequence of (L2-M) below, and the CDRL3 is a polypeptide that includes the amino acid sequence of (L3-M) below.

(L1-M) An amino acid sequence of (L1-M1), (L1-M2), or (L1-M3) below:
  (L1-M1) an amino acid sequence of Sequence ID No. 78 (GSDVGAYDY),
  (L1-M2) an amino acid sequence having 80% or more identity to the amino acid sequence of Sequence ID No. 78, and
  (L1-M3) an amino acid sequence consisting of the amino acid sequence of Sequence ID No. 78 with deletion, substitution, insertion, and/or addition of one or several amino acids.

(L2-M) An amino acid sequence of (L2-M1), (L2-M2), or (L2-M3) below:
  (L2-M1) an amino acid sequence of Sequence ID No. 79 (DVS),
  (L2-M2) an amino acid sequence having 80% or more identity to the amino acid sequence of Sequence ID No. 79, and
  (L2-M3) an amino acid sequence consisting of the amino acid sequence of Sequence ID No. 79 with deletion, substitution, insertion, and/or addition of one or several amino acids.

(L3-M) An amino acid sequence of (L3-M1), (L3-M2), or (L3-M3) below:
  (L3-M1) an amino acid sequence of Sequence ID No. 80 (SSYSGSSTWV),
  (L3-M2) an amino acid sequence having 80% or more identity to the amino acid sequence of Sequence ID No. 80, and
  (L3-M3) an amino acid sequence consisting of the amino acid sequence of Sequence ID No. 80 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (13) above, the heavy-chain variable region of (HB) above includes a polypeptide consisting of the amino acid sequence of (H-B) above, for example. The light-chain variable region of (LM) above includes a polypeptide consisting of the amino acid sequence of (L-M) below, for example.

(L-M) An amino acid sequence of (L-M1), (L-M2), or (L-M3) below:
  (L-M1) an amino acid sequence of Sequence ID No. 81:

```
Sequence ID No. 81:
QSALTQPASVSGSPGQSITISCTGTGSDVGAYDYVSWYQHHPGRAPRLII
RDVSVRPSGVPDRFSGSKSGNTASLTISGLQAEDEADYYCSSYSGSSTWV
FGGGTKLTVL,
```

(L-M2) an amino acid sequence having 80% or more identity to the amino acid sequence of Sequence ID No. 81, and
  (L-M3) an amino acid sequence consisting of the amino acid sequence of Sequence ID No. 81 with deletion, substitution, insertion, and/or addition of one or several amino acids.

The amino acid sequence of (L-M1) above is a sequence that includes the amino acid sequences of (L1-M1) of the CDRL1, (L2-M1) of the CDRL2, and (L3-M1) of the CDRL3, for example. The amino acid sequence of (L-M2) above may be an amino acid sequence that includes the amino acid sequences of (L1-M1) of the CDRL1, (L2-M1) of the CDRL2, and (L3-M1) of the CDRL3 and that has 80% or more identity to the amino acid sequence of Sequence ID No. 81, for example. The amino acid sequence of (L-M3) above may be an amino acid sequence that includes the amino acid sequences of (L1-M1) of the CDRL1, (L2-M1) of the CDRL2, and (L3-M1) of the CDRL3 and that consists of the amino acid sequence of Sequence ID No. 81 with deletion, substitution, insertion, and/or addition of one or several amino acids, for example.

In the antibody of the present invention, the heavy-chain variable region is (H-B1) above, and the light-chain variable region is (L-M1) above, for example. The antibody that includes this combination is also referred to as an "antibody 3M4E5H-L73" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (14)

The antibodies or the like of Combination (14) are also referred to as an antibody 3M4E5H-L80 group, for example. In Combination (14) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B) above, and the CDRH3 is a polypeptide that includes the amino acid sequence of (H3-B) above. The light-chain variable region of (LN) above includes the CDRL1, the CDRL2, and the CDRL3, the CDRL1 is a polypeptide that includes the amino acid sequence of (L1-N) below, the CDRL2 is a polypeptide that includes the amino acid sequence of (L2-N) below, and the CDRL3 is a polypeptide that includes the amino acid sequence of (L3-N) below.

(L1-N) An amino acid sequence of (L1-N1), (L1-N2), or (L1-N3) below:
  (L1-N1) an amino acid sequence of Sequence ID No. 82 (SSDVGSYNL),
  (L1-N2) an amino acid sequence having 80% or more identity to the amino acid sequence of Sequence ID No. 82, and
  (L1-N3) an amino acid sequence consisting of the amino acid sequence of Sequence ID No. 82 with deletion, substitution, insertion, and/or addition of one or several amino acids.

(L2-N) An amino acid sequence of (L2-N1), (L2-N2), or (L2-N3) below:
  (L2-N1) an amino acid sequence of Sequence ID No. 83 (DVS), (L2-N2) an amino acid sequence having 80% or more identity to the amino acid sequence of Sequence ID No. 83, and (L2-N3) an amino acid sequence consisting of the amino acid sequence of Sequence ID No. 83 with deletion, substitution, insertion, and/or addition of one or several amino acids.

(L3-N) An amino acid sequence of (L3-N1), (L3-N2), or (L3-N3) below:

(L3-N1) an amino acid sequence of Sequence ID No. 84 (SSYTSSSTFAV), (L3-N2) an amino acid sequence having 80% or more identity to the amino acid sequence of Sequence ID No. 84, and (L3-N3) an amino acid sequence consisting of the amino acid sequence of Sequence ID No. 84 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (14) above, the heavy-chain variable region of (HB) above includes a polypeptide consisting of the amino acid sequence of (H-B) above, for example. The light-chain variable region of (LN) above includes a polypeptide consisting of the amino acid sequence of (L-N) below, for example.

(L-N) An amino acid sequence of (L-N1), (L-N2), or (L-N3) below:

(L-N1) an amino acid sequence of Sequence ID No. 85:

```
Sequence ID No. 85:
QSALTQPASVSGSPGQSITISCTGTSSDVGSYNLVSWYQQHPGKAPKLMI
YDVSNRPSGVSYRFSGSKSGNTASLTISGLQAEDEADYYCSSYTSSSTFA
VFGGGTQLTVL
```

(L-N2) an amino acid sequence having 80% or more identity to the amino acid sequence of Sequence ID No. 85, and (L-N3) an amino acid sequence consisting of the amino acid sequence of Sequence ID No. 85 with deletion, substitution, insertion, and/or addition of one or several amino acids.

The amino acid sequence of (L-N1) above is a sequence that includes the amino acid sequences of (L1-N1) of the CDRL1, (L2-N1) of the CDRL2, and (L3-N1) of the CDRL3, for example. The amino acid sequence of (L-N2) above may be an amino acid sequence that includes the amino acid sequences of (L1-N1) of the CDRL1, (L2-N1) of the CDRL2, and (L3-N1) of the CDRL3 and that has 80% or more identity to the amino acid sequence of Sequence ID No. 85, for example. The amino acid sequence of (L-N3) above may be an amino acid sequence that includes the amino acid sequences of (L1-N1) of the CDRL1, (L2-N1) of the CDRL2, and (L3-N1) of the CDRL3 and that consists of the amino acid sequence of Sequence ID No. 85 with deletion, substitution, insertion, and/or addition of one or several amino acids, for example.

In the antibody of the present invention, the heavy-chain variable region is (H-B1) above, and the light-chain variable region is (L-N1) above, for example. The antibody that includes this combination is also referred to as an "antibody 3M4E5H-L80" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (15)

The antibodies or the like of Combination (15) are also referred to as an antibody 3M4E5H-L88 group, for example. In Combination (15) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B) above, and the CDRH3 is a polypeptide that includes the amino acid sequence of (H3-B) above. The light-chain variable region of (LO) above includes the CDRL1, the CDRL2, and the CDRL3, the CDRL1 is a polypeptide that includes the amino acid sequence of (L1-O) below, the CDRL2 is a polypeptide that includes the amino acid sequence of (L2-O) below, and the CDRL3 is a polypeptide that includes the amino acid sequence of (L3-O) below.

(L1-O) An amino acid sequence of (L1-O1), (L1-O2), or (L1-O3) below:

(L1-O1) an amino acid sequence of Sequence ID No. 86 (SSDVGGYNY), (L1-O2) an amino acid sequence having 80% or more identity to the amino acid sequence of Sequence ID No. 86, and (L1-O3) an amino acid sequence consisting of the amino acid sequence of Sequence ID No. 86 with deletion, substitution, insertion, and/or addition of one or several amino acids.

(L2-O) An amino acid sequence of (L2-O1), (L2-O2), or (L2-O3) below:

(L2-O1) an amino acid sequence of Sequence ID No. 87 (DVS), (L2-O2) an amino acid sequence having 80% or more identity to the amino acid sequence of Sequence ID No. 87, and (L2-O3) an amino acid sequence consisting of the amino acid sequence of Sequence ID No. 87 with deletion, substitution, insertion, and/or addition of one or several amino acids.

(L3-O) An amino acid sequence of (L3-O1), (L3-O2), or (L3-O3) below:

(L3-O1) an amino acid sequence of Sequence ID No. 88 (CSYAGGYYV), (L3-O2) an amino acid sequence having 80% or more identity to the amino acid sequence of Sequence ID No. 88, and (L3-O3) an amino acid sequence consisting of the amino acid sequence of Sequence ID No. 88 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (15) above, the heavy-chain variable region of (HB) above includes a polypeptide consisting of the amino acid sequence of (H-B) above, for example. The light-chain variable region of (LO) above includes a polypeptide consisting of the amino acid sequence of (L-O) below, for example.

(L-O) An amino acid sequence of (L-O1), (L-O2), or (L-O3) below:

(L-O1) an amino acid sequence of Sequence ID No. 89:

```
Sequence ID No. 89:
QSALPQPASVSGSPGQSVTISCTGTSSDVGGYNYVSWYQQHPGKAPKLMI
YDVSKRPSGVPDRFSGSKSGNTASLTVSGLQAEDEADYFCCSYAGGYYVF
GTGTKLTVL,
```

(L-O2) an amino acid sequence having 80% or more identity to the amino acid sequence of Sequence ID No. 89, and (L-O3) an amino acid sequence consisting of the amino acid sequence of Sequence ID No. 89 with deletion, substitution, insertion, and/or addition of one or several amino acids.

The amino acid sequence of (L-O1) above is a sequence that includes the amino acid sequences of (L1-O1) of the CDRL1, (L2-O1) of the CDRL2, and (L3-O1) of the CDRL3, for example. The amino acid sequence of (L-O2) above may be an amino acid sequence that includes the amino acid sequences of (L1-O1) of the CDRL1, (L2-O1) of the CDRL2, and (L3-O1) of the CDRL3 and that has 80% or more identity to the amino acid sequence of Sequence ID No. 89, for example. The amino acid sequence of (L-O3) above may be an amino acid sequence that includes the amino acid sequences of (L1-O1) of the CDRL1, (L2-O1) of the CDRL2, and (L3-O1) of the CDRL3 and that consists of the amino acid sequence of Sequence ID No. 89 with deletion, substitution, insertion, and/or addition of one or several amino acids, for example.

In the antibody of the present invention, the heavy-chain variable region is (H-B1) above, and the light-chain variable region is (L-O1) above, for example. The antibody that includes this combination is also referred to as an "antibody 3M4E5H-L88" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (16)

The antibodies or the like of Combination (16) are also referred to as an antibody 3M4E5H-L102 group, for example. In Combination (16) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B) above, and the CDRH3 is a polypeptide that includes the amino acid sequence of (H3-B) above. The light-chain variable region of (LP) above includes the CDRL1, the CDRL2, and the CDRL3, the CDRL1 is a polypeptide that includes the amino acid sequence of (L1-P) below, the CDRL2 is a polypeptide that includes the amino acid sequence of (L2-P) below, and the CDRL3 is a polypeptide that includes the amino acid sequence of (L3-P) below.

(L1-P) An amino acid sequence of (L1-P1), (L1-P2), or (L1-P3) below:

(L1-P1) an amino acid sequence of Sequence ID No. 90 (SSDVGGYNY), (L1-P2) an amino acid sequence having 80% or more identity to the amino acid sequence of Sequence ID No. 90, and (L1-P3) an amino acid sequence consisting of the amino acid sequence of Sequence ID No. 90 with deletion, substitution, insertion, and/or addition of one or several amino acids.

(L2-P) An amino acid sequence of (L2-P1), (L2-P2), or (L2-P3) below:

(L2-P1) an amino acid sequence of Sequence ID No. 91 (DVS), (L2-P2) an amino acid sequence having 80% or more identity to the amino acid sequence of Sequence ID No. 91, and (L2-P3) an amino acid sequence consisting of the amino acid sequence of Sequence ID No. 91 with deletion, substitution, insertion, and/or addition of one or several amino acids.

(L3-P) An amino acid sequence of (L3-P1), (L3-P2), or (L3-P3) below:

(L3-P1) an amino acid sequence of Sequence ID No. 92 (SSYAGSGSTPFV), (L3-P2) an amino acid sequence having 80% or more identity to the amino acid sequence of Sequence ID No. 92, and (L3-P3) an amino acid sequence consisting of the amino acid sequence of Sequence ID No. 92 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (16) above, the heavy-chain variable region of (HB) above includes a polypeptide consisting of the amino acid sequence of (H-B) above, for example. The light-chain variable region of (LP) above includes a polypeptide consisting of the amino acid sequence of (L-P) below, for example.

(L-P) An amino acid sequence of (L-P1), (L-P2), or (L-P3) below:

(L-P1) an amino acid sequence of Sequence ID No. 93

```
Sequence ID No. 93:
QSALTQPPSASGSPGQSVTISCTGTSSDVGGYNYVSWYQQHPGKAPKLMI
YDVSKRPSGVPDRFSGSKSGNTASLTISGLQTEDEADYYCSSYAGSGSTP
FVFGTGTKLTVL,
```

(L-P2) an amino acid sequence having 80% or more identity to the amino acid sequence of Sequence ID No. 93, and (L-P3) an amino acid sequence consisting of the amino acid sequence of Sequence ID No. 93 with deletion, substitution, insertion, and/or addition of one or several amino acids.

The amino acid sequence of (L-P1) above is a sequence that includes the amino acid sequences of (L1-P1) of the CDRL1, (L2-P1) of the CDRL2, and (L3-P1) of the CDRL3, for example. The amino acid sequence of (L-P2) above may be an amino acid sequence that includes the amino acid sequences of (L1-P1) of the CDRL1, (L2-P1) of the CDRL2, and (L3-P1) of the CDRL3 and that has 80% or more identity to the amino acid sequence of Sequence ID No. 93, for example. The amino acid sequence of (L-P3) above may be an amino acid sequence that includes the amino acid sequences of (L1-P1) of the CDRL1, (L2-P1) of the CDRL2, and (L3-P1) of the CDRL3 and that consists of the amino acid sequence of Sequence ID No. 93 with deletion, substitution, insertion, and/or addition of one or several amino acids, for example.

In the antibody of the present invention, the heavy-chain variable region is (H-B1) above, and the light-chain variable region is (L-P1) above, for example. The antibody that includes this combination is also referred to as an "antibody 3M4E5H-L102" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (17)

The antibodies or the like of Combination (17) are also referred to as an antibody 3M4E5H-L124 group, for example. In Combination (17) above, the heavy-chain variable region of (HB) above includes the CDRH1, the CDRH2, and the CDRH3, the CDRH1 is a polypeptide that includes the amino acid sequence of (H1-B) above, the CDRH2 is a polypeptide that includes the amino acid sequence of (H2-B) above, and the CDRH3 is a polypeptide that includes the amino acid sequence of (H3-B) above. The light-chain variable region of (LQ) above includes the CDRL1, the CDRL2, and the CDRL3, the CDRL1 is a polypeptide that includes the amino acid sequence of (L1-Q) below, the CDRL2 is a polypeptide that includes the amino acid sequence of (L2-Q) below, and the CDRL3 is a polypeptide that includes the amino acid sequence of (L3-Q) below.

(L1-Q) An amino acid sequence of (L1-Q1), (L1-Q2), or (L1-Q3) below:
 (L1-Q1) an amino acid sequence of Sequence ID No. 94 (SSDVGGYNY),
 (L1-Q2) an amino acid sequence having 80% or more identity to the amino acid sequence of Sequence ID No. 94, and
 (L1-Q3) an amino acid sequence consisting of the amino acid sequence of Sequence ID No. 94 with deletion, substitution, insertion, and/or addition of one or several amino acids.

(L2-Q) An amino acid sequence of (L2-Q1), (L2-Q2), or (L2-Q3) below:
 (L2-Q1) an amino acid sequence of Sequence ID No. 95 (DVS),
 (L2-Q2) an amino acid sequence having 80% or more identity to the amino acid sequence of Sequence ID No. 95, and
 (L2-Q3) an amino acid sequence consisting of the amino acid sequence of Sequence ID No. 95 with deletion, substitution, insertion, and/or addition of one or several amino acids.

(L3-Q) An amino acid sequence of (L3-Q1), (L3-Q2), or (L3-Q3) below:
 (L3-Q1) an amino acid sequence of Sequence ID No. 96 (CSYAGRRYV),
 (L3-Q2) an amino acid sequence having 80% or more identity to the amino acid sequence of Sequence ID No. 96, and
 (L3-Q3) an amino acid sequence consisting of the amino acid sequence of Sequence ID No. 96 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (17) above, the heavy-chain variable region of (HB) above includes a polypeptide consisting of the amino acid sequence of (H-B) above, for example. The light-chain variable region of (LQ) above includes a polypeptide consisting of the amino acid sequence of (L-Q) below, for example.

(L-Q) An amino acid sequence of (L-Q1), (L-Q2), or (L-Q3) below:
 (L-Q1) an amino acid sequence of Sequence ID No. 97:

```
Sequence ID No. 97:
QSALTQPASVSGSPGQSITISCTGTSSDVGGYNYVSWYQQHPGKAPKLMI
YDVSNRPSRVPDRFAGSKSGNTASLTISGLQAEDEADYYCCSYAGRRYVF
GTGTKLTVL,
```

(L-Q2) an amino acid sequence having 80% or more identity to the amino acid sequence of Sequence ID No. 97, and
 (L-Q3) an amino acid sequence consisting of the amino acid sequence of Sequence ID No. 97 with deletion, substitution, insertion, and/or addition of one or several amino acids.

The amino acid sequence of (L-Q1) above is a sequence that includes the amino acid sequences of (L1-Q1) of the CDRL1, (L2-Q1) of the CDRL2, and (L3-Q1) of the CDRL3, for example. The amino acid sequence of (L-Q2) above may be an amino acid sequence that includes the amino acid sequences of (L1-Q1) of the CDRL1, (L2-Q1) of the CDRL2, and (L3-Q1) of the CDRL3 and that has 80% or more identity to the amino acid sequence of Sequence ID No. 97, for example. The amino acid sequence of (L-Q3) above may be an amino acid sequence that includes the amino acid sequences of (L1-Q1) of the CDRL1, (L2-Q1) of the CDRL2, and (L3-Q1) of the CDRL3 and that consists of the amino acid sequence of Sequence ID No. 97 with deletion, substitution, insertion, and/or addition of one or several amino acids, for example.

In the antibody of the present invention, the heavy-chain variable region is (H-B1) above, and the light-chain variable region is (L-Q1) above, for example. The antibody that includes this combination is also referred to as an "antibody 3M4E5H-L124" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination (18)

The antibodies or the like of Combination (18) are also referred to as an antibody H73-3M4E5L group, for example. In Combination (18) above, the heavy-chain variable region of (HC) above includes the CDRH1, the CDRH2, and the CDRH3, the CDRH1 is a polypeptide that includes the amino acid sequence of (H1-C) below, the CDRH2 is a polypeptide that includes the amino acid sequence of (H2-C) below, and the CDRH3 is a polypeptide that includes the amino acid sequence of (H3-C) below. The light-chain variable region of (LA) above includes the CDRL1, the CDRL2, and the CDRL3, the CDRL1 is a polypeptide that includes the amino acid sequence of (L1-A) above, the CDRL2 is a polypeptide that includes the amino acid sequence of (L2-A) above, and the CDRL3 is a polypeptide that includes the amino acid sequence of (L3-A) above.

(H1-C) An amino acid sequence of (H1-C1), (H1-C2), or (H1-C3) below:
- (H1-C1) an amino acid sequence of Sequence ID No. 25 (GGSISSYY),
- (H1-C2) an amino acid sequence having 80% or more identity to the amino acid sequence of Sequence ID No. 25, and
- (H1-C3) an amino acid sequence consisting of the amino acid sequence of Sequence ID No. 25 with deletion, substitution, insertion, and/or addition of one or several amino acids.

(H2-C) An amino acid sequence of (H2-C1), (H2-C2), or (H2-C3) below:
- (H2-C1) an amino acid sequence of Sequence ID No. 26 (INHSGST),
- (H2-C2) an amino acid sequence having 80% or more identity to the amino acid sequence of Sequence ID No. 26, and
- (H2-C3) an amino acid sequence consisting of the amino acid sequence of Sequence ID No. 26 with deletion, substitution, insertion, and/or addition of one or several amino acids.

(H3-C) An amino acid sequence of (H3-C1), (H3-C2), or (H3-C3) below:
- (H3-C1) an amino acid sequence of Sequence ID No. 27 (ARCPIYYYGMDV),
- (H3-C2) an amino acid sequence having 80% or more identity to the amino acid sequence of Sequence ID No. 27, and
- (H3-C3) an amino acid sequence consisting of the amino acid sequence of Sequence ID No. 27 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (18) above, the heavy-chain variable region of (HC) above includes a polypeptide consisting of the amino acid sequence of (H-C) below, for example. The light-chain variable region of (LA) above includes a polypeptide consisting of the amino acid sequence of (L-A) above, for example.

(H-C) An amino acid sequence of (H-C1), (H-C2), or (H-C3) below:
(H-C1) an amino acid sequence of Sequence ID No. 28:

```
Sequence ID No. 28:
QLQLQESGPGLVKPSQTLSLTCTVSGGSISSYYWSWIRQPPGKGLEWIG
EINHSGSTNYNPSLKSRVTISVDTSKNQFSLKLSSVTAADTAVYYCARC
PIYYYGMDVWGQGTTVTVSS,
```

(H-C2) an amino acid sequence having 80% or more identity to the amino acid sequence of Sequence ID No. 28, and (H-C3) an amino acid sequence consisting of the amino acid sequence of Sequence ID No. 28 with deletion, substitution, insertion, and/or addition of one or several amino acids.

The amino acid sequence of (H-C1) above is a sequence that includes the amino acid sequences of (H1-C1) of the CDRH1, (H2-C1) of the CDRH2, and (H3-C1) of the CDRH3, for example. The amino acid sequence of (H-C2) above may be an amino acid sequence that includes the amino acid sequences of (H1-C1) of the CDRH1, (H2-C1) of the CDRH2, and (H3-C1) of the CDRH3 and that has 80% or more identity to the amino acid sequence of Sequence ID No. 28, for example. The amino acid sequence of (H-C3) above may be an amino acid sequence that includes the amino acid sequences of (H1-C1) of the CDRH1, (H2-C1) of the CDRH2, and (H3-C1) of the CDRH3 and that consists of the amino acid sequence of Sequence ID No. 28 with deletion, substitution, insertion, and/or addition of one or several amino acids, for example.

In the antibody of the present invention, the heavy-chain variable region is (H-C1) above, and the light-chain variable region is (L-A1) above, for example. The antibody that includes this combination is also referred to as an "antibody H73-3M4E5L" hereinafter.

The "identity" as used for the polypeptide of the heavy-chain variable region refers to 80% or more, 85% or more, 90% or more, 95% or more, 96% or more, 97% or more, 98% or more, or 99% or more identity, for example.

The term "one or several" as used for the polypeptide of the heavy-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

In the present invention, the amino acid sequences of Sequence ID Nos. 17 to 97 are human-derived amino acid sequences, for example.

The binding of the antibody of the present invention or the like to A2/NY-ESO-1$_{157}$ can be confirmed using a technique for detecting the binding of an antibody to an antigen such as surface plasmon resonance (SPR) or flow cytometry, for example.

The antibody of the present invention or the like may further include a labeling substance, for example. There is no particular limitation on the labeling substance, and examples thereof include fluorescent substances, dyes, isotopes, and enzymes. Examples of the fluorescent substances include fluorophores such as pyrene, TAMRA, fluorescein, Cy3 dyes, Cy5 dyes, FAM dyes, rhodamine dyes, Texas red dyes, JOE, MAX, HEX, and TYE, and examples of the dyes include Alexa dyes such as Alexa488 and Alexa647. The antibody of the present invention or the like may be modified by a low-molecular compound such as a pharmaceutical compound. Examples of the low-molecular compound include anticancer agents such as tubulin inhibitors. The antibody of the present invention or the like is modified directly or indirectly by the low-molecular compound, for example. In the latter case, the antibody of the present invention or the like is modified by the low-molecular compound via a linker, for example.

The antibody of the present invention or the like may be immobilized on a carrier, a porous body, or the like, for example. There is no particular limitation on the carrier, and examples thereof include a substrate, a bead, and a container. Examples of the container include a microplate and a tube.

There is no particular limitation on a method for manufacturing the antibody of the present invention or the like, and the antibody or the like can be manufactured using genetic engineering techniques based on the amino acid sequence information described above, for example. Specifically, the antibody or the like can be manufactured as follows, for example. It should be noted that the present invention is not limited to this example.

First, a vector that includes nucleic acid sequences coding for the amino acid sequences of the above-mentioned regions, heavy chain, and/or light chain in the antibody of the present invention or the like is introduced into a host, and thus a transformant is obtained. Then, the transformant is cultured, a fraction containing an antibody capable of binding to A2/NY-ESO-$1_{157}$ is collected, and the antibody is isolated or purified from the obtained collected fraction.

Examples of the vector include a vector that includes a nucleic acid sequence coding for the heavy-chain variable region, a vector that includes a nucleic acid sequence coding for the light-chain variable region, a vector that includes a nucleic acid sequence coding for the heavy chain, and a vector that includes a nucleic acid sequence coding for the light chain. There is no particular limitation on the host as long as the vector can be introduced into the host, and the nucleic acid sequence in the vector can be expressed in the host. Examples of the host include mammalian cells such as HEK cells, CHO cells, COS cells, NSO cells, and SP2/0 cells. There is no particular limitation on a method for introducing the vector into a host, and a known method can be employed.

There is no particular limitation on a method for culturing the transformant, and it is possible to determine as appropriate which method is employed, in accordance with the type of host. The fraction containing an antibody can be collected as a liquid fraction after the cultured transformant is lysed, for example. There is no particular limitation on a method for isolating or purifying the antibody, and a known method can be employed.

In the present invention, the antibody is a monoclonal antibody, for example. Examples of the monoclonal antibody include monoclonal antibodies obtained through immunization of an animal, chimeric antibodies, humanized antibodies, and human antibodies (also referred to as "fully human antibodies").

The chimeric antibody is an antibody formed by coupling a variable region of an antibody derived from a non-human animal and a constant region of a human antibody. The chimeric antibody can be produced as follows, for example. First, the gene of the variable region (V region) of a monoclonal antibody derived from a non-human animal capable of binding to the A2/NY-ESO-$1_{157}$ protein is prepared, the gene of the variable region and the gene of the constant region (C region) of a human antibody are coupled to each other, and then the resultant product is coupled to an expression vector. Cells transfected with the expression vector are cultured, and the chimeric antibody secreted into the culture medium is collected. The chimeric antibody can thus be prepared. There is no particular limitation on the animal from which the variable region is derived, and examples thereof include a rat and a mouse. The method for manufacturing a chimeric antibody is not limited to the above-mentioned method, and a chimeric antibody can be manufactured with reference to a known method such as the method disclosed in JP H3-73280B, for example.

The humanized antibody is an antibody in which only the CDRs are derived from a non-human animal and the other regions are derived from a human. The humanized antibody can be manufactured as follows, for example. First, the genes of the CDRs of a monoclonal antibody derived from a non-human animal are prepared and grafted into a gene of a human antibody (e.g., a region that corresponds to the constant region) (CDR grafting), and then the resultant product is coupled to an expression vector. Cells transfected with the expression vector are cultured, and a humanized antibody into which the target CDRs are grafted is secreted into the culture medium, and is then collected. The humanized antibody can thus be prepared. There is no particular limitation on the animal from which the CDRs are derived, and examples thereof include a rat and a mouse. The method for manufacturing a humanized antibody is not limited to the above-mentioned method, and a humanized antibody can be manufactured with reference to a known method such as the method disclosed in JP H4-506458A or the method disclosed in JP S62-296890A, for example.

The human antibody is an antibody in which the entire region is derived from a human. The human antibody can be produced by introducing the gene of a human antibody into a non-human animal, for example. Examples of an animal into which the gene of a human antibody is to be introduced include transgenic animals for producing a human antibody. There is no particular limitation on the type of animal, and an example thereof is a mouse. The human antibody can be manufactured with reference to known methods disclosed in Nature Genetics, Vol. 7, p. 13-21, 1994; Nature Genetics, Vol. 15, p. 146-156, 1997; JP H4-504365A; JP H7-509137A; WO 94/25585; Nature, Vol. 368, p. 856-859, 1994; JP H6-500233A; and the like, for example. The human antibody can also be manufactured using a phage display technique, for example, and can be manufactured with reference to a known method disclosed in Marks, J. D. et al.: J. Mol. Biol., Vol. 222, p. 581-597, 1991, or the like, for example.

The antibody of the present invention or the like can also be prepared through immunization of an animal with an antigen, for example. An example of the antigen is the A2/NY-ESO-$1_{157}$ protein. It is preferable to repeat the immunization with the antigen a plurality of times. The peptide fragment may be a peptide fragment constituted by only an antigenic determinant (epitope) or a peptide fragment that includes the antigenic determinant, for example.

The monoclonal antibody obtained through immunization of an animal can be manufactured with reference to known methods such as the methods disclosed in "Current Protocols in Molecular Biology" (John Wiley & Sons (1987)), Antibodies: A Laboratory Manual, Ed. Harlow and David Lane, Cold Spring Harbor Laboratory (1988)), and the like, for example. Specifically, an animal is immunized with an antigen, and antibody-producing cells collected from the immunized animal and myeloma cells lacking antibody producibility are fused to produce hybridomas, for example. Subsequently, antibody-producing cells are screened from the hybridomas, and a monoclonal hybridoma is produced through cloning. Then, this hybridoma clone is administered to an animal, and a monoclonal antibody obtained from the abdominal cavity is purified. Alternatively, the hybridoma is cultured, and then a monoclonal antibody is purified from the hybridoma culture solution. Producing the hybridoma clone in this manner makes it possible to stably supply monoclonal antibodies having uniform specificity.

It is preferable that the myeloma cells are derived from a mouse, a rat, a human, or the like, for example. The myeloma cells and the antibody-producing cells may be derived from the same species or different species, for example, and are preferably derived from the same species.

In the first antibody of the present invention or the like, the heavy-chain variable region of (H) above and the light-chain variable region of (L) above may be a heavy-chain variable region of (H) below and a light-chain variable region of (L) below.

(H) A heavy-chain variable region that includes
 a heavy-chain complementarity determining region (CDRH) 1, a CDRH2, and a CDRH3,
 wherein the CDRH1 is a polypeptide that includes an amino acid sequence of (H1),
 the CDRH2 is a polypeptide that includes an amino acid sequence of (H2),
 the CDRH3 is a polypeptide that includes an amino acid sequence of (H3),
 the amino acid sequences of (H1), (H2), and (H3) are as follows:
 (H1) an amino acid sequence of (H1-1), (H1-2), or (H1-3) below:
  (H1-1) any one of amino acid sequences of CDRH1 shown in Condition (H1) below,
  (H1-2) an amino acid sequence having 80% or more identity to the amino acid sequence of (H1-1), and
  (H1-3) an amino acid sequence consisting of the amino acid sequence of (H1-1) with deletion, substitution, insertion, and/or addition of one or several amino acids;
 (H2) an amino acid sequence of (H2-1), (H2-2), or (H2-3) below:
  (H2-1) any one of amino acid sequences of CDRH2 shown in Condition (H1) below,
  (H2-2) an amino acid sequence having 80% or more identity to the amino acid sequence of (H2-1), and
  (H2-3) an amino acid sequence consisting of the amino acid sequence of (H2-1) with deletion, substitution, insertion, and/or addition of one or several amino acids; and
 (H3) an amino acid sequence of (H3-1), (H3-2), or (H3-3) below:
  (H3-1) any one of amino acid sequences of CDRH3 shown in Condition (H1) below,
  (H3-2) an amino acid sequence having 80% or more identity to the amino acid sequence of (H3-1), and
  (H3-3) an amino acid sequence consisting of the amino acid sequence of (H3-1) with deletion, substitution, insertion, and/or addition of one or several amino acids, and
 Condition (H1) is as follows:
 the CDRH1 is $GX_1X_2X_3SX_4X_5X_6$ (Sequence ID No. 322),
 the CDRH2 is $X_7X_8X_9X_{10}SX_{11}GST$ (Sequence ID No. 323),
 the CDRH3 is $AX_{12}X_{13}X_{14}X_{15}X_{16}GMDV$ (Sequence ID No. 324),
 $X_1$ is G or F,
 $X_2$ is S or T,
 $X_3$ is I or F,
 $X_4$ is S or T,
 $X_5$ is N or Y,
 $X_6$ is Y or Q,
 $X_7$ is not present or is I,
 $X_8$ is V or N,
 $X_9$ is S or H,
 $X_{10}$ is not present or is Y,
 $X_{11}$ is not present or is G,
 $X_{12}$ is R or G,
 $X_{13}$ is E or C,
 $X_{14}$ is S, L, or P,
 $X_{15}$ is Y, L, or I, and
 $X_{16}$ is Y or P.

(L) A light-chain variable region that includes
 a light-chain complementarity determining region (CDRL) 1, a CDRL2, and a CDRL3,
 wherein the CDRL1 is a polypeptide that includes an amino acid sequence of (L1),
 the CDRL2 is a polypeptide that includes an amino acid sequence of (L2),
 the CDRL3 is a polypeptide that includes an amino acid sequence of (L3),
 the amino acid sequences of (L1), (L2), and (L3) are as follows:
 (L1) an amino acid sequence of (L1-1), (L1-2), or (L1-3) below:
  (L1-1) any one of amino acid sequences of CDRL1 shown in Conditions (L1) and (L2) below,
  (L1-2) an amino acid sequence having 80% or more identity to the amino acid sequence of (L1-1), and
  (L1-3) an amino acid sequence consisting of the amino acid sequence of (L1-1) with deletion, substitution, insertion, and/or addition of one or several amino acids;
 (L2) an amino acid sequence of (L2-1), (L2-2), or (L2-3) below:
  (L2-1) any one of amino acid sequences of CDRL2 shown in Conditions (L1) and (L2) below,
  (L2-2) an amino acid sequence having 80% or more identity to the amino acid sequence of (L2-1), and
  (L2-3) an amino acid sequence consisting of the amino acid sequence of (L2-1) with deletion, substitution, insertion, and/or addition of one or several amino acids; and
 (L3) an amino acid sequence of (L3-1), (L3-2), or (L3-3) below:
  (L3-1) any one of amino acid sequences of CDRL3 shown in Conditions (L1) and (L2) below,
  (L3-2) an amino acid sequence having 80% or more identity to the amino acid sequence of (L3-1), and
  (L3-3) an amino acid sequence consisting of the amino acid sequence of (L3-1) with deletion, substitution, insertion, and/or addition of one or several amino acids,
 Condition (L1) is as follows:
 the CDRL1 is $QX_1X_2SX_3X_4$ (Sequence ID No. 313),
 the CDRL2 is AAS (Sequence ID No. 34) or GAS (Sequence ID No. 63),
 the CDRL3 is $QQYX_5X_6X_7X_8X_9X_{10}Xu$ (Sequence ID No. 314),
 $X_1$ is S or D,
 $X_2$ is I or V,
 $X_3$ is S or R,
 $X_4$ is Y or N,
 $X_5$ is Y, E, N, or D,
 $X_6$ is S or N,
 $X_7$ is not present or is T, Y, or S,
 $X_8$ is P, S, R, or L,
 $X_9$ is Q, R, P, or I,
 $X_{10}$ is not present or is S or C, and
 $X_{11}$ is not present or is T, and Condition (L2) is as follows:
the CDRL1 is $X_1X_2DVGX_3YX_4X_5$ (Sequence ID No. 315),
the CDRL2 is DVN (Sequence ID No. 71), DVI (Sequence ID No. 75), or DVS (Sequence ID No. 79),
the CDRL3 is $X_6SX_7X_8X_9X_{10}X_{11}X_{12}X_{13}X_{14}X_{15}V$ (Sequence ID No. 316),
$X_1$ is S or G,
$X_2$ is R or S,
$X_3$ is G, A, or S,
$X_4$ is N, D, E, or Q,
$X_5$ is Y, F, L, or W,
$X_6$ is W, S, or C,
$X_7$ is F, Y, or W,
$X_8$ is not present or is A or T,
$X_9$ is not present or is G,
$X_{10}$ is not present or is S,
$X_{11}$ is G or S,
$X_{12}$ is not present or is S,
$X_{13}$ is S, T, or R,
$X_{14}$ is Y, N, T, F, P, or R, and
$X_{15}$ is Y, S, W, A, or F.

Examples of heavy-chain variable regions that meet Condition (H1) above include the heavy-chain variable regions of (HA), (HB), and (HC) above.

Regarding the light-chain variable region of (L) above, (L1-1), (L2-1), and (L3-1) meet the same condition or different conditions of Conditions (L1) and (L2), and preferably meet the same condition.

In Condition (L1), it is preferable that $X_7$ is not present or is T or Y.

In Condition (L2), it is preferable that $X_4$ is N, D, or E. It is preferable that $X_5$ is Y, F, or L. It is preferable that $X_7$ is F or Y.

Examples of light-chain variable regions that meet Condition (L1) above include the light-chain variable regions of (LB) to (U) above.

Examples of light-chain variable regions that meet Condition (L2) above include the light-chain variable regions of (LA) and (LK) to (LQ) above.

Regarding the heavy-chain variable region of (H) above and the light-chain variable region of (L) above, if the CDRH1 is GFTFSTYQ (Sequence ID No. 21), the CDRH2 is IVSSGGST (Sequence ID No. 22), and the CDRH3 is AGELLPYYGMDV (Sequence ID No. 23) in the heavy-chain variable region of (H) above, it is preferable that the CDRL1 is SRDVGGYNY (Sequence ID No. 29), the CDRL2 is DVI (Sequence ID No. 30), and the CDRL3 is an amino acid sequence other than WSFAGSYYV (Sequence ID No. 31) in the light-chain variable region of (L) above.

Second Antibody and Antigen-Binding Fragment Thereof

The antibody of the present invention against CD19 or the antigen-binding fragment thereof (also referred to as a "second antigen or the like" hereinafter) includes the heavy-chain variable region of (H) below and the light-chain variable region of (L) below. The antibody of the present invention or the like is characterized by including the heavy-chain variable region of (H) below and the light-chain variable region of (L) below, and there is no particular limitation on the other configurations and conditions. The antibody of the present invention or the like is capable of binding to CD19. It is known that CD19 is expressed in normal B cells and specific cancer cells derived from B-cell lymphoma and the like, for example. Accordingly, the antibody of the present invention or the like can be favorably used as a bispecific antibody against CD19-expressing cancer cells, the antigen-binding domain of a CAR in CAR-T cells, and the like, for example. The descriptions of the CAR library, the first screening method, the first antibody or antigen-binding fragment thereof, and the like of the present invention can be applied.

(H) A heavy-chain variable region that includes
a heavy-chain complementarity determining region (CDRH) 1, a CDRH2, and a CDRH3,
wherein the CDRH1 is a polypeptide that includes an amino acid sequence of (H1),
the CDRH2 is a polypeptide that includes an amino acid sequence of (H2),
the CDRH3 is a polypeptide that includes an amino acid sequence of (H3), and
the amino acid sequences of (H1), (H2), and (H3) are as follows:
(H1) an amino acid sequence of (H1-1), (H1-2), or (H1-3) below:
(H1-1) any one of amino acid sequences of CDRH1 shown in Table 3A below,
(H1-2) an amino acid sequence having 80% or more identity to the amino acid sequence of (H1-1), and
(H1-3) an amino acid sequence consisting of the amino acid sequence of (H1-1) with deletion, substitution, insertion, and/or addition of one or several amino acids;
(H2) an amino acid sequence of (H2-1), (H2-2), or (H2-3) below:
(H2-1) any one of amino acid sequences of CDRH2 shown in Table 3A below,
(H2-2) an amino acid sequence having 80% or more identity to the amino acid sequence of (H2-1), and
(H2-3) an amino acid sequence consisting of the amino acid sequence of (H2-1) with deletion, substitution, insertion, and/or addition of one or several amino acids; and
(H3) an amino acid sequence of (H3-1), (H3-2), or (H3-3) below:
(H3-1) any one of amino acid sequences of CDRH3 shown in Table 3A below,
(H3-2) an amino acid sequence having 80% or more identity to the amino acid sequence of (H3-1), and
(H3-3) an amino acid sequence consisting of the amino acid sequence of (H3-1) with deletion, substitution, insertion, and/or addition of one or several amino acids.

(L) A light-chain variable region that includes
a light-chain complementarity determining region (CDRL) 1, a CDRL2, and a CDRL3,
wherein the CDRL1 is a polypeptide that includes an amino acid sequence of (L1),
the CDRL2 is a polypeptide that includes an amino acid sequence of (L2),
the CDRL3 is a polypeptide that includes an amino acid sequence of (L3), and
the amino acid sequences of (L1), (L2), and (L3) are as follows:
(L1) an amino acid sequence of (L1-1), (L1-2), or (L1-3) below:
(L1-1) any one of amino acid sequences of CDRL1 shown in Table 3B below,
(L1-2) an amino acid sequence having 80% or more identity to the amino acid sequence of (L1-1), and
(L1-3) an amino acid sequence consisting of the amino acid sequence of (L1-1) with deletion, substitution, insertion, and/or addition of one or several amino acids;
(L2) an amino acid sequence of (L2-1), (L2-2), or (L2-3) below:
(L2-1) any one of amino acid sequences of CDRL2 shown in Table 3B below, (L2-2) an amino acid sequence having 80% or more identity to the amino acid sequence of (L2-1), and
(L2-3) an amino acid sequence consisting of the amino acid sequence of (L2-1) with deletion, substitution, insertion, and/or addition of one or several amino acids; and
(L3) an amino acid sequence of (L3-1), (L3-2), or (L3-3) below:
(L3-1) any one of amino acid sequences of CDRL3 shown in Table 3B below,
(L3-2) an amino acid sequence having 80% or more identity to the amino acid sequence of (L3-1), and
(L3-3) an amino acid sequence consisting of the amino acid sequence of (L3-1) with deletion, substitution, insertion, and/or addition of one or several amino acids.

Human CD19 has an amino acid sequence that corresponds to the amino acid sequence registered as NCBI Accession No. NM_001770.6, for example. Mouse CD19 has an amino acid sequence that corresponds to the amino acid sequence registered as NCBI Accession No. NM_009844.2, for example.

In the heavy-chain variable region of (H) above, the CDRH1 is the CDRH1 of (HA) above. The CDRH2 is the CDRH2 of (HA) above. The CDRH3 is the CDRH3 of (HA) above.

In the light-chain variable region of (L) above, the CDRL1 is the CDRL1 of any one of (LA) to (LL) and (LM) above. The CDRL2 is the CDRL2 of any one of (LA) to (LL) and (LM) above. The CDRL3 is the CDRL3 of any one of (LA) to (LL) and (LM) above.

TABLE 3A

| Heavy-chain variable region | CDRH1 | CDRH2 | CDRH3 | |
|---|---|---|---|---|
| (HA) | GFTFDDYA (Sequence ID No. 216) | ISWNSGRI (Sequence ID No. 217) | ARDQGYHYYDSAEHAFDI (Sequence ID No. 218) | 18H |

TABLE 3B

| Light-chain variable region | CDRL1 | CDRL2 | CDRL3 | |
|---|---|---|---|---|
| (LA) | KLGDKY (Sequence ID No. 220) | QDS (Sequence ID No. 221) | QAWDSSTHVV (Sequence ID No. 222) | L4 |
| (LB) | SSDVGGYNY (Sequence ID No. 224) | DVS (Sequence ID No. 225) | GTWDTSLTAVNT (Sequence ID No. 226) | L7 |
| (LC) | WSNIGDDH (Sequence ID No. 228) | DTS (Sequence ID No. 229) | GTWESSLSGAN (Sequence ID No. 230) | L9 |
| (LD) | SSDVGGYDY (Sequence ID No. 232) | DVT (Sequence ID No. 233) | SSYTTSTTWV (Sequence ID No. 234) | L13 |
| (LE) | TSDVGTTNY (Sequence ID No. 236) | DVT (Sequence ID No. 237) | SYAGSYTFVV (Sequence ID No. 238) | L14 |
| (LF) | SSDVGVYNY (Sequence ID No. 240) | DVS (Sequence ID No. 241) | AAWDDSLNGAN (Sequence ID No. 242) | L16 |
| (LG) | SSNIGNNY (Sequence ID No. 244) | DNY (Sequence ID No. 245) | AAWDDSLSAI (Sequence ID No. 246) | L17 |
| (LH) | SSDVGGYNY (Sequence ID No. 248) | DVS (Sequence ID No. 249) | HSYDSSLSHV (Sequence ID No. 250) | L22 |
| (LI) | QSVSSN (Sequence ID No. 252) | GAS (Sequence ID No. 253) | QQYNNWPPLYT (Sequence ID No. 254) | K4 |
| (LJ) | QSVSSY (Sequence ID No. 256) | DAS (Sequence ID No. 257) | QQSYSTLLYT (Sequence ID No. 258) | K5 |
| (LK) | QSVSSY (Sequence ID No. 260) | DAS (Sequence ID No. 261) | QQYDSLPLT (Sequence ID No. 262) | K6 |
| (LL) | QTISASS (Sequence ID No. 264) | GAS (Sequence ID No. 265) | QQFNEWPLT (Sequence ID No. 266) | K9 |
| (LM) | QSVSSN (Sequence ID No. 268) | GAS (Sequence ID No. 269) | QQYGSSPDIFT (Sequence ID No. 270) | K10 |

In the present invention, "CD19" is a type-I transmembrane glycoprotein having a molecular weight of 95 kDa, for example. It is known that CD19 is involved in the generation, activation, differentiation regulation, and the like of B cells, for example, and CD19 is mainly expressed in B cells.

The CDRL1, the CDRL2, and the CDRL3 may belong to the same one or different ones of (LA) to (LL) and (LM) above, and they preferably belong to the same one. If the CDRL1, the CDRL2, and the CDRL3 belong to the same one of (LA) to (LL) and (LM) above, the CDRL1, the CDRL2, and the CDRL3 are those of any one of (LA) to (LL) and (LM) above.

The term "identity" as used for the CDRs refers to the degree of identity when appropriately aligning sequences to be compared, for example, and means the ratio (%) of exactly the same amino acids in these sequences. The "identity" in each case refers to 80% or more, 85% or more, 90% or more, 95% or more, 96% or more, 97% or more, 98% or more, or 99% or more identity, for example. The identity can be calculated with default parameters using analysis software such as BLAST or FASTA (the same applies hereinafter).

The term "one or several" as used for the CDRs regarding substitution and the like refers to 1 to 5, 1 to 4, 1 to 3, 1 or 2, or 1, for example.

The amino acid substitution may be conservative substitution, for example (the same applies hereinafter). The term "conservative substitution" means that one or several amino acids are substituted by other amino acids and/or amino acid derivatives such that the functions of a protein are not substantially modified. It is preferable that a "substituting amino acid" and an "amino acid to be substituted" have similar properties and/or functions, for example. Specifically, it is preferable that they are similar in chemical properties such as a hydrophobicity/hydrophilicity index (hydropathy), a polarity, and an electric charge, physical properties such as a secondary structure, and the like, for example. Amino acids or amino acid derivatives having similar properties and/or functions are known in the art, for example. Specific examples of nonpolar amino acids (hydrophobic amino acids) include alanine, valine, isoleucine, leucine, proline, tryptophan, phenylalanine, and methionine; specific examples of polar amino acids (neutral amino acids) include glycine, serine, threonine, tyrosine, glutamine, asparagine, and cysteine; specific examples of positively charged amino acids (basic amino acids) include arginine, histidine, and lysine; and specific examples of negatively charged amino acids (acidic amino acids) include aspartic acid and glutamic acid.

In the light-chain variable region of (L) above, there is no particular limitation on the combination of (L1-1), (L2-1), and (L3-1) above, and the CDRL1 of any one of (LA) to (LL) and (LM) above, the CDRL2 of any one of (LA) to (LL) and (LM) above, and the CDRL3 of any one of (LA) to (LL) and (LM) above can be combined as desired, for example. The combination of (L1-1), (L2-1), and (L3-1) above is preferably a combination of the CDRL1, the CDRL2, and the CDRL3 of any one of (LA) to (LL) and (LM) above.

Hereinafter, the combination of the heavy-chain variable region or heavy chain and the light-chain variable region or light chain in the antibody of the present invention or the like will be described more specifically. In this combination, the descriptions of the heavy-chain variable region can be applied to the heavy chain, and vice versa. Also, in this combination, the descriptions of the light-chain variable region can be applied to the light chain, and vice versa. In the amino acid sequences and the base sequences shown below, underlined amino acid sequences and base sequences are amino acid sequences that correspond to the CDRs and base sequences coding for the amino acid sequences that correspond to the CDRs, respectively, unless otherwise stated.

As described above, the combination of the heavy-chain variable region and the light-chain variable region in the antibody of the present invention or the like is a combination of (HA) above and any one of (LA) to (LL) and (LM) above, for example.

Combination of (HA) and (LA) (Combination (LA))

The antibodies or the like of Combination (LA) are also referred to as an antibody 18H-L4 group, for example. In Combination (LA) above, the heavy-chain variable region of (HA) above includes the CDRH1, the CDRH2, and the CDRH3, the CDRH1 is a polypeptide that includes the amino acid sequence of (H1-A) below, the CDRH2 is a polypeptide that includes the amino acid sequence of (H2-A) below, and the CDRH3 is a polypeptide that includes the amino acid sequence of (H3-A) below. The light-chain variable region of (LA) above includes the CDRL1, the CDRL2, and the CDRL3, the CDRL1 is a polypeptide that includes the amino acid sequence of (L1-A) below, the CDRL2 is a polypeptide that includes the amino acid sequence of (L2-A) below, and the CDRL3 is a polypeptide that includes the amino acid sequence of (L3-A) below.

(H1-A) An amino acid sequence of (H1-A1), (H1-A2), or (H1-A3) below:
  (H1-A1) an amino acid sequence of Sequence ID No. 216 (GFTFDDYA),
  (H1-A2) an amino acid sequence having 80% or more identity to the amino acid sequence of Sequence ID No. 216, and
  (H1-A3) an amino acid sequence consisting of the amino acid sequence of Sequence ID No. 216 with deletion, substitution, insertion, and/or addition of one or several amino acids.

(H2-A) An amino acid sequence of (H2-A1), (H2-A2), or (H2-A3) below:
  (H2-A1) an amino acid sequence of Sequence ID No. 217 (ISWNSGRI),
  (H2-A2) an amino acid sequence having 80% or more identity to the amino acid sequence of Sequence ID No. 217, and
  (H2-A3) an amino acid sequence consisting of the amino acid sequence of Sequence ID No. 217 with deletion, substitution, insertion, and/or addition of one or several amino acids.

(H3-A) An amino acid sequence of (H3-A1), (H3-A2), or (H3-A3) below:
  (H3-A1) an amino acid sequence of Sequence ID No. 218 (ARDQGYHYYDSAEHAFDI),
  (H3-A2) an amino acid sequence having 80% or more identity to the amino acid sequence of Sequence ID No. 218, and
  (H3-A3) an amino acid sequence consisting of the amino acid sequence of Sequence ID No. 218 with deletion, substitution, insertion, and/or addition of one or several amino acids.

(L1-A) An amino acid sequence of (L1-A1), (L1-A2), or (L1-A3) below:
  (L1-A1) an amino acid sequence of Sequence ID No. 220 (KLGDKY),
  (L1-A2) an amino acid sequence having 80% or more identity to the amino acid sequence of Sequence ID No. 220, and
  (L1-A3) an amino acid sequence consisting of the amino acid sequence of Sequence ID No. 220 with deletion, substitution, insertion, and/or addition of one or several amino acids.

(L2-A) An amino acid sequence of (L2-A1), (L2-A2), or (L2-A3) below:
  (L2-A1) an amino acid sequence of Sequence ID No. 221 (QDS), (L2-A2) an amino acid sequence having 80% or more identity to the amino acid sequence of Sequence ID No. 221, and (L2-A3) an amino acid sequence consisting of the amino acid sequence of Sequence ID No. 221 with deletion, substitution, insertion, and/or addition of one or several amino acids.

(L3-A) An amino acid sequence of (L3-A1), (L3-A2), or (L3-A3) below:

(L3-A1) an amino acid sequence of Sequence ID No. 222 (QAWDSSTHVV), (L3-A2) an amino acid sequence having 80% or more identity to the amino acid sequence of Sequence ID No. 222, and (L3-A3) an amino acid sequence consisting of the amino acid sequence of Sequence ID No. 222 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LA) above, the heavy-chain variable region of (HA) above includes a polypeptide consisting of the amino acid sequence of (H-A) below, for example. The light-chain variable region of (LA) above includes a polypeptide consisting of the amino acid sequence of (L-A) below, for example.

(H-A) An amino acid sequence of (H-A1), (H-A2), or (H-A3) below:

(H-A1) an amino acid sequence of Sequence ID No. 219:

```
Sequence ID No. 219:
EVQLVESGGGLVQPGRSLRLSCAASGFTFDDYAMHWVRQAPGKGLEWVS
GISWNSGRIGYADSVKGRFTISRDNAKNSLFLQMNSLRAEDTAVYYCAR
DQGYHYYDSAEHAFDIWGQGTVVTVSS,
```

(H-A2) an amino acid sequence having 80% or more identity to the amino acid sequence of Sequence ID No. 219, and (H-A3) an amino acid sequence consisting of the amino acid sequence of Sequence ID No. 219 with deletion, substitution, insertion, and/or addition of one or several amino acids.

(L-A) An amino acid sequence of (L-A1), (L-A2), or (L-A3) below:

(L-A1) an amino acid sequence of Sequence ID No. 223:

```
Sequence ID No. 223:
SYELTQPPSVSVSPGQTASITCSGDKLGDKYACWYQQKPGQSPVLVIYQ
DSKRPSGIPERFSGSNSGNTATLTISGTQAMDEADYYCQAWDSSTHVVF
GGGTKLTVL,
```

(L-A2) an amino acid sequence having 80% or more identity to the amino acid sequence of Sequence ID No. 223, and (L-A3) an amino acid sequence consisting of the amino acid sequence of Sequence ID No. 223 with deletion, substitution, insertion, and/or addition of one or several amino acids.

The amino acid sequence of (H-A) above is a sequence that includes the amino acid sequences of (H1-A1) of the CDRH1, (H2-A1) of the CDRH2, and (H3-A1) of the CDRH3, for example. The amino acid sequence of (H-A2) above may be an amino acid sequence that includes the amino acid sequences of (H1-A1) of the CDRH1, (H2-A1) of the CDRH2, and (H3-A1) of the CDRH3 and that has 80% or more identity to the amino acid sequence of Sequence ID No. 219, for example. The amino acid sequence of (H-A3) above may be an amino acid sequence that includes the amino acid sequences of (H1-A1) of the CDRH1, (H2-A1) of the CDRH2, and (H3-A1) of the CDRH3 and that consists of the amino acid sequence of Sequence ID No. 219 with deletion, substitution, insertion, and/or addition of one or several amino acids, for example.

The amino acid sequence of (L-A1) above is a sequence that includes the amino acid sequences of (L1-A1) of the CDRL1, (L2-A1) of the CDRL2, and (L3-A1) of the CDRL3, for example. The amino acid sequence of (L-A2) above may be an amino acid sequence that includes the amino acid sequences of (L1-A1) of the CDRL1, (L2-A1) of the CDRL2, and (L3-A1) of the CDRL3 and that has 80% or more identity to the amino acid sequence of Sequence ID No. 223, for example. The amino acid sequence of (L-A3) above may be an amino acid sequence that includes the amino acid sequences of (L1-A1) of the CDRL1, (L2-A1) of the CDRL2, and (L3-A1) of the CDRL3 and that consists of the amino acid sequence of Sequence ID No. 223 with deletion, substitution, insertion, and/or addition of one or several amino acids, for example.

In the antibody of the present invention, the heavy-chain variable region is (H-A1) above, and the light-chain variable region is (L-A1) above, for example. The antibody that includes this combination is also referred to as an "antibody 18H-L4" hereinafter.

The "identity" as used for the polypeptide of the heavy-chain variable region and the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the heavy-chain variable region and the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LB) (Combination (LB))

The antibodies or the like of Combination (LB) are also referred to as an antibody 18H-L7 group, for example. In Combination (LB) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LB) above includes the CDRL1, the CDRL2, and the CDRL3, the CDRL1 is a polypeptide that includes the amino acid sequence of (L1-B) below, the CDRL2 is a polypeptide that includes the amino acid sequence of (L2-B) below, and the CDRL3 is a polypeptide that includes the amino acid sequence of (L3-B) below.

(L1-B) An amino acid sequence of (L1-B1), (L1-B2), or (L1-B3) below:

(L1-B1) an amino acid sequence of Sequence ID No. 224 (SSDVGGYNY), (L1-B2) an amino acid sequence having 80% or more identity to the amino acid sequence of Sequence ID No. 224, and (L1-B3) an amino acid sequence consisting of the amino acid sequence of Sequence ID No. 224 with deletion, substitution, insertion, and/or addition of one or several amino acids.

(L2-B) An amino acid sequence of (L2-B1), (L2-B2), or (L2-B3) below:
  (L2-B1) an amino acid sequence of Sequence ID No. 225 (DVS),
  (L2-B2) an amino acid sequence having 80% or more identity to the amino acid sequence of Sequence ID No. 225, and
  (L2-B3) an amino acid sequence consisting of the amino acid sequence of Sequence ID No. 225 with deletion, substitution, insertion, and/or addition of one or several amino acids.

(L3-B) An amino acid sequence of (L3-B1), (L3-B2), or (L3-B3) below:
  (L3-B1) an amino acid sequence of Sequence ID No. 226 (GTWDTSLTAVV),
  (L3-B2) an amino acid sequence having 80% or more identity to the amino acid sequence of Sequence ID No. 226, and
  (L3-B3) an amino acid sequence consisting of the amino acid sequence of Sequence ID No. 226 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LB) above, the heavy-chain variable region of (HA) above includes a polypeptide consisting of the amino acid sequence of (H-A) above, for example. The light-chain variable region of (LB) above includes a polypeptide consisting of the amino acid sequence of (L-B) below, for example.

(L-B) An amino acid sequence of (L-B1), (L-B2), or (L-B3) below:
  (L-B1) an amino acid sequence of Sequence ID No. 227:

```
Sequence ID No. 227:
QSALTQPRSVSGSPGQSVTISCTGTSSDVGGYNYVSWYQQHPGKAPKLM
IYDVSNRPSGVSNRFSGSKSGNTASLTISGLQTGDEADYYCGTWDTSLT
AVVFGGGTELTVL,
```

(L-B2) an amino acid sequence having 80% or more identity to the amino acid sequence of Sequence ID No. 227, and
  (L-B3) an amino acid sequence consisting of the amino acid sequence of Sequence ID No. 227 with deletion, substitution, insertion, and/or addition of one or several amino acids.

The amino acid sequence of (L-B1) above is a sequence that includes the amino acid sequences of (L1-B1) of the CDRL1, (L2-B1) of the CDRL2, and (L3-B1) of the CDRL3, for example. The amino acid sequence of (L-B2) above may be an amino acid sequence that includes the amino acid sequences of (L-B1) of the CDRL1, (L2-B1) of the CDRL2, and (L3-B1) of the CDRL3 and that has 80% or more identity to the amino acid sequence of Sequence ID No. 227, for example. The amino acid sequence of (L-B3) above may be an amino acid sequence that includes the amino acid sequences of (L1-B1) of the CDRL1, (L2-B1) of the CDRL2, and (L3-B1) of the CDRL3 and that consists of the amino acid sequence of Sequence ID No. 227 with deletion, substitution, insertion, and/or addition of one or several amino acids, for example.

In the antibody of the present invention, the heavy-chain variable region is (H-A1) above, and the light-chain variable region is (L-B1) above, for example. The antibody that includes this combination is also referred to as an "antibody 18H-L7" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LC) (Combination (LC))

The antibodies or the like of Combination (LC) are also referred to as an antibody 18H-L9 group, for example. In Combination (LC) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LC) above includes the CDRL1, the CDRL2, and the CDRL3, the CDRL1 is a polypeptide that includes the amino acid sequence of (L1-C) below, the CDRL2 is a polypeptide that includes the amino acid sequence of (L2-C) below, and the CDRL3 is a polypeptide that includes the amino acid sequence of (L3-C) below.

(L1-C) An amino acid sequence of (L1-C1), (L1-C2), or (L1-C3) below:
  (L1-C1) an amino acid sequence of Sequence ID No. 228 (WSNIGDDH),
  (L1-C2) an amino acid sequence having 80% or more identity to the amino acid sequence of Sequence ID No. 228, and
  (L1-C3) an amino acid sequence consisting of the amino acid sequence of Sequence ID No. 228 with deletion, substitution, insertion, and/or addition of one or several amino acids.

(L2-C) An amino acid sequence of (L2-C1), (L2-C2), or (L2-C3) below:
  (L2-C1) an amino acid sequence of Sequence ID No. 229 (DTS),
  (L2-C2) an amino acid sequence having 80% or more identity to the amino acid sequence of Sequence ID No. 229, and
  (L2-C3) an amino acid sequence consisting of the amino acid sequence of Sequence ID No. 229 with deletion, substitution, insertion, and/or addition of one or several amino acids.

(L3-C) An amino acid sequence of (L3-C1), (L3-C2), or (L3-C3) below:
  (L3-C1) an amino acid sequence of Sequence ID No. 230 (GTWESSLSGVV),
  (L3-C2) an amino acid sequence having 80% or more identity to the amino acid sequence of Sequence ID No. 230, and
  (L3-C3) an amino acid sequence consisting of the amino acid sequence of Sequence ID No. 230 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LC) above, the heavy-chain variable region of (HA) above includes a polypeptide consisting of the amino acid sequence of (H-A) above, for example. The light-chain variable region of (LC) above includes a polypeptide consisting of the amino acid sequence of (L-C) below, for example.

(L-C) An amino acid sequence of (L-C1), (L-C2), or (L-C3) below:
(L-C1) an amino acid sequence of Sequence ID No. 231:

```
Sequence ID No. 231:
QSVLTQPPSVSAAPGQKVTISCSGSWSNIGDDHVSWYQQFPGAAPKLLI
YDTSKRPSRVADRFSGSKSGASATLAITGLQAGDEADYYCGTWESSLSG
VVFGGGTELTVL,
```

(L-C2) an amino acid sequence having 80% or more identity to the amino acid sequence of Sequence ID No. 231, and (L-C3) an amino acid sequence consisting of the amino acid sequence of Sequence ID No. 231 with deletion, substitution, insertion, and/or addition of one or several amino acids.

The amino acid sequence of (L-C1) above is a sequence that includes the amino acid sequences of (L1-C1) of the CDRL1, (L2-C1) of the CDRL2, and (L3-C1) of the CDRL3, for example. The amino acid sequence of (L-C2) above may be an amino acid sequence that includes the amino acid sequences of (L1-C1) of the CDRL1, (L2-C1) of the CDRL2, and (L3-C1) of the CDRL3 and that has 80% or more identity to the amino acid sequence of Sequence ID No. 231, for example. The amino acid sequence of (L-C3) above may be an amino acid sequence that includes the amino acid sequences of (L1-C1) of the CDRL1, (L2-C1) of the CDRL2, and (L3-C1) of the CDRL3 and that consists of the amino acid sequence of Sequence ID No. 231 with deletion, substitution, insertion, and/or addition of one or several amino acids, for example.

In the antibody of the present invention, the heavy-chain variable region is (H-A1) above, and the light-chain variable region is (L-C1) above, for example. The antibody that includes this combination is also referred to as an "antibody 18H-L9" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LD) (Combination (LD))

The antibodies or the like of Combination (LD) are also referred to as an antibody 18H-L13 group, for example. In Combination (LD) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LD) above includes the CDRL1, the CDRL2, and the CDRL3, the CDRL1 is a polypeptide that includes the amino acid sequence of (L1-D) below, the CDRL2 is a polypeptide that includes the amino acid sequence of (L2-D) below, and the CDRL3 is a polypeptide that includes the amino acid sequence of (L3-D) below.

(L1-D) An amino acid sequence of (L1-D1), (L1-D2), or (L1-D3) below:
(L1-D1) an amino acid sequence of Sequence ID No. 232 (SSDVGGYDY),
(L1-D2) an amino acid sequence having 80% or more identity to the amino acid sequence of Sequence ID No. 232, and
(L1-D3) an amino acid sequence consisting of the amino acid sequence of Sequence ID No. 232 with deletion, substitution, insertion, and/or addition of one or several amino acids.

(L2-D) An amino acid sequence of (L2-D1), (L2-D2), or (L2-D3) below:
(L2-D1) an amino acid sequence of Sequence ID No. 233 (DVT),
(L2-D2) an amino acid sequence having 80% or more identity to the amino acid sequence of Sequence ID No. 233, and
(L2-D3) an amino acid sequence consisting of the amino acid sequence of Sequence ID No. 233 with deletion, substitution, insertion, and/or addition of one or several amino acids.

(L3-D) An amino acid sequence of (L3-D1), (L3-D2), or (L3-D3) below:
(L3-D1) an amino acid sequence of Sequence ID No. 234 (SSYTTSTTWV),
(L3-D2) an amino acid sequence having 80% or more identity to the amino acid sequence of Sequence ID No. 234, and
(L3-D3) an amino acid sequence consisting of the amino acid sequence of Sequence ID No. 234 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LD) above, the heavy-chain variable region of (HA) above includes a polypeptide consisting of the amino acid sequence of (H-A) above, for example. The light-chain variable region of (LD) above includes a polypeptide consisting of the amino acid sequence of (L-D) below, for example.

(L-D) An amino acid sequence of (L-D1), (L-D2), or (L-D3) below:
(L-D1) an amino acid sequence of Sequence ID No. 235:

```
Sequence ID No. 235:
QSALTQPRSVSGSPGQSVTISCTGTSSDVGGYNYVSWYQQHPGKAPKLM
IYDVSNRPSGVSNRFSGSKSGNTASLTISGLQTGDEADYYCGTWDTSLT
AVVFGGGTELTVL,
```

(L-D2) an amino acid sequence having 80% or more identity to the amino acid sequence of Sequence ID No. 235, and (L-D3) an amino acid sequence consisting of the amino acid sequence of Sequence ID No. 235 with deletion, substitution, insertion, and/or addition of one or several amino acids.

The amino acid sequence of (L-D1) above is a sequence that includes the amino acid sequences of (L1-D1) of the CDRL1, (L2-D1) of the CDRL2, and (L3-D1) of the CDRL3, for example. The amino acid sequence of (L-D2) above may be an amino acid sequence that includes the amino acid sequences of (L1-D1) of the CDRL1, (L2-D1) of the CDRL2, and (L3-D1) of the CDRL3 and that has 80% or more identity to the amino acid sequence of Sequence ID No. 235, for example. The amino acid sequence of (L-D3) above may be an amino acid sequence that includes the amino acid sequences of (L1-D1) of the CDRL1, (L2-D1) of the CDRL2, and (L3-D1) of the CDRL3 and that consists of the amino acid sequence of Sequence ID No. 235 with deletion, substitution, insertion, and/or addition of one or several amino acids, for example.

In the antibody of the present invention, the heavy-chain variable region is (H-A1) above, and the light-chain variable region is (L-D1) above, for example. The antibody that includes this combination is also referred to as an "antibody 18H-L13" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LE) (Combination (LE))

The antibodies or the like of Combination (LE) are also referred to as an antibody 18H-L14 group, for example. In Combination (LE) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LE) above includes the CDRL1, the CDRL2, and the CDRL3, the CDRL1 is a polypeptide that includes the amino acid sequence of (L1-E) below, the CDRL2 is a polypeptide that includes the amino acid sequence of (L2-E) below, and the CDRL3 is a polypeptide that includes the amino acid sequence of (L3-E) below.

(L1-E) An amino acid sequence of (L1-E1), (L1-E2), or (L1-E3) below:
 (L1-E1) an amino acid sequence of Sequence ID No. 236 (TSDVGTTNY),
 (L1-E2) an amino acid sequence having 80% or more identity to the amino acid sequence of Sequence ID No. 236, and
 (L1-E3) an amino acid sequence consisting of the amino acid sequence of Sequence ID No. 236 with deletion, substitution, insertion, and/or addition of one or several amino acids.

(L2-E) An amino acid sequence of (L2-E1), (L2-E2), or (L2-E3) below:
 (L2-E1) an amino acid sequence of Sequence ID No. 237 (DVT),
 (L2-E2) an amino acid sequence having 80% or more identity to the amino acid sequence of Sequence ID No. 237, and
 (L2-E3) an amino acid sequence consisting of the amino acid sequence of Sequence ID No. 237 with deletion, substitution, insertion, and/or addition of one or several amino acids.

(L3-E) An amino acid sequence of (L3-E1), (L3-E2), or (L3-E3) below:
 (L3-E1) an amino acid sequence of Sequence ID No. 238 (SYAGSYTFVV),
 (L3-E2) an amino acid sequence having 80% or more identity to the amino acid sequence of Sequence ID No. 238, and
 (L3-E3) an amino acid sequence consisting of the amino acid sequence of Sequence ID No. 238 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LE) above, the heavy-chain variable region of (HA) above includes a polypeptide consisting of the amino acid sequence of (H-A) above, for example. The light-chain variable region of (LE) above includes a polypeptide consisting of the amino acid sequence of (L-E) below, for example.

(L-E) An amino acid sequence of (L-E1), (L-E2), or (L-E3) below:
 (L-E1) an amino acid sequence of Sequence ID No. 239:

```
Sequence ID No. 239:
QSALTQPASVSGSPGQSITISCTGTTSDVGTTNYVSWYQQHPGKAPKLL
IYDVTNRPSGVPDRFSGSKSANTASLTISGLQAEDEADYYCCSYAGSYT
FVVFGGGTELTVL,
```

(L-E2) an amino acid sequence having 80% or more identity to the amino acid sequence of Sequence ID No. 239, and
 (L-E3) an amino acid sequence consisting of the amino acid sequence of Sequence ID No. 239 with deletion, substitution, insertion, and/or addition of one or several amino acids.

The amino acid sequence of (L-E1) above is a sequence that includes the amino acid sequences of (L1-E1) of the CDRL1, (L2-E1) of the CDRL2, and (L3-E1) of the CDRL3, for example. The amino acid sequence of (L-E2) above may be an amino acid sequence that includes the amino acid sequences of (L1-E1) of the CDRL1, (L2-E1) of the CDRL2, and (L3-E1) of the CDRL3 and that has 80% or more identity to the amino acid sequence of Sequence ID No. 239, for example. The amino acid sequence of (L-E3) above may be an amino acid sequence that includes the amino acid sequences of (L1-E1) of the CDRL1, (L2-E1) of the CDRL2, and (L3-E1) of the CDRL3 and that consists of the amino acid sequence of Sequence ID No. 239 with deletion, substitution, insertion, and/or addition of one or several amino acids, for example.

In the antibody of the present invention, the heavy-chain variable region is (H-A1) above, and the light-chain variable region is (L-E1) above, for example. The antibody that includes this combination is also referred to as an "antibody 18H-L14" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LF) (Combination (LF))

The antibodies or the like of Combination (LF) are also referred to as an antibody 18H-L16 group, for example. In Combination (LF) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LF) above includes the CDRL1, the CDRL2, and the CDRL3, the CDRL1 is a polypeptide that includes the amino acid sequence of (L1-F) below, the CDRL2 is a polypeptide that includes the amino acid sequence of (L2-F) below, and the CDRL3 is a polypeptide that includes the amino acid sequence of (L3-F) below.

(L1-F) An amino acid sequence of (L1-F1), (L1-F2), or (L1-F3) below:
(L1-F1) an amino acid sequence of Sequence ID No. 240 (SSDVGVYNY),
(L1-F2) an amino acid sequence having 80% or more identity to the amino acid sequence of Sequence ID No. 240, and
(L1-F3) an amino acid sequence consisting of the amino acid sequence of Sequence ID No. 240 with deletion, substitution, insertion, and/or addition of one or several amino acids.

(L2-F) An amino acid sequence of (L2-F1), (L2-F2), or (L2-F3) below:
(L2-F1) an amino acid sequence of Sequence ID No. 241 (DVS),
(L2-F2) an amino acid sequence having 80% or more identity to the amino acid sequence of Sequence ID No. 241, and
(L2-F3) an amino acid sequence consisting of the amino acid sequence of Sequence ID No. 241 with deletion, substitution, insertion, and/or addition of one or several amino acids.

(L3-F) An amino acid sequence of (L3-F1), (L3-F2), or (L3-F3) below:
(L3-F1) an amino acid sequence of Sequence ID No. 242 (AAWDDSLNGVV),
(L3-F2) an amino acid sequence having 80% or more identity to the amino acid sequence of Sequence ID No. 242, and
(L3-F3) an amino acid sequence consisting of the amino acid sequence of Sequence ID No. 242 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LF) above, the heavy-chain variable region of (HA) above includes a polypeptide consisting of the amino acid sequence of (H-A) above, for example. The light-chain variable region of (LF) above includes a polypeptide consisting of the amino acid sequence of (L-F) below, for example.

(L-F) An amino acid sequence of (L-F1), (L-F2), or (L-F3) below:
(L-F1) an amino acid sequence of Sequence ID No. 243:

```
Sequence ID No. 243:
QSALTQPPSASGSPGQSVTISCTGTSSDVGVYNYVSWYQQHPGKAPKLM
IYDVSKRPSGVPDRFSGSKSANTASLTISGLQAEDEADYYCAAWDDSLN
GVVFGGGTQLTVL,
```

(L-F2) an amino acid sequence having 80% or more identity to the amino acid sequence of Sequence ID No. 243, and
(L-F3) an amino acid sequence consisting of the amino acid sequence of Sequence ID No. 243 with deletion, substitution, insertion, and/or addition of one or several amino acids.

The amino acid sequence of (L-F1) above is a sequence that includes the amino acid sequences of (L1-F1) of the CDRL1, (L2-F1) of the CDRL2, and (L3-F1) of the CDRL3, for example. The amino acid sequence of (L-F2) above may be an amino acid sequence that includes the amino acid sequences of (L1-F1) of the CDRL1, (L2-F1) of the CDRL2, and (L3-F1) of the CDRL3 and that has 80% or more identity to the amino acid sequence of Sequence ID No. 243, for example. The amino acid sequence of (L-F3) above may be an amino acid sequence that includes the amino acid sequences of (L1-F1) of the CDRL1, (L2-F1) of the CDRL2, and (L3-F1) of the CDRL3 and that consists of the amino acid sequence of Sequence ID No. 243 with deletion, substitution, insertion, and/or addition of one or several amino acids, for example.

In the antibody of the present invention, the heavy-chain variable region is (H-A1) above, and the light-chain variable region is (L-F1) above, for example. The antibody that includes this combination is also referred to as an "antibody 18H-L16" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LG) (Combination (LG))

The antibodies or the like of Combination (LG) are also referred to as an antibody 18H-L17 group, for example. In Combination (LG) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LG) above includes the CDRL1, the CDRL2, and the CDRL3, the CDRL1 is a polypeptide that includes the amino acid sequence of (L1-G) below, the CDRL2 is a polypeptide that includes the amino acid sequence of (L2-G) below, and the CDRL3 is a polypeptide that includes the amino acid sequence of (L3-G) below.

(L1-G) An amino acid sequence of (L1-G1), (L1-G2), or (L1-G3) below:
(L1-G1) an amino acid sequence of Sequence ID No. 244 (SSNIGNNY),
(L1-G2) an amino acid sequence having 80% or more identity to the amino acid sequence of Sequence ID No. 244, and (L1-G3) an amino acid sequence consisting of the amino acid sequence of Sequence ID No. 244 with deletion, substitution, insertion, and/or addition of one or several amino acids.

(L2-G) An amino acid sequence of (L2-G1), (L2-G2), or (L2-G3) below:
 (L2-G1) an amino acid sequence of Sequence ID No. 245 (DNV),
 (L2-G2) an amino acid sequence having 80% or more identity to the amino acid sequence of Sequence ID No. 245, and
 (L2-G3) an amino acid sequence consisting of the amino acid sequence of Sequence ID No. 245 with deletion, substitution, insertion, and/or addition of one or several amino acids.

(L3-G) An amino acid sequence of (L3-G1), (L3-G2), or (L3-G3) below:
 (L3-G1) an amino acid sequence of Sequence ID No. 246 (AAWDDSLSAI),
 (L3-G2) an amino acid sequence having 80% or more identity to the amino acid sequence of Sequence ID No. 246, and
 (L3-G3) an amino acid sequence consisting of the amino acid sequence of Sequence ID No. 246 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LG) above, the heavy-chain variable region of (HA) above includes a polypeptide consisting of the amino acid sequence of (H-A) above, for example. The light-chain variable region of (LG) above includes a polypeptide consisting of the amino acid sequence of (L-G) below, for example.

(L-G) An amino acid sequence of (L-G1), (L-G2), or (L-G3) below:
 (L-G1) an amino acid sequence of Sequence ID No. 247:

```
Sequence ID No. 247:
QSVLTQPPSASGTPGQRVTISCSGSSSNIGNNYVCWYQHLPGTAPKLLI
YDNVKRPSGIPDRFSGSKSGTSASLAISGLRSEDEADYYCAAWDDSLSA
IFGGGTELTVL,
```

(L-G2) an amino acid sequence having 80% or more identity to the amino acid sequence of Sequence ID No. 247, and
 (L-G3) an amino acid sequence consisting of the amino acid sequence of Sequence ID No. 247 with deletion, substitution, insertion, and/or addition of one or several amino acids.

The amino acid sequence of (L-G1) above is a sequence that includes the amino acid sequences of (L1-G1) of the CDRL1, (L2-G1) of the CDRL2, and (L3-G1) of the CDRL3, for example. The amino acid sequence of (L-G2) above may be an amino acid sequence that includes the amino acid sequences of (L1-G1) of the CDRL1, (L2-G1) of the CDRL2, and (L3-G1) of the CDRL3 and that has 80% or more identity to the amino acid sequence of Sequence ID No. 247, for example. The amino acid sequence of (L-G3) above may be an amino acid sequence that includes the amino acid sequences of (L1-G1) of the CDRL1, (L2-G1) of the CDRL2, and (L3-G1) of the CDRL3 and that consists of the amino acid sequence of Sequence ID No. 247 with deletion, substitution, insertion, and/or addition of one or several amino acids, for example.

In the antibody of the present invention, the heavy-chain variable region is (H-A1) above, and the light-chain variable region is (L-G1) above, for example. The antibody that includes this combination is also referred to as an "antibody 18H-L17" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LH) (Combination (LH))

The antibodies or the like of Combination (LH) are also referred to as an antibody 18H-L22 group, for example. In Combination (LH) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LH) above includes the CDRL1, the CDRL2, and the CDRL3, the CDRL1 is a polypeptide that includes the amino acid sequence of (L1-H) below, the CDRL2 is a polypeptide that includes the amino acid sequence of (L2-H) below, and the CDRL3 is a polypeptide that includes the amino acid sequence of (L3-H) below.

(L1-H) An amino acid sequence of (L1-H1), (L1-H2), or (L1-H3) below:
 (L1-H1) an amino acid sequence of Sequence ID No. 248 (SSDVGGYNY),
 (L1-H2) an amino acid sequence having 80% or more identity to the amino acid sequence of Sequence ID No. 248, and
 (L1-H3) an amino acid sequence consisting of the amino acid sequence of Sequence ID No. 248 with deletion, substitution, insertion, and/or addition of one or several amino acids.

(L2-H) An amino acid sequence of (L2-H1), (L2-H2), or (L2-H3) below:
 (L2-H1) an amino acid sequence of Sequence ID No. 249 (DVS),
 (L2-H2) an amino acid sequence having 80% or more identity to the amino acid sequence of Sequence ID No. 249, and
 (L2-H3) an amino acid sequence consisting of the amino acid sequence of Sequence ID No. 249 with deletion, substitution, insertion, and/or addition of one or several amino acids.

(L3-H) An amino acid sequence of (L3-H1), (L3-H2), or (L3-H3) below:
 (L3-H1) an amino acid sequence of Sequence ID No. 250 (HSYDSSLSHV),
 (L3-H2) an amino acid sequence having 80% or more identity to the amino acid sequence of Sequence ID No. 250, and
 (L3-H3) an amino acid sequence consisting of the amino acid sequence of Sequence ID No. 250 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LH) above, the heavy-chain variable region of (HA) above includes a polypeptide consisting of the amino acid sequence of (H-A) above, for example. The light-chain variable region of (LH) above includes a polypeptide consisting of the amino acid sequence of (L-H) below, for example.

(L-H) An amino acid sequence of (L-H1), (L-H2), or (L-H3) below:

(L-H1) an amino acid sequence of Sequence ID No. 251:

```
Sequence ID No. 251:
QSALTQPASVSGSPGQSITISCTGTSSDVGGYNYVSWYQQHPGKAPKLM
IYDVSNRPSGVPDRFSGSKSGTSASLAISGLQSEDEADYYCHSYDSSLS
HVFGTGTKVTVL,
```

(L-H2) an amino acid sequence having 80% or more identity to the amino acid sequence of Sequence ID No. 251, and (L-H3) an amino acid sequence consisting of the amino acid sequence of Sequence ID No. 251 with deletion, substitution, insertion, and/or addition of one or several amino acids.

The amino acid sequence of (L-H1) above is a sequence that includes the amino acid sequences of (L1-H1) of the CDRL1, (L2-H1) of the CDRL2, and (L3-H1) of the CDRL3, for example. The amino acid sequence of (L-H2) above may be an amino acid sequence that includes the amino acid sequences of (L1-H1) of the CDRL1, (L2-H1) of the CDRL2, and (L3-H1) of the CDRL3 and that has 80% or more identity to the amino acid sequence of Sequence ID No. 251, for example. The amino acid sequence of (L-H3) above may be an amino acid sequence that includes the amino acid sequences of (L1-H1) of the CDRL1, (L2-H1) of the CDRL2, and (L3-H1) of the CDRL3 and that consists of the amino acid sequence of Sequence ID No. 251 with deletion, substitution, insertion, and/or addition of one or several amino acids, for example.

In the antibody of the present invention, the heavy-chain variable region is (H-A1) above, and the light-chain variable region is (L-H1) above, for example. The antibody that includes this combination is also referred to as an "antibody 18H-L22" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LI) (Combination (LI))

The antibodies or the like of Combination (LI) are also referred to as an antibody 18H-K4 group, for example. In Combination (LI) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LI) above includes the CDRL1, the CDRL2, and the CDRL3, the CDRL1 is a polypeptide that includes the amino acid sequence of (L1-I) below, the CDRL2 is a polypeptide that includes the amino acid sequence of (L2-I) below, and the CDRL3 is a polypeptide that includes the amino acid sequence of (L3-I) below.

(L1-I) An amino acid sequence of (L1-I1), (L1-I2), or (L1I3) below:

(L1-I1) an amino acid sequence of Sequence ID No. 252 (QSVSSN), (L1I2) an amino acid sequence having 80% or more identity to the amino acid sequence of Sequence ID No. 252, and (L1I3) an amino acid sequence consisting of the amino acid sequence of Sequence ID No. 252 with deletion, substitution, insertion, and/or addition of one or several amino acids.

(L2-I) An amino acid sequence of (L2-I1), (L2-I2), or (L2-I3) below:

(L2-I1) an amino acid sequence of Sequence ID No. 253 (GAS), (L2-I2) an amino acid sequence having 80% or more identity to the amino acid sequence of Sequence ID No. 253, and (L2-I3) an amino acid sequence consisting of the amino acid sequence of Sequence ID No. 253 with deletion, substitution, insertion, and/or addition of one or several amino acids.

(L3-I) An amino acid sequence of (L3-I1), (L3-I2), or (L3-I3) below:

(L3-I1) an amino acid sequence of Sequence ID No. 254 (QQYNNWPPLYT), (L3-I2) an amino acid sequence having 80% or more identity to the amino acid sequence of Sequence ID No. 254, and (L3-I3) an amino acid sequence consisting of the amino acid sequence of Sequence ID No. 254 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LI) above, the heavy-chain variable region of (HA) above includes a polypeptide consisting of the amino acid sequence of (H-A) above, for example. The light-chain variable region of (LI) above includes a polypeptide consisting of the amino acid sequence of (L-I) below, for example.

(L-I) An amino acid sequence of (L-I1), (L-I2), or (L-I3) below:

(L-I1) an amino acid sequence of Sequence ID No. 255:

```
Sequence ID No. 255:
EIVLTQSPGTLSLSPGERATLSCRASQSVSSNLAWYQQKPGQAPRLLIY
GASTRATGIPARFSGSGSGTEFTLTISSLQSEDFAVYYCQQYNNWPPLY
TFGQGTKLEIK,
```

(L-I2) an amino acid sequence having 80% or more identity to the amino acid sequence of Sequence ID No. 255, and (L-I3) an amino acid sequence consisting of the amino acid sequence of Sequence ID No. 255 with deletion, substitution, insertion, and/or addition of one or several amino acids.

The amino acid sequence of (L-I1) above is a sequence that includes the amino acid sequences of (L1-I1) of the CDRL1, (L2-I1) of the CDRL2, and (L3-I1) of the CDRL3, for example. The amino acid sequence of (L-I2) above may be an amino acid sequence that includes the amino acid sequences of (L1-I1) of the CDRL1, (L2-I1) of the CDRL2, and (L3-I1) of the CDRL3 and that has 80% or more identity to the amino acid sequence of Sequence ID No. 255, for example. The amino acid sequence of (L-I3) above may be an amino acid sequence that includes the amino acid sequences of (L1-I1) of the CDRL1, (L2-I1) of the CDRL2, and (L3-I1) of the CDRL3 and that consists of the amino acid sequence of Sequence ID No. 255 with deletion, substitution, insertion, and/or addition of one or several amino acids, for example.

In the antibody of the present invention, the heavy-chain variable region is (H-A1) above, and the light-chain variable region is (L-I1) above, for example. The antibody that includes this combination is also referred to as an "antibody 18H-K4" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LJ) (Combination (LJ))

The antibodies or the like of Combination (LJ) are also referred to as an antibody 18H-K5 group, for example. In Combination (LJ) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LJ) above includes the CDRL1, the CDRL2, and the CDRL3, the CDRL1 is a polypeptide that includes the amino acid sequence of (L1-J) below, the CDRL2 is a polypeptide that includes the amino acid sequence of (L2-J) below, and the CDRL3 is a polypeptide that includes the amino acid sequence of (L3-J) below.

(L1-J) An amino acid sequence of (L1-J1), (L1-J2), or (L1-J3) below:
  (L1-J1) an amino acid sequence of Sequence ID No. 256 (QSVSSY),
  (L1-J2) an amino acid sequence having 80% or more identity to the amino acid sequence of Sequence ID No. 256, and
  (L1-J3) an amino acid sequence consisting of the amino acid sequence of Sequence ID No. 256 with deletion, substitution, insertion, and/or addition of one or several amino acids.

(L2-J) An amino acid sequence of (L2-J1), (L2-J2), or (L2-J3) below:
  (L2-J1) an amino acid sequence of Sequence ID No. 257 (DAS),
  (L2-J2) an amino acid sequence having 80% or more identity to the amino acid sequence of Sequence ID No. 257, and
  (L2-J3) an amino acid sequence consisting of the amino acid sequence of Sequence ID No. 257 with deletion, substitution, insertion, and/or addition of one or several amino acids.

(L3-J) An amino acid sequence of (L3-J1), (L3-J2), or (L3-J3) below:
  (L3-J1) an amino acid sequence of Sequence ID No. 258 (QQSYSTLLYT),
  (L3-J2) an amino acid sequence having 80% or more identity to the amino acid sequence of Sequence ID No. 258, and
  (L3-J3) an amino acid sequence consisting of the amino acid sequence of Sequence ID No. 258 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LJ) above, the heavy-chain variable region of (HA) above includes a polypeptide consisting of the amino acid sequence of (H-A) above, for example. The light-chain variable region of (LJ) above includes a polypeptide consisting of the amino acid sequence of (L-J) below, for example.

(L-J) An amino acid sequence of (L-J1), (L-J2), or (L-J3) below:
  (L-J1) an amino acid sequence of Sequence ID No. 259:

Sequence ID No. 259:
EIVLTQSPGTLSLSPGERATLSCRAS<u>QSVSSY</u>LAWYQQKPGQAPRLLIY
<u>DAS</u>NRATGIPARFSGSGSGTDFTLTI<u>SSLEPEDFATYYCQQSYSTLLYT</u>
FGQGTKLEIK, (L-J2) an amino acid sequence having 80% or more identity to the amino acid sequence of Sequence ID No. 259, and
  (L-J3) an amino acid sequence consisting of the amino acid sequence of Sequence ID No. 259 with deletion, substitution, insertion, and/or addition of one or several amino acids.

The amino acid sequence of (L-J1) above is a sequence that includes the amino acid sequences of (L1-J1) of the CDRL1, (L2-J1) of the CDRL2, and (L3-J1) of the CDRL3, for example. The amino acid sequence of (L-J2) above may be an amino acid sequence that includes the amino acid sequences of (L1-J1) of the CDRL1, (L2-J1) of the CDRL2, and (L3-J1) of the CDRL3 and that has 80% or more identity to the amino acid sequence of Sequence ID No. 259, for example. The amino acid sequence of (L-J3) above may be an amino acid sequence that includes the amino acid sequences of (L1-J1) of the CDRL1, (L2-J1) of the CDRL2, and (L3-J1) of the CDRL3 and that consists of the amino acid sequence of Sequence ID No. 259 with deletion, substitution, insertion, and/or addition of one or several amino acids, for example.

In the antibody of the present invention, the heavy-chain variable region is (H-A1) above, and the light-chain variable region is (L-J1) above, for example. The antibody that includes this combination is also referred to as an "antibody 18H-K5" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LK) (Combination (LK))

The antibodies or the like of Combination (LK) are also referred to as an antibody 18H-K6 group, for example. In Combination (LK) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LK) above includes the CDRL1, the CDRL2, and the CDRL3, the CDRL1 is a polypeptide that includes the amino acid sequence of (L1-K) below, the CDRL2 is a polypeptide that includes the amino acid sequence of (L2-K) below, and the CDRL3 is a polypeptide that includes the amino acid sequence of (L3-K) below.

(L1-K) An amino acid sequence of (L1-K1), (L1-K2), or (L1-K3) below:
(L1-K1) an amino acid sequence of Sequence ID No. 260 (QSVSSY),
(L1-K2) an amino acid sequence having 80% or more identity to the amino acid sequence of Sequence ID No. 260, and
(L1-K3) an amino acid sequence consisting of the amino acid sequence of Sequence ID No. 260 with deletion, substitution, insertion, and/or addition of one or several amino acids.

(L2-K) An amino acid sequence of (L2-K1), (L2-K2), or (L2-K3) below:
(L2-K1) an amino acid sequence of Sequence ID No. 261 (DAS),
(L2-K2) an amino acid sequence having 80% or more identity to the amino acid sequence of Sequence ID No. 261, and
(L2-K3) an amino acid sequence consisting of the amino acid sequence of Sequence ID No. 261 with deletion, substitution, insertion, and/or addition of one or several amino acids.

(L3-K) An amino acid sequence of (L3-K1), (L3-K2), or (L3-K3) below:
(L3-K1) an amino acid sequence of Sequence ID No. 262 (QQYDSLPLT),
(L3-K2) an amino acid sequence having 80% or more identity to the amino acid sequence of Sequence ID No. 262, and
(L3-K3) an amino acid sequence consisting of the amino acid sequence of Sequence ID No. 262 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LK) above, the heavy-chain variable region of (HA) above includes a polypeptide consisting of the amino acid sequence of (H-A) above, for example. The light-chain variable region of (LK) above includes a polypeptide consisting of the amino acid sequence of (L-K) below, for example.

(L-K) An amino acid sequence of (L-K1), (L-K2), or (L-K3) below:
(L-K1) an amino acid sequence of Sequence ID No. 263:

```
Sequence ID No. 263:
EIVLTRSPATLSLSPGERATLSCRASQSVSSYLAWYQQKPGQAPRLLIY
DASNRATGISARFSGSGSGTEFTLTISSLQSEDIATYYCQQYDSLPLTF
GGGTKLEIK,
```

(L-K2) an amino acid sequence having 80% or more identity to the amino acid sequence of Sequence ID No. 263, and
(L-K3) an amino acid sequence consisting of the amino acid sequence of Sequence ID No. 263 with deletion, substitution, insertion, and/or addition of one or several amino acids.

The amino acid sequence of (L-K1) above is a sequence that includes the amino acid sequences of (L1-K1) of the CDRL1, (L2-K1) of the CDRL2, and (L3-K1) of the CDRL3, for example. The amino acid sequence of (L-K2) above may be an amino acid sequence that includes the amino acid sequences of (L1-K1) of the CDRL1, (L2-K1) of the CDRL2, and (L3-K1) of the CDRL3 and that has 80% or more identity to the amino acid sequence of Sequence ID No. 263, for example. The amino acid sequence of (L-K3) above may be an amino acid sequence that includes the amino acid sequences of (L1-K1) of the CDRL1, (L2-K1) of the CDRL2, and (L3-K1) of the CDRL3 and that consists of the amino acid sequence of Sequence ID No. 263 with deletion, substitution, insertion, and/or addition of one or several amino acids, for example.

In the antibody of the present invention, the heavy-chain variable region is (H-A1) above, and the light-chain variable region is (L-K1) above, for example. The antibody that includes this combination is also referred to as an "antibody 18H-K6" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LL) (Combination (LL))

The antibodies or the like of Combination (LL) are also referred to as an antibody 18H-K9 group, for example. In Combination (LL) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LL) above includes the CDRL1, the CDRL2, and the CDRL3, the CDRL1 is a polypeptide that includes the amino acid sequence of (L1-L) below, the CDRL2 is a polypeptide that includes the amino acid sequence of (L2-L) below, and the CDRL3 is a polypeptide that includes the amino acid sequence of (L3-L) below.

(L1-L) An amino acid sequence of (L1-L1), (L1-L2), or (L1-L3) below:
(L1-L1) an amino acid sequence of Sequence ID No. 264 (QTISASS),
(L1-L2) an amino acid sequence having 80% or more identity to the amino acid sequence of Sequence ID No. 264, and (L1-L3) an amino acid sequence consisting of the amino acid sequence of Sequence ID No. 264 with deletion, substitution, insertion, and/or addition of one or several amino acids.

(L2-L) An amino acid sequence of (L2-L1), (L2-L2), or (L2-L3) below:
- (L2-L1) an amino acid sequence of Sequence ID No. 265 (GAS),
- (L2-L2) an amino acid sequence having 80% or more identity to the amino acid sequence of Sequence ID No. 265, and
- (L2-L3) an amino acid sequence consisting of the amino acid sequence of Sequence ID No. 265 with deletion, substitution, insertion, and/or addition of one or several amino acids.

(L3-L) An amino acid sequence of (L3-L1), (L3-L2), or (L3-L3) below:
- (L3-L1) an amino acid sequence of Sequence ID No. 266 (QQFNEWPLT),
- (L3-L2) an amino acid sequence having 80% or more identity to the amino acid sequence of Sequence ID No. 266, and
- (L3-L3) an amino acid sequence consisting of the amino acid sequence of Sequence ID No. 266 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LL) above, the heavy-chain variable region of (HA) above includes a polypeptide consisting of the amino acid sequence of (H-A) above, for example. The light-chain variable region of (LL) above includes a polypeptide consisting of the amino acid sequence of (L-L) below, for example.

(L-L) An amino acid sequence of (L-L1), (L-L2), or (L-L3) below:
- (L-L1) an amino acid sequence of Sequence ID No. 267:

```
Sequence ID No. 267:
EIVLTQSPATLSLSPGERATVSCRPSQTISASSVAWYQQKAGQAPRLLIY

GASSRATGIPDRFSGSGSGTDFTLTISRLEPEDFAVYYCQQFNEWPLTFG

GGTKVEIK
```

- (L-L2) an amino acid sequence having 80% or more identity to the amino acid sequence of Sequence ID No. 267, and
- (L-L3) an amino acid sequence consisting of the amino acid sequence of Sequence ID No. 267 with deletion, substitution, insertion, and/or addition of one or several amino acids.

The amino acid sequence of (L-L1) above is a sequence that includes the amino acid sequences of (L1-L1) of the CDRL1, (L2-L1) of the CDRL2, and (L3-L1) of the CDRL3, for example. The amino acid sequence of (L-L2) above may be an amino acid sequence that includes the amino acid sequences of (L1-L1) of the CDRL1, (L2-L1) of the CDRL2, and (L3-L1) of the CDRL3 and that has 80% or more identity to the amino acid sequence of Sequence ID No. 267, for example. The amino acid sequence of (L-L3) above may be an amino acid sequence that includes the amino acid sequences of (L1-L1) of the CDRL1, (L2-L1) of the CDRL2, and (L3-L1) of the CDRL3 and that consists of the amino acid sequence of Sequence ID No. 267 with deletion, substitution, insertion, and/or addition of one or several amino acids, for example.

In the antibody of the present invention, the heavy-chain variable region is (H-A1) above, and the light-chain variable region is (L-L1) above, for example. The antibody that includes this combination is also referred to as an "antibody 18H-K9" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

Combination of (HA) and (LM) (Combination (LM))

The antibodies or the like of Combination (LM) are also referred to as an antibody 18H-K10 group, for example. In Combination (LM) above, the heavy-chain variable region of (HA) above includes the CDRH1, the CDRH2, and the CDRH3, the CDRH1 is a polypeptide that includes the amino acid sequence of (H1-A) above, the CDRH2 is a polypeptide that includes the amino acid sequence of (H2-A) above, and the CDRH3 is a polypeptide that includes the amino acid sequence of (H3-A) above. The light-chain variable region of (LM) above includes the CDRL1, the CDRL2, and the CDRL3, the CDRL1 is a polypeptide that includes the amino acid sequence of (L1-M) below, the CDRL2 is a polypeptide that includes the amino acid sequence of (L2-M) below, and the CDRL3 is a polypeptide that includes the amino acid sequence of (L3-M) below.

(L1-M) An amino acid sequence of (L1-M1), (L1-M2), or (L1-M3) below:
- (L1-M1) an amino acid sequence of Sequence ID No. 268 (QSVSSN),
- (L1-M2) an amino acid sequence having 80% or more identity to the amino acid sequence of Sequence ID No. 268, and
- (L1-M3) an amino acid sequence consisting of the amino acid sequence of Sequence ID No. 268 with deletion, substitution, insertion, and/or addition of one or several amino acids.

(L2-M) An amino acid sequence of (L2-M1), (L2-M2), or (L2-M3) below:
- (L2-M1) an amino acid sequence of Sequence ID No. 269 (GAS),
- (L2-M2) an amino acid sequence having 80% or more identity to the amino acid sequence of Sequence ID No. 269, and
- (L2-M3) an amino acid sequence consisting of the amino acid sequence of Sequence ID No. 269 with deletion, substitution, insertion, and/or addition of one or several amino acids.

(L3-M) An amino acid sequence of (L3-M1), (L3-M2), or (L3-M3) below:
- (L3-M1) an amino acid sequence of Sequence ID No. 270 (QQYGSSPDIFT),
- (L3-M2) an amino acid sequence having 80% or more identity to the amino acid sequence of Sequence ID No. 270, and
- (L3-M3) an amino acid sequence consisting of the amino acid sequence of Sequence ID No. 270 with deletion, substitution, insertion, and/or addition of one or several amino acids.

The "identity" as used for the CDRs refers to 80% or more, 85% or more, 90% or more, 95% or more, 96% or more, 97% or more, 98% or more, or 99% or more identity, for example.

The term "one or several" as used for the CDRs regarding substitution and the like refers to 1 to 5, 1 to 4, 1 to 3, 1 or 2, or 1, for example.

In Combination (LM) above, the heavy-chain variable region of (HA) above includes a polypeptide consisting of the amino acid sequence of (H-A) above, for example. The light-chain variable region of (LM) above includes a polypeptide consisting of the amino acid sequence of (L-M) below, for example.

(L-M) An amino acid sequence of (L-M1), (L-M2), or (L-M3) below:

(L-M1) an amino acid sequence of Sequence ID No. 271:

```
Sequence ID No. 271:
EIVLTQSPATLSLSPGERATLSCRASQSVSSNLAWYQQKLGQAPRLLIYG

ASSRATGIPDRFSGSGSGTDFTLTISRLEPEDFAVYYCQQYGSSPDIFTF

GPGTKVDIK
```

(L-M2) an amino acid sequence having 80% or more identity to the amino acid sequence of Sequence ID No. 271, and (L-M3) an amino acid sequence consisting of the amino acid sequence of Sequence ID No. 271 with deletion, substitution, insertion, and/or addition of one or several amino acids.

The amino acid sequence of (L-M1) above is a sequence that includes the amino acid sequences of (L1-M1) of the CDRL1, (L2-M1) of the CDRL2, and (L3-M1) of the CDRL3, for example. The amino acid sequence of (L-M2) above may be an amino acid sequence that includes the amino acid sequences of (L1-M1) of the CDRL1, (L2-M1) of the CDRL2, and (L3-M1) of the CDRL3 and that has 80% or more identity to the amino acid sequence of Sequence ID No. 271, for example. The amino acid sequence of (L-M3) above may be an amino acid sequence that includes the amino acid sequences of (L1-M1) of the CDRL1, (L2-M1) of the CDRL2, and (L3-M1) of the CDRL3 and that consists of the amino acid sequence of Sequence ID No. 271 with deletion, substitution, insertion, and/or addition of one or several amino acids, for example.

In the antibody of the present invention, the heavy-chain variable region is (H-A1) above, and the light-chain variable region is (L-M1) above, for example. The antibody that includes this combination is also referred to as an "antibody 18H-K10" hereinafter.

The "identity" as used for the polypeptide of the light-chain variable region refers to 80% or more, 85% or more, 90% or more, 95% or more, 96% or more, 97% or more, 98% or more, or 99% or more identity, for example.

The term "one or several" as used for the polypeptide of the light-chain variable region regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

In the present invention, the amino acid sequences of Sequence ID Nos. 216 to 271 are human-derived amino acid sequences, for example.

The binding of the antibody of the present invention or the like to CD19 can be confirmed using a technique for detecting the binding of an antibody to an antigen such as surface plasmon resonance (SPR) or flow cytometry, for example.

The antibody of the present invention or the like may be labeled with a labeling substance or immobilized on a carrier, a porous body, or the like, for example. The descriptions above can be applied to the above-mentioned labeling and immobilization.

There is no particular limitation on a method for manufacturing the antibody of the present invention or the like, and the antibody or the like can be manufactured using genetic engineering techniques based on the amino acid sequence information described above, for example. Specifically, the antibody or the like can be manufactured as follows, for example. It should be noted that the present invention is not limited to this example.

First, a vector that includes nucleic acid sequences coding for the amino acid sequences of the above-mentioned regions, heavy chain, and/or light chain in the antibody of the present invention or the like is introduced into a host, and thus a transformant is obtained. Then, the transformant is cultured, a fraction containing an antibody capable of binding to CD19 is collected, and the antibody is isolated or purified from the obtained collected fraction.

The descriptions above can be applied to the above-mentioned vector and the above-mentioned method for culturing a transformant into which the vector has been introduced.

In the present invention, the antibody is a monoclonal antibody, for example. Examples of the monoclonal antibody include monoclonal antibodies obtained through immunization of an animal, chimeric antibodies, humanized antibodies, and human antibodies (also referred to as "fully human antibodies"). The descriptions above can be applied to the above-mentioned chimeric antibodies and humanized antibodies.

The antibody of the present invention or the like can also be prepared through immunization of an animal with an antigen, for example. An example of the antigen is the CD19 protein. It is preferable to repeat the immunization with the antigen a plurality of times. The peptide fragment may be a peptide fragment constituted by only an antigenic determinant (epitope) or a peptide fragment that includes the antigenic determinant, for example. The descriptions above can be applied to the above-mentioned method for manufacturing a monoclonal antibody.

In the second antibody of the present invention or the like, the light-chain variable region of (L) above may be a light-chain variable region of (L) below.

(L) A light-chain variable region that includes
a light-chain complementarity determining region (CDRL) 1, a CDRL2, and a CDRL3,
wherein the CDRL1 is a polypeptide that includes an amino acid sequence of (L1),
the CDRL2 is a polypeptide that includes an amino acid sequence of (L2),
the CDRL3 is a polypeptide that includes an amino acid sequence of (L3),
the amino acid sequences of (L1), (L2), and (L3) are as follows:
(L1) an amino acid sequence of (L1-1), (L1-2), or (L1-3) below:
(L1-1) any one of amino acid sequences of CDRL1 shown in Conditions (L1) to (L3) and (L4) below,
(L1-2) an amino acid sequence having 80% or more identity to the amino acid sequence of (L1-1), and
(L1-3) an amino acid sequence consisting of the amino acid sequence of (L1-1) with deletion, substitution, insertion, and/or addition of one or several amino acids;

(L2) an amino acid sequence of (L2-1), (L2-2), or (L2-3) below:
  (L2-1) any one of amino acid sequences of CDRL2 shown in Conditions (L1) to (L3) and (L4) below,
  (L2-2) an amino acid sequence having 80% or more identity to the amino acid sequence of (L2-1), and
  (L2-3) an amino acid sequence consisting of the amino acid sequence of (L2-1) with deletion, substitution, insertion, and/or addition of one or several amino acids;
(L3) an amino acid sequence of (L3-1), (L3-2), or (L3-3) below:
  (L3-1) any one of amino acid sequences of CDRL3 shown in Conditions (L1) to (L3) and (L4) below,
  (L3-2) an amino acid sequence having 80% or more identity to the amino acid sequence of (L3-1), and
  (L3-3) an amino acid sequence consisting of the amino acid sequence of (L3-1) with deletion, substitution, insertion, and/or addition of one or several amino acids Condition (L1) is as follows:
the CDRL1 is KLGDKY (Sequence ID No. 220),
the CDRL2 is QDS (Sequence ID No. 221), and
the CDRL3 is QAWDSSTHV (Sequence ID No. 222), Condition (L2) is as follows:
the CDRL1 is WSNIGDDH (Sequence ID No. 228),
the CDRL2 is DTS (Sequence ID No. 229), and
the CDRL3 is GTWESSLSGVV (Sequence ID No. 230), Condition (L3) is as follows:
the CDRL1 is $X_1SX_2X_3GX_4X_5NY$ (Sequence ID No. 317),
the CDRL2 is $DX_6X_7$ (Sequence ID No. 318),
the CDRL3 is $X_8X_9X_{10}X_{11}X_{12}SX_{13}X_{14}X_{15}X_{16}X_{17}$ (Sequence ID No. 319),
$X_1$ is S or T,
$X_2$ is D or N,
$X_3$ is V, I, L, or A,
$X_4$ is G, T, V, or N,
$X_5$ is not present, or is Y, T, or S,
$X_6$ is V or N,
$X_7$ is S, I, or V,
$X_8$ is not present, or is G, A, or H,
$X_9$ is T, S, or A,
$X_{10}$ is W, Y, or F,
$X_{11}$ is A or D,
$X_{12}$ is T, G, D, or S,
$X_{13}$ is L or Y,
$X_{14}$ is T, N, or S,
$X_{15}$ is A, F, G, or H,
$X_{16}$ is V or I, and
$X_{17}$ is not present or is V, and Condition (L4) is as follows:
the CDRL1 is $QX_1X_2SX_3SX_4$ (Sequence ID No. 320),
the CDRL2 is GAS (Sequence ID No. 253) or DAS (Sequence ID No. 257),
the CDRL3 is $QQX_5X_6X_7X_8X_9X_{10}X_{11}LX_{12}T$ (Sequence ID No. 321),
$X_1$ is S, T, N, or Q,
$X_2$ is V, I, L, or A,
$X_3$ is not present, or is A, I, V, L, or G,
$X_4$ is N, Y, or S,
$X_5$ is not present or is S,
$X_6$ is Y, F, or W,
$X_7$ is N, S, D, or G,
$X_8$ is N, T, S, or E,
$X_9$ is W, L, or S,
$X_{10}$ is not present or is P,
$X_{11}$ is not present, or is P or D, and
$X_{12}$ is not present, or is Y, F, or W.

Regarding the light-chain variable region of (L) above, (L1-1), (L2-1), and (L3-1) meet the same condition or different conditions of Conditions (L1) to (L4), and preferably meet the same condition.

In Condition (L3), it is preferable that $X_3$ is V or I. It is preferable that $X_5$ is not present, or is Y or T. It is preferable that $X_{10}$ is W or Y.

In Condition (L4), it is preferable that $X_1$ is S or T. It is preferable that $X_2$ is V or I. It is preferable that $X_6$ is Y or F. It is preferable that $X_{12}$ is not present, or is Y or F.

An example of light-chain variable regions that meet Condition (L1) above include the light-chain variable region of (LA) above.

An example of light-chain variable regions that meet Condition (L2) above include the light-chain variable region of (LC) above.

Examples of light-chain variable regions that meet Condition (L3) above include the light-chain variable regions of (LB), (LE), (LF), (LG), and (LH) above.

Examples of light-chain variable regions that meet Condition (L4) above include the light-chain variable regions of (LI), (LJ), (LK), (LL), and (LM) above.

Gene, Expression Vector, and Transformant

The coding gene of the present invention is a gene coding for an antibody against a complex of HLA-A*02:01 and NY-ESO-1$_{157-165}$ or an antigen-binding fragment thereof, or an antibody against CD19 or an antigen-binding fragment (also collectively referred to as "an antibody of the present invention or an antigen-binding fragment thereof" or "an antibody of the present invention or the like" hereinafter), and includes a nucleic acid (polynucleotide) coding for the amino acid sequence of the first antibody of the present invention or the antigen-binding fragment, or the second antibody of the present invention or the antigen-binding fragment.

The above-described antibody of the present invention or the like can be obtained through the expression of the coding gene of the present invention. There is no particular limitation on the sequence of the coding gene of the present invention, and it is sufficient that the sequence thereof codes for the amino acid sequence of the antibody of the present invention or the like. The sequence thereof may be a sense sequence or an antisense sequence.

The expression vector of the present invention is an expression vector for expressing an antibody against A2/NY-ESO-1$_{157}$ or an antigen-binding fragment thereof, or an antibody against CD19 or an antigen-binding fragment, and includes the coding gene of the present invention. In the expression vector, the coding gene is coupled to the linking vector such that the antibody of the present invention or the antigen-binding fragment thereof can be expressed. It is sufficient that the expression vector of the present invention can express the antibody of the present invention or the like, and there is no particular limitation on the other configurations.

The expression vector of the present invention may be an expression vector that includes a nucleic acid sequence coding for the heavy-chain variable region and a nucleic acid sequence coding for the light-chain variable region, or a set of an expression vector that includes a nucleic acid sequence coding for the heavy-chain variable region and an expression vector that includes a nucleic acid sequence coding for the light-chain variable region, for example. The expression vector of the present invention can be prepared by coupling the coding gene of the present invention to a linking vector, for example. The descriptions of the expression vector in the CAR library of the present invention can be applied to the linking vector, for example. There is no particular limitation on the type of linking vector to which the coding gene is to be coupled, and examples thereof include pUC and pMX. The linking vector can also be selected as appropriate in accordance with a host into which the expression vector is to be introduced, for example. There is no particular limitation on the host, and examples thereof include mammalian cells such as CHO cells.

The transformant of the present invention is a transformant that expresses the antibody of the present invention or the like, and includes a host and the coding gene of the present invention. It is sufficient that the transformant of the present invention includes the coding gene of the present invention so as to be capable of expressing the coding gene. It is preferable that the transformant includes the expression vector of the present invention, for example. There is no particular limitation on a method for introducing the expression vector into the host, and a known method can be employed.

The descriptions of the CAR library of the present invention, the first screening method, the first antibody or the like, the second antibody of the present invention or the like can be applied to the gene, the expression vector, and the transformant of the present invention, for example.

First Chimeric Antigen Receptor

As described above, the first chimeric antigen receptor (CAR) of the present invention includes an antigen-binding domain, a transmembrane domain, and an intracellular signaling domain, and the antigen-binding domain includes the antibody of the present invention or the antigen-binding fragment thereof. The first CAR of the present invention is characterized in that the antigen-binding domain includes the first antibody of the present invention or the like, and there is no particular limitation on the other configurations and conditions. The descriptions of the CAR library, the first screening method, the first antibody or the like, the second antibody or the like, the gene, the expression vector, and the transformant of the present invention can be applied to the first CAR of the present invention. The first CAR of the present invention can be favorably used as a CAR for CAR-T cells against A2/NY-ESO-1$_{157}$-expressing cancer cells, for example.

The antigen-binding domain may be the first antibody of the present invention or the antigen-binding fragment of the first antibody of the present invention, for example. The antigen-binding fragment is preferably a single-chain antibody (scFv). If the antigen-binding domain is an scFv, the heavy-chain variable region and the light-chain variable region are arranged in this order from the C terminus or N terminus in the antigen-binding domain.

A specific example of the antigen-binding domain is a polypeptide of (BD) below.
(BD) A polypeptide of (BD1), (BD2), or (BD3) below:
(BD1) a polypeptide consisting of the amino acid sequence of any one of Sequence ID Nos. 98 to 117,
(BD2) a polypeptide consisting of an amino acid sequence having 80% or more identity to the amino acid sequence of any one of Sequence ID Nos. 98 to 117, the polypeptide being capable of binding to A2/NY-ESO-1$_{157}$, and
(BD3) a polypeptide consisting of an amino acid sequence consisting of the amino acid sequence of any one of Sequence ID Nos. 98 to 117 with deletion, substitution, insertion, and/or addition of one or several amino acids, the polypeptide being capable of binding to A2/NY-ESO-1$_{157}$.

In the polypeptide of (BD1) above, each of the amino acid sequences of Sequence ID Nos. 98 to 117 is an amino acid sequence that includes a combination of the heavy-chain variable region and the light-chain variable region that corresponds to any one of Combinations (1) to (18) for the first antibody of the present invention or the like, for example. Regarding the amino acid sequences of the heavy-chain variable region and the light-chain variable region in each of the amino acid sequences of Sequence ID Nos. 98 to 117, the amino acid sequences that include the combinations of the heavy-chain variable region and the light-chain variable region that correspond to Combinations (1) to (18) for the first antibody of the present invention or the like can be referred to, for example. In the polypeptides of (BD2) and (BD3) above, the amino acid sequences that correspond to the CDRH1, the CDRH2, the CDRH3, the CDRL1, the CDRL2, and the CDRL3 are conserved in the amino acid sequences of Sequence ID Nos. 98 to 117, for example. Regarding the amino acid sequences of the CDRs in the amino acid sequences of Sequence ID Nos. 98 to 117, the amino acid sequences of the CDRs included in the amino acid sequences that include the combinations of the heavy-chain variable region and the light-chain variable region that correspond to Combinations (1) to (18) for the first antibody of the present invention or the like can be referred to, for example.

```
Antigen-Binding Domain of H1-3M4E5L
                                                   (Sequence ID No. 98)
QVQLQESGPGLVKPSDTLSLTCLVSGGSISSNYWSWIRQAPGKGLEWIG

HVSYSGSTNYNPSLKSRVTISVDTSKNQFSLKLSSVTAADTAVYYCARESYYYY

GMDVWGQGTTVTVSSGSTSGSGKPGSGEGSTKGQSELTQPRSVSGSPGQSVTI

SCTGTSRDVGGYNYVSWYQQHPGKAPKLIIHDVIERSSGVPDRFSGSKSGNTAS

LTISGLQAEDEADYYCWSFAGSYYVFGTGTDVTVL

Antigen-Binding Domain of K52-H1
                                                   (Sequence ID No. 99)
DIQMTQSPSAMSASVGDRVTITCRASQSISSYLNWYQQKPGKAPKLLIY

AASSLQSGVPSRFSGSGSGTDFTLTISSLQPEDFATYYCQQYYSTPQTFGPGTKV

DIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS
```

-continued

Antigen-Binding Domain of K73-H1
(Sequence ID No. 100)
DIQMTQSPSSLSASVGDRVTITCRASQSISSYLNWYQQKAGKAPKLLIY

AASSLQSGVPSRFSGSGSGTDFTLTISCLQSEDVATYYCQQYESYRRSFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS

Antigen-Binding Domain of K121-H1
(Sequence ID No. 101)
DIQMTQSPSSLSASVGDRVTITCRASQSISSYLNWYQQKPGKAPKLLIYA

ASSLQSGVPSRFSGSGSGTDFTLTISCLQSEDFATYYCQQYNSYSRTFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS

Antigen-Binding Domain of K124-H1
(Sequence ID No. 102)
DIQMTQSPSSLSASVGDRVTITCRASQSISSYLNWYQQKPGKAPKLLIYA

ASRLESGVPSRFSGSGSGTDFTLTISCLQSEDFATYYCQQYNSYSRTFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS

Antigen-Binding Domain of K125-H1
(Sequence ID No. 103)
DIQMTQSPSSLSASVGDRVTITCRASQSISSYLNWYQQKPGKAPKLLLY

AASRLESGVPSRFSGSGSGTEFTLTISSLQPDDFATYYCQQYNSYSPCTFGPGTK

VDIKGSTSGSGKPGSGEGSTKGQVQLQESGPGLVKPSDTLSLTCLVSGGSISSN

YVVSWIRQAPGKGLEWIGHVSYSGSTNYNPSLKSRVTISVDTSKNQFSLKLSSVT

AADTAVYYCARESYYYYGMDVWGQGTTVTVSS

Antigen-Binding Domain of K131-H1
(Sequence ID No. 104)
DIQMTQSPSSLSASVGDRVSITCRASQDISRYLNWYQQKPGKAPKLLLY

AASRLESGVPSRFSGSGSGTDFTLTITSLQPDDFATYYCQQYDNLITFGQGTRLE

IKGSTSGSGKPGSGEGSTKGQVQLQESGPGLVKPSDTLSLTCLVSGGSISSNYW

SWIRQAPGKGLEWIGHVSYSGSTNYNPSLKSRVTISVDTSKNQFSLKLSSVTAA

DTAVYYCARESYYYYGMDVWGQGTTVTVSS

Antigen-Binding Domain of K145-H1
(Sequence ID No. 105)
DIQMTQSPSSLSASVGDRVSITCRASQDISRYLNWYQQKPGKAPKLLLY

AASRLESGVPSRFSGSGSGTDFTLTITSLQPDDFATYYCQQYNSYSRTFGQGTK

VEIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS

Antigen-Binding Domain of K151-H1
(Sequence ID No. 106)
DIQMTQSPSSLSASVGDRVTITCRASQSISSYLNWYQQKPGKAPKLLIYA

ASSLQSGVPSRFSGSGSGTDFTLTITSLQPDDFATYYCQQYDNLITFGQGTRLEI

KGSTSGSGKPGSGEGSTKGQVQLQESGPGLVKPSDTLSLTCLVSGGSISSNYWS

-continued

WIRQAPGKGLEWIGHVSYSGSTNYNPSLKSRVTISVDTSKNQFSLKLSSVTAAD

TAVYYCARESYYYYGMDVWGQGTTVTVSS

Antigen-Binding Domain of K160-H1

(Sequence ID No. 107)

EIVLTQSPATLSVSPGERATLSCRASQSVSSNLAWYQQKPGQAPRLLIYG

ASTRATGIPARFSGSGSGTEFTLTISRLEPEDFATYYCQQYNSYSRTFGQGTKVE

IKGSTSGSGKPGSGEGSTKGQVQLQESGPGLVKPSDTLSLTCLVSGGSISSNYW

SWIRQAPGKGLEWIGHVSYSGSTNYNPSLKSRVTISVDTSKNQFSLKLSSVTAA

DTAVYYCARESYYYYGMDVWGQGTTVTVSS

Antigen-Binding Domain of K173-H1

(Sequence ID No. 108)

DIQMTQSPSSLSASVGDRVTITCRASQSISSYLNWYQQKAGKAPKLLIY

AASSLQSGVPSRFSGSGSGTDFTLTISCLQSEDVATYYCQQYESYSRTFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSS

Antigen-Binding Domain of L1-3M4E511

(Sequence ID No. 109)

QSALTQPPSASGSPGQSVTISCTGTSSDVGGYDFVSVVYQQHPGEAPKLL

VYDVNNRPSGVSNRFSGSKSGNTASLTISGLQAEDEGDYYCSSYAGSNSVFGTG

TKVTVLGSTSGSGKPGSGEGSTKGEVQLLESGGGLVQPGGSLRLSCAASGFTFS

TYQMSWVRQAPGKGLEWVSGIVSSGGSTAYADSVKGRFTISRDNSKNTLYLQM

NSLRAEDTAVYYCAGELLPYYGMDVWGQGTTVTVSS

Antigen-Binding Domain of 3M4E511-L1

(Sequence ID No. 110)

EVQLLESGGGLVQPGGSLRLSCAASGFTFSTYQMSWVRQAPGKGLEW

VSGIVSSGGSTAYADSVKGRFTISRDNSKNTLYLQMNSLRAEDTAVYYCAGELL

PYYGMDVWGQGTTVTVSSGSTSGSGKPGSGEGSTKGQSALTQPPSASGSPGQS

VTISCTGTSSDVGGYDFVSWYQQHPGEAPKLLVYDVNNRPSGVSNRFSGSKSG

NTASLTISGLQAEDEGDYYCSSYAGSNSVFGTGTKVTVL

Antigen-Binding Domain of L66-3M4E511

(Sequence ID No. 111)

QSALTQPASVSGSPGQSITISCTGTSSDVGGYEFVSWYQQHPGSAPKLII

YDVIERPFGVSYRFSASKSGNTASLTISGLQEDEADYFCSSYTSSSTYVFGTGT

KVTVLGSTSGSGKPGSGEGSTKGEVQLLESGGGLVQPGGSLRLSCAASGFTFST

YQMSWVRQAPGKGLEWVSGIVSSGGSTAYADSVKGRFTISRDNSKNTLYLQMN

SLRAEDTAVYYCAGELLPYYGMDVWGQGTTVTVSS

Antigen-Binding Domain of L73-3M4E511

(Sequence ID No. 112)

QSALTQPASVSGSPGQSITISCTGTGSDVGAYDYVSWYQHHPGRAPRLII

RDVSVRPSGVPDRFSGSKSGNTASLTISGLQAEDEADYYCSSYSGSSTWVFGGG

TKLTVLGSTSGSGKPGSGEGSTKGEVQLLESGGGLVQPGGSLRLSCAASGFTFS

TYQMSWVRQAPGKGLEWVSGIVSSGGSTAYADSVKGRFTISRDNSKNTLYLQM

NSLRAEDTAVYYCAGELLPYYGMDVWGQGTTVTVSS

Antigen-Binding Domain of L80-3M4E511

(Sequence ID No. 113)

QSALTQPASVSGSPGQSITISCTGTSSDVGSYNLVSVVYQQHPGKAPKLM

IYDVSNRPSGVSYRFSGSKSGNTASLTISGLQAEDEADYYCSSYTSSSTFAVFGG

```
GTQLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSS

Antigen-Binding Domain of L88-3M4E5l1
                                              (Sequence ID No. 114)
QSALPQPASVSGSPGQSVTISCTGTSSDVGGYNYVSWYQQHPGKAPKL

MIYDVSKRPSGVPDRFSGSKSGNTASLTVSGLQAEDEADYFCCSYAGGYYVFGT

GTKLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSS

Antigen-Binding Domain of L102-3M4E5H
                                              (Sequence ID No. 115)
QSALTQPPSASGSPGQSVTISCTGTSSDVGGYNYVSVVYQQHPGKAPKL

MIYDVSKRPSGVPDRFSGSKSGNTASLTISGLQTEDEADYYCSSYAGSGSTPFVF

GTGTKLTVLGSTSGSGKPGSGEGSTKGEVQLLESGGGLVQPGGSLRLSCAASG

FTFSTYQMSWVRQAPGKGLEWVSGIVSSGGSTAYADSVKGRFTISRDNSKNTL

YLQMNSLRAEDTAVYYCAGELLPYYGMDVWGQGTTVTVSS

Antigen-Binding Domain of L124-3M4E5H
                                              (Sequence ID No. 116)
QSALTQPASVSGSPGQSITISCTGTSSDVGGYNYVSVVYQQHPGKAPKL

MIYDVSNRPSRVPDRFAGSKSGNTASLTISGLQAEDEADYYCCSYAGRRYVFGT

GTKLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSS

Antigen-Binding Domain of 1173-3M4E5L
                                              (Sequence ID No. 117)
QLQLQESGPGLVKPSQTLSLTCTVSGGSISSYYWSWIRQPPGKGLEWIG

EINHSGSTNYNPSLKSRVTISVDTSKNQFSLKLSSVTAADTAVYYCARCPIYYYG

MDVWGQGTTVTVSSGSTSGSGKPGSGEGSTKGQSELTQPRSVSGSPGQSVTIS

CTGTSRDVGGYNYVSVVYQQHPGKAPKLIIHDVIERSSGVPDRFSGSKSGNTASL

TISGLQAEDEADYYCWSFAGSYYVFGTGTDVTVL
```

In the polypeptide of (BD1) above, the amino acid sequences of the heavy-chain variable region and the light-chain variable region may also be arranged in the reverse order. In a specific example, the polypeptide of (BD1) above may be a polypeptide obtained by exchanging the amino acid sequences of the heavy-chain variable region and the light-chain variable region in the amino acid sequences of Sequence ID Nos. 98 to 117.

The "identity" as used for the polypeptide of (BD2) above refers to 80% or more, 85% or more, 90% or more, 95% or more, 96% or more, 97% or more, 98% or more, or 99% or more identity, for example.

The term "one or several" as used for the polypeptide of (BD3) above regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

The descriptions of the first transmembrane domain and the first intracellular signaling domain of the CAR library of the present invention can be respectively applied to the above-mentioned transmembrane domain and intracellular signaling domain, for example.

A specific example of the first CAR of the present invention is a polypeptide of (C) below, for example.

(C) A polypeptide of (C1), (C2), or (C3) below:
  (C1) a polypeptide consisting of the amino acid sequence of any one of Sequence ID Nos. 118 to 137,
  (C2) a polypeptide consisting of an amino acid sequence having 80% or more identity to the amino acid sequence of any one of Sequence ID Nos. 118 to 137, the polypeptide being capable of binding to A2/NY-ESO-1$_{157}$, and
  (C3) a polypeptide consisting of an amino acid sequence consisting of the amino acid sequence of any one of Sequence ID Nos. 118 to 137 with deletion, substitution, insertion, and/or addition of one or several amino acids, the polypeptide being capable of binding to A2/NY-ESO-1$_{157}$.

H1-3M4E5L CAR
(Sequence ID No. 118)
QVQLQESGPGLVKPSDTLSLTCLVSGGSISSNYWSWIRQAPGKGLEWIG

HVSYSGSTNYNPSLKSRVTISVDTSKNQFSLKLSSVTAADTAVYYCARESYYYY

GMDVWGQGTTVTVSSGSTSGSGKPGSGEGSTKGQSELTQPRSVSGSPGQSVTI

SCTGTSRDVGGYNYVSWYQQHPGKAPKLIIHDVIERSSGVPDRFSGSKSGNTAS

LTISGLQAEDEADYYCWSFAGSYYVFGTGTDVTVLAAAIEVMYPPPYLDNEKS

NGTIIHVKGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAPAYQG

QNQLYNELNLGRREEYDVLDKRRGRDPEMGGKPRRKNPQEGLYNELQKDKM

AEAYSEIGMKGERRRGKGHDGLYQGLSTATKDTYDALHMQALPPR

K52-H1 CAR
(Sequence ID No. 119)
DIQMTQSPSAMSASVGDRVTITCRASQSISSYLNWYQQKPGKAPKLLIY

AASSLQSGVPSRFSGSGSGTDFTLTISSLQPEDFATYYCQQYYSTPQTFGPGTKV

DIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSSAAAIEVMYPPPYLDNEKSNGTI

IHVKGKHLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQGQNQL

YNELNLGRREEYDVLDKRRGRDPEMGGKPRRKNPQEGLYNELQKDKMAEAY

SEIGMKGERRRGKGHDGLYQGLSTATKDTYDALHMQALPPR

K73-H1 CAR
(Sequence ID No. 120)
DIQMTQSPSSLSASVGDRVTITCRASQSISSYLNWYQQKAGKAPKLLIY

AASSLQSGVPSRFSGSGSGTDFTLTISCLQSEDVATYYCQQYESYRRSFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSSAAAIEVMYPPPYLDNEKSNGTI

IHVKGKHLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQGQNQL

YNELNLGRREEYDVLDKRRGRDPEMGGKPRRKNPQEGLYNELQKDKMAEAY

SEIGMKGERRRGKGHDGLYQGLSTATKDTYDALHMQALPPR

K121-H1 CAR
(Sequence ID No. 121)
DIQMTQSPSSLSASVGDRVTITCRASQSISSYLNWYQQKPGKAPKLLIYA

ASSLQSGVPSRFSGSGSGTDFTLTISCLQSEDFATYYCQQYNSYSRTFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSSAAAIEVMYPPPYLDNEKSNGTI

IHVKGKHLCPSPLFPGPSKPFWVLVVVGGVLACYSLLVTVAFIIFWVRSKRSRLL

HSDYNINMTPRRPGPTRKHYPYAPPRDFAAYRSRVKFSRSADAPAYQQGQNQL

YNELNLGRREEYDVLDKRRGRDPEMGGKPRRKNPQEGLYNELQKDKNIAEAY

SEIGMKGERRRGKGHDGLYQGLSTATKDTYDALHMQALPPR

-continued

K124-H1 CAR
(Sequence ID No. 122)
DIQMTQSPSSLSASVGDRVTITCRAS<u>QSISSYLNWYQQKPGKAPKLLIYA</u>
<u>ASRLESGVPSRFSGSGSGTDFTLTISCLQSEDFATYYC<u>QQYNSYSRT</u>FGQGTKV
EIKGSTSGSGKPGSGEGSTKGQVQLQESGPGLVKPSDTLSLTCLVS<u>GGSISSNY</u>
WSWIRQAPGKGLEWIGH<u>VSYSGST</u>NYNPSLKSRVTISVDTSKNQFSLKLSSVTA
ADTAVYYC<u>ARESYYYYGMDV</u>WGQGTTVTVSSAAAIEVNIYPPPYLDNEKSNGTI
IHVKGKHLCPSPLFPGPSKPFWVLVVVGGVLACYSLLVTVAFIIFWVRSKRSRLL
HSDYNINMTPRRPGPTRKHYQPYAPPRDFAAYRSRVKFSRSADAPAYQQGQNQL
YNELNLGRREEYDVLDKRRGRDPEMGGKPRRKNPQEGLYNELQKDKNIAEAY
SEIGMKGERRRGKGHDGLYQGLSTATKDTYDALHMQALPPR K125-H1 CAR
(Sequence ID No. 123)
DIQMTQSPSSLSASVGDRVTITCRAS<u>QSISSYLNWYQQKPGKAPKLLLY</u>
<u>AASR</u>LESGVPSRFSGSGSGTEFTLTISSLQPDDFATYYC<u>QQYNSYSPCT</u>FGPGTK
VDIKGSTSGSGKPGSGEGSTKGQVQLQESGPGLVKPSDTLSLTCLVS<u>GGSISSN</u>
<u>YVVS</u>WIRQAPGKGLEWIGH<u>VSYSGST</u>NYNPSLKSRVTISVDTSKNQFSLKLSSVT
AADTAVYYC<u>ARESYYYYGMDV</u>WGQGTTVTVSSAAAIEVNIYPPPYLDNEKSNGT
IIHVKGKHLCPSPLFPGPSKPFVVVLVVVGGVLACYSLLVTVAFIIFWVRSKRSRL
LHSDYNINMTPRRPGPTRKHYQPYAPPRDFAAYRSRVKFSRSADAPAYQQGQNQ
LYNELNLGRREEYDVLDKRRGRDPEMGGKPRRKNPQEGLYNELQKDKNIAEA
YSEIGMKGERRRGKGHDGLYQGLSTATKDTYDALHMQALPPR K131-H1 CAR
(Sequence ID No. 124)
DIQMTQSPSSLSASVGDRVSITCRAS<u>QDISRY</u>LNWYQQKPGKAPKLLLY
<u>AASR</u>LESGVPSRFSGSGSGTDFTLTITSLQPDDFATYYC<u>QQYDNLIT</u>FGQGTRLE
IKGSTSGSGKPGSGEGSTKGQVQLQESGPGLVKPSDTLSLTCLVS<u>GGSISSNYW</u>
SWIRQAPGKGLEWIGH<u>VSYSGST</u>NYNPSLKSRVTISVDTSKNQFSLKLSSVTAA
DTAVYYC<u>ARESYYYYGMDV</u>WGQGTTVTVSSAAAIEVNIYPPPYLDNEKSNGTII
HVKGKHLCPSPLFPGPSKPFWVLVVVGGVLACYSLLVTVAFIIFWVRSKRSRLL
HSDYMNMTPRRPGPTRKHYQPYAPPRDFAAYRSRVKFSRSADAPAYQQGQNQL
YNELNLGRREEYDVLDKRRGRDPEMGGKPRRKNPQEGLYNELQKDKMAEAY
SEIGMKGERRRGKGHDGLYQGLSTATKDTYDALHMQALPPR K145-H1 CAR
(Sequence ID No. 125)
DIQMTQSPSSLSASVGDRVSITCRAS<u>QDISRY</u>LNWYQQKPGKAPKLLLY
<u>AASR</u>LESGVPSRFSGSGSGTDFTLTITSLQPDDFATYYC<u>QQYNSYSRT</u>FGQGTK
VEIKGSTSGSGKPGSGEGSTKGQVQLQESGPGLVKPSDTLSLTCLVS<u>GGSISSNY</u>
WSWIRQAPGKGLEWIGH<u>VSYSGST</u>NYNPSLKSRVTISVDTSKNQFSLKLSSVTA
ADTAVYYC<u>ARESYYYYGMDV</u>WGQGTTVTVSSAAAIEVMYPPPYLDNEKSNGTI
IHVKGKHLCPSPLFPGPSKPFWVLVVVGGVLACYSLLVTVAFIIFWVRSKRSRLL
HSDYMNMTPRRPGPTRKHYQPYAPPRDFAAYRSRVKFSRSADAPAYQQGQNQL
YNELNLGRREEYDVLDKRRGRDPEMGGKPRRKNPQEGLYNELQKDKMAEAY
SEIGMKGERRRGKGHDGLYQGLSTATKDTYDALHMQALPPR

```
K151-H1 CAR
                                          (Sequence ID No. 126)
DIQMTQSPSSLSASVGDRVTITCRASQSISSYLNWYQQKPGKAPKLLIYA

ASSLQSGVPSRFSGSGSGTDFTLTITSLQPDDFATYYCQQYDNLITFGQGTRLEI

KGSTSGSGKPGSGEGSTKGQVQLQESGPGLVKPSDTLSLTCLVSGGSISSNYWS

WIRQAPGKGLEWIGHVSYSGSTNYNPSLKSRVTISVDTSKNQFSLKLSSVTAAD

TAVYYCARESYYYYGMDVWGQGTTVTVSSAAAIEVMYPPPYLDNEKSNGTIIH

VKGKHLCPSPLFPGPSKPFWVLVVVGGVLACYSLLVTVAFIIFWVRSKRSRLLH

SDYMNMTPRRPGPTRKHYQPYAPPRDFAAYRSRVKFSRSADAPAYQQGQNQLY

NELNLGRREEYDVLDKRRGRDPEMGGKPRRKNPQEGLYNELQKDKMAEAYS

EIGMKGERRRGKGHDGLYQGLSTATKDTYDALHMQALPPR

K160-H1 CAR
                                          (Sequence ID No. 127)
EIVLTQSPATLSVSPGERATLSCRASQSVSSNLAWYQQKPGQAPRLLIYG

ASTRATGIPARFSGSGSGTEFTLTISRLEPEDFATYYCQQYNSYSRTFGQGTKVE

IKGSTSGSGKPGSGEGSTKGQVQLQESGPGLVKPSDTLSLTCLVSGGSISSNYW

SWIRQAPGKGLEWIGHVSYSGSTNYNPSLKSRVTISVDTSKNQFSLKLSSVTAA

DTAVYYCARESYYYYGMDVWGQGTTVTVSSAAAIEVMYPPPYLDNEKSNGTII

HVKGKHLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQGQNQL

YNELNLGRREEYDVLDKRRGRDPEMGGKPRRKNPQEGLYNELQKDKMAEAY

SEIGMKGERRRGKGHDGLYQGLSTATKDTYDALHMQALPPR

K173-H1 CAR
                                          (Sequence ID No. 128)
DIQMTQSPSSLSASVGDRVTITCRASQSISSYLNWYQQKAGKAPKLLIY

AASSLQSGVPSRFSGSGSGTDFTLTISCLQSEDVATYYCQQYESYSRTFGQGTKV

EIKGSTSGSGKPGSGEGSTKGQVQLQESGPGLVKPSDTLSLTCLVSGGSISSNY

WSWIRQAPGKGLEWIGHVSYSGSTNYNPSLKSRVTISVDTSKNQFSLKLSSVTA

ADTAVYYCARESYYYYGMDVWGQGTTVTVSSAAAIEVMYPPPYLDNEKSNGTI

IHVKGKHLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQGQNQL

YNELNLGRREEYDVLDKRRGRDPEMGGKPRRKNPQEGLYNELQKDKMAEAY

SEIGMKGERRRGKGHDGLYQGLSTATKDTYDALHMQALPPR

L1-3M4E5H CAR
                                          (Sequence ID No. 129)
QSALTQPPSASGSPGQSVTISCTGTSSDVGGYDFVSWYQQHPGEAPKLL

VYDVNNRPSGVSNRFSGSKSGNTASLTISGLQAEDEGDYYCSSYAGSNSVFGTG

TKVTVLGSTSGSGKPGSGEGSTKGEVQLLESGGGLVQPGGSLRLSCAASGFTFS

TYQMSWVRQAPGKGLEWVSGIVSSGGSTAYADSVKGRFTISRDNSKNTLYLQM

NSLRAEDTAVYYCAGELLPYYGMDVWGQGTTVTVSSAAAIEVMYPPPYLDNEK

SNGTIIHVKGKHLCPSPLFPGPSKPFWVLVVVGGVLACYSLLVTVAFIIFWVRSK

RSRLLHSDYMNMTPRRPGPTRKHYQPYAPPRDFAAYRSRVKFSRSADAPAYQQ

GQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR
```

3M4E5H-L1 CAR
(Sequence ID No. 130)
EVQLLESGGGLVQPGGSLRLSCAASGFTFSTYQMSWVRQAPGKGLEW

VSGIVSSGGSTAYADSVKGRFTISRDNSKNTLYLQMNSLRAEDTAVYYCAGELL

PYYGMDVWGQGTTVTVSSEVQLLESGGGLVQPGGSLRLSCAASGFTFSTYQMS

WVRQAPGKGLEWVSGIVSSGGSTAYADSVKGRFTISRDNSKNTLYLQMNSLRA

EDTAVYYCAGELLPYYGMDVWGQGTTVTVSSQSALTQPPSASGSPGQSVTISCT

GTSSDVGGYDFVSWYQQHPGEAPKLLVYDVNNRPSGVSNRFSGSKSGNTASLT

ISGLQAEDEGDYYCSSYAGSNSVFGTGTKVTVLAAAIEVNIYPPPYLDNEKSNGT

IIHVKGKHLCPSPLFPGPSKPFWVLVVVGGVLACYSLLVTVAFIIFWVRSKRSRL

LHSDYNINMTPRRPGPTRKHYQPYAPPRDFAAYRSRVKFSRSADAPAYQQGQNQ

LYNELNLGRREEYDVLDKRRGRDPEMGGKPRRKNPQEGLYNELQKDKNIAEA

YSEIGMKGERRRGKGHDGLYQGLSTATKDTYDALHMQALPPR

L66-3M4E5H CAR
(Sequence ID No. 131)
QSALTQPASVSGSPGQSITISCTGTSSDVGGYEFVSWYQQHPGSAPKLII

YDVIERPFGVSYRFSASKSGNTASLTISGLQEDEADYFCSSYTSSSTYVFGTGT

KVTVLGSTSGSGKPGSGEGSTKGEVQLLESGGGLVQPGGSLRLSCAASGFTFST

YQMSWVRQAPGKGLEWVSGIVSSGGSTAYADSVKGRFTISRDNSKNTLYLQMN

SLRAEDTAVYYCAGELLPYYGMDVWGQGTTVTVSSAAAIEVNIYPPPYLDNEKS

NGTIIHVKGKHLCPSPLFPGPSKPFWVLVVVGGVLACYSLLVTVAFIIFWVRSKR

SRLLHSDYNINMTPRRPGPTRKHYQPYAPPRDFAAYRSRVKFSRSADAPAYQQG

QNQLYNELNLGRREEYDVLDKRRGRDPEMGGKPRRKNPQEGLYNELQKDKNI

AEAYSEIGMKGERRRGKGHDGLYQGLSTATKDTYDALHMQALPPR

L73-3M4E5H CAR
(Sequence ID No. 132)
QSALTQPASVSGSPGQSITISCTGTGSDVGAYDYVSWYQHHPGRAPRLII

RDVSVRPSGVPDRFSGSKSGNTASLTISGLQAEDEADYYCSSYSGSSTWVFGGG

TKLTVLGSTSGSGKPGSGEGSTKGEVQLLESGGGLVQPGGSLRLSCAASGFTFS

TYQMSWVRQAPGKGLEWVSGIVSSGGSTAYADSVKGRFTISRDNSKNTLYLQM

NSLRAEDTAVYYCAGELLPYYGMDVWGQGTTVTVSSAAAIEVNIYPPPYLDNEK

SNGTIIHVKGKHLCPSPLFPGPSKPFWVLVVVGGVLACYSLLVTVAFIIFWVRSK

RSRLLHSDYNINMTPRRPGPTRKHYQPYAPPRDFAAYRSRVKFSRSADAPAYQQ

GQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

L80-3M4E5H CAR
(Sequence ID No. 133)
QSALTQPASVSGSPGQSITISCTGTSSDVGSYNLVSVVYQQHPGKAPKLM

IYDVSNRPSGVSYRFSGSKSGNTASLTISGLQAEDEADYYCSSYTSSSTFAVFGG

GTQLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSSAAAIEVMYPPPYLDN

EKSNGTIIHVKGKHLCPSPLFPGPSKPFWVLVVVGGVLACYSLLVTVAFIIFWVR

SKRSRLLHSDYMNMTPRRPGPTRKHYQPYAPPRDFAAYRSRVKFSRSADAPAY

```
QQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

L88-3M4E5H CAR
                                    (Sequence ID No. 134)
QSALPQPASVSGSPGQSVTISCTGTSSDVGGYNYVSWYQQHPGKAPKL

MIYDVSKRPSGVPDRFSGSKSGNTASLTVSGLQAEDEADYFCCSYAGGYYVFGT

GTKLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSSAAAIEVMYPPPYLDN

EKSNGTIIHVKGKHLCPSPLFPGPSKPFWVLVVVGGVLACYSLLVTVAFIIFWVR

SKRSRLLHSDYMNMTPRRPGPTRKHYQPYAPPRDFAAYRSRVKFSRSADAPAY

QQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

L102-3M4E5H CAR
                                    (Sequence ID No. 135)
QSALTQPPSASGSPGQSVTISCTGTSSDVGGYNYVSVVYQQHPGKAPKL

MIYDVSKRPSGVPDRFSGSKSGNTASLTISGLQTEDEADYYCSSYAGSGSTPFVF

GTGTKLTVLGSTSGSGKPGSGEGSTKGEVQLLESGGGLVQPGGSLRLSCAASG

FTFSTYQMSWVRQAPGKGLEWVSGIVSSGGSTAYADSVKGRFTISRDNSKNTL

YLQMNSLRAEDTAVYYCAGELLPYYGMDVWGQGTTVTVSSAAAIEVMYPPPYL

DNEKSNGTIIHVKGKHLCPSPLFPGPSKPFWVLVVVGGVLACYSLLVTVAFIIF

WVRSKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

L124-3M4E5H CAR
                                    (Sequence ID No. 136)
QSALTQPASVSGSPGQSITISCTGTSSDVGGYNYVSVVYQQHPGKAPKL

MIYDVSNRPSRVPDRFAGSKSGNTASLTISGLQAEDEADYYCCSYAGRRYVFGT

GTKLTVLGSTSGSGKPGSGEGSTKGEVQLLESGGGLVQPGGSLRLSCAASGFTF

STYQMSWVRQAPGKGLEWVSGIVSSGGSTAYADSVKGRFTISRDNSKNTLYLQ

MNSLRAEDTAVYYCAGELLPYYGMDVWGQGTTVTVSSAAAIEVMYPPPYLDN

EKSNGTIIHVKGKHLCPSPLFPGPSKPFWVLVVVGGVLACYSLLVTVAFIIFWVR

SKRSRLLHSDYMNMTPRRPGPTRKHYQPYAPPRDFAAYRSRVKFSRSADAPAY

QQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR 1173-3M4E5L CAR
                                    (Sequence ID No. 137)
QLQLQESGPGLVKPSQTLSLTCTVSGGSISSYYWSWIRQPPGKGLEWIG

EINHSGSTNYNPSLKSRVTISVDTSKNQFSLKLSSVTAADTAVYYCARCPIYYYG

MDVWGQGTTVTVSSGSTSGSGKPGSGEGSTKGQSELTQPRSVSGSPGQSVTIS

CTGTSRDVGGYNYVSVVYQQHPGKAPKLIIHDVIERSSGVPDRFSGSKSGNTASL

TISGLQAEDEADYYCWSFAGSYYVFGTGTDVTVLAAAIEVMYPPPYLDNEKSN

GTIIHVKGKHLCPSPLFPGPSKPFWVLVVVGGVLACYSLLVTVAFIIFWVRSKRS

RLLHSDYMNMTPRRPGPTRKHYQPYAPPRDFAAYRSRVKFSRSADAPAYQQGQ
```

-continued

NQLYNELNLGRREEYDVLDKRRGRDPEMGGKPRRKNPQEGLYNELQKDKMA

EAYSEIGMKGERRRGKGHDGLYQGLSTATKDTYDALHMQALPPR

In the polypeptide of (C1) above, each of the amino acid sequences of Sequence ID Nos. 118 to 137 is an amino acid sequence that includes a combination of the heavy-chain variable region and the light-chain variable region that corresponds to any one of Combinations (1) to (18) for the first antibody of the present invention or the like, for example. In the polypeptides of (C2) and (C3) above, the amino acid sequences that correspond to the CDRH1, the CDRH2, the CDRH3, the CDRL1, the CDRL2, and the CDRL3 are conserved in the amino acid sequences of Sequence ID Nos. 118 to 137, for example. Regarding the amino acid sequences of the CDRs in the amino acid sequences of Sequence ID Nos. 118 to 137, the amino acid sequences that include the combinations of the heavy-chain variable region and the light-chain variable region that correspond to Combinations (1) to (18) for the first antibody of the present invention or the like can be referred to, for example.

The "identity" as used for the polypeptide of (C2) above refers to 80% or more, 85% or more, 90% or more, 95% or more, 96% or more, 97% or more, 98% or more, or 99% or more identity, for example.

The term "one or several" as used for the polypeptide of (C3) above regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

There is no particular limitation on a method for manufacturing the first CAR of the present invention, and the first CAR can be manufactured using genetic engineering techniques based on the amino acid sequence information described above, for example. Specifically, the first CAR can be manufactured as follows, for example. It should be noted that the present invention is not limited to this example.

First, an expression vector that includes a nucleic acid coding for the first CAR of the present invention is introduced into a host to obtain a transformant. Then, the transformant is cultured, and thus a first CAR-expressing transformant is obtained.

An example of the expression vector is a vector that includes a nucleic acid coding for the first CAR, and the descriptions of the above-described expression vector can be applied, for example. There is no particular limitation on the host, and the descriptions of the above-described host can be applied, for example.

Second Chimeric Antigen Receptor

As described above, the second chimeric antigen receptor (CAR) of the present invention includes an antigen-binding domain, a transmembrane domain, and an intracellular signaling domain, and the antigen-binding domain includes the antibody of the present invention or the antigen-binding fragment thereof. The second CAR of the present invention is characterized in that the antigen-binding domain includes the second antibody of the present invention or the like, and there is no particular limitation on the other configurations and conditions. The descriptions of the CAR library, the first screening method, the first antibody or the like, the second antibody or the like, the gene, the expression vector, and the transformant of the present invention can be applied to the second CAR of the present invention. The second CAR of the present invention can be favorably used as a CAR for CAR-T cells against CD19-expressing cancer cells, for example.

The antigen-binding domain may be the second antibody of the present invention or the antigen-binding fragment of the second antibody of the present invention, for example. The antigen-binding fragment is preferably a single-chain antibody (scFv). If the antigen-binding domain is an scFv, the heavy-chain variable region and the light-chain variable region are arranged in this order from the C terminus or N terminus in the antigen-binding domain.

A specific example of the antigen-binding domain is a polypeptide of (bd) below.

(bd) A polypeptide of (bd1), (bd2), or (bd3) below:

(bd1) a polypeptide consisting of the amino acid sequence of any one of Sequence ID Nos. 272 to 284, (bd2) a polypeptide consisting of an amino acid sequence having 80% or more identity to the amino acid sequence of any one of Sequence ID Nos. 272 to 284, the polypeptide being capable of binding to CD19, and (bd3) a polypeptide consisting of an amino acid sequence consisting of the amino acid sequence of any one of Sequence ID Nos. 272 to 284 with deletion, substitution, insertion, and/or addition of one or several amino acids, the polypeptide being capable of binding to CD19.

In the polypeptide of (bd1) above, each of the amino acid sequences of Sequence ID Nos. 272 to 284 is an amino acid sequence that includes a combination of the heavy-chain variable region and the light-chain variable region that corresponds to any one of Combinations (LA) to (LM) for the second antibody of the present invention or the like, for example. Regarding the amino acid sequences of the heavy-chain variable region and the light-chain variable region in each of the amino acid sequences of Sequence ID Nos. 272 to 284, the amino acid sequences that include the combinations of the heavy-chain variable region and the light-chain variable region that correspond to Combinations (LA) to (LM) for the second antibody of the present invention or the like can be referred to, for example. In the polypeptides of (bd2) and (bd3) above, the amino acid sequences that correspond to the CDRH1, the CDRH2, the CDRH3, the CDRL1, the CDRL2, and the CDRL3 are conserved in the amino acid sequences of Sequence ID Nos. 272 to 284, for example. Regarding the amino acid sequences of the CDRs in the amino acid sequences of Sequence ID Nos. 272 to 284, the amino acid sequences of the CDRs included in the amino acid sequences that include the combinations of the heavy-chain variable region and the light-chain variable region that correspond to Combinations (LA) to (LM) for the second antibody of the present invention or the like can be referred to, for example.

Antigen-Binding Domain of L4-1811
(Sequence ID No. 272)
SYELTQPPSVSVSPGQTASITCSGDKLGDKYACWYQQKPGQSPVLVIYQ
DSKRPSGIPERFSGSNSGNTATLTISGTQAMDEADYYCQAWDSSTHVVFGGGT
KLTVLGSTSGSGKPGSGEGSTKGEVQLVESGGGLVQPGRSLRLSCAASGFTFDD
YAMHWVRQAPGKGLEWVSGISWNSGRIGYADSVKGRFTISRDNAKNSLFLQM
NSLRAEDTAVYYCARDQGYHYYDSAEHAFDIWGQGTVVTVSS Antigen-Binding Domain of L7-1811
(Sequence ID No. 273)
QSALTQPRSVSGSPGQSVTISCTGTSSDVGGYNYVSWYQQHPGKAPKL
MIYDVSNRPSGVSNRFSGSKSGNTASLTISGLQTGDEADYYCGTWDTSLTAVVF
GGGTELTVLGSTSGSGKPGSGEGSTKGEVQLVESGGGLVQPGRSLRLSCAASG
FTFDDYAMHVVRQAPGKGLEWVSGISWNSGRIGYADSVKGRFTISRDNAKNS
LFLQMNSLRAEDTAVYYCARDQGYHYYDSAEHAFDIWGQGTVVTVSS Antigen-Binding Domain of L9-1811
(Sequence ID No. 274)
QSVLTQPPSVSAAPGQKVTISCSGSWSNIGDDHVSWYQQFPGAAPKLLI
YDTSKRPSRVADRFSGSKSGASATLAITGLQAGDEADYYCGTWESSLSGVVFGG
GTELTVLGSTSGSGKPGSGEGSTKGEVQLVESGGGLVQPGRSLRLSCAASGFTF
DDYAMHVVRQAPGKGLEWVSGISWNSGRIGYADSVKGRFTISRDNAKNSLFL
QMNSLRAEDTAVYYCARDQGYHYYDSAEHAFDIWGQGTVVTVSS Antigen-Binding Domain of L13-1811
(Sequence ID No. 275)
QSALTQPASVSGSPGQSITISCTGLSSDVGGYDYVSWYQQHPGIAPKLM
IYDVTNRPSGVSSRFSGSKSGNTASLTISGLQAEDEADYYCSSYTTSTTWVFGA
GTKLTVLGSTSGSGKPGSGEGSTKGEVQLVESGGGLVQPGRSLRLSCAASGFTF
DDYAMHVVRQAPGKGLEWVSGISWNSGRIGYADSVKGRFTISRDNAKNSLFL
QMNSLRAEDTAVYYCARDQGYHYYDSAEHAFDIWGQGTVVTVSS Antigen-Binding Domain of L14-18E1
(Sequence ID No. 276)
QSALTQPASVSGSPGQSITISCTGTTSDVGTTNYVSWYQQHPGKAPKLL
IYDVTNRPSGVPDRFSGSKSANTASLTISGLQAEDEADYYCCSYAGSYTFVVFG
GGTELTVLGSTSGSGKPGSGEGSTKGEVQLVESGGGLVQPGRSLRLSCAASGFT
FDDYAMHWVRQAPGKGLEWVSGISWNSGRIGYADSVKGRFTISRDNAKNSLF
LQMNSLRAEDTAVYYCARDQGYHYYDSAEHAFDIWGQGTVVTVSS Antigen-Binding Domain of L16-18E1
(Sequence ID No. 277)
QSALTQPPSASGSPGQSVTISCTGTSSDVGVYNYVSWYQQHPGKAPKL
MIYDVSKRPSGVPDRFSGSKSANTASLTISGLQAEDEADYYCAAWDDSLNGVV
FGGGTQLTVLGSTSGSGKPGSGEGSTKGEVQLVESGGGLVQPGRSLRLSCAAS
GFTFDDYAMHWVRQAPGKGLEWVSGISWNSGRIGYADSVKGRFTISRDNAKN
SLFLQMNSLRAEDTAVYYCARDQGYHYYDSAEHAFDIWGQGTVVTVSS Antigen-Binding Domain of L17-18H
(Sequence ID No. 278)
QSVLTQPPSASGTPGQRVTISCSGSSSNIGNNYVCWYQHLPGTAPKLLI
YDNVKRPSGIPDRFSGSKSGTSASLAISGLRSEDEADYYCAAWDDSLSAIFGGG
TELTVLGSTSGSGKPGSGEGSTKGEVQLVESGGGLVQPGRSLRLSCAASGFTFD
DYAMHWVRQAPGKGLEWVSGISWNSGRIGYADSVKGRFTISRDNAKNSLFLQ

```
MNSLRAEDTAVYYCARDQGYHYYDSAEHAFDIWGQGTVVTVSS

Antigen-Binding Domain of L22-18E1
                                        (Sequence ID No. 279)
QSALTQPASVSGSPGQSITISCTGTSSDVGGYNYVSWYQQHPGKAPKL

MIYDVSNRPSGVPDRFSGSKSGTSASLAISGLQSEDEADYYCHSYDSSLSHVFG

TGTKVTVLGSTSGSGKPGSGEGSTKGEVQLVESGGGLVQPGRSLRLSCAASGFT

FDDYAMHWVRQAPGKGLEWVSGISWNSGRIGYADSVKGRFTISRDNAKNSLF

LQMNSLRAEDTAVYYCARDQGYHYYDSAEHAFDIWGQGTVVTVSS

Antigen-Binding Domain of K4-18H
                                        (Sequence ID No. 280)
EIVLTQSPGTLSLSPGERATLSCRASQSVSSNLAWYQQKPGQAPRLLIYG

ASTRATGIPARFSGSGSGTEFTLTISSLQSEDFAVYYCQQYNNWPPLYTFGQGTK

LEIKGSTSGSGKPGSGEGSTKGEVQLVESGGGLVQPGRSLRLSCAASGFTFDDY

AMHWVRQAPGKGLEWVSGISWNSGRIGYADSVKGRFTISRDNAKNSLFLQMN

SLRAEDTAVYYCARDQGYHYYDSAEHAFDIWGQGTVVTVSS

Antigen-Binding Domain of K5-18H
                                        (Sequence ID No. 281)
EIVLTQSPGTLSLSPGERATLSCRASQSVSSYLAWYQQKPGQAPRLLIYD

ASNRATGIPARFSGSGSGTDFTLTISSLEPEDFATYYCQQSYSTLLYTFGQGTKL

EIKGSTSGSGKPGSGEGSTKGEVQLVESGGGLVQPGRSLRLSCAASGFTFDDYA

MHWVRQAPGKGLEWVSGISWNSGRIGYADSVKGRFTISRDNAKNSLFLQMNS

LRAEDTAVYYCARDQGYHYYDSAEHAFDIWGQGTVVTVSS

Antigen-Binding Domain of K6-18H
                                        (Sequence ID No. 282)
EIVLTRSPATLSLSPGERATLSCRASQSVSSYLAWYQQKPGQAPRLLIYD

ASNRATGISARFSGSGSGTEFTLTISSLQSEDIATYYCQQYDSLPLTFGGGTKLEI

KGSTSGSGKPGSGEGSTKGEVQLVESGGGLVQPGRSLRLSCAASGFTFDDYAM

HWVRQAPGKGLEWVSGISWNSGRIGYADSVKGRFTISRDNAKNSLFLQMNSL

RAEDTAVYYCARDQGYHYYDSAEHAFDIWGQGTVVTVSS

Antigen-Binding Domain of K10-18H
                                        (Sequence ID No. 283)
EIVLTQSPATLSLSPGERATVSCRPSQTISASSVAWYQQKAGQAPRLLIY

GASSRATGIPDRFSGSGSGTDFTLTISRLEPEDFAVYYCQQFNEWPLTFGGGTK

VEIKGSTSGSGKPGSGEGSTKGEVQLVESGGGLVQPGRSLRLSCAASGFTFDDY

AMHWVRQAPGKGLEWVSGISWNSGRIGYADSVKGRFTISRDNAKNSLFLQMN

SLRAEDTAVYYCARDQGYHYYDSAEHAFDIWGQGTVVTVSS

Antigen-Binding Domain of K10-18H
                                        (Sequence ID No. 284)
EIVLTQSPATLSLSPGERATLSCRASQSVSSNLAWYQQKLGQAPRLLIYG

ASSRATGIPDRFSGSGSGTDFTLTISRLEPEDFAVYYCQQYGSSPDIFTFGPGTK

VDIKGSTSGSGKPGSGEGSTKGEVQLVESGGGLVQPGRSLRLSCAASGFTFDDY

AMHWVRQAPGKGLEWVSGISWNSGRIGYADSVKGRFTISRDNAKNSLFLQMN

SLRAEDTAVYYCARDQGYHYYDSAEHAFDIWGQGTVVTVSS
```

In the polypeptide of (bd1) above, the amino acid sequences of the heavy-chain variable region and the light-chain variable region may also be arranged in the reverse order. In a specific example, the polypeptide of (bd1) above may be a polypeptide obtained by exchanging the amino acid sequences of the heavy-chain variable region and the light-chain variable region in the amino acid sequences of Sequence ID Nos. 272 to 284.

The "identity" as used for the polypeptide of (bd2) above refers to 80% or more, 85% or more, 90% or more, 95% or more, 96% or more, 97% or more, 98% or more, or 99% or more identity, for example.

The term "one or several" as used for the polypeptide of (bd3) above regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

The descriptions of the first transmembrane domain and the first intracellular signaling domain of the CAR library of the present invention can be respectively applied to the above-mentioned transmembrane domain and intracellular signaling domain, for example.

A specific example of the second CAR of the present invention is a polypeptide of (CA) below, for example.

(CA) A polypeptide of (CA1), (CA2), or (CA3) below:
(CA1) a polypeptide consisting of the amino acid sequence of any one of Sequence ID Nos. 285 to 297,
(CA2) a polypeptide consisting of an amino acid sequence having 80% or more identity to the amino acid sequence of any one of Sequence ID Nos. 285 to 297, the polypeptide being capable of binding to CD19, and
(CA3) a polypeptide consisting of an amino acid sequence consisting of the amino acid sequence of any one of Sequence ID Nos. 285 to 297 with deletion, substitution, insertion, and/or addition of one or several amino acids, the polypeptide being capable of binding to CD19.

```
L4-18H CAR
                                        (Sequence ID No. 285)
SYELTQPPSVSVSPGQTASITCSGDKLGDKYACWYQQKPGQSPVLVIYQ

DSKRPSGIPERFSGSNSGNTATLTISGTQAMDEADYYCQAWDSSTHVVFGGGT

KLTVLGSTSGSGKPGSGEGSTKGEVQLVESGGGLVQPGRSLRLSCAASGFTFDD

YAMHWVRQAPGKGLEWVSGISWNSGRIGYADSVKGRFTISRDNAKNSLFLQM

NSLRAEDTAVYYCARDQGYHYYDSAEHAFDIWGQGTVVTVSSAAAIEVMYPPP

YLDNEKSNGTIIHVKGKHLCPSPLFPGPSKPFWVLVVVGGVLACYSLLVTVAFII

FWVRSKRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR

L7-18H CAR
                                        (Sequence ID No. 286)
QSALTQPRSVSGSPGQSVTISCTGTSSDVGGYNYVSWYQQHPGKAPKL

MIYDVSNRPSGVSNRFSGSKSGNTASLTISGLQTGDEADYYCGTWDTSLTAVVF

GGGTELTVLGSTSGSGKPGSGEGSTKGEVQLVESGGGLVQPGRSLRLSCAASG

FTFDDYAMHWVRQAPGKGLEWVSGISWNSGRIGYADSVKGRFTISRDNAKNS

LFLQMNSLRAEDTAVYYCARDQGYHYYDSAEHAFDIWGQGTVVTVSSAAAIEV

MYPPPYLDNEKSNGTIIHVKGKHLCPSPLFPGPSKPFWVLVVVGGVLACYSLLV

TVAFIIFWVRSKRSRLLHSDYMNMTPRRPGPTRKHYQPYAPPRDFAAYRSRVKF

SRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQA

LPPR

L9-18H CAR
                                        (Sequence ID No. 287)
QSVLTQPPSVSAAPGQKVTISCSGSWSNIGDDHVSWYQQFPGAAPKLLI

YDTSKRPSRVADRFSGSKSGASATLAITGLQAGDEADYYCGTWESSLSGVVFGG

GTELTVLGSTSGSGKPGSGEGSTKGEVQLVESGGGLVQPGRSLRLSCAASGFTF

DDYAMHVVVRQAPGKGLEWVSGISWNSGRIGYADSVKGRFTISRDNAKNSLFL

QMNSLRAEDTAVYYCARDQGYHYYDSAEHAFDIWGQGTVVTVSSAAAIEVMY

PPPYLDNEKSNGTIIHVKGKHLCPSPLFPGPSKPFWVLVVVGGVLACYSLLVTV

AFIIFWVRSKRSRLLHSDYMNMTPRRPGPTRKHYQPYAPPRDFAAYRSRVKFSR
```

SADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQAL

PPR

L13-18H CAR (Sequence ID No. 288)
QSALTQPASVSGSPGQSITISCTGLSSDVGGYDYVSWYQQHPGIAPKLM

IYDVTNRPSGVSSRFSGSKSGNTASLTISGLQAEDEADYYCSSYTTSTTWVFGA

GTKLTVLGSTSGSGKPGSGEGSTKGEVQLVESGGGLVQPGRSLRLSCAASGFTF

DDYAMHVVVRQAPGKGLEWVSGISWNSGRIGYADSVKGRFTISRDNAKNSLFL

QMNSLRAEDTAVYYCARDQGYHYYDSAEHAFDIWGQGTVVTVSSAAAIEVMY

PPPYLDNEKSNGTIIHVKGKHLCPSPLFPGPSKPFWVLVVVGGVLACYSLLVTV

AFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQAL

PPR

L14-18H CAR (Sequence ID No. 289)
QSALTQPASVSGSPGQSITISCTGTTSDVGTTNYVSWYQQHPGKAPKLL

IYDVTNRPSGVPDRFSGSKSANTASLTISGLQAEDEADYYCSYAGSYTFVVFG

GGTELTVLGSTSGSGKPGSGEGSTKGEVQLVESGGGLVQPGRSLRLSCAASGFT

FDDYAMHWVRQAPGKGLEWVSGISWNSGRIGYADSVKGRFTISRDNAKNSLF

LQMNSLRAEDTAVYYCARDQGYHYYDSAEHAFDIWGQGTVVTVSSAAAIEVM

YPPPYLDNEKSNGTIIHVKGKHLCPSPLFPGPSKPFWVLVVVGGVLACYSLLVT

VAFIIFWVRSKRSRLLHSDYMNMTPRRPGPTRKHYQPYAPPRDFAAYRSRVKFS

RSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQA

LPPR

L16-18H CAR (Sequence ID No. 290)
QSALTQPPSASGSPGQSVTISCTGTSSDVGVYNYVSWYQQHPGKAPKL

MIYDVSKRPSGVPDRFSGSKSANTASLTISGLQAEDEADYYCAAWDDSLNGVV

FGGGTQLTVLGSTSGSGKPGSGEGSTKGEVQLVESGGGLVQPGRSLRLSCAAS

GFTFDDYAMHWVRQAPGKGLEWVSGISWNSGRIGYADSVKGRFTISRDNAKN

SLFLQMNSLRAEDTAVYYCARDQGYHYYDSAEHAFDIWGQGTVVTVSSAAAIE

VMYPPPYLDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAAYRSRV

KFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHM

QALPPR

L17-18H CAR (Sequence ID No. 291)
QSVLTQPPSASGTPGQRVTISCSGSSSNIGNNYVCWYQHLPGTAPKLLI

YDNVKRPSGIPDRFSGSKSGTSASLAISGLRSEDEADYYCAAWDDSLSAIFGGG

TELTVLGSTSGSGKPGSGEGSTKGEVQLVESGGGLVQPGRSLRLSCAASGFTFD

DYAMHWVRQAPGKGLEWVSGISWNSGRIGYADSVKGRFTISRDNAKNSLFLQ

-continued

```
MNSLRAEDTAVYYCARDQGYHYYDSAEHAFDIWGQGTVVTVSSAAAIEVNIYPP
PYLDNEKSNGTIIHVKGKHLCPSPLFPGPSKPFWVLVVVGGVLACYSLLVTVAF
IIFWVRSKRSRLLHSDYNINMTPRRPGPTRKHYQPYAPPRDFAAYRSRVKFSRSA
DAPAYQQGQNQLYNELNLGRREEYDVLDKRRGRDPEMGGKPRRKNPQEGLY
NELQKDKNIAEAYSEIGMKGERRRGKGHDGLYQGLSTATKDTYDALHMQALPP
R
```

L22-18H CAR
(Sequence ID No. 292)

```
QSALTQPASVSGSPGQSITISCTGTSSDVGGYNYVSVVYQQHPGKAPKL
MIYDVSNRPSGVPDRFSGSKSGTSASLAISGLQSEDEADYYCHSYDSSLSHVFG
TGTKVTVLGSTSGSGKPGSGEGSTKGEVQLVESGGGLVQPGRSLRLSCAASGFT
FDDYAMHVVVRQAPGKGLEWVSGISWNSGRIGYADSVKGRFTISRDNAKNSLF
LQMNSLRAEDTAVYYCARDQGYHYYDSAEHAFDIWGQGTVVTVSSAAAIEVNI
YPPPYLDNEKSNGTIIHVKGKHLCPSPLFPGPSKPFWVLVVVGGVLACYSLLVT
VAFIIFWVRSKRSRLLHSDYNINMTPRRPGPTRKHYQPYAPPRDFAAYRSRVKFS
RSADAPAYQQGQNQLYNELNLGRREEYDVLDKRRGRDPEMGGKPRRKNPQE
GLYNELQKDKNIAEAYSEIGMKGERRRGKGHDGLYQGLSTATKDTYDALHMQA
LPPR
```

K4-18H CAR
(Sequence ID No. 293)

```
EIVLTQSPGTLSLSPGERATLSCRASQSVSSNLAWYQQKPGQAPRLLIYG
ASTRATGIPARFSGSGSGTEFTLTISSLQSEDFAVYYCQQYNNWPPLYTFGQGTK
LEIKGSTSGSGKPGSGEGSTKGEVQLVESGGGLVQPGRSLRLSCAASGFTFDDY
AMHWVRQAPGKGLEWVSGISWNSGRIGYADSVKGRFTISRDNAKNSLFLQMN
SLRAEDTAVYYCARDQGYHYYDSAEHAFDIWGQGTVVTVSSAAAIEVNIYPPPY
LDNEKSNGTIIHVKGKHLCPSPLFPGPSKPFWVLVVVGGVLACYSLLVTVAFIIF
WVRSKRSRLLHSDYNINMTPRRPGPTRKHYQPYAPPRDFAAYRSRVKFSRSADA
PAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
```

K5-18H CAR
(Sequence ID No. 294)

```
EIVLTQSPGTLSLSPGERATLSCRASQSVSSYLAWYQQKPGQAPRLLIYD
ASNRATGIPARFSGSGSGTDFTLTISSLEPEDFATYYCQQSYSTLLYTFGQGTKL
EIKGSTSGSGKPGSGEGSTKGEVQLVESGGGLVQPGRSLRLSCAASGFTFDDYA
MHWVRQAPGKGLEWVSGISWNSGRIGYADSVKGRFTISRDNAKNSLFLQMNS
LRAEDTAVYYCARDQGYHYYDSAEHAFDIWGQGTVVTVSSAAAIEVMYPPPYL
DNEKSNGTIIHVKGKHLCPSPLFPGPSKPFWVLVVVGGVLACYSLLVTVAFIIF
WVRSKRSRLLHSDYMNMTPRRPGPTRKHYQPYAPPRDFAAYRSRVKFSRSADA
PAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
```

K6-18H CAR
(Sequence ID No. 295)

```
EIVLTRSPATLSLSPGERATLSCRASQSVSSYLAWYQQKPGQAPRLLIYD
ASNRATGISARFSGSGSGTEFTLTISSLQSEDIATYYCQQYDSLPLTFGGGTKLEI
```

-continued

```
KGSTSGSGKPGSGEGSTKGEVQLVESGGGLVQPGRSLRLSCAASGFTFDDYAM

HWVRQAPGKGLEWVSGISWNSGRIGYADSVKGRFTISRDNAKNSLFLQMNSL

RAEDTAVYYCARDQGYHYYDSAEHAFDIWGQGTVVTVSSAAAIEVMYPPPYLD

NEKSNGTIIHVKGKHLCPSPLFPGPSKPFWVLVVVGGVLACYSLLVTVAFIIFW

VRSKRSRLLHSDYMNMTPRRPGPTRKHYQPYAPPRDFAAYRSRVKFSRSADAP

AYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

K9-18H CAR
                                       (Sequence ID No. 296)
EIVLTQSPATLSLSPGERATVSCRPSQTISASSVAWYQQKAGQAPRLLIY

GASSRATGIPDRFSGSGSGTDFTLTISRLEPEDFAVYYCQQFNEWPLTFGGGTK

VEIKGSTSGSGKPGSGEGSTKGEVQLVESGGGLVQPGRSLRLSCAASGFTFDDY

AMHWVRQAPGKGLEWVSGISWNSGRIGYADSVKGRFTISRDNAKNSLFLQMN

SLRAEDTAVYYCARDQGYHYYDSAEHAFDIWGQGTVVTVSSAAAIEVMYPPPY

LDNEKSNGTIIHVKGKHLCPSPLFPGPSKPFWVLVVVGGVLACYSLLVTVAFIIF

WVRSKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

K10-18H CAR
                                       (Sequence ID No. 297)
EIVLTQSPATLSLSPGERATLSCRASQSVSSNLAWYQQKLGQAPRLLIYG

ASSRATGIPDRFSGSGSGTDFTLTISRLEPEDFAVYYCQQYGSSPDIFTFGPGTK

VDIKGSTSGSGKPGSGEGSTKGEVQLVESGGGLVQPGRSLRLSCAASGFTFDDY

AMHWVRQAPGKGLEWVSGISWNSGRIGYADSVKGRFTISRDNAKNSLFLQMN

SLRAEDTAVYYCARDQGYHYYDSAEHAFDIWGQGTVVTVSSAAAIEVMYPPPY

LDNEKSNGTIIHVKGKHLCPSPLFPGPSKPFWVLVVVGGVLACYSLLVTVAFIIF

WVRSKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR
```

In the polypeptide of (CA1) above, each of the amino acid sequences of Sequence ID Nos. 285 to 297 is an amino acid sequence that includes a combination of the heavy-chain variable region and the light-chain variable region that corresponds to any one of Combinations (LA) to (LM) for the second antibody of the present invention or the like, for example. In the polypeptides of (CA2) and (CA3) above, the amino acid sequences that correspond to the CDRH1, the CDRH2, the CDRH3, the CDRL1, the CDRL2, and the CDRL3 are conserved in the amino acid sequences of Sequence ID Nos. 285 to 297, for example. Regarding the amino acid sequences of the CDRs in the amino acid sequences of Sequence ID Nos. 285 to 297, the amino acid sequences that include the combinations of the heavy-chain variable region and the light-chain variable region that correspond to Combinations (LA) to (LM) for the second antibody of the present invention or the like can be referred to, for example.

The "identity" as used for the polypeptide of (CA2) above refers to 80% or more, 85% or more, 90% or more, 95% or more, 96% or more, 97% or more, 98% or more, or 99% or more identity, for example.

The term "one or several" as used for the polypeptide of (CA3) above regarding substitution and the like refers to 1 to 20, 1 to 15, 1 to 10, 1 to 9, 1 to 8, 1 to 7, 1 to 6, 1 to 5, 1 to 4, 1 to 3, 1 or 2, or 1, for example.

There is no particular limitation on a method for manufacturing the second CAR of the present invention, and the second CAR can be manufactured using genetic engineering techniques based on the amino acid sequence information described above, for example. Specifically, the second CAR can be manufactured as follows, for example. It should be noted that the present invention is not limited to this example.

First, an expression vector that includes a nucleic acid coding for the second CAR of the present invention is introduced into a host to obtain a transformant. Then, the transformant is cultured, and thus a second CAR-expressing transformant is obtained.

An example of the expression vector is a vector that includes a nucleic acid coding for the second CAR, and the descriptions of the above-described expression vector can be applied, for example. There is no particular limitation on the host, and the descriptions of the above-described host can be applied, for example.

Nucleic Acid

As described above, the nucleic acid of the present invention codes for the chimeric antigen receptor of the present invention. The nucleic acid of the present invention is characterized by coding for the first chimeric antigen receptor or second chimeric antigen receptor of the present invention (also collectively referred to as the "chimeric antigen receptor of the present invention" hereinafter), and there is no particular limitation on the other configurations and conditions. With the nucleic acid of the present invention, the CAR of the present invention can be expressed in cells, for example. The descriptions of the CAR library, the first screening method, the first antibody or the like, the first antibody or the like, the gene, the expression vector, the transformant, the first chimeric antigen receptor, and the second chimeric antigen receptor of the present invention can be applied to the nucleic acid of the present invention, for example.

The nucleic acid of the present invention can be prepared based on the amino acid sequence of the CAR of the present invention using an ordinary method, for example. In a specific example, the nucleic acid coding for the CAR of the present invention can be prepared based on the base sequence coding for the amino acid sequence obtained from the database in which the amino acid sequences of the above-described domains are registered, using a molecular biological technique and/or a chemical synthesis method, for example. The base sequence of the nucleic acid may be subjected to codon optimization in accordance with the source of cells in which the CAR of the present invention is to be expressed, for example.

A specific example of the nucleic acid of the present invention is a polynucleotide of (c) below.

(c) A polynucleotide (nucleic acid) of (c1), (c2), (c3), (c4), (c5), or (c6) below:
- (c1) a polynucleotide coding for a polypeptide consisting of the amino acid sequence of any one of Sequence ID Nos. 118 to 137,
- (c2) a polynucleotide coding for a polypeptide consisting of an amino acid sequence having 80% or more identity to the amino acid sequence of any one of Sequence ID Nos. 118 to 137, the polypeptide being capable of binding to A2/NY-ESO-1$_{157}$,
- (c3) a polynucleotide coding for a polypeptide consisting of an amino acid sequence consisting of the amino acid sequence of any one of Sequence ID Nos. 118 to 137 with deletion, substitution, insertion, and/or addition of one or several amino acids, the polypeptide being capable of binding to A2/NY-ESO-1$_{157}$,
- (c4) a polynucleotide consisting of the base sequence of any one of Sequence ID Nos. 138 to 157,
- (c5) a polynucleotide consisting of a base sequence having 80% or more identity to the base sequence of any one of Sequence ID Nos. 138 to 157, and coding for a polypeptide capable of binding to A2/NY-ESO-1$_{157}$, and
- (c6) a polynucleotide consisting of a base sequence consisting of the base sequence of any one of Sequence ID Nos. 138 to 157 with deletion, substitution, insertion, and/or addition of one or several bases, and coding for a polypeptide capable of binding to A2/NY-ESO-1$_{157}$.

The polynucleotides of (c1) to (c3) above are nucleic acids coding for the polypeptides of (C1) to (C3) above, respectively, and the descriptions of the polypeptides of (C1) to (C3) above can be applied.

In the polynucleotide of (c4) above, each of the base sequences of Sequence ID Nos. 138 to 157 is a polynucleotide coding for a polypeptide that includes an amino acid sequence that includes a combination of the heavy-chain variable region and the light-chain variable region that corresponds to any one of Combinations (1) to (18) for the first antibody of the present invention or the like, for example. In the polynucleotides of (c5) and (c6) above, the polynucleotides coding for the amino acid sequences that correspond to the CDRH1, the CDRH2, the CDRH3, the CDRL1, the CDRL2, and the CDRL3 are conserved in the base sequences of Sequence ID Nos. 138 to 157, for example. Regarding the base sequences coding for the amino acid sequences of the CDRs in the base sequences of Sequence ID Nos. 138 to 157, the amino acid sequences of the CDRs included in the amino acid sequences that include the combinations of the heavy-chain variable region and the light-chain variable region that correspond to Combinations (1) to (18) for the first antibody of the present invention or the like can be referred to, for example.

The "identity" as used for the polynucleotide of (c5) above refers to 80% or more, 85% or more, 90% or more, 95% or more, 96% or more, 97% or more, 98% or more, or 99% or more identity, for example.

The term "one or several" as used for the polynucleotide of (c6) above regarding substitution and the like refers to 1 to 280, 1 to 210, 1 to 140, 1 to 70, 1 to 63, 1 to 56, 1 to 49, 1 to 35, 1 to 28, 1 to 21, 1 to 14, 1 to 7, 1 to 6, 1 to 5, 1 to 4, 1 to 3, 1 or 2, or 1, for example.

```
Polynucleotide Coding for H1-3M4E5L CAR
                                        (Sequence ID No. 138)
5'-CAGGTGCAGCTGCAGGAGTCGGGCCCAGGACTGGTGAAGCCTTCGGATACCC

TGTCCCTCACCTGTCTTGTCTCTGGTGGCTCCATCAGTAGTAATTACTGGAGC

TGGATCCGGCAGGCCCCAGGGAAGGGACTGGAGTGGATTGGACATGTCTCCT

ACAGTGGGAGCACCAACTACAACCCCTCCCTCAAGAGTCGAGTTACCATATCA

GTAGACACGTCTAAGAACCAGTTCTCCCTGAAGCTGAGCTCTGTGACTGCCG

CGGACACGGCCGTGTATTACTGTGCGAGAGAGTCCTACTACTACTACGGTATG

GACGTCTGGGGCCAAGGGACCACGGTCACCGTCTCCTCAGGCTCTACAAGCG

GCTCTGGCAAGCCTGGATCTGGCGAGGGAAGCACCAAGGGCCAGAGCGAGC

TGACACAGCCTAGATCCGTGTCTGGCAGCCCTGGCCAGAGCGTGACCATCAG

CTGTACCGGCACCAGCAGAGATGTGGGCGGCTACAACTACGTGTCCTGGTAT
```

CAGCAGCATCCCGGCAAGGCCCCCAAGCTGATCATCCAC<u>GACGTGATCGAGC</u>

GGAGCAGCGGCGTGCCCGATAGATTCAGCGGCAGCAAGAGCGGCAACACCG

CCAGCCTGACAATCAGCGGACTGCAGGCCGAGGACGAGGCCGACTACTACTG

<u>TTGGAGCTTCGCCGGCAGCTACTACGT</u>GTTCGGCACCGGCACCGATGTGACC

GTGCTGGCGGCCGCAATCGAAGTGATGTACCCCCCTCCCTACCTGGACAACG

AGAAGTCCAACGGCACCATTATCCACGTGAAGGGAAAGCACCTGTGCCCCAG

CCCTCTGTTCCCTGGCCCTAGCAAGCCTTTCTGGGTGCTGGTGGTCGTGGGC

GGAGTGCTGGCCTGTTATAGCCTGCTCGTGACCGTGGCCTTCATCATCTTTTG

GGTGCGCAGCAAGCGGAGCCGGCTGCTGCACAGCGACTACATGAACATGACC

CCCAGACGGCCCGGACCCACCAGAAAGCACTACCAGCCTTACGCCCCTCCCA

GAGACTTCGCCGCCTACAGATCTCGAGTGAAGTTCAGCAGAAGCGCCGACGC

CCCTGCCTATCAGCAGGGCCAGAACCAGCTGTACAACGAGCTGAACCTGGGC

AGACGGGAAGAGTACGACGTGCTGGACAAGCGGAGAGGCAGGGACCCTGAG

ATGGGCGGCAAGCCCAGAAGAAAGAACCCCCAGGAAGGCCTGTATAACGAAC

TGCAGAAAGACAAGATGGCCGAGGCCTACAGCGAGATCGGCATGAAGGGCGA

GCGGAGAAGAGGCAAGGGCCACGATGGCCTGTACCAGGGCCTGAGCACCGC

CACCAAGGACACCTATGACGCCCTGCACATGCAGGCCCTGCCCCCCAGA-3'

Polynucleotide Coding for K52-H1 CAR (Sequence ID No. 139)

5'-GACATCCAGATGACCCAGTCTCCATCTGCCATGTCTGCATCTGTAGGAGACAG

AGTCACCATCACTTGCCGGGCAAGT<u>CAGAGCATTAGCAGCTATTTAAATTGGT</u>

ATCAGCAGAAACCAGGGAAAGCCCCTAAGCTCCTGATCTAT<u>GCTGCATCCAGT</u>

TTGCAAAGTGGGGTCCCATCAAGGTTCAGTGGCAGTGGATCTGGGACAGATT

TCACTCTCACCATCAGCAGTCTGCAGCCTGAAGATTTTGCAACTTACTATTGT

<u>CAGCAATATTATAGTACTCCTCAAACT</u>TTCGGCCCTGGGACCAAAGTGGATAT

CAAAGGCTCTACAAGCGGCTCTGGCAAGCCTGGATCTGGCGAGGGAAGCACC

AAGGGCCAGGTGCAGCTGCAGGAGTCGGGCCCAGGACTGGTGAAGCCTTCG

GATACCCTGTCCCTCACCTGTCTTGTCTCT<u>GGTGGCTCCATCAGTAGTAATTAC</u>

TGGAGCTGGATCCGGCAGGCCCCAGGGAAGGGACTGGAGTGGATTGGACAT

<u>GTCTCCTACAGTGGGAGCACC</u>AACTACAACCCCTCCCTCAAGAGTCGAGTTAC

CATATCAGTAGACACGTCTAAGAACCAGTTCTCCCTGAAGCTGAGCTCTGTGA

CTGCCGCGGACACGGCCGTGTATTACTGT<u>GCGAGAGAGTCCTACTACTACTAC</u>

<u>GGTATGGACGTC</u>TGGGGCCAAGGGACCACGGTCACCGTCTCCTCAGCGGCCG

CAATCGAAGTGATGTACCCCCCTCCCTACCTGGACAACGAGAAGTCCAACGG

CACCATTATCCACGTGAAGGGAAAGCACCTGTGCCCCAGCCCTCTGTTCCCTG

GCCCTAGCAAGCCTTTCTGGGTGCTGGTGGTCGTGGGCGGAGTGCTGGCCTG

TTATAGCCTGCTCGTGACCGTGGCCTTCATCATCTTTTGGGTGCGCAGCAAGC

GGAGCCGGCTGCTGCACAGCGACTACATGAACATGACCCCCAGACGGCCCGG

ACCCACCAGAAAGCACTACCAGCCTTACGCCCCTCCCAGAGACTTCGCCGCC

TACAGATCTCGAGTGAAGTTCAGCAGAAGCGCCGACGCCCCTGCCTATCAGC

AGGGCCAGAACCAGCTGTACAACGAGCTGAACCTGGGCAGACGGGAAGAGTA

```
CGACGTGCTGGACAAGCGGAGAGGCAGGGACCCTGAGATGGGCGGCAAGCC

CAGAAGAAAGAACCCCCAGGAAGGCCTGTATAACGAACTGCAGAAAGACAAG

ATGGCCGAGGCCTACAGCGAGATCGGCATGAAGGGCGAGCGGAGAAGAGGC

AAGGGCCACGATGGCCTGTACCAGGGCCTGAGCACCGCCACCAAGGACACCT

ATGACGCCCTGCACATGCAGGCCCTGCCCCCCAGA-3'
```

Polynucleotide Coding for K73-H1 CAR
                                                        (Sequence ID No. 140)
```
5'-GACATCCAGATGACCCAGTCTCCATCCTCCCTGTCTGCATCTGTAGGAGACAG

AGTCACCATCACTTGCCGGGCAAGTCAGAGCATTAGCAGCTATTTAAATTGGT

ATCAGCAGAAAGCAGGGAAAGCCCCTAAGCTTCTGATCTATGCTGCATCCAGT

TTGCAAAGTGGGGTCCCATCAAGGTTCAGCGGCAGTGGATCTGGGACAGATT

TCACTCTCACCATCAGCTGCCTGCAGTCTGAAGATGTTGCAACCTATTACTGC

CAACAGTATGAAAGTTATCGAAGGTCGTTCGGCCAAGGGACCAAGGTGGAAA

TCAAAGGCTCTACAAGCGGCTCTGGCAAGCCTGGATCTGGCGAGGGAAGCAC

CAAGGGCCAGGTGCAGCTGCAGGAGTCGGGCCCAGGACTGGTGAAGCCTTC

GGATACCCTGTCCCTCACCTGTCTTGTCTCTGGTGGCTCCATCAGTAGTAATT

ACTGGAGCTGGATCCGGCAGGCCCCAGGGAAGGGACTGGAGTGGATTGGAC

ATGTCTCCTACAGTGGGAGCACCAACTACAACCCCTCCCTCAAGAGTCGAGTT

ACCATATCAGTAGACACGTCTAAGAACCAGTTCTCCCTGAAGCTGAGCTCTGT

GACTGCCGCGGACACGGCCGTGTATTACTGTGCGAGAGAGTCCTACTACTACT

ACGGTATGGACGTCTGGGGCCAAGGGACCACGGTCACCGTCTCCTCAGCGGC

CGCAATCGAAGTGATGTACCCCCCTCCCTACCTGGACAACGAGAAGTCCAAC

GGCACCATTATCCACGTGAAGGGAAAGCACCTGTGCCCCAGCCCTCTGTTCC

CTGGCCCTAGCAAGCCTTTCTGGGTGCTGGTGGTCGTGGGCGGAGTGCTGGC

CTGTTATAGCCTGCTCGTGACCGTGGCCTTCATCATCTTTTGGGTGCGCAGCA

AGCGGAGCCGGCTGCTGCACAGCGACTACATGAACATGACCCCCAGACGGCC

CGGACCCACCAGAAAGCACTACCAGCCTTACGCCCCTCCCAGAGACTTCGCC

GCCTACAGATCTCGAGTGAAGTTCAGCAGAAGCGCCGACGCCCCTGCCTATC

AGCAGGGCCAGAACCAGCTGTACAACGAGCTGAACCTGGGCAGACGGGAAG

AGTACGACGTGCTGGACAAGCGGAGAGGCAGGGACCCTGAGATGGGCGGCA

AGCCCAGAAGAAAGAACCCCCAGGAAGGCCTGTATAACGAACTGCAGAAAGA

CAAGATGGCCGAGGCCTACAGCGAGATCGGCATGAAGGGCGAGCGGAGAAG

AGGCAAGGGCCACGATGGCCTGTACCAGGGCCTGAGCACCGCCACCAAGGAC

ACCTATGACGCCCTGCACATGCAGGCCCTGCCCCCCAGA-3'
```

Polynucleotide Coding for K121-H1 CAR
                                                        (Sequence ID No. 141)
```
5'-GACATCCAGATGACCCAGTCTCCATCCTCCCTGTCTGCATCTGTAGGAGACAG

AGTCACCATCACTTGCCGGGCAAGTCAGAGCATTAGCAGCTATTTAAATTGGT

ATCAGCAGAAACCAGGGAAAGCCCCTAAGCTTCCTGATCTATGCTGCATCCAGT

TTGCAAAGTGGGGTCCCATCAAGGTTCAGTGGCAGTGGATCTGGGACAGATT

TCACTCTCACCATCAGCTGCCTGCAGTCTGAAGATTTTGCAACTTATTACTGC

CAACAGTATAATAGTTATTCCCGGACGTTCGGCCAAGGGACCAAGGTGGAAAT

CAAAGGCTCTACAAGCGGCTCTGGCAAGCCTGGATCTGGCGAGGGAAGCACC
```

-continued

AAGGGCCAGGTGCAGCTGCAGGAGTCGGGCCCAGGACTGGTGAAGCCTTCG
GATACCCTGTCCCTCACCTGTCTTGTCTCT<u>GGTGGCTCCATCAGTAGTAATTAC</u>
TGGAGCTGGATCCGGCAGGCCCCAGGGAAGGGACTGGAGTGGATTGGACAT
<u>GTCTCCTACAGTGGGAGCACC</u>AACTACAACCCCTCCCTCAAGAGTCGAGTTAC
CATATCAGTAGACACGTCTAAGAACCAGTTCTCCCTGAAGCTGAGCTCTGTGA
CTGCCGCGGACACGGCCGTGTATTACTGT<u>GCGAGAGAGTCCTACTACTACTAC</u>
GGTATGGACGTCTGGGGCCAAGGGACCACGGTCACCGTCTCCTCAGCGGCCG
CAATCGAAGTGATGTACCCCCCTCCCTACCTGGACAACGAGAAGTCCAACGG
CACCATTATCCACGTGAAGGGAAAGCACCTGTGCCCCAGCCCTCTGTTCCCTG
GCCCTAGCAAGCCTTTCTGGGTGCTGGTGGTCGTGGGCGGAGTGCTGGCCTG
TTATAGCCTGCTCGTGACCGTGGCCTTCATCATCTTTTGGGTGCGCAGCAAGC
GGAGCCGGCTGCTGCACAGCGACTACATGAACATGACCCCCAGACGGCCCGG
ACCCACCAGAAAGCACTACCAGCCTTACGCCCCTCCCAGAGACTTCGCCGCC
TACAGATCTCGAGTGAAGTTCAGCAGAAGCGCCGACGCCCCTGCCTATCAGC
AGGGCCAGAACCAGCTGTACAACGAGCTGAACCTGGGCAGACGGGAAGAGTA
CGACGTGCTGGACAAGCGGAGAGGCAGGGACCCTGAGATGGGCGGCAAGCC
CAGAAGAAAGAACCCCCAGGAAGGCCTGTATAACGAACTGCAGAAAGACAAG
ATGGCCGAGGCCTACAGCGAGATCGGCATGAAGGGCGAGCGGAGAAGAGGC
AAGGGCCACGATGGCCTGTACCAGGGCCTGAGCACCGCCACCAAGGACACCT
ATGACGCCCTGCACATGCAGGCCCTGCCCCCCAGA-3'

Polynucleotide Coding for K124-H1 CAR (Sequence ID No. 142)
5'-GACATCCAGATGACCCAGTCTCCATCCTCCCTGTCTGCATCTGTAGGAGACAG
AGTCACCATCACTTGCCGGGCAAGT<u>CAGAGCATTAGCAGCT</u>ATTTAAATTGGT
ATCAGCAGAAACCAGGGAAAGCCCCTAAGCTCCTGATCTAT<u>GCTGCATCC</u>AGA
TTGGAAAGTGGGGTCCCATCAAGGTTCAGTGGCAGTGGATCTGGGACAGATT
TCACTCTCACCATCAGCTGCCTGCAGTCTGAAGATTTTGCAACTTATTACTGC
<u>CAACAGTATAATAGTTATTCCCGGACG</u>TTCGGCCAAGGGACCAAGGTGGAAAT
CAAAGGCTCTACAAGCGGCTCTGGCAAGCCTGGATCTGGCGAGGGAAGCACC
AAGGGCCAGGTGCAGCTGCAGGAGTCGGGCCCAGGACTGGTGAAGCCTTCG
GATACCCTGTCCCTCACCTGTCTTGTCTCT<u>GGTGGCTCCATCAGTAGTAATTAC</u>
TGGAGCTGGATCCGGCAGGCCCCAGGGAAGGGACTGGAGTGGATTGGACAT
<u>GTCTCCTACAGTGGGAGCACC</u>AACTACAACCCCTCCCTCAAGAGTCGAGTTAC
CATATCAGTAGACACGTCTAAGAACCAGTTCTCCCTGAAGCTGAGCTCTGTGA
CTGCCGCGGACACGGCCGTGTATTACTGT<u>GCGAGAGAGTCCTACTACTACTAC</u>
<u>GGTATGGACGTC</u>TGGGGCCAAGGGACCACGGTCACCGTCTCCTCAGCGGCCG
CAATCGAAGTGATGTACCCCCCTCCCTACCTGGACAACGAGAAGTCCAACGG
CACCATTATCCACGTGAAGGGAAAGCACCTGTGCCCCAGCCCTCTGTTCCCTG
GCCCTAGCAAGCCTTTCTGGGTGCTGGTGGTCGTGGGCGGAGTGCTGGCCTG
TTATAGCCTGCTCGTGACCGTGGCCTTCATCATCTTTTGGGTGCGCAGCAAGC
GGAGCCGGCTGCTGCACAGCGACTACATGAACATGACCCCCAGACGGCCCGG

```
ACCCACCAGAAAGCACTACCAGCCTTACGCCCCTCCCAGAGACTTCGCCGCC

TACAGATCTCGAGTGAAGTTCAGCAGAAGCGCCGACGCCCCTGCCTATCAGC

AGGGCCAGAACCAGCTGTACAACGAGCTGAACCTGGGCAGACGGGAAGAGTA

CGACGTGCTGGACAAGCGGAGAGGCAGGGACCCTGAGATGGGCGGCAAGCC

CAGAAGAAAGAACCCCCAGGAAGGCCTGTATAACGAACTGCAGAAAGACAAG

ATGGCCGAGGCCTACAGCGAGATCGGCATGAAGGGCGAGCGGAGAAGAGGC

AAGGGCCACGATGGCCTGTACCAGGGCCTGAGCACCGCCACCAAGGACACCT

ATGACGCCCTGCACATGCAGGCCCTGCCCCCCAGA-3'
```
Polynucleotide Coding for K125-H1 CAR
                                            (Sequence ID No. 143)
```
5'-GACATCCAGATGACCCAGTCTCCATCCTCCCTGTCTGCATCTGTAGGAGACAG

AGTCACCATCACTTGCCGGGCAAGTCAGAGCATTAGCAGCTATTTAAATTGGT

ATCAGCAGAAACCAGGGAAAGCCCCTAAGCTCCTGCTCTATGCTGCATCCAGA

TTGGAAAGTGGGGTCCCATCAAGGTTCAGCGGCAGTGGATCTGGGACAGAAT

TCACTCTCACCATCAGCAGCCTGCAGCCTGATGATTTTGCAACTTATTACTGC

CAACAGTATAATAGTTATTCTCCGTGCACTTTCGGCCCTGGGACCAAAGTGGA

TATCAAAGGCTCTACAAGCGGCTCTGGCAAGCCTGGATCTGGCGAGGGAAGC

ACCAAGGGCCAGGTGCAGCTGCAGGAGTCGGGCCCAGGACTGGTGAAGCCT

TCGGATACCCTGTCCCTCACCTGTCTTGTCTCTGGTGGCTCCATCAGTAGTAA

TTACTGGAGCTGGATCCGGCAGGCCCCAGGGAAGGGACTGGAGTGGATTGGA

CATGTCTCCTACAGTGGGAGCACCAACTACAACCCCTCCCTCAAGAGTCGAGT

TACCATATCAGTAGACACGTCTAAGAACCAGTTCTCCCTGAAGCTGAGCTCTG

TGACTGCCGCGGACACGGCCGTGTATTACTGTGCGAGAGAGTCCTACTACTAC

TACGGTATGGACGTCTGGGGCCAAGGGACCACGGTCACCGTCTCCTCAGCGG

CCGCAATCGAAGTGATGTACCCCCCTCCCTACCTGGACAACGAGAAGTCCAAC

GGCACCATTATCCACGTGAAGGGAAAGCACCTGTGCCCCAGCCCTCTGTTCC

CTGGCCCTAGCAAGCCTTTCTGGGTGCTGGTGGTCGTGGGCGGAGTGCTGGC

CTGTTATAGCCTGCTCGTGACCGTGGCCTTCATCATCTTTTGGGTGCGCAGCA

AGCGGAGCCGGCTGCTGCACAGCGACTACATGAACATGACCCCCAGACGGCC

CGGACCCACCAGAAAGCACTACCAGCCTTACGCCCCTCCCAGAGACTTCGCC

GCCTACAGATCTCGAGTGAAGTTCAGCAGAAGCGCCGACGCCCCTGCCTATC

AGCAGGGCCAGAACCAGCTGTACAACGAGCTGAACCTGGGCAGACGGGAAG

AGTACGACGTGCTGGACAAGCGGAGAGGCAGGGACCCTGAGATGGGCGGCA

AGCCCAGAAGAAAGAACCCCCAGGAAGGCCTGTATAACGAACTGCAGAAAGA

CAAGATGGCCGAGGCCTACAGCGAGATCGGCATGAAGGGCGAGCGGAGAAG

AGGCAAGGGCCACGATGGCCTGTACCAGGGCCTGAGCACCGCCACCAAGGAC

ACCTATGACGCCCTGCACATGCAGGCCCTGCCCCCCAGA-3'
```
Polynucleotide Coding for K131-H1 CAR
                                            (Sequence ID No. 144)
```
5'-GACATCCAGATGACCCAGTCTCCATCCTCCCTGTCTGCATCTGTAGGGGACAG

AGTCTCCATCACTTGCCGGGCAAGTCAGGACATTAGCAGGTATTTAAATTGGT

ATCAGCAGAAACCAGGGAAAGCCCCTAAGCTCCTGCTCTATGCTGCATCCAGA

TTGGAAAGTGGGGTCCCATCCAGGTTCAGTGGCAGTGGATCTGGGACAGACT
```

-continued

TCACTCTCACCATCACCAGCCTGCAGCCTGATGACTTTGCAACTTATTACTGC

CAACAGTATGATAATCTGATCACCTTCGGCCAAGGGACACGACTGGAGATTAA

AGGCTCTACAAGCGGCTCTGGCAAGCCTGGATCTGGCGAGGGAAGCACCAAG

GGCCAGGTGCAGCTGCAGGAGTCGGGCCCAGGACTGGTGAAGCCTTCGGATA

CCCTGTCCCTCACCTGTCTTGTCTCTGGTGGCTCCATCAGTAGTAATTACTGG

AGCTGGATCCGGCAGGCCCCAGGGAAGGGACTGGAGTGGATTGGACATGTCT

CCTACAGTGGGAGCACCAACTACAACCCCTCCCTCAAGAGTCGAGTTACCATA

TCAGTAGACACGTCTAAGAACCAGTTCTCCCTGAAGCTGAGCTCTGTGACTGC

CGCGGACACGGCCGTGTATTACTGTGCGAGAGAGTCCTACTACTACTACGGTA

TGGACGTCTGGGGCCAAGGGACCACGGTCACCGTCTCCTCAGCGGCCGCAAT

CGAAGTGATGTACCCCCCTCCCTACCTGGACAACGAGAAGTCCAACGGCACC

ATTATCCACGTGAAGGGAAAGCACCTGTGCCCCAGCCCTCTGTTCCCTGGCCC

TAGCAAGCCTTTCTGGGTGCTGGTGGTCGTGGGCGGAGTGCTGGCCTGTTAT

AGCCTGCTCGTGACCGTGGCCTTCATCATCTTTTGGGTGCGCAGCAAGCGGA

GCCGGCTGCTGCACAGCGACTACATGAACATGACCCCCAGACGGCCCGGACC

CACCAGAAAGCACTACCAGCCTTACGCCCCTCCCAGAGACTTCGCCGCCTACA

GATCTCGAGTGAAGTTCAGCAGAAGCGCCGACGCCCCTGCCTATCAGCAGGG

CCAGAACCAGCTGTACAACGAGCTGAACCTGGGCAGACGGGAAGAGTACGAC

GTGCTGGACAAGCGGAGAGGCAGGGACCCTGAGATGGGCGGCAAGCCCAGA

AGAAAGAACCCCCAGGAAGGCCTGTATAACGAACTGCAGAAAGACAAGATGG

CCGAGGCCTACAGCGAGATCGGCATGAAGGGCGAGCGGAGAAGAGGCAAGG

GCCACGATGGCCTGTACCAGGGCCTGAGCACCGCCACCAAGGACACCTATGA

CGCCCTGCACATGCAGGCCCTGCCCCCCAGA-3'

Polynucleotide Coding for K145-H1 CAR
(Sequence ID No. 145)
5'-GACATCCAGATGACCCAGTCTCCATCCTCCCTGTCTGCATCTGTAGGGGACAG

AGTCTCCATCACTTGCCGGGCAAGTCAGGACATTAGCAGGTATTTAAATTGGT

ATCAGCAGAAACCAGGGAAAGCCCCTAAGCTCCTGCTCTATGCTGCATCCAGA

TTGGAAAGTGGGGTCCCATCCAGGTTCAGTGGCAGTGGATCTGGGACAGACT

TCACTCTCACCATCACCAGCCTGCAGCCTGATGACTTTGCAACTTATTACTGC

CAACAGTATAATAGTTATTCCCGGACGTTCGGCCAAGGGACCAAGGTGGAAAT

CAAAGGCTCTACAAGCGGCTCTGGCAAGCCTGGATCTGGCGAGGGAAGCACC

AAGGGCCAGGTGCAGCTGCAGGAGTCGGGCCCAGGACTGGTGAAGCCTTCG

GATACCCTGTCCCTCACCTGTCTTGTCTCTGGTGGCTCCATCAGTAGTAATTAC

TGGAGCTGGATCCGGCAGGCCCCAGGGAAGGGACTGGAGTGGATTGGACAT

GTCTCCTACAGTGGGAGCACCAACTACAACCCCTCCCTCAAGAGTCGAGTTAC

CATATCAGTAGACACGTCTAAGAACCAGTTCTCCCTGAAGCTGAGCTCTGTGA

CTGCCGCGGACACGGCCGTGTATTACTGTGCGAGAGAGTCCTACTACTACTAC

GGTATGGACGTCTGGGGCCAAGGGACCACGGTCACCGTCTCCTCAGCGGCCG

CAATCGAAGTGATGTACCCCCCTCCCTACCTGGACAACGAGAAGTCCAACGG

CACCATTATCCACGTGAAGGGAAAGCACCTGTGCCCCAGCCCTCTGTTCCCTG

-continued

GCCCTAGCAAGCCTTTCTGGGTGCTGGTGGTCGTGGGCGGAGTGCTGGCCTG

TTATAGCCTGCTCGTGACCGTGGCCTTCATCATCTTTTGGGTGCGCAGCAAGC

GGAGCCGGCTGCTGCACAGCGACTACATGAACATGACCCCCAGACGGCCCGG

ACCCACCAGAAAGCACTACCAGCCTTACGCCCCTCCCAGAGACTTCGCCGCC

TACAGATCTCGAGTGAAGTTCAGCAGAAGCGCCGACGCCCCTGCCTATCAGC

AGGGCCAGAACCAGCTGTACAACGAGCTGAACCTGGGCAGACGGGAAGAGTA

CGACGTGCTGGACAAGCGGAGAGGCAGGGACCCTGAGATGGGCGGCAAGCC

CAGAAGAAAGAACCCCCAGGAAGGCCTGTATAACGAACTGCAGAAAGACAAG

ATGGCCGAGGCCTACAGCGAGATCGGCATGAAGGGCGAGCGGAGAAGAGGC

AAGGGCCACGATGGCCTGTACCAGGGCCTGAGCACCGCCACCAAGGACACCT

ATGACGCCCTGCACATGCAGGCCCTGCCCCCCAGA-3'

Polynucleotide Coding for K151-H1 CAR (Sequence ID No. 146)

5'-GACATCCAGATGACCCAGTCTCCATCCTCCCTGTCTGCATCTGTAGGGGACAG

AGTCACCATCACTTGCCGGGCAAGTCAGAGCATTAGCAGCTATTTAAATTGGT

ATCAGCAGAAACCAGGGAAAGCCCCTAAGCTCCTGATCTATGCTGCATCCAGT

TTGCAAAGTGGGGTCCCATCAAGGTTCAGTGGCAGTGGATCTGGGACAGACT

TCACTCTCACCATCACCAGCCTGCAGCCTGATGACTTTGCAACTTATTACTGC

CAACAGTATGATAATCTGATCACCTTCGGCCAAGGGACACGACTGGAGATTAA

AGGCTCTACAAGCGGCTCTGGCAAGCCTGGATCTGGCGAGGGAAGCACCAAG

GGCCAGGTGCAGCTGCAGGAGTCGGGCCCAGGACTGGTGAAGCCTTCGGATA

CCCTGTCCCTCACCTGTCTTGTCTCTGGTGGCTCCATCAGTAGTAATTACTGG

AGCTGGATCCGGCAGGCCCCAGGGAAGGGACTGGAGTGGATTGGACATGTCT

CCTACAGTGGGAGCACCAACTACAACCCCTCCCTCAAGAGTCGAGTTACCATA

TCAGTAGACACGTCTAAGAACCAGTTCTCCCTGAAGCTGAGCTCTGTGACTGC

CGCGGACACGGCCGTGTATTACTGTGCGAGAGAGTCCTACTACTACTACGGTA

TGGACGTCTGGGGCCAAGGGACCACGGTCACCGTCTCCTCAGCGGCCGCAAT

CGAAGTGATGTACCCCCCTCCCTACCTGGACAACGAGAAGTCCAACGGCACC

ATTATCCACGTGAAGGGAAAGCACCTGTGCCCCAGCCCTCTGTTCCCTGGCCC

TAGCAAGCCTTTCTGGGTGCTGGTGGTCGTGGGCGGAGTGCTGGCCTGTTAT

AGCCTGCTCGTGACCGTGGCCTTCATCATCTTTTGGGTGCGCAGCAAGCGGA

GCCGGCTGCTGCACAGCGACTACATGAACATGACCCCCAGACGGCCCGGACC

CACCAGAAAGCACTACCAGCCTTACGCCCCTCCCAGAGACTTCGCCGCCTACA

GATCTCGAGTGAAGTTCAGCAGAAGCGCCGACGCCCCTGCCTATCAGCAGGG

CCAGAACCAGCTGTACAACGAGCTGAACCTGGGCAGACGGGAAGAGTACGAC

GTGCTGGACAAGCGGAGAGGCAGGGACCCTGAGATGGGCGGCAAGCCCAGA

AGAAAGAACCCCCAGGAAGGCCTGTATAACGAACTGCAGAAAGACAAGATGG

CCGAGGCCTACAGCGAGATCGGCATGAAGGGCGAGCGGAGAAGAGGCAAGG

GCCACGATGGCCTGTACCAGGGCCTGAGCACCGCCACCAAGGACACCTATGA

CGCCCTGCACATGCAGGCCCTGCCCCCCAGA-3'

-continued

Polynucleotide Coding for K160-H1 CAR
(Sequence ID No. 147)
5'-GAAATTGTGTTGACGCAGTCTCCAGCCACCCTGTCTGTGTCTCCAGGGGAAA
GAGCCACCCTCTCCTGCAGGGCCAGTCAGAGTGTTAGCAGCAACTTAGCCTG
GTACCAGCAGAAACCTGGCCAGGCTCCCAGGCTCCTCATCTATGGTGCATCCA
CCAGGGCCACTGGTATCCCAGCCAGGTTCAGTGGCAGTGGGTCTGGGACAGA
GTTCACTCTCACCATCAGCAGACTGGAGCCTGAAGATTTTGCAACCTATTACT
GCCAACAGTATAATAGTTATTCCCGGACGTTCGGCCAAGGGACCAAGGTGGAA
ATCAAAGGCTCTACAAGCGGCTCTGGCAAGCCTGGATCTGGCGAGGGAAGCA
CCAAGGGCCAGGTGCAGCTGCAGGAGTCGGGCCCAGGACTGGTGAAGCCTT
CGGATACCCTGTCCCTCACCTGTCTTGTCTCTGGTGGCTCCATCAGTAGTAAT
TACTGGAGCTGGATCCGGCAGGCCCCAGGGAAGGGACTGGAGTGGATTGGAC
ATGTCTCCTACAGTGGGAGCACCAACTACAACCCCTCCCTCAAGAGTCGAGTT
ACCATATCAGTAGACACGTCTAAGAACCAGTTCTCCCTGAAGCTGAGCTCTGT
GACTGCCGCGGACACGGCCGTGTATTACTGTGCGAGAGAGTCCTACTACTACT
ACGGTATGGACGTCTGGGGCCAAGGGACCACGGTCACCGTCTCCTCAGCGGC
CGCAATCGAAGTGATGTACCCCCCTCCCTACCTGGACAACGAGAAGTCCAAC
GGCACCATTATCCACGTGAAGGGAAAGCACCTGTGCCCCAGCCCTCTGTTCC
CTGGCCCTAGCAAGCCTTTCTGGGTGCTGGTGGTCGTGGGCGGAGTGCTGGC
CTGTTATAGCCTGCTCGTGACCGTGGCCTTCATCATCTTTTGGGTGCGCAGCA
AGCGGAGCCGGCTGCTGCACAGCGACTACATGAACATGACCCCCAGACGGCC
CGGACCCACCAGAAAGCACTACCAGCCTTACGCCCCTCCCAGAGACTTCGCC
GCCTACAGATCTCGAGTGAAGTTCAGCAGAAGCGCCGACGCCCCTGCCTATC
AGCAGGGCCAGAACCAGCTGTACAACGAGCTGAACCTGGGCAGACGGGAAG
AGTACGACGTGCTGGACAAGCGGAGAGGCAGGGACCCTGAGATGGGCGGCA
AGCCCAGAAGAAAGAACCCCCAGGAAGGCCTGTATAACGAACTGCAGAAAGA
CAAGATGGCCGAGGCCTACAGCGAGATCGGCATGAAGGGCGAGCGGAGAAG
AGGCAAGGGCCACGATGGCCTGTACCAGGGCCTGAGCACCGCCACCAAGGAC
ACCTATGACGCCCTGCACATGCAGGCCCTGCCCCCCAGA-3'

Polynucleotide Coding for K173-H1 CAR
(Sequence ID No. 148)
5'-GACATCCAGATGACCCAGTCTCCATCCTCCCTGTCTGCATCTGTAGGAGACAG
AGTCACCATCACTTGCCGGGCAAGTCAGAGCATTAGCAGCTATTTAAATTGGT
ATCAGCAGAAAGCAGGGAAAGCCCCTAAGCTTCTGATCTATGCTGCATCCAGT
TTGCAAAGTGGGGTCCCATCAAGGTTCAGCGGCAGTGGATCTGGGACAGATT
TCACTCTCACCATCAGCTGCCTGCAGTCTGAAGATGTTGCAACCTATTACTGC
CAACAGTATGAAAGTTATTCCCGGACGTTCGGCCAAGGGACCAAGGTGGAAA
TCAAAGGCTCTACAAGCGGCTCTGGCAAGCCTGGATCTGGCGAGGGAAGCAC
CAAGGGCCAGGTGCAGCTGCAGGAGTCGGGCCCAGGACTGGTGAAGCCTTC
GGATACCCTGTCCCTCACCTGTCTTGTCTCTGGTGGCTCCATCAGTAGTAATT
ACTGGAGCTGGATCCGGCAGGCCCCAGGGAAGGGACTGGAGTGGATTGGAC
ATGTCTCCTACAGTGGGAGCACCAACTACAACCCCTCCCTCAAGAGTCGAGTT -continued

ACCATATCAGTAGACACGTCTAAGAACCAGTTCTCCCTGAAGCTGAGCTCTGT

GACTGCCGCGGACACGGCCGTGTATTACTGT<u>GCGAGAGAGTCCTACTACTACT</u>

<u>ACGGTATGGACGT</u>CTGGGGCCAAGGGACCACGGTCACCGTCTCCTCAGCGGC

CGCAATCGAAGTGATGTACCCCCCTCCCTACCTGGACAACGAGAAGTCCAAC

GGCACCATTATCCACGTGAAGGGAAAGCACCTGTGCCCCAGCCCTCTGTTCC

CTGGCCCTAGCAAGCCTTTCTGGGTGCTGGTGGTCGTGGGCGGAGTGCTGGC

CTGTTATAGCCTGCTCGTGACCGTGGCCTTCATCATCTTTTGGGTGCGCAGCA

AGCGGAGCCGGCTGCTGCACAGCGACTACATGAACATGACCCCCAGACGGCC

CGGACCCACCAGAAAGCACTACCAGCCTTACGCCCCTCCCAGAGACTTCGCC

GCCTACAGATCTCGAGTGAAGTTCAGCAGAAGCGCCGACGCCCCTGCCTATC

AGCAGGGCCAGAACCAGCTGTACAACGAGCTGAACCTGGGCAGACGGGAAG

AGTACGACGTGCTGGACAAGCGGAGAGGCAGGGACCCTGAGATGGGCGGCA

AGCCCAGAAGAAAGAACCCCCAGGAAGGCCTGTATAACGAACTGCAGAAAGA

CAAGATGGCCGAGGCCTACAGCGAGATCGGCATGAAGGGCGAGCGGAGAAG

AGGCAAGGGCCACGATGGCCTGTACCAGGGCCTGAGCACCGCCACCAAGGAC

ACCTATGACGCCCTGCACATGCAGGCCCTGCCCCCCAGA-3'

Polynucleotide Coding for L1-3M4E5H CAR (Sequence ID No. 149)

5'-CAGTCTGCCCTGACTCAGCCTCCCTCCGCGTCCGGGTCTCCTGGACAGTCAG

TCACCATCTCCTGCACTGGAACC<u>AGCAGTGACGTTGGTGGTTATGACTTT</u>GTC

TCCTGGTACCAACAGCACCCAGGCGAAGCCCCCAAACTCCTCGTTTAT<u>GATGT</u>

<u>CAAT</u>AACCGGCCCTCAGGGGTTTCTAATCGCTTCTCTGGCTCCAAGTCTGGCA

ACACGGCCTCCCTGACCATCTCTGGGCTCCAGGCTGAGGACGAGGGTGACTA

TTACTGC<u>AGCTCATATGCAGGCAGCAACAGCGTCTT</u>CGGAACTGGGACCAAG

GTCACCGTCCTAGGCTCTACAAGCGGCTCTGGCAAGCCTGGATCTGGCGAGG

GAAGCACCAAGGGCGAAGTGCAGCTGCTGGAATCTGGCGGCGGACTGGTGC

AGCCTGGCGGATCTCTGAGACTGAGCTGTGCCGCCAGCGGCTTCACCTTCAG

CACCTACCAGATGAGCTGGGTGCGCCAGGCCCCTGGCAAAGGACTGGAATGG

GTGTCCGG<u>CATCGTGTCCAGCGGCGGCTCTAC</u>AGCCTACGCCGATAGCGTGA

AGGGCCGGTTCACCATCAGCCGGGACAACAGCAAGAACACCCTGTACCTGCA

GATGAACAGCCTGAGAGCCGAGGACACCGCCGTGTACTATTGT<u>GCCGGGGAG</u>

<u>CTGCTGCCCTACTACGGCATGGATGTGT</u>GGGGCCAGGGCACCACCGTGACAG

TGTCCTCAGCGGCCGCAATCGAAGTGATGTACCCCCCTCCCTACCTGGACAAC

GAGAAGTCCAACGGCACCATTATCCACGTGAAGGGAAAGCACCTGTGCCCCA

GCCCTCTGTTCCCTGGCCCTAGCAAGCCTTTCTGGGTGCTGGTGGTCGTGGG

CGGAGTGCTGGCCTGTTATAGCCTGCTCGTGACCGTGGCCTTCATCATCTTTT

GGGTGCGCAGCAAGCGGAGCCGGCTGCTGCACAGCGACTACATGAACATGAC

CCCCAGACGGCCCGGACCCACCAGAAAGCACTACCAGCCTTACGCCCCTCCC

AGAGACTTCGCCGCCTACAGATCTCGAGTGAAGTTCAGCAGAAGCGCCGACG

CCCCTGCCTATCAGCAGGGCCAGAACCAGCTGTACAACGAGCTGAACCTGGG

CAGACGGGAAGAGTACGACGTGCTGGACAAGCGGAGAGGCAGGGACCCTGA

GATGGGCGGCAAGCCCAGAAGAAAGAACCCCCAGGAAGGCCTGTATAACGAA

CTGCAGAAAGACAAGATGGCCGAGGCCTACAGCGAGATCGGCATGAAGGGCG

AGCGGAGAAGAGGCAAGGGCCACGATGGCCTGTACCAGGGCCTGAGCACCG

CCACCAAGGACACCTATGACGCCCTGCACATGCAGGCCCTGCCCCCCAGA-3'

Polynucleotide Coding for 3M4E5H-L1 CAR
(Sequence ID No. 150)
5'-GAAGTGCAGCTGCTGGAATCTGGCGGCGGACTGGTGCAGCCTGGCGGATCTC

TGAGACTGAGCTGTGCCGCCAGCGGCTTCACCTTCAGCACCTACCAGATGAG

CTGGGTGCGCCAGGCCCCTGGCAAAGGACTGGAATGGGTGTCCGGCATCGTG

TCCAGCGGCGGCTCTACAGCCTACGCCGATAGCGTGAAGGGCCGGTTCACCA

TCAGCCGGGACAACAGCAAGAACACCCTGTACCTGCAGATGAACAGCCTGAG

AGCCGAGGACACCGCCGTGTACTATTGTGCCGGGGAGCTGCTGCCCTACTAC

GGCATGGATGTGTGGGGCCAGGGCACCACCGTGACAGTGTCCTCAGGCTCTA

CAAGCGGCTCTGGCAAGCCTGGATCTGGCGAGGGAAGCACCAAGGGCCAGT

CTGCCCTGACTCAGCCTCCCTCCGCGTCCGGGTCTCCTGGACAGTCAGTCAC

CATCTCCTGCACTGGAACCAGCAGTGACGTTGGTGGTTATGACTTTGTCTCCT

GGTACCAACAGCACCCAGGCGAAGCCCCCAAACTCCTCGTTTATGATGTCAAT

AACCGGCCCTCAGGGGTTTCTAATCGCTTCTCTGGCTCCAAGTCTGGCAACAC

GGCCTCCCTGACCATCTCTGGGCTCCAGGCTGAGGACGAGGGTGACTATTAC

TGCAGCTCATATGCAGGCAGCAACAGCGTCTTCGGAACTGGGACCAAGGTCA

CCGTCCTAGCGGCCGCAATCGAAGTGATGTACCCCCCTCCCTACCTGGACAAC

GAGAAGTCCAACGGCACCATTATCCACGTGAAGGGAAAGCACCTGTGCCCCA

GCCCTCTGTTCCCTGGCCCTAGCAAGCCTTTCTGGGTGCTGGTGGTCGTGGG

CGGAGTGCTGGCCTGTTATAGCCTGCTCGTGACCGTGGCCTTCATCATCTTTT

GGGTGCGCAGCAAGCGGAGCCGGCTGCTGCACAGCGACTACATGAACATGAC

CCCCAGACGGCCCGGACCCACCAGAAAGCACTACCAGCCTTACGCCCCTCCC

AGAGACTTCGCCGCCTACAGATCTCGAGTGAAGTTCAGCAGAAGCGCCGACG

CCCCTGCCTATCAGCAGGGCCAGAACCAGCTGTACAACGAGCTGAACCTGGG

CAGACGGGAAGAGTACGACGTGCTGGACAAGCGGAGAGGCAGGGACCCTGA

GATGGGCGGCAAGCCCAGAAGAAAGAACCCCCAGGAAGGCCTGTATAACGAA

CTGCAGAAAGACAAGATGGCCGAGGCCTACAGCGAGATCGGCATGAAGGGCG

AGCGGAGAAGAGGCAAGGGCCACGATGGCCTGTACCAGGGCCTGAGCACCG

CCACCAAGGACACCTATGACGCCCTGCACATGCAGGCCCTGCCCCCCAGA-3'

Polynucleotide Coding for L66-3M4E5H CAR
(Sequence ID No. 151)
5'-CAGTCTGCCCTGACTCAGCCTGCCTCCGTGTCTGGGTCTCCTGGACAGTCGA

TCACCATCTCCTGCACTGGGACCAGCAGTGACGTTGGTGGTTATGAATTTGTC

TCCTGGTACCAACAACACCCAGGCAGCGCCCCCAAACTCATTATTTATGACGT

AATAGAGCGTCCCTTCGGTGTCTCCTATCGGTTCTCTGCCTCCAAGTCAGGCA

ACACGGCCTCCCTGACGATCTCTGGGCTCCAGGGTGAAGACGAGGCTGATTA

CTTCTGCAGCTCATATACAAGCAGCAGCACTTATGTCTTCGGAACTGGGACCA

AGGTCACCGTCCTAGGCTCTACAAGCGGCTCTGGCAAGCCTGGATCTGGCGA

GGGAAGCACCAAGGGCGAAGTGCAGCTGCTGGAATCTGGCGGCGGACTGGT

-continued

GCAGCCTGGCGGATCTCTGAGACTGAGCTGTGCCGCCAGCGGCTTCACCTTC
AGCACCTACCAGATGAGCTGGGTGCGCCAGGCCCCTGGCAAAGGACTGGAAT
GGGTGTCCGGCATCGTGTCCAGCGGCGGCTCTACAGCCTACGCCGATAGCGT
GAAGGGCCGGTTCACCATCAGCCGGGACAACAGCAAGAACACCCTGTACCTG
CAGATGAACAGCCTGAGAGCCGAGGACACCGCCGTGTACTATTGTGCCGGGG
AGCTGCTGCCCTACTACGGCATGGATGTGTGGGGCCAGGGCACCACCGTGAC
AGTGTCCTCAGCGGCCGCAATCGAAGTGATGTACCCCCCTCCCTACCTGGACA
ACGAGAAGTCCAACGGCACCATTATCCACGTGAAGGGAAAGCACCTGTGCCC
CAGCCCTCTGTTCCCTGGCCCTAGCAAGCCTTTCTGGGTGCTGGTGGTCGTG
GGCGGAGTGCTGGCCTGTTATAGCCTGCTCGTGACCGTGGCCTTCATCATCTT
TTGGGTGCGCAGCAAGCGGAGCCGGCTGCTGCACAGCGACTACATGAACATG
ACCCCCAGACGGCCCGGACCCACCAGAAAGCACTACCAGCCTTACGCCCCTC
CCAGAGACTTCGCCGCCTACAGATCTCGAGTGAAGTTCAGCAGAAGCGCCGA
CGCCCCTGCCTATCAGCAGGGCCAGAACCAGCTGTACAACGAGCTGAACCTG
GGCAGACGGGAAGAGTACGACGTGCTGGACAAGCGGAGAGGCAGGGACCCT
GAGATGGGCGGCAAGCCCAGAAGAAAGAACCCCCAGGAAGGCCTGTATAACG
AACTGCAGAAAGACAAGATGGCCGAGGCCTACAGCGAGATCGGCATGAAGGG
CGAGCGGAGAAGAGGCAAGGGCCACGATGGCCTGTACCAGGGCCTGAGCAC
CGCCACCAAGGACACCTATGACGCCCTGCACATGCAGGCCCTGCCCCCCAGA-3'

Polynucleotide Coding for L73-3M4E5H CAR
(Sequence ID No. 152)
5'-CAGTCTGCCCTGACTCAGCCTGCCTCCGTGTCTGGGTCTCCTGGACAGTCGA
TCACCATCTCCTGCACTGGAACCGGCAGTGACGTTGGTGCTTATGACTATGTC
TCCTGGTACCAACATCACCCAGGCAGAGCCCCCAGACTCATCATTCGTGATGT
CAGTGTGCGGCCCTCAGGGGTCCCTGATCGCTTCTCTGGCTCCAAGTCTGGC
AACACGGCCTCCCTGACCATCTCTGGGCTCCAGGCTGAGGACGAGGCTGATT
ATTACTGCTCCTCATATTCAGGCAGCAGCACTTGGGTGTTCGGCGGGGGGAC
CAAGCTGACCGTCCTAGGCTCTACAAGCGGCTCTGGCAAGCCTGGATCTGGC
GAGGGAAGCACCAAGGGCGAAGTGCAGCTGCTGGAATCTGGCGGCGGACTG
GTGCAGCCTGGCGGATCTCTGAGACTGAGCTGTGCCGCCAGCGGCTTCACCT
TCAGCACCTACCAGATGAGCTGGGTGCGCCAGGCCCCTGGCAAAGGACTGGA
ATGGGTGTCCGGCATCGTGTCCAGCGGCGGCTCTACAGCCTACGCCGATAGC
GTGAAGGGCCGGTTCACCATCAGCCGGGACAACAGCAAGAACACCCTGTACC
TGCAGATGAACAGCCTGAGAGCCGAGGACACCGCCGTGTACTATTGTGCCGG
GGAGCTGCTGCCCTACTACGGCATGGATGTGTGGGGCCAGGGCACCACCGTG
ACAGTGTCCTCAGCGGCCGCAATCGAAGTGATGTACCCCCCTCCCTACCTGGA
CAACGAGAAGTCCAACGGCACCATTATCCACGTGAAGGGAAAGCACCTGTGC
CCCAGCCCTCTGTTCCCTGGCCCTAGCAAGCCTTTCTGGGTGCTGGTGGTCG
TGGGCGGAGTGCTGGCCTGTTATAGCCTGCTCGTGACCGTGGCCTTCATCATC
TTTTGGGTGCGCAGCAAGCGGAGCCGGCTGCTGCACAGCGACTACATGAACA
TGACCCCCAGACGGCCCGGACCCACCAGAAAGCACTACCAGCCTTACGCCCC
TCCCAGAGACTTCGCCGCCTACAGATCTCGAGTGAAGTTCAGCAGAAGCGCC

```
GACGCCCCTGCCTATCAGCAGGGCCAGAACCAGCTGTACAACGAGCTGAACC

TGGGCAGACGGGAAGAGTACGACGTGCTGGACAAGCGGAGAGGCAGGGACC

CTGAGATGGGCGGCAAGCCCAGAAGAAAGAACCCCCAGGAAGGCCTGTATAA

CGAACTGCAGAAAGACAAGATGGCCGAGGCCTACAGCGAGATCGGCATGAAG

GGCGAGCGGAGAAGAGGCAAGGGCCACGATGGCCTGTACCAGGGCCTGAGC

ACCGCCACCAAGGACACCTATGACGCCCTGCACATGCAGGCCCTGCCCCCCA

GA-3'

Polynucleotide Coding for L80-3M4E5H CAR
                                             (Sequence ID No. 153)
5'-CAGTCTGCCCTGACTCAGCCTGCCTCCGTGTCTGGGTCTCCTGGACAGTCGA

TCACCATCTCCTGCACTGGAACCAGCAGTGATGTTGGGAGTTATAACCTTGTC

TCCTGGTACCAACAACACCCAGGCAAAGCCCCCAAACTCATGATTTATGATGT

CAGTAATCGGCCCTCAGGGGTTTCTTATCGCTTCTCTGGCTCCAAGTCTGGCA

ACACGGCCTCCCTGACCATCTCTGGGCTCCAGGCTGAGGACGAGGCTGATTA

TTACTGCAGCTCATATACAAGCAGCAGCACTTTCGCGGTGTTCGGCGGAGGG

ACCCAGCTGACCGTCCTCGGCTCTACAAGCGGCTCTGGCAAGCCTGGATCTG

GCGAGGGAAGCACCAAGGGCGAAGTGCAGCTGCTGGAATCTGGCGGCGGAC

TGGTGCAGCCTGGCGGATCTCTGAGACTGAGCTGTGCCGCCAGCGGCTTCAC

CTTCAGCACCTACCAGATGAGCTGGGTGCGCCAGGCCCCTGGCAAAGGACTG

GAATGGGTGTCCGGCATCGTGTCCAGCGGCGGCTCTACAGCCTACGCCGATA

GCGTGAAGGGCCGGTTCACCATCAGCCGGGACAACAGCAAGAACACCCTGTA

CCTGCAGATGAACAGCCTGAGAGCCGAGGACACCGCCGTGTACTATTGTGCC

GGGGAGCTGCTGCCCTACTACGGCATGGATGTGTGGGGCCAGGGCACCACCG

TGACAGTGTCCTCAGCGGCCGCAATCGAAGTGATGTACCCCCCTCCCTACCTG

GACAACGAGAAGTCCAACGGCACCATTATCCACGTGAAGGGAAAGCACCTGT

GCCCCAGCCCTCTGTTCCCTGGCCCTAGCAAGCCTTTCTGGGTGCTGGTGGT

CGTGGGCGGAGTGCTGGCCTGTTATAGCCTGCTCGTGACCGTGGCCTTCATC

ATCTTTTGGGTGCGCAGCAAGCGGAGCCGGCTGCTGCACAGCGACTACATGA

ACATGACCCCCAGACGGCCCGGACCCACCAGAAAGCACTACCAGCCTTACGC

CCCTCCCAGAGACTTCGCCGCCTACAGATCTCGAGTGAAGTTCAGCAGAAGC

GCCGACGCCCCTGCCTATCAGCAGGGCCAGAACCAGCTGTACAACGAGCTGA

ACCTGGGCAGACGGGAAGAGTACGACGTGCTGGACAAGCGGAGAGGCAGGG

ACCCTGAGATGGGCGGCAAGCCCAGAAGAAAGAACCCCCAGGAAGGCCTGTA

TAACGAACTGCAGAAAGACAAGATGGCCGAGGCCTACAGCGAGATCGGCATG

AAGGGCGAGCGGAGAAGAGGCAAGGGCCACGATGGCCTGTACCAGGGCCTG

AGCACCGCCACCAAGGACACCTATGACGCCCTGCACATGCAGGCCCTGCCCC

CCAGA-3'

Polynucleotide Coding for L88-3M4E5H CAR
                                             (Sequence ID No. 154)
5'-CAATCTGCCCTGCCTCAGCCTGCCTCCGTGTCTGGGTCTCCTGGACAGTCAGT
CACCATCTCCTGCACTGGAACCAGCAGTGATGTTGGTGGTTATAACTATGTCT
CCTGGTACCAACAGCACCCAGGCAAAGCCCCCAAACTCATGATTTATGATGTC
AGTAAGCGGCCCTCAGGGGTCCCTGATCGCTTCTCTGGTTCCAAGTCTGGCA
ACACGGCCTCCCTGACCGTCTCTGGGCTCCAGGCTGAGGATGAGGCTGATTA
TTTCTGCTGTTCGTATGCAGGCGGCTATTATGTCTTCGGAACTGGGACCAAGC
```

-continued

```
TGACCGTCCTAGGCTCTACAAGCGGCTCTGGCAAGCCTGGATCTGGCGAGGG
AAGCACCAAGGGCGAAGTGCAGCTGCTGGAATCTGGCGGCGGACTGGTGCA
GCCTGGCGGATCTCTGAGACTGAGCTGTGCCGCCAGCGGCTTCACCTTCAGC
ACCTACCAGATGAGCTGGGTGCGCCAGGCCCCTGGCAAAGGACTGGAATGGG
TGTCCGGCATCGTGTCCAGCGGCGGCTCTACAGCCTACGCCGATAGCGTGAA
GGGCCGGTTCACCATCAGCCGGGACAACAGCAAGAACACCCTGTACCTGCAG
ATGAACAGCCTGAGAGCCGAGGACACCGCCGTGTACTATTGTGCCGGGGAGC
TGCTGCCCTACTACGGCATGGATGTGTGGGGCCAGGGCACCACCGTGACAGT
GTCCTCAGCGGCCGCAATCGAAGTGATGTACCCCCCTCCCTACCTGGACAAC
GAGAAGTCCAACGGCACCATTATCCACGTGAAGGGAAAGCACCTGTGCCCCA
GCCCTCTGTTCCCTGGCCCTAGCAAGCCTTTCTGGGTGCTGGTGGTCGTGGG
CGGAGTGCTGGCCTGTTATAGCCTGCTCGTGACCGTGGCCTTCATCATCTTTT
GGGTGCGCAGCAAGCGGAGCCGGCTGCTGCACAGCGACTACATGAACATGAC
CCCCAGACGGCCCGGACCCACCAGAAAGCACTACCAGCCTTACGCCCCTCCC
AGAGACTTCGCCGCCTACAGATCTCGAGTGAAGTTCAGCAGAAGCGCCGACG
CCCCTGCCTATCAGCAGGGCCAGAACCAGCTGTACAACGAGCTGAACCTGGG
CAGACGGGAAGAGTACGACGTGCTGGACAAGCGGAGAGGCAGGGACCCTGA
GATGGGCGGCAAGCCCAGAAGAAGAACCCCCAGGAAGGCCTGTATAACGAA
CTGCAGAAAGACAAGATGGCCGAGGCCTACAGCGAGATCGGCATGAAGGGCG
AGCGGAGAAGAGGCAAGGGCCACGATGGCCTGTACCAGGGCCTGAGCACCG
CCACCAAGGACACCTATGACGCCCTGCACATGCAGGCCCTGCCCCCCAGA-3'
```

Polynucleotide Coding for L102-3M4E5H CAR (Sequence ID No. 155)

```
5'-CAGTCTGCCCTGACTCAGCCTCCCTCCGCGTCCGGGTCTCCTGGACAGTCAG
TCACCATCTCCTGCACTGGAACCAGCAGTGACGTTGGTGGTTATAACTATGTC
TCCTGGTACCAACAGCACCCAGGCAAAGCCCCCAAACTCATGATTTATGATGT
CAGTAAGCGGCCCTCAGGGGTCCCTGATCGCTTCTCTGGCTCCAAGTCTGGC
AACACGGCCTCCCTGACCATCTCTGGGCTCCAGACTGAGGACGAGGCTGATT
ACTATTGCAGCTCATATGCAGGCAGCGGCAGCACCCCCTTTGTCTTCGGAACT
GGGACCAAGCTGACCGTCCTAGGCTCTACAAGCGGCTCTGGCAAGCCTGGAT
CTGGCGAGGGAAGCACCAAGGGCGAAGTGCAGCTGCTGGAATCTGGCGGCG
GACTGGTGCAGCCTGGCGGATCTCTGAGACTGAGCTGTGCCGCCAGCGGCTT
CACCTTCAGCACCTACCAGATGAGCTGGGTGCGCCAGGCCCCTGGCAAAGGA
CTGGAATGGGTGTCCGGCATCGTGTCCAGCGGCGGCTCTACAGCCTACGCCG
ATAGCGTGAAGGGCCGGTTCACCATCAGCCGGGACAACAGCAAGAACACCCT
GTACCTGCAGATGAACAGCCTGAGAGCCGAGGACACCGCCGTGTACTATTGT
GCCGGGGAGCTGCTGCCCTACTACGGCATGGATGTGTGGGGCCAGGGCACCA
CCGTGACAGTGTCCTCAGCGGCCGCAATCGAAGTGATGTACCCCCCTCCCTAC
CTGGACAACGAGAAGTCCAACGGCACCATTATCCACGTGAAGGGAAAGCACC
TGTGCCCCAGCCCTCTGTTCCCTGGCCCTAGCAAGCCTTTCTGGGTGCTGGT
GGTCGTGGGCGGAGTGCTGGCCTGTTATAGCCTGCTCGTGACCGTGGCCTTC
ATCATCTTTTGGGTGCGCAGCAAGCGGAGCCGGCTGCTGCACAGCGACTACA
TGAACATGACCCCCAGACGGCCCGGACCCACCAGAAAGCACTACCAGCCTTA
CGCCCCTCCCAGAGACTTCGCCGCCTACAGATCTCGAGTGAAGTTCAGCAGA
AGCGCCGACGCCCCTGCCTATCAGCAGGGCCAGAACCAGCTGTACAACGAGC
TGAACCTGGGCAGACGGGAAGAGTACGACGTGCTGGACAAGCGGAGAGGCA
GGGACCCTGAGATGGGCGGCAAGCCCAGAAGAAAGAACCCCCAGGAAGGCC
TGTATAACGAACTGCAGAAAGACAAGATGGCCGAGGCCTACAGCGAGATCGG
CATGAAGGGCGAGCGGAGAAGAGGCAAGGGCCACGATGGCCTGTACCAGGG
CCTGAGCACCGCCACCAAGGACACCTATGACGCCCTGCACATGCAGGCCCTG
CCCCCCAGA-3'
```

Polynucleotide Coding for L124-3M4E5H CAR (Sequence ID No. 156)

```
5'-CAGTCTGCCCTGACTCAGCCTGCCTCCGTGTCTGGGTCTCCTGGACAGTCGA
TCACCATCTCCTGCACTGGAACCAGCAGTGACGTTGGTGGTTATAACTATGTC
TCCTGGTACCAACAACACCCAGGCAAAGCCCCCAAACTCATGATTTATGATGT
CAGTAATCGGCCCTCAAGGGTCCCTGATCGCTTCGCTGGCTCCAAGTCTGGC
AACACGGCCTCCCTGACCATCTCTGGGCTCCAGGCTGAAGACGAGGCTGATT
ATTACTGCTGCTCATATGCCGGCAGACGTTATGTGTTCGGAACTGGGACCAAG
CTGACCGTCCTAGGCTCTACAAGCGGCTCTGGCAAGCCTGGATCTGGCGAGG
GAAGCACCAAGGGCGAAGTGCAGCTGCTGGAATCTGGCGGCGGACTGGTGC
AGCCTGGCGGATCTCTGAGACTGAGCTGTGCCGCCAGCGGCTTCACCTTCAG
CACCTACCAGATGAGCTGGGTGCGCCAGGCCCCTGGCAAAGGACTGGAATGG
GTGTCCGGCATCGTGTCCAGCGGCGGCTCTACAGCCTACGCCGATAGCGTGA
AGGGCCGGTTCACCATCAGCCGGGACAACAGCAAGAACACCCTGTACCTGCA
GATGAACAGCCTGAGAGCCGAGGACACCGCCGTGTACTATTGTGCCGGGGAG
CTGCTGCCCTACTACGGCATGGATGTGTGGGGCCAGGGCACCACCGTGACAG
TGTCCTCAGCGGCCGCAATCGAAGTGATGTACCCCCCTCCCTACCTGGACAAC
GAGAAGTCCAACGGCACCATTATCCACGTGAAGGGAAAGCACCTGTGCCCCA
GCCCTCTGTTCCCTGGCCCTAGCAAGCCTTTCTGGGTGCTGGTGGTCGTGGG
CGGAGTGCTGGCCTGTTATAGCCTGCTCGTGACCGTGGCCTTCATCATCTTTT
GGGTGCGCAGCAAGCGGAGCCGGCTGCTGCACAGCGACTACATGAACATGAC
CCCCAGACGGCCCGGACCCACCAGAAAGCACTACCAGCCTTACGCCCCTCCC
AGAGACTTCGCCGCCTACAGATCTCGAGTGAAGTTCAGCAGAAGCGCCGACG
CCCCTGCCTATCAGCAGGGCCAGAACCAGCTGTACAACGAGCTGAACCTGGG
```

```
                         -continued
CAGACGGGAAGAGTACGACGTGCTGGACAAGCGGAGAGGCAGGGACCCTGA
GATGGGCGGCAAGCCCAGAAGAAAGAACCCCCAGGAAGGCCTGTATAACGAA
CTGCAGAAAGACAAGATGGCCGAGGCCTACAGCGAGATCGGCATGAAGGGCG
AGCGGAGAAGAGGCAAGGGCCACGATGGCCTGTACCAGGGCCTGAGCACCG
CCACCAAGGACACCTATGACGCCCTGCACATGCAGGCCCTGCCCCCCAGA-3'
Polynucleotide Coding for 1173-3M4E5L CAR
                                            (Sequence ID No. 157)
5'-CAGCTGCAGCTGCAGGAGTCGGGCCCAGGACTGGTGAAGCCTTCACAGACCC
TGTCCCTCACCTGCACTGTCTCTGGTGGCTCCATCAGTAGTTACTACTGGAGC
TGGATCCGGCAGCCCCCAGGGAAGGGACTGGAGTGGATTGGGGAAATCAATC
ATAGTGGAAGCACCAACTACAACCCGTCCCTCAAGAGTCGAGTCACCCATATCA
GTAGACACGTCTAAGAACCAGTTCTCCCTGAAGCTGAGCTCTGTGACTGCCG
CGGACACGGCCGTGTATTACTGTGCGAGGTGCCCTATCTACTACTACGGTATG
GACGTCTGGGGCCAAGGGACCACGGTCACCGTCTCCTCAGGCTCTACAAGCG
GCTCTGGCAAGCCTGGATCTGGCGAGGGAAGCACCAAGGGCCAGAGCGAGC
TGACACAGCCTAGATCCGTGTCTGGCAGCCCTGGCCAGAGCGTGACCATCAG
CTGTACCGGCACCAGCAGAGATGTGGGCGGCTACAACTACGTGTCCTGGTAT
CAGCAGCATCCCGGCAAGGCCCCCAAGCTGATCATCCACGACGTGATCGAGC
GGAGCAGCGGCGTGCCCGATAGATTCAGCGGCAGCAAGAGCGGCAACACCG
CCAGCCTGACAATCAGCGGACTGCAGGCCGAGGACGAGGCCGACTACTACTG
TTGGAGCTTCGCCGGCAGCTACTACGTGTTCGGCACCGGCACCGATGTGACC
GTGCTGGCGGCCGCAATCGAAGTGATGTACCCCCCTCCCTACCTGGACAACG
AGAAGTCCAACGGCACCATTATCCACGTGAAGGGAAAGCACCTGTGCCCCAG
CCCTCTGTTCCCTGGCCCTAGCAAGCCTTTCTGGGTGCTGGTGGTCGTGGGC
GGAGTGCTGGCCTGTTATAGCCTGCTCGTGACCGTGGCCTTCATCATCTTTTG
GGTGCGCAGCAAGCGGAGCCGGCTGCTGCACAGCGACTACATGAACATGACC
CCCAGACGGCCCGGACCCACCCAGAAAGCACTACCAGCCTTACGCCCCTCCCA
GAGACTTCGCCGCCTACAGATCTCGAGTGAAGTTCAGCAGAAGCGCCGACGC
CCCTGCCTATCAGCAGGGCCAGAACCAGCTGTACAACGAGCTGAACCTGGGC
AGACGGGAAGAGTACGACGTGCTGGACAAGCGGAGAGGCAGGGACCCTGAG
ATGGGCGGCAAGCCCAGAAGAAAGAACCCCCAGGAAGGCCTGTATAACGAAC
TGCAGAAAGACAAGATGGCCGAGGCCTACAGCGAGATCGGCATGAAGGGCGA
GCGGAGAAGAGGCAAGGGCCACGATGGCCTGTACCAGGGCCTGAGCACCGC
CACCAAGGACACCTATGACGCCCTGCACATGCAGGCCCTGCCCCCCAGA-3'
```

Another specific example of the nucleic acid of the present invention is a polynucleotide of (ca) below.

(ca) A polynucleotide (nucleic acid) of (ca1), (ca2), (ca3), (ca4), (ca5), or (ca6) below:

(ca1) a polynucleotide coding for a polypeptide consisting of the amino acid sequence of any one of Sequence ID Nos. 272 to 284, (ca2) a polynucleotide coding for a polypeptide consisting of an amino acid sequence having 80% or more identity to the amino acid sequence of any one of Sequence ID Nos. 272 to 284, the polypeptide being capable of binding to CD19, (ca3) a polynucleotide coding for a polypeptide consisting of an amino acid sequence consisting of the amino acid sequence of any one of Sequence ID Nos. 272 to 284 with deletion, substitution, insertion, and/or addition of one or several amino acids, the polypeptide being capable of binding to CD19, (ca4) a polynucleotide consisting of the base sequence of any one of Sequence ID Nos. 298 to 310, (ca5) a polynucleotide consisting of a base sequence having 80% or more identity to the base sequence of any one of Sequence ID Nos. 298 to 310, and coding for a polypeptide capable of binding to CD19, and (ca6) a polynucleotide consisting of a base sequence consisting of the base sequence of any one of Sequence ID Nos. 298 to 310 with deletion, substitution, insertion, and/or addition of one or several bases, and coding for a polypeptide capable of binding to CD19.

The polynucleotides of (ca1) to (ca3) above are nucleic acids coding for the polypeptides of (CA1) to (CA3) above, respectively, and the descriptions of the polypeptides of (CA1) to (CA3) above can be applied.

In the polynucleotide of (ca4) above, each of the base sequences of Sequence ID Nos. 298 to 310 is a polynucleotide coding for a polypeptide that includes an amino acid sequence that includes a combination of the heavy-chain variable region and the light-chain variable region that corresponds to any one of Combinations (LA) to (LM) for the second antibody of the present invention or the like, for example. In the polynucleotides of (ca5) and (ca6) above, the polynucleotides coding for the amino acid sequences that correspond to the CDRH1, the CDRH2, the CDRH3, the CDRL1, the CDRL2, and the CDRL3 are conserved in the base sequences of Sequence ID Nos. 298 to 310, for example. Regarding the base sequences coding for the amino acid sequences of the CDRs in the base sequences of Sequence ID Nos. 298 to 310, the amino acid sequences of the CDRs included in the amino acid sequences that include the combinations of the heavy-chain variable region and the light-chain variable region that correspond to Combinations (LA) to (LM) for the second antibody of the present invention or the like can be referred to, for example.

The "identity" as used for the polynucleotide of (ca5) above refers to 80% or more, 85% or more, 90% or more, 95% or more, 96% or more, 97% or more, 98% or more, or 99% or more identity, for example.

The term "one or several" as used for the polynucleotide of (ca6) above regarding substitution and the like refers to 1 to 280, 1 to 210, 1 to 140, 1 to 70, 1 to 63, 1 to 56, 1 to 49, 1 to 35, 1 to 28, 1 to 21, 1 to 14, 1 to 7, 1 to 6, 1 to 5, 1 to 4, 1 to 3, 1 or 2, or 1, for example.

```
Polynucleotide Coding for L4-18H CAR
                                            (Sequence ID No. 298)
5'-TCCTATGAGCTGACTCAGCCACCCTCAGTGTCCGTGTCTCCAGGACAGACAG

CCAGCATCACCTGCTCTGGAGATAAATTGGGGGATAAATATGCTTGCTGGTAT
```

-continued

CAGCAGAAGCCAGGCCAGTCCCCTGTGCTGGTCATCTATCAAGATAGCAAGC

GGCCCTCAGGGATCCCTGAGCGATTCTCTGGCTCCAACTCTGGGAACACAGC

CACTCTGACCATCAGCGGGACCCAGGCTATGGATGAGGCTGACTATTACTGTC

AGGCGTGGGACAGCAGCACACATGTGGTATTCGGCGGAGGGACCAAGCTGAC

CGTCCTAGGCTCTACAAGCGGCTCTGGCAAGCCTGGATCTGGCGAGGGAAGC

ACCAAGGGCGAAGTGCAGCTTGTGGAATCTGGCGGAGGACTGGTGCAGCCTG

GAAGAAGCCTGAGACTGTCTTGTGCCGCCAGCGGCTTCACCTTCGACGATTAT

GCCATGCACTGGGTCCGACAGGCCCCTGGAAAAGGCCTTGAATGGGTGTCCG

GCATCTCTTGGAACAGCGGCAGAATCGGCTACGCCGACTCTGTGAAGGGCAG

ATTCACCATCAGCCGGGACAACGCCAAGAACAGCCTGTTCCTGCAGATGAAC

TCCCTGAGAGCCGAGGACACCGCCGTGTACTACTGTGCCAGAGATCAGGGCT

ACCACTACTACGACTCTGCCGAGCACGCCTTCGATATCTGGGGCCAGGGAAC

AGTGGTCACCGTTAGTTCTGCGGCCGCAATCGAAGTGATGTACCCCCCTCCCT

ACCTGGACAACGAGAAGTCCAACGGCACCATTATCCACGTGAAGGGAAAGCA

CCTGTGCCCCAGCCCTCTGTTCCCTGGCCCTAGCAAGCCTTTCTGGGTGCTG

GTGGTCGTGGGCGGAGTGCTGGCCTGTTATAGCCTGCTCGTGACCGTGGCCT

TCATCATCTTTTGGGTGCGCAGCAAGCGGAGCCGGCTGCTGCACAGCGACTA

CATGAACATGACCCCCAGACGGCCCGGACCCACCAGAAAGCACTACCAGCCT

TACGCCCCTCCCAGAGACTTCGCCGCCTACAGATCTCGAGTGAAGTTCAGCA

GAAGCGCCGACGCCCCTGCCTATCAGCAGGGCCAGAACCAGCTGTACAACGA

GCTGAACCTGGGCAGACGGGAAGAGTACGACGTGCTGGACAAGCGGAGAGG

CAGGGACCCTGAGATGGGCGGCAAGCCCAGAAGAAAGAACCCCCAGGAAGG

CCTGTATAACGAACTGCAGAAAGACAAGATGGCCGAGGCCTACAGCGAGATC

GGCATGAAGGGCGAGCGGAGAAGAGGCAAGGGCCACGATGGCCTGTACCAG

GGCCTGAGCACCGCCACCAAGGACACCTATGACGCCCTGCACATGCAGGCCC

TGCCCCCCAGA-3'

Polynucleotide Coding for L7-18H CAR
(Sequence ID No. 299)
5'-CAGTCTGCCCTGACTCAGCCTCGCTCAGTGTCCGGGTCTCCTGGACAGTCAG

TCACCATCTCCTGCACTGGAACCAGCAGTGATGTTGGTGGTTATAACTATGTC

TCCTGGTACCAACAACACCCAGGCAAAGCCCCCAAACTCATGATTTATGATGT

CAGTAATCGGCCCTCAGGGGTTTCTAATCGCTTCTCTGGCTCCAAGTCTGGCA

ACACGGCCTCCCTGACCATCTCTGGGCTCCAGACTGGGGACGAGGCCGATTA

TTACTGCGGAACATGGGATACCAGCCTGACTGCTGTGGTATTCGGCGGAGGG

ACCGAGCTGACCGTCCTCGGCTCTACAAGCGGCTCTGGCAAGCCTGGATCTG

GCGAGGGAAGCACCAAGGGCGAAGTGCAGCTTGTGGAATCTGGCGGAGGAC

TGGTGCAGCCTGGAAGAAGCCTGAGACTGTCTTGTGCCGCCAGCGGCTTCAC

CTTCGACGATTATGCCATGCACTGGGTCCGACAGGCCCCTGGAAAAGGCCTT

GAATGGGTGTCCGGCATCTCTTGGAACAGCGGCAGAATCGGCTACGCCGACT

CTGTGAAGGGCAGATTCACCATCAGCCGGGACAACGCCAAGAACAGCCTGTT

CCTGCAGATGAACTCCCTGAGAGCCGAGGACACCGCCGTGTACTACTGTGCC

AGAGATCAGGGCTACCACTACTACGACTCTGCCGAGCACGCCTTCGATATCTG

-continued

```
GGGCCAGGGAACAGTGGTCACCGTTAGTTCTGCGGCCGCAATCGAAGTGATG
TACCCCCCTCCCTACCTGGACAACGAGAAGTCCAACGGCACCATTATCCACGT
GAAGGGAAAGCACCTGTGCCCCAGCCCTCTGTTCCCTGGCCCTAGCAAGCCT
TTCTGGGTGCTGGTGGTCGTGGGCGGAGTGCTGGCCTGTTATAGCCTGCTCG
TGACCGTGGCCTTCATCATCTTTTGGGTGCGCAGCAAGCGGAGCCGGCTGCT
GCACAGCGACTACATGAACATGACCCCCAGACGGCCCGGACCCACCAGAAAG
CACTACCAGCCTTACGCCCCTCCCAGAGACTTCGCCGCCTACAGATCTCGAGT
GAAGTTCAGCAGAAGCGCCGACGCCCCTGCCTATCAGCAGGGCCAGAACCAG
CTGTACAACGAGCTGAACCTGGGCAGACGGGAAGAGTACGACGTGCTGGACA
AGCGGAGAGGCAGGGACCCTGAGATGGGCGGCAAGCCCAGAAGAAAGAACC
CCCAGGAAGGCCTGTATAACGAACTGCAGAAAGACAAGATGGCCGAGGCCTA
CAGCGAGATCGGCATGAAGGGCGAGCGGAGAAGAGGCAAGGGCCACGATGG
CCTGTACCAGGGCCTGAGCACCGCCACCAAGGACACCTATGACGCCCTGCAC
ATGCAGGCCCTGCCCCCCAGA-3'
```

Polynucleotide Coding for L9-18H CAR (Sequence ID No. 300)

```
5'-CAGTCTGTGTTGACGCAGCCGCCCTCAGTGTCTGCGGCCCCAGGACAGAAGG
TCACCATCTCCTGCTCTGGAAGCTGGTCCAACATTGGAGATGATCATGTCTCC
TGGTACCAGCAGTTCCCAGGAGCAGCCCCCAAACTCCTCATTTATGACACTTC
TAAGCGACCCTCACGCGTTGCTGACCGATTCTCTGGCTCCAAGTCTGGCGCG
TCAGCCACCCTGGCCATCACTGGACTCCAGGCTGGGGACGAGGCCGACTATT
ATTGCGGAACATGGGAAAGCAGCCTGAGTGGTGTGGTTTTCGGCGGAGGGAC
CGAGCTGACCGTCCTAGGCTCTACAAGCGGCTCTGGCAAGCCTGGATCTGGC
GAGGGAAGCACCAAGGGCGAAGTGCAGCTTGTGGAATCTGGCGGAGGACTG
GTGCAGCCTGGAAGAAGCCTGAGACTGTCTTGTGCCGCCAGCGGCTTCACCT
TCGACGATTATGCCATGCACTGGGTCCGACAGGCCCCTGGAAAAGGCCTTGA
ATGGGTGTCCGGCATCTCTTGGAACAGCGGCAGAATCGGCTACGCCGACTCT
GTGAAGGGCAGATTCACCATCAGCCGGGACAACGCCAAGAACAGCCTGTTCC
TGCAGATGAACTCCCTGAGAGCCGAGGACACCGCCGTGTACTACTGTGCCAG
AGATCAGGGCTACCACTACTACGACTCTGCCGAGCACGCCTTCGATATCTGGG
GCCAGGGAACAGTGGTCACCGTTAGTTCTGCGGCCGCAATCGAAGTGATGTA
CCCCCCTCCCTACCTGGACAACGAGAAGTCCAACGGCACCATTATCCACGTGA
AGGGAAAGCACCTGTGCCCCAGCCCTCTGTTCCCTGGCCCTAGCAAGCCTTT
CTGGGTGCTGGTGGTCGTGGGCGGAGTGCTGGCCTGTTATAGCCTGCTCGTG
ACCGTGGCCTTCATCATCTTTTGGGTGCGCAGCAAGCGGAGCCGGCTGCTGC
ACAGCGACTACATGAACATGACCCCCAGACGGCCCGGACCCACCAGAAAGCA
CTACCAGCCTTACGCCCCTCCCAGAGACTTCGCCGCCTACAGATCTCGAGTGA
AGTTCAGCAGAAGCGCCGACGCCCCTGCCTATCAGCAGGGCCAGAACCAGCT
GTACAACGAGCTGAACCTGGGCAGACGGGAAGAGTACGACGTGCTGGACAAG
CGGAGAGGCAGGGACCCTGAGATGGGCGGCAAGCCCAGAAGAAAGAACCCC
CAGGAAGGCCTGTATAACGAACTGCAGAAAGACAAGATGGCCGAGGCCTACA
```

-continued
GCGAGATCGGCATGAAGGGCGAGCGGAGAAGAGGCAAGGGCCACGATGGCC

TGTACCAGGGCCTGAGCACCGCCACCAAGGACACCTATGACGCCCTGCACAT

GCAGGCCCTGCCCCCCAGA-3'

Polynucleotide Coding for L13-18H CAR
(Sequence ID No. 301)
5'-CAGTCTGCCCTGACTCAGCCTGCCTCCGTGTCTGGGTCTCCTGGACAGTCGA

TCACCATCTCCTGCACTGGACTCAGCAGTGACGTTGGTGGTTATGACTATGTC

TCCTGGTACCAACAACACCCAGGCATAGCCCCCAAACTCATGATTTATGATGT

CACTAATCGGCCCTCAGGGGTTTCTAGTCGCTTCTCTGGCTCCAAGTCTGGCA

ACACGGCCTCCCTGACCATCTCTGGGCTCCAGGCTGAGGACGAGGCTGATTA

TTACTGCAGCTCATATACAACCAGCACGACTTGGGTCTTCGGAGCTGGGACCA

AGCTGACCGTCCTAGGCTCTACAAGCGGCTCTGGCAAGCCTGGATCTGGCGA

GGGAAGCACCAAGGGCGAAGTGCAGCTTGTGGAATCTGGCGGAGGACTGGT

GCAGCCTGGAAGAAGCCTGAGACTGTCTTGTGCCGCCAGCGGCTTCACCTTC

GACGATTATGCCATGCACTGGGTCCGACAGGCCCCTGGAAAAGGCCTTGAAT

GGGTGTCCGGCATCTCTTGGAACAGCGGCAGAATCGGCTACGCCGACTCTGT

GAAGGGCAGATTCACCATCAGCCGGGACAACGCCAAGAACAGCCTGTTCCTG

CAGATGAACTCCCTGAGAGCCGAGGACACCGCCGTGTACTACTGTGCCAGAG

ATCAGGGCTACCACTACTACGACTCTGCCGAGCACGCCTTCGATATCTGGGGC

CAGGGAACAGTGGTCACCGTTAGTTCTGCGGCCGCAATCGAAGTGATGTACC

CCCCTCCCTACCTGGACAACGAGAAGTCCAACGGCACCATTATCCACGTGAAG

GGAAAGCACCTGTGCCCCAGCCCTCTGTTCCCTGGCCCTAGCAAGCCTTTCT

GGGTGCTGGTGGTCGTGGGCGGAGTGCTGGCCTGTTATAGCCTGCTCGTGAC

CGTGGCCTTCATCATCTTTTGGGTGCGCAGCAAGCGGAGCCGGCTGCTGCAC

AGCGACTACATGAACATGACCCCCAGACGGCCCGGACCCACCAGAAAGCACT

ACCAGCCTTACGCCCCTCCCAGAGACTTCGCCGCCTACAGATCTCGAGTGAA

GTTCAGCAGAAGCGCCGACGCCCCTGCCTATCAGCAGGGCCAGAACCAGCTG

TACAACGAGCTGAACCTGGGCAGACGGGAAGAGTACGACGTGCTGGACAAGC

GGAGAGGCAGGGACCCTGAGATGGGCGGCAAGCCCAGAAGAAAGAACCCCC

AGGAAGGCCTGTATAACGAACTGCAGAAAGACAAGATGGCCGAGGCCTACAG

CGAGATCGGCATGAAGGGCGAGCGGAGAAGAGGCAAGGGCCACGATGGCCT

GTACCAGGGCCTGAGCACCGCCACCAAGGACACCTATGACGCCCTGCACATG

CAGGCCCTGCCCCCCAGA-3'

Polynucleotide Coding for L14-18H CAR
(Sequence ID No. 302)
5'-CAGTCTGCCCTGACTCAGCCTGCCTCCGTGTCTGGGTCTCCTGGACAGTCGA

TCACCATCTCCTGCACTGGAACCACCAGTGACGTTGGTACTACTAATTATGTC

TCCTGGTACCAGCAACACCCAGGCAAAGCCCCCAAACTCCTAATTTATGATGT

CACTAATCGGCCCTCAGGGGTCCCTGATCGCTTCTCTGGCTCCAAGTCTGCCA

ACACGGCCTCCCTGACCATCTCTGGGCTCCAGGCTGAGGACGAGGCTGATTA

TTACTGCTGCTCATATGCAGGCAGCTACACCTTCGTGGTATTCGGCGGAGGGA

CCGAGCTGACCGTCCTAGGCTCTACAAGCGGCTCTGGCAAGCCTGGATCTGG

CGAGGGAAGCACCAAGGGCGAAGTGCAGCTTGTGGAATCTGGCGGAGGACT

-continued

GGTGCAGCCTGGAAGAAGCCTGAGACTGTCTTGTGCCGCCAGCGGCTTCACC

TTCGACGATTATGCCATGCACTGGGTCCGACAGGCCCCTGGAAAAGGCCTTG

AATGGGTGTCCGGCATCTCTTGGAACAGCGGCAGAATCGGCTACGCCGACTC

TGTGAAGGGCAGATTCACCATCAGCCGGGACAACGCCAAGAACAGCCTGTTC

CTGCAGATGAACTCCCTGAGAGCCGAGGACACCGCCGTGTACTACTGTGCCA

GAGATCAGGGCTACCACTACTACGACTCTGCCGAGCACGCCTTCGATATCTGG

GGCCAGGGAACAGTGGTCACCGTTAGTTCTGCGGCCGCAATCGAAGTGATGT

ACCCCCCTCCCTACCTGGACAACGAGAAGTCCAACGGCACCATTATCCACGTG

AAGGGAAAGCACCTGTGCCCCAGCCCTCTGTTCCCTGGCCCTAGCAAGCCTT

TCTGGGTGCTGGTGGTCGTGGGCGGAGTGCTGGCCTGTTATAGCCTGCTCGT

GACCGTGGCCTTCATCATCTTTTGGGTGCGCAGCAAGCGGAGCCGGCTGCTG

CACAGCGACTACATGAACATGACCCCCAGACGGCCCGGACCCACCAGAAAGC

ACTACCAGCCTTACGCCCCTCCCAGAGACTTCGCCGCCTACAGATCTCGAGTG

AAGTTCAGCAGAAGCGCCGACGCCCCTGCCTATCAGCAGGGCCAGAACCAGC

TGTACAACGAGCTGAACCTGGGCAGACGGGAAGAGTACGACGTGCTGGACAA

GCGGAGAGGCAGGGACCCTGAGATGGGCGGCAAGCCCAGAAGAAAGAACCC

CCAGGAAGGCCTGTATAACGAACTGCAGAAAGACAAGATGGCCGAGGCCTAC

AGCGAGATCGGCATGAAGGGCGAGCGGAGAAGAGGCAAGGGCCACGATGGC

CTGTACCAGGGCCTGAGCACCGCCACCAAGGACACCTATGACGCCCTGCACA

TGCAGGCCCTGCCCCCCAGA-3'

Polynucleotide Coding for L16-18H CAR (Sequence ID No. 303)

5'-CAGTCTGCCCTGACTCAGCCTCCCTCCGCGTCCGGGTCTCCTGGACAGTCAG

TCACCATCTCCTGCACTGGAACCAGCAGTGACGTTGGTGTTTATAACTATGTC

TCCTGGTACCAACAACACCCAGGCAAAGCCCCCAAACTCATGATTTATGATGT

CAGTAAGCGGCCCTCAGGGGTCCCTGATCGCTTCTCTGGCTCCAAGTCTGCC

AACACGGCCTCCCTGACCATCTCTGGGCTCCAGGCTGAGGATGAGGCTGATT

ATTACTGTGCAGCATGGGATGACAGCCTGAATGGTGTGGTATTCGGCGGAGG

CACCCAGCTGACCGTCCTCGGCTCTACAAGCGGCTCTGGCAAGCCTGGATCT

GGCGAGGGAAGCACCAAGGGCGAAGTGCAGCTTGTGGAATCTGGCGGAGGA

CTGGTGCAGCCTGGAAGAAGCCTGAGACTGTCTTGTGCCGCCAGCGGCTTCA

CCTTCGACGATTATGCCATGCACTGGGTCCGACAGGCCCCTGGAAAAGGCCT

TGAATGGGTGTCCGGCATCTCTTGGAACAGCGGCAGAATCGGCTACGCCGAC

TCTGTGAAGGGCAGATTCACCATCAGCCGGGACAACGCCAAGAACAGCCTGT

TCCTGCAGATGAACTCCCTGAGAGCCGAGGACACCGCCGTGTACTACTGTGC

CAGAGATCAGGGCTACCACTACTACGACTCTGCCGAGCACGCCTTCGATATCT

GGGGCCAGGGAACAGTGGTCACCGTTAGTTCTGCGGCCGCAATCGAAGTGAT

GTACCCCCCTCCCTACCTGGACAACGAGAAGTCCAACGGCACCATTATCCACG

TGAAGGGAAAGCACCTGTGCCCCAGCCCTCTGTTCCCTGGCCCTAGCAAGCC

TTTCTGGGTGCTGGTGGTCGTGGGCGGAGTGCTGGCCTGTTATAGCCTGCTC

GTGACCGTGGCCTTCATCATCTTTTGGGTGCGCAGCAAGCGGAGCCGGCTGC

-continued
TGCACAGCGACTACATGAACATGACCCCCAGACGGCCCGGACCCACCAGAAA

GCACTACCAGCCTTACGCCCCTCCCAGAGACTTCGCCGCCTACAGATCTCGAG

TGAAGTTCAGCAGAAGCGCCGACGCCCCTGCCTATCAGCAGGGCCAGAACCA

GCTGTACAACGAGCTGAACCTGGGCAGACGGGAAGAGTACGACGTGCTGGAC

AAGCGGAGAGGCAGGGACCCTGAGATGGGCGGCAAGCCCAGAAGAAAGAAC

CCCCAGGAAGGCCTGTATAACGAACTGCAGAAAGACAAGATGGCCGAGGCCT

ACAGCGAGATCGGCATGAAGGGCGAGCGGAGAAGAGGCAAGGGCCACGATG

GCCTGTACCAGGGCCTGAGCACCGCCACCAAGGACACCTATGACGCCCTGCA

CATGCAGGCCCTGCCCCCCAGA-3'

Polynucleotide Coding for L17-18H CAR (Sequence ID No. 304)

5'-CAGTCTGTACTGACTCAACCACCCTCAGCGTCTGGGACCCCCGGGCAGAGGG

TCACCATCTCTTGCTCTGGCAGC<u>AGCTCCAACATCGGAAATAATTATGTATGCT</u>

GGTACCAACACCTCCCAGGAACGGCCCCCAAACTTCTCATTTATG<u>ACAATGTT</u>

AAGCGACCCTCAGGGATTCCTGACCGATTCTCTGGCTCCAAGTCTGGCACGT

CAGCCTCCCTGGCCATCAGTGGGCTCCGGTCCGAGGATGAGGCTGATTATTAC

TGTGC<u>AGCATGGGATGACAGCCTGAGTGCCATATT</u>CGGCGGAGGGACCGAGC

TGACCGTCCTAGGCTCTACAAGCGGCTCTGGCAAGCCTGGATCTGGCGAGGG

AAGCACCAAGGGCGAAGTGCAGCTTGTGGAATCTGGCGGAGGACTGGTGCA

GCCTGGAAGAAGCCTGAGACTGTCTTGTGCCGCCAGC<u>GGCTTCACCTTCGAC</u>

<u>GATTATGCC</u>ATGCACTGGGTCCGACAGGCCCCTGGAAAAGGCCTTGAATGGG

TGTCCGGC<u>ATCTCTTGGAACAGCGGCAGAATCGG</u>CTACGCCGACTCTGTGAA

GGGCAGATTCACCATCAGCCGGGACAACGCCAAGAACAGCCTGTTCCTGCAG

ATGAACTCCCTGAGAGCCGAGGACACCGCCGTGTACTACTGT<u>GCCAGAGATC</u>

<u>AGGGCTACCACTACTACGACTCTGCCGAGCACGCCTTCGATATC</u>TGGGGCCAG

GGAACAGTGGTCACCGTTAGTTCTGCGGCCGCAATCGAAGTGATGTACCCCC

CTCCCTACCTGGACAACGAGAAGTCCAACGGCACCATTATCCACGTGAAGGG

AAAGCACCTGTGCCCCAGCCCTCTGTTCCCTGGCCCTAGCAAGCCTTTCTGG

GTGCTGGTGGTCGTGGGCGGAGTGCTGGCCTGTTATAGCCTGCTCGTGACCG

TGGCCTTCATCATCTTTTGGGTGCGCAGCAAGCGGAGCCGGCTGCTGCACAG

CGACTACATGAACATGACCCCAGACGGCCCGGACCCACCAGAAAGCACTAC

CAGCCTTACGCCCCTCCCAGAGACTTCGCCGCCTACAGATCTCGAGTGAAGTT

CAGCAGAAGCGCCGACGCCCCTGCCTATCAGCAGGGCCAGAACCAGCTGTAC

AACGAGCTGAACCTGGGCAGACGGGAAGAGTACGACGTGCTGGACAAGCGG

AGAGGCAGGGACCCTGAGATGGGCGGCAAGCCCAGAAGAAAGAACCCCCAG

GAAGGCCTGTATAACGAACTGCAGAAAGACAAGATGGCCGAGGCCTACAGCG

AGATCGGCATGAAGGGCGAGCGGAGAAGAGGCAAGGGCCACGATGGCCTGT

ACCAGGGCCTGAGCACCGCCACCAAGGACACCTATGACGCCCTGCACATGCA

GGCCCTGCCCCCCAGA-3'

Polynucleotide Coding for L22-18H CAR (Sequence ID No. 305)

5'-CAGTCTGCCCTGACTCAGCCTGCCTCCGTGTCTGGGTCTCCTGGACAGTCGA

TCACCATCTCCTGCACTGGAACC<u>AGCAGTGACGTTGGTGGTTATAACTATGTC</u>

-continued

TCCTGGTACCAACAACACCCAGGCAAAGCCCCCAAACTCATGATTTATGATGT
CAGTAATCGGCCCTCAGGGGTCCCTGATCGCTTCTCTGGCTCCAAGTCTGGC
ACCTCAGCCTCCCTGGCCATCAGTGGGCTCCAGTCTGAGGATGAGGCTGATT
ATTACTGCCACTCCTATGACAGCAGCCTGAGTCATGTCTTCGGAACTGGGACC
AAGGTCACCGTCCTAGGCTCTACAAGCGGCTCTGGCAAGCCTGGATCTGGCG
AGGGAAGCACCAAGGGCGAAGTGCAGCTTGTGGAATCTGGCGGAGGACTGG
TGCAGCCTGGAAGAAGCCTGAGACTGTCTTGTGCCGCCAGCGGCTTCACCTT
CGACGATTATGCCATGCACTGGGTCCGACAGGCCCCTGGAAAAGGCCTTGAA
TGGGTGTCCGGCATCTCTTGGAACAGCGGCAGAATCGGCTACGCCGACTCTG
TGAAGGGCAGATTCACCATCAGCCGGGACAACGCCAAGAACAGCCTGTTCCT
GCAGATGAACTCCCTGAGAGCCGAGGACACCGCCGTGTACTACTGTGCCAGA
GATCAGGGCTACCACTACTACGACTCTGCCGAGCACGCCTTCGATATCTGGGG
CCAGGGAACAGTGGTCACCGTTAGTTCTGCGGCCGCAATCGAAGTGATGTAC
CCCCCTCCCTACCTGGACAACGAGAAGTCCAACGGCACCATTATCCACGTGAA
GGGAAAGCACCTGTGCCCCAGCCCTCTGTTCCCTGGCCCTAGCAAGCCTTTC
TGGGTGCTGGTGGTCGTGGGCGGAGTGCTGGCCTGTTATAGCCTGCTCGTGA
CCGTGGCCTTCATCATCTTTTGGGTGCGCAGCAAGCGGAGCCGGCTGCTGCA
CAGCGACTACATGAACATGACCCCCAGACGGCCCGGACCCACCAGAAAGCAC
TACCAGCCTTACGCCCCTCCCAGAGACTTCGCCGCCTACAGATCTCGAGTGAA
GTTCAGCAGAAGCGCCGACGCCCCTGCCTATCAGCAGGGCCAGAACCAGCTG
TACAACGAGCTGAACCTGGGCAGACGGGAAGAGTACGACGTGCTGGACAAGC
GGAGAGGCAGGGACCCTGAGATGGGCGGCAAGCCCAGAAGAAAGAACCCCC
AGGAAGGCCTGTATAACGAACTGCAGAAAGACAAGATGGCCGAGGCCTACAG
CGAGATCGGCATGAAGGGCGAGCGGAGAAGAGGCAAGGGCCACGATGGCCT
GTACCAGGGCCTGAGCACCGCCACCAAGGACACCTATGACGCCCTGCACATG
CAGGCCCTGCCCCCCAGA-3'

Polynucleotide Coding for K4-18H CAR
(Sequence ID No. 306)
5'-GAAATTGTGTTGACGCAGTCTCCAGGCACCCTGTCTTTGTCTCCAGGGGAAA
GAGCCACCCTCTCCTGCAGGGCCAGTCAGAGTGTTAGCAGCAACTTAGCCTG
GTACCAGCAGAAACCTGGCCAGGCTCCCAGGCTCCTCATCTATGGTGCATCCA
CCAGGGCCACTGGTATCCCAGCCAGGTTCAGTGGCAGTGGGTCTGGGACAGA
GTTCACTCTCACCATCAGCAGCCTGCAGTCTGAAGATTTTGCAGTTTATTACT
GTCAGCAGTATAATAACTGGCCTCCCTTGTACACTTTTGGCCAGGGGACCAAG
CTGGAGATCAAAGGCTCTACAAGCGGCTCTGGCAAGCCTGGATCTGGCGAGG
GAAGCACCAAGGGCGAAGTGCAGCTTGTGGAATCTGGCGGAGGACTGGTGC
AGCCTGGAAGAAGCCTGAGACTGTCTTGTGCCGCCAGCGGCTTCACCTTCGA
CGATTATGCCATGCACTGGGTCCGACAGGCCCCTGGAAAAGGCCTTGAATGG
GTGTCCGGCATCTCTTGGAACAGCGGCAGAATCGGCTACGCCGACTCTGTGA
AGGGCAGATTCACCATCAGCCGGGACAACGCCAAGAACAGCCTGTTCCTGCA
GATGAACTCCCTGAGAGCCGAGGACACCGCCGTGTACTACTGTGCCAGAGAT -continued <u>CAGGGCTACCACTACTACGACTCTGCCGAGCACGCCTTCGATATC</u>TGGGGCCA

GGGAACAGTGGTCACCGTTAGTTCTGCGGCCGCAATCGAAGTGATGTACCCC

CCTCCCTACCTGGACAACGAGAAGTCCAACGGCACCATTATCCACGTGAAGG

GAAAGCACCTGTGCCCCAGCCCTCTGTTCCTGGCCCTAGCAAGCCTTTCTG

GGTGCTGGTGGTCGTGGGCGGAGTGCTGGCCTGTTATAGCCTGCTCGTGACC

GTGGCCTTCATCATCTTTTGGGTGCGCAGCAAGCGGAGCCGGCTGCTGCACA

GCGACTACATGAACATGACCCCCAGACGGCCCGGACCCACCAGAAAGCACTA

CCAGCCTTACGCCCCTCCCAGAGACTTCGCCGCCTACAGATCTCGAGTGAAGT

TCAGCAGAAGCGCCGACGCCCCTGCCTATCAGCAGGGCCAGAACCAGCTGTA

CAACGAGCTGAACCTGGGCAGACGGGAAGAGTACGACGTGCTGGACAAGCG

GAGAGGCAGGGACCCTGAGATGGGCGGCAAGCCCAGAAGAAAGAACCCCCA

GGAAGGCCTGTATAACGAACTGCAGAAAGACAAGATGGCCGAGGCCTACAGC

GAGATCGGCATGAAGGGCGAGCGGAGAAGAGGCAAGGGCCACGATGGCCTG

TACCAGGGCCTGAGCACCGCCACCAAGGACACCTATGACGCCCTGCACATGC

AGGCCCTGCCCCCCAGA-3'

Polynucleotide Coding for K5-18H CAR (Sequence ID No. 307)

5'-GAAATTGTGTTGACGCAGTCTCCAGGCACCCTGTCTTTGTCTCCAGGGGAAA

GAGCCACCCTCTCCTGCAGGGCCAGT<u>CAGAGTGTTAGCAGCTACT</u>TAGCCTG

GTACCAACAGAAACCTGGCCAGGCTCCCAGGCTCCTCATCTAT<u>GATGCATCCA</u>

ACAGGGCCACTGGCATCCCAGCCAGGTTCAGTGGCAGTGGGTCTGGGACAGA

CTTCACTCTCACCATCAGCAGCCTAGAGCCTGAAGATTTTGCAACTTACTACT

GT<u>CAACAGAGTTACAGTACCCTTTTGTACACT</u>TTTGGCCAGGGGACCAAGCTG

GAGATCAAAGGCTCTACAAGCGGCTCTGGCAAGCCTGGATCTGGCGAGGGAA

GCACCAAGGGCGAAGTGCAGCTTGTGGAATCTGGCGGAGGACTGGTGCAGC

CTGGAAGAAGCCTGAGACTGTCTTGTGCCGCCAGC<u>GGCTTCACCTTCGACGA</u>

<u>TTATGCC</u>ATGCACTGGGTCCGACAGGCCCCTGGAAAAGGCCTTGAATGGGTG

TCCGGC<u>ATCTCTTGGAACAGCGGCAGA</u>ATCGGCTACGCCGACTCTGTGAAGG

GCAGATTCACCATCAGCCGGGACAACGCCAAGAACAGCCTGTTCCTGCAGAT

GAACTCCCTGAGAGCCGAGGACACCGCCGTGTACTACTGT<u>GCCAGAGATCAG</u>

<u>GGCTACCACTACTACGACTCTGCCGAGCACGCCTTCGATATC</u>TGGGGCCAGG

GAACAGTGGTCACCGTTAGTTCTGCGGCCGCAATCGAAGTGATGTACCCCCT

CCCTACCTGGACAACGAGAAGTCCAACGGCACCATTATCCACGTGAAGGGAA

AGCACCTGTGCCCCAGCCCTCTGTTCCTGGCCCTAGCAAGCCTTTCTGGGT

GCTGGTGGTCGTGGGCGGAGTGCTGGCCTGTTATAGCCTGCTCGTGACCGTG

GCCTTCATCATCTTTTGGGTGCGCAGCAAGCGGAGCCGGCTGCTGCACAGCG

ACTACATGAACATGACCCCCAGACGGCCCGGACCCACCAGAAAGCACTACCA

GCCTTACGCCCCTCCCAGAGACTTCGCCGCCTACAGATCTCGAGTGAAGTTCA

GCAGAAGCGCCGACGCCCCTGCCTATCAGCAGGGCCAGAACCAGCTGTACAA

CGAGCTGAACCTGGGCAGACGGGAAGAGTACGACGTGCTGGACAAGCGGAG

AGGCAGGGACCCTGAGATGGGCGGCAAGCCCAGAAGAAAGAACCCCCAGGA

AGGCCTGTATAACGAACTGCAGAAAGACAAGATGGCCGAGGCCTACAGCGAG

ATCGGCATGAAGGGCGAGCGGAGAAGAGGCAAGGGCCACGATGGCCTGTAC

CAGGGCCTGAGCACCGCCACCAAGGACACCTATGACGCCCTGCACATGCAGG

CCCTGCCCCCCAGA-3'

Polynucleotide Coding for K6-18H CAR (Sequence ID No. 308)

5'-GAAATTGTGTTGACACGGTCTCCACCACCCTGTCTTTGTCTCCAGGGGAAA

GAGCCACCCTCTCCTGCAGGGCCAGTCAGAGTGTTAGCAGCTACTTAGCCTG

GTACCAACAGAAACCTGGCCAGGCTCCCAGGCTCCTCATCTATGATGCCTCCA

ACAGGGCCACTGGTATTTCAGCCAGGTTCAGTGGCAGTGGGTCTGGGACAGA

GTTCACTCTCACCATCAGCAGCCTGCAGTCTGAAGATATTGCAACATATTACT

GTCAACAGTATGATAGTCTCCCACTCACTTTCGGCGGAGGGACCAAGCTGGA

GATCAAAGGCTCTACAAGCGGCTCTGGCAAGCCTGGATCTGGCGAGGGAAGC

ACCAAGGGCGAAGTGCAGCTTGTGGAATCTGGCGGAGGACTGGTGCAGCCTG

GAAGAAGCCTGAGACTGTCTTGTGCCGCCAGCGGCTTCACCTTCGACGATTAT

GCCATGCACTGGGTCCGACAGGCCCCTGGAAAAGGCCTTGAATGGGTGTCCG

GCATCTCTTGGAACAGCGGCAGAATCGGCTACGCCGACTCTGTGAAGGGCAG

ATTCACCATCAGCCGGGACAACGCCAAGAACAGCCTGTTCCTGCAGATGAAC

TCCCTGAGAGCCGAGGACACCGCCGTGTACTACTGTGCCAGAGATCAGGGCT

ACCACTACTACGACTCTGCCGAGCACGCCTTCGATATCTGGGGCCAGGGAAC

AGTGGTCACCGTTAGTTCTGCGGCCGCAATCGAAGTGATGTACCCCCCTCCCT

ACCTGGACAACGAGAAGTCCAACGGCACCATTATCCACGTGAAGGGAAAGCA

CCTGTGCCCCAGCCCTCTGTTCCCTGGCCCTAGCAAGCCTTTCTGGGTGCTG

GTGGTCGTGGGCGGAGTGCTGGCCTGTTATAGCCTGCTCGTGACCGTGGCCT

TCATCATCTTTTGGGTGCGCAGCAAGCGGAGCCGGCTGCTGCACAGCGACTA

CATGAACATGACCCCCAGACGGCCCGGACCCACCAGAAAGCACTACCAGCCT

TACGCCCCTCCCAGAGACTTCGCCGCCTACAGATCTCGAGTGAAGTTCAGCA

GAAGCGCCGACGCCCCTGCCTATCAGCAGGGCCAGAACCAGCTGTACAACGA

GCTGAACCTGGGCAGACGGGAAGAGTACGACGTGCTGGACAAGCGGAGAGG

CAGGGACCCTGAGATGGGCGGCAAGCCCAGAAGAAAGAACCCCCAGGAAGG

CCTGTATAACGAACTGCAGAAAGACAAGATGGCCGAGGCCTACAGCGAGATC

GGCATGAAGGGCGAGCGGAGAAGAGGCAAGGGCCACGATGGCCTGTACCAG

GGCCTGAGCACCGCCACCAAGGACACCTATGACGCCCTGCACATGCAGGCCC

TGCCCCCCAGA-3'

Polynucleotide Coding for K9-18H CAR (Sequence ID No. 309)

5'-GAAATAGTGTTGACACAGTCTCCAGCCACCCTGTCTTTGTCTCCAGGGGAAAG

AGCCACCGTCTCCTGTAGGGCCCAGTCAGACCATTAGTGCCAGTTCCGTAGCCT

GGTATCAGCAGAAAGCTGGCCAGGCTCCACGGCTCCTCATCTATGGTGCATCC

AGCAGGGCCACTGGCATCCCAGACAGGTTCAGTGGCAGTGGGTCTGGGACAG

ACTTCACTCTCACCATCAGCAGACTGGAGCCTGAAGATTTTGCAGTTTATTAC

TGTCAGCAATTTAATGAATGGCCTCTCACTTTCGGCGGAGGGACCAAGGTGG

AAATCAAAGGCTCTACAAGCGGCTCTGGCAAGCCTGGATCTGGCGAGGGAAG

-continued

CACCAAGGGCGAAGTGCAGCTTGTGGAATCTGGCGGAGGACTGGTGCAGCCT

GGAAGAAGCCTGAGACTGTCTTGTGCCGCCAGCGGCTTCACCTTCGACGATT

ATGCCATGCACTGGGTCCGACAGGCCCCTGGAAAAGGCCTTGAATGGGTGTC

CGGCATCTCTTGGAACAGCGGCAGAATCGGCTACGCCGACTCTGTGAAGGGC

AGATTCACCATCAGCCGGGACAACGCCAAGAACAGCCTGTTCCTGCAGATGA

ACTCCCTGAGAGCCGAGGACACCGCCGTGTACTACTGTGCCAGAGATCAGGG

CTACCACTACTACGACTCTGCCGAGCACGCCTTCGATATCTGGGGCCAGGGAA

CAGTGGTCACCGTTAGTTCTGCGGCCGCAATCGAAGTGATGTACCCCCCTCCC

TACCTGGACAACGAGAAGTCCAACGGCACCATTATCCACGTGAAGGGAAAGC

ACCTGTGCCCCAGCCCTCTGTTCCCTGGCCCTAGCAAGCCTTTCTGGGTGCTG

GTGGTCGTGGGCGGAGTGCTGGCCTGTTATAGCCTGCTCGTGACCGTGGCCT

TCATCATCTTTTGGGTGCGCAGCAAGCGGAGCCGGCTGCTGCACAGCGACTA

CATGAACATGACCCCCAGACGGCCCGGACCCACCAGAAAGCACTACCAGCCT

TACGCCCCTCCCAGAGACTTCGCCGCCTACAGATCTCGAGTGAAGTTCAGCA

GAAGCGCCGACGCCCCTGCCTATCAGCAGGGCCAGAACCAGCTGTACAACGA

GCTGAACCTGGGCAGACGGGAAGAGTACGACGTGCTGGACAAGCGGAGAGG

CAGGGACCCTGAGATGGGCGGCAAGCCCAGAAGAAAGAACCCCCAGGAAGG

CCTGTATAACGAACTGCAGAAAGACAAGATGGCCGAGGCCTACAGCGAGATC

GGCATGAAGGGCGAGCGGAGAAGAGGCAAGGGCCACGATGGCCTGTACCAG

GGCCTGAGCACCGCCACCAAGGACACCTATGACGCCCTGCACATGCAGGCCC

TGCCCCCCAGA-3'

Polynucleotide Coding for K10-18H CAR (Sequence ID No. 310)

5'-GAAATTGTGTTGACACAGTCTCCAGCCACCCTGTCTTTGTCTCCAGGGGAAAG

AGCCACCCTCTCCTGCAGGGCCAGTCAGAGTGTTAGCAGCAACTTAGCCTGG

TACCAGCAAAAACTTGGCCAGGCTCCCAGGCTCCTCATCTATGGTGCATCCAG

CAGGGCCACTGGCATCCCAGACAGGTTCAGTGGCAGTGGGTCTGGGACAGAC

TTCACTCTCACCATCAGCAGACTGGAGCCTGAAGATTTTGCAGTGTATTACTG

TCAGCAGTATGGTAGCTCACCCGATATATTCACTTTCGGCCCTGGGACCAAAG

TGGATATCAAAGGCTCTACAAGCGGCTCTGGCAAGCCTGGATCTGGCGAGGG

AAGCACCAAGGGCGAAGTGCAGCTTGTGGAATCTGGCGGAGGACTGGTGCA

GCCTGGAAGAAGCCTGAGACTGTCTTGTGCCGCCAGCGGCTTCACCTTCGAC

GATTATGCCATGCACTGGGTCCGACAGGCCCCTGGAAAAGGCCTTGAATGGG

TGTCCGGCATCTCTTGGAACAGCGGCAGAATCGGCTACGCCGACTCTGTGAA

GGGCAGATTCACCATCAGCCGGGACAACGCCAAGAACAGCCTGTTCCTGCAG

ATGAACTCCCTGAGAGCCGAGGACACCGCCGTGTACTACTGTGCCAGAGATC

AGGGCTACCACTACTACGACTCTGCCGAGCACGCCTTCGATATCTGGGGCCAG

GGAACAGTGGTCACCGTTAGTTCTGCGGCCGCAATCGAAGTGATGTACCCCC

CTCCCTACCTGGACAACGAGAAGTCCAACGGCACCATTATCCACGTGAAGGG

AAAGCACCTGTGCCCCAGCCCTCTGTTCCCTGGCCCTAGCAAGCCTTTCTGG

GTGCTGGTGGTCGTGGGCGGAGTGCTGGCCTGTTATAGCCTGCTCGTGACCG

TGGCCTTCATCATCTTTTGGGTGCGCAGCAAGCGGAGCCGGCTGCTGCACAG

-continued

```
CGACTACATGAACATGACCCCCAGACGGCCCGGACCCACCAGAAAGCACTAC

CAGCCTTACGCCCCTCCCAGAGACTTCGCCGCCTACAGATCTCGAGTGAAGTT

CAGCAGAAGCGCCGACGCCCCTGCCTATCAGCAGGGCCAGAACCAGCTGTAC

AACGAGCTGAACCTGGGCAGACGGGAAGAGTACGACGTGCTGGACAAGCGG

AGAGGCAGGGACCCTGAGATGGGCGGCAAGCCCAGAAGAAAGAACCCCCAG

GAAGGCCTGTATAACGAACTGCAGAAAGACAAGATGGCCGAGGCCTACAGCG

AGATCGGCATGAAGGGCGAGCGGAGAAGAGGCAAGGGCCACGATGGCCTGT

ACCAGGGCCTGAGCACCGCCACCAAGGACACCTATGACGCCCTGCACATGCA

GGCCCTGCCCCCCAGA-3'
```

The nucleic acid of the present invention may be introduced into an expression vector, for example. The descriptions above can be applied to the above-mentioned expression vector, for example.

Regarding the nucleic acid of the present invention, the various polynucleotides above can be manufactured using a known genetic engineering technique and/or a known synthesis technique, for example.

Cell

As described above, the cell of the present invention includes the chimeric antigen receptor of the present invention. The cell of the present invention is characterized by including the chimeric antigen receptor of the present invention, and there is no particular limitation on the other configurations and conditions. The cell of the present invention can be used to treat cancer, for example. The descriptions of the CAR library, the first screening method, the first antibody or the like, the second antibody or the like, the gene, the expression vector, the transformant, the first chimeric antigen receptor, the second chimeric antigen receptor, the nucleic acid, and the like of the present invention can be applied to the cell of the present invention, for example.

The cell of the present invention may also express a CAR other than the CAR of the present invention. The cell is preferably a T cell. The T cell may be a T cell-like cell, for example.

Cell-Manufacturing Method

As described above, the cell-manufacturing method of the present invention includes an introduction step of introducing the nucleic acid of the present invention into cells. The cell-manufacturing method of the present invention is characterized in that the nucleic acid of the present invention is introduced into cells in the introduction step, and there is no particular limitation on the other steps and conditions. The cell-manufacturing method of the present invention can be used to manufacture cells capable of treating cancer, for example. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, and the like of the present invention can be applied to the cell-manufacturing method of the present invention, for example.

The cell are preferably a T cell or T cell-like cell.

There is no particular limitation on the nucleic acid-introducing method performed in the introduction step, and the descriptions of the first expression step in the first screening method of the present invention can be applied, for example.

The cell-manufacturing method of the present invention may also include an expression step of expressing a chimeric antigen receptor encoded by the nucleic acid in the cells after the introduction step, for example. The expression step can be performed by culturing the cells that have been subjected to the introduction step, for example.

Cancer Therapeutic Agent

A cancer therapeutic agent (also referred to as a "therapeutic agent" hereinafter) of the present invention includes the cell, gene, expression vector, or nucleic acid of the present invention. The therapeutic agent of the present invention is characterized by including the cell, gene, expression vector, or nucleic acid of the present invention, and there is no particular limitation on the other configurations and conditions. The therapeutic agent of the present invention can be used to treat cancer, for example. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, the cell-manufacturing method, and the like of the present invention can be applied to the cancer therapeutic agent of the present invention, for example.

In the present invention, cancer to be treated is not particularly limited and can be determined as appropriate in accordance with the type of chimeric antigen receptor to be expressed, or the like, for example. When the cancer therapeutic agent of the present invention is a cell, gene, expression vector, or nucleic acid involving a CAR capable of binding to A2/NY-ESO-$1_{157}$, examples of the cancer to be treated include malignant melanoma, lung cancer, synovial sarcoma, breast cancer, esophageal cancer, ovarian cancer, bladder cancer, neuroblastoma, and myeloma. When the cancer therapeutic agent of the present invention is a cell, gene, expression vector, or nucleic acid involving a CAR capable of binding to CD19, examples of the cancer to be treated include B-cell lymphoma, acute lymphatic leukemia, chronic lymphatic leukemia, and multiple myeloma.

There is no particular limitation on the conditions for administrating the therapeutic agent of the present invention, and the administration form, the administration method, the timing of administration, the dosage amount, and the like can be determined as appropriate in accordance with the type of target cancer, the stage of cancer progression, the age of a patient, and the like, for example. There is no particular limitation on a method for using the therapeutic agent of the present invention, and it is sufficient that the therapeutic agent of the present invention is administered to the administration target, for example.

Examples of the administration target include cells, tissues, and organs. Examples of the administration target include humans and non-human animals other than humans. Examples of the non-human animals include mammals such as mice, rats, dogs, monkeys, rabbits, sheep, horses, and pigs. The administration may be in vivo administration or in vitro administration, for example.

The administration method is not particularly limited and can be determined as appropriate in accordance with the administration target, for example. Examples of the administration method include parenteral administration and oral administration. Examples of the parenteral administration include topical administration, subcutaneous administration, intracutaneous administration, intramuscular administration, intraperitoneal administration, intravenous administration, intralymphatic administration, and intratumoral administration.

There is no particular limitation on the administration form of the therapeutic agent of the present invention, and an example thereof is a liquid agent such as an injection solution (an injection) or a drip infusion solution, or the like.

There is no particular limitation on the amount of the cells blended in the therapeutic agent of the present invention. Also, there is no particular limitation on the administration conditions of the cells. When the administration method is intravenous administration, the administration conditions of the cells are as follows: the dose (total) for an adult male human is $1 \times 10^8$ to $3 \times 10^{10}$ cells, and preferably $1 \times 10^9$ to $1 \times 10^{10}$ cells, for example, and the administration frequency is once a week to once every four weeks, for example. It is preferable that the cells are blended in the therapeutic agent of the present invention in such an amount that achieves a concentration at which the administration conditions shown as an example can be realized.

There is no particular limitation on the amount of the gene, expression vector, or nucleic acid blended in the therapeutic agent of the present invention. Also, there is no particular limitation on the administration conditions of the gene, expression vector, or nucleic acid. When the administration method is subcutaneous injection, intravenous injection, or the like, and is systemic administration to a human, the dose (total) is 5 to 5000 mg or 50 to 500 mg, for example, and the administration frequency is once every two weeks to once every eight weeks, for example.

The therapeutic agent of the present invention may include only one of, or a plurality of, the cell, gene, expression vector, and nucleic acid. Also, the therapeutic agent of the present invention may further include other additives. There is no particular limitation on the blend amounts of the additives as long as the functions of the therapeutic agent of the present invention is not inhibited. There is no particular limitation on the additives, and pharmaceutically acceptable additives are preferable, for example. The types of additives are not particularly limited and can be selected as appropriate in accordance with the type of administration target, for example. Examples of the additives include bases, stabilizers, and preservatives.

Cancer Treatment Method

A cancer treatment method of the present invention includes an administration step of administering the cell, gene, expression vector, or nucleic acid of the present invention to an administration target. The cancer treatment method of the present invention is characterized by administering the cell, gene, expression vector, or nucleic acid of the present invention to an administration target in the administration step, and there is no particular limitation on the other steps and conditions. The treatment method of the present invention can be used to treat cancer. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, the cell-manufacturing method, the therapeutic agent, and the like of the present invention can be applied to the cancer treatment method of the present invention, for example.

In the administration step, any one of, or a plurality of, the cell, gene, expression vector, and nucleic acid of the present invention may be administered.

Use of Antibody or the Like, or Cell, Gene, Expression Vector, or Nucleic Acid

The present invention is directed to the antibody of the present invention or the antigen-binding fragment thereof to be used in a cancer treatment method, or the antibody of the present invention or the antigen-binding fragment thereof to be used to treat cancer. Also, the present invention is directed to use of the antibody of the present invention or the antigen-binding fragment to manufacture a cancer treatment medicine. Furthermore, the present invention is directed to the cell, gene, expression vector, or nucleic acid of the present invention to be used in a cancer treatment method, or the cell, gene, expression vector, or nucleic acid of the present invention to be used to treat cancer. Also, the present invention is directed to use of the cell, gene, expression vector, or nucleic acid of the present invention to manufacture a cancer treatment medicine. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, the cell-manufacturing method, the therapeutic agent, the treatment method, and the like of the present invention can be applied to the use of the present invention, for example.

BsAb Library

A bispecific antibody (BsAb) library of the present invention includes nucleic acids coding for first bispecific antibodies (BsAbs), wherein each of the first BsAbs includes a first antigen-binding domain and a second antigen-binding domain, the first antigen-binding domain includes a first single-chain antibody (scFv) capable of binding to a first target antigen, the second antigen-binding domain includes a second scFv to be screened for the ability to bind to a second target antigen, the second scFv includes a second heavy-chain variable region and a second light-chain variable region, the second heavy-chain variable region and the second light-chain variable region meet Condition 1 or Condition 2 below, and the first target antigen or the second target antigen is an immune cell-activating receptor.

Condition 1

The heavy-chain complementarity determining region (CDRH) 1, the CDRH2, and the CDRH3 in the second heavy-chain variable region include the CDRH1, the CDRH2, and the CDRH3 in the heavy-chain variable region of an antibody capable of binding to the second target antigen or an antigen-binding fragment of the antibody, respectively, and the light-chain complementarity determining region (CDRL) 1, the CDRL2, and the CDRL3 in the second light-chain variable region include the CDRL1, the CDRL2, and the CDRL3 in the light-chain variable region of a first B cell receptor, respectively.

Condition 2

The heavy-chain complementarity determining region (CDRH) 1, the CDRH2, and the CDRH3 in the second heavy-chain variable region include the CDRH1, the CDRH2, and the CDRH3 in the heavy-chain variable region of a first B cell receptor, respectively, and
the light-chain complementarity determining region (CDRL) 1, the CDRL2, and the CDRL3 in the second light-chain variable region include the CDRL1, the CDRL2, and the CDRL3 in the light-chain variable region of an antibody capable of binding to the second target antigen or an antigen-binding fragment of the antibody, respectively.

In the BsAb library of the present invention, each of the first BsAbs included in the BsAb library of the present invention includes a first antigen-binding domain and a second antigen-binding domain, the first antigen-binding domain includes a first scFv capable of binding to a first target antigen, the second antigen-binding domain includes a second scFv to be screened for the ability to bind to a second target antigen, the second scFv includes a second heavy-chain variable region and a second light-chain variable region, the second heavy-chain variable region and the second light-chain variable region meet Condition 1 or Condition 2 above, the first target antigen or the second target antigen is an immune cell-activating receptor, and there is no particular limitation on the other configurations and conditions. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, the cell-manufacturing method, the therapeutic agent, the treatment method, and the like of the present invention can be applied to the BsAb library of the present invention, for example.

In the BsAb library of the present invention, the first BsAb is a protein that includes the first antigen-binding domain and the second antigen-binding domain. The first antigen-binding domain and the second antigen-binding domain include a first single-chain antibody (scFv) capable of binding to a first target antigen, and a second scFv to be screened for the ability to bind to a second target antigen, respectively. The second scFv has a structure similar to that of an scFv, for example, and the extracellular domain capable of binding to the antigen is changed to the second antigen-binding domain to be screened for the ability to bind to the second target antigen. Moreover, in the BsAb library of the present invention, the first target antigen or the second target antigen is an immune cell-activating receptor. Accordingly, when the first target antigen is the immune cell-activating receptor, if the first BsAb capable of binding to the second target antigen coexists with an immune cell capable of expressing the second target antigen and the first target antigen (the immune cell-activating receptor), the first BsAb can induce signal via the immune cell-activating receptor of the immune cell, thus making it possible to activate the immune cell (e.g., cause the proliferation of the immune cell, the expression of an activation marker, and the like), for example. That is, with the BsAb library of the present invention, when the first target antigen is the immune cell-activating receptor, a second screening method, which will be described later, can be used to select, from the BsAb group expressed from the BsAb library, a first BsAb capable of activating the immune cell as a BsAb capable of binding to the second target antigen. Accordingly, with the BsAb library of the present invention, scFvs capable of binding to the second target antigen can be screened more easily compared with a method in which hybridomas are used and a method in which phage display is used, for example. Moreover, a first BsAb capable of binding to the second target antigen can activate the immune cell in the second screening method, which will be described later, for example, and thus it can be said that the first BsAb is a BsAb capable of activating the immune cell. Therefore, with the BsAb library of the present invention, BsAbs that can induce cytotoxic activity and the like against cells expressing the second target antigen via the immune cell can be screened, for example.

When the second target antigen is the immune cell-activating receptor, if the first BsAb capable of binding to the second target antigen coexists with an immune cell capable of expressing the first target antigen and the second target antigen (the immune cell-activating receptor), the first BsAb can induce signal via the immune cell-activating receptor of the immune cell, thus making it possible to activate the immune cell (e.g., cause the proliferation of the immune cell, the expression of an activation marker, and the like), for example. That is, with the BsAb library of the present invention, when the second target antigen is the immune cell-activating receptor, the second screening method, which will be described later, can be used to select, from the BsAb group expressed from the BsAb library, a first BsAb capable of activating the immune cell as a BsAb capable of binding to the second target antigen. Accordingly, with the BsAb library of the present invention, scFvs capable of binding to the second target antigen can be screened more easily compared with a method in which hybridomas are used and a method in which phage display is used, for example. Moreover, a first BsAb capable of binding to the second target antigen can activate the immune cell in the second screening method, which will be described later, for example, and thus it can be said that the first BsAb is a BsAb capable of activating the immune cell. Therefore, with the BsAb library of the present invention, BsAbs that can induce, via the immune cell, cytotoxic activity and the like against cells expressing the first target antigen can be screened, for example.

In the BsAb library of the present invention, the second antigen-binding domain includes the second scFv to be screened for the ability to bind to the target antigen. The second scFv is a single-chain polypeptide derived from an antigen capable of binding to an antigen, for example, and has a structure similar to that of an scFv that has an ability to bind to the antigen. The scFv is a polypeptide obtained by coupling the fragments (Fvs) of variable regions of the heavy chain (H chain) and the light chain (L chain) of the antibody capable of binding to the antigen. On the other hand, in the second scFv, either the heavy-chain variable region or the light-chain variable region is a variable region of the antibody or the like capable of binding to the second target antigen, and the other one is a variable region derived from a B cell receptor, namely a variable region that may or may not bind to the second target antigen, as described later, for example. With the BsAb library of the present invention in which the second scFv has such a configuration, heavy-chain variable regions or light-chain variable regions capable of binding to the second target antigen can be screened, for example. Therefore, with the BsAb library of the present invention, scFvs capable of binding to the second target antigen can be screened using a smaller number of, or a smaller number of types of, nucleic acids compared with a phage display technique in which heavy-chain variable regions and light-chain variable regions capable of binding to the second target antigen are screened at a time, for example.

Regarding the BsAb library of the present invention, the term "nucleic acid coding for the first BsAb" refers to a nucleic acid (polynucleotide) coding for the amino acid sequence of the first BsAb, for example, and the descriptions above can be applied.

The term "BsAb" as used in the present invention refers to an antibody in which two antigen-binding sites in the antibody molecule are capable of binding to different target antigens, or an antigen-binding fragment of the antibody, for example. The term "different target antigens" means that the epitopes are different, for example, and the epitopes may be epitopes of different antigens, or different epitopes in one antigen. The structure of a known bispecific antibody can be employed as that of the "BsAb", for example, and specific examples of the structure to be employed include the structures of a dual-variable-domain antibody (DVD-Ig (trademark)), a diabody, a triabody, a tetrabody, a tandab, a flexibody (a combination of an scFv and a diabody), a tandem scFv (e.g., BiTE (registered trademark) manufactured by Micromet), DART (registered trademark) (manufactured by MacroGenics), Fcab (trademark) or mAb$^2$ (trademark) (manufactured by F-star), an Fc engineering antibody (manufactured by Xencor), and DuoBody (registered trademark) (manufactured by Genmab). The tandem scFv is preferable because the library can be easily constructed. The tandem scFv is a protein in which two scFvs are coupled to each other via a linker peptide (inter-Fv linker peptide), for example, and in each of the two scFvs, the heavy-chain variable region and the light-chain variable region are coupled to each other via a linker peptide (Fv linker peptide).

Hereinafter, regarding the first BsAb, a case where the first target antigen is an immune cell-activating receptor and a case where the second target antigen is an immune cell-activating receptor will be described.

(1) First Target Antigen: Immune Cell-Activating Receptor

The term "immune cell-activating receptor" above refers to a receptor that is expressed in the immune cell and that can activate the immune cell capable of expressing the immune cell-activating receptor due to binding to a ligand or cross-linking between a plurality of immune cell-activating receptors, for example. The immune cell-activating receptor can be determined in accordance with the type of immune cell, for example. When the immune cell is a T cell, a specific example of the immune cell-activating receptor is CD3. Example of the CD3 include CD3γ, CD3δ, CD3ε, CD3ζ, CD3η, and complexes thereof. When the immune cell is an NK cell, an example of the immune cell-activating receptor is an NK cell-activating receptor. Examples of the NK cell-activating receptor include CD94/NKG2C, CD94/NKG2E, and NKG2D/NKG2D. When the immune cell is an NKT cell, examples of the immune cell-activating receptor include CD3 and the NK cell-activating receptor. When the immune cell is a B cell, examples of the immune cell-activating receptor include CD19, CD79α, and CD79β.

When the first target antigen is the above-mentioned immune cell-activating receptor, there is no particular limitation on the second target antigen, and the descriptions of the target antigen in the CAR library can be applied, for example.

In the BsAb library of the present invention, the first scFv includes a first heavy-chain variable region and a first light-chain variable region, for example. The first heavy-chain variable region and the first light-chain variable region have structures similar to those of the heavy-chain variable region and the light-chain variable region in an antibody molecule, respectively. In general, the heavy-chain variable region and the light-chain variable region in an antibody molecule each include three complementarity determining regions (CDRs). The CDRs are also referred to as "hypervariable domains". The CDRs are regions in which the primary structure is particularly likely to be variable in the variable regions of the heavy chain and the light chain, and the primary structure generally includes three CDRs. In the present invention, the three CDRs in the heavy-chain variable region are referred to as a heavy-chain CDR 1 (CDRH1), a heavy-chain CDR 2 (CDRH2), and a heavy-chain CDR 3 (CDRH3), in this order from the amino terminus (N terminus) of the amino acid sequence of the heavy-chain variable region, and the three CDRs in the light-chain variable region are referred to as a light-chain CDR 1 (CDRL1), a light-chain CDR 2 (CDRL2), and a light-chain CDR 3 (CDRL3), in this order from the amino terminus of the amino acid sequence of the light-chain variable region. These sites are close to one another in the three-dimensional structure and determine the binding specificity for an antigen.

The first heavy-chain variable region includes the CDRH1, the CDRH2, and the CDRH3. The first light-chain variable region includes the CDRL1, the CDRL2, and the CDRL3.

An antibody capable of binding to an immune cell-activating receptor such as CD3 or an antigen-binding fragment of the antibody is used for the CDRH1, the CDRH2, and the CDRH3 in the first heavy-chain variable region and the CDRL1, the CDRL2, and the CDRL3 in the first light-chain variable region. For example, the descriptions of an antibody and an antigen-binding fragment regarding the above-described antibody of the present invention or the like can be applied to specific examples of the antibody or the antigen-binding fragment thereof.

Known antibodies or the like can be used as the antibody or the like capable of binding to the immune cell-activating receptor in accordance with the type of immune cell-activating receptor, for example. In a specific example, when the immune cell-activating receptor is CD3, examples of an antibody against CD3ε include an OKT3 antibody, a UCHT1 antibody, an L2K antibody, an HIT3a antibody, a 28F11 antibody, and a 27H5 antibody, for example. When the immune cell-activating receptor is CD19, examples of an antibody against CD19 include an FMC63 antibody and SJ25C1. The antibody or the like capable of binding to the immune cell-activating receptor may be an antibody obtained through immunization with the immune cell-activating receptor, for example. The antibody or the like capable of binding to the immune cell-activating receptor may be an scFv obtained using the second screening method of the present invention, which will be described later, for example. The CDRH1, the CDRH2, and the CDRH3 in the first heavy-chain variable region may respectively be polypeptides that consist of the amino acid sequences of the CDRH1, the CDRH2, and the CDRH3 of the antibody or the like capable of binding to the immune cell-activating receptor, or polypeptides that include the amino acid sequences of the CDRH1, the CDRH2, and the CDRH3 of the antibody or the like capable of binding to the immune cell-activating receptor, for example.

Regions in the first heavy-chain variable region other than the CDRH1, the CDRH2, and the CDRH3, namely framework regions (FRs), may include the FRs in the heavy-chain variable region of the antibody or the like capable of binding to the immune cell-activating receptor, for example. The number of the FRs above in the primary structure is generally four. In the present invention, the four FRs in the heavy-chain variable region are referred to as a heavy-chain FR 1 (FRH1), a heavy-chain FR 2 (FRH2), a heavy-chain FR 3 (FRH3), and a heavy-chain FR 4 (FRH4), in this order from the N terminus of the amino acid sequence of the heavy-chain variable region. It should be noted that the CDRHs and the FRHs are arranged such that the FRH1, the CDRH1, the FRH2, the CDRH2, the FRH3, the CDRH3, and the FRH4 are lined up in this order from the N terminus of the amino acid sequence of the heavy-chain variable region, for example. The FRH1, the FRH2, the FRH3, and the FRH4 in the first heavy-chain variable region may respectively be polypeptides that consist of the amino acid sequences of the FRH1, the FRH2, the FRH3, and the FRH4 of the antibody or the like capable of binding to the immune cell-activating receptor, or polypeptides that include the amino acid sequences of the FRH1, the FRH2, the FRH3, and the FRH4 of the antibody or the like capable of binding to the immune cell-activating receptor, for example. It is preferable that "the antibody or the like capable of binding to the immune cell-activating receptor" in the descriptions of the CDRHs and "the antibody or the like capable of binding to the immune cell-activating receptor" in the descriptions of the FRHs are the same antibody or the like.

The first heavy-chain variable region may include the heavy-chain variable region of the antibody or the like capable of binding to the immune cell-activating receptor, for example. In this case, the first heavy-chain variable region may be a polypeptide that consists of the amino acid sequence of the heavy-chain variable region of the antibody or the like capable of binding to the immune cell-activating receptor, or a polypeptide that includes the amino acid sequence of the heavy-chain variable region of the antibody or the like capable of binding to the immune cell-activating receptor, for example.

The CDRL1, the CDRL2, and the CDRL3 in the first light-chain variable region may respectively be polypeptides that consist of the amino acid sequences of the CDRL1, the CDRL2, and the CDRL3 of the antibody or the like capable of binding to the immune cell-activating receptor, or polypeptides that include the amino acid sequences of the CDRL1, the CDRL2, and the CDRL3 of the antibody or the like capable of binding to the immune cell-activating receptor, for example.

The FRs in the first light-chain variable region may include the FRs in the light-chain variable region of the antibody or the like capable of binding to the immune cell-activating receptor, for example. The number of the FRs above in the primary structure is generally four. In the present invention, the four FRs in the light-chain variable region are referred to as a light-chain FR 1 (FRL1), a light-chain FR 2 (FRL2), a light-chain FR 3 (FRL3), and a light-chain FR 4 (FRL4), in this order from the N terminus of the amino acid sequence of the light-chain variable region. It should be noted that the CDRLs and the FRLs are arranged such that the FRL1, the CDRL1, the FRL2, the CDRL2, the FRL3, the CDRL3, and the FRL4 are lined up in this order from the N terminus of the amino acid sequence of the light-chain variable region, for example. The FRL1, the FRL2, the FRL3, and the FRL4 in the first light-chain variable region may respectively be polypeptides that consist of the amino acid sequences of the FRL1, the FRL2, the FRL3, and the FRL4 of the antibody or the like capable of binding to the immune cell-activating receptor, or polypeptides that include the amino acid sequences of the FRL1, the FRL2, the FRL3, and the FRL4 of the antibody or the like capable of binding to the immune cell-activating receptor, for example. It is preferable that "the antibody or the like capable of binding to the immune cell-activating receptor" in the descriptions of the CDRLs and "the antibody or the like capable of binding to the immune cell-activating receptor" in the descriptions of the FRLs are the same antibody or the like.

The first light-chain variable region may include the light-chain variable region of the antibody or the like capable of binding to the immune cell-activating receptor, for example. In this case, the first light-chain variable region may be a polypeptide that consists of the amino acid sequence of the light-chain variable region of the antibody or the like capable of binding to the immune cell-activating receptor, or a polypeptide that includes the amino acid sequence of the light-chain variable region of the antibody or the like capable of binding to the immune cell-activating receptor, for example.

In the first scFv, the first heavy-chain variable region and the first light-chain variable region are coupled to each other via a first linker peptide (first Fv linker peptide), for example. It is preferable that the first Fv linker peptide does not inhibit the first scFv from binding to the immune cell-activating receptor, for example. The first Fv linker peptide is constituted by 1 to 40, 1 to 18, 1 to 15, 1 to 7, 1 to 3, or 1 or 2 amino acids, for example. The first Fv linker peptide is constituted by amino acids such as glycine and serine, for example, and a specific example thereof is $(GGGGS)_n$. n in this formula is an integer from 1 to 6, for example. The amino acid sequence of the first Fv linker peptide may be the amino acid sequence of the polypeptide represented by Sequence ID No. 1 or 2 above, for example.

In the BsAb library of the present invention, the second scFv includes a second heavy-chain variable region and a second light-chain variable region. The second heavy-chain variable region and the second light-chain variable region have structures similar to those of the heavy-chain variable region and the light-chain variable region in an antibody molecule, respectively, and the descriptions of the first scFv above can be applied to the structures thereof.

The second heavy-chain variable region includes the CDRH1, the CDRH2, and the CDRH3. The second light-chain variable region includes the CDRL1, the CDRL2, and the CDRL3. The second heavy-chain variable region and the second light-chain variable region meet Condition 1 or Condition 2 above.

In Condition 1 above, the CDRH1, the CDRH2, and the CDRH3 of an antibody or the like capable of binding to the second target antigen are used as those in the second heavy-chain variable region, and the CDRL1, the CDRL2, and the CDRL3 in the second light-chain variable region are screened for the ability to bind to the second target antigen. For example, the descriptions of an antibody and an antigen-binding fragment regarding the above-described antibody of the present invention or the like can be applied to specific examples of the antibody or the antigen-binding fragment thereof.

Known antibodies or the like can be used as the antibody or the like capable of binding to the second target antigen in accordance with the second target antigen, for example. As a specific example, a 3M4E5 antibody can be used as an antibody against a complex of HLA-A*02:01 and NY-ESO- $1_{157-165}$, for example. An FMC63 antibody can be used as an antibody against human CD19, for example. The antibody or the like capable of binding to the second target antigen may be an scFv obtained using the second screening method of the present invention, which will be described later, or an antibody obtained through immunization with the second target antigen, for example. The CDRH1, the CDRH2, and the CDRH3 in the second heavy-chain variable region may respectively be polypeptides that consist of the amino acid sequences of the CDRH1, the CDRH2, and the CDRH3 of the antibody or the like capable of binding to the second target antigen, or polypeptides that include the amino acid sequences of the CDRH1, the CDRH2, and the CDRH3 of the antibody or the like capable of binding to the second target antigen, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the antibody or the like capable of binding to the second target antigen, or polypeptides that include the amino acid sequences of the FRH1, the FRH2, the FRH3, and the FRH4 of the antibody or the like capable of binding to the second target antigen, for example.

It is preferable that "the antibody or the like capable of binding to the second target antigen" in the descriptions of the CDRHs and "the antibody or the like capable of binding to the second target antigen" in the descriptions of the FRHs are the same antibody or the like.

The second heavy-chain variable region may include the heavy-chain variable region of the antibody or the like capable of binding to the second target antigen, for example. In this case, the second heavy-chain variable region may be a polypeptide that consists of the amino acid sequence of the heavy-chain variable region of the antibody or the like capable of binding to the second target antigen, or a polypeptide that includes the amino acid sequence of the heavy-chain variable region of the antibody or the like capable of binding to the second target antigen, for example.

The second light-chain variable region is encoded by a VJ gene fragment formed through VJ gene recombination of a V gene fragment and a J gene fragment, for example. Therefore, the first B cell receptor may be a B cell receptor that includes a polypeptide encoded by an artificial VJ gene fragment designed as an artificial combination of a V gene fragment and a J gene fragment, for example. B cells in a living organism express a light-chain variable region encoded by a product formed through VJ gene recombination, for example.

Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the BsAb library of the present invention, the first B cell receptor is preferably the light-chain variable region of the B cell receptor derived from isolated B cells for the reason that the BsAb library can be more easily prepared.

The CDRL1, the CDRL2, and the CDRL3 in the second light-chain variable region may respectively be polypeptides that consist of the amino acid sequences of the CDRL1, the CDRL2, and the CDRL3 of the first B cell receptor, or polypeptides that include the amino acid sequences of the CDRL1, the CDRL2, and the CDRL3 of the first B cell receptor, for example.

The FRL1, the FRL2, the FRL3, and the FRL4 in the second light-chain variable region may respectively be polypeptides that consist of the amino acid sequences of the FRL1, the FRL2, the FRL3, and the FRL4 of the first B cell receptor, or polypeptides that include the amino acid sequences of the FRL1, the FRL2, the FRL3, and the FRL4 of the first B cell receptor, for example. It is preferable that "the first B cell receptor" in the descriptions of the CDRLs and "the first B cell receptor" in the descriptions of the FRLs are the same B cell receptor.

The second light-chain variable region may include the light-chain variable region of the first B cell receptor, for example. In this case, the second light-chain variable region may be a polypeptide that consists of the amino acid sequence of the light-chain variable region of the first B cell receptor, or a polypeptide that includes the amino acid sequence of the light-chain variable region of the first B cell receptor, for example.

In the second scFv, the second heavy-chain variable region and the second light-chain variable region are coupled to each other via a second linker peptide (second Fv linker peptide), for example. It is preferable that the second Fv linker peptide does not inhibit the second scFv from binding to the second target antigen, for example. The second Fv linker peptide is constituted by 1 to 40, 1 to 18, 1 to 15, 1 to 7, 1 to 3, or 1 or 2 amino acids, for example. The second Fv linker peptide is constituted by amino acids such as glycine and serine, for example, and a specific example thereof is $(GGGGS)_n$. n in this formula is an integer from 1 to 6, for example. The amino acid sequence of the second Fv linker peptide may be the amino acid sequence of the polypeptide represented by Sequence ID No. 1 or 2 above, for example. The second Fv linker peptide may be the same as or different from the first Fv linker peptide, for example.

Next, in Condition 2 above, the CDRL1, the CDRL2, and the CDRL3 in the second light-chain variable region are derived from the antibody or the like capable of binding to the second target antigen, and the CDRH1, the CDRH2, and the CDRH3 in the second heavy-chain variable region are screened for the ability to bind to the second target antigen.

The second heavy-chain variable region is encoded by a VDJ gene fragment formed through VDJ gene recombination of a V gene fragment, a D gene fragment, and a J gene fragment, for example. Therefore, the first B cell receptor may be a B cell receptor that includes a polypeptide encoded by an artificial VDJ gene fragment designed as an artificial combination of a V gene fragment, a D gene fragment, and a J gene fragment, for example. B cells in a living organism express a heavy-chain variable region encoded by a product formed through VDJ gene recombination, for example. Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the BsAb library of the present invention, the first B cell receptor is preferably the heavy-chain variable region of the B cell receptor derived from isolated B cells for the reason that the BsAb library can be more easily prepared.

The CDRH1, the CDRH2, and the CDRH3 in the second heavy-chain variable region may respectively be polypeptides that consist of the amino acid sequences of the CDRH1, the CDRH2, and the CDRH3 of the first B cell receptor, or polypeptides that include the amino acid sequences of the CDRH1, the CDRH2, and the CDRH3 of the first B cell receptor, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the first B cell receptor, or polypeptides that include the amino acid sequences of the FRH1, the FRH2, the FRH3, and the FRH4 of the first B cell receptor, for example. It is preferable that "the first B cell receptor" in the descriptions of the CDRHs and "the first B cell receptor" in the descriptions of the FRHs are the same B cell receptor.

The second heavy-chain variable region may include the heavy-chain variable region of the first B cell receptor, for example. In this case, the second heavy-chain variable region may be a polypeptide that consists of the amino acid sequence of the heavy-chain variable region of the first B cell receptor, or a polypeptide that includes the amino acid sequence of the heavy-chain variable region of the first B cell receptor, for example.

Regarding the second light-chain variable region, the descriptions of the antibody or the like capable of binding to the second target antigen in Condition 1 can be applied to the above-mentioned antibody or the like capable of binding to the second target antigen, for example. The CDRL1, the CDRL2, and the CDRL3 in the second light-chain variable region may respectively be polypeptides that consist of the amino acid sequences of the CDRL1, the CDRL2, and the CDRL3 of the antibody or the like capable of binding to the second target antigen, or polypeptides that include the amino acid sequences of the CDRL1, the CDRL2, and the CDRL3 of the antibody or the like capable of binding to the second target antigen, for example.

The FRs in the second light-chain variable region may include the FRs in the light-chain variable region of the antibody or the like capable of binding to the second target antigen, for example. The FRL1, the FRL2, the FRL3, and the FRL4 in the second light-chain variable region may respectively be polypeptides that consist of the amino acid sequences of the FRL1, the FRL2, the FRL3, and the FRL4 of the antibody or the like capable of binding to the second target antigen, or polypeptides that include the amino acid sequences of the FRL1, the FRL2, the FRL3, and the FRL4 of the antibody or the like capable of binding to the second target antigen, for example. It is preferable that "the antibody or the like capable of binding to the second target antigen" in the descriptions of the CDRLs and "the antibody or the like capable of binding to the second target antigen" in the descriptions of the FRLs are the same antibody or the like.

The second light-chain variable region may include the light-chain variable region of the antibody or the like capable of binding to the second target antigen, for example. In this case, the second light-chain variable region may be a polypeptide that consists of the amino acid sequence of the light-chain variable region of the antibody or the like capable of binding to the second target antigen, or a polypeptide that includes the amino acid sequence of the light-chain variable region of the antibody or the like capable of binding to the second target antigen, for example.

In the second scFv, the second heavy-chain variable region and the second light-chain variable region are coupled to each other via a second linker peptide (second Fv linker peptide), for example. It is preferable that the second Fv linker peptide does not inhibit the second scFv from binding to the second target antigen, for example. The descriptions of the first Fv linker peptide can be applied to the descriptions of the second Fv linker peptide, for example. The second Fv linker peptide may be the same as or different from the first Fv linker peptide, for example.

The first scFv and the second scFv are directly or indirectly coupled to each other, for example. The coupling between the first scFv and the second scFv can be designed as appropriate in accordance with the type of first BsAb, for example. In a specific example, when the first BsAb is a tandem scFv, the first scFv and the second scFv are coupled to each other via a linker peptide (inter-Fv linker peptide). The inter-Fv linker peptide is constituted by 1 to 40, 1 to 18, 1 to 15, 1 to 7, 1 to 3, or 1 or 2 amino acids, for example. The inter-Fv linker peptide is constituted by amino acids such as glycine and serine, for example, and a specific example thereof is $(GGGGS)_n$. n in this formula is an integer from 1 to 6, for example. The amino acid sequence of the inter-Fv linker peptide may be the amino acid sequence of the polypeptide represented by Sequence ID No. 1 or 2 above, for example.

(2) Second Target Antigen: Immune Cell-Activating Receptor

There is no particular limitation on the first target antigen, and the descriptions of the target antigen in the CAR library can be applied, for example.

The descriptions of the first target antigen of the BsAb library of the present invention in "(1) First Target Antigen: Immune Cell-Activating Receptor" can be applied to the second target antigen.

In the BsAb library of the present invention, the first scFv includes a first heavy-chain variable region and a first light-chain variable region, for example. The first heavy-chain variable region and the first light-chain variable region have structures similar to those of the heavy-chain variable region and the light-chain variable region in an antibody molecule, respectively, and the descriptions of the first scFv of the BsAb library of the present invention in "(1) First Target Antigen: Immune Cell-Activating Receptor" can be applied. The first heavy-chain variable region includes the CDRH1, the CDRH2, and the CDRH3, for example. The first light-chain variable region includes the CDRL1, the CDRL2, and the CDRL3, for example.

An antibody capable of binding to the first target antigen or an antigen-binding fragment of the antibody is used for the CDRH1, the CDRH2, and the CDRH3 in the first heavy-chain variable region and the CDRL1, the CDRL2, and the CDRL3 in the first light-chain variable region. For example, the descriptions of an antibody and an antigen-binding fragment regarding the above-described antibody of the present invention or the like can be applied to specific examples of the antibody or the antigen-binding fragment thereof.

Known antibodies or the like capable of binding to the first target antigen can be used as the antibody or the like capable of binding to the first target antigen in accordance with the type of first target antigen, for example. The antibody or the like capable of binding to the first target antigen may be an antibody obtained through immunization with the first target antigen, for example. The antibody or the like capable of binding to the first target antigen may be an scFv obtained using the second screening method of the present invention, which will be described later, for example. The CDRH1, the CDRH2, and the CDRH3 in the first heavy-chain variable region may respectively be polypeptides that consist of the amino acid sequences of the CDRH1, the CDRH2, and the CDRH3 of the antibody or the like capable of binding to the first target antigen, or polypeptides that include the amino acid sequences of the CDRH1, the CDRH2, and the CDRH3 of the antibody or the like capable of binding to the first target antigen, for example.

The FRH1, the FRH2, the FRH3, and the FRH4 in the first heavy-chain variable region may respectively be polypeptides that consist of the amino acid sequences of the FRH1, the FRH2, the FRH3, and the FRH4 of the antibody or the like capable of binding to the first target antigen, or polypeptides that include the amino acid sequences of the FRH1, the FRH2, the FRH3, and the FRH4 of the antibody or the like capable of binding to the first target antigen, for example. It is preferable that "the antibody or the like capable of binding to the first target antigen" in the descriptions of the CDRHs and "the antibody or the like capable of binding to the first target antigen" in the descriptions of the FRHs are the same antibody or the like.

The first heavy-chain variable region may include the heavy-chain variable region of the antibody or the like capable of binding to the first target antigen, for example. In this case, the first heavy-chain variable region may be a polypeptide that consists of the amino acid sequence of the heavy-chain variable region of the antibody or the like capable of binding to the first target antigen, or a polypeptide that includes the amino acid sequence of the heavy-chain variable region of the antibody or the like capable of binding to the first target antigen, for example.

The CDRL1, the CDRL2, and the CDRL3 in the first light-chain variable region may respectively be polypeptides that consist of the amino acid sequences of the CDRL1, the CDRL2, and the CDRL3 of the antibody or the like capable of binding to the first target antigen, or polypeptides that include the amino acid sequences of the CDRL1, the CDRL2, and the CDRL3 of the antibody or the like capable of binding to the first target antigen, for example.

The FRL1, the FRL2, the FRL3, and the FRL4 in the first light-chain variable region may respectively be polypeptides that consist of the amino acid sequences of the FRL1, the FRL2, the FRL3, and the FRL4 of the antibody or the like capable of binding to the first target antigen, or polypeptides that include the amino acid sequences of the FRL1, the FRL2, the FRL3, and the FRL4 of the antibody or the like capable of binding to the first target antigen, for example. It is preferable that "the antibody or the like capable of binding to the first target antigen" in the descriptions of the CDRLs and "the antibody or the like capable of binding to the first target antigen" in the descriptions of the FRLs are the same antibody or the like.

The first light-chain variable region may include the light-chain variable region of the antibody or the like capable of binding to the first target antigen, for example. In this case, the first light-chain variable region may be a polypeptide that consists of the amino acid sequence of the light-chain variable region of the antibody or the like capable of binding to the first target antigen, or a polypeptide that includes the amino acid sequence of the light-chain variable region of the antibody or the like capable of binding to the first target antigen, for example.

In the first scFv, the first heavy-chain variable region and the first light-chain variable region are coupled to each other via a first linker peptide (first Fv linker peptide), for example. It is preferable that the first Fv linker peptide does not inhibit the first scFv from binding to the first target antigen, for example. The first Fv linker peptide is constituted by 1 to 40, 1 to 18, 1 to 15, 1 to 7, 1 to 3, or 1 or 2 amino acids, for example. The first Fv linker peptide is constituted by amino acids such as glycine and serine, for example, and a specific example thereof is $(GGGGS)_n$. n in this formula is an integer from 1 to 6, for example. The amino acid sequence of the first Fv linker peptide may be the amino acid sequence of the polypeptide represented by Sequence ID No. 1 or 2 above, for example.

In the BsAb library of the present invention, the second scFv includes a second heavy-chain variable region and a second light-chain variable region. The second heavy-chain variable region and the second light-chain variable region have structures similar to those of the heavy-chain variable region and the light-chain variable region in an antibody molecule, respectively, and the descriptions of the first scFv in (1) above can be applied to the structures.

The second heavy-chain variable region includes the CDRH1, the CDRH2, and the CDRH3. The second light-chain variable region includes the CDRL1, the CDRL2, and the CDRL3. The second heavy-chain variable region and the second light-chain variable region meet Condition 1 or Condition 2 above.

In Condition 1 above, an antibody or the like capable of binding to the immune cell-activating receptor is used for the CDRH1, the CDRH2, and the CDRH3 in the second heavy-chain variable region, and the CDRL1, the CDRL2, and the CDRL3 in the second light-chain variable region are screened for the ability to bind to the immune cell-activating receptor. For example, the descriptions of an antibody and an antigen-binding fragment regarding the above-described antibody of the present invention or the like can be applied to specific examples of the antibody or the antigen-binding fragment thereof.

The descriptions of the antibody or the like capable of binding to the immune cell-activating receptor of the BsAb library of the present invention in "(1) First Target Antigen: Immune Cell-Activating Receptor" can be applied to the above-mentioned antibody or the like capable of binding to the immune cell-activating receptor. The CDRH1, the CDRH2, and the CDRH3 in the second heavy-chain variable region may respectively be polypeptides that consist of the amino acid sequences of the CDRH1, the CDRH2, and the CDRH3 of the antibody or the like capable of binding to the immune cell-activating receptor, or polypeptides that include the amino acid sequences of the CDRH1, the CDRH2, and the CDRH3 of the antibody or the like capable of binding to the immune cell-activating receptor, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the antibody or the like capable of binding to the immune cell-activating receptor, or polypeptides that include the amino acid sequences of the FRH1, the FRH2, the FRH3, and the FRH4 of the antibody or the like capable of binding to the immune cell-activating receptor, for example. It is preferable that "the antibody or the like capable of binding to the immune cell-activating receptor" in the descriptions of the CDRHs and "the antibody or the like capable of binding to the immune cell-activating receptor" in the descriptions of the FRHs are the same antibody or the like.

The second heavy-chain variable region may include the heavy-chain variable region of the antibody or the like capable of binding to the immune cell-activating receptor, for example. In this case, the second heavy-chain variable region may be a polypeptide that consists of the amino acid sequence of the heavy-chain variable region of the antibody or the like capable of binding to the immune cell-activating receptor, or a polypeptide that includes the amino acid sequence of the heavy-chain variable region of the antibody or the like capable of binding to the immune cell-activating receptor, for example.

The second light-chain variable region is encoded by a VJ gene fragment formed through VJ gene recombination of a V gene fragment and a J gene fragment, for example. Therefore, the first B cell receptor may be a B cell receptor that includes a polypeptide encoded by an artificial VJ gene fragment designed as an artificial combination of a V gene fragment and a J gene fragment, for example. B cells in a living organism express a light-chain variable region encoded by a product formed through VJ gene recombination, for example. Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the BsAb library of the present invention, the first B cell receptor is preferably the light-chain variable region of the B cell receptor derived from isolated B cells for the reason that the BsAb library can be more easily prepared.

The CDRL1, the CDRL2, and the CDRL3 in the second light-chain variable region may respectively be polypeptides that consist of the amino acid sequences of the CDRL1, the CDRL2, and the CDRL3 of the first B cell receptor, or polypeptides that include the amino acid sequences of the CDRL1, the CDRL2, and the CDRL3 of the first B cell receptor, for example.

The FRL1, the FRL2, the FRL3, and the FRL4 in the second light-chain variable region may respectively be polypeptides that consist of the amino acid sequences of the FRL1, the FRL2, the FRL3, and the FRL4 of the first B cell receptor, or polypeptides that include the amino acid sequences of the FRL1, the FRL2, the FRL3, and the FRL4 of the first B cell receptor, for example. It is preferable that "the first B cell receptor" in the descriptions of the CDRLs and "the first B cell receptor" in the descriptions of the FRLs are the same B cell receptor.

The second light-chain variable region may include the light-chain variable region of the first B cell receptor, for example. In this case, the second light-chain variable region may be a polypeptide that consists of the amino acid sequence of the light-chain variable region of the first B cell receptor, or a polypeptide that includes the amino acid sequence of the light-chain variable region of the first B cell receptor, for example.

In the first scFv, the first heavy-chain variable region and the first light-chain variable region are coupled to each other via a first linker peptide (first Fv linker peptide), for example. It is preferable that the first Fv linker peptide does not inhibit the first scFv from binding to the first target antigen, for example. The first Fv linker peptide is constituted by 1 to 40, 1 to 18, 1 to 15, 1 to 7, 1 to 3, or 1 or 2 amino acids, for example. The first Fv linker peptide is constituted by amino acids such as glycine and serine, for example, and a specific example thereof is $(GGGGS)_n$. n in this formula is an integer from 1 to 6, for example. The amino acid sequence of the first Fv linker peptide may be the amino acid sequence of the polypeptide represented by Sequence ID No. 1 or 2 above, for example.

Next, in Condition 2 above, the CDRL1, the CDRL2, and the CDRL3 in the second light-chain variable region are derived from the antibody or the like capable of binding to the immune cell-activating receptor, and the CDRH1, the CDRH2, and the CDRH3 in the second heavy-chain variable region are screened for the ability to bind to the immune cell-activating receptor.

The second heavy-chain variable region is encoded by a VDJ gene fragment formed through VDJ gene recombination of a V gene fragment, a D gene fragment, and a J gene fragment, for example. Therefore, the first B cell receptor may be a B cell receptor that includes a polypeptide encoded by an artificial VDJ gene fragment designed as an artificial combination of a V gene fragment, a D gene fragment, and a J gene fragment, for example. B cells in a living organism express a heavy-chain variable region encoded by a product formed through VDJ gene recombination, for example. Therefore, the first B cell receptor may be a B cell receptor derived from isolated B cells, for example. In this case, the first B cell receptor may be a B cell receptor of B cells derived from a human, for example, and is preferably a B cell receptor derived from human peripheral blood B cells. In the BsAb library of the present invention, the first B cell receptor is preferably the heavy-chain variable region of the B cell receptor derived from isolated B cells for the reason that the BsAb library can be more easily prepared.

The CDRH1, the CDRH2, and the CDRH3 in the second heavy-chain variable region may respectively be polypeptides that consist of the amino acid sequences of the CDRH1, the CDRH2, and the CDRH3 of the first B cell receptor, or polypeptides that include the amino acid sequences of the CDRH1, the CDRH2, and the CDRH3 of the first B cell receptor, for example.

The FRH1, the FRH2, the FRH3, and the FRH4 in the second heavy-chain variable region may respectively be polypeptides that consist of the amino acid sequences of the FRH1, the FRH2, the FRH3, and the FRH4 of the first B cell receptor, or polypeptides that include the amino acid sequences of the FRH1, the FRH2, the FRH3, and the FRH4 of the first B cell receptor, for example. It is preferable that "the first B cell receptor" in the descriptions of the CDRHs and "the first B cell receptor" in the descriptions of the FRHs are the same B cell receptor.

The second heavy-chain variable region may include the heavy-chain variable region of the first B cell receptor, for example. In this case, the second heavy-chain variable region may be a polypeptide that consists of the amino acid sequence of the heavy-chain variable region of the first B cell receptor, or a polypeptide that includes the amino acid sequence of the heavy-chain variable region of the first B cell receptor, for example.

Regarding the second light-chain variable region, the descriptions of the antibody or the like capable of binding to the immune cell-activating receptor of the BsAb library of the present invention in "(1) First Target Antigen: Immune Cell-Activating Receptor" can be applied to the above-mentioned antibody or the like capable of binding to the immune cell-activating receptor, for example. The CDRL1, the CDRL2, and the CDRL3 in the second light-chain variable region may respectively be polypeptides that consist of the amino acid sequences of the CDRL1, the CDRL2, and the CDRL3 of the antibody or the like capable of binding to the immune cell-activating receptor, or polypeptides that include the amino acid sequences of the CDRL1, the CDRL2, and the CDRL3 of the antibody or the like capable of binding to the immune cell-activating receptor, for example.

The FRs in the second light-chain variable region may include the FRs in the light-chain variable region of the antibody or the like capable of binding to the immune cell-activating receptor, for example. The FRL1, the FRL2, the FRL3, and the FRL4 in the second light-chain variable region may respectively be polypeptides that consist of the amino acid sequences of the FRL1, the FRL2, the FRL3, and the FRL4 of the antibody or the like capable of binding to the immune cell-activating receptor, or polypeptides that include the amino acid sequences of the FRL1, the FRL2, the FRL3, and the FRL4 of the antibody or the like capable of binding to the immune cell-activating receptor, for example. It is preferable that "the antibody or the like capable of binding to the immune cell-activating receptor" in the descriptions of the CDRLs and "the antibody or the like capable of binding to the immune cell-activating receptor" in the descriptions of the FRLs are the same antibody or the like.

The second light-chain variable region may include the light-chain variable region of the antibody or the like capable of binding to the immune cell-activating receptor, for example. In this case, the second light-chain variable region may be a polypeptide that consists of the amino acid sequence of the light-chain variable region of the antibody or the like capable of binding to the immune cell-activating receptor, or a polypeptide that includes the amino acid sequence of the light-chain variable region of the antibody or the like capable of binding to the immune cell-activating receptor, for example.

In the second scFv, the second heavy-chain variable region and the second light-chain variable region are coupled to each other via a second linker peptide (second Fv linker peptide), for example. It is preferable that the second Fv linker peptide does not inhibit the second scFv from binding to the immune cell-activating receptor, for example. The descriptions of the first Fv linker peptide can be applied to the descriptions of the second Fv linker peptide, for example. The second Fv linker peptide may be the same as or different from the first Fv linker peptide, for example.

The first scFv and the second scFv may be directly or indirectly coupled to each other, or be formed such that, when the first scFv and the second scFv coexist, the third scFv and the fourth scFv are associated with (bind to) each other, for example. The coupling between the first scFv and the second scFv can be designed as appropriate in accordance with the type of first BsAb, for example. In a specific example, when the first BsAb is a tandem scFv, the first scFv and the second scFv are coupled to each other via a linker peptide (inter-Fv linker peptide). The inter-Fv linker peptide is constituted by 1 to 40, 1 to 18, 1 to 15, 1 to 7, 1 to 3, or 1 or 2 amino acids, for example. The inter-Fv linker peptide is constituted by amino acids such as glycine and serine, for example, and a specific example thereof is $(GGGGS)_n$. n in this formula is an integer from 1 to 6, for example. In a specific example, the amino acid sequence of the inter-Fv linker peptide may be the amino acid sequence of the polypeptide represented by Sequence ID No. 1 or 2 above, for example. The electric charges of the amino acid side chains can be used for the above-mentioned association, for example. In a specific example, the association can be induced by adding a domain that includes positively charged amino acids to one binding domain and adding a domain that includes negatively charged amino acids to the other binding domain, for example. Moreover, a combination of a tag sequence and a polypeptide capable of recognizing the tag sequence, or the like can also be used for the association, for example.

Regarding the arrangement order of the first scFv and the second scFv of each of the first BsAbs in the BsAb library of the present invention, the first scFv and the second scFv may be arranged in this order from the N-terminal side, or the second scFv and the first scFv may be arranged in this order from the N-terminal side. The latter case is preferable because the first BsAb library can be prepared more easily.

An example of the first BsAb is a polypeptide consisting of the amino acid sequence represented by Formula (3) (Sequence ID No. 158) below. Examples of the combination of $V_1$, $V_2$, $V_3$, and $V_4$ in Formula (3) below include combinations (V1) to (V8) below. When the second scFv meets Condition 1 above, the combination of $V_1$, $V_2$, $V_3$, and $V_4$ is preferably the combination (V7) or (V8) below. When the second scFv meets Condition 2 above, the combination of $V_1$, $V_2$, $V_3$, and $V_4$ is preferably the combination (V5) or (V6) below. In Formula (3) below, the amino acid sequence between $V_1$ and $V_2$ is the amino acid sequence of the first Fv linker peptide, the amino acid sequence between $V_2$ and $V_3$ is the amino acid sequence of the inter-Fv linker peptide, and the amino acid sequence between $V_3$ and $V_4$ is the amino acid sequence of the second Fv linker peptide. In Formula (3) below, the first Fv linker peptide and the second Fv linker peptide are Fv linker peptides 1, but may also be independently an Fv linker peptide 2.

(3)
[V$_1$]-[GSTSGSGKPGSGEGSTKG]-[V$_2$]-[SGSG]-[V$_3$]-[GSTSGSGKPGSGEGSTKG]-[V$_4$]...

(V1) $V_1$: $V_{H1}$, $V_2$: $V_{L1}$, $V_3$: $V_{H2}$, $V_4$: $V_{L2}$
(V2) $V_1$: $V_{L1}$, $V_2$: $V_{H1}$, $V_3$: $V_{H2}$, $V_4$: $V_{L2}$
(V3) $V_1$: $V_{H1}$, $V_2$: $V_{L1}$, $V_3$: $V_{L2}$, $V_4$: $V_{H2}$
(V4) $V_1$: $V_{L1}$, $V_2$: $V_{H1}$, $V_3$: $V_{L2}$, $V_4$: $V_{H2}$
(V5) $V_1$: $V_{H2}$, $V_2$: $V_{L2}$, $V_3$: $V_{H1}$, $V_5$: $V_{L1}$
(V6) $V_1$: $V_{H2}$, $V_2$: $V_{L2}$, $V_3$: $V_{L1}$, $V_4$: $V_{H1}$
(V7) $V_1$: $V_{L2}$, $V_2$: $V_{H2}$, $V_3$: $V_{H1}$, $V_4$: $V_{L1}$
(V8) $V_1$: $V_{L2}$, $V_2$: $V_{H2}$, $V_3$: $V_{L1}$, $V_4$: $V_{H1}$ $V_{H1}$: first heavy-chain variable region
$V_{L1}$: first light-chain variable region
$V_{H2}$: second heavy-chain variable region
$V_{L2}$: second light-chain variable region An example of the nucleic acid coding for the first BsAb is a polynucleotide consisting of the base sequence represented by Formula (4) (Sequence ID No. 159) below. Examples of the combination of $N_1$, $N_2$, $N_3$, and $N_4$ in Formula (4) below include combinations (N1) to (N8) below. The combinations (N1) to (N8) below are nucleic acids coding for the first BsAbs of the combinations (V1) to (V8) above, respectively. In Formula (4) below, the base sequence between $N_1$ and $N_2$ is the base sequence coding for the first Fv linker peptide, the base sequence between $N_2$ and $N_3$ is the base sequence coding for the inter-Fv linker peptide, and the base sequence between $N_3$ and $N_4$ is the base sequence coding for the second Fv linker peptide. In Formula (4) below, the base sequences coding for the first Fv linker peptide and the second Fv linker peptide are base sequences coding for Fv linker peptides 1, but may also be independently a base sequence coding for an Fv linker peptide 2.

(4)
5'-[N$_1$]-

[GGCTCTACAAGCGGCTCTGGCAAGCCTGGATCTGGCGAGGGAAGCACC

AAGGGC]-[N$_2$]-[AGCGGATCTGGC]-[N$_3$]-

[GGCTCTACAAGCGGCTCTGGCAAGCCTGGATCTGGCGAGGGAAGCACC

AAGGGC]-[N$_4$]-3'...

(N1) $N_1$: $N_{H1}$, $N_2$: $N_{L1}$, $N_3$: $N_{H2}$, $N_4$: $N_{L2}$
(N2) $N_1$: $N_{L1}$, $N_2$: $N_{H1}$, $N_3$: $N_{H2}$, $N_4$: $N_{L2}$
(N3) $N_1$: $N_{H1}$, $N_2$: $N_{L1}$, $N_3$: $N_{L2}$, $N_4$: $N_{H2}$
(N4) $N_1$: $N_{L1}$, $N_2$: $N_{H1}$, $N_3$: $N_{L2}$, $N_4$: $N_{H2}$
(N5) $N_1$: $N_{H2}$, $N_2$: $N_{L2}$, N3: $N_{H1}$, $N_4$: $N_{L1}$
(N6) $N_1$: $N_{H2}$, $N_2$: $N_{L2}$, $N_3$: $N_{L1}$, $N_4$: $N_{H1}$ (N7) $N_1$: $N_{L2}$, $N_2$: $N_{H2}$, $N_3$: $N_{H1}$, $N_4$: $N_{L1}$
(N8) $N_1$: $N_{L2}$, $N_2$: $N_{H2}$, $N_3$: $N_{L1}$, $N_4$: $N_{H1}$ $N_{H1}$: base sequence coding for first heavy-chain variable region $N_{L1}$: base sequence coding for first light-chain variable region $N_{H2}$: base sequence coding for second heavy-chain variable region $N_{L2}$: base sequence coding for second light-chain variable region It is preferable that the BsAb library of the present invention includes a plurality of types of nucleic acids, for example. In this case, the BsAb library of the present invention is a mixture of a plurality of types of nucleic acids, for example. It is preferable that some or all of the plurality of types of nucleic acids code for different first BsAbs, and preferably code for different second antigen-binding domains, for example. When the plurality of types of nucleic acids code for different second antigen-binding domains, the regions other than the second antigen-binding domains in the first BsAbs have the same amino acid sequence or different amino acid sequences, for example. The number of types of nucleic acids included in the BsAb library of the present invention is $1 \times 10^5$ to $1 \times 10^6$ or $1 \times 10^6$ to $5 \times 10^6$, for example, and preferably about $1 \times 10^6$ (e.g., $8 \times 10^5$ to $2 \times 10^6$). In the phage display technique, the number of types of nucleic acids required to screen scFv capable of binding to the target antigen is about $1 \times 10^8$. On the other hand, with the BsAb library of the present invention, scFvs capable of binding to the second target antigen can be screened using as few as about $1 \times 10^6$ types of nucleic acids, for example. Accordingly, with the BsAb library of the present invention, scFvs capable of binding to the second target antigen can be screened using a smaller number of, or a smaller number of types of, nucleic acids compared with the phage display technique, for example.

The first BsAb may include a signal peptide at the N terminus, for example. An example of the signal peptide is a signal peptide serving as an endoplasmic reticulum transport signal. The first BsAb may include a tag, for example. Examples of the tag include a peptide tag and a protein tag. Examples of the tag include a FLAG (registered trademark) tag, a HA tag, a His tag, a Myc tag, a V5 tag, and a truncated NGFR (nerve growth factor receptor). The tag peptide is added to at least either of the N terminus or the C terminus of the first BsAb, for example. When the truncated NGFR is used as the tag, the tag is arranged at the C-terminal side of the first BsAb. Thus, with the BsAb library of the present invention, the nucleic acid introduction efficiency can be adjusted such that one type of nucleic acid coding for a first BsAb is introduced per cell, for example. The first BsAb and the tag may be coupled to each other via a linker peptide.

In the present invention, the nucleic acids coding for the first BsAbs can be prepared based on the amino acid sequences of the first BsAbs using an ordinary method, for example. In a specific example, the nucleic acids coding for the first BsAbs can be prepared based on the base sequences coding for the amino acid sequences obtained from the database in which the amino acid sequences of the above-described domains are registered, using a molecular biological technique and/or a chemical synthesis method, for example. The base sequences of the nucleic acids may be subjected to codon optimization in accordance with the source of cells in which the BsAb library of the present invention is to be expressed, for example.

The nucleic acids coding for the first BsAbs may be introduced into expression vectors, for example. The expression vectors can be prepared by coupling the nucleic acids coding for the first BsAbs to linking vectors, for example. There is no particular limitation on the types of linking vectors, and examples thereof include: retroviral vectors such as oncoretroviral vectors, lentiviral vectors, and pseudo type vectors; and viral vectors such as adenoviral vectors, adeno-associated viral (AAV) vectors, simian viral vectors, vaccinia viral vectors, Sendai viral vectors, Epstein-Barr viral (EBV) vectors, and HSV vectors. Specific examples of the linking vectors include pUC, pCMV, pMX, and pELP. The linking vectors can also be determined as appropriate in accordance with hosts into which the expression vectors are to be introduced, for example. There is no particular limitation on the hosts, and examples thereof include mammalian-derived cultured cells such as CHO cells, Jurkat cells, and Jurkat 76 cells, and immune cells. Examples of the immune cells include lymphocytes, granulocytes, and macrophages. Examples of the lymphocytes include T cells, NK cells, NKT cells, and B cells. The immune cells are cells isolated from a living organism, immune cells induced from stem cells such as multipotent stem cells, or cultured cells derived from immune cells, for example. The T cells may be T cell-like cells. Examples of the T cell-like cells include cultured cells derived from T cells, and specific examples thereof include Jurkat cells and Jurkat 76 cells.

It is preferable that each of the expression vectors includes a regulatory sequence for regulating at least either the expression of the nucleic acid coding for the first BsAb or the expression of the first BsAb encoded by the nucleic acid coding for the first BsAb, for example. Examples of the regulatory sequence include a promoter, a terminator, an enhancer, a polyadenylation signal sequence, and a replication origin sequence (ori). There is no particular limitation on the arrangement of the regulatory sequence in the expression vector. It is sufficient that the regulatory sequence is arranged in the expression vector such that at least either the expression of the nucleic acid coding for the first BsAb or the expression of the first BsAb encoded by the nucleic acid can be functionally regulated, for example, and the regulatory sequence can be arranged based on a known method. For example, a predetermined sequence included in the linking vector may be used as the regulatory sequence, or an additional regulatory sequence may be inserted into the linking vector, or a regulatory sequence included in the linking vector may be replaced with another regulatory sequence.

The expression vector may further include a sequence coding for a selective marker, for example. Examples of the selective marker include drug-resistant markers, fluorescent protein markers, enzymatic markers, and cell-surface receptor markers.

Second Screening Method

A second scFv-screening method (also referred to as a "second screening method" hereinafter) of the present invention includes:

a first production step of producing first BsAbs from the BsAb library of the present invention;

a first contact step in which, when the first target antigen is an immune cell-activating receptor, the first BsAbs, the second target antigen, and immune cells capable of expressing the immune cell-activating receptor are brought into contact with one another, and when the second target antigen is an immune cell-activating receptor, the first BsAbs, the first target antigen, and immune cells capable of expressing the immune cell-activating receptor are brought into contact with one another; and a first selection step of selecting second scFvs of the first BsAbs that have bound to the second target antigen in the first contact step as first candidate scFvs capable of binding to the second target antigen.

The second screening method of the present invention is characterized by including the first production step, the first contact step, and the first selection step, and using the BsAb library of the present invention in the first production step, and there is no particular limitation on the other configurations and conditions. With the second screening method of the present invention, scFvs capable of binding to the second target antigen can be screened more easily compared with a method in which hybridomas are used and a method in which phage display is used, for example. Moreover, with the second screening method of the present invention, BsAbs that can induce cytotoxic activity and the like against cells expressing the first target antigen or second target antigen via T cells can be screened, for example. Furthermore, an antibody capable of binding to the target antigen or an antigen-binding fragment thereof can be produced based on the amino acid sequences of the CDRs in the heavy-chain variable regions and the light-chain variable regions of scFvs capable of binding to the second target antigen, for example. Accordingly, the second screening method can also be considered as a method for screening an antibody capable of binding to the target antigen or an antigen-binding fragment of the antibody, for example. The descriptions of the CAR library, the first screening method, the first antibody or the like, the second antibody or the like, the gene, the expression vector, the transformant, the first chimeric antigen receptor, the second chimeric antigen receptor, the nucleic acid, the cell, the cell-manufacturing method, the therapeutic agent, the treatment method, the BsAb library, and the like of the present invention can be applied to the second screening method of the present invention, for example. The second screening method of the present invention can be used to manufacture new scFvs capable of binding to a target antigen, for example. Accordingly, the second screening method of the present invention can also be considered as an scFv-manufacturing method, for example.

When BsAbs and the like capable of binding to a target antigen are manufactured using a phage display technique or the like, an antibody library in which the number of types of antibodies is about $1 \times 10^{10}$ is produced, and antibodies capable of binding to the target antigen are obtained, followed by preparation of BsAbs and the like that include scFvs from the antibodies. Then, the effectiveness of the BsAbs and the like is examined using immune cells or the like. On the other hand, in the second screening method of the present invention, the BsAb library of the present invention and the immune cells are used, thus making it possible to simultaneously perform screening of scFvs capable of binding to the target antigen and examination of the effectiveness of the BsAbs expressed from the library in the immune cells, for example. Accordingly, with the second screening method of the present invention, scFvs capable of binding to a target antigen and being used for BsAbs that are functional in immune cells and the like can be more easily screened compared with a phage display technique and the like used to obtain antibodies capable of binding to a target antigen, for example.

The first production step is a step of producing first BsAbs from the BsAb library of the present invention. There is no particular limitation on the method for producing first BsAbs, and a known method in which a protein is synthesized from a nucleic acid can be used, for example. In a specific example, in the first production step, the BsAb library (first BsAb library) of the present invention is introduced into hosts, for example. Then, in the first production step, the BsAbs are expressed in the hosts by culturing the hosts into which the first BsAb library has been introduced, for example. The method for introducing the first BsAb library is not particularly limited, and can be determined as appropriate in accordance with the type of hosts, for example. When the hosts are cells, a known method for introducing a nucleic acid into cells can be used as the above-mentioned introducing method, for example, and the description of the introducing method in the above-mentioned first expression step of the first screening method of the present invention can be applied. The host culture conditions are not particularly limited, and can be determined as appropriate in accordance with the type of hosts, for example. In a specific example, when the hosts are cells, the cells are cultured for 24 hours to 2 weeks, 24 to 48 hours, or 1 to 2 weeks, for example, but there is no particular limitation thereto. The cells are cultured at a temperature of 28 to 37° C., for example.

The first BsAb library may include nucleic acids coding for the first BsAbs, or expression vectors into which nucleic acids coding for the first BsAbs have been introduced, for example. The descriptions of the BsAb library of the present invention can be applied to the above-mentioned hosts, for example. The hosts are preferably 293 cells. The first BsAbs are preferably tandem scFvs because the library can be easily constructed.

Next, in the first contact step, the first BsAbs, the target antigen, and the immune cells capable of expressing the immune cell-activating receptor are brought into contact with one another. Specifically, when the first target antigen of the first BsAbs is an immune cell-activating receptor, the first BsAbs, the second target antigen, and the immune cells are brought into contact with one another in the first contact step. On the other hand, when the second target antigen of the first BsAbs is an immune cell-activating receptor, the first BsAbs, the first target antigen, and the immune cells are brought into contact with one another in the first contact step. The first BsAbs, the target antigen, and the immune cells can be brought into contact with one another by culturing the first BsAbs, the target antigen, and the immune cells together, for example. These are cultured for 1 to 96 hours, 1 to 6 hours, or 6 to 96 hours, for example. These are cultured at a temperature of 28 to 37° C., for example. It is preferable that the ratio between the number of the immune cells and the number of molecules of the first BsAbs is determined such that the number of molecules of the first BsAbs is 0.1 pmol or more for $1 \times 10^6$ immune cells, for example.

The immune cells capable of expressing the immune cell-activating receptor may by immune cells expressing the immune cell-activating receptor, or immune cells capable of expressing the immune cell-activating receptor under predetermined conditions. The predetermined conditions can be determined as appropriate in accordance with the type of immune cells, for example. The immune cells can be selected as appropriate in accordance with the type of immune cell-activating receptor. When the immune cell-activating receptor is CD3, examples of the immune cells include T cells and NKT cells. When the immune cell-activating receptor is an NK cell-activating receptor, examples of the immune cells include NK cells and NKT cells. When the immune cell-activating receptor is CD19, CD79α, or CD79β, examples of the immune cells include B cells. The above-mentioned T cells, NK cells, NKT cells, and B cells may be the above-described T cell-like cultured cells, NK cell-like cultured cells, NKT cell-like cultured cells, and B cell-like cultured cells, respectively. It is preferable that the immune cell-activating receptor and immune cells are CD3, and T cells or T cell-like cultured cells, respectively. Accordingly, with the second screening method of the present invention, BsAbs that are likely to induce cytotoxic activity against cells expressing the first target antigen or second target antigen via T cells can be screened, for example.

The number of the types of first BsAbs may be one or two or more, for example. In the latter case, a mixture of a plurality of types of first BsAbs having different amino acid sequences is used as the first BsAbs in the first contact step, for example.

When the first target antigen is an immune cell-activating receptor, examples of the second target antigen to be used in the contact in the first contact step include a second target antigen monomer, a second target antigen complex, and a second target antigen-expressing cell, and a second target antigen-expressing cell is preferable. An example of the second target antigen complex is a second target antigen multimer, and specific examples thereof include a target antigen dimer and a target antigen tetramer. The second target antigen multimer can be prepared using a method in which tagged target antigens are cross-linked via an antibody, a method in which a complex of biotinylated target antigens is formed using avidin, or the like, for example. Examples of the second target antigen-expressing cell include cells that intrinsically express the second target antigen, and cells that express the second target antigen due to the introduction of a nucleic acid coding for the second target antigen. Examples of the second target antigen-expressing cell include 293 cells, 293 T cells, and K562 cells. The cell in which the second target antigen is to be expressed may be the same as or different from the above-mentioned host, for example.

When the second target antigen is an immune cell-activating receptor, examples of the first target antigen to be used in the contact in the first contact step include a first target antigen monomer, a first target antigen complex, and a first target antigen-expressing cell, and a first target antigen-expressing cell is preferable. An example of the first target antigen complex is a first target antigen multimer, and specific examples thereof include a target antigen dimer and a target antigen tetramer. The first target antigen multimer can be prepared using a method in which tagged target antigens are cross-linked via an antibody, a method in which a complex of biotinylated target antigens is formed using avidin, or the like, for example. Examples of the first target antigen-expressing cell include cells that intrinsically express the first target antigen, and cells that express the first target antigen due to the introduction of a nucleic acid coding for the first target antigen. Examples of the first target antigen-expressing cell include cultured cells such as 293 cells, 293 T cells, and K562 cells. The cell in which the first target antigen is to be expressed may be the same as or different from the above-mentioned hosts, for example.

Then, in the first selection step, the second scFvs of the first BsAbs that have bound to the second target antigen in the first contact step are selected as first candidate scFvs capable of binding to the second target antigen. The binding of the first BsAbs to the second target antigen can be evaluated directly or indirectly, for example, and indirect evaluation is preferable because BsAbs that can induce cytotoxic activity and the like against cells expressing the first target antigen or second target antigen via T cells can be screened, for example.

The direct evaluation method can be performed using a technique for detecting the binding of an antibody to an antigen such as surface plasmon resonance (SPR) or flow cytometry, for example. In a specific example, the direct evaluation method can be performed using a labeled first target antigen monomer or multimer, or a labeled second target antigen monomer or multimer, for example. In this case, in the first selection step, the first BsAbs, the labeled first target antigen or second target antigen, and the immune cells are brought into contact with one another, for example. When the first BsAbs bind to the second target antigen, the first BsAb, the labeled first target antigen or second target antigen, and the immune cell form a complex. Accordingly, in the first selection step, it can be determined that the first BsAb have bound to the second target antigen if some of the immune cells form a complex that includes the above-mentioned label, for example.

The indirect evaluation method can be implemented as follows, for example. The first BsAbs capable of binding to the second target antigen form cross-links between the immune cell-activating receptors of the immune cells, for example. As a result, the immune cells that include the cross-linked immune cell-activating receptors are activated by the signal generated in the immune cell-activating receptors, for example. Accordingly, in the indirect evaluation method, the activation of the immune cells is used as an evaluation index, for example. In a specific example, when the first BsAbs bind to the second target antigen, the expression of activation markers is increased in the immune cells, the production amounts of cytokines and/or chemokines are increased in the immune cells, and the immune cells are proliferated, for example, compared with the case where the first BsAbs that do not bind to the second target antigen are present, for example. In a specific example, when the immune cells are T cells, NK cells, NKT cells, or B cells, the expression of the following activation markers is increased in the cells, the production amounts of the following cytokines and/or chemokines are increased in the cells, and the cells are proliferated, for example. Accordingly, in the first selection step, when it is determined based on any one or more of the indices that the immune cells are activated, it can be determined that the first BsAbs that have activated the immune cells have bound to the second target antigen. The increase in the production amounts of cytokines and/or chemokines may be evaluated using a reporter whose mRNA or protein expression level increases when the expression of the cytokines and/or chemokines is induced, for example. An example of the reporter is a fluorescent protein.

T cells
   Activation marker: CD69, CD107a, etc.
   Cytokine, chemokine: IFN-γ, IL-12, IL-2, TNFα, MIP-1β, etc.

NK cells
   Activation marker: CD69, CD107a, etc.
   Cytokine, chemokine: INF-γ, IL-12, etc.

NKT cells
   Activation marker: CD69, CD107a, CD25, etc.
   Cytokine, chemokine: INF-γ, IL-2, etc.

B cells
   Activation marker: CD28, CD69, CD80, CD138, B220, etc.
   Cytokine, chemokine: CXCR4, etc.

Then, the second scFvs of the first BsAbs that have bound to the second target antigen are selected as first candidate scFvs capable of binding to the second target antigen. The first candidate scFvs can be selected by selecting hosts expressing the first BsAbs capable of binding to the second target antigen and reading the base sequences coding for the scFvs or BsAbs in the selected hosts, for example. In the first selection step, the CDRH1, the CDRH2, and the CDRH3 in the heavy-chain variable region and the CDRL1, the CDRL2, and the CDRL3 in the light-chain variable region in each of the first candidate scFvs may also be identified, for example. The CDRs can be identified using a known method referring to the genome information, for example.

Accordingly, new scFvs capable of binding to the second target antigen can be screened. If a first BsAb of the first BsAb library meets Condition 1 above, the first screening method of the present invention can be used to screen new light-chain variable regions capable of binding to the second target antigen. If a first BsAb of the first BsAb library meets Condition 2 above, the first screening method of the present invention can be used to screen new heavy-chain variable regions capable of binding to the second target antigen.

When the first BsAbs include a plurality of types of BsAbs, the first contact step and the first selection step may be performed once or a plurality of times, and are preferably performed a plurality of times. The term "plurality of times" refers to two to five times or two to four times, for example, and preferably two to three times. In this case, it is preferable that the first contact step and the first selection step are performed as one set, and this set is performed a plurality of times. When the first contact step and the first selection step are performed a plurality of times, the first round of the first contact step and the first selection step is performed, and then new first BsAbs are produced from the hosts expressing first BsAbs capable of binding to the second target antigen, for example. In this case, it is preferable that the number of types of BsAbs included in the new first BsAbs is smaller than the number of types of BsAbs subjected to the previous round of the first contact step and the first selection step. The new first BsAbs are diluted after the hosts expressing the first BsAbs have been collected, for example. The new first BsAbs can be prepared by reseeding the diluted hosts at a cell density lower than that at the time of collection, culturing the hosts, and collecting the culture supernatant. In the second screening method of the present invention, the first contact step and the first selection step are performed using the new first BsAbs, for example. The contact step and the selection step are repeatedly performed a desired number of times in the same manner, and thus a monoclonal host expressing a first BsAb capable of binding to the second target antigen is obtained, for example. Accordingly, with the second screening method of the present invention, first BsAbs capable of binding to the second target antigen can be identified more reliably, for example.

In the second screening method of the present invention, the new heavy-chain variable region or light-chain variable region of the first candidate scFv may be used as the heavy-chain variable region or light-chain variable region of an antibody or the like capable of binding to the second target antigen out of the second scFvs of the first BsAb library to screen the other region, for example. In this case, the second screening method of the present invention further includes a preparation step of preparing a second BsAb library based on the first candidate scFvs, for example.

The second BsAb library includes nucleic acids coding for second BsAbs, for example. Each of the second BsAbs includes a third antigen-binding domain and a fourth antigen-binding domain, for example. The third antigen-binding domain includes a third scFv capable of binding to the first target antigen, for example. The fourth antigen-binding domain includes a fourth scFv to be screened for the ability to bind to the second target antigen, for example.

The nucleic acids coding for the second BsAbs are nucleic acids (polynucleotides) coding for the amino acid sequences of the second BsAbs, for example.

In the second screening method of the present invention, the second BsAbs and the first BsAbs may have the same structure or different structures, for example. The second BsAbs are preferably tandem scFvs because the library can be easily constructed.

When the first target antigen is an immune cell-activating receptor, the first target antigen of the second BsAbs may be the same as or different from the first target antigen of the first BsAbs of the above-mentioned BsAb library of the present invention described in "(1) First Target Antigen: Immune Cell-Activating Receptor". In the latter case, the first target antigen of the second BsAbs is a subunit or complex different from the first target antigen of the first BsAbs, for example.

When the second target antigen is an immune cell-activating receptor, the first target antigen of the second BsAbs is the same as the first target antigen of the first BsAbs of the above-mentioned BsAb library of the present invention described in "(2) Second Target Antigen: Immune Cell-Activating Receptor", and the descriptions thereof can be applied.

When the first target antigen is an immune cell-activating receptor, the second target antigen of the second BsAbs is the same as the second target antigen of the first BsAbs of the above-mentioned BsAb library of the present invention described in "(1) First Target Antigen: Immune Cell-Activating Receptor", and the descriptions thereof can be applied.

When the second target antigen is an immune cell-activating receptor, the second target antigen of the second BsAbs may be the same as or different from the second target antigen of the first BsAbs of the above-mentioned BsAb library of the present invention described in "(2) Second Target Antigen: Immune Cell-Activating Receptor". In the latter case, the second target antigen of the second BsAbs is a subunit or complex different from the first target antigen of the first BsAbs, for example.

If the "first scFv" is changed to the "third scFv", the "first heavy-chain variable region" is changed to a "third heavy-chain variable region", and the "first light-chain variable region" is changed to a "third light-chain variable region", the descriptions of the first scFv of the BsAb library of the present invention described in "(1) First Target Antigen: Immune Cell-Activating Receptor" can be applied to the third scFv, for example. The third scFv of the second BsAb may be the same as or different from the first scFv of the first BsAb.

In each of the third scFvs, the third heavy-chain variable region and the third light-chain variable region are coupled to each other via a third linker peptide (third Fv linker peptide), for example. It is preferable that the third Fv linker peptide does not inhibit the third scFv from binding to the second target antigen, for example. The third Fv linker peptide is constituted by 1 to 40, 1 to 18, 1 to 15, 1 to 7, 1 to 3, or 1 or 2 amino acids, for example. The third Fv linker peptide is constituted by amino acids such as glycine and serine, for example, and a specific example thereof is $(GGGGS)_n$. n in this formula is an integer from 1 to 6, for example. The amino acid sequence of the third Fv linker peptide may be the amino acid sequence of the polypeptide represented by Sequence ID No. 1 or 2 above, for example.

In each of the second BsAbs, the fourth scFv includes a fourth heavy-chain variable region and a fourth light-chain variable region. The fourth heavy-chain variable region and the fourth light-chain variable region have structures similar to those of the heavy-chain variable region and the light-chain variable region in an antibody molecule, respectively, and the descriptions of the first scFv can be applied to the structures.

The fourth heavy-chain variable region includes a CDRH1, a CDRH2, and a CDRH3. The fourth light-chain variable region includes a CDRL1, a CDRL2, and a CDRL3. The fourth heavy-chain variable region and the fourth light-chain variable region meet Condition 3 or Condition 4 below.

Condition 3

If the BsAb library in the first production step meets Condition 1 above,
the CDRH1, the CDRH2, and the CDRH3 in the fourth heavy-chain variable region include the CDRH1, the CDRH2, and the CDRH3 in the heavy-chain variable region of a second B cell receptor, respectively, and
the CDRL1, the CDRL2, and the CDRL3 in the fourth light-chain variable region include the CDRL1, the CDRL2, and the CDRL3 in the light-chain variable region of the first candidate BsAb, respectively.

Condition 4

If the BsAb library in the first production step meets Condition 2 above,
the CDRH1, the CDRH2, and the CDRH3 in the fourth heavy-chain variable region include the CDRH1, the CDRH2, and the CDRH3 in the heavy-chain variable region of the first candidate BsAb, respectively, and
the CDRL1, the CDRL2, and the CDRL3 in the fourth light-chain variable region include the CDRL1, the CDRL2, and the CDRL3 in the light-chain variable region of a second B cell receptor, respectively.

Condition 3 above is employed in the case where the second BsAb library is prepared using the first candidate scFvs screened using the first BsAb library that meets Condition 1 above, for example. In Condition 3 above, the first candidate scFv is used for the CDRL1, the CDRL2, and the CDRL3 in the fourth light-chain variable region, and the CDRH1, the CDRH2, and the CDRH3 in the fourth heavy-chain variable region are screened for the ability to bind to the second target antigen, for example.

If the "first B cell receptor" is changed to the "second B cell receptor", and the "second heavy-chain variable region" is changed to the "fourth heavy-chain variable region", the descriptions of the second heavy-chain variable region of the above-mentioned BsAb library of the present invention described in Condition 2 in "(1) First Target Antigen: Immune Cell-Activating Receptor" can be applied to the second B cell receptor in the fourth heavy-chain variable region, for example.

The CDRH1, the CDRH2, and the CDRH3 in the fourth heavy-chain variable region may respectively be polypeptides that consist of the amino acid sequences of the CDRH1, the CDRH2, and the CDRH3 of the second B cell receptor, or polypeptides that include the amino acid sequences of the CDRH1, the CDRH2, and the CDRH3 of the second B cell receptor, for example.

The FRH1, the FRH2, the FRH3, and the FRH4 in the fourth heavy-chain variable region may respectively be polypeptides that consist of the amino acid sequences of the FRH1, the FRH2, the FRH3, and the FRH4 of the second B cell receptor, or polypeptides that include the amino acid sequences of the FRH1, the FRH2, the FRH3, and the FRH4 of the second B cell receptor, for example. It is preferable that "the second B cell receptor" in the descriptions of the CDRHs and "the second B cell receptor" in the descriptions of the FRHs are the same B cell receptor.

The fourth heavy-chain variable region may include the heavy-chain variable region of the second B cell receptor, for example. In this case, the fourth heavy-chain variable region may be a polypeptide that consists of the amino acid sequence of the heavy-chain variable region of the second B cell receptor, or a polypeptide that includes the amino acid sequence of the heavy-chain variable region of the second B cell receptor, for example.

The CDRL1, the CDRL2, and the CDRL3 in the fourth light-chain variable region may respectively be polypeptides that consist of the amino acid sequences of the CDRL1, the CDRL2, and the CDRL3 of the first candidate scFv, or polypeptides that include the amino acid sequences of the CDRL1, the CDRL2, and the CDRL3 of the first candidate scFv, for example.

The FRs in the fourth light-chain variable region may include the FRs in the light-chain variable region of the first candidate scFv, for example. The FRL1, the FRL2, the FRL3, and the FRL4 in the fourth light-chain variable region may respectively be polypeptides that consist of the amino acid sequences of the FRL1, the FRL2, the FRL3, and the FRL4 of the first candidate scFv, or polypeptides that include the amino acid sequences of the FRL1, the FRL2, the FRL3, and the FRL4 of the first candidate scFv, for example. It is preferable that "the first candidate scFv" in the descriptions of the CDRLs and "the first candidate scFv" in the descriptions of the FRLs are the same scFv.

The fourth light-chain variable region may include the light-chain variable region of the first candidate scFv, for example. In this case, the fourth light-chain variable region may be a polypeptide that consists of the amino acid sequence of the light-chain variable region of the first candidate scFv, or a polypeptide that includes the amino acid sequence of the light-chain variable region of the first candidate scFv, for example.

Next, Condition 4 above is employed in the case where the second BsAb library is prepared using the first candidate scFvs screened using the first BsAb library that meets Condition 2 above, for example. In Condition 4 above, the first candidate scFv is used for the CDRH1, the CDRH2, and the CDRH3 in the fourth heavy-chain variable region, and the CDRL1, the CDRL2, and the CDRL3 in the fourth light-chain variable region are screened for the ability to bind to the second target antigen, for example.

The CDRH1, the CDRH2, and the CDRH3 in the fourth heavy-chain variable region may respectively be polypeptides that consist of the amino acid sequences of the CDRH1, the CDRH2, and the CDRH3 of the first candidate scFv, or polypeptides that include the amino acid sequences of the CDRH1, the CDRH2, and the CDRH3 of the first candidate scFv, for example.

The FRH1, the FRH2, the FRH3, and the FRH4 in the fourth heavy-chain variable region may respectively be polypeptides that consist of the amino acid sequences of the FRH1, the FRH2, the FRH3, and the FRH4 of the first candidate scFv, or polypeptides that include the amino acid sequences of the FRH1, the FRH2, the FRH3, and the FRH4 of the first candidate scFv, for example. It is preferable that "the first candidate scFv" in the descriptions of the CDRHs and "the first candidate scFv" in the descriptions of the FRHs are the same scFv.

The fourth heavy-chain variable region may include the heavy-chain variable region of the first candidate scFv, for example. In this case, the fourth heavy-chain variable region may be a polypeptide that consists of the amino acid sequence of the heavy-chain variable region of the first candidate scFv, or a polypeptide that includes the amino acid sequence of the heavy-chain variable region of the first candidate scFv, for example.

If the "first B cell receptor" is changed to the "second B cell receptor", and the "second light-chain variable region" is changed to the "fourth light-chain variable region", the descriptions of the second light-chain variable region of the above-mentioned BsAb library of the present invention described in Condition 1 in "(1) First Target Antigen: Immune Cell-Activating Receptor" can be applied to the second B cell receptor in the fourth light-chain variable region, for example.

The CDRL1, the CDRL2, and the CDRL3 in the fourth light-chain variable region may respectively be polypeptides that consist of the amino acid sequences of the CDRL1, the CDRL2, and the CDRL3 of the second B cell receptor, or polypeptides that include the amino acid sequences of the CDRL1, the CDRL2, and the CDRL3 of the second B cell receptor, for example.

The FRL1, the FRL2, the FRL3, and the FRL4 in the fourth light-chain variable region may respectively be polypeptides that consist of the amino acid sequences of the FRL1, the FRL2, the FRL3, and the FRL4 of the second B cell receptor, or polypeptides that include the amino acid sequences of the FRL1, the FRL2, the FRL3, and the FRL4 of the second B cell receptor, for example. It is preferable that "the second B cell receptor" in the descriptions of the CDRLs and "the second B cell receptor" in the descriptions of the FRLs are the same B cell receptor.

The fourth light-chain variable region may include the light-chain variable region of the second B cell receptor, for example. In this case, the fourth light-chain variable region may be a polypeptide that consists of the amino acid sequence of the light-chain variable region of the second B cell receptor, or a polypeptide that includes the amino acid sequence of the light-chain variable region of the second B cell receptor, for example.

In each of the fourth scFvs, the fourth heavy-chain variable region and the fourth light-chain variable region are coupled to each other via a fourth linker peptide (fourth Fv linker peptide), for example. It is preferable that the fourth Fv linker peptide does not inhibit the fourth scFv from binding to the immune cell-activating receptor, for example. The fourth Fv linker peptide is constituted by 1 to 40, 1 to 18, 1 to 15, 1 to 7, 1 to 3, or 1 or 2 amino acids, for example. The fourth Fv linker peptide is constituted by amino acids such as glycine and serine, for example, and a specific example thereof is $(GGGGS)_n$. n in this formula is an integer from 1 to 6, for example. The amino acid sequence of the fourth Fv linker peptide may be the amino acid sequence of the polypeptide represented by Sequence ID No. 1 or 2 above, for example. The fourth Fv linker peptide in the fourth scFv may be the same as or different from the first Fv linker peptide in the first scFv, for example.

The third scFv and the fourth scFv may be directly or indirectly coupled to each other, or be formed such that, when the third scFv and the fourth scFv coexist, the third scFv and the fourth scFv are associated with (bind to) each other, for example. The coupling between the third scFv and the fourth scFv can be designed as appropriate in accordance with the type of second BsAb, for example. In a specific example, when the second BsAb is a tandem scFv, the third scFv and the fourth scFv are coupled to each other via a linker peptide (inter-Fv linker peptide). The inter-Fv linker peptide is constituted by 1 to 40, 1 to 18, 1 to 15, 1 to 7, 1 to 3, or 1 or 2 amino acids, for example. The inter-Fv linker peptide is constituted by amino acids such as glycine and serine, for example, and a specific example thereof is $(GGGGS)_n$. n in this formula is an integer from 1 to 6, for example. In a specific example, the amino acid sequence of the inter-Fv linker peptide may be the amino acid sequence of the polypeptide represented by Sequence ID No. 1 or 2 above, for example. The electric charges of the amino acid side chains can be used for the above-mentioned association, for example. In a specific example, the association can be induced by adding a domain that includes positively charged amino acids to one binding domain and adding a domain that includes negatively charged amino acids to the other binding domain, for example. Moreover, a combination of a tag sequence and a polypeptide capable of recognizing the tag sequence, or the like can also be used for the association, for example.

Regarding the arrangement order of the third scFv and the fourth scFv of each of the second BsAbs, the third scFv and the fourth scFv may be arranged in this order from the N-terminal side, or the fourth scFv and the third scFv may be arranged in this order from the N-terminal side.

An example of the second BsAb is a polypeptide consisting of the amino acid sequence represented by Formula (5) (Sequence ID No. 160) below. Examples of the combination of $V_5$, $V_6$, $V_7$, and Vs in Formula (5) below include combinations (V9) to (V16) below. When the fourth scFv meets Condition 3 above, the combination of $V_5$, $V_6$, $V_7$, and Vs is preferably the combination (V13) or (V14) below. When the fourth scFv meets Condition 4 above, the combination of $V_5$, $V_6$, $V_7$, and Vs is preferably the combination (V15) or (V16) below. In Formula (5) below, the amino acid sequence between $V_5$ and $V_6$ is the amino acid sequence of the first Fv linker peptide, the amino acid sequence between $V_6$ and $V_7$ is the amino acid sequence of the inter-Fv linker peptide, and the amino acid sequence between $V_7$ and Vs is the amino acid sequence of the second Fv linker peptide. In Formula (5) below, the first Fv linker peptide and the second Fv linker peptide are Fv linker peptides 1, but may also be independently an Fv linker peptide 2.

(5)
[V$_5$]-[GSTSGSGKPGSGEGSTKG]-[V$_6$]-[SGSG]-[V$_7$]-
[GSTSGSGKPGSGEGSTKG]-[V$_8$]...

(V9) $V_5$: $V_{H3}$, $V_6$: $V_{L3}$, $V_7$: $V_{H4}$, $V_8$: $V_{L4}$
(V10) $V_5$: $V_{L3}$, $V_6$: $V_{H3}$, $V_7$: $V_{H4}$, $V_8$: $V_{L4}$
(V11) $V_5$: $V_{H3}$, $V_6$: $V_{L3}$, $V_7$: $V_{L4}$, $V_8$: $V_{H4}$
(V12) $V_5$: $V_{L3}$, $V_6$: $V_{H3}$, $V_7$: $V_{L4}$, $V_8$: $V_{H4}$
(V13) $V_5$: $V_{H4}$, $V_6$: $V_{L4}$, $V_7$: $V_{H3}$, $V_8$: $V_{L3}$
(V14) $V_5$: $V_{H4}$, $V_6$: $V_{L4}$, $V_7$: $V_{L3}$, $V_8$: $V_{H3}$
(V15) $V_5$: $V_{L4}$, $V_6$: $V_{H4}$, $V_7$: $V_{H3}$, $V_8$: $V_{L3}$
(V16) $V_5$: $V_{L4}$, $V_6$: $V_{H4}$, $V_7$: $V_{L3}$, $V_8$: $V_{H3}$ $V_{H3}$: third heavy-chain variable region
$V_{L3}$: third light-chain variable region
$V_{H4}$: fourth heavy-chain variable region
$V_{L4}$: fourth light-chain variable region An example of the nucleic acid coding for the second BsAb is a polynucleotide consisting of the base sequence represented by Formula (6) (Sequence ID No. 161) below.

Examples of the combination of $N_5$, $N_6$, $N_7$, and $N_8$ in Formula (6) below include combinations (N9) to (N16) below. The combinations (N9) to (N16) below are nucleic acids coding for the second BsAbs of the combinations (V9) to (V16) above, respectively. In Formula (6) below, the base sequence between $N_5$ and $N_6$ is the base sequence coding for the first Fv linker peptide, the base sequence between $N_6$ and $N_7$ is the base sequence coding for the inter-Fv linker peptide, and the base sequence between $N_7$ and $N_8$ is the base sequence coding for the second Fv linker peptide. In Formula (6) below, the base sequences coding for the first Fv linker peptide and the second Fv linker peptide are base sequences coding for Fv linker peptides 1, but may also be independently a base sequence coding for an Fv linker peptide 2.

(6)

5'-[$N_5$]-

[GGCTCTACAAGCGGCTCTGGCAAGCCTGGATCTGGCGAGGGAAGCACC

AAGGGC]-[$N_6$]-[AGCGGATCTGGC]-[$N_7$]-

[GGCTCTACAAGCGGCTCTGGCAAGCCTGGATCTGGCGAGGGAAGCACC

AAGGGC]-[$N_8$]-3'...

(N9) $N_5$: $N_{H3}$, $N_6$: $N_{L3}$, $N_7$: $N_{H4}$, $N_8$: $N_{L4}$
    (N10) $N_5$: $N_{L3}$, $N_6$: $N_{H3}$, $N_7$: $N_{H4}$, $N_8$: $N_{L4}$
    (N11) $N_5$: $N_{H3}$, $N_6$: $N_{L3}$, $N_7$: $N_{L4}$, $N_8$: $N_{H4}$
    (N12) $N_5$: $N_{L3}$, $N_6$: $N_{H3}$, $N_7$: $N_{L4}$, $N_8$: $N_{H4}$
    (N13) $N_5$: $N_{H4}$, $N_6$: $N_{L4}$, $N_7$: $N_{H3}$, $N_8$: $N_{L3}$
    (N14) $N_5$: $N_{H4}$, $N_6$: $N_{L4}$, $N_7$: $N_{L3}$, $N_8$: $N_{H3}$
    (N15) $N_5$: $N_{L4}$, $N_6$: $N_{H4}$, $N_7$: $N_{H3}$, $N_8$: $N_{L3}$
    (N16) $N_5$: $N_{L4}$, $N_6$: $N_{H4}$, $N_7$: $N_{L3}$, $N_8$: $N_{H3}$ $N_{H3}$: base sequence coding for third heavy-chain variable region
    $N_{L3}$: base sequence coding for third light-chain variable region
    $N_{H4}$: base sequence coding for fourth heavy-chain variable region
    $N_{L4}$: base sequence coding for fourth light-chain variable region It is preferable that the second BsAb library includes a plurality of types of nucleic acids, for example. In this case, the second BsAb library is a mixture of a plurality of types of nucleic acids, for example. It is preferable that some or all of the plurality of types of nucleic acids code for different second BsAbs, and preferably code for different fourth antigen-binding domains, for example. When the plurality of types of nucleic acids code for different fourth antigen-binding domains, the regions other than the fourth antigen-binding domains in the second BsAbs have the same amino acid sequence or different amino acid sequences, for example. The number of types of nucleic acids included in the second BsAb library is $1\times10^5$ to $1\times10^6$ or $1\times10^6$ to $5\times10^6$, for example, and preferably about $1\times10^6$ (e.g., $8\times10S$ to $2\times10^6$).

The second BsAb may include a signal peptide at the N terminus, for example. The second BsAb may include a tag, for example. If the "first BsAb" is changed to the "second BsAb", the descriptions of the signal peptide and the tag in the first BsAb can be applied to the above-mentioned signal peptide and the tag, for example.

In the present invention, the nucleic acids coding for the second BsAbs can be prepared based on the amino acid sequences of the second BsAbs using an ordinary method, for example. In a specific example, the nucleic acids coding for the second BsAbs can be prepared based on the base sequences coding for the amino acid sequences obtained from the database in which the amino acid sequences of the above-described domains are registered, using a molecular biological technique and/or a chemical synthesis method, for example. The base sequences of the nucleic acids may be subjected to codon optimization in accordance with the source of cells in which the second BsAb library is to be expressed, for example.

The nucleic acids coding for the second BsAbs may be introduced into expression vectors, for example. The descriptions of the expression vectors for the BsAb library of the present invention can be applied to the above-mentioned expression vectors, for example.

Next, in the second screening method of the present invention, a production step, a contact step, and a selection step are performed in the same manner, except that the second BsAb library prepared in the above-mentioned preparation step is used instead of the first BsAb library, for example. Specifically, the second screening method of the present invention further includes a second production step of producing the second BsAbs from the second BsAb library, a second contact step of bringing the second BsAbs, the target antigen, and immune cells capable of expressing the immune cell-activating receptor into contact with one another, and a second selection step of selecting fourth scFvs of the second BsAbs that have bound to the second target antigen in the second contact step as second candidate scFvs capable of binding to the second target antigen, for example. When the first target antigen of the second BsAbs is an immune cell-activating receptor, the second BsAbs, the second target antigen, and the immune cells are brought into contact with one another in the second contact step, for example. On the other hand, when the second target antigen of the second BsAbs is an immune cell-activating receptor, the second BsAbs, the first target antigen, and the immune cells are brought into contact with one another in the second contact step, for example.

If the "first production step" is changed to the "second production step", the "first BsAb library" is changed to the "second BsAb library", and the "first BsAb" is changed to the "second BsAb", the descriptions of the first production step can be applied to the second production step, for example.

If the "first production step" is changed to the "second production step", and the "first contact step" is changed to the "second contact step", the descriptions of the first contact step can be applied to the second contact step, for example.

If the "first contact step" is changed to the "second contact step", the "first selection step" is changed to the "second selection step", the "second scFv" is changed to the "fourth scFv", the "first candidate scFv" is changed to the "second candidate scFv", and the "first BsAb" is changed to the "second BsAb", the descriptions of the first selection step can be applied to the second selection step, for example.

Accordingly, the second screening method of the present invention can be used to screen scFvs that include new heavy-chain variable regions and light-chain variable regions capable of binding to the second target antigen, for example.

Method for Manufacturing Third scFv

As described above, the scFv-manufacturing method of the present invention includes: a first administration step of administering cells expressing a first chimeric antigen receptor (CAR) library to an animal, and a first collection step of collecting the cells expressing the first CAR library that accumulate in a tissue expressing a target antigen in the animal as cells expressing CARs specific to the target antigen, wherein the first CAR library includes nucleic acids coding for first CARs, each of the first CARs includes a first antigen-binding domain, a first transmembrane domain, and a first intracellular signaling domain, the first antigen-binding domain includes a first single-chain antibody (scFv) to be screened for the ability to bind to the target antigen, the first scFv includes a first heavy-chain variable region and a first light-chain variable region, and the first heavy-chain variable region and the first light-chain variable region meet Condition 1 or Condition 2 below.

Condition 1

The heavy-chain complementarity determining region (CDRH) 1, the CDRH2, and the CDRH3 in the first heavy-chain variable region include the CDRH1, the CDRH2, and the CDRH3 in the heavy-chain variable region of an antibody capable of binding to the target antigen or an antigen-binding fragment of the antibody, respectively, and the light-chain complementarity determining region (CDRL) 1, the CDRL2, and the CDRL3 in the first light-chain variable region include the CDRL1, the CDRL2, and the CDRL3 in the light-chain variable region of a first B cell receptor, respectively.

Condition 2

The heavy-chain complementarity determining region (CDRH) 1, the CDRH2, and the CDRH3 in the first heavy-chain variable region include the CDRH1, the CDRH2, and the CDRH3 in the heavy-chain variable region of a first B cell receptor, respectively, and the light-chain complementarity determining region (CDRL) 1, the CDRL2, and the CDRL3 in the first light-chain variable region include the CDRL1, the CDRL2, and the CDRL3 in the light-chain variable region of an antibody capable of binding to the target antigen or an antigen-binding fragment of the antibody, respectively.

A third scFv-manufacturing method of the present invention is characterized by including the first administration step of administering cells expressing a first CAR library to an animal, and the first collection step of collecting the cells expressing the first CAR library that accumulate in a tissue expressing a target antigen in the animal as cells expressing CARs specific to the target antigen, and there is no particular limitation on the other steps and conditions. The descriptions of the CAR library, the first screening method, and the CAR library cells of the present invention can be applied to the third scFv-manufacturing method of the present invention.

Cells expressing CARs that include scFvs capable of binding to the target antigen out of the cells expressing the CAR library are activated in a target antigen-dependent manner in the animal. The cells expressing the CAR library that have been activated move to and accumulate at a site expressing the target antigen in the animal. Accordingly, with the manufacturing method of the present invention, scFvs that can be functional in CAR-T cells and can also be involved in local invasion can be manufactured by collecting cells expressing the first CAR library that accumulate in a tissue expressing the target antigen in the animal as cells expressing CARs specific to the target antigen. The cells are activated in a target antigen-dependent manner, and therefore, it can be said that the scFvs in the cells that express the CAR library and accumulate in a tissue expressing the target antigen are more likely to recognize the target antigen. Therefore, it can be said that the manufacturing method of the present invention can be used to manufacture scFvs that are capable of binding to the target antigen and activating immune cells such as T cells, for example.

Furthermore, in the first CAR library used in the manufacturing method of the present invention, each of the first CARs is a protein that includes the first antigen-binding domain, the first transmembrane domain, and the first intracellular signaling domain. The first CAR has a structure similar to that of a CAR that includes an extracellular domain capable of binding to an antigen, a transmembrane domain, and an intracellular signaling domain, for example, and the extracellular domain capable of binding to an antigen is changed to a first antigen-binding domain to be screened for the ability to bind to the target antigen. Therefore, with the manufacturing method of the present invention, new scFvs capable of binding to the target antigen and activating immune cells such as T cells can be screened.

In the third scFv-manufacturing method of the present invention, cells expressing the first CAR library (also referred to as "first expressing cells" hereinafter) can be prepared by introducing, into cells, the first CAR library that includes nucleic acids coding for the first CARs, for example. Accordingly, the third scFv-manufacturing method of the present invention may include a first production step of producing the first CAR library prior to the first administration step. Also, the third scFv-manufacturing method of the present invention may include a first preparation step of preparing cells expressing the first CAR library prior to the first administration step by introducing the first CAR library into cells.

In the first production step, the first CAR library is produced. As described above, the first CAR library includes nucleic acids coding for the first CARs. The nucleic acids coding for the first CARs are nucleic acids (polynucleotides) coding for the amino acid sequences of the first CARs, for example. The first CAR library is the same as the first CAR library in the CAR library of the present invention, and the descriptions thereof can be applied.

The descriptions of the CAR library of the present invention can be applied to the target antigen of the first scFvs, for example.

In the first preparation step, cells expressing the first CAR library are prepared by introducing the first CAR library into cells. Specifically, in the first preparation step, the first CAR library is introduced into the above-mentioned cells, for example. In the first preparation step, the first CAR library is expressed in the cells by culturing the cells into which the first CAR library has been introduced, for example. There is no particular limitation on a method for introducing the first CAR library, and a known method for introducing nucleic acids into cells can be used, for example. Specific examples of the method for introducing the first CAR library include a method in which a nucleic acid introducing reagent such as a liposome or a cationic lipid is used; and a method in which virus such as retrovirus or lentivirus is used. The cells are cultured for 6 hours to 30 days, 6 to 96 hours, or 1 to 30 days, for example, but there is no particular limitation thereto. The cells are cultured at a temperature of 28 to 37° C., for example.

The first CAR library may include nucleic acids coding for the first CARs, or expression vectors into which nucleic acids coding for the first CARs have been introduced, for example.

Examples of the cells include, but are not particularly limited to, mammalian-derived cultured cells such as CHO cells, Jurkat cells, and Jurkat 76 cells, and immune cells. Examples of the immune cells include, but are not particularly limited to, T cells, NK cells, NKT cells, and B cells. Examples of the immune cells include cells isolated from a living organism, immune cells induced from stem cells such as multipotent stem cells, and cultured cells derived from immune cells. The isolated immune cells may be immune cell-like cultured cells, for example, and specific examples thereof include T cell-like cultured cells, NK cell-like cultured cells, NKT cell-like cultured cells, and B cell-like cultured cells. The immune cells are immune cells isolated from a living organism, for example, and specific examples thereof include immune cells derived from human peripheral blood. Examples of the T cell-like cultured cells include Jurkat cells and Jurkat 76 cells. The cells are preferably T cells or T cell-like cultured cells because scFvs that are more likely to be functional in CAR-T cells can be screened, for example.

Next, in the first administration step, the cells expressing the first CAR library are administered to an animal. In the first administration step, it is preferable to administer a plurality of types of cells expressing the first CAR library. In this case, a mixture of a plurality of types of expressing cells is used as the cells expressing the first CAR library, for example. It is preferable that some or all of the plurality of types of expressing cells code for different first CARs, and preferably code for different first antigen-binding domains, for example. When the plurality of types of expressing cells code for different first antigen-binding domains, the regions other than the first antigen-binding domains in the first CARs have the same amino acid sequence or different amino acid sequences, for example. It can also be said that the types of cells expressing the first CAR library correspond to the types of first CARs included in the cells expressing the first CAR library, for example. The number of types of first CARs included in the cells expressing the first CAR library is $1\times10^5$ to $1\times10^7$, $1\times10^5$ to $1\times10^6$, or $1\times10^6$ to $5\times10^6$, for example, and preferably about $2\times10^6$ (e.g., $1\times10^6$ to $3\times10^6$). The number of types of first CARs is the number of types for $1\times10^6$ cells, for example. The number of types of first CARs can also be referred to as the heterogeneity of the nucleic acids coding for the first CARs, for example. As described above, the heterogeneity can be measured through restriction enzyme mapping, sequencing of the CDRs and/or the FRHs using the Sanger's method etc., or the like, for example.

There is no particular limitation on the conditions for administrating the first expressing cells, and the administration form, the administration method, the timing of administration, the dosage amount, and the like can be determined as appropriate in accordance with the type and amount of target antigen, and the site of the animal at which the target antigen is expressed, for example.

Examples of the animal (administration target) include humans and non-human animals other than humans. Examples of the non-human animals include mammals such as mice, rats, dogs, monkeys, rabbits, sheep, horses, and pigs.

The animal is preferably an immune-suppressed animal. When the animal is a mouse, examples of the immune-suppressed mouse include nude mice, SCID (severe combined immunodeficiency) mice, and NOG (NOD/Shi-scid, IL-2Rγ KO) mice.

The administration method is not particularly limited and can be determined as appropriate in accordance with the administration target, for example. Examples of the administration method include parenteral administration and oral administration. Examples of the parenteral administration include topical administration, subcutaneous administration, intracutaneous administration, intramuscular administration, intraperitoneal administration, intravenous administration, intralymphatic administration, and intratumoral administration. The administration method is preferably intravenous administration or intralymphatic administration.

There is no particular limitation on the administration conditions of the first expressing cells. When the administration method is intravenous administration, the administration conditions of the first expressing cells are as follows: the dose (total) for a mouse is $1\times10^6$ to $3\times10^{10}$ cells, and preferably $1\times10^6$ to $1\times10^8$ cells, $1\times10^6$ to $1\times10^7$ cells, or about $5\times10^6$ cells, for example. The administration frequency of the first expressing cells is once a week to once every four weeks, for example.

The animal may express the target antigen intrinsically or extrinsically, for example. In the latter case, the expression in the animal may be achieved by introducing a nucleic acid or expression vector coding for the target antigen or introducing cells expressing the target antigen, for example.

When the cells expressing the target antigen are introduced, the third scFv-manufacturing method of the present invention may include a first formation step of forming a tissue expressing a target antigen prior to the first administration step by introducing cells expressing the target antigen into the animal. The cells to be introduced may be cells expressing a target antigen or cells that express a target antigen after differentiation or under specific conditions, for example. Examples of the cells that express a target antigen under specific conditions include cells in which the expression of a target antigen is induced by treatment with an inducing substance such as doxycycline. The type of tissue formed by the introduced cells is not particularly limited and can be determined as appropriate in accordance with the target antigen. One or two or more types of tissues may be formed. In the latter case, the introduced cells may form an organ. In a specific example, when the target antigen is a tumor antigen, tumor cells expressing the target antigen are introduced into the animal to form a tumor tissue expressing the target antigen in the first formation step. In the present invention, the term "tissue" refers to a cell aggregate, for example. One or two or more types of cells may be included in the aggregate.

The third scFv-manufacturing method of the present invention includes a first stimulation step of administering the target antigen to the animal after the first administration step, for example. Since the third scFv-manufacturing method of the present invention includes the first stimulation step, cells expressing CARs specific to the target antigen out of the first expressing cells can be primed, thus making it possible to allow the cells expressing CARs specific to the target antigen to accumulate in a tissue expressing the target antigen. The first stimulation step is performed before the first collection step, which will be described later, after the first administration step, for example.

The first stimulation step can be performed in the same manner as the immunization of an animal with the target antigen, for example. Specifically, the first stimulation step can be performed by administering the target antigen, a nucleic acid molecule coding for the target antigen, or cells expressing the target antigen to the animal. An immunostimulant (adjuvant) may be administered together with the target antigen, for example.

Next, in the first collection step, the cells expressing the first CAR library that have accumulated in a tissue expressing the target antigen in the animal are collected as cells expressing CARs specific to the target antigen. In the first collection step, the first expressing cells that have accumulated in the tissue may be collected, or the tissue in which the first expressing cells have accumulated is collected, followed by collection of the first expressing cells from the tissue. As described above, this step may be performed on one or two or more types of tissues. In the latter case, it is preferable to collect the first expressing cells that have accumulated in two or more types of tissues in the first collection step. In this case, in the first collection step, two or more types of tissues in which the first expressing cells have accumulated may be collected, followed by collection of the first expressing cells from the two or more types of tissues. When the tissue is collected in the first collection step, a portion or all of the tissue is collected. In the first collection step, it may be confirmed if the first expressing cells accumulate in the tissue, prior to the collection of the first expressing cells. The above-mentioned confirmation can be performed using a microscope capable of live imaging, such as a two-photon excitation microscope, for example. When the confirmation is performed, it is preferable that the first expressing cells express luciferase such as SLR. Moreover, when the confirmation is performed, the first expressing cells may be labeled with a labeling substance such as a fluorescent protein prior to the confirmation, for example.

The first collection step may be performed after a desired period of time has elapsed since the first administration step was finished. Examples of the period from the completion of the first administration step to the start of the first collection step include 8 hours to 1 month, 1 day to 2 weeks, and 1 day to 1 week. When the first collection step is performed subsequently to the first stimulation step, the period from the completion of the first administration step to the start of the first collection step is a time that elapses before cells expressing CARs specific to the target antigen are activated and accumulate, for example, and specific examples thereof include 1 day to 2 weeks and 1 day to 1 week.

It is preferable that the third scFv-manufacturing method of the present invention includes a first restimulation step of restimulating cells expressing CARs specific to the target antigen with the target antigen after the first collection step. With this configuration, in the first restimulation step, it is possible to cause the proliferation of cells expressing CARs specific to the target antigen out of the cells expressing the first CAR library that have accumulated in a tissue expressing the target antigen. Accordingly, if the third scFv-manufacturing method of the present invention includes the first restimulation step, cells expressing CARs specific to the target antigen can be enriched, and the amino acid sequences of the first heavy-chain variable regions and the first light-chain variable regions of the cells expressing CARs specific to the target antigen, and the base sequences coding for the first heavy-chain variable regions and the first light-chain variable regions can be easily determined, for example.

In the first restimulation step, there is no particular limitation on the method of restimulation with the target antigen, and the restimulation can be performed by causing the cells expressing the first CAR library that have been collected from the tissue to coexist with the target antigen, for example. When the above-mentioned cells are caused to coexist with the target antigen, the target antigen may exist in the form of a monomer, a polymer such as a dimer or trimer, or a cell, for example. When the target antigen exists in the form of a cell, the cell is a cell expressing the target antigen.

The third scFv-manufacturing method of the present invention may include a first sequence determination step of determining the amino acid sequences of the first heavy-chain variable regions and the first light-chain variable regions of the first expressing cells collected in the first collection step, for example. The amino acid sequences of the first heavy-chain variable regions and the first light-chain variable regions can be determined by determining the base sequences coding for the amino acid sequences of the first heavy-chain variable regions and the first light-chain variable regions, for example. Specifically, the first sequence determination step can be performed by extracting nucleic acids from the first expressing cells collected in the first collection step, amplifying the base sequences coding for the first heavy-chain variable regions and the first light-chain variable regions in the nucleic acids, and determining the base sequences. Accordingly, with the third scFv-manufacturing method of the present invention, the amino acid sequence of the first heavy-chain variable region or the first light-chain variable region derived from the first B cell receptor can be determined, for example.

Furthermore, in the first sequence determination step, the CDRH1, the CDRH2, and the CDRH3 in each of the first heavy-chain variable regions and the CDRL1, the CDRL2, and the CDRL3 in each of the first light-chain variable regions may be identified, for example. The CDRs can be identified using a known method referring to the genome information (e.g., the website of the IMGT (http://www.imgt.org/)), for example.

The third scFv-manufacturing method of the present invention may be configured such that the first heavy-chain variable regions or first light-chain variable regions derived from the first B cell receptors in the first expressing cells collected in the first collection step are considered as the heavy-chain variable regions or light-chain variable regions of antigens and the like capable of binding to the target antigen in the first CAR library, and then the other regions are screened, for example. That is, the third scFv-manufacturing method of the present invention may be configured such that first heavy-chain variable regions or first light-chain variable regions that are newly identified in the first scFvs screened using the first CAR library (first scFvs of the first expressing cells collected in the first collection step) are used to screen the other regions. In this case, the third scFv-manufacturing method of the present invention may also be configured such that cells expressing a second CAR library are prepared based on the first heavy-chain variable regions or first light-chain variable regions derived from the first B cell receptors in the first expressing cells collected in the first collection step, and then steps similar to the first administration step and the first collection step are performed, for example. In this case, the third scFv-manufacturing method of the present invention includes a second administration step of administering cells expressing the second CAR library to an animal, and a second collection step of collecting the cells expressing the second CAR library that have accumulated in a tissue expressing a target antigen in the animal as cells expressing CARs specific to the target antigen, for example.

The second CAR library includes nucleic acids coding for second CARs, for example. Each of the second CARs includes a second antigen-binding domain, a second transmembrane domain, and a second intracellular signaling domain, for example. The second antigen-binding domain includes a second scFv to be screened for the ability to bind to the target antigen, for example.

The nucleic acids coding for the second CARs are nucleic acids (polynucleotides) coding for the amino acid sequences of the second CARs, for example.

The target antigen of the second scFvs is the same as the target antigen of the first scFvs. The second scFvs have structures similar to those of the first scFvs, for example.

Each of the second scFvs includes a second heavy-chain variable region and a second light-chain variable region, for example. The second heavy-chain variable region includes a CDRH1, a CDRH2, and a CDRH3, for example. The second light-chain variable region includes a CDRL1, a CDRL2, and a CDRL3, for example. The second heavy-chain variable region and the second light-chain variable region meet Condition 3 or Condition 4 below, for example.

Condition 3

If the first CAR library meets Condition 1 above,
the CDRH1, the CDRH2, and the CDRH3 in the second heavy-chain variable region include the CDRH1, the CDRH2, and the CDRH3 in the heavy-chain variable region of a second B cell receptor, respectively, and
the CDRL1, the CDRL2, and the CDRL3 in the second light-chain variable region include the CDRL1, the CDRL2, and the CDRL3 in the light-chain variable region of the scFv of a cell expressing a CAR specific to the target antigen, respectively.

Condition 4

If the first CAR library meets Condition 2 above,
the CDRH1, the CDRH2, and the CDRH3 in the second heavy-chain variable region include the CDRH1, the CDRH2, and the CDRH3 in the heavy-chain variable region of the scFv of a cell expressing a CAR specific to the target antigen, respectively, and
the CDRL1, the CDRL2, and the CDRL3 in the second light-chain variable region include the CDRL1, the CDRL2, and the CDRL3 in the light-chain variable region of a second B cell receptor, respectively.

In the third scFv-manufacturing method of the present invention, cells expressing the second CAR library (also referred to as "second expressing cells" hereinafter) can be prepared by introducing, into cells, the second CAR library that includes nucleic acids coding for the second CARs, for example. Accordingly, the third scFv-manufacturing method of the present invention may include a second production step of producing the second CAR library prior to the second administration step. Also, the third scFv-manufacturing method of the present invention may include a second preparation step of preparing cells expressing the second CAR library prior to the second administration step by introducing the second CAR library into cells.

In the second production step, the second CAR library is produced. As described above, the second CAR library includes nucleic acids coding for the second CARs. The nucleic acids coding for the second CARs are nucleic acids (polynucleotides) coding for the amino acid sequences of the second CARs, for example. The second CAR library is the same as the second CAR library in the CAR library of the present invention, and the descriptions thereof can be applied.

As described above, the second heavy-chain variable region includes the CDRH1, the CDRH2, and the CDRH3. The second light-chain variable region includes the CDRL1, the CDRL2, and the CDRL3. The second heavy-chain variable region and the second light-chain variable region meet Condition 3 or Condition 4 above.

Condition 3 above is employed in the case where the second CAR library is prepared using the first light-chain variable regions screened using the first CAR library that meets Condition 1 above, for example. In Condition 3 above, the CDRL1, the CDRL2, and the CDRL3 of the first light-chain variable region screened using the first CAR library are used as those in the second light-chain variable region, and the CDRH1, the CDRH2, and the CDRH3 in the second heavy-chain variable region are screened for the ability to bind to the target antigen, for example.

Next, Condition 4 above is employed in the case where the second CAR library is prepared using the heavy-chain variable regions screened using the first CAR library that meets Condition 2 above, for example. In Condition 4 above, the CDRH1, the CDRH2, and the CDRH3 of the heavy-chain variable region screened using the first CAR library are used as those in the second heavy-chain variable region, and the CDRL1, the CDRL2, and the CDRL3 in the second light-chain variable region are screened for the ability to bind to the target antigen, for example.

Next, in the second preparation step, cells expressing the second CAR library are prepared by introducing the second CAR library into cells. Specifically, in the second preparation step, the second CAR library is introduced into the above-mentioned cells, for example. In the second preparation step, the second CAR library is expressed in the cells by culturing the cells into which the second CAR library has been introduced, for example. The descriptions of the method for introducing the first CAR library can be applied to the method for introducing the second CAR library, for example.

The second CAR library may include nucleic acids coding for the second CARs, or expression vectors into which nucleic acids coding for the second CARs have been introduced, for example.

There is no particular limitation on the cells, and the descriptions of the cells into which the first CAR library is to be introduced can be applied, for example.

Next, in the second administration step, the cells expressing the second CAR library are administered to an animal. In the second administration step, it is preferable to administer a plurality of types of cells expressing the second CAR library. In this case, a mixture of a plurality of types of expressing cells is used as the cells expressing the second CAR library, for example. It is preferable that some or all of the plurality of types of expressing cells code for different second CARs, and preferably code for different second antigen-binding domains, for example. When the plurality of types of expressing cells code for different second antigen-binding domains, the regions other than the second antigen-binding domains in the second CARs have the same amino acid sequence or different amino acid sequences, for example. It can also be said that the types of cells expressing the second CAR library correspond to the types of second CARs included in the cells expressing the second CAR library, for example. The number of types of second CARs included in the cells expressing the second CAR library is $1 \times 10^5$ to $1 \times 10^7$, $1 \times 10^5$ to $1 \times 10^6$, or $1 \times 10^6$ to $5 \times 10^6$, for example, and preferably about $2 \times 10^6$ (e.g., $1 \times 10^6$ to $3 \times 10^6$). The number of types of second CARs can also be referred to as the heterogeneity of the nucleic acids coding for the second CARs, for example. As described above, the heterogeneity can be measured through restriction enzyme mapping, sequencing of the CDRs and/or the FRHs using the Sanger's method etc., or the like, for example.

There is no particular limitation on the administration conditions of the second expressing cells, and the descriptions of the above-mentioned administration conditions of the second expressing cells can be applied, for example.

In the second administration step, the animal may express the target antigen intrinsically or extrinsically, for example. In the latter case, the expression in the animal may be achieved by introducing a nucleic acid or expression vector coding for the target antigen or introducing cells expressing the target antigen, for example.

When the cells expressing the target antigen are introduced, the third scFv-manufacturing method of the present invention may include a second formation step of forming a tissue expressing a target antigen prior to the second administration step by introducing cells expressing the target antigen into the animal. The cells to be introduced may be cells expressing a target antigen or cells that express a target antigen after differentiation or under specific conditions, for example. Examples of the cells that express a target antigen under specific conditions include cells in which the expression of a target antigen is induced by treatment with an inducing substance such as doxycycline. The type of tissue formed by the introduced cells is not particularly limited and can be determined as appropriate in accordance with the target antigen. One or two or more types of tissues may be formed. In the latter case, the introduced cells may form an organ. In a specific example, when the target antigen is a tumor antigen, tumor cells expressing the target antigen are introduced into the animal to form a tumor tissue expressing the target antigen in the second formation step.

The third scFv-manufacturing method of the present invention includes a second stimulation step of administering the target antigen to the animal after the second administration step, for example. Since the third scFv-manufacturing method of the present invention includes the second stimulation step, cells expressing CARs specific to the target antigen out of the second expressing cells can be primed, thus making it possible to allow the cells expressing CARs specific to the target antigen to accumulate in a tissue expressing the target antigen. The second stimulation step is performed in the second collection step, which will be described later, after the second administration step, for example.

The second stimulation step can be performed in the same manner as the immunization of an animal with the target antigen, for example. Specifically, the second stimulation step can be performed by administering the target antigen, a nucleic acid molecule coding for the target antigen, or cells expressing the target antigen to the animal. An immunostimulant (adjuvant) may be administered together with the target antigen, for example.

Next, in the second collection step, the cells expressing the second CAR library that have accumulated in a tissue expressing the target antigen in the animal are collected as cells expressing CARs specific to the target antigen. In the second collection step, the second expressing cells that have accumulated in the tissue may be collected, or the tissue in which the second expressing cells have accumulated is collected, followed by collection of the second expressing cells from the tissue. As described above, this step may be performed on one or two or more types of tissues. In the latter case, it is preferable to collect the second expressing cells that have accumulated in two or more types of tissues in the second collection step. In this case, in the second collection step, two or more types of tissues in which the second expressing cells have accumulated may be collected, followed by collection of the second expressing cells from the two or more types of tissues. When the tissue is collected in the second collection step, a portion or all of the tissue is collected. In the second collection step, it may be confirmed if the second expressing cells accumulate in the tissue, prior to the collection of the second expressing cells. The above-mentioned confirmation can be performed using a microscope capable of live imaging, such as a two-photon excitation microscope, for example. When the confirmation is performed, it is preferable that the second expressing cells express luciferase such as SLR. Moreover, when the confirmation is performed, the second expressing cells may be labeled with a labeling substance such as a fluorescent protein prior to the confirmation, for example.

The second collection step may be performed after a desired period of time has elapsed since the second administration step was finished. Examples of the period from the completion of the second administration step to the start of the second collection step include 8 hours to 1 month, 1 day to 2 weeks, and 1 day to 1 week. When the second collection step is performed subsequently to the second stimulation step, the period from the completion of the second administration step to the start of the second collection step is a time that elapses before cells expressing CARs specific to the target antigen are activated and accumulate, for example, and specific examples thereof include 1 day to 2 weeks and 1 day to 1 week.

It is preferable that the third scFv-manufacturing method of the present invention includes a second restimulation step of restimulating cells expressing CARs specific to the target antigen with the target antigen after the second collection step. With this configuration, in the second restimulation step, it is possible to cause the proliferation of cells expressing CARs specific to the target antigen out of the cells expressing the second CAR library that have accumulated in a tissue expressing the target antigen. Accordingly, if the third scFv manufacturing method of the present invention includes the second restimulation step, cells expressing CARs specific to the target antigen can be enriched, and the amino acid sequences of the second heavy-chain variable regions and the second light-chain variable regions of the cells expressing CARs specific to the target antigen, and the base sequences coding for the second heavy-chain variable regions and the second light-chain variable regions can be easily determined, for example.

In the second restimulation step, there is no particular limitation on the method of restimulation with the target antigen, and if the "first CAR library" is changed to the "second CAR library", the descriptions of the first restimulation step can be applied, for example.

The third scFv-manufacturing method of the present invention may include a second sequence determination step of determining the amino acid sequences of the second heavy-chain variable regions and the second light-chain variable regions of the second expressing cells collected in the second collection step, for example. The amino acid sequences of the second heavy-chain variable regions and the second light-chain variable regions can be determined by determining the base sequences coding for the amino acid sequences of the second heavy-chain variable regions and the second light-chain variable regions, for example. Specifically, the second sequence determination step can be performed by extracting nucleic acids from the second expressing cells collected in the second collection step, amplifying the base sequences coding for the second heavy-chain variable regions and the second light-chain variable regions in the nucleic acids, and determining the base sequences. Accordingly, with the third scFv-manufacturing method of the present invention, the amino acid sequence of the second heavy-chain variable region or the second light-chain variable region derived from the second B cell receptor can be determined, for example.

Furthermore, in the second sequence determination step, the CDRH1, the CDRH2, and the CDRH3 in each of the second heavy-chain variable regions and the CDRL1, the CDRL2, and the CDRL3 in each of the second light-chain variable regions may be identified, for example. The CDRs can be identified using a known method referring to the genome information (e.g., the website of the IMGT (http://www.imgt.org/)), for example.

EXAMPLES

Next, examples of the present invention will be described. However, the present invention is not limited to the examples below. Commercially available reagents were used according to their protocols unless otherwise stated.

Example 1

It was confirmed that the screening method of the present invention in which the CAR library of the present invention is used could be used to screen scFvs capable of binding to A2/NY-ESO-1$_{157}$.

(1) Preparation of 3M4E5 CAR

A 3M4E5 CAR was prepared using an A2/NY-ESO-1$_{157}$-specific antibody (clone: 3M4E5). Specifically, a nucleic acid coding for a 3M4E5 scFv was prepared by coupling a nucleic acid (Sequence ID No. 162) coding for the heavy-chain variable region derived from the immunoglobulin heavy chain of 3M4E5 and a nucleic acid (Sequence ID No. 163) coding for the light-chain variable region derived from the immunoglobulin light chain of 3M4E5 to each other via a nucleic acid (Sequence ID No. 3) coding for an Fv linker peptide (GSTSGSGKPGSGEGSTKG: Sequence ID No. 1). An scFv obtained by coupling the heavy-chain variable region of 3M4E5, the Fv linker peptide, and the light-chain variable region of 3M4E5 in this order is referred to as a "3M4E5HL scFv". An scFv obtained by coupling the light-chain variable region of 3M4E5, the Fv linker peptide, and the heavy-chain variable region of 3M4E5 in this order is referred to as a "3M4E5LH scFv".

```
Nucleic Acid Coding for Heavy-Chain Variable Region Derived from
Immunoglobulin Heavy Chain of 3M4E5
                                            (Sequence ID No. 162)
5'-GAAGTGCAGCTGCTGGAATCTGGCGGCGGACTGGTGCAGCCTGGCGGATCTC

TGAGACTGAGCTGTGCCGCCAGCGGCTTCACCTTCAGCACCTACCAGATGAG

CTGGGTGCGCCAGGCCCCTGGCAAAGGACTGGAATGGGTGTCCGGCATCGTG

TCCAGCGGCGGCTCTACAGCCTACGCCGATAGCGTGAAGGGCCGGTTCACCA

TCAGCCGGGACAACAGCAAGAACACCCTGTACCTGCAGATGAACAGCCTGAG

AGCCGAGGACACCGCCGTGTACTATTGTGCCGGGGAGCTGCTGCCCTACTAC

GGCATGGATGTGTGGGGCCAGGGCACCACCGTGACAGTGTCCTCA-3'

Nucleic Acid Coding for Light-Chain Variable Region Derived from
Immunoglobulin Light Chain of 3M4E5
                                            (Sequence ID No. 163)
5'-CAGAGCGAGCTGACACAGCCTAGATCCGTGTCTGGCAGCCCTGGCCAGAGCG

TGACCATCAGCTGTACCGGCACCAGCAGAGATGTGGGCGGCTACAACTACGT

GTCCTGGTATCAGCAGCATCCCGGCAAGGCCCCCAAGCTGATCATCCACGAC

GTGATCGAGCGGAGCAGCGGCGTGCCCGATAGATTCAGCGGCAGCAAGAGCG

GCAACACCGCCAGCCTGACAATCAGCGGACTGCAGGCCGAGGACGAGGCCG

ACTACTACTGTTGGAGCTTCGCCGGCAGCTACTACGTGTTCGGCACCGGCACC

GATGTGACCGTGCTG-3'

3M4E5HL scFv
                                            (Sequence ID No. 164)
EVQLLESGGGLVQPGGSLRLSCAASGFTFSTYQMSWVRQAPGKGLEW

VSGIVSSGGSTAYADSVKGRFTISRDNSKNTLYLQMNSLRAEDTAVYYCAGELL

PYYGMDVWGQGTTVTVSSGSTSGSGKPGSGEGSTKGQSELTQPRSVSGSPGQS

VTISCTGTSRDVGGYNYVSWYQQHPGKAPKLIIHDVIERSSGVPDRFSGSKSGN

TASLTISGLQAEDEADYYCWSFAGSYYVFGTGTDVTVL

Nucleic Acid Coding for 3M4E5HL scFv
                                            (Sequence ID No. 165)
5'-GAAGTGCAGCTGCTGGAATCTGGCGGCGGACTGGTGCAGCCTGGCGGATCTC

TGAGACTGAGCTGTGCCGCCAGCGGCTTCACCTTCAGCACCTACCAGATGAG
```

```
CTGGGTGCGCCAGGCCCCTGGCAAAGGACTGGAATGGGTGTCCGGCATCGTG

TCCAGCGGCGGCTCTACAGCCTACGCCGATAGCGTGAAGGGCCGGTTCACCA

TCAGCCGGGACAACAGCAAGAACACCCTGTACCTGCAGATGAACAGCCTGAG

AGCCGAGGACACCGCCGTGTACTATTGTGCCGGGGAGCTGCTGCCCTACTAC

GGCATGGATGTGTGGGGCCAGGGCACCACCGTGACAGTGTCCTCAGGCTCTA

CAAGCGGCTCTGGCAAGCCTGGATCTGGCGAGGGAAGCACCAAGGGCCAGA

GCGAGCTGACACAGCCTAGATCCGTGTCTGGCAGCCCTGGCCAGAGCGTGAC

CATCAGCTGTACCGGCACCAGCAGAGATGTGGGCGGCTACAACTACGTGTCC

TGGTATCAGCAGCATCCCGGCAAGGCCCCCAAGCTGATCATCCACGACGTGAT

CGAGCGGAGCAGCGGCGTGCCCGATAGATTCAGCGGCAGCAAGAGCGGCAA

CACCGCCAGCCTGACAATCAGCGGACTGCAGGCCGAGGACGAGGCCGACTAC

TACTGTTGGAGCTTCGCCGGCAGCTACTACGTGTTCGGCACCGGCACCGATG

TGACCGTGCTG-3'
```

3M4E5LH scFv (Sequence ID No. 166)

```
QSELTQPRSVSGSPGQSVTISCTGTSRDVGGYNYVSWYQQHPGKAPKLI

IHDVIERSSGVPDRFSGSKSGNTASLTISGLQAEDEADYYCWSFAGSYYVFGTG

TDVTVLGSTSGSGKPGSGEGSTKGEVQLLESGGGLVQPGGSLRLSCAASGFTFS

TYQMSWVRQAPGKGLEWVSGIVSSGGSTAYADSVKGRFTISRDNSKNTLYLQM

NSLRAEDTAVYYCAGELLPYYGMDVWGQGTTVTVSS
```

Nucleic Acid Coding for 3M4E5LH scFv (Sequence ID No. 167)

```
5'-CAGAGCGAGCTGACACAGCCTAGATCCGTGTCTGGCAGCCCTGGCCAGAGCG

TGACCATCAGCTGTACCGGCACCAGCAGAGATGTGGGCGGCTACAACTACGT

GTCCTGGTATCAGCAGCATCCCGGCAAGGCCCCCAAGCTGATCATCCACGAC

GTGATCGAGCGGAGCAGCGGCGTGCCCGATAGATTCAGCGGCAGCAAGAGCG

GCAACACCGCCAGCCTGACAATCAGCGGACTGCAGGCCGAGGACGAGGCCG

ACTACTACTGTTGGAGCTTCGCCGGCAGCTACTACGTGTTCGGCACCGGCACC

GATGTGACCGTGCTGGGCTCTACAAGCGGCTCTGGCAAGCCTGGATCTGGCG

AGGGAAGCACCAAGGGCGAAGTGCAGCTGCTGGAATCTGGCGGCGGACTGG

TGCAGCCTGGCGGATCTCTGAGACTGAGCTGTGCCGCCAGCGGCTTCACCTT

CAGCACCTACCAGATGAGCTGGGTGCGCCAGGCCCCTGGCAAAGGACTGGAA

TGGGTGTCCGGCATCGTGTCCAGCGGCGGCTCTACAGCCTACGCCGATAGCG

TGAAGGGCCGGTTCACCATCAGCCGGGACAACAGCAAGAACACCCTGTACCT

GCAGATGAACAGCCTGAGAGCCGAGGACACCGCCGTGTACTATTGTGCCGGG

GAGCTGCTGCCCTACTACGGCATGGATGTGTGGGGCCAGGGCACCACCGTGA

CAGTGTCCTCA-3'
```

Next, a nucleic acid (Sequence ID No. 169) coding for a sequence (Sequence ID No. 168) that included a partial region, the transmembrane domain, and the intracellular signaling domain of human CD28, and a nucleic acid coding for the intracellular signaling domain of human CD3ζ were coupled to the 3' ends of the nucleic acids coding for the 3M4E5HL scFv and the 3M4E5LH scFv, such that these nucleic acids were arranged in the stated order from the 5' end side. Thus, a nucleic acid coding for a 3M4E5HL CAR that included the 3M4E5HL scFv and a nucleic acid coding for a 3M4E5LH CAR that included the 3M4E5LH scFv were prepared. It should be noted that the nucleic acid coding for the partial region, the transmembrane domain, and the intracellular signaling domain of human CD28 and the nucleic acid coding for the intracellular signaling domain of human CD3ζ were obtained using the GeneArt (trademark) artificial gene synthesis service (provided by Thermo Fisher Scientific). A NotI restriction enzyme site was added to the 5' end of the nucleic acid coding for the partial region, the transmembrane domain, and the intracellular signaling domain of human CD28.

```
Partial Region, Transmembrane Domain, Intra-
cellular Signaling Domain of Human CD28
                                (Sequence ID No. 168)
AAAIEVNIYPPPYLDNEKSNGTIIHVKGKHLCPSPLFPGPSKPFWVLVV
VGGVLACYSLLVTVAFIIFWVRSKRSRLLHSDYNINMTPRRPGPTRKHY
QPYAPPRDFAAYRS Nucleic Acid Coding for Partial Region, Trans-
membrane Domain, Intracellular Signaling
Domain of Human CD28
                                (Sequence ID No. 169)
5'-GCGGCCGCAATCGAAGTGATGTACCCCCCTCCCTACCTGGACAACG

AGAAGTCCAACGGCACCATTATCCACGTGAAGGGAAAGCACCTGTGCCC

CAGCCCTCTGTTCCCTGGCCCTAGCAAGCCTTTCTGGGTGCTGGTGGTC

GTGGGCGGAGTGCTGGCCTGTTATAGCCTGCTCGTGACCGTGGCCTTCA

TCATCTTTTGGGTGCGCAGCAAGCGGAGCCGGCTGCTGCACAGCGACTA

CATGAACATGACCCCCAGACGGCCCGGACCCACCAGAAAGCACTACCAG

CCTTACGCCCCTCCCAGAGACTTCGCCGCCTACAGATCT-3'

Intracellular Signaling Domain of Human CD3
                                (Sequence ID No. 170)
RVKFSRSADAPAYQQGQNQLYNELNLGRREEYDVLDKRRGRDPEMGG
KPRRKNPQEGLYNELQKDKNIAEAYSEIGMKGERRRGKGHDGLYQGLST
ATKDTYDALHMQALPPR Nucleic Acid Coding for Intracellular Signaling
Domain of Human CD4
                                (Sequence ID No. 171)
5'-CGAGTGAAGTTCAGCAGAAGCGCCGACGCCCCTGCCTATCAGCAGG

GCCAGAACCAGCTGTACAACGAGCTGAACCTGGGCAGACGGGAAGAGTA

CGACGTGCTGGACAAGCGGAGAGGCAGGGACCCTGAGATGGGCGGCAAG

CCCAGAAGAAAGAACCCCCAGGAAGGCCTGTATAACGAACTGCAGAAAG

ACAAGATGGCCGAGGCCTACAGCGAGATCGGCATGAAGGGCGAGCGGAG

AAGAGGCAAGGGCCACGATGGCCTGTACCAGGGCCTGAGCACCGCCACC

AAGGACACCTATGACGCCCTGCACATGCAGGCCCTGCCCCCCAGA-3'
```

Furthermore, a nucleic acid coding for the truncated-NGFR gene (ΔNGFR) was coupled to the 3' ends of the nucleic acid coding for the 3M4E5HL CAR and the nucleic acid coding for the 3M4E5LH CAR via a nucleic acid coding for a furin cleavage site (RAKR: Sequence ID No. 172), a spacer sequence (SGSG: Sequence ID No. 173), and a codon-optimized P2A sequence (ATNFSLLKQAGD-VEENPGP: Sequence ID No. 174). Thus, a nucleic acid coding for a tagged 3M4E5HL CAR and a nucleic acid coding for a tagged 3M4E5LH CAR were prepared. The nucleic acids were introduced into pMX expression vectors.
(2) Preparation of First CAR Library A B-cell purification kit (CD19-positive selection kit, MACS (registered trademark) beads, manufactured by Miltenyi Biotec) was used to purify 1×10$^6$ to 3×10$^6$ human peripheral blood B cells from human peripheral blood monocytes. After the obtained CD19$^+$ B cells were collected, RNA was extracted using a cDNA synthesis kit (SMARTer (trademark) RACE cDNA amplification kit, manufactured by Takara Bio), and then cDNA was synthesized from the RNA.

A nucleic acid coding for a protein that included the heavy-chain variable region and a portion of the constant region derived from the immunoglobulin heavy chain was amplified through PCR in which the above-mentioned cDNA and a mixture of a 5'-RACE primer, a 3'IGHC primer, and a 3'IGHM primer were used. The 3'IGHC primer is capable of hybridizing with the CH1 region of a human IgG.

```
The 3'IGHM primer is capable of hybridizing with
the CH1 region of a human IgM.
5'-RACE Primer
                                (Sequence ID No. 175)
5'-CTAATACGACTCACTATAGGGCAAGCAGTGGTATCAACGCAGAGT-
3'

3'IGHC Primer
                                (Sequence ID No. 176)
5'-TGAGTTCCACGACACCGTCAC-3'

3'IGHM Primer
                                (Sequence ID No. 177)
5'-TCCAGGACAAAGTGATGGAGTC-3'
```

Next, semi-nested PCR was performed in which the first PCR product and a mixture of a modified 5'-RACE primer, a 3'IGHJ1 primer, a 3'IGHJ2 primer, and a 3'IGHJ3 primer were used, and thus a nucleic acid coding for the heavy-chain variable region was amplified. Thus, a library of nucleic acids coding for the heavy-chain variable regions derived from human peripheral blood B cells was prepared. The 3'IGHJ1 primer, the 3'IGHJ2 primer, and the 3'IGHJ3 primer are capable of hybridizing with the J regions (J gene fragments) of the heavy chain.

```
Modified 5'-RACE Primer
                                (Sequence ID No. 178)
5'-GTGTGGTGGTACGGGAATTCAAGCAGTGGTATCAACGCAGAGT-3'

3'IGHJ1 Primer
                                (Sequence ID No. 179)
5'-CTTGCCAGAGCCGCTTGTAGAGCCTGAGGAGACGGTGACCAGG
G-3'

3'IGHJ2 Primer
                                (Sequence ID No. 180)
5'-CTTGCCAGAGCCGCTTGTAGAGCCTGAAGAGACGGTGACCATT
GTC-3'

3'IGHJ3 Primer
                                (Sequence ID No. 181)
5'-CTTGCCAGAGCCGCTTGTAGAGCCTGAGGAGACGGTGACCGTG
GTC-3'
```

Next, a nucleic acid coding for the light-chain variable region derived from the immunoglobulin light chain was amplified in the same manner as in the above-mentioned amplification of the nucleic acid coding for the heavy-chain variable region, except that a 3'IGKC primer and a 3'IGLC primer were used in the first PCR instead of the 3'IGHC primer and the 3'IGHM primer, and a 3'IGKJ1 primer, a 3'IGKJ2 primer, a 3'IGKJ3 primer, a 3'IGKJ4 primer, a 3'IGLJ1 primer, a 3'IGLJ2 primer, a 3'IGLJ4 primer, a 3'IGLJ5 primer, and a 3'IGLJ7 primer were used in the second semi-nested PCR instead of the 3'IGHJ1 primer, the 3'IGHJ2 primer, and the 3'IGHJ3 primer. Thus, a library of nucleic acids coding for the light-chain variable regions derived from human peripheral blood B cells was prepared. The 3'IGKC primer and the 3'IGLC primer are capable of hybridizing with the CH1 regions of a κ chain and a λ chain, respectively. The 3'IGKJ1 primer, the 3'IGKJ2 primer, the 3'IGKJ3 primer, the 3'IGKJ4 primer, the 3'IGLJ1 primer, the 3'IGLJ2 primer, the 3'IGLJ4 primer, the 3'IGLJ5 primer, and the 3'IGLJ7 primer are capable of hybridizing with the J regions (J gene fragments) of the light chain.

```
3'IGKC Primer
                              (Sequence ID No. 182)
5'-AGGGTCAGAGGCCAAAGGATGG-3'

3'IGLC Primer
                              (Sequence ID No. 183)
5'-CTTGGAGCTCCTCAGAGGAG-3'

3'IGKJ1 Primer
                              (Sequence ID No. 184)
5'-CTTGCCAGAGCCGCTTGTAGAGCCTTTGATTTCCACCTTGGTCCC-
3'

3'IGKJ2 Primer
                              (Sequence ID No. 185)
5'-CTTGCCAGAGCCGCTTGTAGAGCCTTTGATCTCCAGCTTGGTCCC-
3'

3'IGKJ3 Primer
                              (Sequence ID No. 186)
5'-CTTGCCAGAGCCGCTTGTAGAGCCTTTGATATCCACTTTGGTCCC-
3'

3'IGKJ4 Primer
                              (Sequence ID No. 187)
5'-CTTGCCAGAGCCGCTTGTAGAGCCTTTAATCTCCAGTCGTGTCCC-
3'

3'IGLJ1 Primer
                              (Sequence ID No. 188)
5'-CTTGCCAGAGCCGCTTGTAGAGCCTAGGACGGTGACCTTGGTCCC-
3'

3'IGLJ2 Primer
                              (Sequence ID No. 189)
5'-CTTGCCAGAGCCGCTTGTAGAGCCTAGGACGGTCAGCTTGGTCCC-
3'

3'IGLJ4 Primer
                              (Sequence ID No. 190)
5'-CTTGCCAGAGCCGCTTGTAGAGCCTAAAATGATCAGCTGGGTTCC-
3'

3'IGLJ5 Primer
                              (Sequence ID No. 191)
5'-CTTGCCAGAGCCGCTTGTAGAGCCTAGGACGGTCAGCTCGGTCCC-
3'

3'IGLJ7 Primer
                              (Sequence ID No. 192)
5'-CTTGCCAGAGCCGCTTGTAGAGCCGAGGACGGTCAGCTGGGTGCC-
3'
```

An hH-3M4E4L scFv library was prepared by substituting the nucleic acid coding for the heavy-chain variable region on the 5' side of the nucleic acid coding for the 3M4E5HL scFv described in (1) above with the above-mentioned library that included the nucleic acids of the heavy-chain variable regions derived from human peripheral blood B cells. Then, a tagged hH-3M4E4L CAR library was prepared in the same manner as in (1) above, except that the hH-3M4E4L scFv library was used instead of the nucleic acid coding for the 3M4E5HL scFv. The tagged hH-3M4E4L CAR library was introduced into pMX expression vectors to prepare expression vectors for expressing the hH-3M4E4L CAR library. It should be noted that, regarding the heterogeneity of the heavy-chain variable regions in the hH-3M4E4L CAR library, it was confirmed through restriction enzyme mapping and sequencing of the regions using the Sanger's method that the number of types of heavy-chain variable regions was about $1 \times 10^6$.

(3) Preparation of First CAR Library-Expressing T Cells (First Candidate CAR-Ts)

The expression vectors for expressing the hH-3M4E4L CAR library were introduced into Plat-A cells (provided by Dr. Toshio KITAMURA, the Institute of Medical Science, the University of Tokyo, National University Corporation) using a transfection reagent (TransIT293, manufactured by Takara Bio), and then a culture supernatant containing ecotropic retroviruses was prepared. The Plat-A cells were maintained in a DMEM culture medium containing fetal calf serum (FCS) at a concentration of 10%, puromycin at a concentration of 1 μg/mL, and blasticidin at a concentration of 10 μg/mL until before use. Next, the hH-3M4E4L CAR library was introduced into PG13 cells serving as packaging cells by adding the above-mentioned culture supernatant containing ecotropic viruses, and thus GaLV-pseudotyped retroviruses that included the hH-3M4E4L CAR library were prepared. Then, CAR-Ts were prepared by infecting human peripheral blood T cells with the GaLV-pseudotyped retroviruses. A DMEM culture medium containing FCS at a concentration of 10% was used as the culture medium for PG13 cells, and PG13 cells were cultured under a wet atmosphere in the culture conditions of 37° C. and 5% $CO_2$. The same cell culture conditions were used in the descriptions below unless otherwise stated.

Next, human peripheral blood monocytes were isolated from a healthy subject. The obtained human peripheral blood monocytes were cultured in the presence of an anti-CD3 antibody (clone: OKT3) at a concentration of 50 ng/mL and human IL-2 at a concentration of 100 IU/mL for two days. An RPMI1640 culture medium containing gentamicin at a concentration of 50 μg/mL and human AB serum (manufactured by Sigma) at a concentration of 10% was used as the culture medium for the human peripheral blood monocytes. After the above-mentioned culture, T cells were centrifuged in the presence of the GaLV-pseudotyped retroviruses under the conditions of 1000×g and 32° C. for 1 hour and thus infected with the retroviruses, and thus the hH-3M4E4L CAR library was introduced into the T cells. The infection with the retroviruses and the introduction of the hH-3M4E4L CAR library were performed in the same manner five more times (six times in total). After the resulting T cells were stained with a PE-labeled anti-human NGFR mAb (clone: ME20.4), it was examined using a flow cytometer (Gallios flow cytometer, manufactured by Beckman Coulter) if the tags were expressed on the T cells, and it was thus confirmed that a single hH-3M4E4L CAR was expressed in a single T cell at an introduction efficiency of 30%. Analysis software (FlowJo Version 7.6.5 software, manufactured by TreeStar) was used to analyze data obtained using the flow cytometer (the same applies hereinafter).

The T cells into which the hH-3M4E4 CAR library had been introduced were reacted with the PE-labeled anti-human NGFR mAb. After the above-mentioned reaction, the T cells into which the hH-3M4E4 CAR library had been introduced were purified using anti-PE microbeads (manufactured by Miltenyi Biotec), and the purified T cells were used as first candidate CAR-Ts.

(4) Preparation of Target Antigen-Expressing Cells

Retroviruses were used to introduce a nucleic acid coding for HLA-A*02:01 and nucleic acids coding for CD80, CD83, CD40, and 4-1BBL into K562 cells (HLA and CD19 are not expressed; available from ATCC), and thus antigen-presenting cells (APCs, K562/A2) were obtained.

```
Nucleic Acid Coding for HLA-A*02:01
                              (Sequence ID No. 193)
5'-ATGGCCGTCATGGCGCCCCGAACCCTCGTCCTGCTACTCTCGGGGG

CTCTGGCCCTGACCCAGACCTGGGCGGGCTCTCACTCCATGAGGTATTT
```

CTTCACATCCGTGTCCCGGCCCGGCCGCGGGGAGCCCCGCTTCATCGCA

GTGGGCTACGTGGACGACACGCAGTTCGTGCGGTTCGACAGCGACGCCG

CGAGCCAGAGGATGGAGCCGCGGGCGCCGTGGATAGAGCAGGAGGGTCC

GGAGTATTGGGACGGGGAGACACGGAAAGTGAAGGCCCACTCACAGACT

CACCGAGTGGACCTGGGGACCCTGCGCGGCTACTACAACCAGAGCGAGG

CCGGTTCTCACACCGTCCAGAGGATGTATGGCTGCGACGTGGGGTCGGA

CTGGCGCTTCCTCCGCGGGTACCACCAGTACGCCTACGACGGCAAGGAT

TACATCGCCCTGAAAGAGGACCTGCGCTCTTGGACCGCGGCGGACATGG

CAGCTCAGACCACCAAGCACAAGTGGGAGGCGGCCCATGTGGCGGAGCA

GTTGAGAGCCTACCTGGAGGGCACGTGCGTGGAGTGGCTCCGCAGATAC

CTGGAGAACGGGAAGGAGACGCTGCAGCGCACGGACGCCCCAAAACGC

ATATGACTCACCACGCTGTCTCTGACCATGAAGCCACCCTGAGGTGCTG

GGCCCTGAGCTTCTACCCTGCGGAGATCACACTGACCTGGCAGCGGGAT

GGGGAGGACCAGACCCAGGACACGGAGCTCGTGGAGACCAGGCCTGCAG

GGGATGGAACCTTCCAGAAGTGGGCGGCTGTGGTGGTGCCTTCTGGACA

GGAGCAGAGATACACCTGCCATGTGCAGCATGAGGGTTTGCCCAAGCCC

CTCACCCTGAGATGGGAGCCGTCTTCCCAGCCCACCATCCCCATCGTGG

GCATCATTGCTGGCCTGGTTCTCTTTGGAGCTGTGATCACTGGAGCTGT

GGTCGCTGCTGTGATGTGGAGGAGGAAGAGCTCAGATAGAAAGGAGGG

AGCTACTCTCAGGCTGCAAGCAGTGACAGTGCCCAGGGCTCTGATGTGT

CTCTCACAGCTTGTAAAGTG-3'

Nucleic Acid Coding for CD80
(Sequence ID No. 194)
5'-ATGGGCCACACACGGAGGCAGGGAACATCACCATCCAAGTGTCCAT

ACCTCAATTTCTTTCAGCTCTTGGTGCTGGCTGGTCTTTCTCACTTCTG

TTCAGGTGTTATCCACGTGACCAAGGAAGTGAAAGAAGTGGCAACGCTG

TCCTGTGGTCACAATGTTTCTGTTGAAGAGCTGGCACAAACTCGCATCT

ACTGGCAAAAGGAGAAGAAAATGGTGCTGACTATGATGTCTGGGGACAT

GAATATATGGCCCGAGTACAAGAACCGGACCATCTTTGATATCACTAAT

AACCTCTCCATTGTGATCCTGGCTCTGCGCCCATCTGACGAGGGCACAT

ACGAGTGTGTTGTTCTGAAGTATGAAAAAGACGCTTTCAAGCGGGAACA

CCTGGCTGAAGTGACGTTATCAGTCAAAGCTGACTTCCCTACACCTAGT

ATATCTGACTTTGAAATTCCAACTTCTAATATTAGAAGGATAATTTGCT

CAACCTCTGGAGGTTTTCCAGAGCCTCACCTCTCCTGGTTGGAAAATGG

AGAAGAATTAAATGCCATCAACACAACAGTTTCCCAAGATCCTGAAACT

GAGCTCTATGCTGTTAGCAGCAAACTGGATTTCAATATGACAACCAACC

ACAGCTTCATGTGTCTCATCAAGTATGGACATTTAAGAGTGAATCAGAC

CTTCAACTGGAATACAACCAAGCAAGAGCATTTTCCTGATAACCTGCTC

CCATCCTGGGCCATTACCTTAATCTCAGTAAATGGAATTTTTGTGATAT

GCTGCCTGACCTACTGCTTTGCCCCAAGATGCAGAGAGAGAAGGAGGAA

TGAGAGATTGAGAAGGGAAAGTGTACGCCCTGTA-3'

Nucleic Acid Coding for CD83
(Sequence ID No. 195)
5'-ATGTCGCGCGGCCTCCAGCTTCTGCTCCTGAGCTGCGCCTACAGCC

TGGCTCCCGCGACGCCGGAGGTGAAGGTGGCTTGCTCCGAAGATGTGGA

CTTGCCCTGCACCGCCCCCTGGGATCCGCAGGTTCCCTACACGGTCTCC

TGGGTCAAGTTATTGGAGGGTGGTGAAGAGAGGATGGAGACACCCCAGG

AAGACCACCTCAGGGGACAGCACTATCATCAGAAGGGGCAAAATGGTTC

TTTCGACGCCCCCAATGAAAGGCCCTATTCCCTGAAGATCCGAAACACT

ACCAGCTGCAACTCGGGGACATACAGGTGCACTCTGCAGGACCCGGATG

GGCAGAGAAACCTAAGTGGCAAGGTGATCTTGAGAGTGACAGGATGCCC

TGCACAGCGTAAAGAAGAGACTTTTAAGAAATACAGAGCGGAGATTGTC

CTGCTGCTGGCTCTGGTTATTTTCTACTTAACACTCATCATTTTCACTT

GTAAGTTTGCACGGCTACAGAGTATCTTCCCAGATTTTTCTAAAGCTGG

CATGGAACGAGCTTTTCTCCCAGTTACCTCCCCAAATAAGCATTTAGGG

CTAGTGACTCCTCACAAGACAGAACTGGTA-3'

Nucleic Acid Coding for CD40
(Sequence ID No. 196)
5'-ATGGTTCGTCTGCCTCTGCAGTGCGTCCTCTGGGGCTGCTTGCTGA

CCGCTGTCCATCCAGAACCACCCACTGCATGCAGAGAAAACAGTACCT

AATAAACAGTCAGTGCTGTTCTTTGTGCCAGCCAGGACAGAAACTGGTG

AGTGACTGCACAGAGTTCACTGAAACGGAATGCCTTCCTTGCGGTGAAA

GCGAATTCCTAGACACCTGGAACAGAGAGACACACTGCCACCAGCACAA

ATACTGCGACCCCAACCTAGGGCTTCGGGTCCAGCAGAAGGGCACCTCA

GAAACAGACACCATCTGCACCTGTGAAGAAGGCTGGCACTGTACGAGTG

AGGCCTGTGAGAGCTGTGTCCTGCACCGCTCATGCTCGCCCGGCTTTGG

GGTCAAGCAGATTGCTACAGGGGTTTCTGATACCATCTGCGAGCCCTGC

CCAGTCGGCTTCTTCTCCAATGTGTCATCTGCTTTCGAAAAATGTCACC

CTTGGACAAGCTGTGAGACCAAAGACCTGGTTGTGCAACAGGCAGGCAC

AAACAAGACTGATGTTGTCTGTGGTCCCCAGGATCGGCTGAGAGCCCTG

GTGGTGATCCCCATCATCTTCGGGATCCTGTTTGCCATCCTCTTGGTGC

TGGTCTTTATCAAAAAGGTGGCCAAGAAGCCAACCAATAAGGCCCCCCA

CCCCAAGCAGGAACCCCAGGAGATCAATTTTCCCGACGATCTTCCTGGC

TCCAACACTGCTGCTCCAGTGCAGGAGACTTTACATGGATGCCAACCGG

TCACCCAGGAGGATGGCAAAGAGAGTCGCATCTCAGTGCAGGAGAGACA

G-3'

Nucleic Acid Coding for 4-1BBL
(Sequence ID No. 197)
5'-ATGGAATACGCCTCTGACGCTTCACTGGACCCCGAAGCCCGTGGC

CTCCCGCGCCCCGCGCTCGCGCCTGCCGCGTACTGCCTTGGGCCCTGGT

CGCGGGGCTGCTGCTGCTGCTGCTCGCTGCCGCCTGCGCCGTCTTC

CTCGCCTGCCCCTGGGCCGTGTCCGGGGCTCGCGCCTCGCCCGGCTCCG

CGGCCAGCCCGAGACTCCGCGAGGGTCCCGAGCTTTCGCCCGACGATCC

CGCCGGCCTCTTGGACCTGCGGCAGGGCATGTTTGCGCAGCTGGTGGCC

CAAAATGTTCTGCTGATCGATGGGCCCCTGAGCTGGTACAGTGACCCAG

-continued

```
GCCTGGCAGGCGTGTCCCTGACGGGGGGCCTGAGCTACAAAGAGGACAC

GAAGGAGCTGGTGGTGGCCAAGGCTGGAGTCTACTATGTCTTCTTTCAA

CTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCT

GGCTTTGACCGTGGACCTGCCACCCGCCTCCTCCGAGGCTCGGAACTCG

GCCTTCGGTTTCCAGGGCCGCTTGCTGCACCTGAGTGCCGGCCAGCGCC

TGGGCGTCCATCTTCACACTGAGGCCAGGGCACGCCATGCCTGGCAGCT

TACCCAGGGCGCCACAGTCTTGGGACTCTTCCGGGTGACCCCCGAAATC

CCAGCCGGACTCCCTTCACCGAGGTCGGAA-3'
```

(5) First Screening Method (First Implementation)

Screening was performed using the first candidate CAR-Ts described in (3) above and the APCs prepared in (4) above. Specifically, the first candidate CAR-Ts and the APCs were seeded in each well (24-well plate) such that the number of the first candidate CAR-Ts was $2 \times 10^6$ and the number of the APCs was $1 \times 10^5$, and then they were cultured together for 7 days. Before use, the APCs were treated with 20 Gy of γ rays and were then pulsed with an NY-ESO-$1_{157-165}$ peptide (NY-ESO-$1_{157}$ peptide, SLLMWITQC: Sequence ID No. 206) at a concentration of 1 to 10 μg/mL, and peptides that did not bind to the HLA-A*02:01 were removed therefrom after the pulsing process. An RPMI1640 culture medium containing gentamicin at a concentration of 50 μg/mL, human AB serum (manufactured by Sigma) at a concentration of 10%, human IL-2 (manufactured by Roche) at a concentration of 10 IU/mL, and human IL-15 (manufactured by PeproTech) at a concentration of 10 ng/mL was used as the culture medium used for the above-mentioned coculture of the first candidate CAR-Ts and the APCs. After the coculture, the first candidate CAR-Ts were collected, and coculture of the first candidate CAR-Ts and the APCs was performed two more times (three times in total) in the same conditions. Thus, the first candidate CAR-Ts expressing the hH-3M4E4L CARs capable of binding to the A2/NY-ESO-$1_{157}$ was enriched.

Next, after the enrichment of the first candidate CAR-Ts, the first candidate CAR-Ts were collected and stained with a PE-labeled A2/NY-ESO-$1_{157}$ tetramer at a concentration of 20 μg/mL. The PE-labeled A2/NY-ESO-$1_{157}$ tetramer was prepared by mixing a biotinylated HLA-A2/NY-ESO-$1_{157}$ monomer and PE-labeled streptavidin (manufactured by Thermo Fisher Scientific). After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). The concentrations of the antibodies were about 10 μg/mL. Then, regarding the first candidate CAR-Ts that had been subjected to tetramer staining, it was confirmed using the flow cytometer if first candidate CAR-Ts expressing CARs capable of binding to the A2/NY-ESO-$1_{157}$ were present (donor 1). The same test was performed using T cells derived from another healthy subject (donor 2). A positive control was performed in the same manner, except that an expression vector that included a nucleic acid coding for a tagged 3M4E5HL CAR was used instead of the expression vectors for expressing the hH-3M4E4L CAR library. A control 1 was performed in the same manner, except that a tetramer consisting of a complex (A2/HIV-Gag$_{77}$) of HLA-A*02:01 and an HIV Gag$_{77-85}$ peptide (SLYNTVATL: Sequence ID No. 198) was used instead of the A2/NY-ESO-$1_{157}$ tetramer. A control 2 was performed in the same manner, except that the expression vectors for expressing the hH-3M4E4L CAR library were not introduced. FIG. 1 shows the results obtained when gating of FSC$^+$-SSC$^+$-NGFR$^+$ cells was performed.

FIG. 1 shows dot plots showing the results of flow cytometry. In FIG. 1, the horizontal axes indicate the average fluorescence intensity of CD8a, and the vertical axes indicate the average fluorescence intensity of the A2 tetramer. As shown in FIG. 1, the T cells (control 2) into which the expression vectors for expressing the hH-3M4E4L CAR library had not been introduced did not include T cells capable of binding to the A2/NY-ESO-$1_{157}$ or A2/HIV-Gag$_{77}$. Moreover, it could be confirmed that the CAR-Ts (3M4E5-CAR, positive control) expressing the 3M4E5HL CAR were capable of binding to the A2/NY-ESO-$1_{157}$ but did not bind to the A2/HIV-Gag$_{77}$ because a CD8$^+$-A2 tetramer$^+$ fraction (the upper right fraction in each dot plot) was present when A2/NY-ESO-$1_{157}$ tetramer staining was performed, and the CD8$^+$-A2 tetramer$^+$ fraction was not present when A2/HIV-Gag$_{77}$ tetramer staining was performed. Furthermore, in the case of the first candidate CAR-Ts (donors 1 and 2), the CD8$^+$-A2 tetramer$^+$ fraction was present when A2/NY-ESO-$1_{157}$ tetramer staining was performed, and the CD8$^+$-A2 tetramer$^+$ fraction was not present when A2/HIV-Gag$_{77}$ tetramer staining was performed. It was found from these results that the first candidate CAR-Ts included first candidate CAR-Ts expressing CARs capable of binding to the A2/NY-ESO-$1_{157}$.

Next, first candidate CAR-Ts expressing CARs capable of binding to the A2/NY-ESO-$1_{157}$ were selected, and the CARs expressed by the first candidate CAR-Ts were identified. Specifically, the first candidate CAR-Ts were stained in the same manner as in (5) above. Then, cell sorting was performed on the first candidate CAR-Ts using a flow cytometer (FACSAria (registered trademark), manufactured by Becton Dickinson), and thus an NGFR$^+$-CD8$^+$-A2/NY-ESO-$1_{157}$ tetramer$^+$ fraction or NGFR$^+$-CD4$^+$-A2/NY-ESO-$1_{157}$ tetramer$^+$ fraction was collected as first candidate CAR-Ts expressing CARs capable of binding to the A2/NY-ESO-$1_{157}$. The total RNA was extracted from the obtained first candidate CAR-Ts using a total RNA extraction reagent (TRIzol (registered trademark), manufactured by Ambion). cDNA was synthesized from the total RNA using a reverse transcriptase (Superscript (registered trademark) III, manufactured by Thermo Fisher Scientific).

PCR in which the obtained cDNA and a mixture of a forward primer 1 below and a reverse primer 1 below were used was performed to amplify nucleic acids coding for scFvs. A cloning kit (Gibson Assembly Master Mix, manufactured by New England Biolab) was used to introduce the obtained nucleic acids coding for scFvs into pMX/CAR expression vectors (pMX/scFv expression vectors) such that the nucleic acid coding for an scFv bound to the 5' end of the partial region of human CD28. The pMX/CAR expression vectors were prepared by linking a nucleic acid (Sequence ID No. 169) coding for the partial region, the transmembrane domain, and the intracellular signaling domain of human CD28 and a nucleic acid (Sequence ID No. 171) coding for the intracellular signaling domain of human CD3ζ such that these nucleic acids were arranged in the stated order from the 5' end side and introducing the thus obtained product into the pMX expression vector. Then, sequencing of the obtained pMX/scFv expression vectors was performed using the Sanger's method, and thus base sequences coding for CARs (a polynucleotide (Sequence ID No. 138) coding for an H1-3M4E5L CAR and a polynucleotide (Sequence ID No. 157) coding for an H73-3M4E5L CAR) were identified. Moreover, the amino acid sequences of the scFvs (H1-3M4E5L (Sequence ID No. 98) and H73-3M4E5L (Sequence ID No. 117)) were identified based on the above-mentioned base sequences. Then, the CDRH1, CDRH2, and the CDRH3 in the new heavy-chain variable region (HA) and those in the new heavy-chain variable region (HC), which are shown in Table 1A above, were identified based on the amino acid sequences of the scFvs. Furthermore, the pMX/scFv expression vectors were used to prepare a pMX/H1-3M4E5L expression vector that included a polynucleotide coding for the H1-3M4E5L and a pMX/H73-3M4E5L expression vector that included a polynucleotide coding for the H73-3M4E5L.

```
Forward Primer 1
                        (Sequence ID No. 199)
5'-ATCCCAGTGTGGTGGTACGGG-3'

Reverse Primer 1
                        (Sequence ID No. 200)
5'-GGGTACATCACTTCGATTGC-3'
```

(6) Analysis of First Candidate scFvs

A culture supernatant containing GaLV-pseudotyped retroviruses was prepared in the same manner as in (3) above, except that the pMX/H1-3M4E5L expression vector or the pMX/H73-3M4E5L expression vector was used instead of the expression vectors for expressing the hH-3M4E4L CAR library. Next, the pMX/H1-3M4E5L expression vector or the pMX/H73-3M4E5L expression vector was introduced into Jurkat 76 cells by adding the above-mentioned culture supernatant containing GaLV-pseudotyped retroviruses, and a CAR (H1-3M4E5L CAR or H73-3M4E5L CAR) that included the H1-3M4E5L or H73-3M4E5L as an scFv was expressed. The Jurkat 76 cells that had expressed the CARs were reacted with the PE-labeled anti-human NGFR mAb. After the above-mentioned reaction, Jurkat 76 cells (H1-3M4E5L CAR-Ts or H73-3M4E5L CAR Ts) expressing the H1-3M4E5L CAR and the H73-3M4E5L CAR were purified using the anti-PE microbeads. The H1-3M4E5L CAR-Ts and the H73-3M4E5L CAR Ts were stained with the PE-labeled A2/NY-ESO-$1_{157}$ tetramer at a concentration of 5 µg/mL, and were then stained with the V450-labeled anti-human NGFR mAb.

Figure 2:
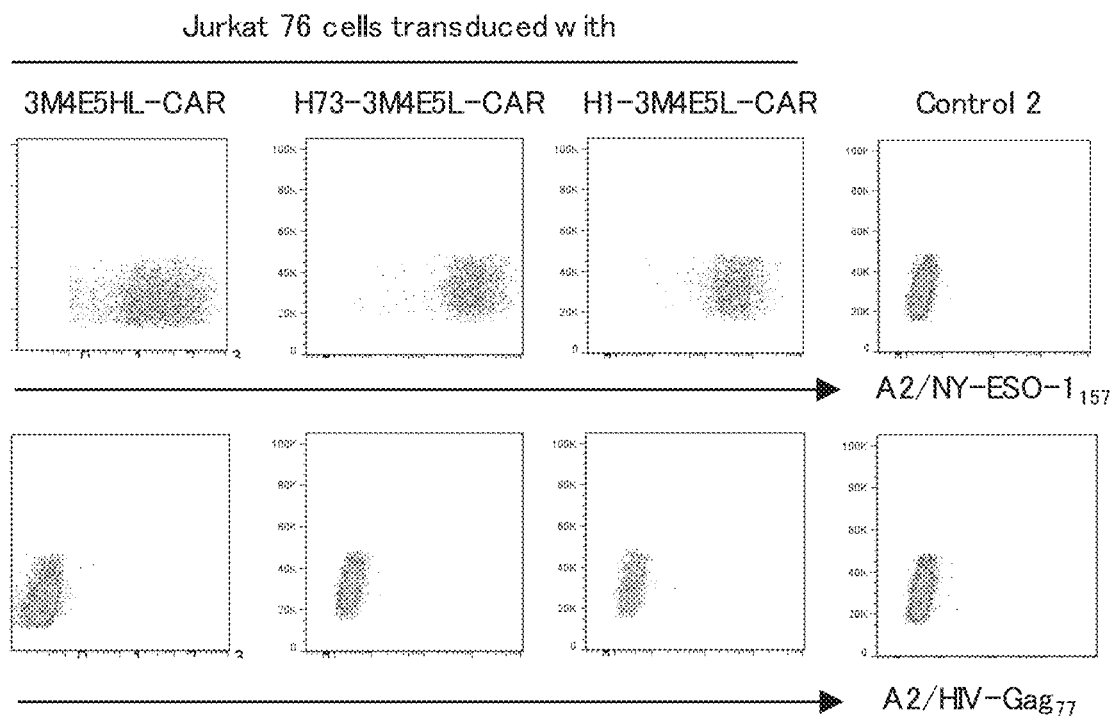
FIG. 2 shows dot plots showing the results of flow cytometry in Example 1.

The stained H1-3M4E5L CAR-Ts and H73-3M4E5L CAR Ts were analyzed by flow cytometry. A positive control was performed in the same manner, except that an expression vector that included a nucleic acid coding for a tagged 3M4E5LH CAR was used instead of the pMX/H1-3M4E5L expression vector or the pMX/H73-3M4E5L expression vector. A control 1 was performed in the same manner, except that the A2/HIV-Gag$_{77}$ tetramer was used instead of the A2/NY-ESO-$1_{157}$ tetramer. A control 2 was performed in the same manner, except that the pMX/H1-3M4E5L expression vector or pMX/H73-3M4E5L expression vector was not introduced. FIG. 2 shows the results obtained when gating of FSC$^+$-SSC$^+$-NGFR$^+$ cells was performed.

FIG. 2 shows dot plots showing the results of flow cytometry. In FIG. 2, the horizontal axes indicate the average fluorescence intensity resulting from A2/NY-ESO-$1_{157}$ tetramer staining or A2/HIV-Gag$_{77}$ tetramer staining, and the vertical axes indicate the average side scatter (SSC) intensity. As shown in FIG. 2, the Jurkat 76 cells (control 2) into which the pMX/H1-3M4E5L expression vector or pMX/H73-3M4E5L expression vector had not been introduced did not include cells capable of binding to the A2/NY-ESO-$1_{157}$ or A2/HIV-Gag$_{77}$. Moreover, it could be confirmed that the 3M4E5HL CAR-Ts (3M4E5 CAR, positive control) were capable of binding to the A2/NY-ESO-$1_{157}$ but did not bind to the A2/HIV-Gag$_{77}$ because substantially all the cells were present as A2 tetramer$^+$ cells when A2/NY-ESO-$1_{157}$ tetramer staining was performed, and substantially all the cells were present as A2 tetramer$^-$ cells when A2/HIV-Gag$_{77}$ tetramer staining was performed. Furthermore, in the case of the H1-3M4E5L CAR-Ts and the H73-3M4E5L CAR-Ts, substantially all the cells were present as A2 tetramer$^+$ cells when A2/NY-ESO-$1_{157}$ tetramer staining was performed, and substantially all the cells were present as A2 tetramer$^-$ cells when A2/HIV-Gag$_{77}$ tetramer staining was performed. It was found from these results that the H1-3M4E5L CAR-Ts and the H73-3M4E5L CAR-Ts were capable of binding to the A2/NY-ESO-$1_{157}$ but did not bind to the A2/HIV-Gag$_{77}$. That is, it was found that the first screening method of the present invention could be used to screen scFvs capable of binding to a target antigen.

(7) Avidity of First Candidate scFvs

Figure 3:
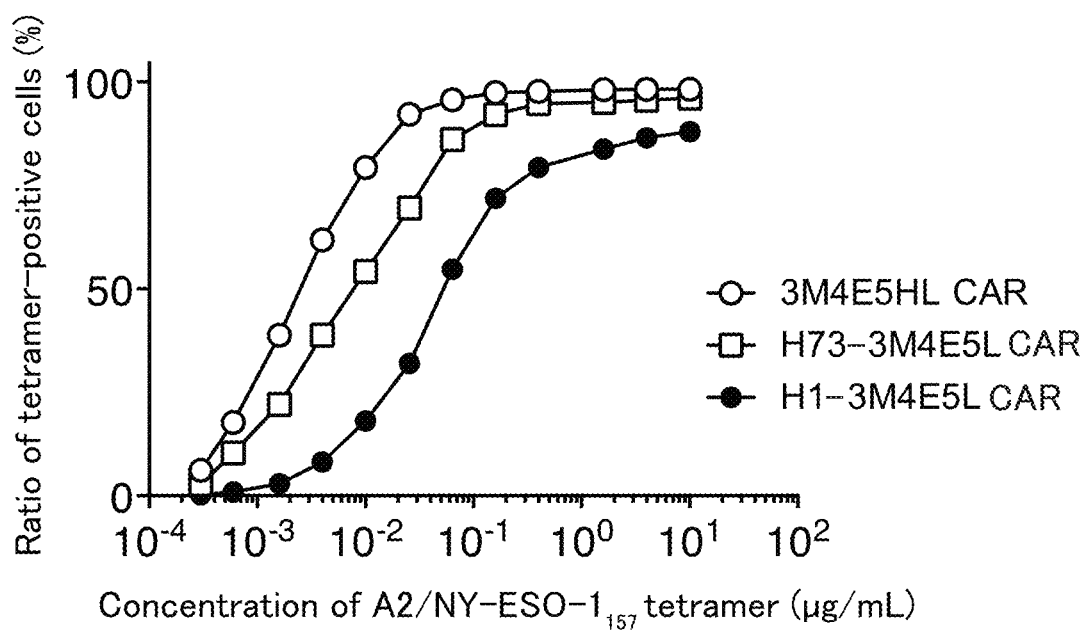
FIG. 3 is a graph indicating the ratios of A2/NY-ESO-$1_{157}$ tetramer-positive cells in Example 1.

Next, flow cytometry analysis was performed on the H1-3M4E5L CAR-Ts and the H73-3M4E5L CAR Ts, which had been obtained in (6) above, and Jurkat 76 cells expressing the 3M4E5LH CAR (3M4E5LH CAR-Ts) in the same manner as in (6) above, except that they were stained with the PE-labeled A2/NY-ESO-$1_{157}$ tetramer at a predetermined concentration (0.0004194304, 0.001048576, 0.00262144, 0.0065536, 0.016384, 0.04096, 0.1024, 0.256, 0.64, 1.6, 4, or 10 µg/mL), and were then stained with the V450-labeled anti-human NGFR mAb. Then, the ratio of A2/NY-ESO-$1_{157}$ tetramer-positive cells was calculated for each A2/NY-ESO-$1_{157}$ tetramer concentration. FIG. 3 shows the results.

FIG. 3 is a graph indicating the ratios of A2/NY-ESO-$1_{157}$ tetramer-positive cells. In FIG. 3, the horizontal axis indicates the concentration of the A2/NY-ESO-$1_{157}$ tetramer, and the vertical axis indicates the ratio of A2/NY-ESO-$1_{157}$ tetramer-positive cells. As shown in FIG. 3, the ratios of the A2/NY-ESO-$1_{157}$ tetramer-positive cells in the CAR-Ts increased in a manner dependent on the concentration of the A2/NY-ESO-$1_{157}$ tetramer. It was necessary to increase the concentration of the A2/NY-ESO-$1_{157}$ tetramer in order to obtain, from the H1-3M4E5L CAR-Ts and the H73-3M4E5L CAR Ts, the A2/NY-ESO-$1_{157}$ tetramer-positive cells at the same level as those from the 3M4E5LH CAR-Ts, and it was thus found that the scFvs in these CAR-Ts were different in avidity for the A2/NY-ESO-$1_{157}$ tetramer. That is, it was found that the first screening method of the present invention could be used to screen scFvs different in binding avidity for a target antigen.

(8) Functions of First Candidate scFvs

Figure 4:
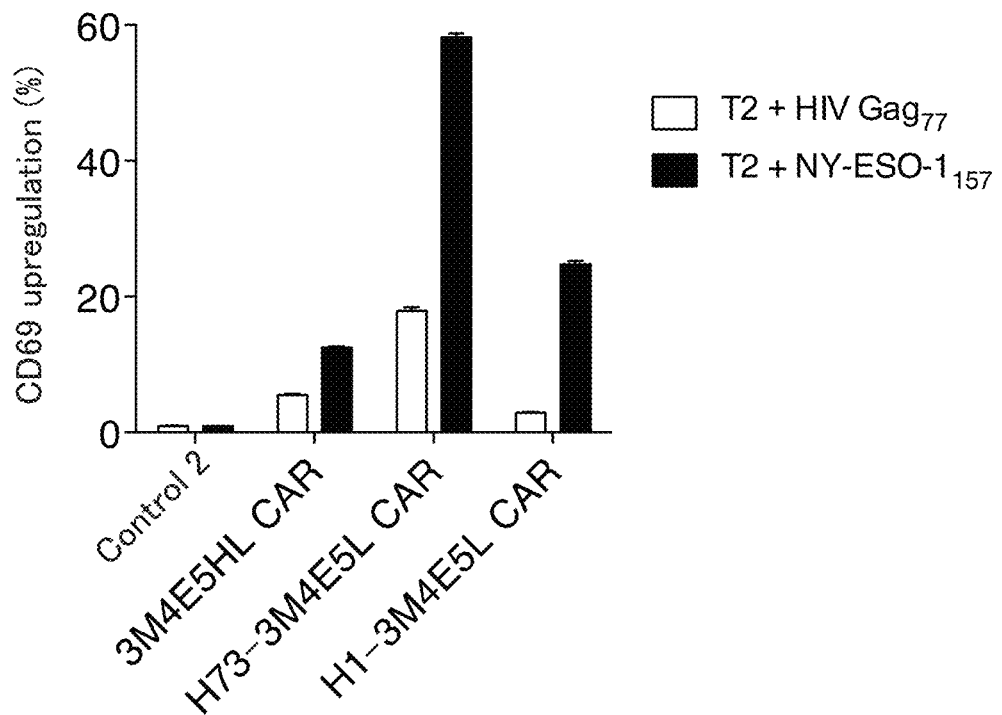
FIG. 4 is a graph indicating changes in a CD69 expression level in Example 1.
Figure 5:
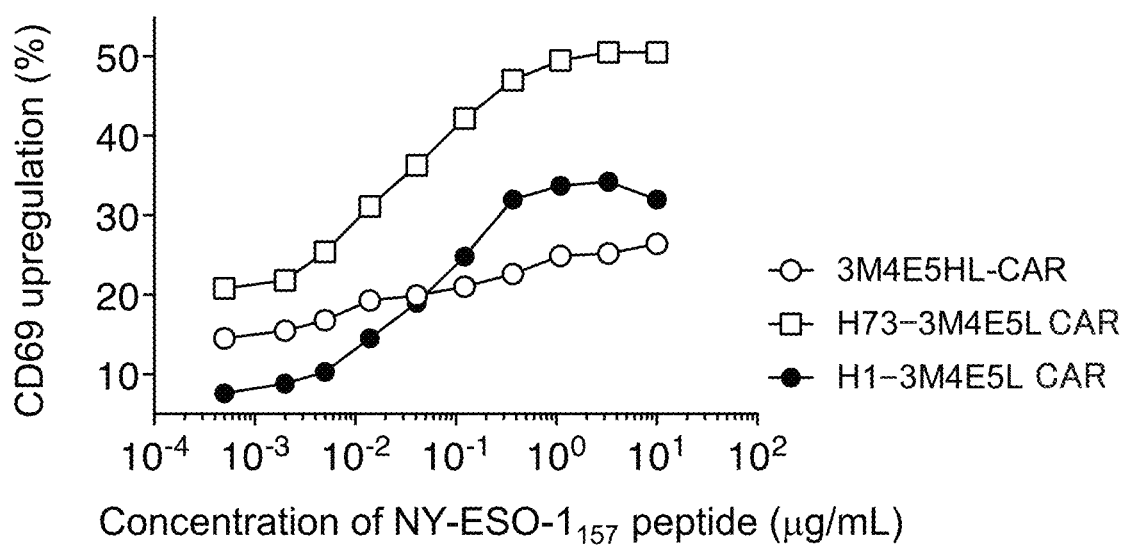
FIG. 5 is a graph indicating changes in a CD69 expression level in Example 1.

Next, it was examined if the H1-3M4E5L CAR-Ts and the H73-3M4E5L CAR-Ts bound to the target antigen and were thus activated. Specifically, the H1-3M4E5L CAR-Ts or H73-3M4E5L CAR-Ts and the T2 cells were seeded in each well (96-well plate) such that the number of the H1-3M4E5L CAR-Ts or H73-3M4E5L CAR-Ts was 3×10$^5$ and the number of the T2 cells was 5×10$^4$, and then they were cultured together for 5 hours. Before use, the T2 cells (HLA-A*02:01-expressing cells) were pulsed with the NY-ESO-$1_{157}$ peptide at a predetermined concentration (0.0005, 0.0015, 0.004, 0.01, 0.04, 0.122, 0.366, 1.11, 3.33, or 10 µg/mL) (T2+NY-ESO-$1_{157}$). An RPMI1640 culture medium containing FCS at a concentration of 10% was used as the culture solution for the coculture. After the above-mentioned coculture, the H1-3M4E5L CAR-Ts and the H73-3M4E5L CAR-Ts were collected, and were then stained with an FITC-labeled anti-human CD69 mAb (clone: FN50) and a V450-labeled anti-human NGFR mAb. The average fluorescence intensity of CD69 in NGFR$^+$ cells from the stained H1-3M4E5L CAR-Ts and H73-3M4E5L CAR-Ts was measured using the flow cytometer. A positive control was performed in the same manner, except that the 3M4E5HL CAR-Ts obtained in (6) above were used. A control 1 was performed in the same manner, except that T2 cells (T2+ HIV Gag$_{77}$) pulsed with the HIV Gag$_{77-85}$ peptide instead of the NY-ESO-1$_{157}$ peptide were used. A control 2 was performed in the same manner, except that the pMX/H1-3M4E5L expression vector was not introduced. Then, the rates of an increase in CD69 expression in the samples were calculated for each peptide concentration using the average fluorescence intensity of CD69 in the control 2 as a standard. FIGS. 4 and 5 show the results.

FIG. 4 is a graph indicating changes in a CD69 expression level obtained when the peptide concentration was 10 μg/mL. In FIG. 4, the horizontal axis indicates the types of samples, and the vertical axis indicates the rate of an increase in CD69 expression. As shown in FIG. 4, the CD69 expression did not increase in the control 2. On the other hand, when the 3M4E5HL CAR-Ts (positive control) were stimulated with the T2+NY-ESO-1$_{157}$, it could be confirmed that the CD69 expression increased compared with the case of the stimulation with the T2+HIV Gag$_{77}$, and the CAR-Ts bound to the A2/NY-ESO-1$_{157}$ and were activated. When the H1-3M4E5L CAR-Ts and the H73-3M4E5L CAR-Ts were stimulated with the T2+NY-ESO-1$_{157}$, the CD69 expression increased compared with the case of the stimulation with the T2+HIV Gag$_{77}$, and the CAR-Ts bound to the A2/NY-ESO-1$_{157}$ and were activated. Furthermore, in the H1-3M4E5L CAR-Ts and the H73-3M4E5L CAR-Ts, the rates of an increase in CD69 expression calculated based on the rates of an increase in CD69 expression level obtained when the stimulation with the T2+HIV Gag$_{77}$ was performed were higher than that in the 3M4E5 HL CAR-Ts. It was thus found that the H1-3M4E5L CAR-Ts and the H73-3M4E5L CAR-Ts were more specific to the A2/NY-ESO-1$_{157}$ than the 3M4E5 HL CAR-Ts. Moreover, it was found that the first screening method of the present invention could be used to screen scFvs that were functional in CAR-T cells and had a higher specificity.

Next, the results of changes in CD69 expression in the case where the NY-ESO-1$_{157}$ peptide was serially diluted are shown in FIG. 5. FIG. 5 is a graph indicating changes in a CD69 expression level. In FIG. 5, the horizontal axis indicates the NY-ESO-1$_{157}$ peptide concentration, and the vertical axis indicates the rate of an increase in CD69 expression. As shown in FIG. 5, in the CAR-Ts, the CD69 expression increased in a manner dependent on the NY-ESO-1$_{157}$ peptide concentration. It was found that, in the H1-3M4E5L CAR-Ts and the H73-3M4E5L CAR Ts, the CD 69 expression increased more sharply and the specificity for the A2/NY-ESO-1$_{157}$ was higher compared with the 3M4E5LH CAR-Ts. That is, it was found that the first screening method of the present invention could be used to screen scFvs that were functional in CAR-T cells and had a higher specificity.

(9) Preparation of Second CAR Library

A second CAR library was prepared using the heavy-chain variable region (HA) screened from the first CAR library. Specifically, the nucleic acid coding for the heavy-chain variable region (3M4E5H) in the pMX expression vector into which the nucleic acid coding for the tagged 3M4E5LH CAR had been introduced was substituted with a nucleic acid coding for the heavy-chain variable region (HA) (3M4E5L-H1 expression vector). Next, the nucleic acid coding for the light-chain variable region (3M4E5L) in the 3M4E5L-H1 expression vectors was substituted with a library that included nucleic acids coding for light-chain variable regions described in (2) above. Thus, the expression vectors that included the second CAR library (expression vectors for expressing the hK-H1 CAR library) were prepared. It should be noted that, regarding the heterogeneity of the heavy-chain variable regions in the hK-H1 CAR library, it was confirmed through restriction enzyme mapping and sequencing of the regions using the Sanger's method that the number of types of heavy-chain variable regions was about $1 \times 10^6$.

(10) Preparation of Second CAR Library-Expressing T Cells (Second Candidate CAR-Ts)

The hK-H1 CAR library was introduced into T cells in the same manner as in (3) above, except that the expression vectors for expressing the hK-H1 CAR library were used instead of the expression vectors for expressing the hH-3M4E4L CAR library. Then, the resulting T cells were purified and used as second candidate CAR-Ts.

(11) First Screening Method (Second Implementation)

Figure 6:
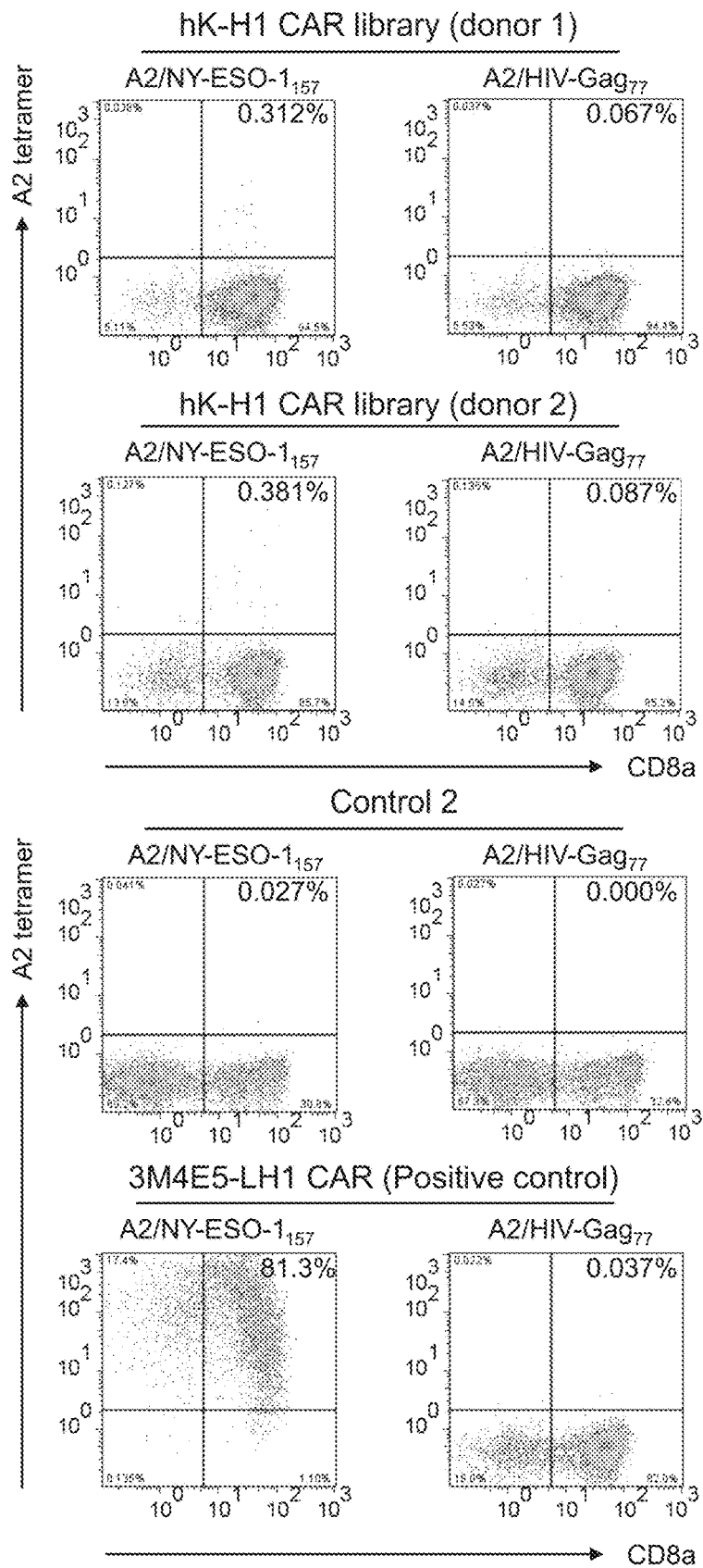
FIG. 6 shows dot plots showing the results of flow cytometry in Example 1.

Next, in the same manner as in (5) above, except that the second candidate CAR-Ts were used instead of the first candidate CAR-Ts, it was confirmed if second candidate CAR-Ts expressing CARs capable of binding to the A2/NY-ESO-1$_{157}$ were present (donor 1). The same test was performed using a library that included nucleic acids of heavy-chain variable regions derived from human peripheral blood B cells obtained from another healthy subject (donor 2). A positive control was performed in the same manner, except that a pMX/3M4E5L-H1 expression vector was used instead of the expression vectors for expressing the hK-H1 CAR library. A control 1 was performed in the same manner, except that the A2/HIV-Gag$_{77}$ tetramer was used instead of the A2/NY-ESO-1$_{157}$ tetramer. A control 2 was performed in the same manner, except that the expression vectors for expressing the hH-3M4E5L CAR library were not introduced. FIG. 6 shows the results obtained when gating of FSC$^+$-SSC$^+$-NGFR$^+$ cells was performed.

FIG. 6 shows dot plots showing the results of flow cytometry. In FIG. 6, the horizontal axes indicate the average fluorescence intensity of CD8a, and the vertical axes indicate the average fluorescence intensity of the A2 tetramer. As shown in FIG. 6, the T cells (control 2) into which the expression vectors for expressing the hK-H1 CAR library had not been introduced did not include T cells capable of binding to the A2/NY-ESO-1$_{157}$ or A2/HIV-Gag$_{77}$. Moreover, it could be confirmed again that the CAR-Ts (3M4E5L-H1 CAR, positive control) expressing the 3M4E5L-H1 CAR were capable of binding to the A2/NY-ESO-1$_{157}$ but did not bind to the A2/HIV-Gag$_{77}$ because a CD8$^+$-A2 tetramer$^+$ fraction (the upper right fraction in each dot plot) was present when A2/NY-ESO-1$_{157}$ tetramer staining was performed, and the CD8$^+$-A2 tetramer$^+$ fraction was not present when A2/HIV-Gag$_{77}$ tetramer staining was performed. Furthermore, in the case of the second candidate CAR-Ts (donors 1 and 2), the CD8$^+$-A2 tetramer$^+$ fraction was present when A2/NY-ESO-1$_{157}$ tetramer staining was performed, and the CD8$^+$-A2 tetramer$^+$ fraction was not present when A2/HIV-Gag$_{77}$ tetramer staining was performed. It was found from these results that the second candidate CAR-Ts included second candidate CAR-Ts expressing CARs capable of binding to the A2/NY-ESO-1$_{157}$.

Next, second candidate CAR-Ts expressing CARs capable of binding to the A2/NY-ESO-1$_{157}$ were selected, and the CARs expressed by the second candidate CAR-Ts were identified. Specifically, the second candidate CAR-Ts were stained with the A2/NY-ESO-1$_{157}$ tetramer. Then, cell sorting was performed on the second candidate CAR-Ts using a flow cytometer, and thus an NGFR$^+$-CD8$^+$-A2/NY-ESO-1$_{157}$ tetramer$^+$ fraction or NGFR$^+$-CD4$^+$-A2/NY-ESO-1$_{157}$-tetramer$^+$ fraction was collected as second candidate CAR-Ts expressing CARs capable of binding to the A2/NY-ESO-1$_{157}$. Then, scFvs were prepared in the same manner as in (5) above, except that second candidate CAR-Ts expressing CARs capable of binding to the A2/NY-ESO-1$_{157}$ were used instead of the first candidate CAR-Ts expressing CARs capable of binding to the A2/NY-ESO-1$_{157}$, and the resulting scFvs were introduced into pMX/CAR expression vectors. Then, sequencing of the obtained pMX/CAR expression vectors into which the scFvs had been introduced was performed using the Sanger's method, and thus base sequences coding for CARs (a polynucleotide coding for K52-H1 CAR (Sequence ID No. 139), a polynucleotide coding for K73-H1 CAR (Sequence ID No. 140), a polynucleotide coding for K121-H1 CAR (Sequence ID No. 141), a polynucleotide coding for K124-H1 CAR (Sequence ID No. 142), a polynucleotide coding for K125-H1 CAR (Sequence ID No. 143), a polynucleotide coding for K131-H1 CAR (Sequence ID No. 144), a polynucleotide coding for K145-H1 CAR (Sequence ID No. 145), a polynucleotide coding for K151-H1 CAR (Sequence ID No. 146), a polynucleotide coding for K160-H1 CAR (Sequence ID No. 147), and a polynucleotide coding for K173-H1 CAR (Sequence ID No. 148)) were identified. Moreover, the amino acid sequences of the scFvs (K52-H1 (Sequence ID No. 99), K73-H1 (Sequence ID No. 100), K121-H1 (Sequence ID No. 101), K124-H1 (Sequence ID No. 102), K125-H1 (Sequence ID No. 103), K131-H1 (Sequence ID No. 104), K145-H1 (Sequence ID No. 105), K151-H1 (Sequence ID No. 106), K160-H1 (Sequence ID No. 107), and K173-H1 (Sequence ID No. 108)) were identified based on the above-mentioned base sequences. Then, the CDRH1, CDRH2, and the CDRH3 in the new light-chain variable regions (LB) to (LJ), which are shown in Table 1B above, were identified based on the amino acid sequences of the scFvs.

(12) Analysis of Second Candidate scFvs

Figure 7A:
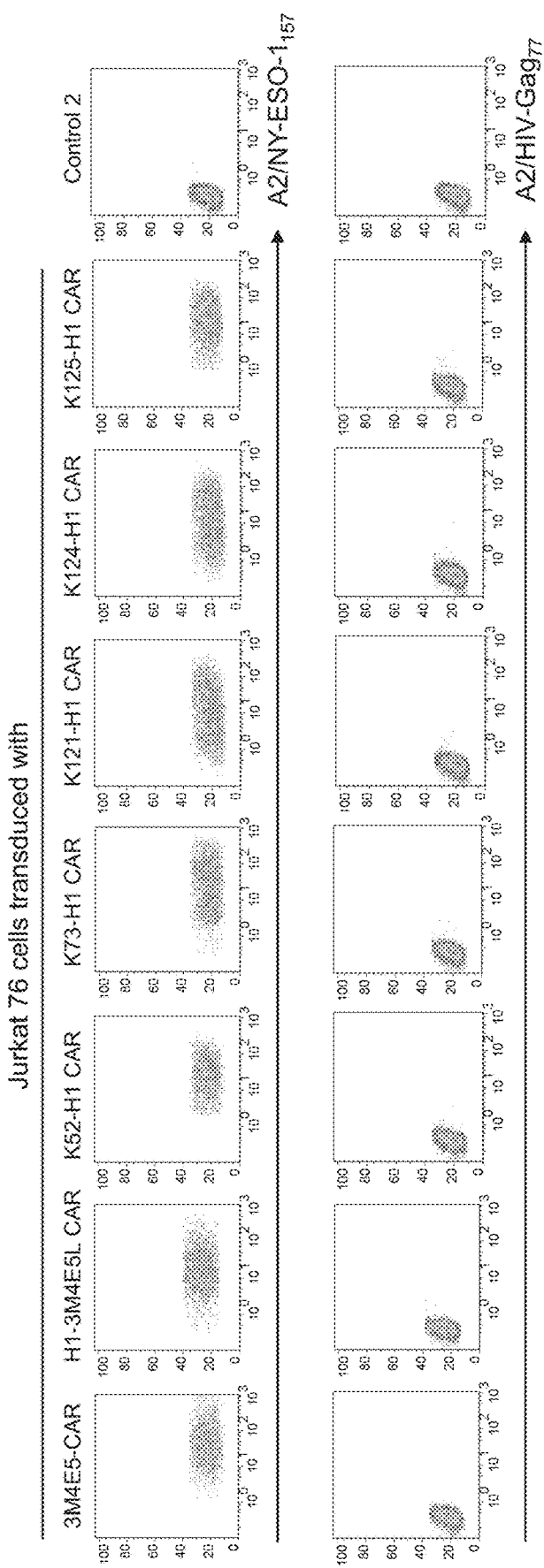
FIG. 7A shows dot plots showing the results of flow cytometry in Example 1.
Figure 7B:
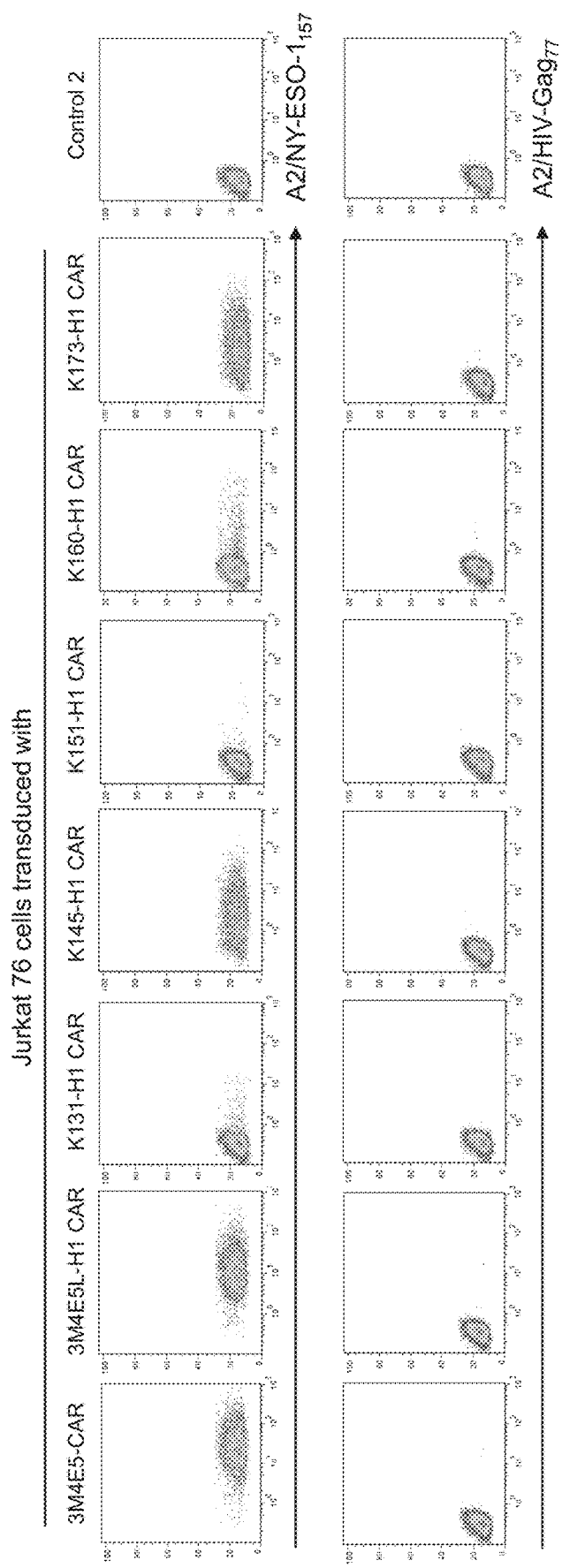
FIG. 7B shows dot plots showing the results of flow cytometry in Example 1.

A culture supernatant containing GaLV-pseudotyped retroviruses was prepared in the same manner as in (3) above, except that the pMX/CAR expression vectors into which polynucleotides coding for the scFvs described in (11) above had been introduced instead of the polynucleotides coding for the scFvs in the expression vectors for expressing the hH-3M4E4L CAR library were used. Next, the pMX/CAR expression vectors into which the polynucleotides coding for the scFvs had been introduced were introduced into Jurkat 76 cells by adding the above-mentioned culture supernatant containing GaLV-pseudotyped retroviruses, and a CAR that included the K52-H1, K73-H1, K121-H1, K124-H1, K125-H1, K131-H1, K145-H1, K151-H1, K160-H1, or K173-H1 as an scFv was expressed. The Jurkat 76 cells that had expressed the CARs were reacted with the PE-labeled anti-human NGFR mAb. After the above-mentioned reaction, Jurkat 76 cells expressing the CARs were purified using the anti-PE microbeads. The purified Jurkat 76 cells expressing the CARs were stained with the PE-labeled A2/NY-ESO-1$_{157}$ tetramer at a concentration of 5 µg/mL, and were then stained with the V450-labeled anti-human NGFR mAb. The stained Jurkat 76 cells expressing the CARs were analyzed by flow cytometry. A process was performed in the same manner, except that the pMX/H1-3M4E5L expression vector was used instead of the pMX/CAR expression vectors into which the scFvs had been introduced. A positive control was performed in the same manner, except that an expression vector that included the nucleic acid coding for the tagged 3M4E5LH CAR was used instead of the pMX/CAR expression vectors into which the scFvs had been introduced. A control 1 was performed in the same manner, except that the A2/HIV-Gag$_{77}$ tetramer was used instead of the A2/NY-ESO-1$_{157}$ tetramer. A control 2 was performed in the same manner, except that the pMX/CAR expression vectors into which the scFvs had been introduced were not introduced. FIGS. 7(A) and 7(B) show the results obtained when gating of NGFR$^+$ cells was performed.

FIGS. 7(A) and 7(B) show dot plots showing the results of flow cytometry. In FIGS. 7(A) and 7(B), the horizontal axes indicate the average fluorescence intensity of the A2 tetramer, and the vertical axes indicate the average side scatter (SSC) intensity. As shown in FIGS. 7(A) and 7(B), the Jurkat 76 cells (control 2) into which the scFv-introduced pMX/CAR expression vectors had not been introduced did not include cells capable of binding to the A2/NY-ESO-1$_{157}$ or A2/HIV-Gag$_{77}$. Moreover, it could be confirmed that the 3M4E5LH CAR-Ts (3M4E5-CAR positive control) were capable of binding to the A2/NY-ESO-1$_{157}$ but did not bind to the A2/HIV-Gag$_{77}$ because substantially all the cells were present in the A2 tetramer$^+$ fraction when A2/NY-ESO-1$_{157}$ tetramer staining was performed, and the A2 tetramer$^+$ fraction was not present when A2/HIV-Gag$_{77}$ tetramer staining was performed. Substantially all or some T cells expressing CARs that included H1-3M4E5L, K52-H1, K73-H1, K121-H1, K124-H1, K125-H1, K131-H1, K145-H1, K151-H1, K160-H1, or K173-H1 were present in the A2 tetramer$^+$ fraction when A2/NY-ESO-1$_{157}$ tetramer staining was performed, and the A2 tetramer$^+$ fraction was not present when A2/HIV-Gag$_{77}$ tetramer staining was performed. It was found from these results that the CARs that included H1-3M4E5L, K52-H1, K73-H1, K121-H1, K124-H1, K125-H1, K131-H1, K145-H1, K151-H1, K160-H1, or K173-H1 were capable of binding to the A2/NY-ESO-1$_{157}$ but did not bind to the A2/HIV-Gag$_{77}$. That is, it was found that the first screening method of the present invention could be used to screen scFvs that included new heavy-chain variable regions and new light-chain variable regions capable of binding to a target antigen. Moreover, since CAR-expressing T cells that were stained with the A2/NY-ESO-1$_{157}$ tetramer to different staining degrees were present, it was found that scFvs that included heavy-chain variable regions and light-chain variable regions having different avidity for a target antigen could be screened.

Example 2

It was confirmed that the screening method of the present invention in which the CAR library of the present invention is used could be used to screen scFvs capable of binding to A2/NY-ESO-1$_{157}$.

(1) Preparation of First CAR Library

An hL-3M4E4H scFv library was prepared by substituting the nucleic acid coding for the light-chain variable region on the 5' side of the nucleic acid coding for the 3M4E5LH scFv described in (1) of Example 1 above with the above-mentioned library that included the nucleic acids of the light-chain variable regions derived from human peripheral blood B cells. Then, a tagged hL-3M4E4H CAR library was prepared in the same manner as in (1) of Example 1 above, except that the hL-3M4E4H scFv library was used instead of the nucleic acid coding for the 3M4E5LH scFv. The tagged hL-3M4E4H CAR library was introduced into pMX expression vectors to prepare expression vectors for expressing the hL-3M4E4H CAR library. It should be noted that the heterogeneity of the heavy-chain variable regions of the hL-3M4E4H CAR library was confirmed through restriction enzyme mapping and sequencing of the regions using the Sanger's method.

(2) Preparation of First CAR Library-Expressing T Cells (First Candidate CAR-Ts)

The hL-3M4E4H CAR library was introduced into T cells in the same manner as in (3) of Example 1 above, except that the expression vectors for expressing the hL-3M4E4H CAR library were used instead of the expression vectors for expressing the hH-3M4E4L CAR library. Then, the resulting T cells were purified and used as first candidate CAR-Ts.

(3) First Screening Method

Figure 8:
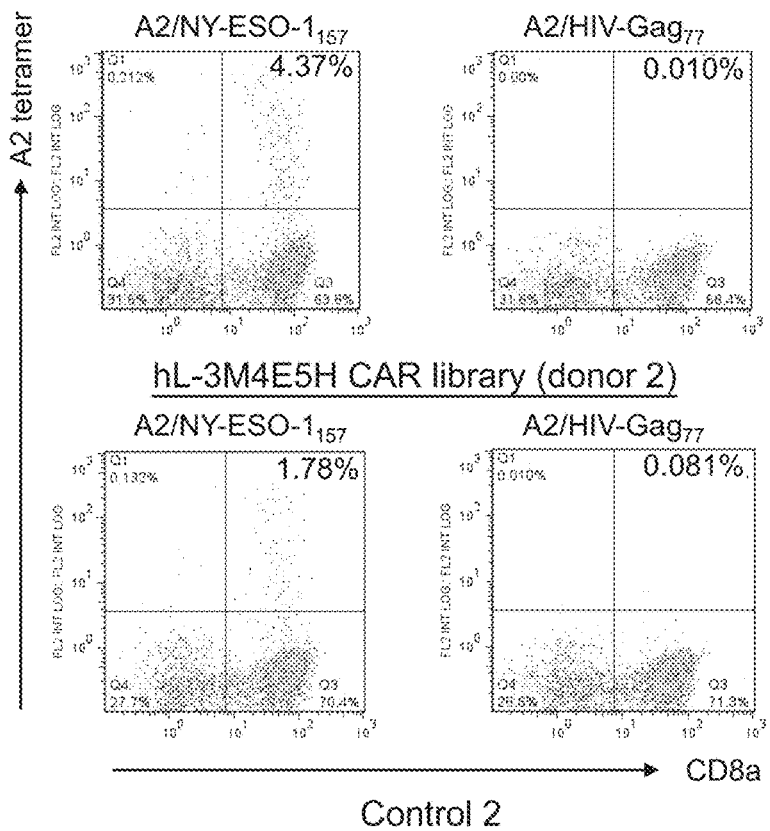
FIG. 8 shows dot plots showing the results of flow cytometry in Example 2.
Figure 8:
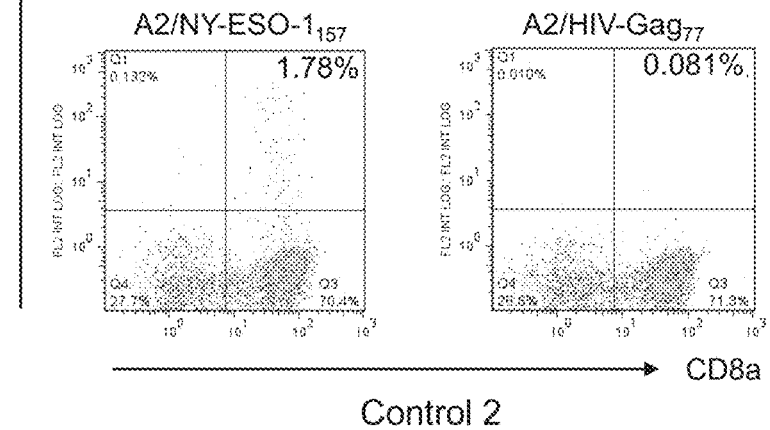
Figure 8:
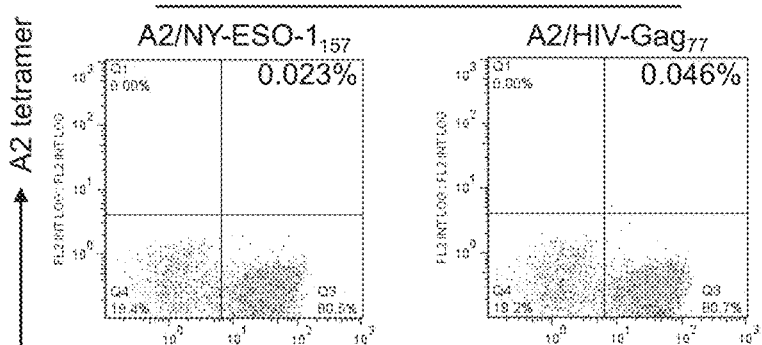
Figure 8:
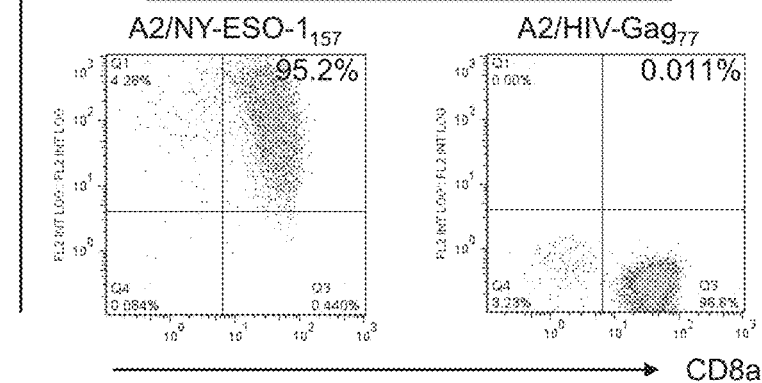

In the same manner as in (5) of Example 1 above, except that the first candidate CAR-Ts described in (2) of Example 2 were used instead of the first candidate CAR-Ts described in (3) of Example 1 above, it was confirmed that first candidate CAR-Ts expressing CARs capable of binding to the A2/NY-ESO-$1_{157}$ were present (donor 1). The same test was performed using a library that included nucleic acids of heavy-chain variable regions derived from human peripheral blood B cells obtained from another healthy subject (donor 2). A positive control was performed in the same manner, except that an expression vector that included a nucleic acid coding for the tagged 3M4E5LH CAR was used instead of the expression vectors for expressing the hH-3M4E4L CAR library. A control 1 was performed in the same manner, except that the A2/HIV-Gag$_{77}$ tetramer was used instead of the A2/NY-ESO-$1_{157}$ tetramer. A control 2 was performed in the same manner, except that the expression vectors for expressing the hL-3M4E4H CAR library were not introduced. FIG. 8 shows the results obtained when gating of FSC$^+$-SSC$^+$-NGFR$^+$ cells was performed.

FIG. 8 shows dot plots showing the results of flow cytometry. In FIG. 8, the horizontal axes indicate the average fluorescence intensity of CD8a, and the vertical axes indicate the average fluorescence intensity of the A2 tetramer. As shown in FIG. 8, the T cells (control 2) into which the expression vectors for expressing the hL-3M4E4H CAR library had not been introduced did not include T cells capable of binding to the A2/NY-ESO-$1_{157}$ or A2/HIV-Gag$_{77}$. Moreover, it could be confirmed that the CAR-Ts (3M4E5-CAR, positive control) expressing the 3M4E5LH CAR were capable of binding to the A2/NY-ESO-$1_{157}$ but did not bind to the A2/HIV-Gag$_{77}$ because a CD8$^+$-A2 tetramer$^+$ fraction (the upper right fraction in each dot plot) was present when A2/NY-ESO-$1_{157}$ tetramer staining was performed, and the CD8$^+$-A2 tetramer$^+$ fraction was not present when A2/HIV-Gag$_{77}$ tetramer staining was performed. Furthermore, in the case of the first candidate CAR-Ts (donors 1 and 2), the CD8$^+$-A2 tetramer$^+$ fraction was present when A2/NY-ESO-$1_{157}$ tetramer staining was performed, and the CD8$^+$-A2 tetramer$^+$ fraction was not present when A2/HIV-Gag$_{77}$ tetramer staining was performed. It was found from these results that the first candidate CAR-Ts included first candidate CAR-Ts expressing CARs capable of binding to the A2/NY-ESO-$1_{157}$.

Next, first candidate CAR-Ts expressing CARs capable of binding to the A2/NY-ESO-$1_{157}$ were selected, and the CARs expressed by the first candidate CAR-Ts were identified. Specifically, the first candidate CAR-Ts were stained in the same manner as in (3) of Example 2 above. Then, cell sorting was performed on the first candidate CAR-Ts using a flow cytometer, and thus an NGFR$^+$-CD8$^+$-A2/NY-ESO-$1_{157}$ tetramer$^+$ fraction or NGFR$^+$-CD4$^+$-A2/NY-ESO-$1_{157}$ tetramer$^+$ fraction was collected as first candidate CAR-Ts expressing CARs capable of binding to the A2/NY-ESO-$1_{157}$. Then, scFvs were prepared in the same manner as in (5) of Example 1 above, except that newly collected first candidate CAR-Ts expressing CARs capable of binding to the A2/NY-ESO-$1_{157}$ were used instead of the first candidate CAR-Ts expressing CARs capable of binding to the A2/NY-ESO-$1_{157}$ described in (5) of Example (1) above, and the resulting scFvs were introduced into pMX/CAR expression vectors. Then, sequencing of the obtained pMX/CAR expression vectors into which the scFvs had been introduced was performed using the Sanger's method, and thus base sequences coding for CARs (a polynucleotide coding for L1-3M4E5 CAR (Sequence ID No. 149), a polynucleotide coding for L66-3M4E5 CAR (Sequence ID No. 151), a polynucleotide coding for L73-3M4E5 CAR (Sequence ID No. 152), a polynucleotide coding for L80-3M4E5 CAR (Sequence ID No. 153), a polynucleotide coding for L88-3M4E5 CAR (Sequence ID No. 154), a polynucleotide coding for L102-3M4E5 CAR (Sequence ID No. 155), and a polynucleotide coding for L124-3M4E5 CAR (Sequence ID No. 156)) were identified. Moreover, the amino acid sequences of the scFvs (L1-3M4E5 (Sequence ID No. 109), L66-3M4E5 (Sequence ID No. 111), L73-3M4E5 (Sequence ID No. 112), L80-3M4E5 (Sequence ID No. 113), L88-3M4E5 (Sequence ID No. 114), L102-3M4E5 (Sequence ID No. 115), and L124-3M4E5 (Sequence ID No. 116)) were identified based on the above-mentioned base sequences. Then, the CDRH1, CDRH2, and the CDRH3 in the new light-chain variable regions (LK) to (LQ), which are shown in Table 1B above, were identified based on the amino acid sequences of the scFvs.

(4) Analysis of First Candidate scFvs

Figure 9:
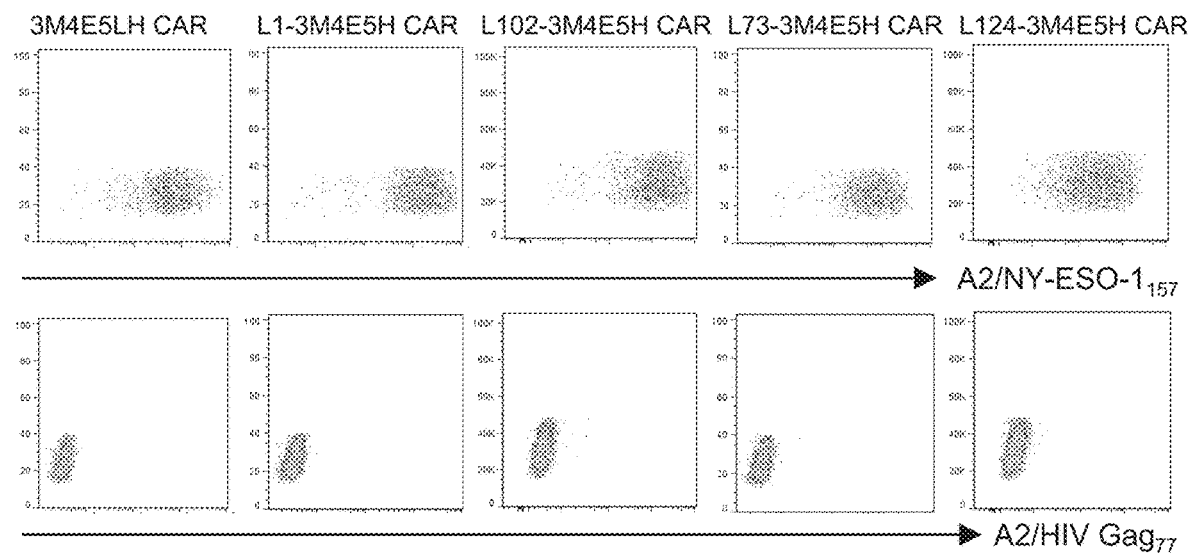
FIG. 9 shows dot plots showing the results of flow cytometry in Example 2.
Figure 9:
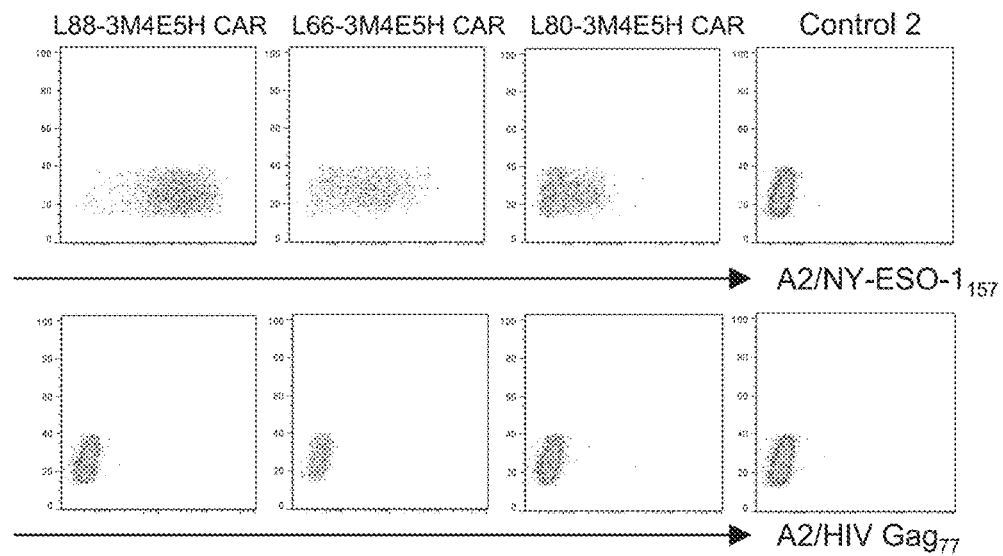

A culture supernatant containing GaLV-pseudotyped retroviruses was prepared in the same manner as in (3) of Example 1 above, except that the pMX/CAR expression vectors into which polynucleotides coding for the scFvs described in (3) of Example 2 above had been introduced instead of the polynucleotides coding for the scFvs in the expression vectors for expressing the hH-3M4E4L CAR library were used. Next, the pMX/CAR expression vectors into which the polynucleotides coding for the scFvs had been introduced were introduced into Jurkat 76 cells by adding the above-mentioned culture supernatant containing GaLV-pseudotyped retroviruses, and a CAR that included the L1-3M4E5, L66-3M4E5, L73-3M4E5, L80-3M4E5, L88-3M4E5, L102-3M4E5, or L124-3M4E5 as an scFv was expressed. The Jurkat 76 cells that had expressed the CARs were reacted with the PE-labeled anti-human NGFR mAb. After the above-mentioned reaction, Jurkat 76 cells expressing the CARs were purified using the anti-PE microbeads. The purified Jurkat 76 cells expressing the CARs were stained with the PE-labeled A2/NY-ESO-$1_{157}$ tetramer at a concentration of 5 μg/mL, and were then stained with the V450-labeled anti-human NGFR mAb. The stained Jurkat 76 cells expressing the CARs were analyzed by flow cytometry. A positive control was performed in the same manner, except that an expression vector that included a nucleic acid coding for the tagged 3M4E5LH CAR was used instead of the pMX/CAR expression vectors into which the scFvs had been introduced. A control 1 was performed in the same manner, except that the A2/HIV-Gag$_{77}$ tetramer was used instead of the A2/NY-ESO-$1_{157}$ tetramer. A control 2 was performed in the same manner, except that the pMX/CAR expression vectors into which the scFvs had been introduced were not introduced. FIG. 9 shows the results obtained when gating of NGFR$^+$ cells was performed.

FIG. 9 shows dot plots showing the results of flow cytometry. In FIG. 9, the horizontal axes indicate the average fluorescence intensity of the A2 tetramer, and the vertical axes indicate the average side scatter (SSC) intensity. As shown in FIG. 9, the Jurkat 76 cells (control 2) into which the scFv-introduced pMX/CAR expression vectors had not been introduced did not include cells capable of binding to the A2/NY-ESO-1$_{157}$ or A2/HIV-Gag$_{77}$. Moreover, it could be confirmed that the 3M4E5LH CAR-Ts (3M4E5 CAR, positive control) were capable of binding to the A2/NY-ESO-1$_{157}$ but did not bind to the A2/HIV-Gag$_{77}$ because substantially all the cells were present in the A2 tetramer$^+$ fraction when A2/NY-ESO-1$_{157}$ tetramer staining was performed, and the A2 tetramer$^+$ fraction was not present when A2/HIV-Gag$_{77}$ tetramer staining was performed. Substantially all or some T cells expressing CARs that included L66-3M4E5, L73-3M4E5, L80-3M4E5, L88-3M4E5, L102-3M4E5, or L124-3M4E5 were present in the A2 tetramer$^+$ fraction when A2/NY-ESO-1$_{157}$ tetramer staining was performed, and the A2 tetramer$^+$ fraction was not present when A2/HIV-Gag$_{77}$ tetramer staining was performed. It was found from these results that the CARs that included L66-3M4E5, L73-3M4E5, L80-3M4E5, L88-3M4E5, L102-3M4E5, or L124-3M4E5 were capable of binding to the A2/NY-ESO-1$_{157}$ but did not bind to the A2/HIV-Gag$_{77}$. That is, it was found that the first screening method of the present invention could be used to screen scFvs that included new heavy-chain variable regions and new light-chain variable regions capable of binding to a target antigen. Moreover, since CAR-expressing T cells that were stained with the A2/NY-ESO-1$_{157}$ tetramer to different staining degrees were present, it was found that scFvs that included heavy-chain variable regions and light-chain variable regions having different avidity for a target antigen could be screened.

(5) Avidity of First Candidate scFvs

Figure 10:
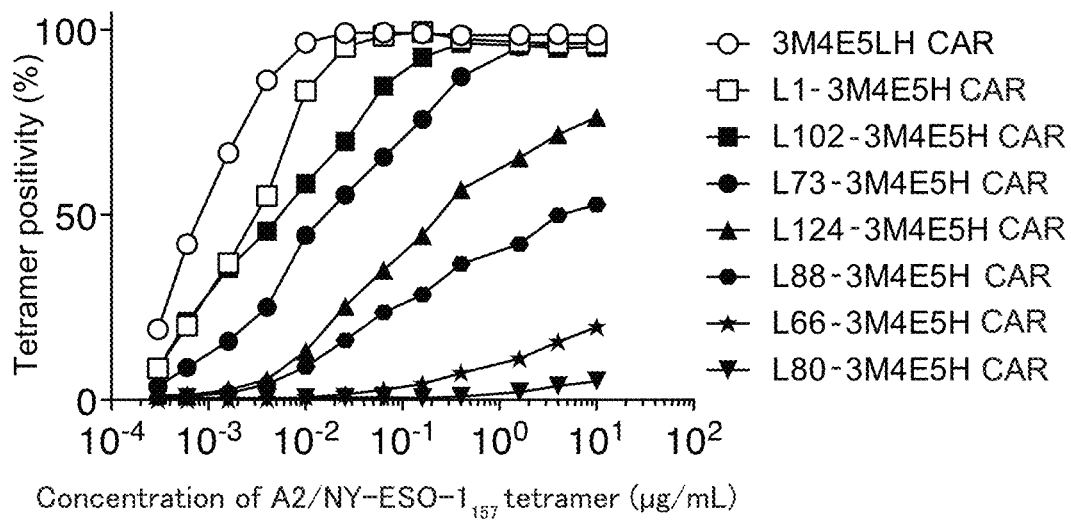
FIG. 10 is a graph indicating the ratios of A2/NY-ESO-$1_{157}$ tetramer-positive cells in Example 2.

Next, flow cytometry analysis was performed in the same manner as in (6) above, except that the 3M4E5LH CAR-Ts and the Jurkat 76 cells expressing the CARs that included L1-3M4E5, L66-3M4E5, L73-3M4E5, L80-3M4E5, L88-3M4E5, L102-3M4E5, or L124-3M4E5, which had been obtained in (4) of Example 2 above, were stained with the PE-labeled A2/NY-ESO-1$_{157}$ tetramer at a predetermined concentration (0.0004194304, 0.001048576, 0.00262144, 0.0065536, 0.016384, 0.04096, 0.1024, 0.256, 0.64, 1.6, 4, or 10 µg/mL), and were then stained with the V450-labeled anti-human NGFR mAb. Then, the ratio of A2/NY-ESO-1$_{157}$ tetramer-positive cells was calculated for each A2/NY-ESO-1$_{157}$ tetramer concentration. FIG. 10 shows the results.

FIG. 10 is a graph indicating the ratios of A2/NY-ESO-1$_{157}$ tetramer-positive cells. In FIG. 10, the horizontal axis indicates the concentration of the A2/NY-ESO-1$_{157}$ tetramer, and the vertical axis indicates the ratio of A2/NY-ESO-1$_{157}$ tetramer-positive cells. As shown in FIG. 10, the ratios of the A2/NY-ESO-1$_{157}$ tetramer-positive cells in the CAR-Ts increased in a manner dependent on the concentration of the A2/NY-ESO-1$_{157}$ tetramer. It was necessary to increase the concentration of the A2/NY-ESO-1$_{157}$ tetramer in order to obtain, from the T cells expressing CARs that included L1-3M4E5, L66-3M4E5, L73-3M4E5, L80-3M4E5, L88-3M4E5, L102-3M4E5, or L124-3M4E5, the A2/NY-ESO-1$_{157}$ tetramer-positive cells at the same level as those from the 3M4E5LH CAR-Ts, and it was thus found that the scFvs in these CAR-Ts were different in avidity for the A2/NY-ESO-1$_{157}$ tetramer. That is, it was found that the first screening method of the present invention could be used to screen scFvs different in binding avidity for a target antigen.

(6) Functions of First Candidate scFvs

Figure 11:
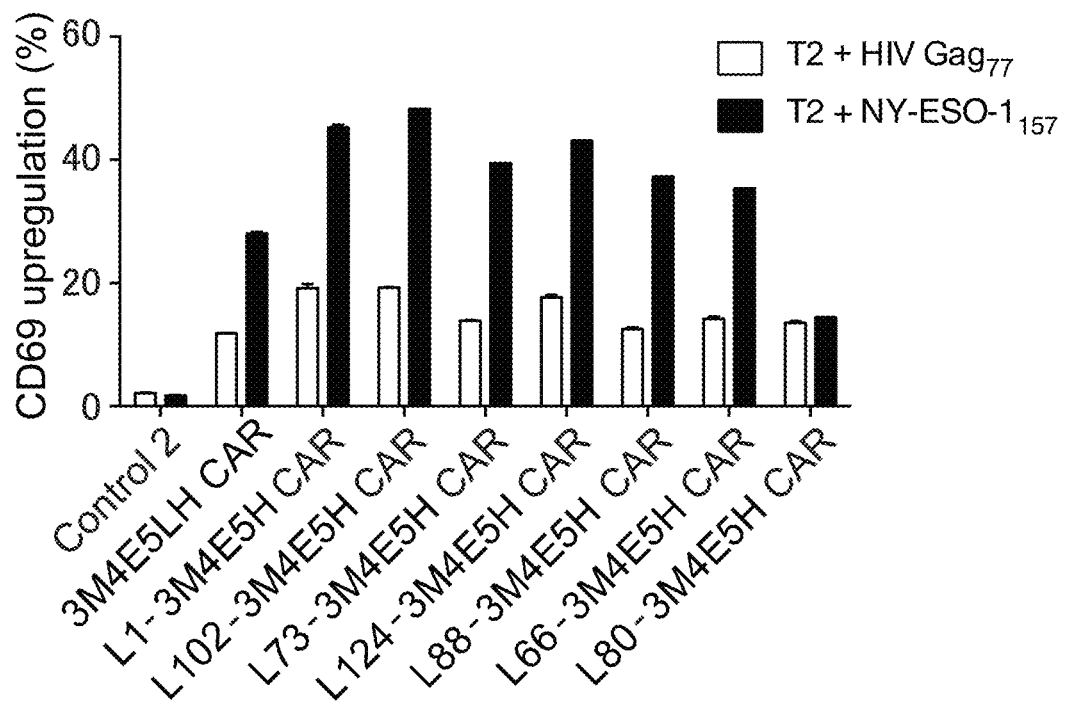
FIG. 11 is a graph indicating changes in a CD69 expression level in the case where the peptide concentration is 10 μg/mL in Example 2.

Next, it was examined if the CAR-Ts expressing L1-3M4E5, L66-3M4E5, L73-3M4E5, L80-3M4E5, L88-3M4E5, L102-3M4E5, or L124-3M4E5 as an scFv bound to the target antigen and were thus activated. Specifically, the CAR-Ts and the T2 cells were seeded in each well (96-well plate) such that the number of the CAR-Ts was 3×10$^5$ and the number of the T2 cells was 5×10$^4$, and then they were cultured together for 5 hours. Before use, the T2 cells (HLA-A*02:01-expressing cells) were pulsed with the NY-ESO-1$_{157-165}$ peptide at a predetermined concentration (0.0005, 0.0015, 0.004, 0.01, 0.04, 0.122, 0.366, 1.11, 3.33, or 10 µg/mL) (T2+NY-ESO-1$_{157}$). An RPMI1640 culture medium containing FCS at a concentration of 10% was used as the culture solution for the coculture. After the above-mentioned coculture, the CAR-Ts were collected, and were then stained with an FITC-labeled anti-human CD69 mAb (clone: FN50) and a V450-labeled anti-human NGFR mAb. The average fluorescence intensity of CD69 in NGFR$^+$ cells from the stained CAR-Ts was measured using the flow cytometer. A positive control was performed in the same manner, except that an expression vector that included a nucleic acid coding for a tagged 3M4E5LH CAR was used instead of the pMX/H1-3M4E5L expression vector. A control 1 was performed in the same manner, except that T2 cells (T2+HIV Gag$_{77}$) pulsed with the HIV Gag$_{77-85}$ peptide instead of the NY-ESO-1$_{157-165}$ peptide were used. A control 2 was performed in the same manner, except that the expression vectors were not introduced. Then, the rates of an increase in CD69 expression in the samples were calculated using the average fluorescence intensity of CD69 in the control 2 as a standard. FIG. 11 shows the results.

FIG. 11 is a graph indicating changes in a CD69 expression level obtained when the peptide concentration was 10 µg/mL. In FIG. 11, the horizontal axis indicates the types of samples, and the vertical axis indicates the rate of an increase in CD69 expression. As shown in FIG. 11, the CD69 expression did not increase in the control 2. On the other hand, when the 3M4E5LH CAR-Ts (positive control) were stimulated with the T2+NY-ESO-1$_{157}$, it could be confirmed that the CD69 expression increased compared with the case of the stimulation with the T2+HIV Gag$_{77}$, and the CAR-Ts bound to the A2/NY-ESO-1$_{157}$ and were activated. When the CAR-Ts expressing L1-3M4E5, L66-3M4E5, L73-3M4E5, L80-3M4E5, L88-3M4E5, L102-3M4E5, or L124-3M4E5 as an scFv were stimulated with the T2+NY-ESO-1$_{157}$, the CD69 expression increased compared with the case of the stimulation with the T2+HIV Gag$_{77}$, and the CAR-Ts bound to the A2/NY-ESO-1$_{157}$ and were activated. Moreover, it was found that the first screening method of the present invention could be used to screen scFvs that were functional in CAR-T cells and had a higher specificity.

Figure 12:
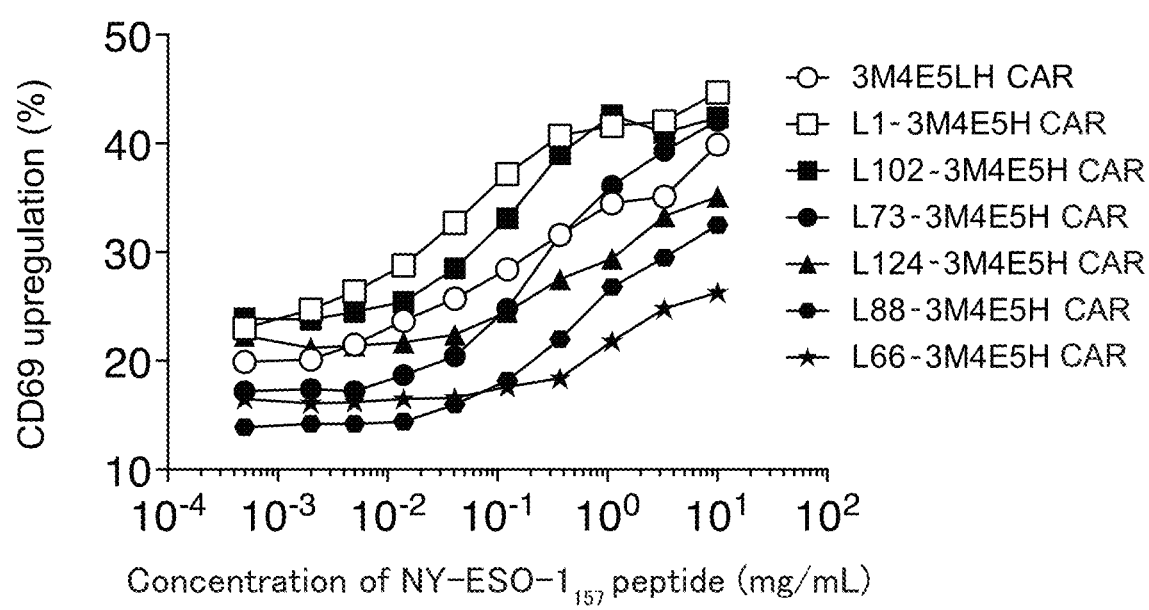
FIG. 12 is a graph indicating changes in a CD69 expression level in Example 2.

Next, the results of changes in CD69 expression in the case where the NY-ESO-1$_{157}$ peptide was serially diluted are shown in FIG. 12. FIG. 12 is a graph indicating changes in a CD69 expression level. In FIG. 12, the horizontal axis indicates the NY-ESO-1$_{157}$ peptide concentration, and the vertical axis indicates the rate of an increase in CD69 expression. As shown in FIG. 12, in the CAR-Ts, the CD69 expression increased in a manner dependent on the NY-ESO-1$_{157}$ peptide concentration. It was found that, in the CAR-Ts expressing L1-3M4E5 or L102-3M4E5 as the scFvs, the CD 69 expression increased more sharply and the specificity for the A2/NY-ESO-1$_{157}$ was higher compared with the 3M4E5LH CAR-Ts. That is, it was found that the first screening method of the present invention could be used to screen scFvs that were functional in CAR-T cells and had a higher specificity.

Example 3

It was confirmed that the screening method of the present invention in which the CAR library of the present invention is used could be used to screen scFvs capable of binding to CD19.

(1) Preparation of FMC63 CAR

A nucleic acid coding for an FMC63HL scFv or FMC63LH scFv was prepared in the same manner as in (1) of Example 1 above, except that the heavy-chain variable region and the light-chain variable region of a human CD19-specific antibody (clone: FMC63) were used instead of the heavy-chain variable region and the light-chain variable region of the A2/NY-ESO-1$_{157}$-specific antibody. Then, nucleic acids coding for a tagged FMC63HL CAR and a tagged FMC63LH CAR were obtained by adding a tag to the 3' ends of the above-mentioned nucleic acids. The nucleic acids were introduced into pMX expression vectors.

FMC63HL scFv
(Sequence ID No. 201)
EVKLQESGPGLVAPSQSLSVTCTVSGVSLPDYGVSWIRQPPRKGLEWL

GVIWGSETTYYNSALKSRLTIIKDNSKSQVFLKNINSLQTDDTAIYYCA

KHYYYGGSYANIDYWGQGTSVTVSSGSTSGSGKPGSGEGSTKGDIQMTQ

TTSSLSASLGDRVTISCRASQDISKYLNWYQQKPDGTVKLLIYHTSRLH

SGVPSRFSGSGSGTDYSLTISNLEQEDIATYFCQQGNTLPYTFGGGTKL

EIT

Nucleic Acid Coding for FMC63HL scFv
(Sequence ID No. 202)
5'-GAAGTGAAACTGCAAGAGTCTGGCCCTGGACTGGTGGCCCCATCTC

AGTCTCTGAGCGTGACCTGTACAGTCAGCGGAGTGTCCCTGCCTGATTA

CGGCGTGTCCTGGATCAGACAGCCTCCTCGGAAAGGCCTGGAATGGCTG

GGAGTGATCTGGGGCAGCGAGACAACCTACTACAACAGCGCCCTGAAGT

CCCGGCTGACCATCATCAAGGACAACTCCAAGAGCCAGGTGTTCCTGAA

GATGAACAGCCTGCAGACCGACGACACCGCCATCTACTATTGCGCCAAG

CACTACTACTACGGCGGCAGCTACGCTATGGACTATTGGGGCCAGGGCA

CCAGCGTTACAGTGTCCTCGGGCTCTACAAGCGGCTCTGGCAAGCCTGG

ATCTGGCGAGGGAAGCACCAAGGGCGATATCCAGATGACCCAGACAACA

AGCAGCCTGAGCGCCAGCCTGGGCGATAGAGTGACCATCAGCTGTAGAG

CCAGCCAGGACATCAGCAAGTACCTGAACTGGTATCAGCAGAAACCCGA

CGGCACCGTGAAGCTGCTGATCTACCACACCAGCAGACTGCACAGCGGC

GTGCCAAGCAGATTTTCTGGCAGCGGCTCTGGCACCGACTACAGCCTGA

CCATCTCCAACCTGGAACAAGAGGATATCGCTACCTACTTCTGCCAGCA

AGGCAACACCCTGCCTTACACCTTTGGCGGAGGCACCAAGCTGGAAATC

ACA-3'

FMC63LH scFv
(Sequence ID No. 203)
DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTC

TVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSS

Nucleic Acid Coding for FMC63LH scFv
(Sequence ID No. 204)
5'-GATATCCAGATGACCCAGACAACAAGCAGCCTGAGCGCCAGCCTGG

GCGATAGAGTGACCATCAGCTGTAGAGCCAGCCAGGACATCAGCAAGTA

CCTGAACTGGTATCAGCAGAAACCCGACGGCACCGTGAAGCTGCTGATC

TACCACACCAGCAGACTGCACAGCGGCGTGCCAAGCAGATTTTCTGGCA

GCGGCTCTGGCACCGACTACAGCCTGACCATCTCCAACCTGGAACAAGA

GGATATCGCTACCTACTTCTGCCAGCAAGGCAACACCCTGCCTTACACC

TTTGGCGGAGGCACCAAGCTGGAAATCACAGGCTCTACAAGCGGCTCTG

GCAAGCCTGGATCTGGCGAGGGAAGCACCAAGGGCGAAGTGAAACTGCA

AGAGTCTGGCCCTGGACTGGTGGCCCCATCTCAGTCTCTGAGCGTGACC

TGTACAGTCAGCGGAGTGTCCCTGCCTGATTACGGCGTGTCCTGGATCA

GACAGCCTCCTCGGAAAGGCCTGGAATGGCTGGGAGTGATCTGGGGCAG

CGAGACAACCTACTACAACAGCGCCCTGAAGTCCCGGCTGACCATCATC

AAGGACAACTCCAAGAGCCAGGTGTTCCTGAAGATGAACAGCCTGCAGA

CCGACGACACCGCCATCTACTATTGCGCCAAGCACTACTACTACGGCGG

CAGCTACGCTATGGACTATTGGGGCCAGGGCACCAGCGTTACAGTGTCC

TCG-3'

(2) Preparation of First CAR Library

An hH-FMC63L scFv library was prepared by substituting the nucleic acid coding for the heavy-chain variable region on the 5' side of the nucleic acids coding for the FMC63HL scFv described in (1) of Example 3 above with a library that included nucleic acids of the heavy-chain variable regions derived from human peripheral blood B cells. Then, a tagged hH-FMC63L CAR library was prepared in the same manner as in (1) of Example 1 above, except that the hH-FMC63L scFv library was used instead of the nucleic acid coding for the 3M4E5LH scFv. The tagged hH-FMC63L CAR library was introduced into pMX expression vectors to prepare expression vectors for expressing the hH-FMC63L CAR library. It should be noted that, regarding the heterogeneity of the heavy-chain variable regions in the hH-FMC63L CAR library, it was confirmed through restriction enzyme mapping and sequencing of the regions using the Sanger's method that the number of types of heavy-chain variable regions was about $1 \times 10^6$.

(3) Preparation of First CAR Library-Expressing T Cells (First Candidate CAR-Ts)

The hH-FMC63L CAR library was introduced into T cells in the same manner as in (3) of Example 1 above, except that the expression vectors for expressing the hH-FMC63L CAR library were used instead of the expression vectors for expressing the hH-3M4E4L CAR library. Then, the resulting T cells were purified and used as first candidate CAR-Ts.

(4) Preparation of Target Antigen-Expressing Cells

Retroviruses were used to introduce a nucleic acid coding for human CD19 into K562 cells, and thus antigen-presenting cells (APCs-CD19) were obtained.

```
Nucleic Acid Coding for Human CD19
                                (Sequence ID No. 205)
5'-ATGCCACCTCCTCGCCTCCTCTTCTTCCTCCTCTTCCTCACCCCCA

TGGAAGTCAGGCCCGAGGAACCTCTAGTGGTGAAGGTGGAAGAGGGAGA

TAACGCTGTGCTGCAGTGCCTCAAGGGGACCTCAGATGGCCCCACTCAG

CAGCTGACCTGGTCTCGGGAGTCCCCGCTTAAACCCTTCTTAAAACTCA

GCCTGGGGCTGCCAGGCCTGGGAATCCACATGAGGCCCTGGCCATCTG

GCTTTTCATCTTCAACGTCTCTCAACAGATGGGGGCTTCTACCTGTGC

CAGCCGGGGCCCCCCTCTGAGAAGGCCTGGCAGCCTGGCTGGACAGTCA

ATGTGGAGGGCAGCGGGGAGCTGTTCCGGTGGAATGTTTCGGACCTAGG

TGGCCTGGGCTGTGGCCTGAAGAACAGGTCCTCAGAGGGCCCCAGCTCC

CCTTCCGGGAAGCTCATGAGCCCCAAGCTGTATGTGTGGGCCAAAGACC

GCCCTGAGATCTGGGAGGGAGAGCCTCCGTGTCTCCCACCGAGGGACAG

CCTGAACCAGAGCCTCAGCCAGGACCTCACCATGGCCCCTGGCTCCACA

CTCTGGCTGTCCTGTGGGGTACCCCCTGACTCTGTGTCCAGGGGCCCCC

TCTCCTGGACCCATGTGCACCCCAAGGGGCCTAAGTCATTGCTGAGCCT

AGAGCTGAAGGACGATCGCCCGGCCAGAGATATGTGGGTAATGGAGACG

GGTCTGTTGTTGCCCCGGGCCACAGCTCAAGACGCTGGAAAGTATTATT

GTCACCGTGGCAACCTGACCATGTCATTCCACCTGGAGATCACTGCTCG

GCCAGTACTATGGCACTGGCTGCTGAGGACTGGTGGCTGGAAGGTCTCA

GCTGTGACTTTGGCTTATCTGATCTTCTGCCTGTGTTCCCTTGTGGGCA

TTCTTCATCTTCAAAGAGCCCTGGTCCTGAGGAGGAAAAGAAAGCGAAT

GACTGACCCCACCAGGAGATTCTTCAAAGTGACGCCTCCCCCAGGAAGC

GGGCCCAGAACCAGTACGGGAACGTGCTGTCTCTCCCCACACCCACCT

CAGGCCTCGGACGCGCCCAGCGTTGGGCCGCAGGCCTGGGGGGCACTGC

CCCGTCTTATGGAAACCCGAGCAGCGACGTCCAGGCGGATGGAGCCTTG

GGGTCCCGGAGCCCGCCGGGAGTGGGCCCAGAAGAAGAGGAAGGGGAGG

GCTATGAGGAACCTGACAGTGAGGAGGACTCCGAGTTCTATGAGAACGA

CTCCAACCTTGGGCAGGACCAGCTCTCCCAGGATGGCAGCGGCTACGAG

AACCCTGAGGATGAGCCCTGGGTCCTGAGGATGAAGACTCCTTCTCCA

ACGCTGAGTCTTATGAGAACGAGGATGAAGAGCTGACCCAGCCGGTCGC

CAGGACAATGGACTTCCTGAGCCCTCATGGGTCAGCCTGGGACCCCAGC

CGGGAAGCAACCTCCCTGGGGTCCCAGTCCTATGAGGATATGAGAGGAA

TCCTGTATGCAGCCCCCCAGCTCCGCTCCATTCGGGGCCAGCCTGGACC

CAATCATGAGGAAGATGCAGACTCTTATGAGAACATGGATAATCCCGAT

GGGCCAGACCCAGCCTGGGGAGGAGGGGGCCGCATGGGCACCTGGAGCA

CCAGG-3'
```

(5) First Screening Method

Screening was performed using the first candidate CAR-Ts described in (3) of Example 3 above and the APCs-CD19 prepared in (4) of Example 3 above. Specifically, the first candidate CAR-Ts and the APCs-CD19 were seeded in each well (24-well plate) such that the number of the first candidate CAR-Ts was 2×10$^6$ and the number of the APCs-CD19 was 1×10$^5$, and then they were cultured together for 7 days. Before use, the APCs-CD19 were treated with 20 Gy of γ rays. An RPMI1640 culture medium containing gentamicin at a concentration of 50 μg/mL, human AB serum (manufactured by Sigma) at a concentration of 10%, human IL-2 (manufactured by Roche) at a concentration of 10 IU/mL, and human IL-15 (manufactured by PeproTech) at a concentration of 10 ng/mL was used as the culture medium used for the above-mentioned coculture of the first candidate CAR-Ts and the APCs-CD19. After the coculture, the first candidate CAR-Ts were collected, and coculture of the first candidate CAR-Ts and the APCs-CD19 was performed two more times (three times in total) in the same conditions. Thus, the first candidate CAR-Ts expressing the hH-FMC63L CARs capable of binding to human CD19 was enriched.

Figure 13:
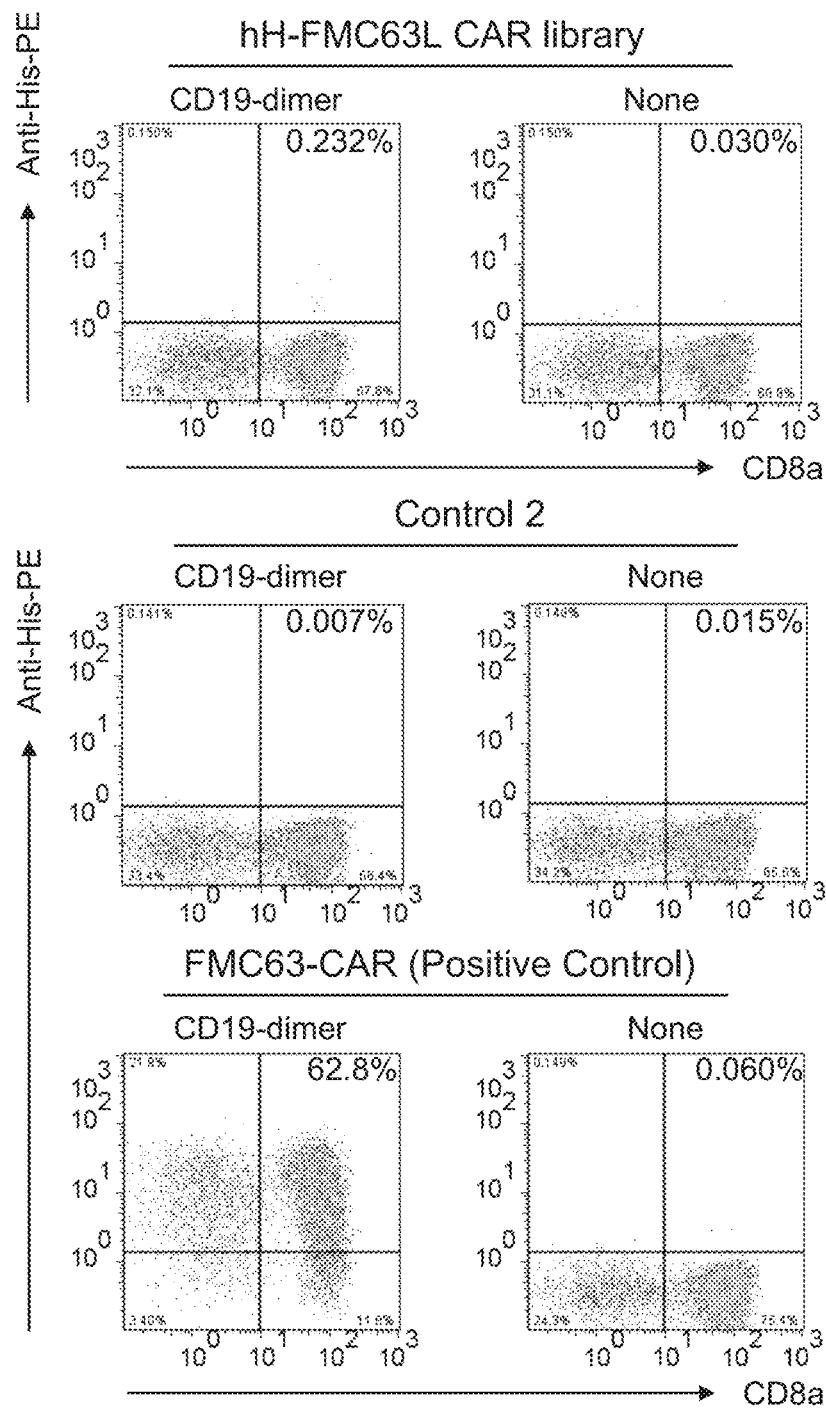
FIG. 13 shows dot plots showing the results of flow cytometry in Example 3.

Next, after the enrichment of the first candidate CAR-Ts, the first candidate CAR-Ts were collected and stained with a PE-labeled CD19 dimer at a concentration of 20 μg/mL. The PE-labeled CD19 dimer was prepared using a soluble CD19, which is human CD19 that includes a His-tag added to the C terminus of the extracellular domain thereof via an SGSG linker. Specifically, the PE-labeled CD19 dimer was prepared by mixing the soluble CD19 and a PE-labeled anti-His mAb (clone: GG11-8F3.5.1) such that the molar ratio therebetween was 2:1. After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). Then, regarding the first candidate CAR-Ts that had been subjected to dimer staining, it was confirmed using the flow cytometer if first candidate CAR-Ts expressing CARs capable of binding to CD19 were present. A positive control was performed in the same manner, except that an expression vector that included a nucleic acid coding for the tagged FMC63HL CAR was used instead of the expression vectors for expressing the hH-FMC63L CAR library. It should be noted that, even when an expression vector that included a nucleic acid coding for the tagged FMC63LH CAR was used, the results were the same as those from the case where the expression vector that included a nucleic acid coding for the tagged FMC63HL CAR was used. A control 1 was performed in the same manner, except that CD19 dimer staining was not performed. A control 2 was performed in the same manner, except that the expression vectors for expressing the hH-FMC63L CAR library were not introduced. FIG. 13 shows the results obtained when gating of FSC$^+$-SSC$^+$-NGFR$^+$ cells was performed.

FIG. 13 shows dot plots showing the results of flow cytometry. In FIG. 13, the horizontal axes indicate the average fluorescence intensity of CD8a, and the vertical axes indicate the average fluorescence intensity of the CD19 dimer. As shown in FIG. 13, the T cells (control 2) into which the expression vectors for expressing the hH-FMC63 CAR library had not been introduced did not include T cells capable of binding to the CD19 dimer. Moreover, it could be confirmed that the CAR-Ts (FMC63-CAR, positive control) expressing the FMC63-CAR were capable of binding to the CD19 dimer because a CD8$^+$-CD19$^+$ dimer fraction (the upper right fraction in each dot plot) was present when CD19 dimer staining was performed, and the CD8$^+$-CD19 dimer$^+$ fraction was not present when CD19 dimer staining was not performed. Furthermore, in the case of the first candidate CAR-Ts, the CD8$^+$-CD19 dimer$^+$ fraction was present when CD19 dimer staining was performed, and the CD8$^+$-CD19 dimer$^+$ fraction was not present when CD19 dimer staining was not performed. It was found from these results that the first candidate CAR-Ts included first candidate CAR-Ts expressing CARs capable of binding to the CD19 dimer. As a result, it was found that the first screening method of the present invention could be used to screen scFvs capable of binding to a target antigen. It should be noted that, although data are not shown, it was confirmed that the CD69 expression increased in cells included in the CD8$^+$-CD19 dimer$^+$ fraction compared with cells included in the CD19 dimer$^-$ fraction, and CARs expressed in the cells included in the CD8$^+$-CD19 dimer$^+$ fraction had a T cell-activating function.

Example 4

It was confirmed that CARs obtained using the screening method of the present invention in which the CAR library of the present invention is used had high specificity for a target antigen.

Figure 14:
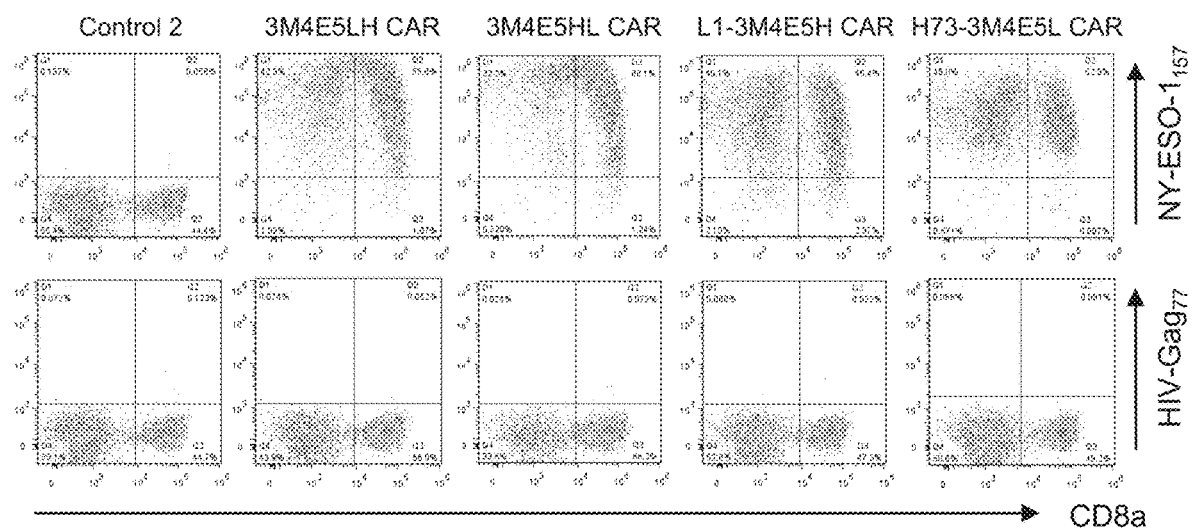
FIG. 14 shows dot plots showing the results of flow cytometry in Example 4.
Figure 16A:
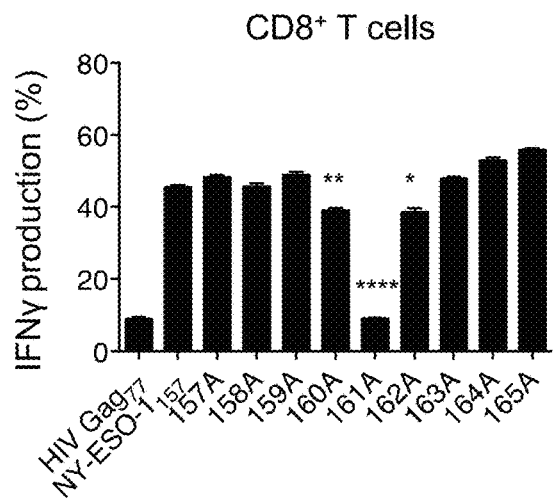
FIG. 16(A) shows the results from T cells expressing a 3M4E5LH CAR.
Figure 16A:
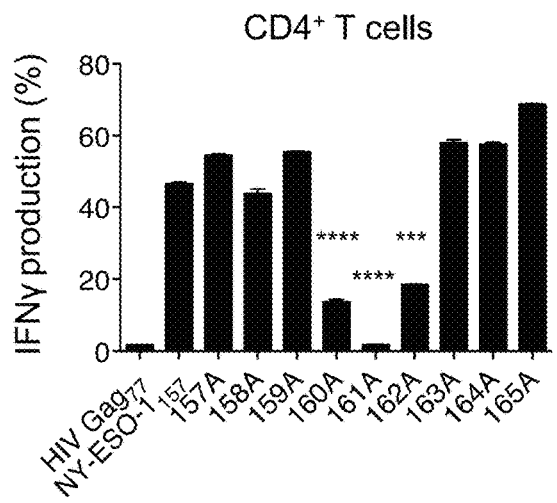
Figure 16B:
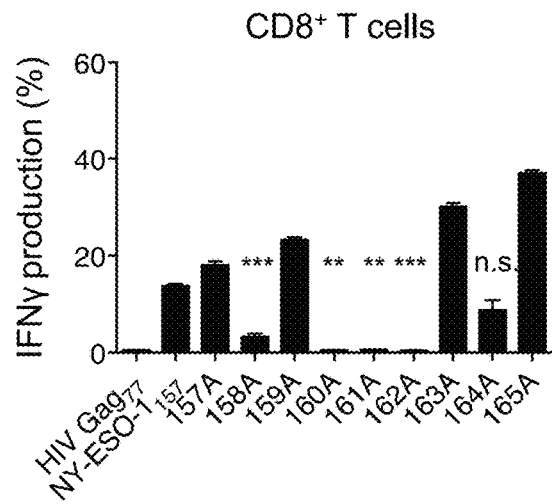
FIG. 16(B) shows the results from T cells expressing an L1-3M4E5H CAR.
Figure 16B:
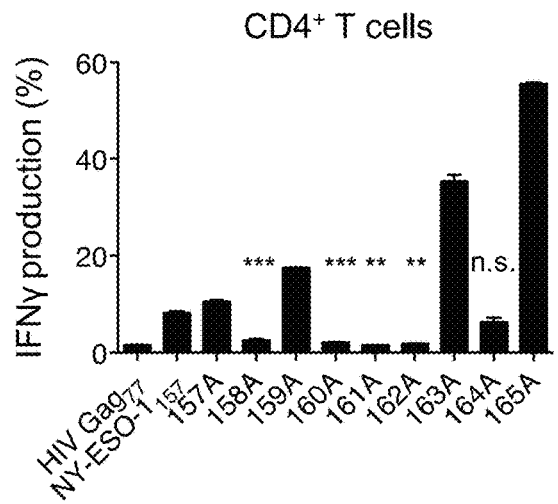

A culture supernatant containing GaLV-pseudotyped retroviruses was prepared in the same manner as in (3) of Example 1 above, except that a pMX/CAR expression vector into which a polynucleotide coding for L1-3M4E5H or H73-3M4E5L as an scFv (antigen-binding domain) had been introduced (respectively referred to as an L1-3M4E5H expression vector and an H73-3M4E5L expression vector) was used instead of the expression vectors for expressing the hH-3M4E4L CAR library. Next, T cells were infected with the retroviruses in the same manner as in (3) of Example 1 above, except that the obtained GaLV-pseudotyped retroviruses were used. Thus, the L1-3M4E5H expression vector or H73-3M4E5L expression vector was introduced into the T cells. The infection with the retroviruses and the introduction of the L1-3M4E5H expression vector or H73-3M4E5L expression vector were performed in the same manner five more times (six times in total). The resulting T cells were stained with the PE-labeled A2/NY-ESO-1$_{157}$ tetramer at a concentration of 20 µg/mL. After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). The concentrations of these antibodies were about 10 µg/mL. Then, it was confirmed using the flow cytometer if the T cells that had been subjected to tetramer staining included T cells expressing CARs capable of binding to the A2/NY-ESO-1$_{157}$. A positive control was performed in the same manner, except that an expression vector that included a nucleic acid coding for the tagged 3M4E5HL CAR or tagged 3M4E5LH CAR was used instead of the expression vectors for expressing the hH-3M4E4L CAR library. A control 1 was performed in the same manner, except that the A2/HIV-Gag$_{77}$ tetramer was used instead of the A2/NY-ESO-1$_{157}$ tetramer. A control 2 was performed in the same manner, except that the expression vectors for expressing the hH-3M4E4L CAR library were not introduced. FIG. 14 shows the results obtained when gating of FSC$^+$-SSC$^+$-NGFR$^+$ cells was performed.

FIG. 14 shows dot plots showing the results of flow cytometry. In FIG. 14, the horizontal axes indicate the average fluorescence intensity of CD8a, and the vertical axes indicate the average fluorescence intensity of the A2 tetramer. As shown in FIG. 14, in the control 2, T cells capable of binding to the A2/NY-ESO-1$_{157}$ or A2/HIV-Gag$_{77}$ were not present. Moreover, it could be confirmed that the CAR-Ts (3M4E5HL CAR or 3M4E5LH CAR, positive control) expressing the 3M4E5HL CAR or 3M4E5LH CAR were capable of binding to the A2/NY-ESO-1$_{157}$ but did not bind to the A2/HIV-Gag$_{77}$ because a CD8$^+$-A2 tetramer$^+$ fraction (the upper right fraction in each dot plot) was present when A2/NY-ESO-1$_{157}$ tetramer staining was performed, and the CD8$^+$-A2 tetramer$^+$ fraction was not present when A2/HIV-Gag$_{77}$ tetramer staining was performed. Furthermore, in the case of the L1-3M4E5H CAR-Ts or H73-3M4E5L CAR-Ts, the CD8$^+$-A2 tetramer$^+$ fraction was present when A2/NY-ESO-1$_{157}$ tetramer staining was performed, and the CD8$^+$-A2 tetramer$^+$ fraction was not present when A2/HIV-Gag$_{77}$ tetramer staining was performed.

Next, it was examined if the T cells that had been infected with the retroviruses bound to the target antigen, and were thus activated to produce cytokines. Specifically, after the infection of T cells (CAR-Ts) with the retroviruses were repeated six times, the T cells and T2 cells were seeded in each well (96-well plate) such that the number of the T cells was 3×10$^5$ and the number of the T2 cells was 5×10$^4$, and then they were cultured together for 5 hours. Before use, the T2 cells (HLA-A*02:01-expressing cells) were pulsed with the NY-ESO-1$_{157}$ peptide at a concentration of 10 µg/mL (T2+NY-ESO-1$_{157}$). An RPMI1640 culture medium containing FCS at a concentration of 10% was used as the culture solution for the coculture. After the above-mentioned coculture, the T cells were collected, fixed with paraformaldehyde, subjected to permeabilization, and stained with an APC-labeled anti-human IL-2 mAb (clone: MQ1-17H12), a PE-labeled anti-human TNFα mAb (clone: Mab11), a PC7-labeled anti-human IFN-γ mAb (clone: B27), an FITC-labeled anti-human CD4 mAb (clone: OKT4), a PC5-labeled anti-human CD8a mAb (clone: B9.11), and a V450-labeled anti-human NGFR mAb (clone: C40-1457). After the CAR-Ts were stained, the amounts of TNF-α, IFN-γ, and IL-2 produced by CD8-positive cells or CD4-positive cells in the CAR-Ts (NGFR-positive fraction) were measured using the flow cytometer. A positive control was performed in the same manner, except that an expression vector that included a nucleic acid coding for the 3M4E5HL or 3M4E5LH as an scFv was used. A control 1 was performed in the same manner, except that the A2/HIV-Gag$_{77}$ peptide was used instead of the NY-ESO-1$_{157}$ peptide. A control 2 was performed in the same manner, except that the expression vectors for expressing the hH-3M4E4L CAR library were not introduced. Then, the rates of an increase in cytokine production in the samples were calculated using the cytokine production amount in the control 2 as a standard. FIG. 15 shows the results.

FIG. 15 shows graphs indicating changes in a cytokine production amount. FIG. 15(A) shows the results from CD8-positive T cells, and FIG. 15(B) shows the results from CD4-positive T cells. In FIG. 15, the horizontal axes indicate the types of samples (CARs), and the vertical axes indicate the rate of an increase in cytokine production. As shown in FIG. 15, the cytokine production did not increase in the control 2. On the other hand, when the 3M4E5LH CAR-Ts or 3M4E5HL CAR-Ts (positive control) were stimulated with the T2+NY-ESO-1$_{157}$, it could be confirmed that the cytokine production amount increased compared with the case of the stimulation with the T2+HIV Gag$_{77}$, and the cytokines bound to the A2/NY-ESO-1$_{157}$ to activate the CAR-Ts. When the 3M4E5HL CAR-Ts or 3M4E5LH CAR-Ts were stimulated with the T2+NY-ESO-1$_{157}$, the cytokine production increased compared with the case of the stimulation with the T2+HIV Gag$_{77}$, and the cytokines bound to the A2/NY-ESO-1$_{157}$ to activate the CAR-Ts, leading to the production of cytokines. Furthermore, when the 3M4E5HL CAR-Ts or 3M4E5LH CAR-Ts were stimulated with the T2+HIV Gag$_{77}$, the cytokine production amount was smaller than or equal to that in the case of the control 2, and was smaller than that in the case of the positive control. It was found from these results that the CARs obtained using the screening method of the present invention in which the CAR library of the present invention is used had high specificity for a target antigen.

Example 5

It was confirmed that CARs obtained using the screening method of the present invention in which the CAR library of the present invention is used differed from antibodies capable of binding to a target antigen used for screening in antigen recognition.

CD8-positive T cells and CD4-positive T cells expressing the L1-3M4E5H CAR were produced in the same manner as in Example 4 above. Next, the T cells and T2 cells were seeded in each well (96-well plate) such that the number of the T cells was 3×10$^5$ and the number of the T2 cells was 5×10$^4$, and then they were cultured together for 5 hours. Before use, the T2 cells (HLA-A*02:01-expressing cells) were pulsed with the NY-ESO-1$_{157}$ peptide or a mutant peptide of the NY-ESO-1$_{157}$ peptide at a concentration of 10 µg/mL (T2+NY-ESO-1$_{157}$). The mutant peptide is a peptide obtained by substituting one of the amino acids in the amino acid sequence of the NY-ESO-1$_{157}$ peptide with alanine. After the above-mentioned coculture, the culture supernatant was collected, and the concentration of IFN-γ in the CAR-Ts was measured in the same manner as in Example 4 above. A control was performed in the same manner, except that CD8-positive T cells or CD4-positive T cells expressing the 3M4E5LH CAR were used. A control 1 was performed in the same manner, except that the A2/HIV-Gag$_{77}$ peptide was used instead of the A2/NY-ESO-1$_{157}$ peptide. A control 2 was performed in the same manner, except that CD8-positive T cells or CD4-positive T cells into which the expression vectors had not been introduced were used. Then, the rates of an increase in cytokine production in the samples were calculated using the cytokine production amount in the control 2 as a standard. FIG. 16 shows the results.

FIG. 16 shows graphs indicating changes in a cytokine production amount. FIG. 16(A) shows the results from T cells expressing the 3M4E5LH CAR, and FIG. 16(B) shows the results from T cells expressing the L1-3M4E5H CAR. In FIGS. 16(A) and 16(B), the horizontal axes indicate the types of peptides, and the vertical axes indicate the changes in a cytokine production amount. The 3M4E5LH CAR recognized the amino acids at positions 160 to 162 of the NY-ESO-1$_{157}$ peptide as shown in FIG. 16(A), whereas the L1-3M4E5H CAR recognized the amino acids at positions 158 and 160 to 162 of the NY-ESO-1$_{157}$ peptide as shown in FIG. 16(B). It was found from these results that CARs obtained using the screening method of the present invention in which the CAR library of the present invention is used differed from antibodies capable of binding to a target antigen used for screening in antigen recognition.

Example 6

It was confirmed that CARs obtained using the screening method of the present invention in which the CAR library of the present invention is used maintained the antigen recognition even when the heavy-chain variable region and the light-chain variable region were arranged in the reverse order.

A 3M4E5H-L1 expression vector was produced by arranging the polynucleotide coding for the heavy-chain variable region and the polynucleotide coding for the light-chain variable region of the L1-3M4E5H expression vector in the reverse order.

Figure 17:
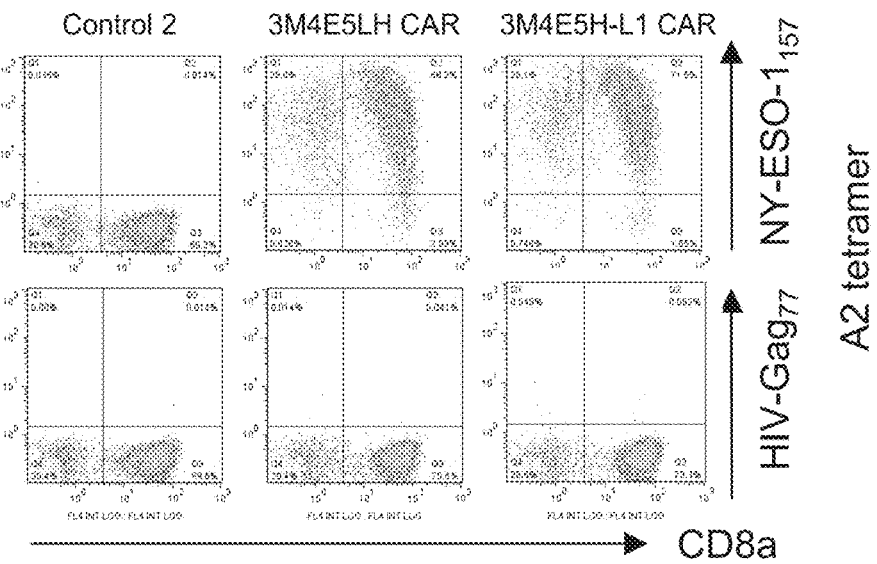
FIG. 17 shows dot plots showing the results of flow cytometry in Example 6.

A culture supernatant containing GaLV-pseudotyped retroviruses was prepared in the same manner as in (3) of Example 1 above, except that the 3M4E5H-L1 expression vector was used instead of the expression vectors for expressing the hH-3M4E4L CAR library. Next, T cells were infected with the retroviruses in the same manner as in (3) of Example 1 above, except that the obtained GaLV-pseudotyped retroviruses were used. Thus, the 3M4E5H-L1 expression vector was introduced into the T cells. The infection with the retroviruses and the introduction of the 3M4E5H-L1 expression vector were performed in the same manner five more times (six times in total). The resulting T cells were stained with the PE-labeled A2/NY-ESO-1$_{157}$ tetramer at a concentration of 20 µg/mL. After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). The concentrations of these antibodies were about 10 µg/mL. Then, it was confirmed using the flow cytometer if the T cells that had been subjected to tetramer staining included T cells expressing CARs capable of binding to the A2/NY-ESO-1$_{157}$. A positive control was performed in the same manner, except that an expression vector that included a nucleic acid coding for the tagged 3M4E5LH CAR was used instead of the expression vectors for expressing the hH-3M4E4L CAR library. A control 1 was performed in the same manner, except that the A2/HIV-Gag$_{77}$ tetramer was used instead of the A2/NY-ESO-1$_{157}$ tetramer. A control 2 was performed in the same manner, except that the expression vectors for expressing the hH-3M4E4L CAR library were not introduced. FIG. 17 shows the results obtained when gating of FSC$^+$-SSC$^+$-NGFR$^+$ cells was performed.

FIG. 17 shows dot plots showing the results of flow cytometry. In FIG. 17, the horizontal axes indicate the average fluorescence intensity of CD8a, and the vertical axes indicate the average fluorescence intensity of the A2 tetramer. As shown in FIG. 17, in the control 2, T cells capable of binding to the A2/NY-ESO-1$_{157}$ or A2/HIV-Gag$_{77}$ were not present. Moreover, it could be confirmed that the CAR-Ts (3M4E5LH CAR, positive control) expressing the 3M4E5LH CAR were capable of binding to the A2/NY-ESO-1$_{157}$ but did not bind to the A2/HIV-Gag$_{77}$ because a CD8$^+$-A2 tetramer$^+$ fraction (the upper right fraction in each dot plot) was present when A2/NY-ESO-1$_{157}$ tetramer staining was performed, and the CD8$^+$-A2 tetramer$^+$ fraction was not present when A2/HIV-Gag$_{77}$ tetramer staining was performed. Furthermore, in the case of the CAR-Ts expressing the 3M4E5H-L1, the CD8$^+$-A2 tetramer$^+$ fraction was present when A2/NY-ESO-1$_{157}$ tetramer staining was performed, and the CD8$^+$-A2 tetramer$^+$ fraction was not present when A2/HIV-Gag$_{77}$ tetramer staining was performed.

Next, it was examined if the T cells that had been infected with the retroviruses bound to the target antigen, and were thus activated to produce cytokines. Specifically, after the infection of T cells (CAR-Ts) with the retroviruses were repeated six times, the T cells, and T2 cells or APCs prepared in (4) of Example 1 above were seeded in each well (96-well plate) such that the number of the T cells was 3×10$^5$ and the number of the T2 cells or APCs was 5×10⁴, and then they were cultured together for 5 hours. Before use, the T2 cells (HLA-A*02:01-expressing cells) and APCs were pulsed with the NY-ESO-1$_{157}$ peptide at a concentration of 10 μg/mL (T2+NY-ESO-1$_{157}$ and K562/A2/NY-ESO-1). An RPMI1640 culture medium containing FCS at a concentration of 10% was used as the culture solution for the coculture. After the above-mentioned coculture, the T cells were collected, fixed with paraformaldehyde, subjected to permeabilization, and stained with an APC-labeled anti-human IL-2 mAb (clone: MQ1-17H12), a PE-labeled anti-human TNFα mAb (clone: Mab11), a PC7-labeled anti-human IFN-γ antibody (clone: B27), an FITC-labeled anti-human CD4 mAb (clone: OKT4), a PC5-labeled anti-human CD8a mAb (clone: B9.11), and a V450-labeled anti-human NGFR mAb (clone: C40-1457). After the CAR-Ts were stained, the amounts of TNF-α, IFN-γ, and IL-2 produced by CD8-positive cells or CD4-positive cells in the CAR-Ts (NGFR-positive fraction) were measured using the flow cytometer. A positive control was performed in the same manner, except that an expression vector that included a nucleic acid coding for the 3M4E5LH as an scFv was used. When the T2 cells were used, a control 1 was performed in the same manner, except that the HIV-Gag$_{77}$ peptide was used instead of the NY-ESO-1$_{157}$ peptide. When the APCs (K562/A2/NY-ESO-1) were used, a control 1 was performed in the same manner, except that K562/A2 into which the NY-ESO-1 gene had not been introduced was used. A control 2 was performed in the same manner, except that the expression vectors for expressing the hH-3M4E4L CAR library were not introduced. Then, the rates of an increase in cytokine production in the samples were calculated using the cytokine production amount in the control 2 as a standard. FIGS. 18 and 19 show the results.

Figure 18A:
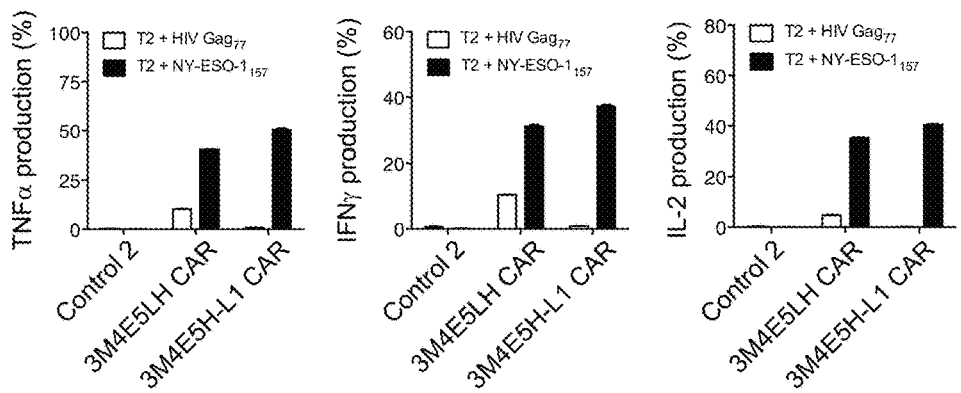
FIG. 18(A) shows the results from CD8-positive T cells.
Figure 18B:
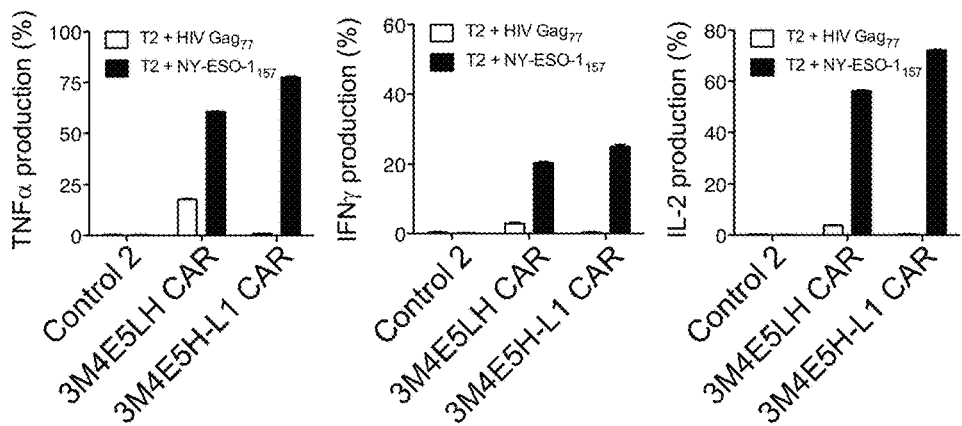
FIG. 18(B) shows the results from CD4-positive T cells.

FIG. 18 shows the results obtained when the T2 cells were used. FIG. 18 shows graphs indicating changes in a cytokine production amount. FIG. 18(A) shows the results from CD8-positive T cells, and FIG. 18(B) shows the results from CD4-positive T cells. In FIG. 18, the horizontal axes indicate the types of samples (CARs), and the vertical axes indicate the rate of an increase in cytokine production. As shown in FIG. 18, the cytokine production did not increase in the control 2. On the other hand, when the 3M4E5LH CAR-Ts (positive control) were stimulated with the T2+NY-ESO-1$_{157}$, it could be confirmed that the cytokine production amount increased compared with the case of the stimulation with the T2+HIV Gag$_{77}$, and the cytokines bound to the A2/NY-ESO-1$_{157}$ to activate the CAR-Ts. When the 3M4E5H-L1 CAR-Ts were stimulated with the T2+NY-ESO-1$_{157}$, the cytokine production increased compared with the case of the stimulation with the T2+HIV Gag$_{77}$, and the cytokines bound to the A2/NY-ESO-1$_{157}$ to activate the CAR-Ts, leading to the production of cytokines. Furthermore, when the 3M4E5H-L1 CAR-Ts were stimulated with the T2+HIV Gag$_{77}$, the cytokine production amount was smaller than or equal to that in the case of the control 2, and was smaller than that in the case of the positive control.

Figure 19A:
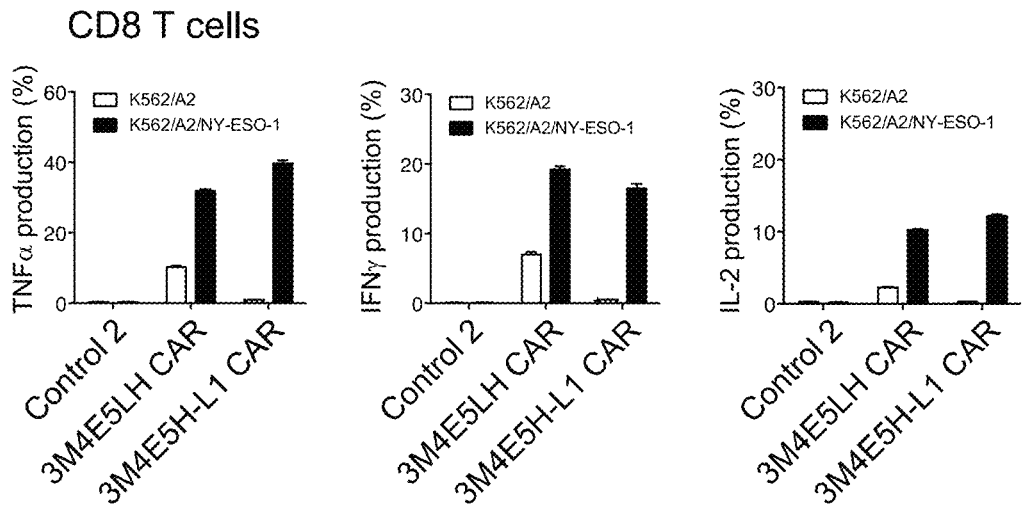
FIG. 19(A) shows the results from CD8-positive T cells.
Figure 19B:
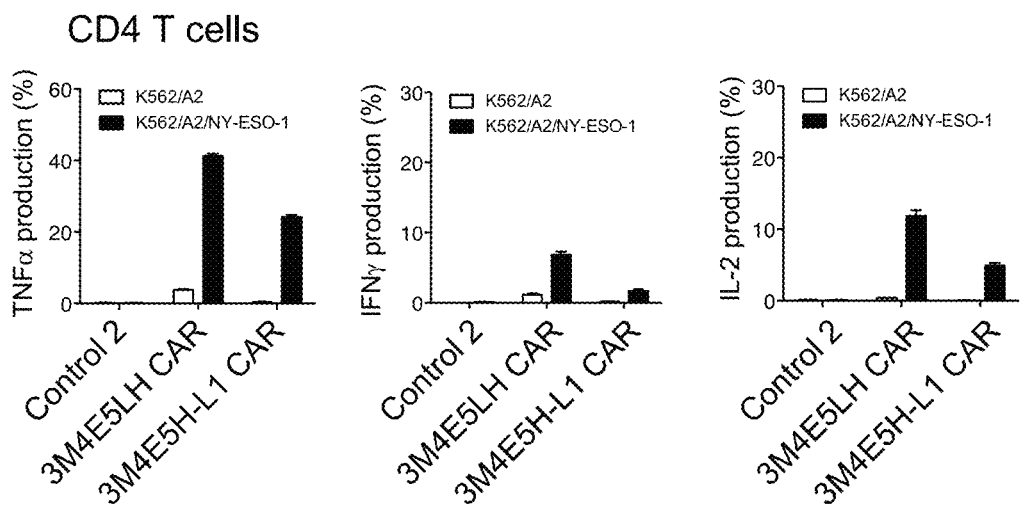
FIG. 19(B) shows the results from CD4-positive T cells.
Figure 20A:
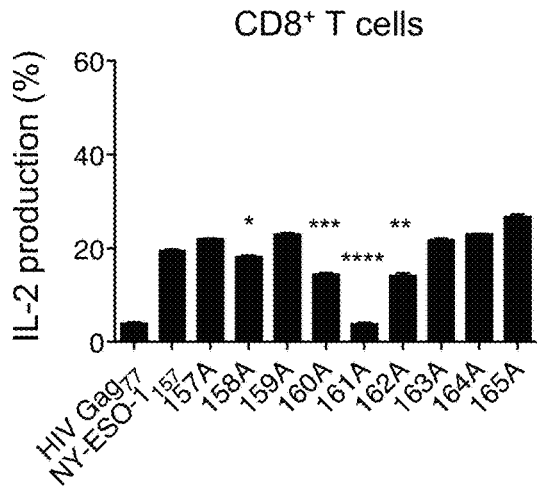
FIG. 20(A) shows the results from T cells expressing a 3M4E5LH CAR.
Figure 20A:
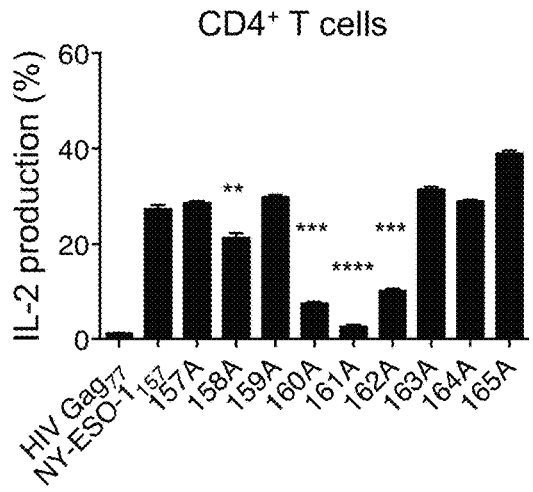
Figure 20B:
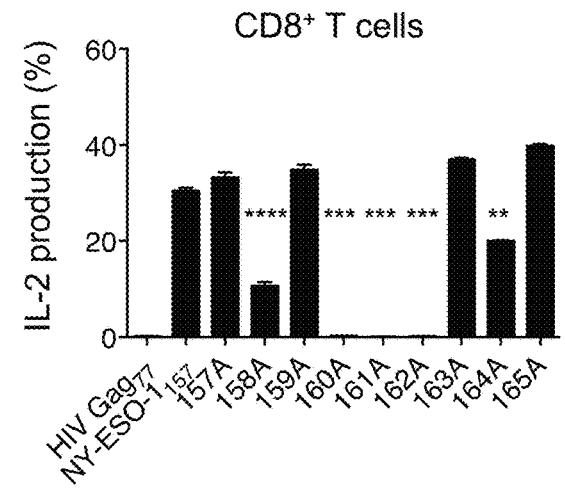
FIG. 20(B) shows the results from T cells expressing a 3M4E5H-L1 CAR.
Figure 20B:
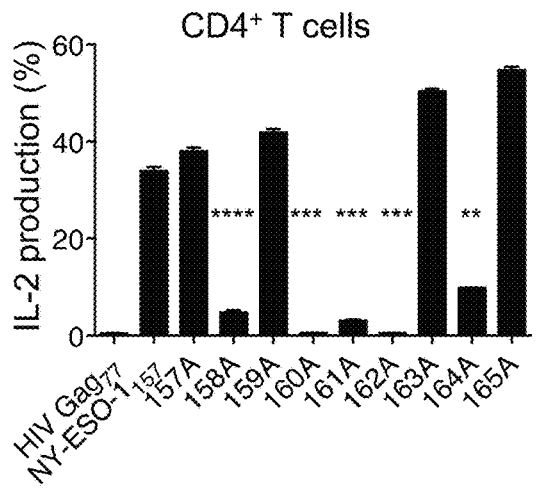

FIG. 19 shows the results obtained when the APCs were used. FIG. 19 shows graphs indicating changes in a cytokine production amount. FIG. 19(A) shows the results from CD8-positive T cells, and FIG. 19(B) shows the results from CD4-positive T cells. In FIG. 19, the horizontal axes indicate the types of samples (CARs), and the vertical axes indicate the rate of an increase in cytokine production. As shown in FIG. 19, the cytokine production did not increase in the control 2. On the other hand, when the 3M4E5LH CAR-Ts (positive control) were stimulated with the K562/A2/NY-ESO-1, it could be confirmed that the cytokine production amount increased compared with the case of the stimulation with the K562/A2, and the cytokines bound to the K562/A2/NY-ESO-1 to activate the CAR-Ts. When the 3M4E5H-L1 CAR-Ts were stimulated with the K562/A2/NY-ESO-1, the cytokine production increased compared with the case of the stimulation with the K562/A2, and the cytokines bound to the K562/A2/NY-ESO-1 to activate the CAR-Ts, leading to the production of cytokines. Furthermore, when the 3M4E5H-L1 CAR-Ts were stimulated with the K562/A2, the cytokine production amount was equal to that in the case of the control 2, and was smaller than that in the case of the positive control. It was found from these results that the CARs obtained using the screening method of the present invention in which the CAR library of the present invention is used could maintain the antigen recognition even when the heavy-chain variable region and the light-chain variable region were arranged in the reverse order.

Example 7

It was confirmed that CARs obtained using the screening method of the present invention in which the CAR library of the present invention is used differed from antibodies capable of binding to a target antigen used for screening in antigen recognition, and could be screened while the cross-reactivity of scFvs in the CARs were controlled.

(1) Antigen Recognition

CD8-positive T cells and CD4-positive T cells expressing the 3M4E5H-L1 CAR were produced in the same manner as in Example 6 above. Next, the T cells and T2 cells were seeded in each well (96-well plate) such that the number of the T cells was 3×10⁵ and the number of the T2 cells was 5×10⁴, and then they were cultured together for 5 hours. Before use, the T2 cells (HLA-A*02:01-expressing cells) were pulsed with the NY-ESO-1$_{157}$ peptide or a mutant peptide of the NY-ESO-1$_{157}$ peptide at a concentration of 10 μg/mL (T2+NY-ESO-1$_{157}$). The mutant peptide is a peptide obtained by substituting one of the amino acids in the amino acid sequence of the NY-ESO-1$_{157}$ peptide with alanine. After the above-mentioned coculture, the culture supernatant was collected, and the concentration of IL-2 in the CAR-Ts was measured in the same manner as in Example 4 above. A control was performed in the same manner, except that CD8-positive T cells or CD4-positive T cells expressing the 3M4E5LH CAR were used. A control 1 was performed in the same manner, except that the A2/HIV-Gag$_{77}$ peptide was used instead of the A2/NY-ESO-1$_{157}$ peptide. A control 2 was performed in the same manner, except that CD8-positive T cells or CD4-positive T cells into which the expression vectors had not been introduced were used. Then, the rates of an increase in cytokine production in the samples were calculated using the cytokine production amount in the control 2 as a standard. FIG. 20 shows the results.

FIG. 20 shows graphs indicating changes in a cytokine production amount. FIG. 20(A) shows the results from T cells expressing the 3M4E5LH CAR, and FIG. 20(B) shows the results from T cells expressing the 3M4E5H-L1 CAR. In FIGS. 20(A) and 20(B), the horizontal axes indicate the types of peptides, and the vertical axes indicate the changes in a cytokine production amount. The 3M4E5LH CAR mainly recognized the amino acids at positions 160 to 162 of the NY-ESO-1$_{157}$ peptide as shown in FIG. 20(A), whereas the 3M4E5H-L1 CAR recognized the amino acids at positions 158, 160 to 162, and 164 of the NY-ESO-1$_{157}$ peptide as shown in FIG. 20(B). It was found from these results that CARs obtained using the screening method of the present invention in which the CAR library of the present invention is used differed from antibodies capable of binding to a target antigen used for screening in antigen recognition.

(2) Crossreactivity

As shown in (1) of Example 7 above, the 3M4E5LH CAR mainly recognized the amino acids at positions 160 to 162 of the NY-ESO-1$_{157}$ peptide, whereas the 3M4E5H-L1 CAR recognized the amino acids at positions 158, 160 to 162, and 164 of the NY-ESO-1$_{157}$ peptide. In order to examine the crossreactivity of the 3M4E5LH CAR and the 3M4E5H-L1 CAR to other peptides, human proteins that include a peptide that is capable of binding to HLA-A*02:01 and that may crossreact with the 3M4E5LH CAR and the 3M4E5H-L1 CAR were predicted using an algorithm (netMHC4.0, http://www.cbs.dtu.dk/services/NetMHC/). The uniprotKB/swissprot was used as the protein database. Moreover, homologous peptides that are highly homologous to the NY-ESO-1$_{157}$ peptide were selected from the peptides in the predicted proteins using an algorithm (ScanProsit, https://prosite.expasy.org/scanprosite/). As a result, Lysophospholipase-like protein 1 (LYPLAL1) protein that included a peptide (Sequence ID No. 207: GLRMWIKQV) that may crossreact therewith was hit. Accordingly, the LYPLAL1 protein was expressed in K562 cells, and the crossreactivity of the 3M4E5LH CAR and the 3M4E5H-L1 CAR was examined.

Retroviruses were used to introduce, into K562 cells (HLA and CD19 were not expressed), a nucleic acid coding for HLA-A*02:01 and a nucleic acid coding for LYPLAL1 (Sequence ID No. 208) or NY-ESO-1 (Sequence ID No. 209) to which ΔNGFR was added via the furin cleavage site, the spacer sequence, and the codon-optimized P2A sequence, and thus antigen-presenting cells (K562/A2/NY-ESO-1 or K562/A2/LYPLAL1) were obtained. Moreover, antigen-presenting cells (K562/A2) were prepared in the same manner, except that the nucleic acid coding for NY-ESO-1 or LYPLAL1 to which ΔNGFR was added was not introduced. The 3M4E5LH CAR-Ts and the 3M4E5H-L1 CAR-Ts were prepared in the same manner as in Example 6, and the CAR-T cells and the antigen-presenting cells were seeded in each well (96-well plate) such that the number of the CAR-T cells was 3×10$^5$ and the number of the antigen-presenting cells was 5×10$^4$, and then they were cultured together for 5 hours. An RPMI1640 culture medium containing FCS at a concentration of 10% was used as the culture solution for the coculture. After the above-mentioned coculture, the CAR-T cells were collected, fixed with paraformaldehyde, subjected to permeabilization, and stained with an APC-labeled anti-human IL-2 mAb (clone: MQ1-17H12), a PE-labeled anti-human TNFα mAb (clone: Mab11), a PC7-labeled anti-human IFN-γ antibody (clone: B27), an FITC-labeled anti-human CD4 mAb (clone: OKT4), a PC5-labeled anti-human CD8α mAb (clone: B9.11), and a V450-labeled anti-human NGFR mAb (clone: C40-1457). After the CAR-Ts were stained, the amounts of TNF-α, IFN-γ, and IL-2 produced by CD8-positive cells or CD4-positive cells in the CAR-Ts (NGFR-positive fraction) were measured using the flow cytometer. In a control 1, K562/A2 into which the NY-ESO-1 gene had not been introduced was used as the APCs. A control 2 was performed in the same manner, except that the expression vectors for expressing the hH-3M4E4L CAR library were not introduced. Then, the rates of an increase in cytokine production in the samples were calculated using the cytokine production amount in the control 2 as a standard. FIG. 21 shows the results.

Nucleic Acid Molecule Coding for LYPLAL1
(Sequence ID No. 208)
5'-ATGGCGGCTGCATCTGGAAGCGTGCTGCAGAGATGTATCGTGTCCC
CAGCCGGCAGACATAGCGCCAGCCTGATTTTTCTGCACGGCAGCGGCGA
TTCTGGCCAGGGACTGAGAATGTGGATCAAACAGGTGCTGAACCAGGAC
CTGACCTTCCAGCACATCAAGATCATCTACCCCACCGCTCCACCTCGGA
GCTACACACCTATGAAGGGCGGCATCAGCAACGTTTGGTTCGACCGGTT
CAAGATCACCAACGACTGCCCCGAGCACCTGGAATCCATCGACGTGATG
TGTCAGGTGCTCACCGACCTGATCGACGAGGAAGTGAAGTCCGGCATCA
AGAAGAACAGAATCCTGATCGGCGGCTTCAGCATGGGCGGCTGTATGGC
CATTCACCTGGCCTACAGAAACCACCAGGATGTGGCTGGCGTGTTCGCC
CTGAGCAGCTTTCTGAACAAAGCCAGCGCCGTGTATCAGGCCCTGCAGA
AATCTAACGGCGTGCTGCCTGAGCTGTTCCAGTGTCATGGCACAGCCGA
TGAGCTGGTGCTGCACTCTTGGGCCGAAGAGACAAATAGCATGCTGAAA
AGCCTGGGCGTGACCACCAAGTTCCACAGCTTCCCCAACGTGTACCACG
AGCTGAGCAAGACCGAGCTGGACATCCTGAAACTGTGGATTCTGACCAA
GCTGCCCGGCGAGATGGAAAAGCAGAAG-3'

Nucleic Acid Molecule Coding for NY-ESO-1
(Sequence ID No. 209)
5'-ATGCAGGCCGAAGGCCGGGGCACAGGGGGTTCGACGGGCGATGCTG
ATGGCCCAGGAGGCCCTGGCATTCCTGATGGCCCAGGGGGCAATGCTGG
CGGCCCAGGAGAGGCGGGTGCCACGGGCGGCAGAGGTCCCCGGGGCGCA
GGGGCAGCAAGGGCCTCGGGGCCGGGAGGAGGCGCCCCGCGGGGTCCGC
ATGGCGGCGCGGCTTCAGGGCTGAATGGATGCTGCAGATGCGGGGCCAG
GGGGCCGGAGAGCCGCCTGCTTGAGTTCTACCTCGCCATGCCTTTCGCG
ACACCCATGGAAGCAGAGCTGGCCCGCAGGAGCCTGGCCCAGGATGCCC
CACCGCTTCCCGTGCCAGGGGTGCTTCTGAAGGAGTTCACTGTGTCCGG
CAACATACTGACTATCCGACTGACTGCTGCAGACCACCGCCAACTGCAG
CTCTCCATCAGCTCCTGTCTCCAGCAGCTTTCCCTGTTGATGTGGATCA
CGCAGTGCTTTCTGCCCGTGTTTTTGGCTCAGCCTCCCTCAGGGCAGAG
GCGC-3'

Figure 21A:
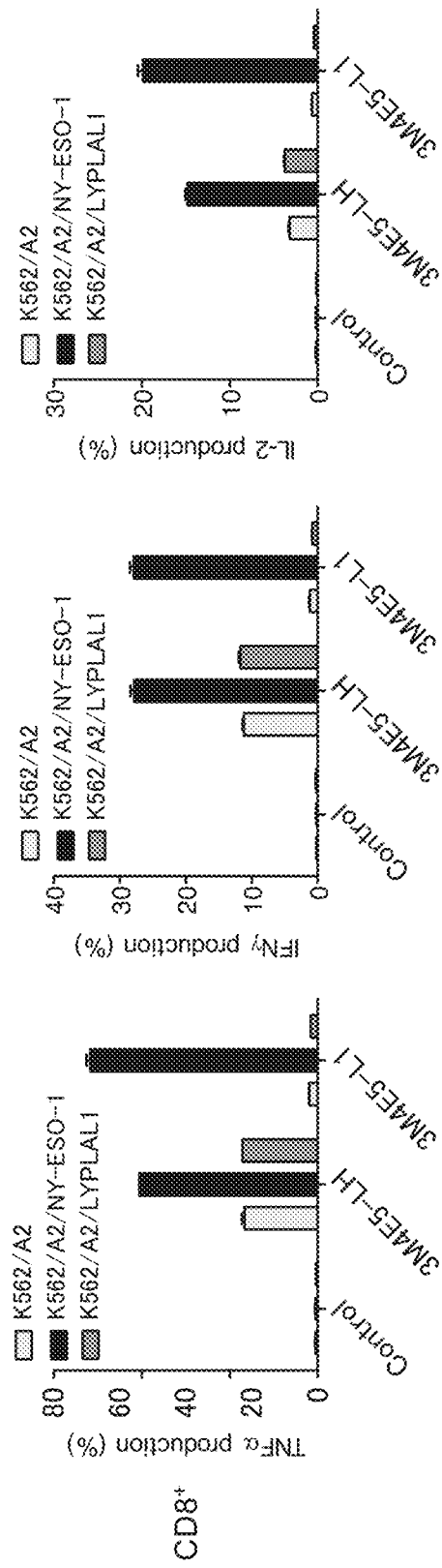
FIG. 21(A) shows the results from CD8-positive T cells.
Figure 21B:
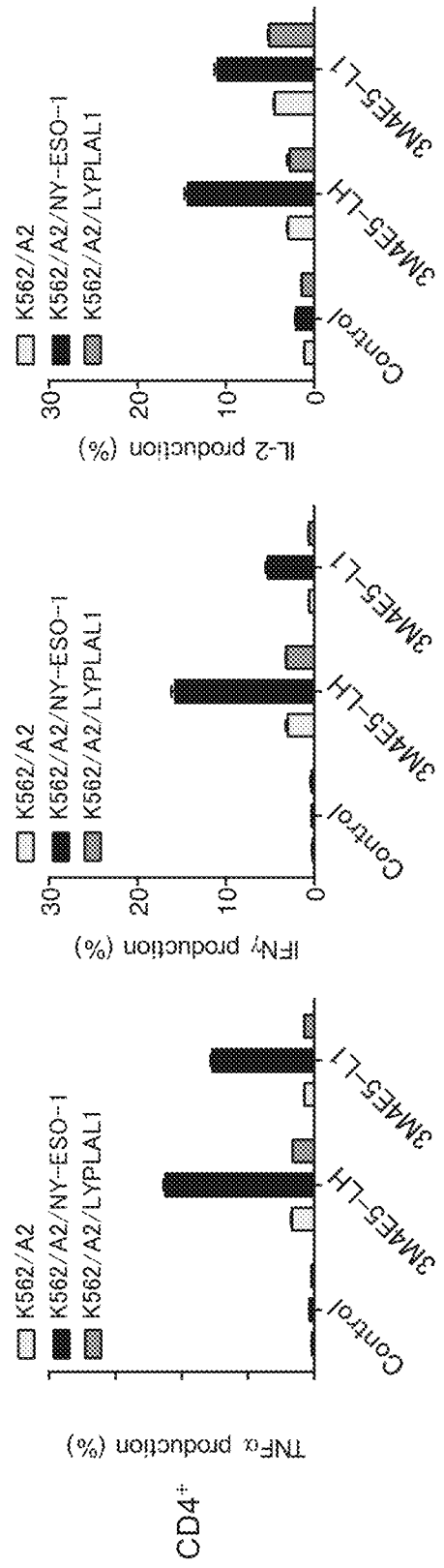
FIG. 21(B) shows the results from CD4-positive T cells.

FIG. 21 shows graphs indicating the ratios of cytokine-producing cells. FIG. 21(A) shows the results from CD8-positive T cells, and FIG. 21(B) shows the results from CD4-positive T cells. In FIG. 21, the horizontal axes of the graphs indicate the types of samples (CARs), and the vertical axes indicate the ratio of TNF-α-positive cells, IFN-γ-positive cells, or IL-2-positive cells. As shown in FIGS. 21(A) and 21(B), the cytokine production did not increase in the control 1 (Control). On the other hand, the T cells expressing the 3M4E5H-L1 CAR or 3M4E5LH CAR produced TNF-α, IFN-γ, and IL-2 in the positive control (K562/A2/NY-ESO-1). Moreover, as shown in FIGS. 21(A) and 21(B), when coculture with the antigen-presenting cell presenting LYPLAL1 (K562/A2/LYPLAL1) was performed, the ratio of cytokine-producing cells in the T cells expressing the 3M4E5LH CAR and 3M4E5H-L1 CAR was nearly equal to that in the case of the control 2 (K562/A2), which corresponds to the background, and no crossreactivity was observed. It was found from these results that the screening method of the present invention in which the CAR library of the present invention is used could control the crossreactivity of scFvs included in CARs.

Example 8

It was confirmed that the antigenic specificity of CARs obtained using the screening method of the present invention in which the CAR library of the present invention is used was changed by arranging the heavy-chain variable region and the light-chain variable region in the reverse order.

Figure 22:
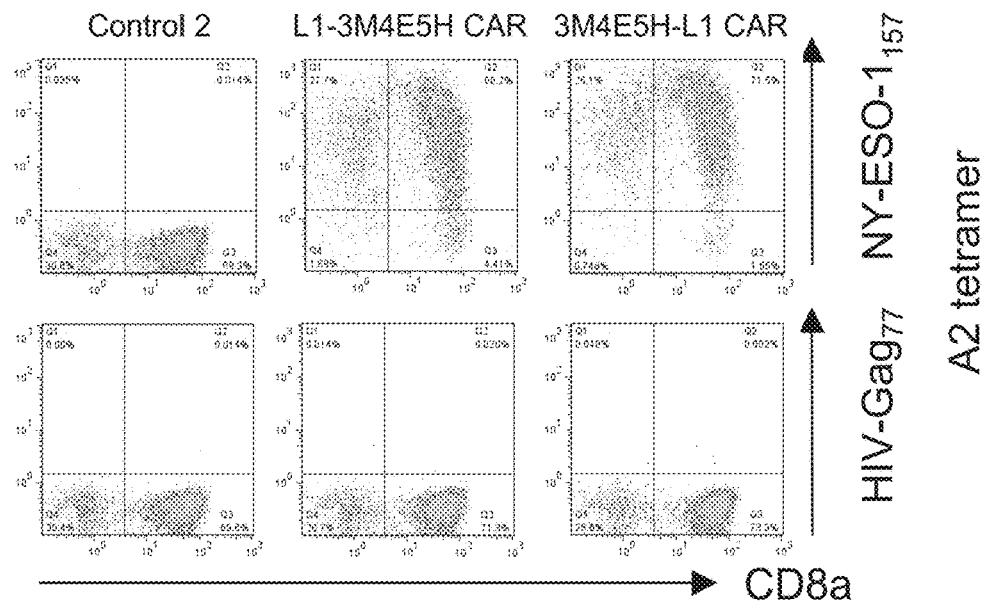
FIG. 22 shows dot plots showing the results of flow cytometry in Example 8.

A culture supernatant containing GaLV-pseudotyped retroviruses was prepared in the same manner as in (3) of Example 1 above, except that the 3M4E5H-L1 expression vector or L1-3M4E5H expression vector was used instead of the expression vectors for expressing the hH-3M4E4L CAR library. Next, T cells were infected with the retroviruses in the same manner as in (3) of Example 1 above, except that the obtained GaLV-pseudotyped retroviruses were used. Thus, the 3M4E5H-L1 expression vector or L1-3M4E5H expression vector was introduced into the T cells. The infection with the retroviruses and the introduction of the 3M4E5H-L1 expression vector or L1-3M4E5H expression vector were performed in the same manner five more times (six times in total). The resulting T cells were stained with the PE-labeled A2/NY-ESO-$1_{157}$ tetramer at a concentration of 20 µg/mL. After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). The concentrations of these antibodies were about 10 µg/mL. Then, it was confirmed using the flow cytometer if the T cells that had been subjected to tetramer staining included T cells expressing CARs capable of binding to the A2/NY-ESO-$1_{157}$. A control 1 was performed in the same manner, except that the A2/HIV-Gag$_{77}$ tetramer was used instead of the A2/NY-ESO-$1_{157}$ tetramer. A control 2 was performed in the same manner, except that the expression vectors for expressing the hH-3M4E4L CAR library were not introduced. FIG. 22 shows the results obtained when gating of FSC$^+$-SSC$^+$-NGFR$^+$ cells was performed.

FIG. 22 shows dot plots showing the results of flow cytometry. In FIG. 22, the horizontal axes indicate the average fluorescence intensity of CD8a, and the vertical axes indicate the average fluorescence intensity of the A2 tetramer. As shown in FIG. 22, in the control 2, T cells capable of binding to the A2/NY-ESO-$1_{157}$ or A2/HIV-Gag$_{77}$ were not present. Moreover, in the case of the CAR-Ts expressing the L1-3M4E5H or 3M4E5H-L1, the CD8$^+$-A2 tetramer$^+$ fraction was present when A2/NY-ESO-$1_{157}$ tetramer staining was performed, and the CD8$^+$-A2 tetramer$^+$ fraction was not present when A2/HIV-Gag$_{77}$ tetramer staining was performed. Furthermore, when the CAR-Ts expressing the L1-3M4E5H and the CAR-Ts expressing the 3M4E5H-L1 included in the CD8$^-$- or CD8$^+$-A2 tetramer$^+$ fraction were compared, the 3M4E5H-L1 CAR-Ts bound more tightly to the A2/NY-ESO-$1_{157}$ than the L1-3M4E5H CAR-Ts did in both the CD8$^-$-A2 tetramer$^+$ fraction and the CD8$^+$-A2 tetramer$^+$ fraction, that is, the antigenic specificity of the 3M4E5H-L1 CAR-Ts was different from that of the L1-3M4E5H CAR-Ts.

Next, it was examined if the T cells that had been infected with the retroviruses bound to the target antigen, and were thus activated to produce cytokines. Specifically, after the infection of T cells (CAR-Ts) with the retroviruses were repeated six times, the T cells, and T2 cells or APCs prepared in (4) of Example 1 above were seeded in each well (96-well plate) such that the number of the T cells was 3×10$^5$ and the number of the T2 cells or APCs was 5×10$^4$, and then they were cultured together for 5 hours. Before use, the T2 cells (HLA-A*02:01-expressing cells) and APCs were pulsed with the NY-ESO-$1_{157}$ peptide at a concentration of 10 µg/mL (T2+NY-ESO-$1_{157}$ and K562/A2/NY-ESO-1). An RPMI1640 culture medium containing FCS at a concentration of 10% was used as the culture solution for the coculture. After the above-mentioned coculture, the T cells were collected, fixed with paraformaldehyde, subjected to permeabilization, and stained with an APC-labeled anti-human IL-2 mAb (clone: MQ1-17H12), a PE-labeled anti-human TNFα mAb (clone: Mab11), a PC7-labeled anti-human IFN-γ antibody (clone: B27), an FITC-labeled anti-human CD4 mAb (clone: OKT4), a PC5-labeled anti-human CD8a mAb (clone: B9.11), and a V450-labeled anti-human NGFR mAb (clone: C40-1457). After the CAR-Ts were stained, the amounts of TNF-α, IFN-γ, and IL-2 produced by CD8-positive cells or CD4-positive cells in the CAR-Ts (NGFR-positive fraction) were measured using the flow cytometer. When the T2 cells were used, a control 1 was performed in the same manner, except that the HIV-Gag$_{77}$ peptide was used instead of the NY-ESO-$1_{157}$ peptide. When the APCs (K562/A2/NY-ESO-1) were used, a control 1 was performed in the same manner, except that K562/A2 into which the NY-ESO-1 gene had not been introduced was used. A control 2 was performed in the same manner, except that the expression vectors for expressing the hH-3M4E4L CAR library were not introduced. Then, the rates of an increase in cytokine production in the samples were calculated using the cytokine production amount in the control 2 as a standard. FIGS. 23 and 24 show the results.

Figure 23A:
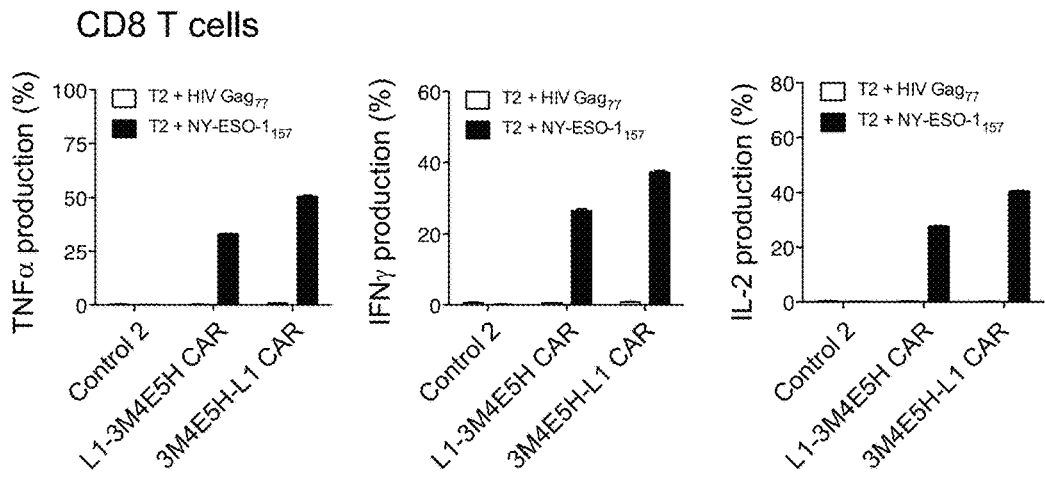
FIG. 23(A) shows the results from CD8-positive T cells.
Figure 23B:
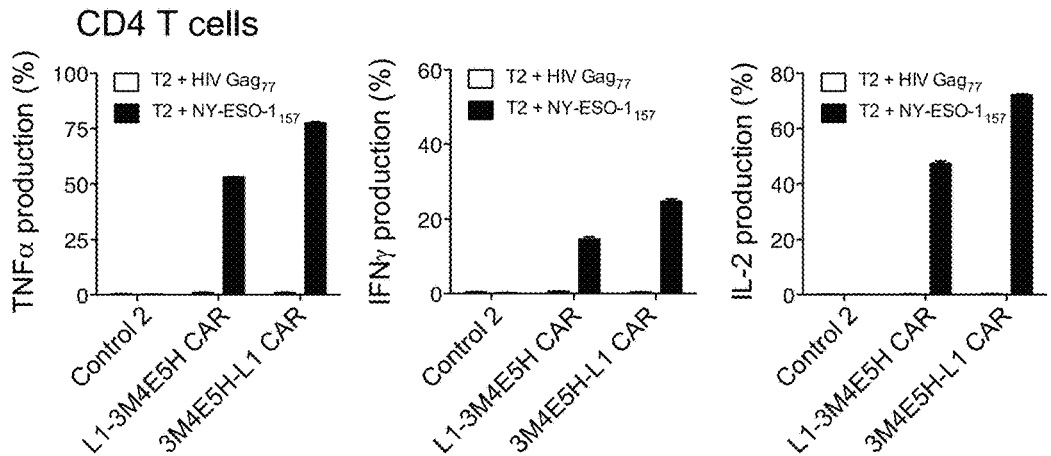
FIG. 23(B) shows the results from CD4-positive T cells.

FIG. 23 shows the results obtained when the T2 cells were used. FIG. 23 shows graphs indicating changes in a cytokine production amount. FIG. 23(A) shows the results from CD8-positive T cells, and FIG. 23(B) shows the results from CD4-positive T cells. In FIG. 23, the horizontal axes indicate the types of samples (CARs), and the vertical axes indicate the rate of an increase in cytokine production. As shown in FIG. 23, the cytokine production did not increase in the control 2. On the other hand, when the L1-3M4E5H CAR-Ts or 3M4E5H-L1 CAR-Ts were stimulated with the T2+NY-ESO-$1_{157}$, it could be confirmed that the cytokine production amount increased compared with the case of the stimulation with the T2+HIV Gag$_{77}$, and the cytokines bound to the A2/NY-ESO-$1_{157}$ to activate the CAR-Ts. Moreover, when the stimulation with T2+NY-ESO-$1_{157}$ was performed, the 3M4E5H-L1 CAR-Ts produced a larger amount of cytokines than the L1-3M4E5H CAR-Ts did.

Figure 24A:
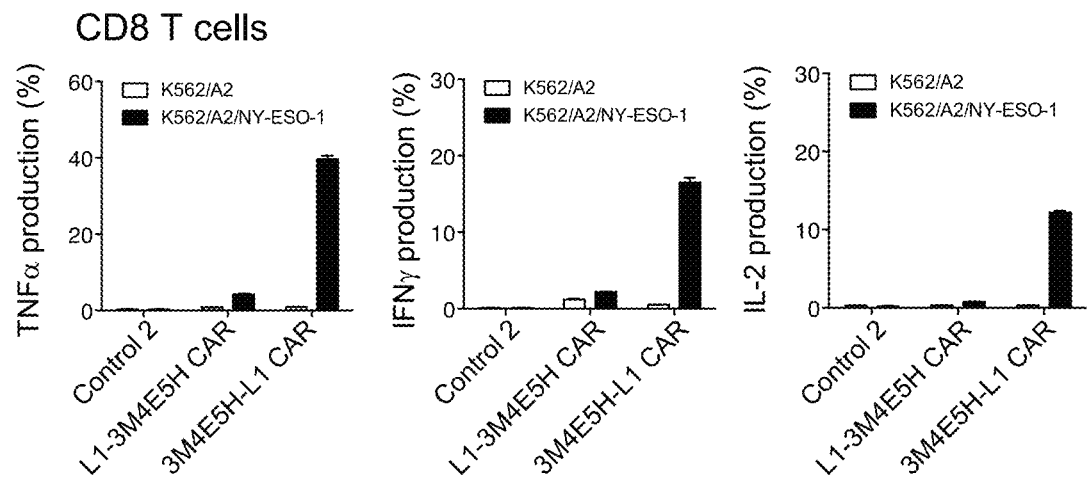
FIG. 24(A) shows the results from CD8-positive T cells.
Figure 24B:
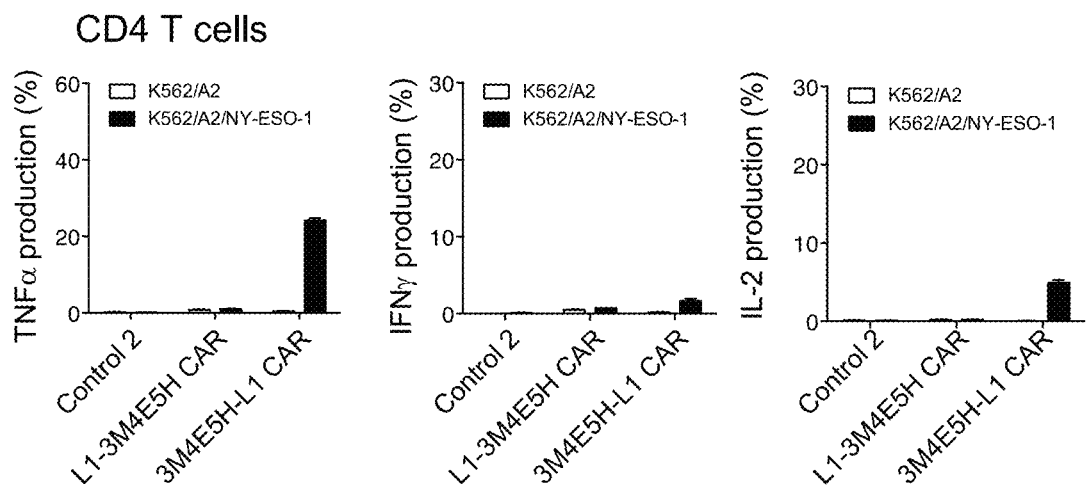
FIG. 24(B) shows the results from CD4-positive T cells.

FIG. 24 shows the results obtained when the APCs were used. FIG. 24 shows graphs indicating changes in a cytokine production amount. FIG. 24(A) shows the results from CD8-positive T cells, and FIG. 24(B) shows the results from CD4-positive T cells. In FIG. 24, the horizontal axes indicate the types of samples (CARs), and the vertical axes indicate the rate of an increase in cytokine production. As shown in FIG. 24, the cytokine production did not increase in the control 2. On the other hand, when the L1-3M4E5H CAR-Ts or 3M4E5H-L1 CAR-Ts were stimulated with the K562/A2/NY-ESO-1, it could be confirmed that the cytokine production amount increased compared with the case of the stimulation with the K562/A2, and the cytokines bound to the K562/A2/NY-ESO-1 to activate the CAR-Ts. Moreover, when the stimulation with the K562/A2/NY-ESO-1 was performed, the 3M4E5H-L1 CAR-Ts produced a larger amount of cytokines than the L1-3M4E5H CAR-Ts did. It was found that the antigenic specificity of CARs obtained using the screening method of the present invention in which the CAR library of the present invention is used was changed by arranging the heavy-chain variable regions and the light-chain variable regions in the reverse order. Moreover, it was found that the specificity, for a target antigen, of CARs obtained using the screening method of the present invention in which the CAR library of the present invention is used could be possibly improved by arranging the heavy-chain variable regions and the light-chain variable regions in the reverse order.

Example 9

It was confirmed that the first screening method of the present invention could be used to screen scFvs that recognize different sites of a target antigen.

First, the CARs expressed by the second candidate CAR-Ts and the CARs expressed by the first candidate CAR-Ts were identified in the same manner as in (9) to (12) of Example 1 above and (1) to (3) of Example 2 above, and thus new CARs (L52-3M4E5H CAR and K156-H1 CAR) were obtained. The underlined sequences in the following amino acid sequences and base sequences correspond to the amino acid sequences or base sequences of the CDRL1, the CDRL2, and the CDRL3 of L52 or L156.

```
L52-3M4E5H CAR
                                    (Sequence ID No. 210)
QSVLTQPPSVSGAPGQRVTISCTGSSSNLGAGYDVHWYQQLPGTAPKL

LIYGSTTRPSGIPDRFSGSKSGTSATLGITGLQTGDEADYYCGTWDSSL

SAGVFGGGTQLTVLGSTSGSGKPGSGEGSTKGEVQLLESGGGLVQPGGS

LRLSCAASGFTFSTYQMSWVRQAPGKGLEWVSGIVSSGGSTAYADSVKG

RFTISRDNSKNTLYLQMNSLRAEDTAVYYCAGELLPYYGMDVWGQGTTV

TVSSAAAIEVMYPPPYLDNEKSNGTIIHVKGKHLCPSPLFPGPSKPFWV

LVVVGGVLACYSLLVTVAFIIFWVRSKRSRLLHSDYMNMTPRRPGPTRK

HYQPYAPPRDFAAYRSRVKFSRSADAPAYQQGQNQLYNELNLGRREEYD

VLDKRRGRDPEMGGKPRRKNPQEGLYNELQKDKMAEAYSEIGMKGERRR

GKGHDGLYQGLSTATKDTYDALHMQALPPR

Polynucleotide Coding for L52-3M4E5H CAR
                                    (Sequence ID No. 211)
5'-CAGTCTGTGCTGACGCAGCCGCCCTCAGTGTCTGGGGCCCCAGGGC

AGAGGGTCACCATCTCCTGCACTGGGAGCAGCTCCAACCTCGGGGCAGG

TTATGATGTACACTGGTACCAGCAGCTTCCAGGAACAGCCCCCAAACTC

CTCATCTATGGTAGCACCACTCGGCCCTCAGGGATTCCTGACCGATTCT

CTGGCTCCAAGTCTGGCACGTCAGCCACCCTGGGCATCACCGGACTCCA

GACTGGGGACGAGGCCGATTATTACTGCGGAACATGGGATAGCAGCCTG

AGTGCTGGGGTGTTCGGCGGAGGCACCCAGCTGACCGTCCTCGGCTCTA

CAAGCGGCTCTGGCAAGCCTGGATCTGGCGAGGGAAGCACCAAGGGCGA

AGTGCAGCTGCTGGAATCTGGCGGCGGACTGGTGCAGCCTGGCGGATCT

CTGAGACTGAGCTGTGCCGCCAGCGGCTTCACCTTCAGCACCTACCAGA

TGAGCTGGGTGCGCCAGGCCCCTGGCAAAGGACTGGAATGGGTGTCCGG

CATCGTGTCCAGCGGCGGCTCTACAGCCTACGCCGATAGCGTGAAGGGC

CGGTTCACCATCAGCCGGGACAACAGCAAGAACACCCTGTACCTGCAGA

TGAACAGCCTGAGAGCCGAGGACACCGCCGTGTACTATTGTGCCGGGGA

GCTGCTGCCCTACTACGGCATGGATGTGTGGGGCCAGGGCACCACCGTG

ACAGTGTCCTCAGCGGCCGCAATCGAAGTGATGTACCCCCCTCCCTACC

TGGACAACGAGAAGTCCAACGGCACCATTATCCACGTGAAGGGAAAGCA

CCTGTGCCCCAGCCCTCTGTTCCCTGGCCCTAGCAAGCCTTTCTGGGTG

CTGGTGGTCGTGGGCGGAGTGCTGGCCTGTTATAGCCTGCTCGTGACCG

TGGCCTTCATCATCTTTTGGGTGCGCAGCAAGCGGAGCCGGCTGCTGCA

CAGCGACTACATGAACATGACCCCCAGACGGCCCGGACCCACCAGAAAG

CACTACCAGCCTTACGCCCCTCCCAGAGACTTCGCCGCCTACAGATCTC

GAGTGAAGTTCAGCAGAAGCGCCGACGCCCCTGCCTATCAGCAGGGCCA

GAACCAGCTGTACAACGAGCTGAACCTGGGCAGACGGGAAGAGTACGAC

GTGCTGGACAAGCGGAGAGGCAGGGACCCTGAGATGGGCGGCAAGCCCA

GAAGAAAGAACCCCCAGGAAGGCCTGTATAACGAACTGCAGAAAGACAA

GATGGCCGAGGCCTACAGCGAGATCGGCATGAAGGGCGAGCGGAGAAGA

GGCAAGGGCCACGATGGCCTGTACCAGGGCCTGAGCACCGCCACCAAGG

ACACCTATGACGCCCTGCACATGCAGGCCCTGCCCCCCAGA-3'

K156-H1 CAR
                                    (Sequence ID No. 212)
EIVLTQSPATLSVSPGERATLSCRASQSVSSNLAWYQQKPGQAPRLLIY

GASTRATGIPARFSGSGSGTEFTLTISRLEPEDFAVYYCQQYNNWPPKF

TFGPGTKVDIRGSTSGSGKPGSGEGSTKGQVQLQESGPGLVKPSDTLSL

TCLVSGGSISSNYWSWIRQAPGKGLEWIGHVSYSGSTNYNPSLKSRVTI

SVDTSKNQFSLKLSSVTAADTAVYYCARESYYYYGMDVWGQGTTVTVSS

AAAIEVMYPPPYLDNEKSNGTIIHVKGKHLCPSPLFPGPSKPFWVLVVV

GGVLACYSLLVTVAFIIFWVRSKRSRLLHSDYMNMTPRRPGPTRKHYQP

YAPPRDFAAYRSRVKFSRSADAPAYQQGQNQLYNELNLGRREEYDVLDK

RRGRDPEMGGKPRRKNPQEGLYNELQKDKMAEAYSEIGMKGERRRGKGH

DGLYQGLSTATKDTYDALHMQALPPR

Polynucleotide Coding for K156-H1 CAR
                                    (Sequence ID No. 213)
5'-GAAATTGTGTTGACGCAGTCTCCAGCCACCCTGTCTGTGTCTCCAG

GGGAAAGAGCCACCCTCTCCTGCAGGGCCAGTCAGAGTGTTAGCAGCAA

CTTAGCCTGGTACCAGCAGAAACCTGGCCAGGCTCCCAGGCTCCTCATC

TATGGTGCATCCACCAGGGCCACTGGTATCCCAGCCAGGTTCAGTGGCA

GTGGGTCTGGGACAGAGTTCACTCTCACCATCAGCAGACTGGAGCCTGA

AGATTTTGCAGTGTATTACTGTCAGCAGTATAATAACTGGCCTCCGAAA

TTCACTTTCGGCCCTGGGACCAAAGTGGATATCAGAGGCTCTACAAGCG

GCTCTGGCAAGCCTGGATCTGGCGAGGGAAGCACCAAGGGCCAGGTGCA

GCTGCAGGAGTCGGGCCCAGGACTGGTGAAGCCTTCGGATACCCTGTCC

CTCACCTGTCTTGTCTCTGGTGGCTCCATCAGTAGTAATTACTGGAGCT

GGATCCGGCAGGCCCCAGGGAAGGGACTGGAGTGGATTGGACATGTCTC
```

-continued
```
CTACAGTGGGAGCACCAACTACAACCCCTCCCTCAAGAGTCGAGTTACC

ATATCAGTAGACACGTCTAAGAACCAGTTCTCCCTGAAGCTGAGCTCTG

TGACTGCCGCGGACACGGCCGTGTATTACTGTGCGAGAGAGTCCTACTA

CTACTACGGTATGGACGTCTGGGGCCAAGGGACCACGGTCACCGTCTCC

TCAGCGGCCGCAATCGAAGTGATGTACCCCCCTCCCTACCTGGACAACG

AGAAGTCCAACGGCACCATTATCCACGTGAAGGGAAAGCACCTGTGCCC

CAGCCCTCTGTTCCCTGGCCCTAGCAAGCCTTTCTGGGTGCTGGTGGTC

GTGGGCGGAGTGCTGGCCTGTTATAGCCTGCTCGTGACCGTGGCCTTCA

TCATCTTTTGGGTGCGCAGCAAGCGGAGCCGGCTGCTGCACAGCGACTA

CATGAACATGACCCCCAGACGGCCCGGACCCACCAGAAAGCACTACCAG

CCTTACGCCCCTCCCAGAGACTTCGCCGCCTACAGATCTCGAGTGAAGT

TCAGCAGAAGCGCCGACGCCCCTGCCTATCAGCAGGGCCAGAACCAGCT

GTACAACGAGCTGAACCTGGGCAGACGGGAAGAGTACGACGTGCTGGAC

AAGCGGAGAGGCAGGGACCCTGAGATGGGCGGCAAGCCCAGAAGAAAGA

ACCCCCAGGAAGGCCTGTATAACGAACTGCAGAAAGACAAGATGGCCGA

GGCCTACAGCGAGATCGGCATGAAGGGCGAGCGGAGAAGAGGCAAGGGC

CACGATGGCCTGTACCAGGGCCTGAGCACCGCCACCAAGGACACCTATG

ACGCCCTGCACATGCAGGCCCTGCCCCCCAGA-3'
```

Figure 25:
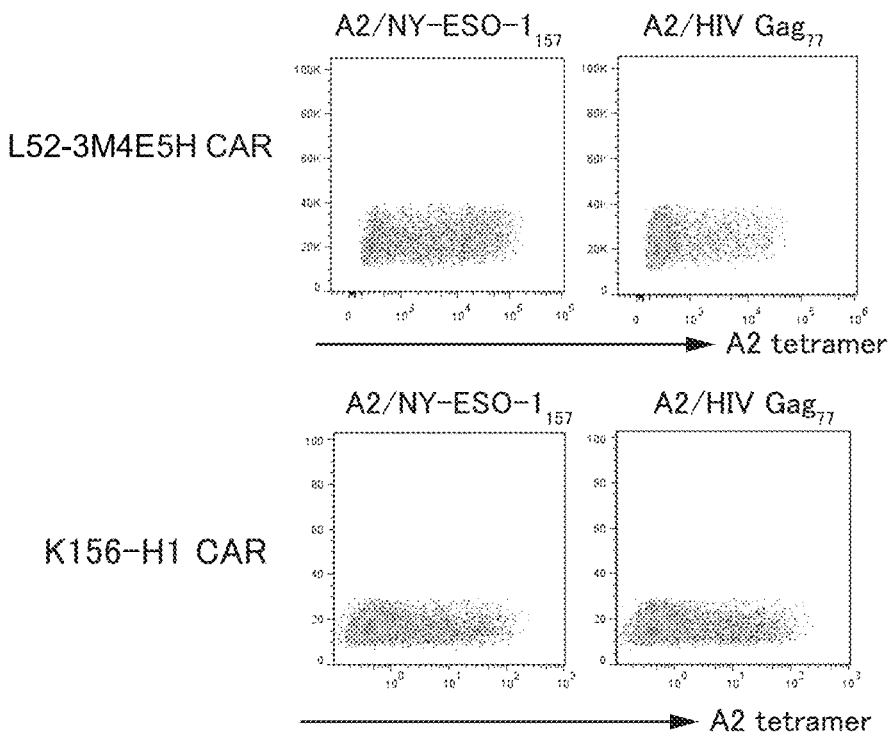
FIG. 25 shows dot plots showing the results of flow cytometry in Example 9.
Figure 26:
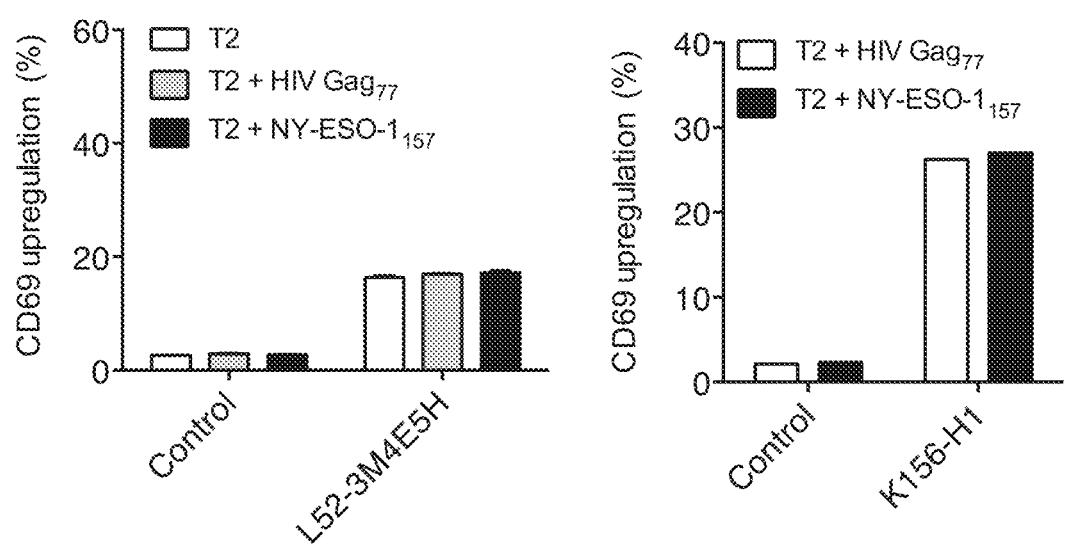
FIG. 26 is graphs indicating changes in a CD69 expression level in Example 9.

The ability to bind to the A2/NY-ESO-1$_{157}$ tetramer and the A2/HIV-Gag$_{77}$ tetramer, and the rate of an increase in CD69 expression were analyzed by flow cytometry in the same manner as in (6) and (8) of Example 1 above, except that a CAR expression vector was used into which a polynucleotide coding for the L52-3M4E5H CAR or K156-H1 CAR had been introduced instead of the polynucleotides coding for scFvs included in the expression vectors for expressing the hH-3M4E4L CAR library. A control 1 was performed in the same manner, except that the rate of an increase in CD69 expression was analyzed without adding the CAR-Ts. A control 2 was performed in the same manner, except that pulsing with the NY-ESO-1$_{157}$ peptide or HIV Gag$_{77-85}$ peptide was not performed. FIGS. 25 and 26 show the results.

FIG. 25 shows dot plots showing the results of flow cytometry. In FIG. 25, the horizontal axes indicate the average fluorescence intensity resulting from A2/NY-ESO-1$_{157}$ tetramer staining or A2/HIV-Gag$_{77}$ tetramer staining, and the vertical axes indicate the average side scatter (SSC) intensity. As shown in FIG. 25, the L52-3M4E5H CAR-Ts and the K156-H1 CAR-Ts included fractions that had been stained with both the A2/NY-ESO-1$_{157}$ tetramer and the A2/HIV-Gag$_{77}$ tetramer. That is, the L52-3M4E5H CAR and the K156-H1 CAR bound to the A2/NY-ESO-1$_{157}$ and the A2/HIV-Gag$_{77}$. It is inferred that this is because the scFvs of the L52-3M4E5H CAR and the K156-H1 CAR recognize and bind to sites closer to an HLA molecule in a complex of the peptide and the HLA molecule compared with the scFv and the like of the L1-3M4E5H CAR.

FIG. 26 shows graphs indicating changes in a CD69 expression level obtained when the peptide concentration was 10 μg/mL. In FIG. 26, the horizontal axes indicate the types of samples, and the vertical axes indicate the rate of an increase in CD69 expression. As shown in FIG. 26, the CD69 expression did not increase in the control 1. On the other hand, when the L52-3M4E5H CAR-Ts and the K156-H1 CAR-Ts were stimulated with the antigen-presenting cells (control 2, T2) that had not been pulsed with the peptide and the antigen-presenting cells that had been pulsed with the A2/NY-ESO-1$_{157}$ (T2+NY-ESO-1$_{157}$) or the A2/HIV-Gag$_{77}$ (T2+HIV Gag$_{57}$), the CD69 expression increased. Since CD69 was also expressed in the control 2, it was corroborated that the scFvs of the L52-3M4E5H CAR and the K156-H1 CAR recognize and bind to sites closer to an HLA molecule in a complex of the peptide and the HLA molecule compared with the scFv and the like of the L1-3M4E5H CAR.

It was found from these results that the first screening method of the present invention could be used to screen scFvs that recognize different sites of a target antigen. That is, it was found that scFvs having the ability to bind to different sites of a target antigen could be screened.

Example 10

It was confirmed that the screening method of the present invention in which the CAR library of the present invention is used could be used to screen scFvs capable of binding to CD19.

(1) Preparation of Clone 18 CARs

A clone 18 scFv or a nucleic acid coding for the clone 18 scFv was prepared in the same manner as in (1) of Example 3 above, except that the heavy-chain variable region and the light-chain variable region of a human CD19-specific antibody (clone18 (see WO 2016/033570)) were used instead of the heavy-chain variable region and the light-chain variable region of the human CD19-specific antibody FMC63. The nucleic acid was introduced into a pMX expression vector. It should be noted that the amino acid sequences that correspond to the heavy-chain variable region and the light-chain variable region in the scFv were underlined.

```
clone18LH scFv
                                (Sequence ID No. 214)
QSALTQPRSVSGFPGQSVTISCTGTTSDDVSWYQQHPGKAPQLMLYDV

SKRPSGVPHRFSGSRSGRAASLIISGLQTEDEADYFCCSYAGRYNSVLF

GGGTKLTVLGSTSGSGKPGSGEGSTKGEVQLVESGGGLVQPGRSLRLSC

AASGFTFDDYAMHWVRQAPGKGLEWVSGISWNSGRIGYADSVKGRFTIS

RDNAKNSLFLQMNSLRAEDTAVYYCARDQGYHYYDSAEHAFDIWGQGTV

VTVSS

Nucleic Acid Coding for clone 18LH scFv
                                (Sequence ID No. 215)
5'-CAATCTGCTCTGACACAGCCTAGAAGCGTGTCCGGCTTTCCTGGCC

AGAGCGTGACCATCAGCTGTACCGGCACCACCTCCGATGACGTGTCCTG

GTATCAGCAGCATCCTGGCAAAGCCCCTCAGCTGATGCTGTACGACGTG

TCCAAAAGACCTAGCGGCGTGCCCCACAGATTCAGCGGATCTAGAAGTG

GCAGAGCCGCCAGCCTGATCATCTCTGGACTGCAGACAGAGGACGAGGC

CGACTACTTCTGCTGTAGCTACGCCGGCAGATACAACAGCGTGCTGTTT

GGCGGCGGAACAAAGCTGACAGTGCTGGGCTCTACAAGCGGCTCTGGCA

AGCCTGGATCTGGCGAGGGAAGCACCAAGGGCGAAGTGCAGCTTGTGGA

ATCTGGCGGAGGACTGGTGCAGCCTGGAAGAAGCCTGAGACTGTCTTGT

GCCGCCAGCGGCTTCACCTTCGACGATTATGCCATGCACTGGGTCCGAC
```

```
-continued
AGGCCCCTGGAAAAGGCCTTGAATGGGTGTCCGGCATCTCTTGGAACAG

CGGCAGAATCGGCTACGCCGACTCTGTGAAGGGCAGATTCACCATCAGC

CGGGACAACGCCAAGAACAGCCTGTTCCTGCAGATGAACTCCCTGAGAG

CCGAGGACACCGCCGTGTACTACTGTGCCAGAGATCAGGGCTACCACTA

CTACGACTCTGCCGAGCACGCCTTCGATATCTGGGGCCAGGGAACAGT

GGTCACCGTTAGTTCT-3'
```

(2) Preparation of First CAR Library

An hK-clone18H scFv library and an hL-clone18H scFv library were prepared by substituting the nucleic acid coding for the light-chain variable region on the 5' side of the nucleic acid coding for the clone18LH scFv described in (1) of Example 10 above with a library that included nucleic acids of the light-chain variable regions derived from human peripheral blood B cells. Then, the hK-clone18H scFv library and the hL-clone18H scFv library were prepared in the same manner as in (2) of Example 1 above, except that the hK-clone18H scFv library and the hL-clone18H scFv library were used instead of the nucleic acid coding for the 3M4E5LH scFv. Next, expression vectors for expressing an hK-clone18H CAR library and an hL-clone18H CAR library were prepared by introducing, into pMX expression vectors, the hK-clone18H scFv library and the hL-clone18H scFv library such that a nucleic acid coding for the partial region, the transmembrane domain, and the intracellular signaling domain of human CD28 described in (1) of Example 1 and a nucleic acid coding for the intracellular signaling domain of human CD3ζ were arranged in the stated order on the 3' end side of the library. It should be noted that, regarding the heterogeneity of the light-chain variable regions in the hK-clone18H CAR library and the hL-clone18H CARs, it was confirmed through restriction enzyme mapping and sequencing of the regions using the Sanger's method that the number of types of light-chain variable regions was about $1\times10^6$.

(3) Preparation of First CAR Library-Expressing T Cells (First Candidate CAR-Ts)

The hK-clone18H CAR library and the hL-clone18H CAR library were introduced into T cells in the same manner as in (3) of Example 1 above, except that the expression vectors for expressing the hK-clone18H CAR library and the hL-clone18H CAR library were used instead of the expression vectors for expressing the hH-3M4E4L CAR library. Then, the resulting T cells were purified and used as first candidate CAR-Ts.

(4) Preparation of Target Antigen-Expressing Cells

In the same manner as in (4) of Example 3 above, retroviruses were used to introduce the nucleic acid coding for human CD19 into K562 cells, and thus antigen-presenting cells (APCs-CD19) were obtained.

(5) First Screening Method

First candidate CAR-Ts expressing hK-clone18H CARs or hL-clone18H CARs capable of binding to human CD19 was enriched in the same manner as in (5) of Example 3 above, except that the first candidate CAR-Ts described in (3) of Example 10 above and the APCs-CD19 prepared in (4) of Example 10 above were used.

Figure 27:
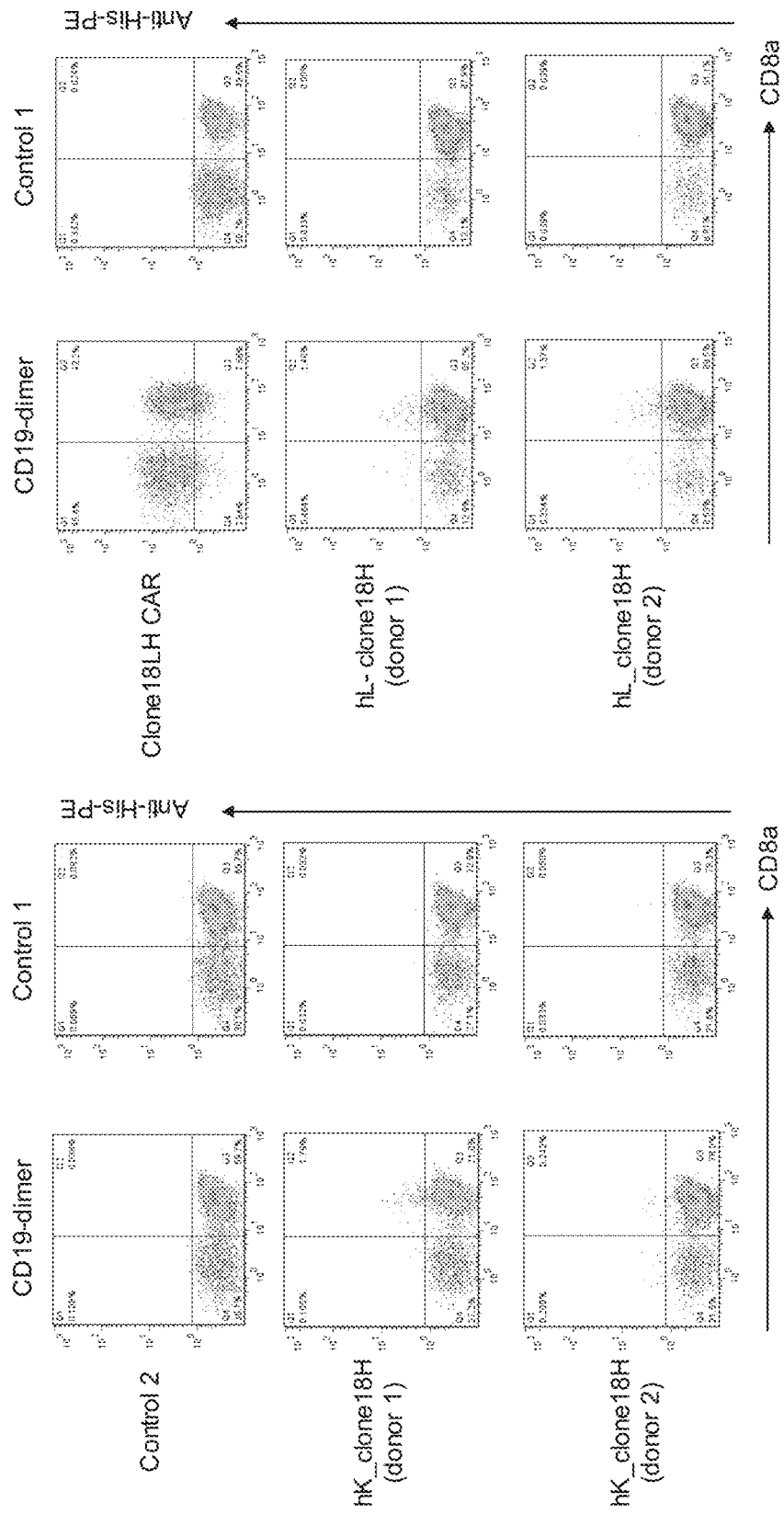
FIG. 27 shows dot plots showing the results of flow cytometry in Example 10.

Next, after the enrichment of the first candidate CAR-Ts, the first candidate CAR-Ts were collected and stained with a PE-labeled CD19 dimer at a concentration of 40 μg/mL. The PE-labeled CD19 dimer was prepared using a soluble CD19, which is human CD19 that includes a His-tag added to the C terminus of the extracellular domain thereof via an SGSG linker. Specifically, the PE-labeled CD19 dimer was prepared by mixing the soluble CD19 and a PE-labeled anti-His mAb (clone: GG11-8F3.5.1) such that the molar ratio therebetween was 2:1. After the above-mentioned staining, the T cells were further stained with a PC5-labeled anti-human CD8a mAb (clone: B9.11), an FITC-labeled anti-human CD4 mAb (clone: OKT4), and a V450-labeled anti-human NGFR mAb (clone: C40-1457). Then, regarding the first candidate CAR-Ts that had been subjected to dimer staining, it was confirmed using the flow cytometer if first candidate CAR-Ts expressing CARs capable of binding to CD19 were present. A positive control was performed in the same manner, except that an expression vector that included a nucleic acid coding for the clone18LH CAR was used instead of the expression vectors for expressing the hK-clone18H CAR library and the hL-clone18H CAR library. A control 1 was performed in the same manner, except that CD19 dimer staining was not performed. A control 2 was performed in the same manner, except that the expression vectors for expressing the hK-clone18H CAR library and the hL-clone18H CAR library were not introduced. The same test was performed using a library that included nucleic acids of light-chain variable regions derived from human peripheral blood B cells obtained from another healthy subject (donor 2). FIG. 27 shows the results obtained when gating of $FSC^+$-$SSC^+$-$NGFR^+$ cells was performed.

FIG. 27 shows dot plots showing the results of flow cytometry. In FIG. 27, the horizontal axes indicate the average fluorescence intensity of CD8a, and the vertical axes indicate the average fluorescence intensity of the CD19 dimer. As shown in FIG. 27, the T cells (control 2) into which the expression vectors for expressing the hK-clone18H CAR library and the hL-clone18H CAR library had not been introduced did not include T cells capable of binding to the CD19 dimer. Moreover, it could be confirmed that the CAR-Ts (clone18LH, positive control) expressing the clone18LH CAR were capable of binding to the CD19 dimer because a $CD19\ dimer^+$ fraction (the upper right fraction in each dot plot) was present when CD19 dimer staining was performed, and the $CD19\ dimer^+$ fraction was not present when CD19 dimer staining was not performed. Furthermore, in all the groups of the first candidate CAR-Ts into which the expression vectors for expressing the hK-clone18H CAR library and the hL-clone18H CAR library had been introduced, the $CD19\ dimer^+$ fraction was present when CD19 dimer staining was performed, and the $CD19\ dimer^+$ fraction was not present when CD19 dimer staining was not performed. As a result, it was found that the first candidate CAR-Ts included first candidate CAR-Ts expressing CARs capable of binding to the CD19 dimer. It was found from these results that the first screening method of the present invention could be used to screen scFvs capable of binding to a target antigen even when different antibodies were used.

Next, first candidate CAR-Ts expressing CARs capable of binding to CD19 were selected, and the CARs expressed by the first candidate CAR-Ts were identified. Specifically, the first candidate CAR-Ts were stained in the same manner as in (5) of Example 10 above. Then, cell sorting was performed on the first candidate CAR-Ts using a flow cytometer (FACSAria (registered trademark), manufactured by Becton Dickinson), and thus an $NGFR^+$-$CD8^+$-$CD19\ dimer^+$ fraction or $NGFR^+$-$CD4^+$-$CD19\ dimer^+$ fraction was collected as first candidate CAR-Ts expressing CARs capable of binding to CD19. The total RNA was extracted from the obtained first candidate CAR-Ts using a total RNA extraction reagent (TRIzol (registered trademark), manufactured by Ambion). cDNA was synthesized from the total RNA using a reverse transcriptase (Superscript (registered trademark) III, manufactured by Thermo Fisher Scientific).

PCR in which the obtained cDNA and a mixture of the forward primer 1 (Sequence ID No. 199) and the reverse primer 1 (Sequence ID No. 200) were used was performed to amplify nucleic acids coding for scFvs. A cloning kit (Gibson Assembly Master Mix, manufactured by New England Biolab) was used to introduce the obtained nucleic acids coding for scFvs into pMX/CAR expression vectors (pMX/scFv expression vectors) such that the nucleic acid coding for an scFv bound to the 5' end of the partial region of human CD28. The pMX/CAR expression vectors were prepared by linking a nucleic acid (Sequence ID No. 169) coding for the partial region, the transmembrane domain, and the intracellular signaling domain of human CD28 and a nucleic acid (Sequence ID No. 171) coding for the intracellular signaling domain of human CD3ζ such that these nucleic acids were arranged in the stated order from the 5' end side and introducing the thus obtained product into the pMX expression vector. Then, sequencing of the obtained pMX/scFv expression vectors was performed using the Sanger's method, and thus base sequences coding for CARs (a polynucleotide (Sequence ID No. 298) coding for an L4-18H CAR, a polynucleotide (Sequence ID No. 299) coding for an L7-18H CAR, a polynucleotide (Sequence ID No. 300) coding for an L9-18H CAR, a polynucleotide (Sequence ID No. 301) coding for an L13-18H CAR, a polynucleotide (Sequence ID No. 302) coding for an L14-18H CAR, a polynucleotide (Sequence ID No. 303) coding for an L16-18H CAR, a polynucleotide (Sequence ID No. 304) coding for an L17-18H CAR, a polynucleotide (Sequence ID No. 305) coding for an L22-18H CAR, a polynucleotide (Sequence ID No. 306) coding for a K4-18H CAR, a polynucleotide (Sequence ID No. 307) coding for a K5-18H CAR, a polynucleotide (Sequence ID No. 308) coding for a K6-18H CAR, a polynucleotide (Sequence ID No. 309) coding for a K9-18H CAR, and a polynucleotide (Sequence ID No. 310) coding for a K10-18H CAR) were identified. Moreover, the amino acid sequences of the scFvs (L4-18H (Sequence ID No. 272), L7-18H (Sequence ID No. 273), L9-18H (Sequence ID No. 274), L13-18H (Sequence ID No. 275), L14-18H (Sequence ID No. 276), L16-18H (Sequence ID No. 277), L17-18H (Sequence ID No. 278), L22-18H (Sequence ID No. 279), K4-18H (Sequence ID No. 280), K5-18H (Sequence ID No. 281), K6-18H (Sequence ID No. 282), K9-18H (Sequence ID No. 283), and K10-18H (Sequence ID No. 284)) were identified based on the above-mentioned base sequences. Then, the CDRL1, CDRL2, and the CDRL3 in the new light-chain variable regions (LA) to (LM), which are shown in Table 3B above, were identified based on the amino acid sequences of the scFvs. Furthermore, the pMX/scFv expression vectors were used to prepare expression vectors that included the polynucleotides coding for the CARs (a pMX/L4-18H expression vector, a pMX/L7-18H expression vector, a pMX/L9-18H expression vector, a pMX/L13-18H expression vector, a pMX/L14-18H expression vector, a pMX/L16-18H expression vector, a pMX/L17-18H expression vector, a pMX/L22-18H expression vector, a pMX/K4-18H expression vector, a pMX/K5-18H expression vector, a pMX/K6-18H expression vector, a pMX/K9-18H expression vector, and a pMX/K10-18H expression vector).

(6) Analysis of First Candidate scFvs

Figure 28:
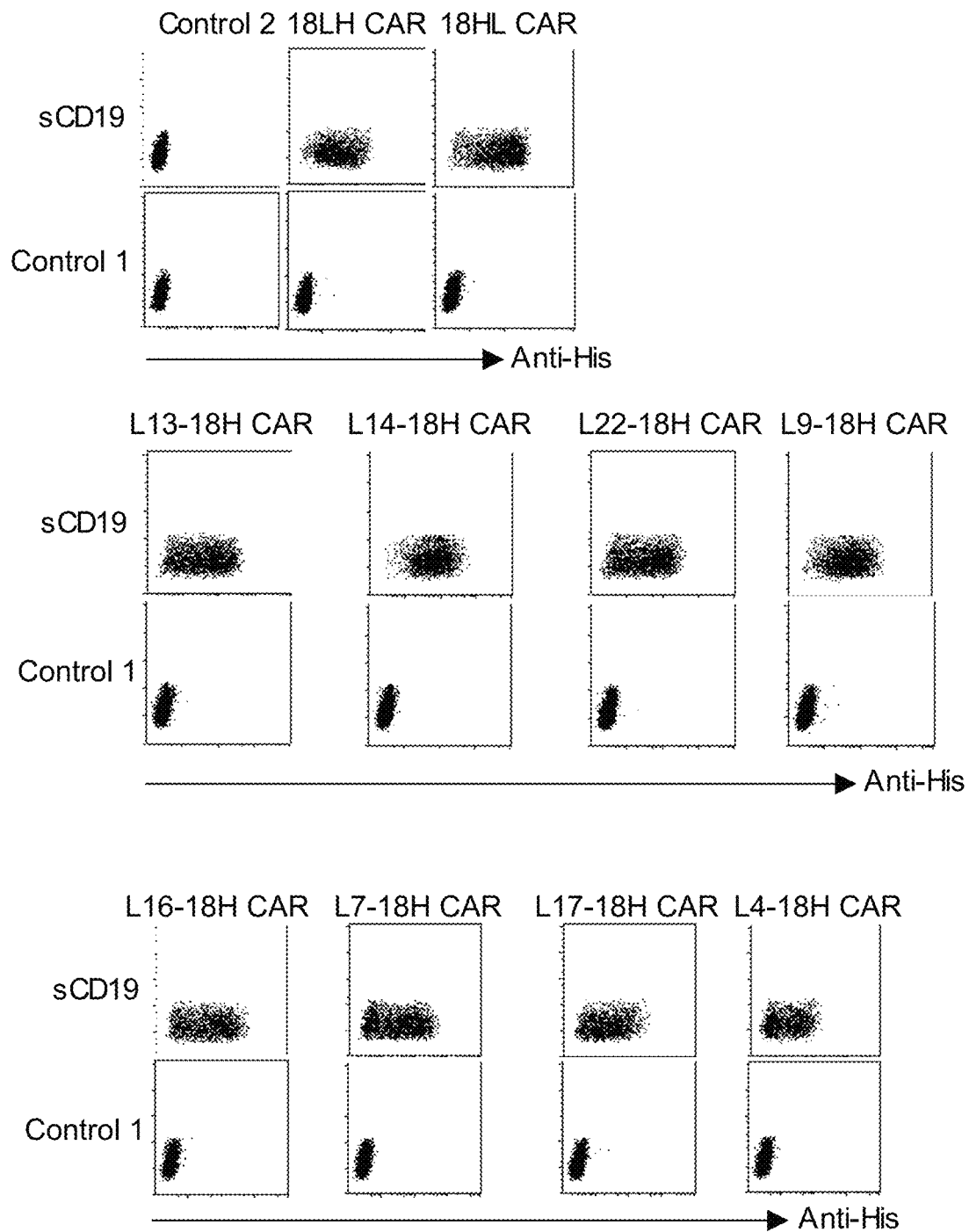
FIG. 28 shows dot plots showing the results of flow cytometry in Example 10.
Figure 29:
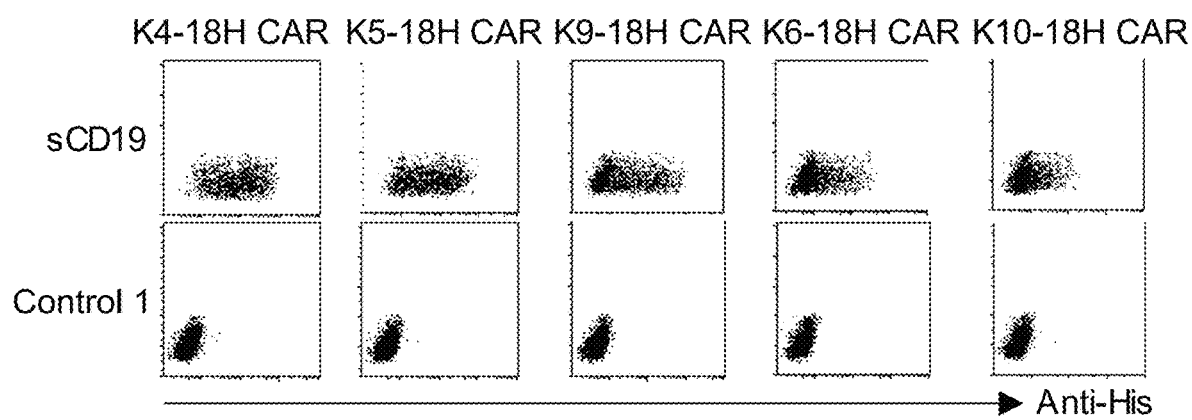
FIG. 29 shows dot plots showing the results of flow cytometry in Example 10.

A culture supernatant containing GaLV-pseudotyped retroviruses was prepared in the same manner as in (3) of Example 10 above, except that the expression vectors that included the polynucleotides coding for the CARs were used instead of the expression vectors for expressing the hK-clone18H CAR library and the hL-clone18H CAR library. Next, the expression vectors that included the polynucleotides coding for the CARs were introduced into Jurkat 76 cells by adding the above-mentioned culture supernatant containing GaLV-pseudotyped retroviruses, and a CAR (an L4-18H CAR, an L7-18H CAR, an L9-18H CAR, an L13-18H CAR, an L14-18H CAR, an L16-18H CAR, an L17-18H CAR, an L22-18H CAR, a K4-18H CAR, a K5-18H CAR, a K6-18H CAR, a K9-18H CAR, or a K10-18H CAR) that included the L4-18H, L7-18H, L9-18H, L13-18H, L14-18H, L16-18H, L17-18H, L22-18H, K4-18H, K5-18H, K6-18H, K9-18H, or K10-18H as an scFv was expressed. The Jurkat 76 cells that had expressed the CARs were reacted with the PE-labeled anti-human NGFR mAb. After the above-mentioned reaction, Jurkat 76 cells (L4-18H CAR-Ts, L7-18H CAR-Ts, L9-18H CAR-Ts, L13-18H CAR-Ts, L14-18H CAR-Ts, L16-18H CAR-Ts, L17-18H CAR-Ts, L22-18H CAR-Ts, K4-18H CAR-Ts, K5-18H CAR-Ts, K6-18H CAR-Ts, K9-18H CAR-Ts, or K10-18H CAR-Ts) expressing the CARs were purified using the anti-PE microbeads. The Jurkat 76 cells expressing the CARs were stained in the same manner as in (5) of Example 10 above. The stained Jurkat 76 cells expressing the CARs were analyzed by flow cytometry. A positive control was performed in the same manner, except that an expression vector that included a nucleic acid coding for a tagged clone18LH CAR or a tagged clone18HL CAR was used instead of the expression vectors that included the polynucleotides coding for the CARs. A control 1 was performed in the same manner, except that CD19 dimer staining was not performed. A control 2 was performed in the same manner, except that the expression vectors that included the polynucleotides coding for the CARs were not introduced. FIGS. 28 and 29 show the results obtained when gating of $FSC^+$-$SSC^+$-$NGFR^+$ cells was performed.

FIGS. 28 and 29 show dot plots showing the results of flow cytometry. In FIGS. 28 and 29, the horizontal axes indicate the average fluorescence intensity resulting from CD19 dimer staining, and the vertical axes indicate the average side scatter (SSC) intensity. As shown in FIGS. 28 and 29, the Jurkat 76 cells (control 2) into which the expression vectors that included the polynucleotides coding for the CARs had not been introduced did not include cells capable of binding to CD19. Moreover, it could be confirmed that the clone18LH CAR-Ts and the clone18HL CAR-Ts (clone18LH CAR or clone18HL CAR, positive control) bound to CD19 because substantially all the cells were present as CD19 dimer$^+$ cells when CD19 dimer staining was performed, and substantially all the cells were present as CD19 dimer$^-$ cells when CD19 dimer staining was performed.

Furthermore, the L4-18H CAR-Ts, L7-18H CAR-Ts, L9-18H CAR-Ts, L13-18H CAR-Ts, L14-18H CAR-Ts, L16-18H CAR-Ts, L17-18H CAR-Ts, L22-18H CAR-Ts, K4-18H CAR-Ts, K5-18H CAR-Ts, K6-18H CAR-Ts, K9-18H CAR-Ts, or K10-18H CAR-Ts were present as CD19 dimer$^+$ CAR-Ts when CD19 dimer staining was performed, and the CAR-Ts were present as CD19 dimer$^-$ CAR-Ts when CD19 dimer staining was not performed. It was found from these results that the L4-18H CAR-Ts, L7-18H CAR-Ts, L9-18H CAR-Ts, L13-18H CAR-Ts, L14-18H CAR-Ts, L16-18H CAR-Ts, L17-18H CAR-Ts, L22-18H CAR-Ts, K4-18H CAR-Ts, K5-18H CAR-Ts, K6-18H CAR-Ts, K9-18H CAR-Ts, or K10-18H CAR-Ts were capable of binding to the CD19 dimer. That is, it was found that the first screening method of the present invention could be used to screen scFvs capable of binding to a target antigen.

(7) Functions of First Candidate scFvs

Figure 30:
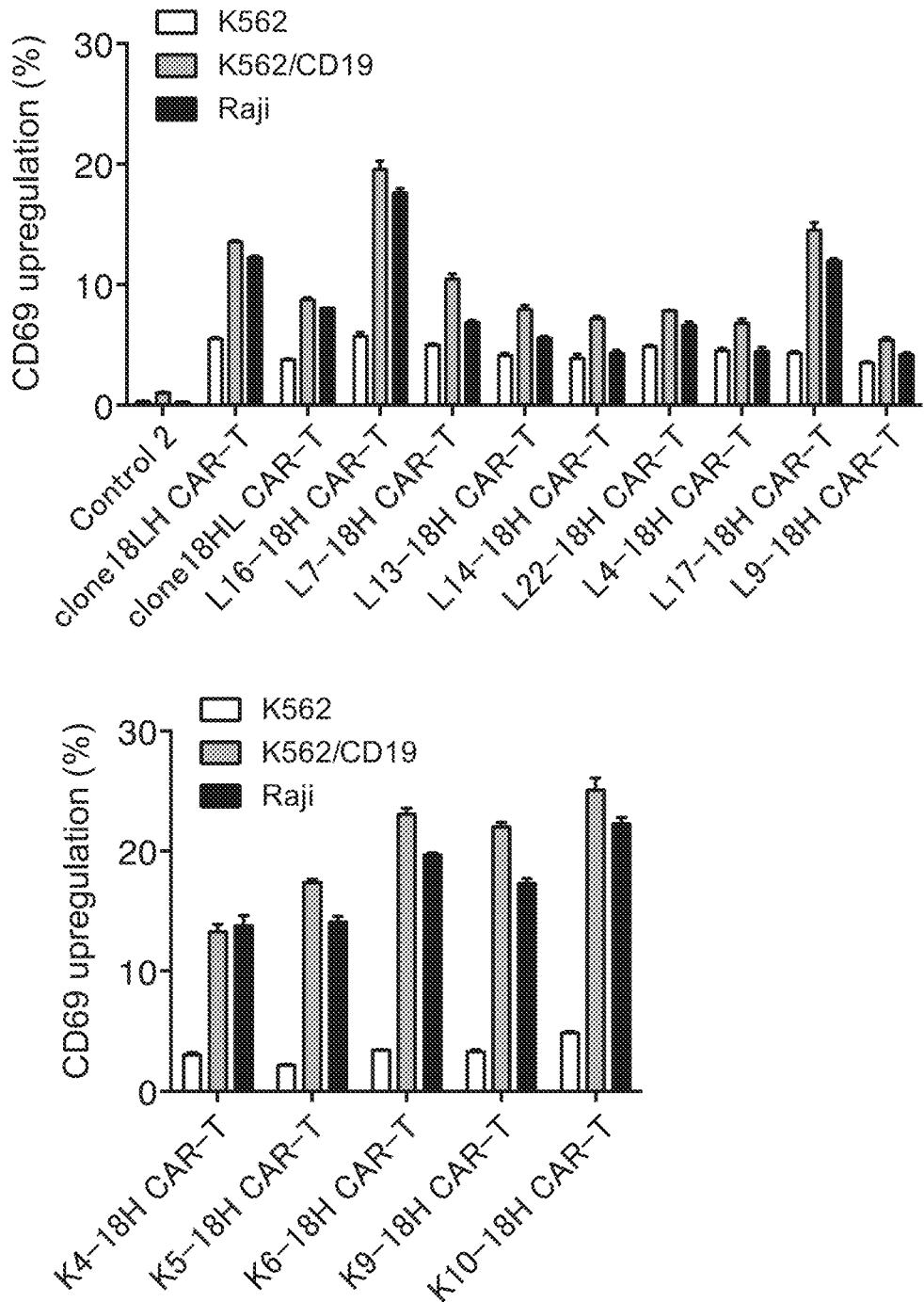
FIG. 30 shows graphs indicating changes in a CD69 expression level in Example 10.

Next, it was examined if the CAR-Ts obtained in (6) of Example 10 above bound to the target antigen and were thus activated. Specifically, the CAR-Ts and antigen-presenting cells (APCs-CD19 or Raji cells) were seeded in each well (96-well plate) such that the number of the CAR-Ts was $2\times10^5$ and the number of the antigen-presenting cells (APCs-CD19 or Raji cells) was $5\times10^4$, and then they were cultured together for 5 hours. The antigen-presenting cells (APCs-CD19) were prepared in the same manner as in (4) of Example 10 above. An RPMI1640 culture medium containing FCS at a concentration of 10% was used as the culture solution for the coculture. After the above-mentioned coculture, the CAR-Ts were collected, and were then stained with an FITC-labeled anti-human CD69 mAb (clone: FN50) and a V450-labeled anti-human NGFR mAb. The average fluorescence intensity of CD69 in NGFR$^+$ cells from the stained CAR-Ts was measured using the flow cytometer. A positive control was performed in the same manner, except that the clone18LH CAR-Ts and the clone18HL CAR-Ts obtained in (6) of Example 10 above were used. A control 1 was performed in the same manner, except that K562 cells into which the nucleic acid coding for CD19 had not been introduced were used. A control 2 was performed in the same manner, except that the expression vectors that included the polynucleotides coding for the CARs were not introduced. Then, the rates of an increase in CD69 expression in the samples were calculated using the average fluorescence intensity of CD69 before the coculture as a standard. FIG. 30 shows the results.

FIG. 30 shows graphs indicating changes in a CD69 expression level. In FIG. 30, the horizontal axes indicate the types of samples, and the vertical axes indicate the rate of an increase in CD69 expression. As shown in FIG. 30, the CD69 expression hardly increases in the control 2. On the other hand, when the clone18LH CAR-Ts and the clone18HL CAR-Ts (positive control) were stimulated with APCs-CD19 (K562/CD19) or Raji cells (Raji), it could be confirmed that the CD69 expression increased compared with the case of the stimulation with the control 1 (K562), and the CAR-Ts bound to CD19 and were activated. Moreover, when the L4-18H CAR-Ts, L7-18H CAR-Ts, L9-18H CAR-Ts, L13-18H CAR-Ts, L14-18H CAR-Ts, L16-18H CAR-Ts, L17-18H CAR-Ts, L22-18H CAR-Ts, K4-18H CAR-Ts, K5-18H CAR-Ts, K6-18H CAR-Ts, K9-18H CAR-Ts, or K10-18H CAR-Ts were stimulated with APCs-CD19 (K562/CD19) or Raji cells (Raji), the CD69 expression increased compared with the case of the stimulation with the control 1 (K562), and the CAR-Ts bound to CD19 and were activated. Furthermore, the rates of an increase in CD69 expression in the CAR-Ts were significantly different, and it was thus found that scFvs different in specificity for CD19 could be screened.

(8) Avidity of First Candidate scFvs

Figure 31:
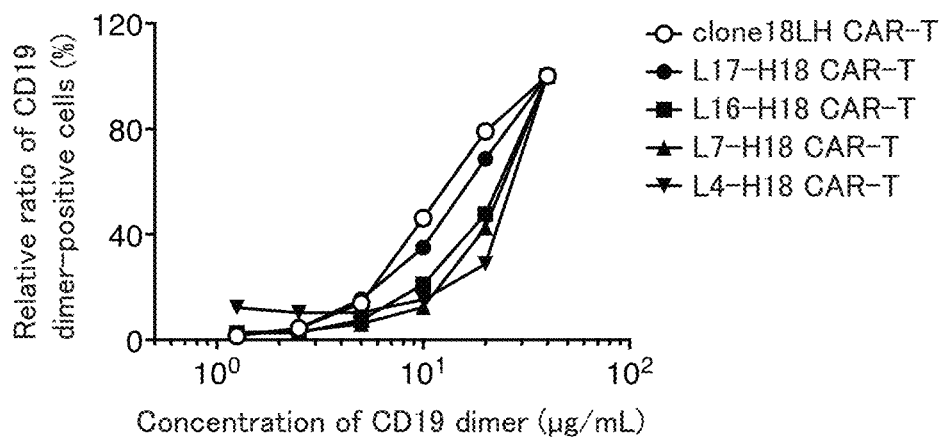
FIG. 31 shows graphs indicating relative ratios of CD19 dimer-positive cells in Example 10.
Figure 31:
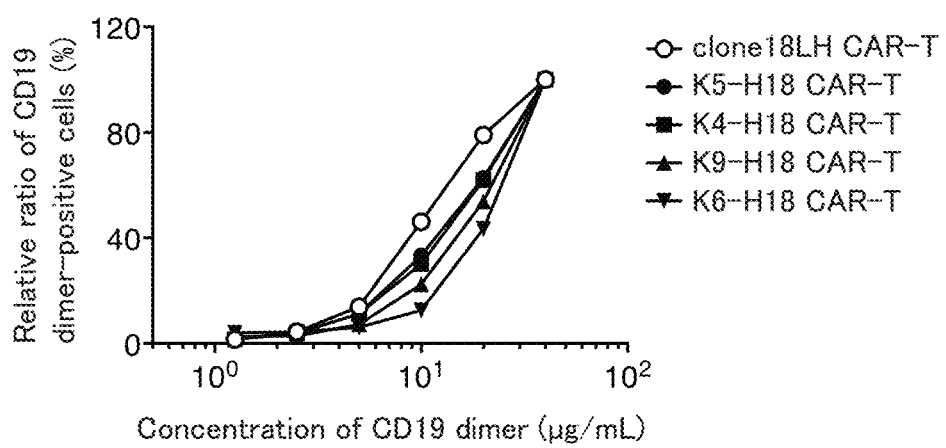

Next, it was examined if the L4-18H CAR-Ts, L7-18H CAR-Ts, L16-18H CAR-Ts, L17-18H CAR-Ts, K4-18H CAR-Ts, K5-18H CAR-Ts, K6-18H CAR-Ts, and K9-18H CAR-Ts, which were obtained in (6) of Example 10 above, were different from the clone18LH CAR-Ts in avidity for the target antigen. Flow cytometry analysis was performed on the CAR-Ts in the same manner as in (6) of Example 10 above, except that the CAR Ts were stained with the PE-labeled CD19 dimer at a predetermined concentration (1.25, 2.5, 5, 10, 20, or 40 µg/mL), and were then stained with the V450-labeled anti-human NGFR mAb. Then, after the ratios of CD19 dimer-positive cells were calculated for each CD19 dimer concentration, the relative ratios of CD19 dimer-positive cells for each CD19 dimer concentration were calculated using the ratio of CD19 dimer-positive cells for a CD19 dimer concentration of 40 µg/mL as a standard. FIG. 31 shows the results.

FIG. 31 shows graphs indicating the relative ratios of CD19 dimer-positive cells. In FIG. 31, the horizontal axes indicate the concentration of the CD19 dimer, and the vertical axes indicate the relative ratio of CD19 dimer-positive cells. As shown in FIG. 31, the ratios of the CD19 dimer-positive cells in the CAR-Ts increased in a manner dependent on the concentration of the CD19 dimer. The staining intensity varied in the CAR-Ts, and it was thus found that the scFvs in these CAR-Ts were different in the avidity for the CD19 dimer. That is, it was found that the first screening method of the present invention could be used to screen scFvs different in binding avidity for a target antigen.

(9) Responsiveness of First Candidate scFvs

Figure 32:
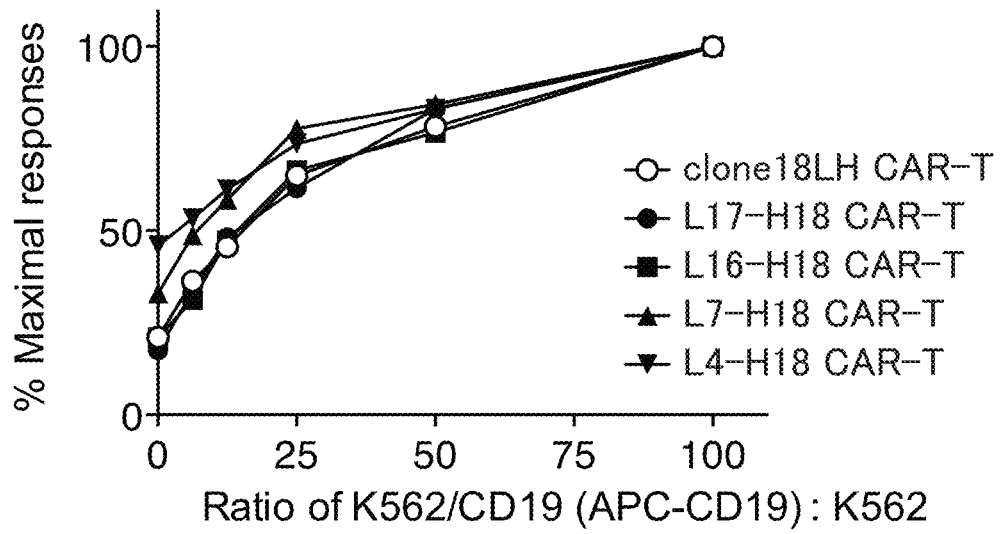
FIG. 32 shows graphs indicating relative values of CD69 expression levels when the amount of target cells is varied in Example 10.
Figure 32:
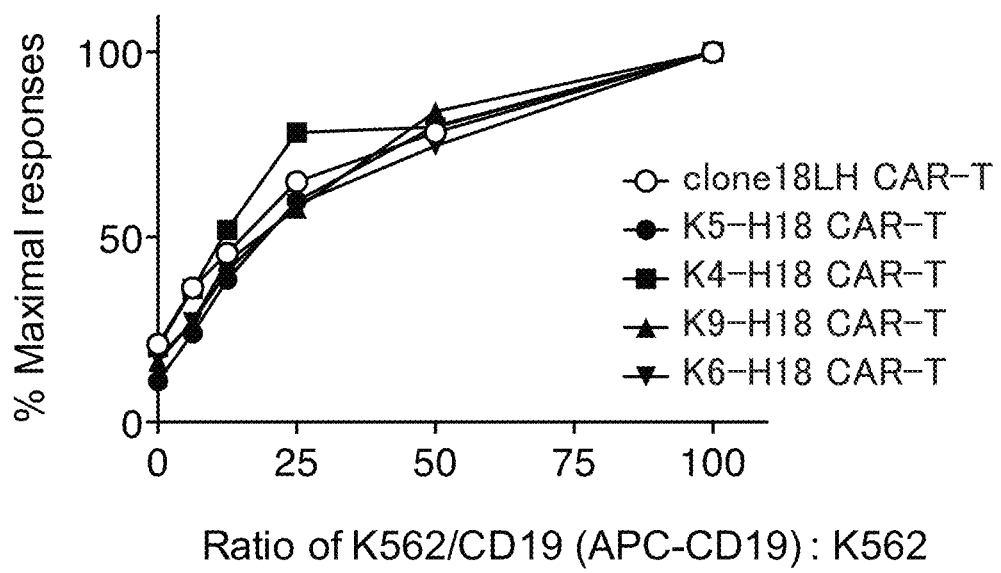

Next, it was examined if the L4-18H CAR-Ts, L7-18H CAR-Ts, L16-18H CAR-Ts, L17-18H CAR-Ts, K4-18H CAR-Ts, K5-18H CAR-Ts, K6-18H CAR-Ts, and K9-18H CAR-Ts, which were obtained in (6) above, were different from the clone18LH CAR-Ts in responsiveness to cells expressing the target antigen. Specifically, the CAR-Ts and mixed cells of the antigen-presenting cells (APCs-CD19) and K562 cells were seeded in each well (96-well plate) such that the number of the CAR-Ts was $2\times10^5$ and the number of the mixed cells was $5\times10^4$, and then they were cultured together for 5 hours. The ratio between the APCs-CD19 (A) and the K562 (K) in the mixed cells (A:K) was set to a predetermined ratio (0:100, 6.25:93.75, 12.5:87.5, 50:50, 100:0). After the above-mentioned coculture, the CAR-Ts were collected and were then stained with an FITC-labeled anti-human CD69 mAb (clone: FN50) and a V450-labeled anti-human NGFR mAb. The ratios of CD69-positive cells in NGFR$^+$ cells from the stained CAR-Ts were measured using the flow cytometer. The relative ratio (% Maximal responses) of CD69-positive cells for each ratio (A:K) was calculated using the ratio of CD69-positive cells for a ratio (A:K) of 100:0 as a standard. FIG. 32 shows the results.

FIG. 32 shows graphs indicating the relative ratios of CD69-positive cells. In FIG. 32, the horizontal axes indicate the ratio (A:K), and the vertical axes indicate the relative ratio (% Maximal responses) of CD69-positive cells. As shown in FIG. 32, the ratios of the CD69-positive cells in the CAR-Ts increased in proportion to the ratio of the APCs-CD19 (A). The reactivity to the APCs-CD19 varied in the CAR-Ts, and it was thus found that the scFvs in these CAR-Ts were different in the avidity for the target antigen. That is, it was found that the first screening method of the present invention could be used to screen scFvs different in binding avidity for a target antigen.

(10) Functions of First Candidate scFvs

Figure 33:
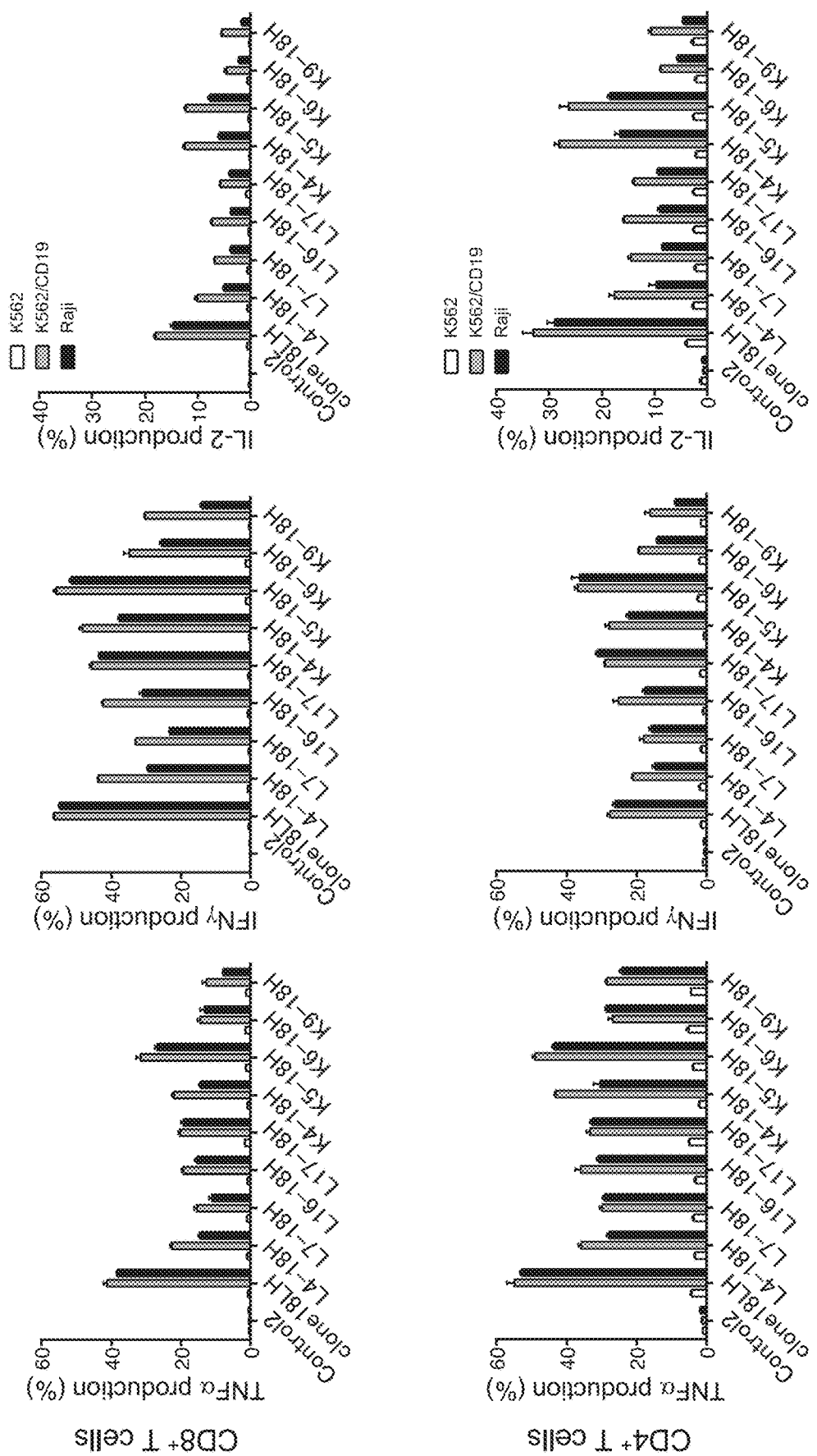
FIG. 33 shows graphs indicating ratios of cytokine-producing cells in Example 10.

Next, it was examined if the L4-18H CAR-Ts, L7-18H CAR-Ts, L16-18H CAR-Ts, L17-18H CAR-Ts, K4-18H CAR-Ts, K5-18H CAR-Ts, K6-18H CAR-Ts, and K9-18H CAR-Ts, which were obtained in (6) above, and the clone18LH CAR-Ts bound to the target antigen and produced cytokines. Specifically, the CAR-Ts and antigen-presenting cells (APCs-CD19 or Raji cells) were seeded in each well (96-well plate) such that the number of the CAR-Ts was $3\times10^5$ and the number of the antigen-presenting cells (APCs-CD19 or Raji cells) was $5\times10^4$, and then they were cultured together for 5 hours. The antigen-presenting cells (APCs-CD19) were prepared in the same manner as in (4) of Example 10 above. An RPMI1640 culture medium containing FCS at a concentration of 10% was used as the culture solution for the coculture. After the above-mentioned culture, BFA was added to a concentration of 5 μmol/L, and then the culture was continued for another 5 hours. Then, after the culture, the cells were fixed with 1% PFA and subjected to cell membrane permeabilization. Moreover, the cells were stained with an APC-labeled anti-human IL-2 mAb (clone: MQ1-17H12), a PE-labeled anti-human TNFα mAb (clone: Mab11), a PC7-labeled anti-human IFN-γ mAb (clone: B27), an FITC-labeled anti-human CD4 mAb (clone: OKT4), a PC5-labeled anti-human CD8a mAb (clone: B9.11), and a V450-labeled anti-human NGFR mAb (clone: C40-1457). The stained cells were measured using the flow cytometer. Then, the ratios of cytokine expression were calculated. A positive control was performed in the same manner, except that the clone18LH CAR-Ts obtained in (6) of Example above were used. A control 1 was performed in the same manner, except that K562 cells into which the nucleic acid coding for CD19 had not been introduced were used. A control 2 was performed in the same manner, except that the expression vectors that included the polynucleotides coding for the CARs were not introduced. FIG. 33 shows the results.

FIG. 33 shows graphs indicating the ratios of cytokine-producing cells. In FIG. 33, the horizontal axes indicate the types of CAR-Ts, and the vertical axes indicate the ratio of cytokine-producing cells. In FIG. 33, the upper graphs show the results from CD8-positive CAR-Ts, and the lower graphs show the results from CD4-positive CAR-Ts. As shown in FIG. 33, it was found that, in the presence of the APCs-CD19 expressing CD19 serving as a target antigen or Raji cells, the ratios of TNF-α-producing cells, IFN-γ-producing cells, and IL-2-producing cells in the CAR-Ts increased compared with the control 1 (K562) and the control 2, which did not express the target antigen, and the CAR-Ts were activated. It was found from these results that the screening method of the present invention could be used to screen scFvs capable of binding to CD19 and inducing an effector function in CAR-Ts.

Example 11

It was confirmed that CARs that included scFvs obtained using the screening method of the present invention in which the CAR library of the present invention is used exhibited anti-tumor effects in vivo.

The L17-18H CAR-Ts, the K5-18H CAR-Ts, and the clone18LH CAR-Ts were prepared in the same manner as in Example 10 above.

Raji cells expressing SLR (Raji/SLR cells) were prepared in the same manner as in (4) of Example 1 above, except that Raji cells were used instead of K562 cells, and a polynucleotide coding for SLR was used instead of the polynucleotide coding for human CD19. It should be noted that, since SLR is an intracellular protein, a nucleic acid coding for a truncated NGFR gene (ΔNGFR) was linked to the polynucleotide coding for SLR via a polynucleotide coding for the furin cleavage site (RAKR: Sequence ID No. 172), the spacer sequence (SGSG: Sequence ID No. 173), and the codon-optimized P2A sequence (ATNFSLLKQAGDVEEN-PGP: Sequence ID No. 174).

SLR Protein (SLR/furin-sgsg-p2a/dNGFR, Sequence ID No. 311)
MEEENIVNGDRPRDLVFPGTAGLQLYQSLYKYSYITDGIIDAHTNEVIS

YAQIFETSCRLAVSLEKYGLDHNNVVAICSENNIHFFGPLIAALYQGIP

-continued

MATSNDMYTEREMIGHLNISKPCLMFCSKKSLPFILKVQKHLDFLKKVI

VIDSMYDINGVECVFSFVSRYTDHAFDPVKFNPKEFDPLERTALIMTSS

GTTGLPKGVVISHRSITIRFVHSSDPIYGTRIAPDTSILAIAPFHHAFG

LFTALAYFPVGLKIVNIVKKFEGEFFLKTIQNYKIASIVVPPPIMVYLA

KSPLVDEYNLSSLTEIACGGSPLGRDIADKVAKRLKVHGILQGYGLTET

CSALILSPNDRELKKGAIGTPMPYVQVKVIDINTGKALGPREKGEICFK

SQMLMKGYHNNPQATRDALDKDGWLHTGDLGYYDEDRFIYVVDRLKELI

KYKGYQVAPAELENLLLQHPNISDAGVIGIPDEFAGQLPSACVVLEPGK

TMTEKEVQDYIAELVTTTKHLRGGVVFIDSIPKGPTGKLMRNELRAIFA

REQAKSKLRAKRSGSGATNFSLLKQAGDVEENPGPMDGPRLLLLLLLGV

SLGGAKEACPTGLYTHSGECCKACNLGEGVAQPCGANQTVCEPCLDSVT

FSDVVSATEPCKPCTECVGLQSMSAPCVEADDAVCRCAYGYYQDETTGR

CEACRVCEAGSGLVFSCQDKQNTVCEECPDGTYSDEANHVDPCLPCTVC

EDTERQLRECTRWADAECEEIPGRWITRSTPPEGSDSTAPSTQEPEAPP

EQDLIASTVAGVVTTVMGSSQPVVTRGTTDNLIPVYCSILAAVVVGLVA

YIAFKRWNS

Polynucleotide Coding for SLR
(Sequence ID No. 312)
5'-ATGGAAGAAGAGAACATCGTGAATGGCGATCGCCCTCGGGATCTGG

TGTTCCCTGGCACAGCCGGCCTGCAGCTGTATCAGTCCCTGTATAAATA

CTCTTACATCACCGACGGAATCATCGACGCCCACACCAACGAGGTGATC

TCCTATGCCCAGATTTTCGAAACAAGTTGCCGCCTGGCCGTGAGCCTGG

AGAAGTATGGCCTGGATCACAACAACGTGGTGGCCATTTGCAGCGAGAA

CAACATCCACTTCTTCGGCCCTCTGATCGCTGCCCTATACCAGGGGATT

CCAATGGCCACATCCAACGATATGTACACCGAGAGGGAGATGATCGGCC

ACCTGAACATCTCCAAGCCATGTCTGATGTTCTGTTCCAAGAAGTCCCT

GCCATTCATCCTGAAGGTGCAGAAGCACCTGGACTTTCTCAAGAAGGTG

ATCGTGATCGACAGCATGTACGACATCAACGGCGTGGAGTGCGTGTTCA

GTTTCGTGTCCCGGTACACCGATCATGCGTTCGATCCAGTGAAGTTCAA

CCCTAAAGAGTTTGATCCCCTGGAGAGAACCGCGCTGATCATGACATCC

TCTGGAACAACCGGCCTGCCTAAGGGCGTGGTGATCAGCCACAGGAGCA

TCACCATCAGATTCGTCCACAGCAGCGATCCCATCTACGGCACCCGCAT

CGCCCCAGATACATCCATCCTGGCCATCGCCCCTTTCCACCACGCCTTC

GGACTGTTTACCGCCCTGGCTTACTTTCCAGTGGGCCTGAAGATCGTGA

TGGTGAAAAAGTTTGAGGGCGAGTTCTTCCTGAAGACCATCCAGAACTA

CAAGATCGCTTCTATCGTGGTGCCTCCTCCAATCATGGTGTATCTGGCC

AAGAGCCCTCTGGTGGATGAGTACAATCTGTCCAGCCTGACAGAGATCG

CCTGTGGCGGCTCCCCTCTGGGCAGAGACATCGCCGACAAGGTGGCCAA

GAGACTGAAGGTCCACGGCATCCTGCAGGGCTATGGCCTGACCGAGACC

```
-continued
TGTAGCGCCCTGATCCTGAGCCCCAACGATAGAGAGCTGAAGAAGGGCG

CCATCGGCACCCCTATGCCCTATGTCCAGGTGAAGGTGATTGACATCAA

CACCGGCAAAGCCCTGGGACCAAGAGAGAAGGGCGAGATTTGCTTCAAG

AGCCAGATGCTGATGAAGGGCTACCACAACAACCCACAGGCCACCAGGG

ATGCCCTGGACAAGGACGGGTGGCTGCACACCGGCGATCTGGGCTACTA

CGACGAGGACAGATTCATCTATGTGGTGGATCGGCTGAAAGAACTCATC

AAGTACAAGGGCTACCAGGTGGCCCCTGCCGAGCTGGAGAACTTGCTTC

TGCAGCACCCTAACATCTCTGATGCCGGCGTCATCGGCATCCCAGACGA

GTTTGCCGGCCAGCTGCCTTCCGCCTGTGTCGTGCTGGAGCCTGGCAAG

ACCATGACCGAGAAGGAGGTGCAGGATTATATCGCCGAGCTGGTGACCA

CCACCAAGCACCTGCGGGCGGCGTGGTGTTCATCGACAGCATTCCGAA

AGGCCCAACAGGCAAGCTGATGAGAAACGAGCTGAGGGCCATCTTTGCC

CGCGAGCAGGCCAAGTCCAAGCTGAGGGCCAAGCGGTCCGGATCCGGAG

CCACCAACTTCAGCCTGCTGAAGCAGGCCGGCGACGTGGAGGAGAACCC

CGGCCCCATGGACGGGCGCGCCTGCTGCTGTTGCTGCTTCTGGGGGTG

TCCCTTGGAGGTGCCAAGGAGGCATGCCCCACAGGCCTGTACACACA

GCGGTGAGTGCTGCAAAGCCTGCAACCTGGGCGAGGGTGTGGCCCAGCC

TTGTGGAGCCAACCAGACCGTGTGTGAGCCCTGCCTGGACAGCGTGACG

TTCTCCGACGTGGTGAGCGCGACCGAGCCGTGCAAGCCGTGCACCGAGT

GCGTGGGGCTCCAGAGCATGTCGGCGCCATGCGTGGAGGCCGACGACGC

CGTGTGCCGCTGCGCCTACGGCTACTACCAGGATGAGACGACTGGGCGC

TGCGAGGCGTGCCGCGTGTGCGAGGCGGGCTCGGGCCTCGTGTTCTCCT

GCCAGGACAAGCAGAACACCGTGTGCGAGGAGTGCCCCGACGGCACGTA

TTCCGACGAGGCCAACCACGTGGACCCGTGCCTGCCCTGCACCGTGTGC

GAGGACACCGAGCGCCAGCTCCGCGAGTGCACACGCTGGGCCGACGCCG

AGTGCGAGGAGATCCCTGGCCGTTGGATTACACGGTCCACACCCCCAGA

GGGCTCGGACAGCACAGCCCCAGCACCCAGGAGCCTGAGGCACCTCCA

GAACAAGACCTCATAGCCAGCACGGTGGCAGGTGTGGTGACCACAGTGA

TGGGCAGCTCCCAGCCCGTGGTGACCCGAGGCACCACCGACAACCTCAT

CCCTGTCTATTGCTCCATCCTGGCTGCTGTGGTTGTGGGTCTTGTGGCC

TACATAGCCTTCAAGAGGTGGAACAGCTGA-3'
```

Figure 34A:
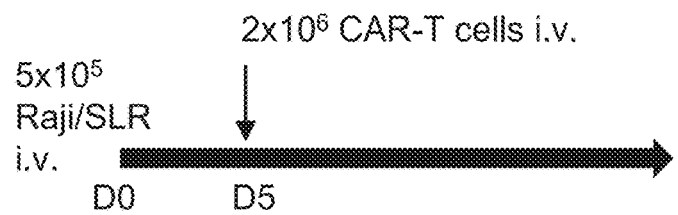
FIG. 34 shows diagrams relating to anti-tumor activity in living organisms in Example 11.

5-week-old NOG mice (NOD/Shi-scid, IL-2RγKO•Jic mice, purchased from In-Vivo Science) were irradiated with 1.5 Gy of γ rays. Next, as shown in FIG. 34(A), the Raji/SLR cells (5×10⁵ cells) were transplanted into the NOG mice through intravenous administration. The day on which the above-mentioned transplantation was performed was taken as Day 0, the CAR-Ts (2×10⁶ cells) were intravenously administered on Day 5. Then, the size of tumor was measured using an image analyzer (AEQUORIA-2D/8600 bioluminescence imaging assays, manufactured by Hamamatsu Photonics) on Days 6, 9, 13, and 17 after the transplantation. A control was measured in the same manner, except that T cells into which the CARs had not been introduced were administered. It should be noted that each group included three mice. FIG. 34 shows the results.

Figure 34B:
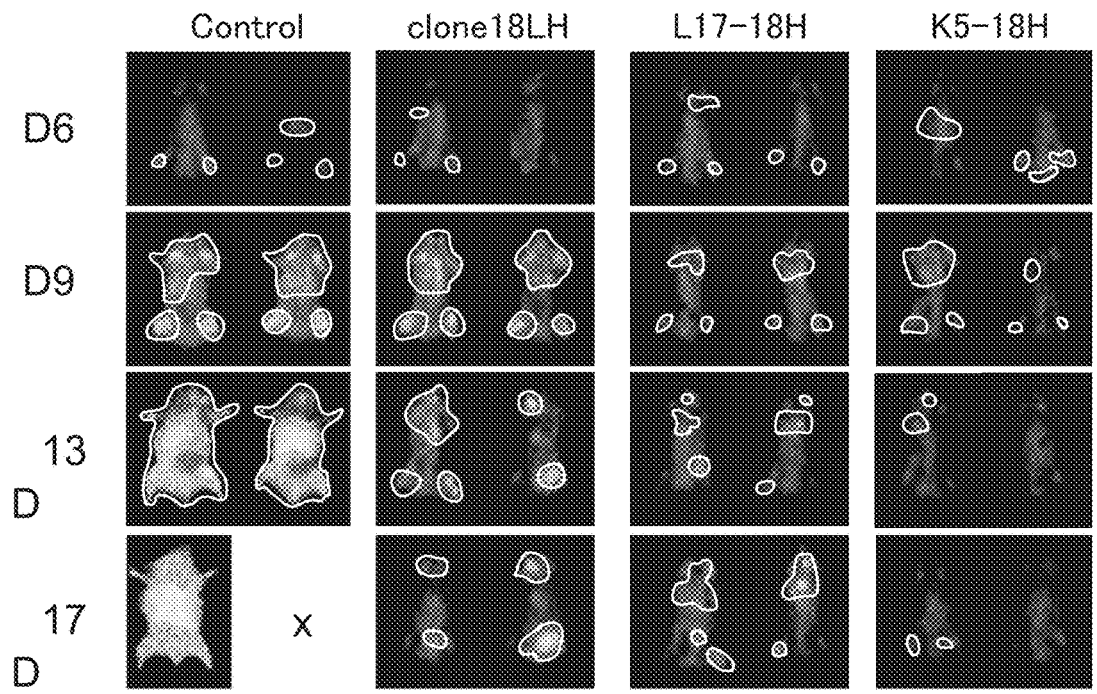
Figure 34C:
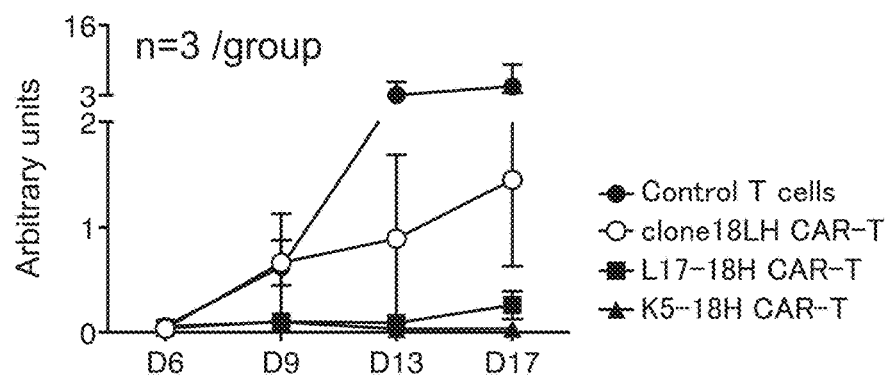

FIG. 34 shows diagrams relating to anti-tumor activity in living organisms. FIG. 34(A) indicates the protocol, FIG. 34(B) shows photographs subjected to measurement using an image analyzer, and FIG. 34(C) shows a graph indicating the sizes of tumors. In FIG. 34(B), the regions surrounded by white lines are regions in which a tumor exists. As shown in FIGS. 34(B) and 34(C), the sizes of tumors of the CAR-T administered groups decreased compared with the control. Moreover, the sizes of the tumors of the L17-18H CAR-T administered group or K5-18H CAR-T administered group significantly decreased compared with the clone18LH CAR-T administered group. It was found from these results that the CARs that included scFvs obtained using the screening method of the present invention in which the CAR library of the present invention is used exhibited anti-tumor effects in vivo. Also, it was found that the screening method of the present invention could be used to screen scFvs capable of inducing a better effector function in vivo compared with scFvs used as templates.

Example 12

It was confirmed that CARs that included scFvs that can functionally activate CAR-T cells could be screened by performing selection based on an indirect evaluation method in the first selection step and the second selection step of the screening method of the present invention in which the CAR library of the present invention is used, that is, by performing selection based on evaluation of activation indices of candidate immune cells resulting from binding between a target antigen and a CAR.

Figure 35:
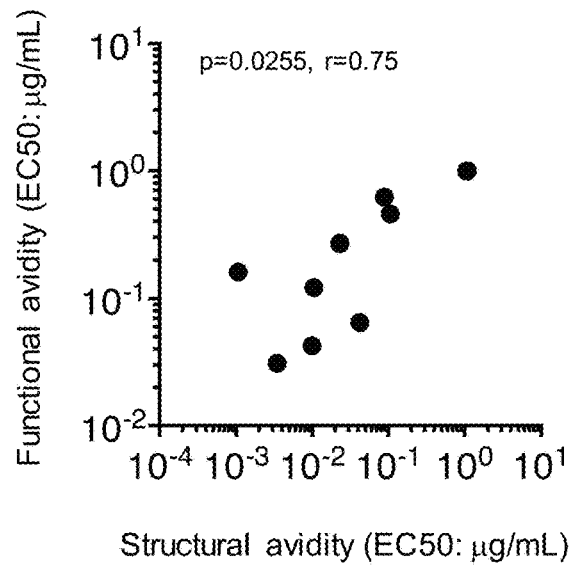
FIG. 35 is a graph indicating a relationship between the structural avidity index value and the functional avidity index value in Example 12.

The results in (5) and (7) of Example 2 were used to calculate, as a structural avidity index value, the tetramer concentration (EC50) at which the ratio of the tetramer positive cells in the L1-3M4E5 CAR-Ts, L66-3M4E5 CAR-Ts, L73-3M4E5 CAR-Ts, L88-3M4E5 CAR-Ts, L102-3M4E5 CAR-Ts, L124-3M4E5 CAR-Ts, H73-3M4E5 CAR-Ts, H1-3M4E5 CAR-Ts, or 3M4E5LH CAR-Ts was half as high as the maximum ratio of the positive cells. The structural avidity can also be considered as specificity of a CAR (scFv) for a target antigen. Moreover, the results in (6) and (8) of Example 2 were used to calculate, as a functional avidity index value, the tetramer concentration (EC) at which the rate of an increase in CD69 expression in the L1-3M4E5 CAR-Ts, L66-3M4E5 CAR-Ts, L73-3M4E5 CAR-Ts, L88-3M4E5 CAR-Ts, L102-3M4E5 CAR-Ts, L124-3M4E5 CAR-Ts, H73-3M4E5 CAR-Ts, H1-3M4E5 CAR-Ts, or 3M4E5LH CAR-Ts was half as high as the maximum rate of an increase in CD69 expression. The functional avidity refers to an ability of a CAR to activate T cells when the CAR binds to a target antigen. Then, the correlation between the structural avidity index value and the functional avidity index value of the L1-3M4E5 CAR-Ts, L66-3M4E5 CAR-Ts, L73-3M4E5 CAR-Ts, L88-3M4E5 CAR-Ts, L102-3M4E5 CAR-Ts, L124-3M4E5 CAR-Ts, H73-3M4E5 CAR-Ts, H1-3M4E5 CAR-Ts, or 3M4E5LH CAR-Ts was examined. FIG. 35 shows the results.

FIG. 35 is a graph indicating a relationship between the structural avidity index value and the functional avidity index value. In FIG. 35, the horizontal axis indicates the structural avidity index value (Structural avidity), and the vertical axis indicates the functional avidity index value (Functional avidity). As shown in FIG. 35, a positive correlation is observed in a region in which the structural avidity index value and the functional avidity index value are high, whereas a correlation between the structural avidity index value and the functional avidity index value is not observed as the structural avidity index value decreases. It was found from these results that CARs that included scFvs capable of functionally activating CAR-T cells could be screened by selecting candidate scFvs based on evaluation of activation indices of candidate immune cells resulting from binding between a target antigen and a CAR compared with the case where candidate scFvs are selected based on binding between a target antigen and a CAR.

Example 13

It was confirmed that CARs that included scFvs obtained using the screening method of the present invention in which the CAR library of the present invention is used exhibited cytotoxic activity in vitro.

The L17-18H CAR-Ts, the K5-18H CAR-Ts, and the clone18LH CAR-Ts were prepared in the same manner as in Example 10 above.

Figure 36:
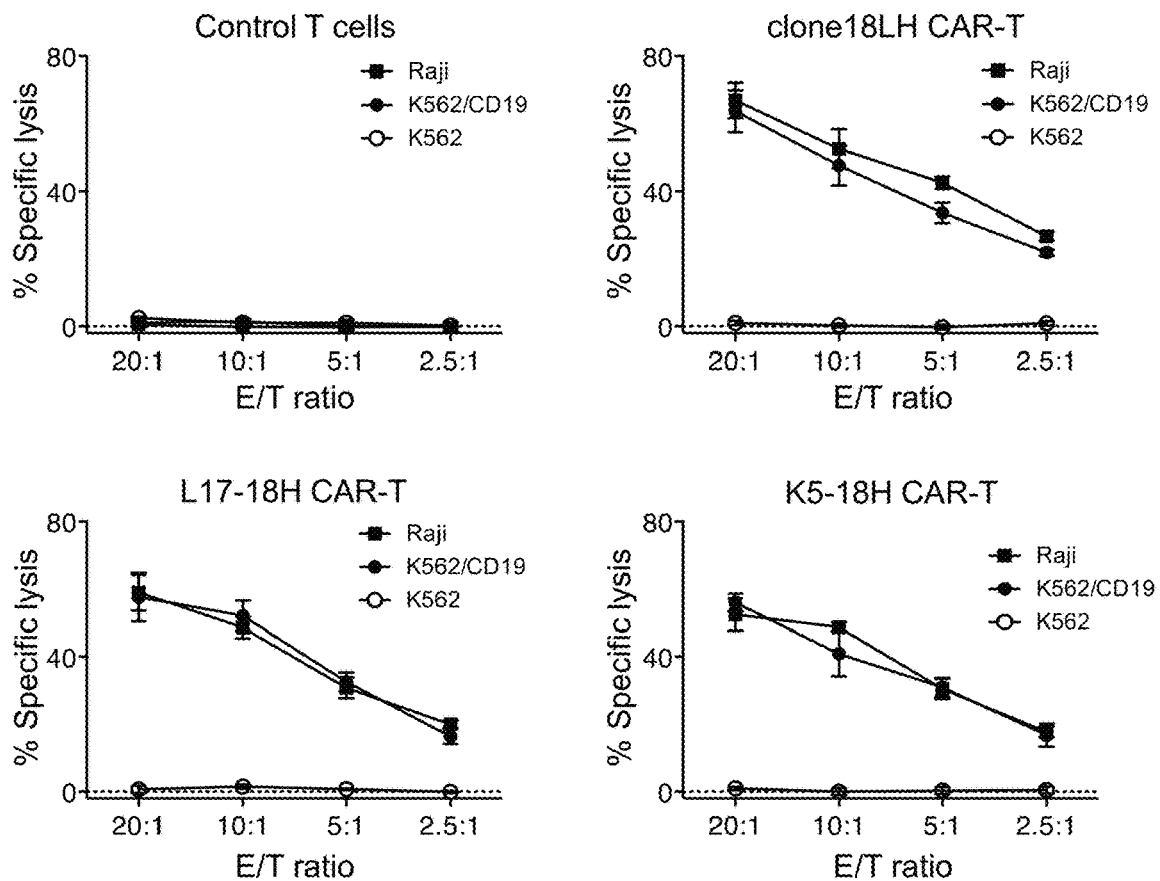
FIG. 36 shows graphs indicating cytotoxicity in Example 13.

Next, $5.0 \times 10^3$ APCs-CD19 (K562/CD19) or Raji cells (Raji) serving as target cells were cultured in the presence of chromium 51 ($^{51}$Cr) for 1.5 hours and were thus labeled with chromium 51. Then, the L17-18H CAR-Ts, K5-18H CAR-Ts, or clone18LH CAR-Ts (E) were added to the well in which the chromium 51-labeled target cells (T) were cultured such that a ratio E:T was 20:1, 10:1, 5:1, or 2.5:1. After the cells were cultured for 5 to 6 hours, the supernatant was collected, and the radiation counting rate per minute (CPM: count per minute) was measured using AccuFLEXg7010 (manufactured by HITACHI). A control 1 was measured in the same manner, except that T cells into which NGFR expression vectors had been introduced were used instead of the CAR-T cells. A control 2 was measured in the same manner, except that K562 cells were used as the target cells. Then, cytotoxicity (ratio of specific lysis) was measured based on Formula (1) below. FIG. 36 shows the results.

$$K=(L_E-L_S)/(L_{Max}-L_S) \times 100(\%) \quad (1)$$

K: cytotoxicity $L_E$: CPM measurement value $L_S$: CPM measurement value obtained when only target cells were present $L_{Max}$: CPM measurement value obtained when PBS containing 0.2% Triton-X was added to well containing only target cells FIG. 36 shows graphs indicating cytotoxicity. In FIG. 36, the horizontal axes indicate the E/T ratios, and the vertical axes indicate cytotoxicity. As shown in FIG. 36, when K562 expressing no target antigen CD19 was used as the target cells (control 2), specific cell damage did not occur, and the equal cytotoxicity was exhibited for all the groups. Moreover, when T cells that did not express CARs specific to CD19 were used (control 1), specific cell damage occurred in none of the target cells. On the other hand, when K562 and Raji cells expressing the target antigen CD19 were used as the target cells, cytotoxicity increased in a manner dependent on the effector level in the L17-18H CAR-T addition group, K5-18H CAR-T addition group, or clone18LH CAR-T addition group. The cytotoxicity was not significantly different between the L17-18H CAR-T addition group, the K5-18H CAR-T addition group, and the clone18LH CAR-T addition group. It was found from these results that the CARs that included the scFvs obtained using the screening method of the present invention in which the CAR library of the present invention is used exhibited cytotoxic activity in vitro, and the cytotoxic activity of the L17-18H CAR-Ts and the K5-18H CAR-Ts was equal to that of the clone18LH CAR-Ts.

Example 14

It was confirmed that CARs that included scFvs obtained using the screening method of the present invention in which the CAR library of the present invention is used exhibited anti-tumor effects in vivo.

The L17-18H CAR-Ts, the K5-18H CAR-Ts, and the clone18LH CAR-Ts were prepared in the same manner as in Example 10. Then, Raji cells expressing SLR were prepared in the same manner as in Example 11.

Figure 37A:
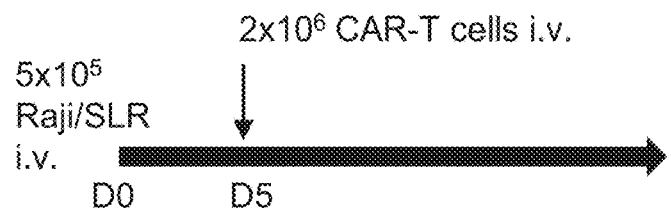
FIG. 37 shows diagrams relating to the overall survival rate in living organisms in Example 14.

5-week-old NOG mice (NOD/Shi-scid, IL-2RγKO•Jic mice, purchased from In-Vivo Science) were radiated with 1.5 Gy of γ rays. Next, as shown in FIGS. 37(A) and 38(A), the Raji/SLR cells ($5 \times 10^5$ cells) were transplanted into the NOG mice through intravenous administration. The day on which the above-mentioned transplantation was performed was taken as Day 0, the CAR-Ts ($2 \times 10^6$ cells) were intravenously administered on Day 5 or Day 7. Then, the size of tumor was measured over time using the image analyzer after the transplantation, and the survival rate of the mice was measured. It should be noted that each group included five mice. A control was performed in the same manner, except that T cells into which NGFR expression vectors had been introduced were used instead of the CAR-T cells. FIGS. 37 and 38 show the results.

Figure 37B:
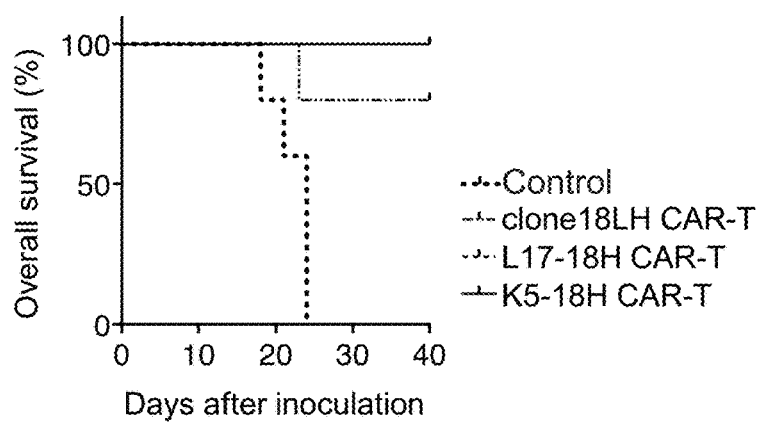
Figure 38A:
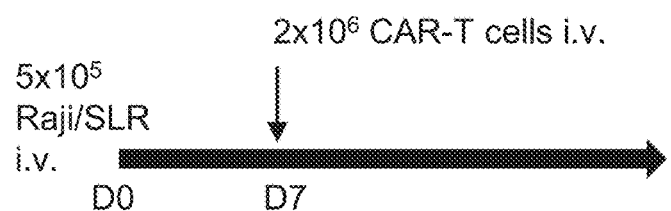
FIG. 38 shows diagrams relating to the overall survival rate in living organisms in Example 14.
Figure 38B:
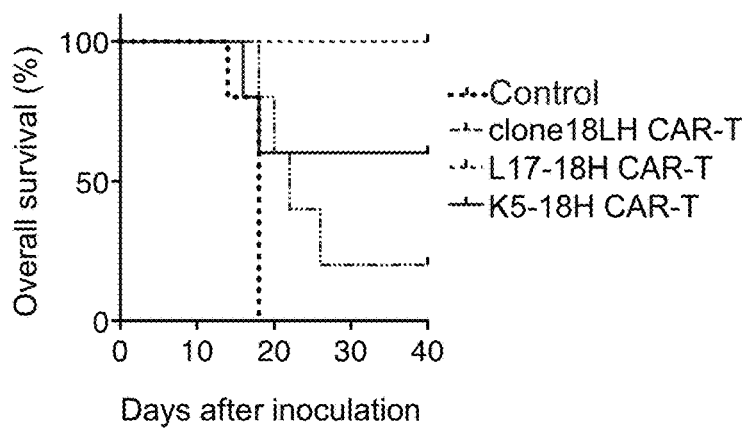

FIGS. 37 and 38 shows diagrams relating to the overall survival of living organisms. FIGS. 37(A) and 38(A) indicate protocols, and FIGS. 37(B) and 38(B) indicate the Kaplan-Meier curves showing the overall survival. As shown in FIG. 37(B), within a period during which the tumors were small, namely in an initial cancer state, the overall survival was not significantly different between the L17-18H CAR-T administered group or K5-18H CAR-T administered group and the clone18LH CAR-T administered group, and these cells exhibited substantially equal anti-tumor effects. Although not shown in the diagrams, the same results were obtained from image analysis performed using an image analyzer. On the other hand, as shown in FIG. 38(B), within a period during which sufficient infiltration of the tumors occurred, namely in an advanced tumor state, the overall survival significantly improved in the L17-18H CAR-T administered group or K5-18H CAR-T administered group compared with the clone18LH CAR-T administered group, and the overall survival was 100% in the L17-18H CAR-T administered group. Although not shown in the diagrams, the same results were obtained from image analysis performed using an image analyzer.

It was found from these results that the CARs that included the scFvs obtained using the screening method of the present invention in which the CAR library of the present invention is used exhibited anti-tumor effects in vivo. Also, it was found that the CARs that included the scFvs obtained using the screening method of the present invention in which the CAR library of the present invention is used exhibited sufficient therapeutic effects for an advanced tumor model in vivo.

Example 15

A mechanism was examined in which scFvs having excellent in-vivo anti-tumor effects can be obtained using the screening method of the present invention.

(1) Comparison of Cell Proliferation Capacity

Figure 39:
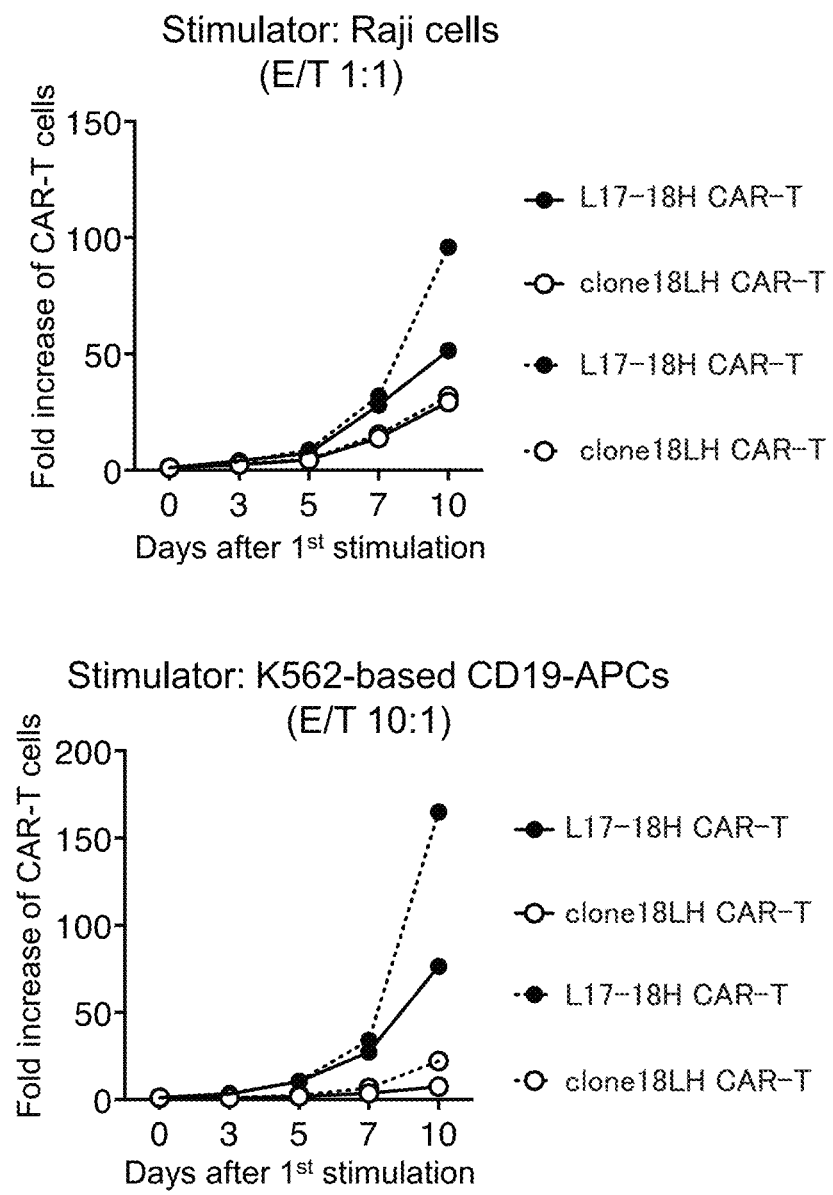
FIG. 39 shows graphs indicating the cell proliferation rates in Example 15.

The L17-18H CAR-Ts and the clone18LH CAR-Ts were prepared in the same manner as in Example 10 above. Next, APCs-CD19 (K562/CD19) or Raji cells (Raji) (T) irradiated with 20 Gy of γ rays were added to the well in which the L17-18H CAR-Ts or clone18LH CAR-Ts (E) were cultured such that a ratio E:T was 1:1 or 10:1. The cells were cultured for 5 days after the addition of the target cells. In the above-mentioned culture, IL-2 and IL-15 were added to the culture medium such that the concentrations thereof were respectively 10 U/mL and 10 ng/mL. Furthermore, on Day 5 after the start of the culture, the CAR-T cells were restimulated in the same conditions as those at the start of the culture. Then, the number of cells at the start of the culture was taken as 1, and a ratio of the number of cells counted when a predetermined period of time (0, 3, 5, 7 or 10 days) elapsed after the start of the culture to those at the start of the culture was calculated as a proliferation rate. FIG. 39 shows the results.

FIG. 39 shows graphs indicating the cell proliferation rates. In FIG. 39, the horizontal axes indicate the period of time after the start of the culture, and the vertical axes indicate the proliferation rate. As shown in FIG. 39, at both ratios (E:T), the CARs obtained using the screening method of the present invention had a better ability to induce the proliferation of T cells. Moreover, the L17-18H CAR-Ts also exhibited a better proliferation rate in the case where E:T=1:1 compared with the clone18LH CAR-Ts, and thus it was found that the L17-18H CAR-Ts had excellent proliferating ability even in the environment in which a large amount of the target antigen was present, such as a situation in which a large number of tumor cells are present due to tumor progression.

(2) Comparison of Cytokine Producibility

Figure 40:
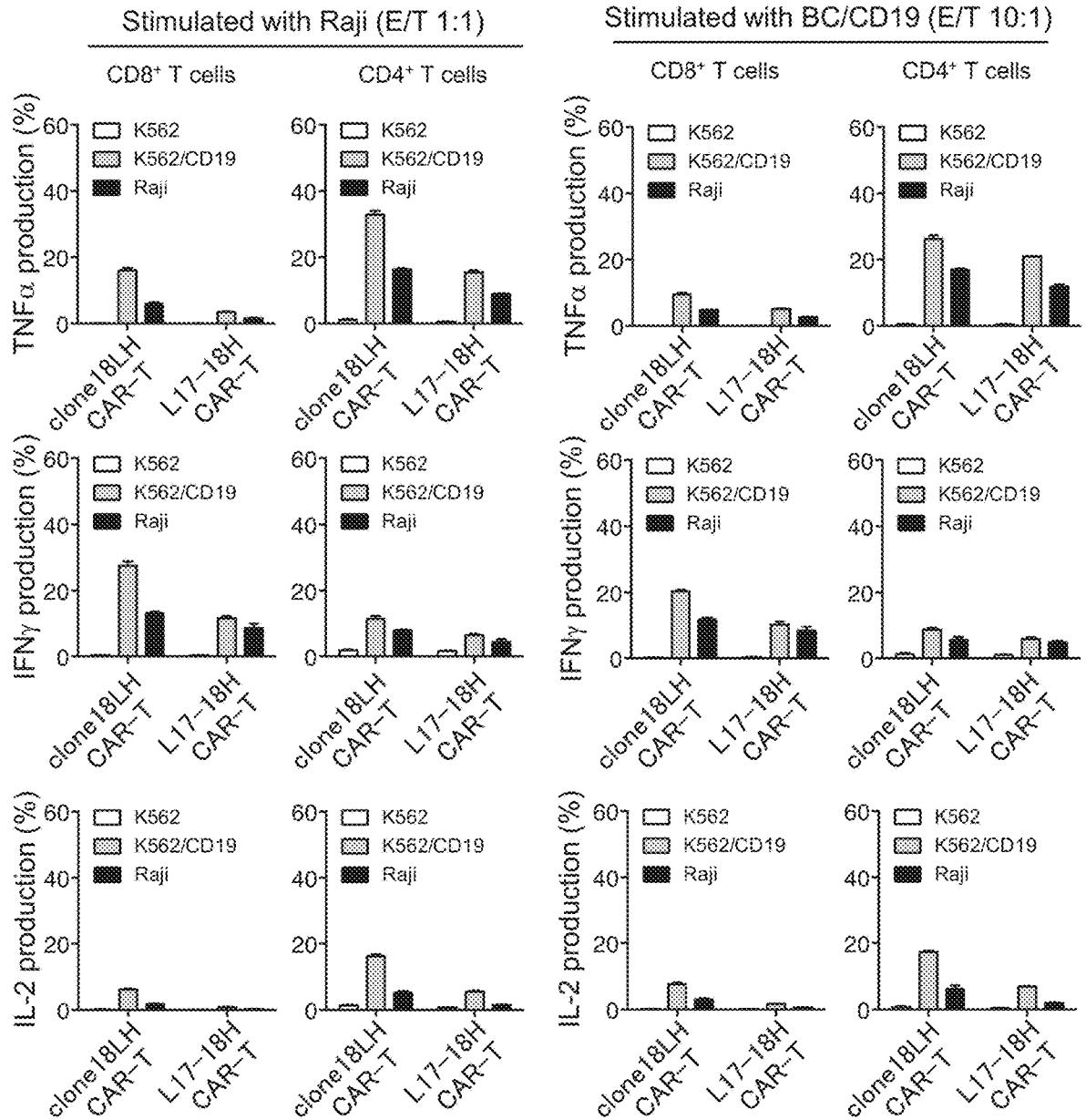
FIG. 40 shows graphs indicating the ratios of cytokine-producing cells in Example 15.

The cytokine producibility of the L17-18H CAR-Ts and the clone18LH CAR-Ts on Day 10 after the start of the culture described in (1) of Example 15 above was examined. Specifically, $3.0 \times 10^5$ CAR-T cells and $5.0 \times 10^4$ target cells (K562 cells, Raji cells, APCs-CD19 (K562/CD19)) were cultured together. After the cells were cultured for 2 hours, Brefeldin A (BFA) was added thereto such that the concentration thereof was 5 μg/mL, and then the cells were cultured for another 14 to 18 hours. After the CAR-T cells had been collected, the CAR-T cells were fixed with 1% paraformaldehyde (PFA), then subjected to cell membrane permeabilization, and stained with a PE-labeled anti-human TNF-α antibody (clone Mab11), an APC-labeled anti-human IL-2 antibody (clone MQ1-17H12), and a PC7-labeled anti-human IFN-γ antibody (clone B27), and a PC5-labeled anti-human CD8 antibody (clone B9.11), an FITC-labeled anti CD4 antibody (clone OKT4), and a V450-labeled anti-human NGFR (clone: C40-1457). The stained CAR-T cells were measured using the flow cytometer, and the ratios of cytokine-producing cells were calculated. FIG. 40 shows the results.

FIG. 40 shows graphs indicating the cytokine producibility. In FIG. 40, the horizontal axes indicate the types of CAR-T cells, the vertical axes indicate the ratio of cytokine-producing cells, and the culture conditions until Day 10 were shown on the upper side of the diagrams. As shown in FIG. 40, it was found that, for all types of cytokines, the ratio of the cytokine-producing cells in the L17-18H CAR-Ts was slightly lower than that in the clone18LH CAR-Ts, that is, the L17-18H CAR-Ts had slightly weak cytokine producibility.

(3) Comparison of Cytotoxic Activity

The cytotoxic activity of the L17-18H CAR-Ts and the clone18LH CAR-Ts on Day 10 after the start of the culture described in (1) of Example 15 above was examined. Next, $5.0 \times 10^3$ APCs-CD19 (K562/CD19) or Raji cells (Raji) and K562 cells serving as target cells were cultured in the presence of chromium 51 ($^{51}$Cr) for 1.5 hours and were thus labeled with chromium 51.

Figure 41:
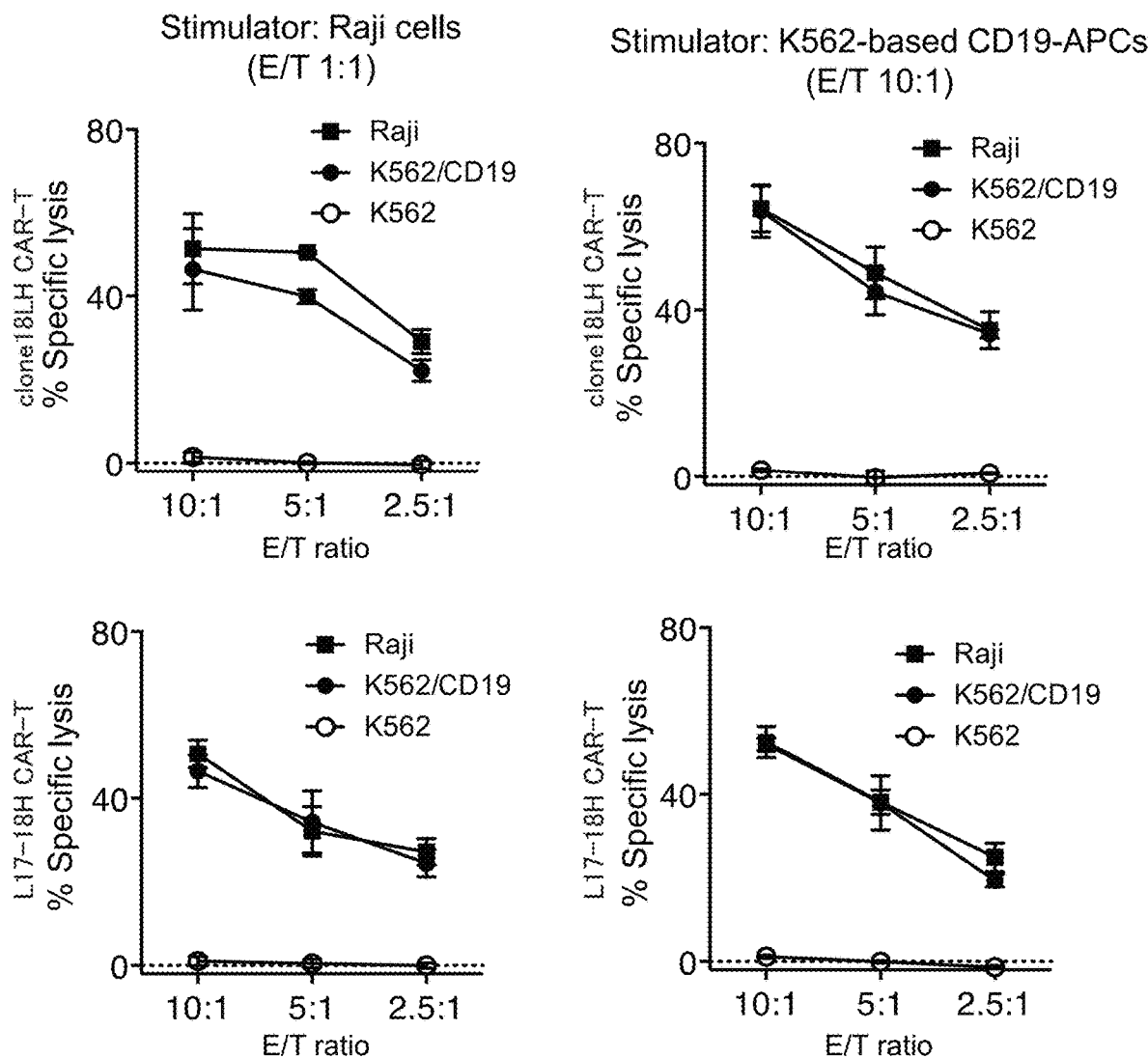
FIG. 41 shows graphs indicating the cytotoxic activity in Example 15.

Next, the L17-18H CAR-Ts or clone18LH CAR-Ts (E) were added to the well in which the chromium 51-labeled target cells (T) were cultured such that a ratio E:T was 10:1, 5:1, or 2.5:1. Then, after the cells were cultured for 5 to 6 hours, the supernatant was collected, and the radiation counting rate per minute (CPM: count per minute) was measured using AccuFLEXg7010. Cytotoxicity (ratio of specific lysis) was measured based on Formula (1) above. FIG. 41 shows the results.

FIG. 41 shows graphs indicating cytotoxic activity. In FIG. 41, the horizontal axes indicate the ratios E:T, the vertical axes indicate cytotoxic activity, and the culture conditions until Day 10 were shown on the upper side of the diagrams. As shown in FIG. 41, it was found that the L17-18H CAR-Ts and the clone18LH CAR-Ts had equivalent cytotoxic activity.

(4) Comparison of T Cell Exhaustion

The L17-18H CAR-Ts and the clone18LH CAR-Ts were prepared in the same manner as in Example 10 above, except that T cells derived from four different donors (humans) were used. The obtained CAR-T cells were incubated in PBS containing CFSE at a concentration of 0.5 μmol/L at 37° C. for 15 minutes, and were thus labeled with CFSE. Next, Raji cells (Raji) (T) irradiated with 20 Gy of γ rays and the L17-18H CAR-Ts or clone18LH CAR-Ts (E) were added to a well such that a ratio E:T was 1:1 or 5:1. The cells were cultured for 3 days after the addition of the target cells.

Figure 42:
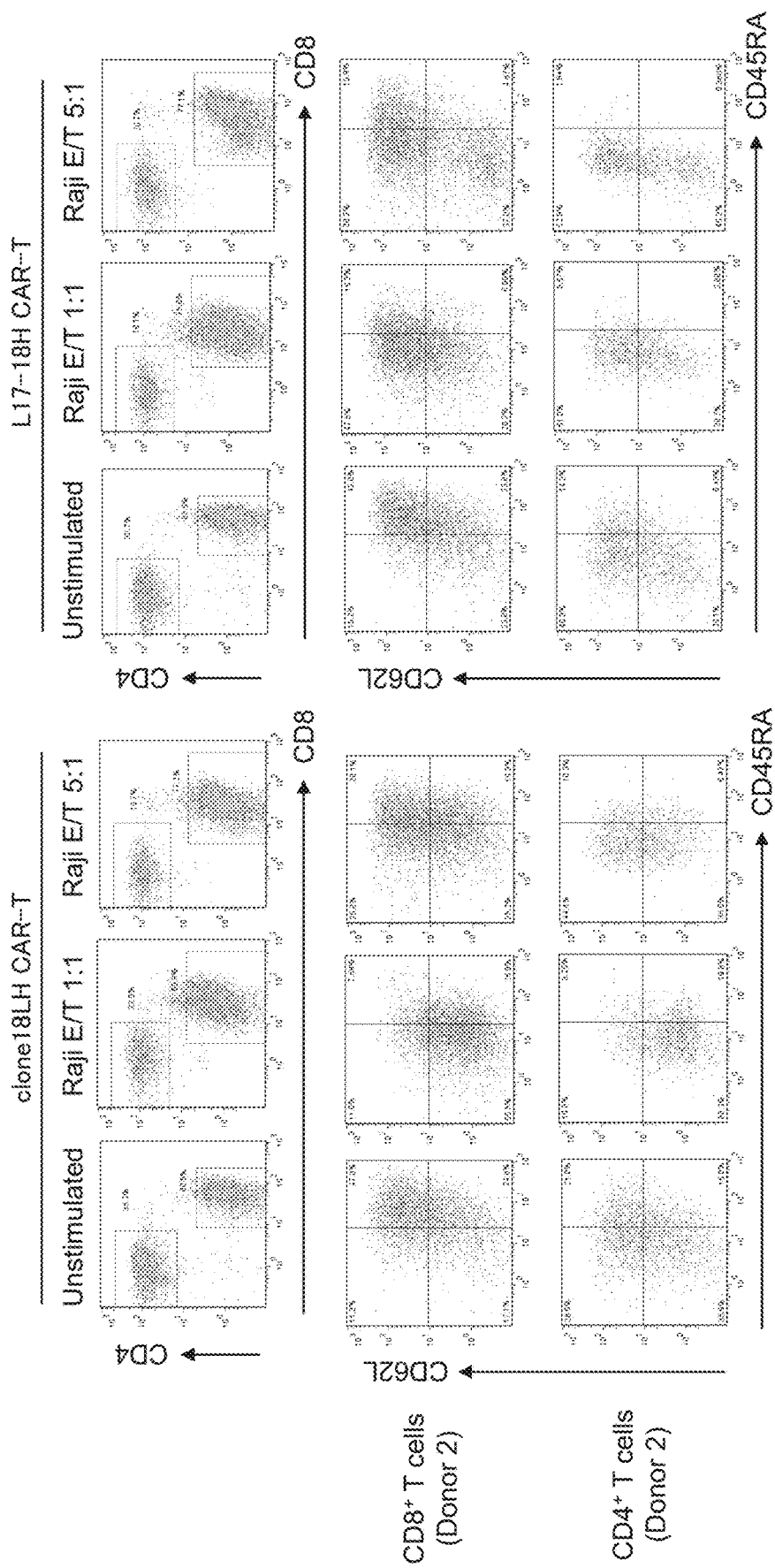
FIG. 42 shows dot plots indicating the distributions of CD45RA/CD62L-positive cells in CD8-positive CAR-T cells and CD4-positive CAR-T cells before and after coculture in Example 15.
Figure 43:
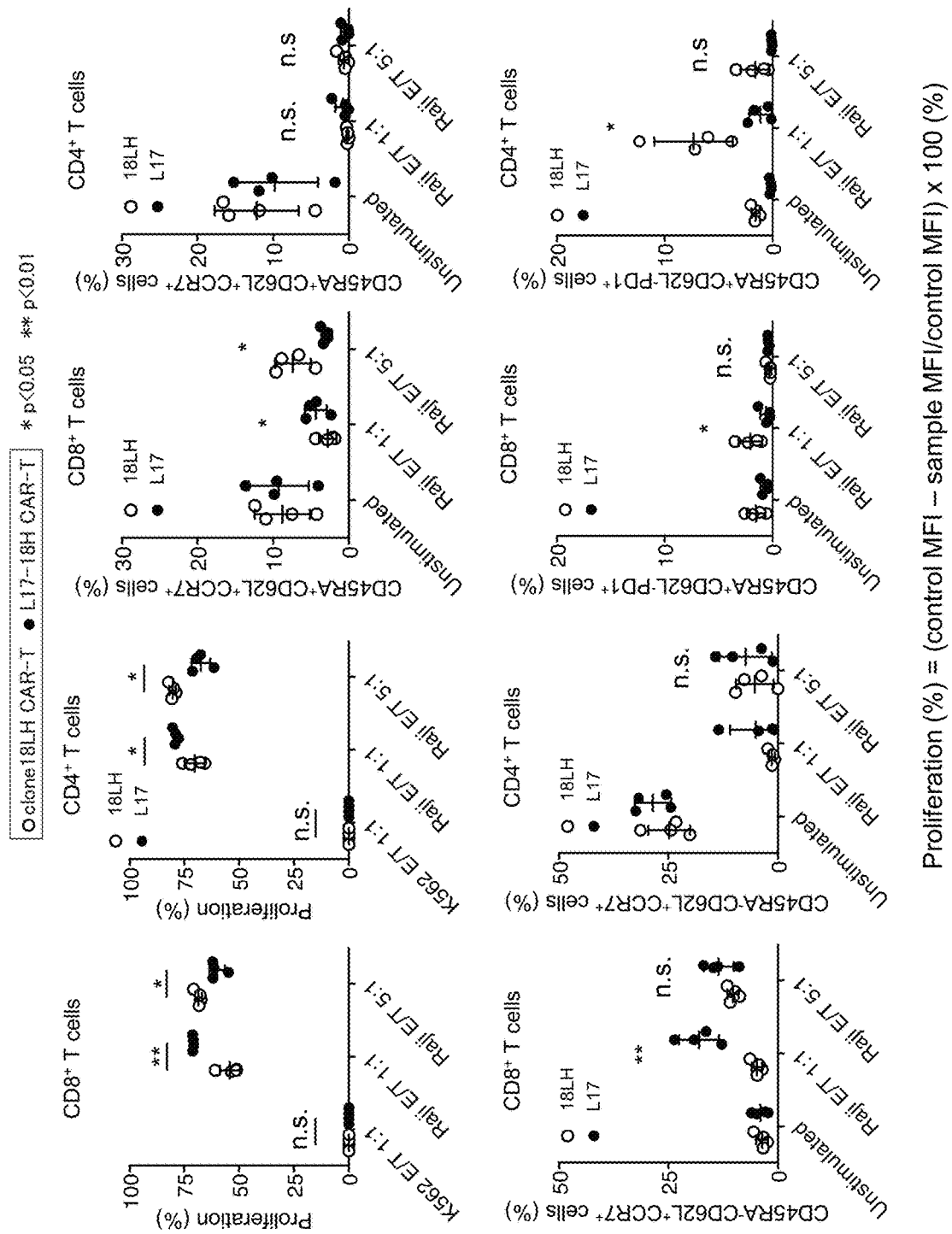
FIG. 43 shows graphs indicating the CAR-T cell division ratios, the ratios of CD45RA-positive CD62L-positive CCR7-positive cells before and after coculture, the ratios of CD45RA-negative CD62L-positive CCR7-positive cells before and after coculture, and the ratios of CD45RA-positive CD62L-negative PD1-positive cells before and after coculture, in Example 15.

After the above-mentioned culture, the CAR-T cells were collected and stained with a PE-labeled anti-PD-1 antibody (clone EH12.2H7), an APC-labeled CD45RA antibody (clone HI100), a PC7-labeled CCR7 antibody (clone G043H7), a BV421-labeled CD62L antibody (clone DREG-56), a PC5-labeled CD8 antibody (clone B9.11), and an APC-Cy7-labeled CD4 antibody (clone RPA-T4), and then the fluorescence intensity was measured using a flow cytometer. The ratio of dividing CAR-T cells was calculated from the obtained MFI of the fluorescence intensity of CFSE based on Formula (2) below. FIG. 42 shows the distributions of CD45RA/CD62L-positive cells in CD8-positive CAR-T cells and CD4-positive CAR-T cells before and after coculture. Furthermore, FIG. 43 shows the CAR-T cell division ratios, the ratios of CD45RA-positive CD62L-positive CCR7-positive cells before and after coculture, the ratios of CD45RA-negative CD62L-positive CCR7-positive cells before and after coculture, and the ratios of CD45RA-positive CD62L-negative PD1-positive cells before and after coculture.

$$\text{Proliferation (\%)} = (\text{control MFI} - \text{sample MFI})/\text{control MFI} \times 100 \quad (2)$$

control MFI: MFI of CAR-T cells cultured together with K562 cell strain on the condition that E:T=1:1 sample MFI: MFI of the CAR-T cells

FIG. 42 shows dot plots indicating the distributions of CD45RA/CD62L-positive cells in CD8-positive CAR-T cells and CD4-positive CAR-T cells before and after coculture. FIG. 43 shows graphs indicating the CAR-T cell division ratios, the ratios of CD45RA-positive CD62L-positive CCR7-positive cells before and after coculture, the ratios of CD45RA-negative CD62L-positive CCR7-positive cells before and after coculture, and the ratios of CD45RA-positive CD62L-negative PD1-positive cells before and after coculture. As shown in FIGS. 42 and 43, the L17-18H CAR-Ts and the clone18LH CAR-Ts had substantially the same character before the coculture. On the other hand, when stimulated in the tumor-rich environment (Raji/CAR-T E/T 1:1) that is considered to simulate the in-vivo environment, the L17-18H CAR-Ts reproducibly exhibited better proliferation capacity compared with the clone18LH CAR-Ts. Furthermore, it became clear that, in the case of the L17-18H CAR-Ts in the same environment, the $CD45RA^+$ $CD62L^+$ $CCR7^+$ character of young T cells was likely to be retained, and the ratio of $CD45RA^-$ $CD62L^+$ $CCR7^+$ central memory T cells increased while the ratio of exhausted $CD45RA^+$ $CD62L^-$ $PD1^+$ T cells decreased, compared with the clone18LH CAR-Ts.

Figure 44:
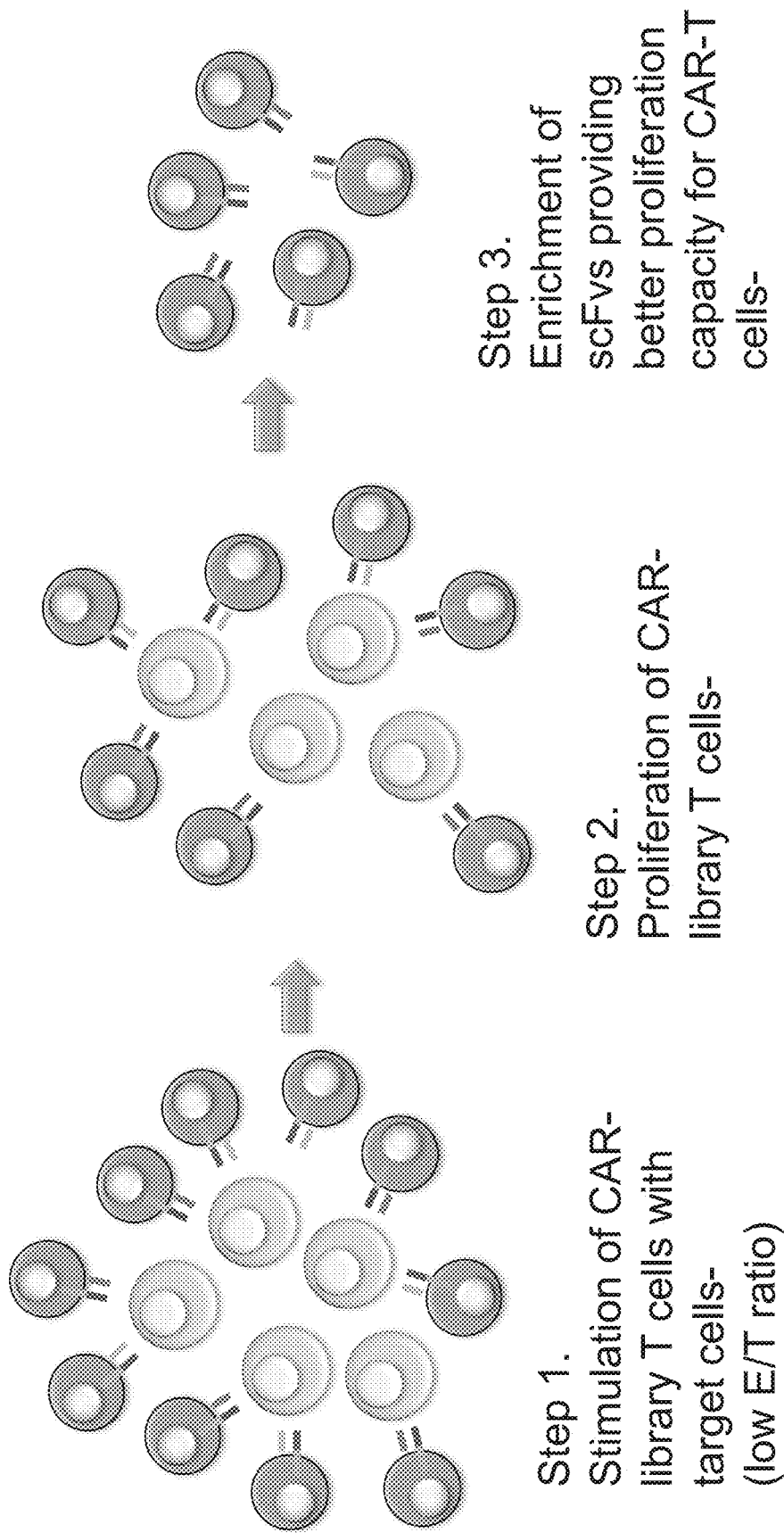
FIG. 44 is a diagram for illustrating a mechanism in which scFvs having an excellent anti-tumor effect in vivo can be obtained using the screening method of the present invention in Example 15.

It is inferred from these results that a mechanism in which scFvs having excellent in-vivo anti-tumor effects can be obtained using the first screening method of the present invention is as follows. It should be noted that the present invention is not limited by the inference above. As shown in FIG. 44, with the screening method of the present invention, immune cells such as T cells into which a CAR library has been introduced (CAR library cells) are brought into contact with a target antigen in the first contact step or second contact step. As a result, cells expressing a CAR specific to the target antigen increase among the CAR library cells. However, each of the E/T ratios of the CAR library cells whose scFvs have different amino acid sequences is significantly low in the first contact step and the second contact step (FIG. 44 Step 1). As a result, CAR library cells characterized by being likely to proliferate even in the case of a low E/T ratio, such as the L17-18H CAR-Ts, are eventually concentrated in the first contact step and the second contact step (FIG. 44 Step 2). Then, the first selection step and the second selection step are performed in the state in which the CAR library cells having such a feature are enriched, and therefore, scFvs derived from CAR library cells characterized by being likely to proliferate even in the case of a low E/T ratio and less likely to be exhausted even when continuing to proliferate are relatively likely to be selected (FIG. 44 Step 3). On the other hand, as in the case of the L17-18H CAR-Ts, CAR library cells capable of proliferating in the case of a low E/T ratio exhibit normal cytotoxic activity. Accordingly, with the screening method of the present invention, CAR library cells that exhibit excellent proliferation capacity and include scFvs exhibiting cytotoxic activity are selected, and it is thus inferred that CARs that included scFvs that are also capable of imparting high anti-tumor activity in vivo can be screened. It should be noted that the above-mentioned mechanism is also effective even when the base skeleton of CAR is changed, and it is thus inferred that scFvs having excellent in-vivo anti-tumor effects can also be obtained even if screening is performed using CARs having intracellular domains other than those of CD28 and CD3ζ.

Although the present invention has been described with reference to the embodiments, the present invention is not limited to the embodiments described above. Various modifications that can be understood by a person skilled in the art can be made in the configurations and details of the present invention without departing from the scope of the present invention.

This application claims priority from Japanese Patent Application No. 2019-018269 filed on Feb. 4, 2019, Japanese Patent Application No. 2019-094188 filed on May 18, 2019, Japanese Patent Application No. 2019-140121 filed on Jul. 30, 2019, and Japanese Patent Application No. 2019-184071 filed on Oct. 4, 2019. The entire subject matter of the Japanese Patent Applications is incorporated herein by reference.

Supplementary Notes

Some or all of the above-mentioned embodiments and examples may also be described as supplementary notes below, but are not limited thereto.

Supplementary Note 1

A chimeric antigen receptor (CAR) library comprising nucleic acids coding for first CARs,
wherein each of the first CARs includes a first antigen-binding domain, a first transmembrane domain, and a first intracellular signaling domain,
the first antigen-binding domain includes a first single-chain antibody (scFv) to be screened for ability to bind to a target antigen,
the first scFv includes a first heavy-chain variable region and a first light-chain variable region,
the first heavy-chain variable region and the first light-chain variable region meet Condition 1 or Condition 2 below,
Condition 1 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of an antibody capable of binding to the target antigen or an antigen-binding fragment of the antibody, respectively, and
a light-chain complementarity determining region (CDRL) 1, a CDRL2, and a CDRL3 in the first light-chain variable region include a CDRL1, a CDRL2, and a CDRL3 in a light-chain variable region of a first B cell receptor, respectively, and
Condition 2 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of a first B cell receptor, respectively, and
a light-chain complementarity determining region (CDRL) 1, a CDRL2, and a CDRL3 in the first light-chain variable region include a CDRL1, a CDRL2, and a CDRL3 in a light-chain variable region of an antibody capable of binding to the target antigen or an antigen-binding fragment of the antibody, respectively.

Supplementary Note 2

The CAR library according to Supplementary Note 1, wherein the first intracellular signaling domain includes an intracellular signaling domain of CD3.

Supplementary Note 3

The CAR library according to Supplementary Note 1 or 2, wherein the first transmembrane domain includes a transmembrane domain of CD28.

Supplementary Note 4

The CAR library according to any one of Supplementary Notes 1 to 3, wherein the first B cell receptor is a B cell receptor of B cells derived from a human.

Supplementary Note 5

An scFv manufacturing method (screening method) comprising:
  a first expression step of expressing the CAR library according to any one of Supplementary Notes 1 to 4 in immune cells;
  a first contact step of bringing the immune cells obtained in the first expression step into contact with a target antigen; and
  a first selection step of selecting a first scFvs of the CARs expressed in the immune cells that have bound to the target antigen in the first contact step as first candidate scFvs capable of binding to the target antigen.

Supplementary Note 6

The manufacturing method (screening method) according to Supplementary Note 5, further comprising
  a preparation step of preparing a second CAR library based on the first candidate scFvs,
  wherein the second CAR library includes nucleic acids coding for second CARs,
  each of the second CARs includes a second antigen-binding domain, a second transmembrane domain, and a second intracellular signaling domain,
  the second antigen-binding domain includes a second scFv to be screened for ability to bind to the target antigen,
  the second scFv includes a second heavy-chain variable region and a second light-chain variable region,
  the second heavy-chain variable region and the second light-chain variable region meet Condition 3 or Condition 4 below,
  the method further comprises:
    a second expression step of expressing the second CAR library in immune cells,
    a second contact step of bringing the immune cells obtained in the second expression step into contact with the target antigen; and
    a second selection step of selecting second scFvs of CARs expressed in immune cells that have bound to the target antigen in the second contact step as second candidate scFvs capable of binding to the target antigen,
  Condition 3 is as follows:
  if the CAR library in the first expression step meets Condition 1 above,
  a CDRH1, a CDRH2, and a CDRH3 in the second heavy-chain variable region include a CDRH1, a CDRH2, and a CDRH3 in a heavy-chain variable region of a second B cell receptor, respectively, and
  a CDRL1, a CDRL2, and a CDRL3 in the second light-chain variable region include a CDRL1, a CDRL2, and a CDRL3 in a light-chain variable region of the first candidate scFv, respectively, and
  Condition 4 is as follows:
  if the CAR library in the first expression step meets Condition 2 above,
  a CDRH1, a CDRH2, and a CDRH3 in the second heavy-chain variable region include a CDRH1, a CDRH2, and a CDRH3 in a heavy-chain variable region of the first candidate scFv, respectively, and
  a CDRL1, a CDRL2, and a CDRL3 in the second light-chain variable region include a CDRL1, a CDRL2, and a CDRL3 in a light-chain variable region of a second B cell receptor, respectively.

Supplementary Note 7

The scFv manufacturing method (screening method) according to Supplementary Note 6, wherein the second contact step is performed a plurality of times.

Supplementary Note 8

The scFv manufacturing method (screening method) according to Supplementary Note 6 or 7,
  wherein immune cells capable of binding to the target antigen are detected using a monomer or multimer of the target antigen in the second selection step, and
  scFvs expressed in the detected immune cells are selected as the second candidate scFvs.

Supplementary Note 9

The scFv manufacturing method (screening method) according to any one of Supplementary Notes 6 to 8, wherein the second B cell receptor is a B cell receptor of B cells derived from a human.

Supplementary Note 10

The scFv manufacturing method (screening method) according to any one of Supplementary Notes 5 to 9, wherein the first contact step is performed a plurality of times.

Supplementary Note 11

The scFv manufacturing method (screening method) according to any one of Supplementary Notes 5 to 10,
  wherein immune cells capable of binding to the target antigen are detected using a monomer or multimer of the target antigen in the first selection step, and
  scFvs expressed in the detected immune cells are selected as the first candidate scFvs.

Supplementary Note 12

The scFv manufacturing method (screening method) according to any one of Supplementary Notes 5 to 11, wherein the immune cells are T cells.

Supplementary Note 13

An antibody against a complex of HLA-A*02:01 and NY-ESO-$1_{157-165}$ or an antigen-binding fragment of the antibody, comprising a heavy-chain variable region of (H) below and a light-chain variable region of (L) below:
  (H) a heavy-chain variable region that includes
    a heavy-chain complementarity determining region (CDRH) 1, a CDRH2, and a CDRH3,
    wherein the CDRH1 is a polypeptide that includes an amino acid sequence of (H1),
    the CDRH2 is a polypeptide that includes an amino acid sequence of (H2), the CDRH3 is a polypeptide that includes an amino acid sequence of (H3), and the amino acid sequences of (H1), (H2), and (H3) are as follows:

(H1) an amino acid sequence of (H1-1), (H1-2), or (H1-3) below:
- (H1-1) any one of amino acid sequences of CDRH1 shown in Table 1A above,
- (H1-2) an amino acid sequence having 80% or more identity to the amino acid sequence of (H1-1), and
- (H1-3) an amino acid sequence consisting of the amino acid sequence of (H1-1) with deletion, substitution, insertion, and/or addition of one or several amino acids, (H2) an amino acid sequence of (H2-1), (H2-2), or (H2-3) below:
- (H2-1) any one of amino acid sequences of CDRH2 shown in Table 1A above,
- (H2-2) an amino acid sequence having 80% or more identity to the amino acid sequence of (H2-1), and
- (H2-3) an amino acid sequence consisting of the amino acid sequence of (H2-1) with deletion, substitution, insertion, and/or addition of one or several amino acids, (H3) an amino acid sequence of (H3-1), (H3-2), or (H3-3) below:
- (H3-1) any one of amino acid sequences of CDRH3 shown in Table 1A above,
- (H3-2) an amino acid sequence having 80% or more identity to the amino acid sequence of (H3-1), and
- (H3-3) an amino acid sequence consisting of the amino acid sequence of (H3-1) with deletion, substitution, insertion, and/or addition of one or several amino acids; and (L) a light-chain variable region that includes
a light-chain complementarity determining region (CDRL) 1, a CDRL2, and a CDRL3, wherein the CDRL1 is a polypeptide that includes an amino acid sequence of (L1), the CDRL2 is a polypeptide that includes an amino acid sequence of (L2), the CDRL3 is a polypeptide that includes an amino acid sequence of (L3), and the amino acid sequences of (L1), (L2), and (L3) are as follows:

(L1) an amino acid sequence of (L1-1), (L1-2), or (L1-3) below:
- (L1-1) any one of amino acid sequences of CDRL1 shown in Table 1B above,
- (L1-2) an amino acid sequence having 80% or more identity to the amino acid sequence of (L1-1), and
- (L1-3) an amino acid sequence consisting of the amino acid sequence of (L1-1) with deletion, substitution, insertion, and/or addition of one or several amino acids, (L2) an amino acid sequence of (L2-1), (L2-2), or (L2-3) below:
- (L2-1) any one of amino acid sequences of CDRL2 shown in Table 1B above,
- (L2-2) an amino acid sequence having 80% or more identity to the amino acid sequence of (L2-1), and
- (L2-3) an amino acid sequence consisting of the amino acid sequence of (L2-1) with deletion, substitution, insertion, and/or addition of one or several amino acids, (L3) an amino acid sequence of (L3-1), (L3-2), or (L3-3) below:
- (L3-1) any one of amino acid sequences of CDRL3 shown in Table 1B above,
- (L3-2) an amino acid sequence having 80% or more identity to the amino acid sequence of (L3-1), and
- (L3-3) an amino acid sequence consisting of the amino acid sequence of (L3-1) with deletion, substitution, insertion, and/or addition of one or several amino acids.

Supplementary Note 14

The antibody or the antigen-binding fragment of the antibody according to Supplementary Note 13, wherein a combination of the heavy-chain variable region and the light-chain variable region is any one of combinations shown in Table 2 above.

Supplementary Note 15

A chimeric antigen receptor comprising
an antigen-binding domain, a transmembrane domain, and an intracellular signaling domain,
wherein the antigen-binding domain includes the antibody or the antigen-binding fragment of the antibody according to Supplementary Note 13 or 14.

Supplementary Note 16

The chimeric antigen receptor according to Supplementary Note 15, wherein the antigen-binding fragment is a single-chain antibody.

Supplementary Note 17

A nucleic acid coding for the chimeric antigen receptor according to Supplementary Note 15 or 16.

Supplementary Note 18

A cell comprising the chimeric antigen receptor according to Supplementary Note 15 or 16.

Supplementary Note 19

The cell according to Supplementary Note 18, wherein the cell includes a T cell.

Supplementary Note 20

A cell manufacturing method comprising an introduction step of introducing the nucleic acid according to Supplementary Note 17 into a cell.

Supplementary Note 21

The cell manufacturing method according to Supplementary Note 20, wherein the cell includes a T cell.

Supplementary Note 22

A bispecific antibody (BsAb) library comprising
nucleic acids coding for first BsAbs,
wherein each of the first BsAbs includes a first antigen-binding domain and a second antigen-binding domain,
the first antigen-binding domain includes a first single-chain antibody (scFv) capable of binding to a first target antigen,
the second antigen-binding domain includes a second scFv to be screened for the ability to bind to a second target antigen,
the second scFv includes a second heavy-chain variable region and a second light-chain variable region, the second heavy-chain variable region and the second light-chain variable region meet Condition 1 or Condition 2 below,
the first target antigen or the second target antigen is an immune cell-activating receptor,
Condition 1 is as follows:
a heavy-chain complementarity determining region (CDRH) 1, a CDRH2, and a CDRH3 in the second heavy-chain variable region include a CDRH1, a CDRH2, and a CDRH3 in a heavy-chain variable region of an antibody capable of binding to the second target antigen or an antigen-binding fragment of the antibody, respectively, and
a light-chain complementarity determining region (CDRL) 1, a CDRL2, and a CDRL3 in the second light-chain variable region include a CDRL1, a CDRL2, and a CDRL3 in a light-chain variable region of a first B cell receptor, respectively, and
Condition 2 is as follows:
a heavy-chain complementarity determining region (CDRH) 1, a CDRH2, and a CDRH3 in the second heavy-chain variable region include a CDRH1, a CDRH2, and a CDRH3 in a heavy-chain variable region of a first B cell receptor, respectively, and
a light-chain complementarity determining region (CDRL) 1, a CDRL2, and a CDRL3 in the second light-chain variable region include a CDRL1, a CDRL2, and a CDRL3 in a light-chain variable region of an antibody capable of binding to the second target antigen or an antigen-binding fragment of the antibody, respectively.

Supplementary Note 23

The BsAb library according to Supplementary Note 22, wherein the first B cell receptor is a B cell receptor of B cells derived from a human.

Supplementary Note 24

The BsAb library according to Supplementary Note 22 or 23, wherein the immune cell-activating receptor is CD3.

Supplementary Note 25

An scFv manufacturing method (screening method) comprising:
a first production step of producing first BsAbs from the BsAb library according to any one of Supplementary Notes 22 to 24;
a first contact step in which, when the first target antigen is an immune cell-activating receptor,
the first BsAbs, the second target antigen, and immune cells capable of expressing the immune cell-activating receptor are brought into contact with one another, and
when the second target antigen is an immune cell-activating receptor,
the first BsAbs, the first target antigen, and immune cells capable of expressing the immune cell-activating receptor are brought into contact with one another; and
a first selection step of selecting second scFvs of the first BsAbs that have bound to the second target antigen in the first contact step as first candidate scFvs capable of binding to the second target antigen.

Supplementary Note 26

The scFv manufacturing method (screening method) according to Supplementary Note 25, further comprising a preparation step of preparing a second BsAb library based on the first candidate scFvs,
wherein the second BsAb library includes nucleic acids coding for the second BsAbs,
each of the second BsABs includes a third antigen-binding domain and a fourth antigen-binding domain,
the third antigen-binding domain includes a third scFv capable of binding to the first target antigen,
the fourth antigen-binding domain includes a fourth scFv to be screened for the ability to bind to the second target antigen,
the fourth scFv includes a fourth heavy-chain variable region and a fourth light-chain variable region,
the fourth heavy-chain variable region and the fourth light-chain variable region meet Condition 3 or Condition 4 below,
the method further comprises:
a second production step of producing the second BsAbs from the second BsAb library;
a second contact step in which, when the first target antigen is the immune cell-activating receptor,
the second BsAbs, the second target antigen, and immune cells capable of expressing the immune cell-activating receptor are brought into contact with one another, and
when the second target antigen is the immune cell-activating receptor,
the second BsAbs, the first target antigen, and immune cells capable of expressing the immune cell-activating receptor are brought into contact with one another; and
a second selection step of selecting fourth scFvs of the second BsAbs that have bound to the second target antigen in the second contact step as second candidate scFvs capable of binding to the second target antigen,
Condition 3 is as follows:
if the BsAb library in the first production step meets Condition 1 above,
a CDRH1, a CDRH2, and a CDRH3 in the fourth heavy-chain variable region include a CDRH1, a CDRH2, and a CDRH3 in a heavy-chain variable region of a second B cell receptor, respectively, and
a CDRL1, a CDRL2, and a CDRL3 in the fourth light-chain variable region include a CDRL1, a CDRL2, and a CDRL3 in a light-chain variable region of the first candidate BsAb, respectively, and
Condition 4 is as follows:
if the BsAb library in the first production step meets Condition 2 above,
a CDRH1, a CDRH2, and a CDRH3 in the fourth heavy-chain variable region include a CDRH1, a CDRH2, and a CDRH3 in a heavy-chain variable region of the first candidate BsAb, respectively, and
a CDRL1, a CDRL2, and a CDRL3 in the fourth light-chain variable region include a CDRL1, a CDRL2, and a CDRL3 in a light-chain variable region of a second B cell receptor, respectively.

Supplementary Note 27

The scFv manufacturing method (screening method) according to Supplementary Note 26, wherein the second contact step and the second selection step are performed as one set, and this set is performed a plurality of times.

Supplementary Note 28

The scFv manufacturing method (screening method) according to Supplementary Note 26 or 27, wherein expression of a molecule capable of activating the immune cells is detected in the second selection step, and a second BsAbs that have induced the molecule capable of activating the immune cells are selected as the second candidate BsAbs.

Supplementary Note 29

The scFv manufacturing method (screening method) according to any one of Supplementary Notes 25 to 28, wherein the second B cell receptor is a B cell receptor of B cells derived from a human.

Supplementary Note 30

The scFv manufacturing method (screening method) according to any one of Supplementary Notes 25 to 29, wherein the first contact step and the first selection step are performed as one set, and this set is performed a plurality of times.

Supplementary Note 31

The scFv manufacturing method (screening method) according to any one of Supplementary Notes 25 to 30,
wherein expression of a molecule capable of activating the immune cells is detected in the first selection step, and
the first BsAbs that have induced the molecule capable of activating the immune cells are selected as the first candidate BsAbs.

Supplementary Note 32

The scFv manufacturing method (screening method) according to any one of Supplementary Notes 25 to 31, wherein the immune cell-activating receptor is CD3.

Supplementary Note 33

The scFv manufacturing method (screening method) according to any one of Supplementary Notes 25 to 32, wherein the immune cells are T cells.

Supplementary Note 34

An antibody against CD19 or an antigen-binding fragment of the antibody, comprising a heavy-chain variable region of (H) below and a light-chain variable region of (L) below:
  (H) a heavy-chain variable region that includes
  a heavy-chain complementarity determining region (CDRH) 1, a CDRH2, and a CDRH3,
  wherein the CDRH1 is a polypeptide that includes an amino acid sequence of (H1),
  the CDRH2 is a polypeptide that includes an amino acid sequence of (H2),
  the CDRH3 is a polypeptide that includes an amino acid sequence of (H3), and
  the amino acid sequences of (H1), (H2), and (H3) are as follows:
  (H1) an amino acid sequence of (H1-1), (H1-2), or (H1-3) below:
    (H1-1) any one of amino acid sequences of CDRH1 shown in Table 3A above,
    (H1-2) an amino acid sequence having 80% or more identity to the amino acid sequence of (H1-1), and
    (H1-3) an amino acid sequence consisting of the amino acid sequence of (H1-1) with deletion, substitution, insertion, and/or addition of one or several amino acids,
  (H2) an amino acid sequence of (H2-1), (H2-2), or (H2-3) below:
    (H2-1) any one of amino acid sequences of CDRH2 shown in Table 3A above,
    (H2-2) an amino acid sequence having 80% or more identity to the amino acid sequence of (H2-1), and
    (H2-3) an amino acid sequence consisting of the amino acid sequence of (H2-1) with deletion, substitution, insertion, and/or addition of one or several amino acids,
  (H3) an amino acid sequence of (H3-1), (H3-2), or (H3-3) below:
    (H3-1) any one of amino acid sequences of CDRH3 shown in Table 3A above,
    (H3-2) an amino acid sequence having 80% or more identity to the amino acid sequence of (H3-1), and
    (H3-3) an amino acid sequence consisting of the amino acid sequence of (H3-1) with deletion, substitution, insertion, and/or addition of one or several amino acids; and
  (L) a light-chain variable region that includes
  a light-chain complementarity determining region (CDRL) 1, a CDRL2, and a CDRL3,
  wherein the CDRL1 is a polypeptide that includes an amino acid sequence of (L1),
  the CDRL2 is a polypeptide that includes an amino acid sequence of (L2),
  the CDRL3 is a polypeptide that includes an amino acid sequence of (L3), and
  the amino acid sequences of (L1), (L2), and (L3) are as follows:
  (L1) an amino acid sequence of (L1-1), (L1-2), or (L1-3) below:
    (L1-1) any one of amino acid sequences of CDRL1 shown in Table 3B above,
    (L1-2) an amino acid sequence having 80% or more identity to the amino acid sequence of (L1-1), and
    (L1-3) an amino acid sequence consisting of the amino acid sequence of (L1-1) with deletion, substitution, insertion, and/or addition of one or several amino acids,
  (L2) an amino acid sequence of (L2-1), (L2-2), or (L2-3) below:
    (L2-1) any one of amino acid sequences of CDRL2 shown in Table 3B above,
    (L2-2) an amino acid sequence having 80% or more identity to the amino acid sequence of (L2-1), and
    (L2-3) an amino acid sequence consisting of the amino acid sequence of (L2-1) with deletion, substitution, insertion, and/or addition of one or several amino acids,
  (L3) an amino acid sequence of (L3-1), (L3-2), or (L3-3) below:
    (L3-1) any one of amino acid sequences of CDRL3 shown in Table 3B above,
    (L3-2) an amino acid sequence having 80% or more identity to the amino acid sequence of (L3-1), and
    (L3-3) an amino acid sequence consisting of the amino acid sequence of (L3-1) with deletion, substitution, insertion, and/or addition of one or several amino acids.

Supplementary Note 35

The antibody or the antigen-binding fragment of the antibody according to Supplementary Note 34, wherein a combination of the heavy-chain variable region and the light-chain variable region is any one of combinations shown in Table 2 above.

Supplementary Note 36

A chimeric antigen receptor comprising
an antigen-binding domain, a transmembrane domain, and an intracellular signaling domain,
wherein the antigen-binding domain includes the antibody or the antigen-binding fragment of the antibody according to Supplementary Note 34 or 35.

Supplementary Note 37

The chimeric antigen receptor according to Supplementary Note 36, wherein the antigen-binding fragment is a single-chain antibody.

Supplementary Note 38

A nucleic acid coding for the chimeric antigen receptor according to Supplementary Note 36 or 37.

Supplementary Note 39

A cell comprising the chimeric antigen receptor according to Supplementary Note 36 or 37.

Supplementary Note 40

The cell according to Supplementary Note 39, wherein the cell includes a T cell.

Supplementary Note 41

A cell manufacturing method comprising an introduction step of introducing the nucleic acid according to Supplementary Note 38 into a cell.

Supplementary Note 42

The cell manufacturing method according to Supplementary Note 41, wherein the cell includes a T cell.

Supplementary Note 43

An scFv manufacturing method comprising:
a first administration step of administering cells expressing a first chimeric antigen receptor (CAR) library to an animal, and
a first collection step of collecting the cells expressing the first CAR library that accumulate in a tissue expressing a target antigen in the animal as cells expressing CARs specific to the target antigen,
wherein the first CAR library includes nucleic acids coding for first CARs,
each of the first CARs includes a first antigen-binding domain, a first transmembrane domain, and a first intracellular signaling domain,
the first antigen-binding domain includes a first single-chain antibody (scFv) to be screened for the ability to bind to the target antigen,
the first scFv includes a first heavy-chain variable region and a first light-chain variable region,
the first heavy-chain variable region and the first light-chain variable region meet Condition 1 or Condition 2 below,
Condition 1 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of an antibody capable of binding to the target antigen or an antigen-binding fragment of the antibody, respectively, and
a light-chain complementarity determining region (CDRL) 1, a CDRL2, and a CDRL3 in the first light-chain variable region include a CDRL1, a CDRL2, and a CDRL3 in a light-chain variable region of a first B cell receptor, respectively, and
Condition 2 is as follows:
a heavy-chain complementarity determining region (CDRH) 1, a CDRH2, and a CDRH3 in the first heavy-chain variable region include a CDRH1, a CDRH2, and a CDRH3 in a heavy-chain variable region of a first B cell receptor, respectively, and
a light-chain complementarity determining region (CDRL) 1, a CDRL2, and a CDRL3 in the first light-chain variable region include a CDRL1, a CDRL2, and a CDRL3 in a light-chain variable region of an antibody capable of binding to the target antigen or an antigen-binding fragment of the antibody, respectively.

Supplementary Note 44

The manufacturing method according to Supplementary Note 43, wherein a plurality of types of cells expressing the first CAR library are administered in the first administration step.

Supplementary Note 45

The manufacturing method according to Supplementary Note 43 or 44, comprising a first stimulation step of administering the target antigen to the animal after the first administration step.

Supplementary Note 46

The manufacturing method according to any one of Supplementary Notes 43 to 45, comprising a first restimulation step of restimulating the cells expressing CARs specific to the target antigen with the target antigen.

Supplementary Note 47

The manufacturing method according to any one of Supplementary Notes 43 to 46, comprising a first formation step of forming a tissue expressing a target antigen prior to the first administration step by introducing cells expressing the target antigen into the animal.

Supplementary Note 48

The manufacturing method according to any one of Supplementary Notes 43 to 47, wherein the cells expressing the first CAR library that accumulate in the expressing tissue are collected as cells expressing CARs specific to the target antigen.

Supplementary Note 49

The manufacturing method according to any one of Supplementary Notes 43 to 48, wherein the first B cell receptor is a B cell receptor of B cells derived from a human.

Supplementary Note 50

The manufacturing method according to any one of Supplementary Notes 43 to 49, further comprising:
a second administration step of administering cells expressing a second CAR library to an animal, and
a second collection step of collecting the cells expressing the second CAR library that accumulate in a tissue expressing a target antigen in the animal as cells expressing CARs specific to the target antigen,
wherein the second CAR library includes nucleic acids coding for second CARs,
each of the second CARs includes a second antigen-binding domain, a second transmembrane domain, and a second intracellular signaling domain,
the second antigen-binding domain includes a second scFv to be screened for the ability to bind to the target antigen,
the second scFv includes a second heavy-chain variable region and a second light-chain variable region,
the second heavy-chain variable region and the second light-chain variable region meet Condition 3 or Condition 4 below,
Condition 3 is as follows:
if the first CAR library meets Condition 1 above,
a CDRH1, a CDRH2, and a CDRH3 in the second heavy-chain variable region include a CDRH1, a CDRH2, and a CDRH3 in a heavy-chain variable region of a second B cell receptor, respectively, and
a CDRL1, a CDRL2, and a CDRL3 in the second light-chain variable region include a CDRL1, a CDRL2, and a CDRL3 in a light-chain variable region of an scFv of the cell expressing the CAR specific to the target antigen, respectively, and
Condition 4 is as follows:
if the first CAR library meets Condition 2 above,
a CDRH1, a CDRH2, and a CDRH3 in the second heavy-chain variable region include a CDRH1, a CDRH2, and a CDRH3 in a heavy-chain variable region of an scFv of the cell expressing the CAR specific to the target antigen, respectively, and
a CDRL1, a CDRL2, and a CDRL3 in the second light-chain variable region include a CDRL1, a CDRL2, and a CDRL3 in a light-chain variable region of a second B cell receptor, respectively.

Supplementary Note 51

The manufacturing method according to Supplementary Note 50, wherein a plurality of types of cells expressing the second CAR library are administered in the second administration step.

Supplementary Note 52

The manufacturing method according to Supplementary Note 50 or 51, further comprising a second stimulation step of administering the target antigen to the animal after the second administration step.

Supplementary Note 53

The manufacturing method according to any one of Supplementary Notes 50 to 52, further comprising a first restimulation step of restimulating the cells expressing CARs specific to the target antigen with the target antigen.

Supplementary Note 54

The manufacturing method according to any one of Supplementary Notes 50 to 53, further comprising a second formation step of forming a tissue expressing a target antigen prior to the second administration step by introducing cells expressing the target antigen into the animal.

Supplementary Note 55

The manufacturing method according to any one of Supplementary Notes 50 to 54, wherein the tissue expressing the target antigen is collected in the second collection step, and the cells expressing the second CAR library that accumulate in the tissue expressing the target antigen are collected as cells expressing CARs specific to the target antigen.

Supplementary Note 56

The manufacturing method according to any one of Supplementary Notes 50 to 55, wherein the second B cell receptor is a B cell receptor of B cells derived from a human.

Supplementary Note 57

The manufacturing method according to any one of Supplementary Notes 43 to 56, wherein the expressing cells are T cells.

Supplementary Note 58

The manufacturing method according to any one of Supplementary Notes 43 to 57, wherein the target antigen is a tumor antigen.

Supplementary Note 59

The manufacturing method according to any one of Supplementary Notes 43 to 58, wherein the animal is a non-human animal.

Supplementary Note 60

The manufacturing method according to any one of Supplementary Notes 43 to 59, wherein the animal is an immune-suppressed animal.

INDUSTRIAL APPLICABILITY

As described above, with the present invention, a CAR library used to screen scFvs that can be functional in CAR-T cells, and an scFv screening method in which the CAR library is used can be provided. Therefore, it can be said that the present invention is significantly useful in the pharmaceutical field and the like.

The invention claimed is:

1. A single-chain antibody (scFv) manufacturing method comprising:

a first expression step of expressing a CAR library in immune cells;

a first contact step of bringing the immune cells obtained in the first expression step into contact with a target antigen; and a first selection step of selecting first scFvs of the CARs expressed in the immune cells that have bound to the target antigen in the first contact step as first candidate scFvs capable of binding to the target antigen, wherein the CAR library comprises nucleic acids coding for different first CARs, wherein each of the first CARs includes a first antigen-binding domain, a first transmembrane domain, and a first intracellular signaling domain, wherein the first antigen-binding domain includes a first single-chain antibody (scFv) to be screened for ability to bind to a target antigen, wherein the first scFv includes a first heavy-chain variable region and a first light-chain variable region, wherein the different CARs include either the heavy-chain variable region or the light-chain variable region of an antibody capable of binding to the target antigen, and the other of the first heavy-chain variable region and the first light-chain variable region is derived from a B cell receptor that may or may not bind to the target antigen, wherein the first heavy-chain variable region includes a heavy-chain complementarity determining region (CDRH) 1, a CDRH2, and a CDRH3 and the first light-chain variable region includes a light-chain complementarity determining region (CDRL) 1, a CDRL2, and a CDRL3, wherein Condition 1 or Condition 2 below is met, Condition 1 is as follows:

the CDRH1, CDRH2, and CDRH3 in the first heavy-chain variable region include a CDRH1, a CDRH2, and a CDRH3 in a heavy-chain variable region of the antibody capable of binding to the target antigen or an antigen-binding fragment of the antibody, respectively, and the CDRL1, CDRL2, and CDRL3 in the first light-chain variable region include a CDRL1, a CDRL2, and a CDRL3 in a light-chain variable region of a first B cell receptor, respectively, and Condition 2 is as follows:

the CDRH1, CDRH2, and CDRH3 in the first heavy-chain variable region include a CDRH1, a CDRH2, and a CDRH3 in a heavy-chain variable region of a first B cell receptor, respectively, and the CDRL1, CDRL2, and CDRL3 in the first light-chain variable region include a CDRL1, a CDRL2, and a CDRL3 in a light-chain variable region of the antibody capable of binding to the target antigen or an antigen-binding fragment of the antibody, respectively, and wherein a number of types of nucleic acids in the CAR library is $1 \times 10^5$ to $1 \times 10^7$.

2. The scFv manufacturing method according to claim 1, wherein the first contact step is performed a plurality of times.

3. The scFv manufacturing method according to claim 1, wherein immune cells capable of binding to the target antigen are detected using a monomer or multimer of the target antigen in the first selection step, and scFvs expressed in the detected immune cells are selected as the first candidate scFvs.

4. The scFv manufacturing method according to claim 1, wherein the immune cells are T cells.

* * * * *

SEQUENCE LISTING

<160> NUMBER OF SEQ ID NOS: 324

<210> SEQ ID NO 1
<211> LENGTH: 18
<212> TYPE: PRT
<213> ORGANISM: Artificial Sequence
<220> FEATURE:
<223> OTHER INFORMATION: FV linker 1

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 15
<212> TYPE: PRT
<213> ORGANISM: Artificial Sequence
<220> FEATURE:
<223> OTHER INFORMATION: FV linker 2

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 54
<212> TYPE: DNA
<213> ORGANISM: Artificial Sequence
<220> FEATURE:
<223> OTHER INFORMATION: FV linker 1

<400> SEQUENCE: 3
ggctctacaa gcggctctgg caagcctgga tctggcgagg gaagcaccaa gggc            54

<210> SEQ ID NO 4
<211> LENGTH: 45
<212> TYPE: DNA
<213> ORGANISM: Artificial Sequence
<220> FEATURE:
<223> OTHER INFORMATION: FV linker 2

<400> SEQUENCE: 4
ggtggaggag gctcaggagg aggtggctct ggtggtggag gctcg                     45

<210> SEQ ID NO 5
<211> LENGTH: 27
<212> TYPE: PRT
<213> ORGANISM: Homo sapiens

<400> SEQUENCE: 5

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 6
<211> LENGTH: 81
<212> TYPE: DNA
<213> ORGANISM: Homo sapiens

<400> SEQUENCE: 6
ttctgggtgc tggtggtcgt gggcggagtg ctggcctgtt atagcctgct cgtgaccgtg      60
gccttcatca tcttttgggt g                                               81

<210> SEQ ID NO 7
<211> LENGTH: 107
<212> TYPE: PRT
<213> ORGANISM: Homo sapiens

<400> SEQUENCE: 7

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 8
<211> LENGTH: 321
<212> TYPE: DNA
<213> ORGANISM: Homo sapiens

<400> SEQUENCE: 8
atcgaagtga tgtaccccccc tccctacctg gacaacgaga gtccaacgg caccattatc      60 cacgtgaagg gaaagcacct gtgccccagc cctctgttcc ctggccctag caagcctttc    120
tgggtgctgg tggtcgtggg cggagtgctg gcctgttata gcctgctcgt gaccgtggcc    180
ttcatcatct tttgggtgcg cagcaagcgg agccggctgc tgcacagcga ctacatgaac    240
atgaccccca gacggcccgg acccaccaga aagcactacc agccttacgc ccctcccaga    300
gacttcgccg cctacagatc t                                              321

<210> SEQ ID NO 9
<211> LENGTH: 111
<212> TYPE: PRT
<213> ORGANISM: Homo sapiens

<400> SEQUENCE: 9

Arg Val Lys Ser Arg Ser Ala Asp Ala Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
        35                  40                  45

Arg Arg Lys Asn Pro Gln Glu Gly Leu Tyr Asn Glu Leu Gln Lys Asp
    50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110

<210> SEQ ID NO 10
<211> LENGTH: 333
<212> TYPE: DNA
<213> ORGANISM: Homo sapiens

<400> SEQUENCE: 10

```
cgagtgaaga gcagaagcgc cgacgcccct gcctatcagc agggccagaa ccagctgtac      60
aacgagctga acctgggcag acgggaagag tacgacgtgc tggacaagcg gagaggcagg     120
gaccctgaga tgggcggcaa gcccagaaga aagaaccccc aggaaggcct gtataacgaa     180
ctgcagaaag acaagatggc cgaggcctac agcgagatcg gcatgaaggg cgagcggaga     240
agaggcaagg gccacgatgg cctgtaccag ggcctgagca ccgccaccaa ggacacctat     300
gacgccctgc acatgcaggc cctgcccccc aga                                  333
```

<210> SEQ ID NO 11
<211> LENGTH: 41
<212> TYPE: PRT
<213> ORGANISM: Homo sapiens

<400> SEQUENCE: 11

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 12
<211> LENGTH: 123
<212> TYPE: DNA
<213> ORGANISM: Homo sapiens

<400> SEQUENCE: 12

```
cgcagcaagc ggagccggct gctgcacagc gactacatga acatgacccc cagacggccc      60
ggacccacca gaaagcacta ccagccttac gcccctccca gagacttcgc cgcctacaga     120
tct                                                                   123
```

<210> SEQ ID NO 13
<211> LENGTH: 39
<212> TYPE: PRT
<213> ORGANISM: Homo sapiens

<400> SEQUENCE: 13

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 14
<211> LENGTH: 117
<212> TYPE: DNA
<213> ORGANISM: Homo sapiens

<400> SEQUENCE: 14

```
atcgaagtga tgtaccccc tccctacctg acaacgaga agtccaacgg caccattatc       60
cacgtgaagg gaaagcacct gtgccccagc cctctgttcc ctggccctag caagcct       117
```

<210> SEQ ID NO 15
<211> LENGTH: 239
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid

<400> SEQUENCE: 15

Xaa Gly Ser Thr Ser Gly Ser Gly Lys Pro Gly Ser Gly Glu Gly Ser
1               5                   10                  15

Thr Lys Gly Xaa Ile Glu Val Met Tyr Pro Pro Tyr Leu Asp Asn
            20                  25                  30

Glu Lys Ser Asn Gly Thr Ile Ile His Val Lys Gly Lys His Leu Cys
        35                  40                  45

Pro Ser Pro Leu Phe Pro Gly Pro Ser Lys Pro Phe Trp Val Leu Val
    50                  55                  60

Val Val Gly Gly Val Leu Ala Cys Tyr Ser Leu Leu Val Thr Val Ala
65                  70                  75                  80

Phe Ile Ile Phe Trp Val Arg Ser Lys Arg Ser Arg Leu Leu His Ser
                85                  90                  95

Asp Tyr Met Asn Met Thr Pro Arg Arg Pro Gly Pro Thr Arg Lys His
            100                 105                 110

Tyr Gln Pro Tyr Ala Pro Pro Arg Asp Phe Ala Ala Tyr Arg Ser Arg
        115                 120                 125

Val Lys Phe Ser Arg Ser Ala Asp Ala Pro Ala Tyr Gln Gln Gly Gln
    130                 135                 140

Asn Gln Leu Tyr Asn Glu Leu Asn Leu Gly Arg Arg Glu Glu Tyr Asp
145                 150                 155                 160

Val Leu Asp Lys Arg Arg Gly Arg Asp Pro Glu Met Gly Gly Lys Pro
                165                 170                 175

Arg Arg Lys Asn Pro Gln Glu Gly Leu Tyr Asn Glu Leu Gln Lys Asp
            180                 185                 190

Lys Met Ala Glu Ala Tyr Ser Glu Ile Gly Met Lys Gly Glu Arg Arg
        195                 200                 205

Arg Gly Lys Gly His Asp Gly Leu Tyr Gln Gly Leu Ser Thr Ala Thr
    210                 215                 220

Lys Asp Thr Tyr Asp Ala Leu His Met Gln Ala Leu Pro Pro Arg
225                 230                 235

<210> SEQ ID NO 16
<211> LENGTH: 713
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is any nucleotide
<220> FEATURE:
<221> NAME/KEY: misc_feature
<222> LOCATION: (56)..(56)
<223> OTHER INFORMATION: n is any nucleotide

<400> SEQUENCE: 16
nggctctaca agcggctctg gcaagcctgg atctggcgag ggaagcacca agggcnatcg    60

```
aagtgatgta ccccctccc tacctggaca acgagaagtc caacggcacc attatccacg    120
tgaagggaaa gcacctgtgc cccagccctc tgttccctgg ccctagcaag cctttctggg    180
tgctggtggt cgtgggcgga gtgctggcct gttatagcct gctcgtgacc gtggccttca    240
tcatcttttg ggtgcgcagc aagcggagcc ggctgctgca cagcgactac atgaacatga    300 ccccagacg gcccggaccc accagaaagc actaccagcc ttacgcccct cccagagact    360
tcgccgccta cagatctcga gtgaagttca gcagaagcgc cgacgcccct gcctatcagc    420
agggccagaa ccagctgtac aacgagctga acctgggcag acgggaagag tacgacgtgc    480
tggacaagcg gagaggcagg gaccctgaga tgggcggcaa gcccagaaga aagaaccccc    540
aggaaggcct gtataacgaa ctgcagaaag acaagatggc cgaggcctac agcgagatcg    600
gcatgaaggg cgagcggaga agaggcaagg gccacgatgg cctgtaccag ggcctgagca    660
ccgccaccaa ggacacctat gacgccctgc acatgcaggc cctgcccccc aga           713
```

<210> SEQ ID NO 17
<211> LENGTH: 8
<212> TYPE: PRT
<213> ORGANISM: Homo sapiens

<400> SEQUENCE: 17

Gly Gly Ser Ile Ser Ser Asn Tyr
1               5

<210> SEQ ID NO 18
<211> LENGTH: 7
<212> TYPE: PRT
<213> ORGANISM: Homo sapiens

<400> SEQUENCE: 18

Val Ser Tyr Ser Gly Ser Thr
1               5

<210> SEQ ID NO 19
<211> LENGTH: 12
<212> TYPE: PRT
<213> ORGANISM: Homo sapiens

<400> SEQUENCE: 19

Ala Arg Glu Ser Tyr Tyr Tyr Tyr Gly Met Asp Val
1               5                   10

<210> SEQ ID NO 20
<211> LENGTH: 118
<212> TYPE: PRT
<213> ORGANISM: Homo sapiens

<400> SEQUENCE: 20

Gln Val Gln Leu Gln Glu Ser Gly Pro Gly Leu Val Lys Pro Ser Asp
1               5                   10                  15

Thr Leu Ser Leu Thr Cys Leu Val Ser Gly Gly Ser Ile Ser Ser Asn
            20                  25                  30

Tyr Trp Ser Trp Ile Arg Gln Ala Pro Gly Lys Gly Leu Glu Trp Ile
        35                  40                  45

Gly His Val Ser Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

-continued

```
Lys Leu Ser Ser Val Thr Ala Ala Asp Thr Ala Val Tyr Tyr Cys Ala
                85                  90                  95

Arg Glu Ser Tyr Tyr Tyr Tyr Gly Met Asp Val Trp Gly Gln Gly Thr
            100                 105                 110

Thr Val Thr Val Ser Ser
        115

<210> SEQ ID NO 21
<211> LENGTH: 8
<212> TYPE: PRT
<213> ORGANISM: Homo sapiens

<400> SEQUENCE: 21

Gly Phe Thr Phe Ser Thr Tyr Gln
1               5

<210> SEQ ID NO 22
<211> LENGTH: 8
<212> TYPE: PRT
<213> ORGANISM: Homo sapiens

<400> SEQUENCE: 22

Ile Val Ser Ser Gly Gly Ser Thr
1               5

<210> SEQ ID NO 23
<211> LENGTH: 12
<212> TYPE: PRT
<213> ORGANISM: Homo sapiens

<400> SEQUENCE: 23

Ala Gly Glu Leu Leu Pro Tyr Tyr Gly Met Asp Val
1               5                   10

<210> SEQ ID NO 24
<211> LENGTH: 119
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Ser Trp Val Arg Gln Ala Pro Gly Lys Gly Leu Glu Trp Val
        35                  40                  45

Ser Gly Ile Val Ser Ser Gly Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Leu Leu Pro Tyr Tyr Gly Met Asp Val Trp Gly Gln Gly
            100                 105                 110

Thr Thr Val Thr Val Ser Ser
        115

<210> SEQ ID NO 25
<211> LENGTH: 8
<212> TYPE: PRT
<213> ORGANISM: Homo sapiens
```

<400> SEQUENCE: 25

Gly Gly Ser Ile Ser Ser Tyr Tyr
1               5

<210> SEQ ID NO 26
<211> LENGTH: 7
<212> TYPE: PRT
<213> ORGANISM: Homo sapiens

<400> SEQUENCE: 26

Ile Asn His Ser Gly Ser Thr
1               5

<210> SEQ ID NO 27
<211> LENGTH: 12
<212> TYPE: PRT
<213> ORGANISM: Homo sapiens

<400> SEQUENCE: 27

Ala Arg Cys Pro Ile Tyr Tyr Tyr Gly Met Asp Val
1               5                   10

<210> SEQ ID NO 28
<211> LENGTH: 118
<212> TYPE: PRT
<213> ORGANISM: Homo sapiens

<400> SEQUENCE: 28

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Cys Pro Ile Tyr Tyr Tyr Gly Met Asp Val Trp Gly Gln Gly Thr
            100                 105                 110

Thr Val Thr Val Ser Ser
        115

<210> SEQ ID NO 29
<211> LENGTH: 9
<212> TYPE: PRT
<213> ORGANISM: Homo sapiens

<400> SEQUENCE: 29

Ser Arg Asp Val Gly Gly Tyr Asn Tyr
1               5

<210> SEQ ID NO 30
<211> LENGTH: 3
<212> TYPE: PRT
<213> ORGANISM: Homo sapiens

<400> SEQUENCE: 30

Asp Val Ile
1

<210> SEQ ID NO 31
<211> LENGTH: 9
<212> TYPE: PRT
<213> ORGANISM: Homo sapiens

<400> SEQUENCE: 31

Trp Ser Phe Ala Gly Ser Tyr Tyr Val
1               5

<210> SEQ ID NO 32
<211> LENGTH: 109
<212> TYPE: PRT
<213> ORGANISM: Homo sapiens

<400> SEQUENCE: 32

Gln Ser Glu Leu Thr Gln Pro Arg Ser Val Ser Gly Ser Pro Gly Gln
1               5                   10                  15

Ser Val Thr Ile Ser Cys Thr Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Ile Ile His Asp Val Ile Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Trp Ser Phe Ala Gly Ser
                85                  90                  95

Tyr Tyr Val Phe Gly Thr Gly Thr Asp Val Thr Val Leu
            100                 105

<210> SEQ ID NO 33
<211> LENGTH: 6
<212> TYPE: PRT
<213> ORGANISM: Homo sapiens

<400> SEQUENCE: 33

Gln Ser Ile Ser Ser Tyr
1               5

<210> SEQ ID NO 34
<211> LENGTH: 3
<212> TYPE: PRT
<213> ORGANISM: Homo sapiens

<400> SEQUENCE: 34

Ala Ala Ser
1

<210> SEQ ID NO 35
<211> LENGTH: 9
<212> TYPE: PRT
<213> ORGANISM: Homo sapiens

<400> SEQUENCE: 35

Gln Gln Tyr Tyr Ser Thr Pro Gln Thr
1               5

<210> SEQ ID NO 36
<211> LENGTH: 107

```
<212> TYPE: PRT
<213> ORGANISM: Homo sapiens

<400> SEQUENCE: 36

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Gln
                85                  90                  95

Thr Phe Gly Pro Gly Thr Lys Val Asp Ile Lys
            100                 105

<210> SEQ ID NO 37
<211> LENGTH: 6
<212> TYPE: PRT
<213> ORGANISM: Homo sapiens

<400> SEQUENCE: 37

Gln Ser Ile Ser Ser Tyr
1               5

<210> SEQ ID NO 38
<211> LENGTH: 3
<212> TYPE: PRT
<213> ORGANISM: Homo sapiens

<400> SEQUENCE: 38

Ala Ala Ser
1

<210> SEQ ID NO 39
<211> LENGTH: 9
<212> TYPE: PRT
<213> ORGANISM: Homo sapiens

<400> SEQUENCE: 39

Gln Gln Tyr Glu Ser Tyr Arg Arg Ser
1               5

<210> SEQ ID NO 40
<211> LENGTH: 107
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60
```

```
Ser Gly Ser Gly Thr Asp Phe Thr Leu Thr Ile Ser Cys Leu Gln Ser
 65                  70                  75                  80

Glu Asp Val Ala Thr Tyr Tyr Cys Gln Gln Tyr Glu Ser Tyr Arg Arg
                 85                  90                  95

Ser Phe Gly Gln Gly Thr Lys Val Glu Ile Lys
            100                 105
```

<210> SEQ ID NO 41
<211> LENGTH: 6
<212> TYPE: PRT
<213> ORGANISM: Homo sapiens

<400> SEQUENCE: 41

```
Gln Ser Ile Ser Ser Tyr
1               5
```

<210> SEQ ID NO 42
<211> LENGTH: 3
<212> TYPE: PRT
<213> ORGANISM: Homo sapiens

<400> SEQUENCE: 42

```
Ala Ala Ser
1
```

<210> SEQ ID NO 43
<211> LENGTH: 9
<212> TYPE: PRT
<213> ORGANISM: Homo sapiens

<400> SEQUENCE: 43

```
Gln Gln Tyr Asn Ser Tyr Ser Arg Thr
1               5
```

<210> SEQ ID NO 44
<211> LENGTH: 107
<212> TYPE: PRT
<213> ORGANISM: Homo sapiens

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys
            100                 105
```

<210> SEQ ID NO 45
<211> LENGTH: 107
<212> TYPE: PRT
<213> ORGANISM: Homo sapiens

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Arg Leu Glu Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105
```

<210> SEQ ID NO 46
<211> LENGTH: 6
<212> TYPE: PRT
<213> ORGANISM: Homo sapiens

<400> SEQUENCE: 46

```
Gln Ser Ile Ser Ser Tyr
1               5
```

<210> SEQ ID NO 47
<211> LENGTH: 3
<212> TYPE: PRT
<213> ORGANISM: Homo sapiens

<400> SEQUENCE: 47

```
Ala Ala Ser
1
```

<210> SEQ ID NO 48
<211> LENGTH: 10
<212> TYPE: PRT
<213> ORGANISM: Homo sapiens

<400> SEQUENCE: 48

```
Gln Gln Tyr Asn Ser Tyr Ser Pro Cys Thr
1               5                   10
```

<210> SEQ ID NO 49
<211> LENGTH: 108
<212> TYPE: PRT
<213> ORGANISM: Homo sapiens

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Leu
            35                  40                  45

Tyr Ala Ala Ser Arg Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95
```

```
Cys Thr Phe Gly Pro Gly Thr Lys Val Asp Ile Lys
            100                 105
```

<210> SEQ ID NO 50
<211> LENGTH: 6
<212> TYPE: PRT
<213> ORGANISM: Homo sapiens

<400> SEQUENCE: 50

```
Gln Asp Ile Ser Arg Tyr
1               5
```

<210> SEQ ID NO 51
<211> LENGTH: 3
<212> TYPE: PRT
<213> ORGANISM: Homo sapiens

<400> SEQUENCE: 51

```
Ala Ala Ser
1
```

<210> SEQ ID NO 52
<211> LENGTH: 8
<212> TYPE: PRT
<213> ORGANISM: Homo sapiens

<400> SEQUENCE: 52

```
Gln Gln Tyr Asp Asn Leu Ile Thr
1               5
```

<210> SEQ ID NO 53
<211> LENGTH: 106
<212> TYPE: PRT
<213> ORGANISM: Homo sapiens

<400> SEQUENCE: 53

```
Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Asp Ile Ser Arg Tyr
            20                  25                  30

Leu Asn Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys
            100                 105
```

<210> SEQ ID NO 54
<211> LENGTH: 6
<212> TYPE: PRT
<213> ORGANISM: Homo sapiens

<400> SEQUENCE: 54

```
Gln Asp Ile Ser Arg Tyr
1               5
```

<210> SEQ ID NO 55

<211> LENGTH: 3
<212> TYPE: PRT
<213> ORGANISM: Homo sapiens

<400> SEQUENCE: 55

Ala Ala Ser
1

<210> SEQ ID NO 56
<211> LENGTH: 9
<212> TYPE: PRT
<213> ORGANISM: Homo sapiens

<400> SEQUENCE: 56

Gln Gln Tyr Asn Ser Tyr Ser Arg Thr
1               5

<210> SEQ ID NO 57
<211> LENGTH: 107
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Asp Ile Ser Arg Tyr
            20                  25                  30

Leu Asn Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 58
<211> LENGTH: 6
<212> TYPE: PRT
<213> ORGANISM: Homo sapiens

<400> SEQUENCE: 58

Gln Ser Ile Ser Ser Tyr
1               5

<210> SEQ ID NO 59
<211> LENGTH: 3
<212> TYPE: PRT
<213> ORGANISM: Homo sapiens

<400> SEQUENCE: 59

Ala Ala Ser
1

<210> SEQ ID NO 60
<211> LENGTH: 8
<212> TYPE: PRT
<213> ORGANISM: Homo sapiens

<400> SEQUENCE: 60

Gln Gln Tyr Asp Asn Leu Ile Thr
1               5

<210> SEQ ID NO 61
<211> LENGTH: 106
<212> TYPE: PRT
<213> ORGANISM: Homo sapiens

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys
            100                 105

<210> SEQ ID NO 62
<211> LENGTH: 6
<212> TYPE: PRT
<213> ORGANISM: Homo sapiens

<400> SEQUENCE: 62

Gln Ser Val Ser Ser Asn
1               5

<210> SEQ ID NO 63
<211> LENGTH: 3
<212> TYPE: PRT
<213> ORGANISM: Homo sapiens

<400> SEQUENCE: 63

Gly Ala Ser
1

<210> SEQ ID NO 64
<211> LENGTH: 9
<212> TYPE: PRT
<213> ORGANISM: Homo sapiens

<400> SEQUENCE: 64

Gln Gln Tyr Asn Ser Tyr Ser Arg Thr
1               5

<210> SEQ ID NO 65
<211> LENGTH: 107
<212> TYPE: PRT
<213> ORGANISM: Homo sapiens

<400> SEQUENCE: 65

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

-continued

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Arg Leu Glu Pro
 65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 66
<211> LENGTH: 6
<212> TYPE: PRT
<213> ORGANISM: Homo sapiens

<400> SEQUENCE: 66

Gln Ser Ile Ser Ser Tyr
1               5

<210> SEQ ID NO 67
<211> LENGTH: 3
<212> TYPE: PRT
<213> ORGANISM: Homo sapiens

<400> SEQUENCE: 67

Ala Ala Ser
1

<210> SEQ ID NO 68
<211> LENGTH: 9
<212> TYPE: PRT
<213> ORGANISM: Homo sapiens

<400> SEQUENCE: 68

Gln Gln Tyr Glu Ser Tyr Ser Arg Thr
1               5

<210> SEQ ID NO 69
<211> LENGTH: 107
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Val Ala Thr Tyr Tyr Cys Gln Gln Tyr Glu Ser Tyr Ser Arg
                85                  90                  95

Thr Phe Gly Gln Gly Thr Lys Val Glu Ile Lys
            100                 105

<210> SEQ ID NO 70

-continued

```
<211> LENGTH: 9
<212> TYPE: PRT
<213> ORGANISM: Homo sapiens

<400> SEQUENCE: 70

Ser Ser Asp Val Gly Gly Tyr Asp Phe
1               5

<210> SEQ ID NO 71
<211> LENGTH: 3
<212> TYPE: PRT
<213> ORGANISM: Homo sapiens

<400> SEQUENCE: 71

Asp Val Asn
1

<210> SEQ ID NO 72
<211> LENGTH: 9
<212> TYPE: PRT
<213> ORGANISM: Homo sapiens

<400> SEQUENCE: 72

Ser Ser Tyr Ala Gly Ser Asn Ser Val
1               5

<210> SEQ ID NO 73
<211> LENGTH: 109
<212> TYPE: PRT
<213> ORGANISM: Homo sapiens

<400> SEQUENCE: 73

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asp Phe Val Ser Trp Tyr Gln Gln His Pro Gly Glu Ala Pro Lys Leu
            35                  40                  45

Leu Val Tyr Asp Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Ala Gly Ser
                85                  90                  95

Asn Ser Val Phe Gly Thr Gly Thr Lys Val Thr Val Leu
            100                 105

<210> SEQ ID NO 74
<211> LENGTH: 9
<212> TYPE: PRT
<213> ORGANISM: Homo sapiens

<400> SEQUENCE: 74

Ser Ser Asp Val Gly Gly Tyr Glu Phe
1               5

<210> SEQ ID NO 75
<211> LENGTH: 3
<212> TYPE: PRT
<213> ORGANISM: Homo sapiens

<400> SEQUENCE: 75
```

```
Asp Val Ile
1

<210> SEQ ID NO 76
<211> LENGTH: 10
<212> TYPE: PRT
<213> ORGANISM: Homo sapiens

<400> SEQUENCE: 76

Ser Ser Tyr Thr Ser Ser Ser Thr Tyr Val
1               5                   10

<210> SEQ ID NO 77
<211> LENGTH: 110
<212> TYPE: PRT
<213> ORGANISM: Homo sapiens

<400> SEQUENCE: 77

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Phe Val Ser Trp Tyr Gln Gln His Pro Gly Ser Ala Pro Lys Leu
        35                  40                  45

Ile Ile Tyr Asp Val Ile Glu Arg Pro Phe Gly Val Ser Tyr Arg Phe
    50                  55                  60

Ser Ala Ser Lys Ser Gly Asn Thr Ala Ser Leu Thr Ile Ser Gly Leu
65                  70                  75                  80

Gln Gly Glu Asp Glu Ala Asp Tyr Phe Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 78
<211> LENGTH: 9
<212> TYPE: PRT
<213> ORGANISM: Homo sapiens

<400> SEQUENCE: 78

Gly Ser Asp Val Gly Ala Tyr Asp Tyr
1               5

<210> SEQ ID NO 79
<211> LENGTH: 3
<212> TYPE: PRT
<213> ORGANISM: Homo sapiens

<400> SEQUENCE: 79

Asp Val Ser
1

<210> SEQ ID NO 80
<211> LENGTH: 10
<212> TYPE: PRT
<213> ORGANISM: Homo sapiens

<400> SEQUENCE: 80

Ser Ser Tyr Ser Gly Ser Ser Thr Trp Val
1               5                   10

<210> SEQ ID NO 81
<211> LENGTH: 110
```

```
<212> TYPE: PRT
<213> ORGANISM: Homo sapiens

<400> SEQUENCE: 81

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ala Tyr
            20                  25                  30

Asp Tyr Val Ser Trp Tyr Gln His His Pro Gly Arg Ala Pro Arg Leu
        35                  40                  45

Ile Ile Arg Asp Val Ser Val Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Gly Ser
                85                  90                  95

Ser Thr Trp Val Phe Gly Gly Gly Thr Lys Leu Thr Val Leu
            100                 105                 110

<210> SEQ ID NO 82
<211> LENGTH: 9
<212> TYPE: PRT
<213> ORGANISM: Homo sapiens

<400> SEQUENCE: 82

Ser Ser Asp Val Gly Ser Tyr Asn Leu
1               5

<210> SEQ ID NO 83
<211> LENGTH: 3
<212> TYPE: PRT
<213> ORGANISM: Homo sapiens

<400> SEQUENCE: 83

Asp Val Ser
1

<210> SEQ ID NO 84
<211> LENGTH: 11
<212> TYPE: PRT
<213> ORGANISM: Homo sapiens

<400> SEQUENCE: 84

Ser Ser Tyr Thr Ser Ser Ser Thr Phe Ala Val
1               5                   10

<210> SEQ ID NO 85
<211> LENGTH: 111
<212> TYPE: PRT
<213> ORGANISM: Homo sapiens

<400> SEQUENCE: 85

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Asp Val Ser Asn Arg Pro Ser Gly Val Ser Tyr Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Phe Ala Val Phe Gly Gly Gly Thr Gln Leu Thr Val Leu
            100                 105                 110
```

<210> SEQ ID NO 86
<211> LENGTH: 9
<212> TYPE: PRT
<213> ORGANISM: Homo sapiens

<400> SEQUENCE: 86

```
Ser Ser Asp Val Gly Gly Tyr Asn Tyr
 1               5
```

<210> SEQ ID NO 87
<211> LENGTH: 3
<212> TYPE: PRT
<213> ORGANISM: Homo sapiens

<400> SEQUENCE: 87

```
Asp Val Ser
 1
```

<210> SEQ ID NO 88
<211> LENGTH: 9
<212> TYPE: PRT
<213> ORGANISM: Homo sapiens

<400> SEQUENCE: 88

```
Cys Ser Tyr Ala Gly Gly Tyr Tyr Val
 1               5
```

<210> SEQ ID NO 89
<211> LENGTH: 109
<212> TYPE: PRT
<213> ORGANISM: Homo sapiens

<400> SEQUENCE: 89

```
Gln Ser Ala Leu Pro Gln Pro Ala Ser Val Ser Gly Ser Pro Gly Gln
 1               5                  10                  15

Ser Val Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Cys Ser Tyr Ala Gly Gly
                 85                  90                  95

Tyr Tyr Val Phe Gly Thr Gly Thr Lys Leu Thr Val Leu
            100                 105
```

<210> SEQ ID NO 90
<211> LENGTH: 9
<212> TYPE: PRT
<213> ORGANISM: Homo sapiens

<400> SEQUENCE: 90

Ser Ser Asp Val Gly Gly Tyr Asn Tyr
1               5

<210> SEQ ID NO 91
<211> LENGTH: 3
<212> TYPE: PRT
<213> ORGANISM: Homo sapiens

<400> SEQUENCE: 91

Asp Val Ser
1

<210> SEQ ID NO 92
<211> LENGTH: 12
<212> TYPE: PRT
<213> ORGANISM: Homo sapiens

<400> SEQUENCE: 92

Ser Ser Tyr Ala Gly Ser Gly Ser Thr Pro Phe Val
1               5                   10

<210> SEQ ID NO 93
<211> LENGTH: 112
<212> TYPE: PRT
<213> ORGANISM: Homo sapiens

<400> SEQUENCE: 93

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Ala Gly Ser
                85                  90                  95

Gly Ser Thr Pro Phe Val Phe Gly Thr Gly Thr Lys Leu Thr Val Leu
                100                 105                 110

<210> SEQ ID NO 94
<211> LENGTH: 9
<212> TYPE: PRT
<213> ORGANISM: Homo sapiens

<400> SEQUENCE: 94

Ser Ser Asp Val Gly Gly Tyr Asn Tyr
1               5

<210> SEQ ID NO 95
<211> LENGTH: 3
<212> TYPE: PRT
<213> ORGANISM: Homo sapiens

<400> SEQUENCE: 95

Asp Val Ser
1

<210> SEQ ID NO 96
<211> LENGTH: 9

```
<212> TYPE: PRT
<213> ORGANISM: Homo sapiens

<400> SEQUENCE: 96

Cys Ser Tyr Ala Gly Arg Arg Tyr Val
1               5

<210> SEQ ID NO 97
<211> LENGTH: 109
<212> TYPE: PRT
<213> ORGANISM: Homo sapiens

<400> SEQUENCE: 97

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Arg Val Pro Asp Arg Phe
    50                  55                  60

Ala Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Arg
                85                  90                  95

Arg Tyr Val Phe Gly Thr Gly Thr Lys Leu Thr Val Leu
            100                 105

<210> SEQ ID NO 98
<211> LENGTH: 245
<212> TYPE: PRT
<213> ORGANISM: Artificial Sequence
<220> FEATURE:
<223> OTHER INFORMATION: Anitigen biding domain

<400> SEQUENCE: 98

Gln Val Gln Leu Gln Glu Ser Gly Pro Gly Leu Val Lys Pro Ser Asp
1               5                   10                  15

Thr Leu Ser Leu Thr Cys Leu Val Ser Gly Gly Ser Ile Ser Ser Asn
            20                  25                  30

Tyr Trp Ser Trp Ile Arg Gln Ala Pro Gly Lys Gly Leu Glu Trp Ile
        35                  40                  45

Gly His Val Ser Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Tyr Tyr Tyr Gly Met Asp Val Trp Gly Gln Gly Thr
            100                 105                 110

Thr Val Thr Val Ser Ser Gly Ser Thr Ser Gly Ser Gly Lys Pro Gly
        115                 120                 125

Ser Gly Glu Gly Ser Thr Lys Gly Gln Ser Glu Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Arg Asp Val Gly Gly Tyr Asn Tyr Val Ser Trp Tyr Gln Gln
                165                 170                 175
```

His Pro Gly Lys Ala Pro Lys Leu Ile Ile His Asp Val Ile Glu Arg
            180                 185                 190

Ser Ser Gly Val Pro Asp Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Trp Ser Phe Ala Gly Ser Tyr Val Phe Gly Thr Gly Thr
225                 230                 235                 240

Asp Val Thr Val Leu
                245

<210> SEQ ID NO 99
<211> LENGTH: 243
<212> TYPE: PRT
<213> ORGANISM: Artificial Sequence
<220> FEATURE:
<223> OTHER INFORMATION: Anitigen biding domain

<400> SEQUENCE: 99

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Gln
                85                  90                  95

Thr Phe Gly Pro Gly Thr Lys Val Asp Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Glu Ser Gly Pro Gly Leu Val Lys Pro Ser Asp Thr Leu Ser
    130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
    210                 215                 220

Tyr Tyr Tyr Tyr Gly Met Asp Val Trp Gly Gln Gly Thr Thr Val Thr
225                 230                 235                 240

Val Ser Ser

<210> SEQ ID NO 100
<211> LENGTH: 243
<212> TYPE: PRT
<213> ORGANISM: Artificial Sequence
<220> FEATURE:

<223> OTHER INFORMATION: Anitigen biding domain

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Val Ala Thr Tyr Tyr Cys Gln Gln Tyr Glu Ser Tyr Arg Arg
                85                  90                  95

Ser Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Glu Ser Gly Pro Gly Leu Val Lys Pro Ser Asp Thr Leu Ser
130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
210                 215                 220

Tyr Tyr Tyr Tyr Gly Met Asp Val Trp Gly Gln Gly Thr Thr Val Thr
225                 230                 235                 240

Val Ser Ser

<210> SEQ ID NO 101
<211> LENGTH: 243
<212> TYPE: PRT
<213> ORGANISM: Artificial Sequence
<220> FEATURE:
<223> OTHER INFORMATION: Anitigen biding domain

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
            115                 120                 125

Leu Gln Glu Ser Gly Pro Gly Leu Val Lys Pro Ser Asp Thr Leu Ser
        130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
            195                 200                 205

Ser Val Thr Ala Ala Asp Thr Ala Val Tyr Tyr Cys Ala Arg Glu Ser
            210                 215                 220

Tyr Tyr Tyr Tyr Gly Met Asp Val Trp Gly Gln Gly Thr Thr Val Thr
225                 230                 235                 240

Val Ser Ser

<210> SEQ ID NO 102
<211> LENGTH: 243
<212> TYPE: PRT
<213> ORGANISM: Artificial Sequence
<220> FEATURE:
<223> OTHER INFORMATION: Anitigen biding domain

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Glu Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
            115                 120                 125

Leu Gln Glu Ser Gly Pro Gly Leu Val Lys Pro Ser Asp Thr Leu Ser
        130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
            195                 200                 205

Ser Val Thr Ala Ala Asp Thr Ala Val Tyr Tyr Cys Ala Arg Glu Ser

```
                210                 215                 220
Tyr Tyr Tyr Tyr Gly Met Asp Val Trp Gly Gln Gly Thr Thr Val Thr
225                 230                 235                 240

Val Ser Ser

<210> SEQ ID NO 103
<211> LENGTH: 244
<212> TYPE: PRT
<213> ORGANISM: Artificial Sequence
<220> FEATURE:
<223> OTHER INFORMATION: Antigen biding domain

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Cys Thr Phe Gly Pro Gly Thr Lys Val Asp Ile Lys Gly Ser Thr Ser
            100                 105                 110

Gly Ser Gly Lys Pro Gly Ser Gly Glu Gly Ser Thr Lys Gly Gln Val
        115                 120                 125

Gln Leu Gln Glu Ser Gly Pro Gly Leu Val Lys Pro Ser Asp Thr Leu
    130                 135                 140

Ser Leu Thr Cys Leu Val Ser Gly Gly Ser Ile Ser Ser Asn Tyr Trp
145                 150                 155                 160

Ser Trp Ile Arg Gln Ala Pro Gly Lys Gly Leu Glu Trp Ile Gly His
                165                 170                 175

Val Ser Tyr Ser Gly Ser Thr Asn Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Glu
    210                 215                 220

Ser Tyr Tyr Tyr Gly Met Asp Val Trp Gly Gln Gly Thr Thr Val
225                 230                 235                 240

Thr Val Ser Ser

<210> SEQ ID NO 104
<211> LENGTH: 242
<212> TYPE: PRT
<213> ORGANISM: Artificial Sequence
<220> FEATURE:
<223> OTHER INFORMATION: Antigen biding domain

<400> SEQUENCE: 104

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Asp Ile Ser Arg Tyr
            20                  25                  30
```

Leu Asn Trp Tyr Gln Gln Lys Pro Gly Lys Ala Pro Lys Leu Leu Leu
            35                  40                  45

Tyr Ala Ala Ser Arg Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys Gly Ser Thr Ser Gly Ser
                100                 105                 110

Gly Lys Pro Gly Ser Gly Glu Gly Ser Thr Lys Gly Gln Val Gln Leu
            115                 120                 125

Gln Glu Ser Gly Pro Gly Leu Val Lys Pro Ser Asp Thr Leu Ser Leu
            130                 135                 140

Thr Cys Leu Val Ser Gly Gly Ser Ile Ser Ser Asn Tyr Trp Ser Trp
145                 150                 155                 160

Ile Arg Gln Ala Pro Gly Lys Gly Leu Glu Trp Ile Gly His Val Ser
                165                 170                 175

Tyr Ser Gly Ser Thr Asn Tyr Asn Pro Ser Leu Lys Ser Arg Val Thr
            180                 185                 190

Ile Ser Val Asp Thr Ser Lys Asn Gln Phe Ser Leu Lys Leu Ser Ser
            195                 200                 205

Val Thr Ala Ala Asp Thr Ala Val Tyr Tyr Cys Ala Arg Glu Ser Tyr
            210                 215                 220

Tyr Tyr Tyr Gly Met Asp Val Trp Gly Gln Gly Thr Thr Val Thr Val
225                 230                 235                 240

Ser Ser

<210> SEQ ID NO 105
<211> LENGTH: 243
<212> TYPE: PRT
<213> ORGANISM: Artificial Sequence
<220> FEATURE:
<223> OTHER INFORMATION: Antigen biding domain

<400> SEQUENCE: 105

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Asp Ile Ser Arg Tyr
            20                  25                  30

Leu Asn Trp Tyr Gln Gln Lys Pro Gly Lys Ala Pro Lys Leu Leu Leu
            35                  40                  45

Tyr Ala Ala Ser Arg Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
                100                 105                 110

Ser Gly Lys Pro Gly Ser Gly Glu Gly Ser Thr Lys Gly Gln Val Gln
            115                 120                 125

Leu Gln Glu Ser Gly Pro Gly Leu Val Lys Pro Ser Asp Thr Leu Ser
            130                 135                 140

```
Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
            165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
            195                 200                 205

Ser Val Thr Ala Ala Asp Thr Ala Val Tyr Tyr Cys Ala Arg Glu Ser
            210                 215                 220

Tyr Tyr Tyr Tyr Gly Met Asp Val Trp Gly Gln Gly Thr Thr Val Thr
225                 230                 235                 240

Val Ser Ser
```

<210> SEQ ID NO 106
<211> LENGTH: 242
<212> TYPE: PRT
<213> ORGANISM: Artificial Sequence
<220> FEATURE:
<223> OTHER INFORMATION: Antigen biding domain

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys Gly Ser Thr Ser Gly Ser
            100                 105                 110

Gly Lys Pro Gly Ser Gly Glu Gly Ser Thr Lys Gly Gln Val Gln Leu
        115                 120                 125

Gln Glu Ser Gly Pro Gly Leu Val Lys Pro Ser Asp Thr Leu Ser Leu
130                 135                 140

Thr Cys Leu Val Ser Gly Gly Ser Ile Ser Ser Asn Tyr Trp Ser Trp
145                 150                 155                 160

Ile Arg Gln Ala Pro Gly Lys Gly Leu Glu Trp Ile Gly His Val Ser
            165                 170                 175

Tyr Ser Gly Ser Thr Asn Tyr Asn Pro Ser Leu Lys Ser Arg Val Thr
        180                 185                 190

Ile Ser Val Asp Thr Ser Lys Asn Gln Phe Ser Leu Lys Leu Ser Ser
        195                 200                 205

Val Thr Ala Ala Asp Thr Ala Val Tyr Tyr Cys Ala Arg Glu Ser Tyr
210                 215                 220

Tyr Tyr Tyr Gly Met Asp Val Trp Gly Gln Gly Thr Thr Val Thr Val
225                 230                 235                 240

Ser Ser
```

<210> SEQ ID NO 107

```
<211> LENGTH: 243
<212> TYPE: PRT
<213> ORGANISM: Artificial Sequence
<220> FEATURE:
<223> OTHER INFORMATION: Antigen biding domain

<400> SEQUENCE: 107

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Glu Ser Gly Pro Gly Leu Val Lys Pro Ser Asp Thr Leu Ser
    130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
    210                 215                 220

Tyr Tyr Tyr Tyr Gly Met Asp Val Trp Gly Gln Gly Thr Thr Val Thr
225                 230                 235                 240

Val Ser Ser

<210> SEQ ID NO 108
<211> LENGTH: 243
<212> TYPE: PRT
<213> ORGANISM: Artificial Sequence
<220> FEATURE:
<223> OTHER INFORMATION: Antigen biding domain

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80
```

```
Glu Asp Val Ala Thr Tyr Tyr Cys Gln Gln Tyr Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
            115                 120                 125

Leu Gln Glu Ser Gly Pro Gly Leu Val Lys Pro Ser Asp Thr Leu Ser
130                 135                 140

Leu Thr Cys Leu Val Ser Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
            195                 200                 205

Ser Val Thr Ala Ala Asp Thr Ala Val Tyr Tyr Cys Ala Arg Glu Ser
    210                 215                 220

Tyr Tyr Tyr Tyr Gly Met Asp Val Trp Gly Gln Gly Thr Thr Val Thr
225                 230                 235                 240

Val Ser Ser

<210> SEQ ID NO 109
<211> LENGTH: 246
<212> TYPE: PRT
<213> ORGANISM: Artificial Sequence
<220> FEATURE:
<223> OTHER INFORMATION: Antigen biding domain

<400> SEQUENCE: 109

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Phe Val Ser Trp Tyr Gln Gln His Pro Gly Glu Ala Pro Lys Leu
        35                  40                  45

Leu Val Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Ala Gly Ser
                85                  90                  95

Asn Ser Val Phe Gly Thr Gly Thr Lys Val Thr Val Leu Gly Ser Thr
            100                 105                 110

Ser Gly Ser Gly Lys Pro Gly Ser Gly Glu Gly Ser Thr Lys Gly Glu
            115                 120                 125

Val Gln Leu Leu Glu Ser Gly Gly Gly Leu Val Gln Pro Gly Gly Ser
130                 135                 140

Leu Arg Leu Ser Cys Ala Ala Ser Gly Phe Thr Phe Ser Thr Tyr Gln
145                 150                 155                 160

Met Ser Trp Val Arg Gln Ala Pro Gly Lys Gly Leu Glu Trp Val Ser
                165                 170                 175

Gly Ile Val Ser Ser Gly Gly Ser Thr Ala Tyr Ala Asp Ser Val Lys
            180                 185                 190
```

```
Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
        210                 215                 220

Gly Glu Leu Leu Pro Tyr Tyr Gly Met Asp Val Trp Gly Gln Gly Thr
225                 230                 235                 240

Thr Val Thr Val Ser Ser
                245

<210> SEQ ID NO 110
<211> LENGTH: 246
<212> TYPE: PRT
<213> ORGANISM: Artificial Sequence
<220> FEATURE:
<223> OTHER INFORMATION: Antigen binding domain

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Ser Trp Val Arg Gln Ala Pro Gly Lys Gly Leu Glu Trp Val
        35                  40                  45

Ser Gly Ile Val Ser Ser Gly Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Leu Leu Pro Tyr Tyr Gly Met Asp Val Trp Gly Gln Gly
            100                 105                 110

Thr Thr Val Thr Val Ser Ser Gly Ser Thr Ser Gly Ser Gly Lys Pro
        115                 120                 125

Gly Ser Gly Glu Gly Ser Thr Lys Gly Gln Ser Ala Leu Thr Gln Pro
    130                 135                 140

Pro Ser Ala Ser Gly Ser Pro Gly Gln Ser Val Thr Ile Ser Cys Thr
145                 150                 155                 160

Gly Thr Ser Ser Asp Val Gly Gly Tyr Asp Phe Val Ser Trp Tyr Gln
                165                 170                 175

Gln His Pro Gly Glu Ala Pro Lys Leu Leu Val Tyr Asp Val Asn Asn
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Gly Asp
    210                 215                 220

Tyr Tyr Cys Ser Ser Tyr Ala Gly Ser Asn Ser Val Phe Gly Thr Gly
225                 230                 235                 240

Thr Lys Val Thr Val Leu
                245

<210> SEQ ID NO 111
<211> LENGTH: 247
<212> TYPE: PRT
<213> ORGANISM: Artificial Sequence
<220> FEATURE:
<223> OTHER INFORMATION: Antigen biding domain

<400> SEQUENCE: 111
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Phe Val Ser Trp Tyr Gln Gln His Pro Gly Ser Ala Pro Lys Leu
        35                  40                  45

Ile Ile Tyr Asp Val Ile Glu Arg Pro Phe Gly Val Ser Tyr Arg Phe
    50                  55                  60

Ser Ala Ser Lys Ser Gly Asn Thr Ala Ser Leu Thr Ile Ser Gly Leu
65              70                  75                  80

Gln Gly Glu Asp Glu Ala Asp Tyr Phe Cys Ser Ser Tyr Thr Ser Ser
            85                  90                  95

Ser Thr Tyr Val Phe Gly Thr Gly Thr Lys Val Thr Val Leu Gly Ser
            100                 105                 110

Thr Ser Gly Ser Gly Lys Pro Gly Ser Gly Glu Gly Ser Thr Lys Gly
            115                 120                 125

Glu Val Gln Leu Leu Glu Ser Gly Gly Leu Val Gln Pro Gly Gly
        130                 135                 140

Ser Leu Arg Leu Ser Cys Ala Ala Ser Gly Phe Thr Phe Ser Thr Tyr
145             150                 155                 160

Gln Met Ser Trp Val Arg Gln Ala Pro Gly Lys Gly Leu Glu Trp Val
            165                 170                 175

Ser Gly Ile Val Ser Gly Gly Ser Thr Ala Tyr Ala Asp Ser Val
            180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
        210                 215                 220

Ala Gly Glu Leu Leu Pro Tyr Tyr Gly Met Asp Val Trp Gly Gln Gly
225             230                 235                 240

Thr Thr Val Thr Val Ser Ser
            245

<210> SEQ ID NO 112
<211> LENGTH: 247
<212> TYPE: PRT
<213> ORGANISM: Artificial Sequence
<220> FEATURE:
<223> OTHER INFORMATION: Antigen biding domain

<400> SEQUENCE: 112

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asp Tyr Val Ser Trp Tyr Gln His His Pro Gly Arg Ala Pro Arg Leu
        35                  40                  45

Ile Ile Arg Asp Val Ser Val Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Ser Gly Ser
            85                  90                  95

Ser Thr Trp Val Phe Gly Gly Gly Thr Lys Leu Thr Val Leu Gly Ser
            100                 105                 110
```

```
Thr Ser Gly Ser Gly Lys Pro Gly Ser Gly Glu Gly Ser Thr Lys Gly
            115                 120                 125

Glu Val Gln Leu Leu Glu Ser Gly Gly Gly Leu Val Gln Pro Gly Gly
        130                 135                 140

Ser Leu Arg Leu Ser Cys Ala Ala Ser Gly Phe Thr Phe Ser Thr Tyr
145                 150                 155                 160

Gln Met Ser Trp Val Arg Gln Ala Pro Gly Lys Gly Leu Glu Trp Val
                165                 170                 175

Ser Gly Ile Val Ser Ser Gly Gly Ser Thr Ala Tyr Ala Asp Ser Val
                180                 185                 190

Lys Gly Arg Phe Thr Ile Ser Arg Asp Asn Ser Lys Asn Thr Leu Tyr
                195                 200                 205

Leu Gln Met Asn Ser Leu Arg Ala Glu Asp Thr Ala Val Tyr Tyr Cys
        210                 215                 220

Ala Gly Glu Leu Leu Pro Tyr Tyr Gly Met Asp Val Trp Gly Gln Gly
225                 230                 235                 240

Thr Thr Val Thr Val Ser Ser
            245

<210> SEQ ID NO 113
<211> LENGTH: 248
<212> TYPE: PRT
<213> ORGANISM: Artificial Sequence
<220> FEATURE:
<223> OTHER INFORMATION: Antigen biding domain

<400> SEQUENCE: 113

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Asp Val Ser Asn Arg Pro Ser Gly Val Ser Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Ala Val Phe Gly Gly Gly Thr Gln Leu Thr Val Leu Gly
            100                 105                 110

Ser Thr Ser Gly Ser Gly Lys Pro Gly Ser Gly Glu Gly Ser Thr Lys
            115                 120                 125

Gly Glu Val Gln Leu Leu Glu Ser Gly Gly Gly Leu Val Gln Pro Gly
            130                 135                 140

Gly Ser Leu Arg Leu Ser Cys Ala Ala Ser Gly Phe Thr Phe Ser Thr
145                 150                 155                 160

Tyr Gln Met Ser Trp Val Arg Gln Ala Pro Gly Lys Gly Leu Glu Trp
                165                 170                 175

Val Ser Gly Ile Val Ser Ser Gly Gly Ser Thr Ala Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220
```

```
Cys Ala Gly Glu Leu Leu Pro Tyr Tyr Gly Met Asp Val Trp Gly Gln
225                 230                 235                 240

Gly Thr Thr Val Thr Val Ser Ser
                245

<210> SEQ ID NO 114
<211> LENGTH: 246
<212> TYPE: PRT
<213> ORGANISM: Artificial Sequence
<220> FEATURE:
<223> OTHER INFORMATION: Antigen biding domain

<400> SEQUENCE: 114

Gln Ser Ala Leu Pro Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Cys Ser Tyr Ala Gly Gly
                85                  90                  95

Tyr Tyr Val Phe Gly Thr Gly Thr Lys Leu Thr Val Leu Gly Ser Thr
                100                 105                 110

Ser Gly Ser Gly Lys Pro Gly Ser Gly Glu Gly Ser Thr Lys Gly Glu
            115                 120                 125

Val Gln Leu Leu Glu Ser Gly Gly Leu Val Gln Pro Gly Gly Ser
    130                 135                 140

Leu Arg Leu Ser Cys Ala Ala Ser Gly Phe Thr Phe Ser Thr Tyr Gln
145                 150                 155                 160

Met Ser Trp Val Arg Gln Ala Pro Gly Lys Gly Leu Glu Trp Val Ser
                165                 170                 175

Gly Ile Val Ser Ser Gly Gly Ser Thr Ala Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Gly Glu Leu Leu Pro Tyr Tyr Gly Met Asp Val Trp Gly Gln Gly Thr
225                 230                 235                 240

Thr Val Thr Val Ser Ser
                245

<210> SEQ ID NO 115
<211> LENGTH: 249
<212> TYPE: PRT
<213> ORGANISM: Artificial Sequence
<220> FEATURE:
<223> OTHER INFORMATION: Antigen biding domain

<400> SEQUENCE: 115

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
```

```
                20                  25                  30
Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Thr Glu Asp Glu Ala Asp Tyr Tyr Cys Ser Ser Tyr Ala Gly Ser
                85                  90                  95

Gly Ser Thr Pro Phe Val Phe Gly Thr Gly Thr Lys Leu Thr Val Leu
                100                 105                 110

Gly Ser Thr Ser Gly Ser Gly Lys Pro Gly Ser Gly Glu Gly Ser Thr
                115                 120                 125

Lys Gly Glu Val Gln Leu Leu Glu Ser Gly Gly Leu Val Gln Pro
                130                 135                 140

Gly Gly Ser Leu Arg Leu Ser Cys Ala Ala Ser Gly Phe Thr Phe Ser
145                 150                 155                 160

Thr Tyr Gln Met Ser Trp Val Arg Gln Ala Pro Gly Lys Gly Leu Glu
                165                 170                 175

Trp Val Ser Gly Ile Val Ser Ser Gly Ser Thr Ala Tyr Ala Asp
                180                 185                 190

Ser Val Lys Gly Arg Phe Thr Ile Ser Arg Asp Asn Ser Lys Asn Thr
                195                 200                 205

Leu Tyr Leu Gln Met Asn Ser Leu Arg Ala Glu Asp Thr Ala Val Tyr
                210                 215                 220

Tyr Cys Ala Gly Glu Leu Leu Pro Tyr Tyr Gly Met Asp Val Trp Gly
225                 230                 235                 240

Gln Gly Thr Thr Val Thr Val Ser Ser
                245
```

<210> SEQ ID NO 116
<211> LENGTH: 246
<212> TYPE: PRT
<213> ORGANISM: Artificial Sequence
<220> FEATURE:
<223> OTHER INFORMATION: Antigen biding domain

<400> SEQUENCE: 116

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Asn Arg Pro Ser Arg Val Pro Asp Arg Phe
 50                  55                  60

Ala Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Arg
                85                  90                  95

Arg Tyr Val Phe Gly Thr Gly Thr Lys Leu Thr Val Leu Gly Ser Thr
                100                 105                 110

Ser Gly Ser Gly Lys Pro Gly Ser Gly Glu Gly Ser Thr Lys Gly Glu
                115                 120                 125

Val Gln Leu Leu Glu Ser Gly Gly Gly Leu Val Gln Pro Gly Gly Ser
```

|     |     |     |     |     | 130 |     |     |     |     | 135 |     |     |     |     | 140 |
| --- | --- | --- | --- | --- | --- | --- | --- | --- | --- | --- | --- | --- | --- | --- | --- |

Leu Arg Leu Ser Cys Ala Ala Ser Gly Phe Thr Phe Ser Thr Tyr Gln
145                 150                 155                 160

Met Ser Trp Val Arg Gln Ala Pro Gly Lys Gly Leu Glu Trp Val Ser
                165                 170                 175

Gly Ile Val Ser Ser Gly Gly Ser Thr Ala Tyr Ala Asp Ser Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
            210                 215                 220

Gly Glu Leu Leu Pro Tyr Tyr Gly Met Asp Val Trp Gly Gln Gly Thr
225                 230                 235                 240

Thr Val Thr Val Ser Ser
                245

<210> SEQ ID NO 117
<211> LENGTH: 245
<212> TYPE: PRT
<213> ORGANISM: Artificial Sequence
<220> FEATURE:
<223> OTHER INFORMATION: Antigen biding domain

<400> SEQUENCE: 117

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Cys Pro Ile Tyr Tyr Gly Met Asp Val Trp Gly Gln Gly Thr
            100                 105                 110

Thr Val Thr Val Ser Ser Gly Ser Thr Ser Gly Ser Gly Lys Pro Gly
            115                 120                 125

Ser Gly Glu Gly Ser Thr Lys Gly Gln Ser Glu Leu Thr Gln Pro Arg
            130                 135                 140

Ser Val Ser Gly Ser Pro Gly Gln Ser Val Thr Ile Ser Cys Thr Gly
145                 150                 155                 160

Thr Ser Arg Asp Val Gly Gly Tyr Asn Tyr Val Ser Trp Tyr Gln Gln
                165                 170                 175

His Pro Gly Lys Ala Pro Lys Leu Ile Ile His Asp Val Ile Glu Arg
            180                 185                 190

Ser Ser Gly Val Pro Asp Arg Phe Ser Gly Ser Lys Ser Gly Asn Thr
            195                 200                 205

Ala Ser Leu Thr Ile Ser Gly Leu Gln Ala Glu Asp Glu Ala Asp Tyr
            210                 215                 220

Tyr Cys Trp Ser Phe Ala Gly Ser Tyr Tyr Val Phe Gly Thr Gly Thr
225                 230                 235                 240

Asp Val Thr Val Leu

245

<210> SEQ ID NO 118
<211> LENGTH: 467
<212> TYPE: PRT
<213> ORGANISM: Artificial Sequence
<220> FEATURE:
<223> OTHER INFORMATION: Chimeric antigen receptor

<400> SEQUENCE: 118

```
Gln Val Gln Leu Gln Glu Ser Gly Pro Gly Leu Val Lys Pro Ser Asp
1               5                   10                  15

Thr Leu Ser Leu Thr Cys Leu Val Ser Gly Gly Ser Ile Ser Ser Asn
            20                  25                  30

Tyr Trp Ser Trp Ile Arg Gln Ala Pro Gly Lys Gly Leu Glu Trp Ile
        35                  40                  45

Gly His Val Ser Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Tyr Tyr Tyr Gly Met Asp Val Trp Gly Gln Gly Thr
            100                 105                 110

Thr Val Thr Val Ser Ser Gly Ser Thr Ser Gly Ser Gly Lys Pro Gly
            115                 120                 125

Ser Gly Glu Gly Ser Thr Lys Gly Gln Ser Glu Leu Thr Gln Pro Arg
130                 135                 140

Ser Val Ser Gly Ser Pro Gly Gln Ser Val Thr Ile Ser Cys Thr Gly
145                 150                 155                 160

Thr Ser Arg Asp Val Gly Gly Tyr Asn Tyr Val Ser Trp Tyr Gln Gln
                165                 170                 175

His Pro Gly Lys Ala Pro Lys Leu Ile Ile His Asp Val Ile Glu Arg
            180                 185                 190

Ser Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Trp Ser Phe Ala Gly Ser Tyr Tyr Val Phe Gly Thr Gly Thr
225                 230                 235                 240

Asp Val Thr Val Leu Ala Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
```

```
                355                 360                 365
Gln Gln Gly Gln Asn Gln Leu Tyr Asn Glu Leu Asn Leu Gly Arg Arg
        370                 375                 380
Glu Glu Tyr Asp Val Leu Asp Lys Arg Arg Gly Arg Asp Pro Glu Met
385                 390                 395                 400
Gly Gly Lys Pro Arg Arg Lys Asn Pro Gln Glu Gly Leu Tyr Asn Glu
                405                 410                 415
Leu Gln Lys Asp Lys Met Ala Glu Ala Tyr Ser Glu Ile Gly Met Lys
        420                 425                 430
Gly Glu Arg Arg Arg Gly Lys Gly His Asp Gly Leu Tyr Gln Gly Leu
                435                 440                 445
Ser Thr Ala Thr Lys Asp Thr Tyr Asp Ala Leu His Met Gln Ala Leu
        450                 455                 460
Pro Pro Arg
465

<210> SEQ ID NO 119
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 119

Asp Ile Gln Met Thr Gln Ser Pro Ser Ala Met Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ser Thr Pro Gln
                85                  90                  95
Thr Phe Gly Pro Gly Thr Lys Val Asp Ile Lys Gly Ser Thr Ser Gly
            100                 105                 110
Ser Gly Lys Pro Gly Ser Gly Glu Gly Ser Thr Lys Gly Gln Val Gln
        115                 120                 125
Leu Gln Glu Ser Gly Pro Gly Leu Val Lys Pro Ser Asp Thr Leu Ser
    130                 135                 140
Leu Thr Cys Leu Val Ser Gly Gly Ser Ile Ser Ser Asn Tyr Trp Ser
145                 150                 155                 160
Trp Ile Arg Gln Ala Pro Gly Lys Gly Leu Glu Trp Ile Gly His Val
                165                 170                 175
Ser Tyr Ser Gly Ser Thr Asn Tyr Asn Pro Ser Leu Lys Ser Arg Val
            180                 185                 190
Thr Ile Ser Val Asp Thr Ser Lys Asn Gln Phe Ser Leu Lys Leu Ser
        195                 200                 205
Ser Val Thr Ala Ala Asp Thr Ala Val Tyr Tyr Cys Ala Arg Glu Ser
    210                 215                 220
Tyr Tyr Tyr Tyr Gly Met Asp Val Trp Gly Gln Gly Thr Thr Val Thr
225                 230                 235                 240
Val Ser Ser Ala Ala Ala Ile Glu Val Met Tyr Pro Pro Pro Tyr Leu
```

-continued

```
                245                 250                 255
Asp Asn Glu Lys Ser Asn Gly Thr Ile Ile His Val Lys Gly Lys His
            260                 265                 270
Leu Cys Pro Ser Pro Leu Phe Pro Gly Pro Ser Lys Pro Phe Trp Val
        275                 280                 285
Leu Val Val Gly Gly Val Leu Ala Cys Tyr Ser Leu Leu Val Thr
    290                 295                 300
Val Ala Phe Ile Ile Phe Trp Val Arg Ser Lys Arg Ser Arg Leu Leu
305                 310                 315                 320
His Ser Asp Tyr Met Asn Met Thr Pro Arg Arg Pro Gly Pro Thr Arg
                325                 330                 335
Lys His Tyr Gln Pro Tyr Ala Pro Pro Arg Asp Phe Ala Ala Tyr Arg
            340                 345                 350
Ser Arg Val Lys Phe Ser Arg Ser Ala Asp Ala Pro Ala Tyr Gln Gln
        355                 360                 365
Gly Gln Asn Gln Leu Tyr Asn Glu Leu Asn Leu Gly Arg Arg Glu Glu
    370                 375                 380
Tyr Asp Val Leu Asp Lys Arg Arg Gly Arg Asp Pro Glu Met Gly Gly
385                 390                 395                 400
Lys Pro Arg Arg Lys Asn Pro Gln Glu Gly Leu Tyr Asn Glu Leu Gln
                405                 410                 415
Lys Asp Lys Met Ala Glu Ala Tyr Ser Glu Ile Gly Met Lys Gly Glu
            420                 425                 430
Arg Arg Arg Gly Lys Gly His Asp Gly Leu Tyr Gln Gly Leu Ser Thr
        435                 440                 445
Ala Thr Lys Asp Thr Tyr Asp Ala Leu His Met Gln Ala Leu Pro Pro
    450                 455                 460
Arg
465

<210> SEQ ID NO 120
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 120

Asp Ile Gln Met Thr Gln Ser Pro Ser Ser Leu Ser Ala Ser Val Gly
1               5                  10                  15
Asp Arg Val Thr Ile Thr Cys Arg Ala Ser Gln Ser Ile Ser Ser Tyr
            20                  25                  30
Leu Asn Trp Tyr Gln Gln Lys Ala Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Cys Leu Gln Ser
65                  70                  75                  80
Glu Asp Val Ala Thr Tyr Tyr Cys Gln Gln Tyr Glu Ser Tyr Arg Arg
                85                  90                  95
Ser Phe Gly Gln Gly Thr Lys Val Glu Ile Lys Gly Ser Thr Ser Gly
            100                 105                 110
Ser Gly Lys Pro Gly Ser Gly Glu Ser Thr Lys Gly Gln Val Gln
        115                 120                 125
Leu Gln Glu Ser Gly Pro Gly Leu Val Lys Pro Ser Asp Thr Leu Ser
```

```
                130                 135                 140
Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
                180                 185                 190

Thr Ile Ser Val Asp Thr Ser Lys Asn Gln Phe Ser Leu Lys Leu Ser
                195                 200                 205

Ser Val Thr Ala Ala Asp Thr Ala Val Tyr Tyr Cys Ala Arg Glu Ser
                210                 215                 220

Tyr Tyr Tyr Tyr Gly Met Asp Val Trp Gly Gln Gly Thr Thr Val Thr
225                 230                 235                 240

Val Ser Ser Ala Ala Ala Ile Glu Val Met Tyr Pro Pro Pro Tyr Leu
                245                 250                 255

Asp Asn Glu Lys Ser Asn Gly Thr Ile Ile His Val Lys Gly Lys His
                260                 265                 270

Leu Cys Pro Ser Pro Leu Phe Pro Gly Pro Ser Lys Pro Phe Trp Val
                275                 280                 285

Leu Val Val Val Gly Gly Val Leu Ala Cys Tyr Ser Leu Leu Val Thr
                290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
                340                 345                 350

Ser Arg Val Lys Phe Ser Arg Ser Ala Asp Ala Pro Ala Tyr Gln Gln
                355                 360                 365

Gly Gln Asn Gln Leu Tyr Asn Glu Leu Asn Leu Gly Arg Arg Glu Glu
                370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
                420                 425                 430

Arg Arg Arg Gly Lys Gly His Asp Gly Leu Tyr Gln Gly Leu Ser Thr
                435                 440                 445

Ala Thr Lys Asp Thr Tyr Asp Ala Leu His Met Gln Ala Leu Pro Pro
                450                 455                 460

Arg
465

<210> SEQ ID NO 121
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

-continued

```
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Cys Leu Gln Ser
 65                  70                  75                  80
Glu Asp Phe Ala Thr Tyr Tyr Cys Gln Gln Tyr Asn Ser Tyr Ser Arg
                85                  90                  95
Thr Phe Gly Gln Gly Thr Lys Val Glu Ile Lys Gly Ser Thr Ser Gly
                100                 105                 110
Ser Gly Lys Pro Gly Ser Gly Glu Gly Ser Thr Lys Gly Gln Val Gln
            115                 120                 125
Leu Gln Glu Ser Gly Pro Gly Leu Val Lys Pro Ser Asp Thr Leu Ser
            130                 135                 140
Leu Thr Cys Leu Val Ser Gly Gly Ser Ile Ser Ser Asn Tyr Trp Ser
145                 150                 155                 160
Trp Ile Arg Gln Ala Pro Gly Lys Gly Leu Glu Trp Ile Gly His Val
                165                 170                 175
Ser Tyr Ser Gly Ser Thr Asn Tyr Asn Pro Ser Leu Lys Ser Arg Val
                180                 185                 190
Thr Ile Ser Val Asp Thr Ser Lys Asn Gln Phe Ser Leu Lys Leu Ser
            195                 200                 205
Ser Val Thr Ala Ala Asp Thr Ala Val Tyr Tyr Cys Ala Arg Glu Ser
            210                 215                 220
Tyr Tyr Tyr Tyr Gly Met Asp Val Trp Gly Gln Gly Thr Thr Val Thr
225                 230                 235                 240
Val Ser Ser Ala Ala Ala Ile Glu Val Met Tyr Pro Pro Pro Tyr Leu
                245                 250                 255
Asp Asn Glu Lys Ser Asn Gly Thr Ile Ile His Val Lys Gly Lys His
                260                 265                 270
Leu Cys Pro Ser Pro Leu Phe Pro Gly Pro Ser Lys Pro Phe Trp Val
            275                 280                 285
Leu Val Val Val Gly Gly Val Leu Ala Cys Tyr Ser Leu Leu Val Thr
            290                 295                 300
Val Ala Phe Ile Ile Phe Trp Val Arg Ser Lys Arg Ser Arg Leu Leu
305                 310                 315                 320
His Ser Asp Tyr Met Asn Met Thr Pro Arg Arg Pro Gly Pro Thr Arg
                325                 330                 335
Lys His Tyr Gln Pro Tyr Ala Pro Pro Arg Asp Phe Ala Ala Tyr Arg
                340                 345                 350
Ser Arg Val Lys Phe Ser Arg Ser Ala Asp Ala Pro Ala Tyr Gln Gln
            355                 360                 365
Gly Gln Asn Gln Leu Tyr Asn Glu Leu Asn Leu Gly Arg Arg Glu Glu
            370                 375                 380
Tyr Asp Val Leu Asp Lys Arg Arg Gly Arg Asp Pro Glu Met Gly Gly
385                 390                 395                 400
Lys Pro Arg Arg Lys Asn Pro Gln Glu Gly Leu Tyr Asn Glu Leu Gln
                405                 410                 415
Lys Asp Lys Met Ala Glu Ala Tyr Ser Glu Ile Gly Met Lys Gly Glu
                420                 425                 430
Arg Arg Arg Gly Lys Gly His Asp Gly Leu Tyr Gln Gly Leu Ser Thr
            435                 440                 445
```

```
Ala Thr Lys Asp Thr Tyr Asp Ala Leu His Met Gln Ala Leu Pro Pro
        450                 455                 460

Arg
465

<210> SEQ ID NO 122
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Glu Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Glu Ser Gly Pro Gly Leu Val Lys Pro Ser Asp Thr Leu Ser
130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
210                 215                 220

Tyr Tyr Tyr Tyr Gly Met Asp Val Trp Gly Gln Gly Thr Thr Val Thr
225                 230                 235                 240

Val Ser Ser Ala Ala Ala Ile Glu Val Met Tyr Pro Pro Pro Tyr Leu
                245                 250                 255

Asp Asn Glu Lys Ser Asn Gly Thr Ile Ile His Val Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335
```

```
Lys His Tyr Gln Pro Tyr Ala Pro Pro Arg Asp Phe Ala Ala Tyr Arg
                340                 345                 350

Ser Arg Val Lys Phe Ser Arg Ser Ala Asp Ala Pro Ala Tyr Gln Gln
            355                 360                 365

Gly Gln Asn Gln Leu Tyr Asn Glu Leu Asn Leu Gly Arg Arg Glu Glu
        370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 123
<211> LENGTH: 466
<212> TYPE: PRT
<213> ORGANISM: Artificial Sequence
<220> FEATURE:
<223> OTHER INFORMATION: Chimeric antigen receptor

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Cys Thr Phe Gly Pro Gly Thr Lys Val Asp Ile Lys Gly Ser Thr Ser
            100                 105                 110

Gly Ser Gly Lys Pro Gly Ser Gly Glu Gly Ser Thr Lys Gly Gln Val
        115                 120                 125

Gln Leu Gln Glu Ser Gly Pro Gly Leu Val Lys Pro Ser Asp Thr Leu
    130                 135                 140

Ser Leu Thr Cys Leu Val Ser Gly Gly Ser Ile Ser Ser Asn Tyr Trp
145                 150                 155                 160

Ser Trp Ile Arg Gln Ala Pro Gly Lys Gly Leu Glu Trp Ile Gly His
                165                 170                 175

Val Ser Tyr Ser Gly Ser Thr Asn Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Glu
    210                 215                 220
```

Ser Tyr Tyr Tyr Tyr Gly Met Asp Val Trp Gly Gln Gly Thr Thr Val
225                 230                 235                 240

Thr Val Ser Ser Ala Ala Ile Glu Val Met Tyr Pro Pro Pro Tyr
        245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
            325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
            405                 410                 415

Gln Lys Asp Lys Met Ala Glu Ala Tyr Ser Glu Ile Gly Met Lys Gly
        420                 425                 430

Glu Arg Arg Arg Gly Lys Gly His Asp Gly Leu Tyr Gln Gly Leu Ser
    435                 440                 445

Thr Ala Thr Lys Asp Thr Tyr Asp Ala Leu His Met Gln Ala Leu Pro
    450                 455                 460

Pro Arg
465

<210> SEQ ID NO 124
<211> LENGTH: 464
<212> TYPE: PRT
<213> ORGANISM: Artificial Sequence
<220> FEATURE:
<223> OTHER INFORMATION: Chimeric antigen receptor

<400> SEQUENCE: 124

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Asp Ile Ser Arg Tyr
            20                  25                  30

Leu Asn Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys Gly Ser Thr Ser Gly Ser
            100                 105                 110

Gly Lys Pro Gly Ser Gly Glu Gly Ser Thr Lys Gly Gln Val Gln Leu
            115                 120                 125

Gln Glu Ser Gly Pro Gly Leu Val Lys Pro Ser Asp Thr Leu Ser Leu
        130                 135                 140

Thr Cys Leu Val Ser Gly Gly Ser Ile Ser Ser Asn Tyr Trp Ser Trp
145                 150                 155                 160

Ile Arg Gln Ala Pro Gly Lys Gly Leu Glu Trp Ile Gly His Val Ser
                165                 170                 175

Tyr Ser Gly Ser Thr Asn Tyr Asn Pro Ser Leu Lys Ser Arg Val Thr
            180                 185                 190

Ile Ser Val Asp Thr Ser Lys Asn Gln Phe Ser Leu Lys Leu Ser Ser
        195                 200                 205

Val Thr Ala Ala Asp Thr Ala Val Tyr Tyr Cys Ala Arg Glu Ser Tyr
    210                 215                 220

Tyr Tyr Tyr Gly Met Asp Val Trp Gly Gln Gly Thr Thr Val Thr Val
225                 230                 235                 240

Ser Ser Ala Ala Ala Ile Glu Val Met Tyr Pro Pro Pro Tyr Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 125
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 125

Asp Ile Gln Met Thr Gln Ser Pro Ser Ser Leu Ser Ala Ser Val Gly
1               5                   10                  15

-continued

Asp Arg Val Ser Ile Thr Cys Arg Ala Ser Gln Asp Ile Ser Arg Tyr
            20                  25                  30

Leu Asn Trp Tyr Gln Gln Lys Pro Gly Lys Ala Pro Lys Leu Leu Leu
         35                  40                  45

Tyr Ala Ala Ser Arg Leu Glu Ser Gly Val Pro Ser Arg Phe Ser Gly
 50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys Gly Ser Thr Ser Gly
             100                 105                 110

Ser Gly Lys Pro Gly Ser Gly Glu Gly Ser Thr Lys Gly Gln Val Gln
         115                 120                 125

Leu Gln Glu Ser Gly Pro Gly Leu Val Lys Pro Ser Asp Thr Leu Ser
130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
             180                 185                 190

Thr Ile Ser Val Asp Thr Ser Lys Asn Gln Phe Ser Leu Lys Leu Ser
         195                 200                 205

Ser Val Thr Ala Ala Asp Thr Ala Val Tyr Tyr Cys Ala Arg Glu Ser
210                 215                 220

Tyr Tyr Tyr Tyr Gly Met Asp Val Trp Gly Gln Gly Thr Thr Val Thr
225                 230                 235                 240

Val Ser Ser Ala Ala Ile Glu Val Met Tyr Pro Pro Pro Tyr Leu
                245                 250                 255

Asp Asn Glu Lys Ser Asn Gly Thr Ile Ile His Val Lys Gly Lys His
             260                 265                 270

Leu Cys Pro Ser Pro Leu Phe Pro Gly Pro Ser Lys Pro Phe Trp Val
         275                 280                 285

Leu Val Val Val Gly Gly Val Leu Ala Cys Tyr Ser Leu Leu Val Thr
290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
             340                 345                 350

Ser Arg Val Lys Phe Ser Arg Ser Ala Asp Ala Pro Ala Tyr Gln Gln
         355                 360                 365

Gly Gln Asn Gln Leu Tyr Asn Glu Leu Asn Leu Gly Arg Arg Glu Glu
370                 375                 380

Tyr Asp Val Leu Asp Lys Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
             420                 425                 430

Arg Arg Arg Gly Lys Gly His Asp Gly Leu Tyr Gln Gly Leu Ser Thr
            435                 440                 445

Ala Thr Lys Asp Thr Tyr Asp Ala Leu His Met Gln Ala Leu Pro Pro
450                 455                 460

Arg
465

<210> SEQ ID NO 126
<211> LENGTH: 464
<212> TYPE: PRT
<213> ORGANISM: Artificial Sequence
<220> FEATURE:
<223> OTHER INFORMATION: Chimeric antigen receptor

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Asp Asn Leu Ile Thr
                85                  90                  95

Phe Gly Gln Gly Thr Arg Leu Glu Ile Lys Gly Ser Thr Ser Gly Ser
            100                 105                 110

Gly Lys Pro Gly Ser Gly Glu Gly Ser Thr Lys Gly Gln Val Gln Leu
        115                 120                 125

Gln Glu Ser Gly Pro Gly Leu Val Lys Pro Ser Asp Thr Leu Ser Leu
130                 135                 140

Thr Cys Leu Val Ser Gly Gly Ser Ile Ser Ser Asn Tyr Trp Ser Trp
145                 150                 155                 160

Ile Arg Gln Ala Pro Gly Lys Gly Leu Glu Trp Ile Gly His Val Ser
                165                 170                 175

Tyr Ser Gly Ser Thr Asn Tyr Asn Pro Ser Leu Lys Ser Arg Val Thr
            180                 185                 190

Ile Ser Val Asp Thr Ser Lys Asn Gln Phe Ser Leu Lys Leu Ser Ser
        195                 200                 205

Val Thr Ala Ala Asp Thr Ala Val Tyr Tyr Cys Ala Arg Glu Ser Tyr
    210                 215                 220

Tyr Tyr Tyr Gly Met Asp Val Trp Gly Gln Gly Thr Thr Val Thr Val
225                 230                 235                 240

Ser Ser Ala Ala Ala Ile Glu Val Met Tyr Pro Pro Pro Tyr Leu Asp
                245                 250                 255

Asn Glu Lys Ser Asn Gly Thr Ile Ile His Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

```
Ser Asp Tyr Met Asn Met Thr Pro Arg Arg Pro Gly Pro Thr Arg Lys
            325                 330                 335

His Tyr Gln Pro Tyr Ala Pro Pro Arg Asp Phe Ala Ala Tyr Arg Ser
        340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 127
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 127

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Gln Glu Ser Gly Pro Gly Leu Val Lys Pro Ser Asp Thr Leu Ser
    130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
    210                 215                 220
```

```
Tyr Tyr Tyr Tyr Gly Met Asp Val Trp Gly Gln Gly Thr Thr Val Thr
225                 230                 235                 240

Val Ser Ser Ala Ala Ala Ile Glu Val Met Tyr Pro Pro Pro Tyr Leu
            245                 250                 255

Asp Asn Glu Lys Ser Asn Gly Thr Ile Ile His Val Lys Gly Lys His
        260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
        290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
                340                 345                 350

Ser Arg Val Lys Phe Ser Arg Ser Ala Asp Ala Pro Ala Tyr Gln Gln
            355                 360                 365

Gly Gln Asn Gln Leu Tyr Asn Glu Leu Asn Leu Gly Arg Arg Glu Glu
        370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
        450                 455                 460

Arg
465

<210> SEQ ID NO 128
<211> LENGTH: 465
<212> TYPE: PRT
<213> ORGANISM: Artificial Sequence
<220> FEATURE:
<223> OTHER INFORMATION: Chimeric antigen receptor

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Val Ala Thr Tyr Tyr Cys Gln Gln Tyr Glu Ser Tyr Ser Arg
                85                  90                  95

Thr Phe Gly Gln Gly Thr Lys Val Glu Ile Lys Gly Ser Thr Ser Gly
            100                 105                 110
```

Ser Gly Lys Pro Gly Ser Gly Glu Gly Ser Thr Lys Gly Gln Val Gln
            115                 120                 125

Leu Gln Glu Ser Gly Pro Gly Leu Val Lys Pro Ser Asp Thr Leu Ser
        130                 135                 140

Leu Thr Cys Leu Val Ser Gly Gly Ser Ile Ser Ser Asn Tyr Trp Ser
145                 150                 155                 160

Trp Ile Arg Gln Ala Pro Gly Lys Gly Leu Glu Trp Ile Gly His Val
                165                 170                 175

Ser Tyr Ser Gly Ser Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Ser
    210                 215                 220

Tyr Tyr Tyr Tyr Gly Met Asp Val Trp Gly Gln Gly Thr Thr Val Thr
225                 230                 235                 240

Val Ser Ser Ala Ala Ala Ile Glu Val Met Tyr Pro Pro Pro Tyr Leu
                245                 250                 255

Asp Asn Glu Lys Ser Asn Gly Thr Ile Ile His Val Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 129
<211> LENGTH: 468
<212> TYPE: PRT
<213> ORGANISM: Artificial Sequence
<220> FEATURE:
<223> OTHER INFORMATION: Chimeric antigen receptor

<400> SEQUENCE: 129

-continued

Gln Ser Ala Leu Thr Gln Pro Pro Ser Ala Gly Ser Pro Gly Gln
1               5                   10                  15

Ser Val Thr Ile Ser Cys Thr Gly Thr Ser Ser Asp Val Gly Gly Tyr
            20                  25                  30

Asp Phe Val Ser Trp Tyr Gln Gln His Pro Gly Glu Ala Pro Lys Leu
            35                  40                  45

Leu Val Tyr Asp Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Ala Gly Ser
                85                  90                  95

Asn Ser Val Phe Gly Thr Gly Thr Lys Val Thr Val Leu Gly Ser Thr
            100                 105                 110

Ser Gly Ser Gly Lys Pro Gly Ser Gly Glu Gly Ser Thr Lys Gly Glu
            115                 120                 125

Val Gln Leu Leu Glu Ser Gly Gly Leu Val Gln Pro Gly Gly Ser
    130                 135                 140

Leu Arg Leu Ser Cys Ala Ala Ser Gly Phe Thr Phe Ser Thr Tyr Gln
145                 150                 155                 160

Met Ser Trp Val Arg Gln Ala Pro Gly Lys Gly Leu Glu Trp Val Ser
            165                 170                 175

Gly Ile Val Ser Ser Gly Gly Ser Thr Ala Tyr Ala Asp Ser Val Lys
            180                 185                 190

Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
    210                 215                 220

Gly Glu Leu Leu Pro Tyr Tyr Gly Met Asp Val Trp Gly Gln Gly Thr
225                 230                 235                 240

Thr Val Thr Val Ser Ser Ala Ala Ala Ile Glu Val Met Tyr Pro Pro
            245                 250                 255

Pro Tyr Leu Asp Asn Glu Lys Ser Asn Gly Thr Ile Ile His Val Lys
            260                 265                 270

Gly Lys His Leu Cys Pro Ser Pro Leu Phe Pro Gly Pro Ser Lys Pro
            275                 280                 285

Phe Trp Val Leu Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met

```
                420               425               430
Lys Gly Glu Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
            450                 455                 460

Leu Pro Pro Arg
465

<210> SEQ ID NO 130
<211> LENGTH: 569
<212> TYPE: PRT
<213> ORGANISM: Artificial Sequence
<220> FEATURE:
<223> OTHER INFORMATION: Chimeric antigen receptor

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Ser Trp Val Arg Gln Ala Pro Gly Lys Gly Leu Glu Trp Val
        35                  40                  45

Ser Gly Ile Val Ser Gly Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Leu Leu Pro Tyr Tyr Gly Met Asp Val Trp Gly Gln Gly
            100                 105                 110

Thr Thr Val Thr Val Ser Ser Glu Val Gln Leu Leu Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Ser Thr Tyr Gln Met Ser Trp Val Arg Gln Ala Pro
145                 150                 155                 160

Gly Lys Gly Leu Glu Trp Val Ser Gly Ile Val Ser Ser Gly Gly Ser
                165                 170                 175

Thr Ala Tyr Ala Asp Ser Val Lys Gly Arg Phe Thr Ile Ser Arg Asp
            180                 185                 190

Asn Ser Lys Asn Thr Leu Tyr Leu Gln Met Asn Ser Leu Arg Ala Glu
        195                 200                 205

Asp Thr Ala Val Tyr Tyr Cys Ala Gly Glu Leu Leu Pro Tyr Tyr Gly
    210                 215                 220

Met Asp Val Trp Gly Gln Gly Thr Thr Val Thr Val Ser Ser Gln Ser
225                 230                 235                 240

Ala Leu Thr Gln Pro Pro Ser Ala Ser Gly Ser Pro Gly Gln Ser Val
                245                 250                 255

Thr Ile Ser Cys Thr Gly Thr Ser Ser Asp Val Gly Gly Tyr Asp Phe
            260                 265                 270

Val Ser Trp Tyr Gln Gln His Pro Gly Glu Ala Pro Lys Leu Leu Val
        275                 280                 285

Tyr Asp Val Asn Asn Arg Pro Ser Gly Val Ser Asn Arg Phe Ser Gly
    290                 295                 300

Ser Lys Ser Gly Asn Thr Ala Ser Leu Thr Ile Ser Gly Leu Gln Ala
```

```
                    305                 310                 315                 320
Glu Asp Glu Gly Asp Tyr Tyr Cys Ser Ser Tyr Ala Gly Ser Asn Ser
                325                 330                 335

Val Phe Gly Thr Gly Thr Lys Val Thr Val Leu Ala Ala Ala Ile Glu
            340                 345                 350

Val Met Tyr Pro Pro Pro Tyr Leu Asp Asn Glu Lys Ser Asn Gly Thr
        355                 360                 365

Ile Ile His Val Lys Gly Lys His Leu Cys Pro Ser Pro Leu Phe Pro
    370                 375                 380

Gly Pro Ser Lys Pro Phe Trp Val Leu Val Val Val Gly Gly Val Leu
385                 390                 395                 400

Ala Cys Tyr Ser Leu Leu Val Thr Val Ala Phe Ile Ile Phe Trp Val
                405                 410                 415

Arg Ser Lys Arg Ser Arg Leu Leu His Ser Asp Tyr Met Asn Met Thr
            420                 425                 430

Pro Arg Arg Pro Gly Pro Thr Arg Lys His Tyr Gln Pro Tyr Ala Pro
        435                 440                 445

Pro Arg Asp Phe Ala Ala Tyr Arg Ser Arg Val Lys Phe Ser Arg Ser
    450                 455                 460

Ala Asp Ala Pro Ala Tyr Gln Gln Gly Gln Asn Gln Leu Tyr Asn Glu
465                 470                 475                 480

Leu Asn Leu Gly Arg Arg Glu Glu Tyr Asp Val Leu Asp Lys Arg Arg
                485                 490                 495

Gly Arg Asp Pro Glu Met Gly Gly Lys Pro Arg Arg Lys Asn Pro Gln
            500                 505                 510

Glu Gly Leu Tyr Asn Glu Leu Gln Lys Asp Lys Met Ala Glu Ala Tyr
        515                 520                 525

Ser Glu Ile Gly Met Lys Gly Glu Arg Arg Arg Gly Lys Gly His Asp
    530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 131
<211> LENGTH: 469
<212> TYPE: PRT
<213> ORGANISM: Artificial Sequence
<220> FEATURE:
<223> OTHER INFORMATION: Chimeric antigen receptor

<400> SEQUENCE: 131

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Phe Val Ser Trp Tyr Gln Gln His Pro Gly Ser Ala Pro Lys Leu
        35                  40                  45

Ile Ile Tyr Asp Val Ile Glu Arg Pro Phe Gly Val Ser Tyr Arg Phe
    50                  55                  60

Ser Ala Ser Lys Ser Gly Asn Thr Ala Ser Leu Thr Ile Ser Gly Leu
65                  70                  75                  80

Gln Gly Glu Asp Glu Ala Asp Tyr Phe Cys Ser Ser Tyr Thr Ser Ser
                85                  90                  95

Ser Thr Tyr Val Phe Gly Thr Gly Thr Lys Val Thr Val Leu Gly Ser
```

```
                    100                 105                 110
Thr Ser Gly Ser Gly Lys Pro Gly Ser Gly Glu Gly Ser Thr Lys Gly
            115                 120                 125
Glu Val Gln Leu Leu Glu Ser Gly Gly Gly Leu Val Gln Pro Gly Gly
    130                 135                 140
Ser Leu Arg Leu Ser Cys Ala Ala Ser Gly Phe Thr Phe Ser Thr Tyr
145                 150                 155                 160
Gln Met Ser Trp Val Arg Gln Ala Pro Gly Lys Gly Leu Glu Trp Val
                165                 170                 175
Ser Gly Ile Val Ser Ser Gly Gly Ser Thr Ala Tyr Ala Asp Ser Val
            180                 185                 190
Lys Gly Arg Phe Thr Ile Ser Arg Asp Asn Ser Lys Asn Thr Leu Tyr
        195                 200                 205
Leu Gln Met Asn Ser Leu Arg Ala Glu Asp Thr Ala Val Tyr Tyr Cys
    210                 215                 220
Ala Gly Glu Leu Leu Pro Tyr Tyr Gly Met Asp Val Trp Gly Gln Gly
225                 230                 235                 240
Thr Thr Val Thr Val Ser Ser Ala Ala Ala Ile Glu Val Met Tyr Pro
                245                 250                 255
Pro Pro Tyr Leu Asp Asn Glu Lys Ser Asn Gly Thr Ile Ile His Val
            260                 265                 270
Lys Gly Lys His Leu Cys Pro Ser Pro Leu Phe Pro Gly Pro Ser Lys
        275                 280                 285
Pro Phe Trp Val Leu Val Val Val Gly Gly Val Leu Ala Cys Tyr Ser
    290                 295                 300
Leu Leu Val Thr Val Ala Phe Ile Ile Phe Trp Val Arg Ser Lys Arg
305                 310                 315                 320
Ser Arg Leu Leu His Ser Asp Tyr Met Asn Met Thr Pro Arg Arg Pro
                325                 330                 335
Gly Pro Thr Arg Lys His Tyr Gln Pro Tyr Ala Pro Pro Arg Asp Phe
            340                 345                 350
Ala Ala Tyr Arg Ser Arg Val Lys Phe Ser Arg Ser Ala Asp Ala Pro
        355                 360                 365
Ala Tyr Gln Gln Gly Gln Asn Gln Leu Tyr Asn Glu Leu Asn Leu Gly
    370                 375                 380
Arg Arg Glu Glu Tyr Asp Val Leu Asp Lys Arg Arg Gly Arg Asp Pro
385                 390                 395                 400
Glu Met Gly Gly Lys Pro Arg Arg Lys Asn Pro Gln Glu Gly Leu Tyr
                405                 410                 415
Asn Glu Leu Gln Lys Asp Lys Met Ala Glu Ala Tyr Ser Glu Ile Gly
            420                 425                 430
Met Lys Gly Glu Arg Arg Arg Gly Lys Gly His Asp Gly Leu Tyr Gln
        435                 440                 445
Gly Leu Ser Thr Ala Thr Lys Asp Thr Tyr Asp Ala Leu His Met Gln
    450                 455                 460
Ala Leu Pro Pro Arg
465

<210> SEQ ID NO 132
<211> LENGTH: 469
<212> TYPE: PRT
<213> ORGANISM: Artificial Sequence
<220> FEATURE:
<223> OTHER INFORMATION: Chimeric antigen receptor
```

<400> SEQUENCE: 132

```
Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ala Tyr
            20                  25                  30

Asp Tyr Val Ser Trp Tyr Gln His Pro Gly Arg Ala Pro Arg Leu
        35                  40                  45

Ile Ile Arg Asp Val Ser Val Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Gly Ser
                85                  90                  95

Ser Thr Trp Val Phe Gly Gly Gly Thr Lys Leu Thr Val Leu Gly Ser
            100                 105                 110

Thr Ser Gly Ser Gly Lys Pro Gly Ser Gly Glu Gly Ser Thr Lys Gly
            115                 120                 125

Glu Val Gln Leu Leu Glu Ser Gly Gly Gly Leu Val Gln Pro Gly Gly
130                 135                 140

Ser Leu Arg Leu Ser Cys Ala Ala Ser Gly Phe Thr Phe Ser Thr Tyr
145                 150                 155                 160

Gln Met Ser Trp Val Arg Gln Ala Pro Gly Lys Gly Leu Glu Trp Val
            165                 170                 175

Ser Gly Ile Val Ser Ser Gly Gly Ser Thr Ala Tyr Ala Asp Ser Val
            180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
210                 215                 220

Ala Gly Glu Leu Leu Pro Tyr Tyr Gly Met Asp Val Trp Gly Gln Gly
225                 230                 235                 240

Thr Thr Val Thr Val Ser Ser Ala Ala Ala Ile Glu Val Met Tyr Pro
            245                 250                 255

Pro Pro Tyr Leu Asp Asn Glu Lys Ser Asn Gly Thr Ile Ile His Val
            260                 265                 270

Lys Gly Lys His Leu Cys Pro Ser Pro Leu Phe Pro Gly Pro Ser Lys
            275                 280                 285

Pro Phe Trp Val Leu Val Val Val Gly Gly Val Leu Ala Cys Tyr Ser
290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
            325                 330                 335

Gly Pro Thr Arg Lys His Tyr Gln Pro Tyr Ala Pro Pro Arg Asp Phe
            340                 345                 350

Ala Ala Tyr Arg Ser Arg Val Lys Phe Ser Arg Ser Ala Asp Ala Pro
            355                 360                 365

Ala Tyr Gln Gln Gly Gln Asn Gln Leu Tyr Asn Glu Leu Asn Leu Gly
            370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
            405                 410                 415
```

```
Asn Glu Leu Gln Lys Asp Lys Met Ala Glu Ala Tyr Ser Glu Ile Gly
                420                 425                 430

Met Lys Gly Glu Arg Arg Gly Lys Gly His Asp Gly Leu Tyr Gln
            435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 133
<211> LENGTH: 470
<212> TYPE: PRT
<213> ORGANISM: Artificial Sequence
<220> FEATURE:
<223> OTHER INFORMATION: Chimeric antigen receptor

<400> SEQUENCE: 133

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Asp Val Ser Asn Arg Pro Ser Gly Val Ser Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Ala Val Phe Gly Gly Gly Thr Gln Leu Thr Val Leu Gly
            100                 105                 110

Ser Thr Ser Gly Ser Gly Lys Pro Gly Ser Gly Glu Gly Ser Thr Lys
        115                 120                 125

Gly Glu Val Gln Leu Leu Glu Ser Gly Gly Gly Leu Val Gln Pro Gly
    130                 135                 140

Gly Ser Leu Arg Leu Ser Cys Ala Ala Ser Gly Phe Thr Phe Ser Thr
145                 150                 155                 160

Tyr Gln Met Ser Trp Val Arg Gln Ala Pro Gly Lys Gly Leu Glu Trp
                165                 170                 175

Val Ser Gly Ile Val Ser Ser Gly Gly Ser Thr Ala Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Gly Glu Leu Leu Pro Tyr Tyr Gly Met Asp Val Trp Gly Gln
225                 230                 235                 240

Gly Thr Thr Val Thr Val Ser Ser Ala Ala Ile Glu Val Met Tyr
                245                 250                 255

Pro Pro Pro Tyr Leu Asp Asn Glu Lys Ser Asn Gly Thr Ile Ile His
            260                 265                 270

Val Lys Gly Lys His Leu Cys Pro Ser Pro Leu Phe Pro Gly Pro Ser
        275                 280                 285

Lys Pro Phe Trp Val Leu Val Val Val Gly Gly Val Leu Ala Cys Tyr
    290                 295                 300
```

-continued

```
Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
                325                 330                 335

Pro Gly Pro Thr Arg Lys His Tyr Gln Pro Tyr Ala Pro Pro Arg Asp
            340                 345                 350

Phe Ala Ala Tyr Arg Ser Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 134
<211> LENGTH: 468
<212> TYPE: PRT
<213> ORGANISM: Artificial Sequence
<220> FEATURE:
<223> OTHER INFORMATION: Chimeric antigen receptor

<400> SEQUENCE: 134

Gln Ser Ala Leu Pro Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Cys Ser Tyr Ala Gly Gly
                85                  90                  95

Tyr Tyr Val Phe Gly Thr Gly Thr Lys Leu Thr Val Leu Gly Ser Thr
            100                 105                 110

Ser Gly Ser Gly Lys Pro Gly Ser Gly Glu Gly Ser Thr Lys Gly Glu
        115                 120                 125

Val Gln Leu Leu Glu Ser Gly Gly Gly Leu Val Gln Pro Gly Gly Ser
    130                 135                 140

Leu Arg Leu Ser Cys Ala Ala Ser Gly Phe Thr Phe Ser Thr Tyr Gln
145                 150                 155                 160

Met Ser Trp Val Arg Gln Ala Pro Gly Lys Gly Leu Glu Trp Val Ser
                165                 170                 175

Gly Ile Val Ser Ser Gly Gly Ser Thr Ala Tyr Ala Asp Ser Val Lys
            180                 185                 190
```

```
Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
        210                 215                 220

Gly Glu Leu Leu Pro Tyr Tyr Gly Met Asp Val Trp Gly Gln Gly Thr
225                 230                 235                 240

Thr Val Thr Val Ser Ser Ala Ala Ile Glu Val Met Tyr Pro Pro
            245                 250                 255

Pro Tyr Leu Asp Asn Glu Lys Ser Asn Gly Thr Ile Ile His Val Lys
            260                 265                 270

Gly Lys His Leu Cys Pro Ser Pro Leu Phe Pro Gly Pro Ser Lys Pro
            275                 280                 285

Phe Trp Val Leu Val Val Val Gly Gly Val Leu Ala Cys Tyr Ser Leu
            290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
            370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
            450                 455                 460

Leu Pro Pro Arg
465

<210> SEQ ID NO 135
<211> LENGTH: 471
<212> TYPE: PRT
<213> ORGANISM: Artificial Sequence
<220> FEATURE:
<223> OTHER INFORMATION: Chimeric antigen receptor

<400> SEQUENCE: 135

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80
```

Gln Thr Glu Asp Glu Ala Asp Tyr Tyr Cys Ser Ser Tyr Ala Gly Ser
                85                  90                  95

Gly Ser Thr Pro Phe Val Phe Gly Thr Gly Thr Lys Leu Thr Val Leu
            100                 105                 110

Gly Ser Ser Gly Ser Gly Lys Pro Gly Ser Gly Glu Gly Ser Thr
        115                 120                 125

Lys Gly Glu Val Gln Leu Leu Glu Ser Gly Gly Gly Leu Val Gln Pro
130                 135                 140

Gly Gly Ser Leu Arg Leu Ser Cys Ala Ala Ser Gly Phe Thr Phe Ser
145                 150                 155                 160

Thr Tyr Gln Met Ser Trp Val Arg Gln Ala Pro Gly Lys Gly Leu Glu
                165                 170                 175

Trp Val Ser Gly Ile Val Ser Ser Gly Gly Ser Thr Ala Tyr Ala Asp
                180                 185                 190

Ser Val Lys Gly Arg Phe Thr Ile Ser Arg Asp Asn Ser Lys Asn Thr
                195                 200                 205

Leu Tyr Leu Gln Met Asn Ser Leu Arg Ala Glu Asp Thr Ala Val Tyr
        210                 215                 220

Tyr Cys Ala Gly Glu Leu Leu Pro Tyr Tyr Gly Met Asp Val Trp Gly
225                 230                 235                 240

Gln Gly Thr Thr Val Thr Val Ser Ser Ala Ala Ile Glu Val Met
                245                 250                 255

Tyr Pro Pro Pro Tyr Leu Asp Asn Glu Lys Ser Asn Gly Thr Ile Ile
                260                 265                 270

His Val Lys Gly Lys His Leu Cys Pro Ser Pro Leu Phe Pro Gly Pro
                275                 280                 285

Ser Lys Pro Phe Trp Val Leu Val Val Val Gly Gly Val Leu Ala Cys
        290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
                340                 345                 350

Asp Phe Ala Ala Tyr Arg Ser Arg Val Lys Phe Ser Arg Ser Ala Asp
                355                 360                 365

Ala Pro Ala Tyr Gln Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 136
<211> LENGTH: 468

```
<212> TYPE: PRT
<213> ORGANISM: Artificial Sequence
<220> FEATURE:
<223> OTHER INFORMATION: Chimeric antigen receptor

<400> SEQUENCE: 136
```

| | | | | | | | | | | | | | | |
|---|---|---|---|---|---|---|---|---|---|---|---|---|---|---|
| Gln | Ser | Ala | Leu | Thr | Gln | Pro | Ala | Ser | Val | Ser | Gly | Ser | Pro | Gly |  Gln |
| 1 | | | | 5 | | | | | 10 | | | | | 15 |
| Ser | Ile | Thr | Ile | Ser | Cys | Thr | Gly | Thr | Ser | Ser | Asp | Val | Gly | Gly | Tyr |
| | | | 20 | | | | | 25 | | | | | 30 | |
| Asn | Tyr | Val | Ser | Trp | Tyr | Gln | Gln | His | Pro | Gly | Lys | Ala | Pro | Lys | Leu |
| | | | 35 | | | | | 40 | | | | | 45 | |
| Met | Ile | Tyr | Asp | Val | Ser | Asn | Arg | Pro | Ser | Arg | Val | Pro | Asp | Arg | Phe |
| | 50 | | | | | 55 | | | | | 60 | | | | |
| Ala | Gly | Ser | Lys | Ser | Gly | Asn | Thr | Ala | Ser | Leu | Thr | Ile | Ser | Gly | Leu |
| 65 | | | | | 70 | | | | | 75 | | | | | 80 |
| Gln | Ala | Glu | Asp | Glu | Ala | Asp | Tyr | Tyr | Cys | Cys | Ser | Tyr | Ala | Gly | Arg |
| | | | | 85 | | | | | 90 | | | | | 95 | |
| Arg | Tyr | Val | Phe | Gly | Thr | Gly | Thr | Lys | Leu | Thr | Val | Leu | Gly | Ser | Thr |
| | | | | 100 | | | | | 105 | | | | | 110 | |
| Ser | Gly | Ser | Gly | Lys | Pro | Gly | Ser | Gly | Glu | Gly | Ser | Thr | Lys | Gly | Glu |
| | | | | 115 | | | | | 120 | | | | | 125 | |
| Val | Gln | Leu | Leu | Glu | Ser | Gly | Gly | Gly | Leu | Val | Gln | Pro | Gly | Gly | Ser |
| | 130 | | | | | 135 | | | | | 140 | | | | |
| Leu | Arg | Leu | Ser | Cys | Ala | Ala | Ser | Gly | Phe | Thr | Phe | Ser | Thr | Tyr | Gln |
| 145 | | | | | 150 | | | | | 155 | | | | | 160 |
| Met | Ser | Trp | Val | Arg | Gln | Ala | Pro | Gly | Lys | Gly | Leu | Glu | Trp | Val | Ser |
| | | | | 165 | | | | | 170 | | | | | 175 | |
| Gly | Ile | Val | Ser | Ser | Gly | Gly | Ser | Thr | Ala | Tyr | Ala | Asp | Ser | Val | Lys |
| | | | | 180 | | | | | 185 | | | | | 190 | |
| Gly | Arg | Phe | Thr | Ile | Ser | Arg | Asp | Asn | Ser | Lys | Asn | Thr | Leu | Tyr | Leu |
| | | | | 195 | | | | | 200 | | | | | 205 | |
| Gln | Met | Asn | Ser | Leu | Arg | Ala | Glu | Asp | Thr | Ala | Val | Tyr | Tyr | Cys | Ala |
| | 210 | | | | | 215 | | | | | 220 | | | | |
| Gly | Glu | Leu | Leu | Pro | Tyr | Tyr | Gly | Met | Asp | Val | Trp | Gly | Gln | Gly | Thr |
| 225 | | | | | 230 | | | | | 235 | | | | | 240 |
| Thr | Val | Thr | Val | Ser | Ser | Ala | Ala | Ala | Ile | Glu | Val | Met | Tyr | Pro | Pro |
| | | | | 245 | | | | | 250 | | | | | 255 | |
| Pro | Tyr | Leu | Asp | Asn | Glu | Lys | Ser | Asn | Gly | Thr | Ile | Ile | His | Val | Lys |
| | | | | 260 | | | | | 265 | | | | | 270 | |
| Gly | Lys | His | Leu | Cys | Pro | Ser | Pro | Leu | Phe | Pro | Gly | Pro | Ser | Lys | Pro |
| | | | | 275 | | | | | 280 | | | | | 285 | |
| Phe | Trp | Val | Leu | Val | Val | Val | Gly | Gly | Val | Leu | Ala | Cys | Tyr | Ser | Leu |
| | 290 | | | | | 295 | | | | | 300 | | | | |
| Leu | Val | Thr | Val | Ala | Phe | Ile | Ile | Phe | Trp | Val | Arg | Ser | Lys | Arg | Ser |
| 305 | | | | | 310 | | | | | 315 | | | | | 320 |
| Arg | Leu | Leu | His | Ser | Asp | Tyr | Met | Asn | Met | Thr | Pro | Arg | Arg | Pro | Gly |
| | | | | 325 | | | | | 330 | | | | | 335 | |
| Pro | Thr | Arg | Lys | His | Tyr | Gln | Pro | Tyr | Ala | Pro | Pro | Arg | Asp | Phe | Ala |
| | | | | 340 | | | | | 345 | | | | | 350 | |
| Ala | Tyr | Arg | Ser | Arg | Val | Lys | Phe | Ser | Arg | Ser | Ala | Asp | Ala | Pro | Ala |
| | | | | 355 | | | | | 360 | | | | | 365 | |
| Tyr | Gln | Gln | Gly | Gln | Asn | Gln | Leu | Tyr | Asn | Glu | Leu | Asn | Leu | Gly | Arg |
| | 370 | | | | | 375 | | | | | 380 | | | | |

-continued

```
Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
        420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
        450                 455                 460

Leu Pro Pro Arg
465

<210> SEQ ID NO 137
<211> LENGTH: 467
<212> TYPE: PRT
<213> ORGANISM: Artificial Sequence
<220> FEATURE:
<223> OTHER INFORMATION: Chimeric antigen receptor

<400> SEQUENCE: 137

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Cys Pro Ile Tyr Tyr Tyr Gly Met Asp Val Trp Gly Gln Gly Thr
        100                 105                 110

Thr Val Thr Val Ser Ser Gly Ser Thr Gly Ser Gly Lys Pro Gly
        115                 120                 125

Ser Gly Glu Gly Ser Thr Lys Gly Gln Ser Glu Leu Thr Gln Pro Arg
    130                 135                 140

Ser Val Ser Gly Ser Pro Gly Gln Ser Val Thr Ile Ser Cys Thr Gly
145                 150                 155                 160

Thr Ser Arg Asp Val Gly Gly Tyr Asn Tyr Val Ser Trp Tyr Gln Gln
                165                 170                 175

His Pro Gly Lys Ala Pro Lys Leu Ile Ile His Asp Val Ile Glu Arg
            180                 185                 190

Ser Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Trp Ser Phe Ala Gly Ser Tyr Tyr Val Phe Gly Thr Gly Thr
225                 230                 235                 240

Asp Val Thr Val Leu Ala Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270
```

```
Lys His Leu Cys Pro Ser Pro Leu Phe Pro Gly Pro Ser Lys Pro Phe
            275                 280                 285
Trp Val Leu Val Val Val Gly Gly Val Leu Ala Cys Tyr Ser Leu Leu
        290                 295                 300
Val Thr Val Ala Phe Ile Ile Phe Trp Val Arg Ser Lys Arg Ser Arg
305                 310                 315                 320
Leu Leu His Ser Asp Tyr Met Asn Met Thr Pro Arg Arg Pro Gly Pro
                325                 330                 335
Thr Arg Lys His Tyr Gln Pro Tyr Ala Pro Pro Arg Asp Phe Ala Ala
            340                 345                 350
Tyr Arg Ser Arg Val Lys Phe Ser Arg Ser Ala Asp Ala Pro Ala Tyr
        355                 360                 365
Gln Gln Gly Gln Asn Gln Leu Tyr Asn Glu Leu Asn Leu Gly Arg Arg
    370                 375                 380
Glu Glu Tyr Asp Val Leu Asp Lys Arg Arg Gly Arg Asp Pro Glu Met
385                 390                 395                 400
Gly Gly Lys Pro Arg Arg Lys Asn Pro Gln Glu Gly Leu Tyr Asn Glu
                405                 410                 415
Leu Gln Lys Asp Lys Met Ala Glu Ala Tyr Ser Glu Ile Gly Met Lys
            420                 425                 430
Gly Glu Arg Arg Arg Gly Lys Gly His Asp Gly Leu Tyr Gln Gly Leu
        435                 440                 445
Ser Thr Ala Thr Lys Asp Thr Tyr Asp Ala Leu His Met Gln Ala Leu
    450                 455                 460
Pro Pro Arg
465

<210> SEQ ID NO 138
<211> LENGTH: 1401
<212> TYPE: DNA
<213> ORGANISM: Artificial Sequence
<220> FEATURE:
<223> OTHER INFORMATION: nucleotide of Chimeric antigen receptor

<400> SEQUENCE: 138
caggtgcagc tgcaggagtc gggcccagga ctggtgaagc cttcggatac cctgtccctc      60
acctgtcttg tctctggtgg ctccatcagt agtaattact ggagctggat ccggcaggcc     120
ccagggaagg gactggagtg gattggacat gtctcctaca gtgggagcac caactacaac     180
ccctccctca gagtcgagt accatatca gtagacacgt ctaagaacca gttctccctg      240
aagctgagct ctgtgactgc cgcggacacg gccgtgtatt actgtgcgag agagtcctac     300
tactactacg gtatggacgt ctggggccaa gggaccacgg tcaccgtctc ctcaggctct     360
acaagcggct ctggcaagcc tggatctggc gagggaagca ccaagggcca gagcgagctg     420
acacagccta gatccgtgtc tggcagccct ggccagagcg tgaccatcag ctgtaccggc     480
accagcagag atgtgggcgg ctacaactac gtgtcctggt atcagcagca tcccggcaag     540 gccccccaagc tgatcatcca cgacgtgatc gagcggagca gcggcgtgcc cgatagattc     600
agcggcagca gagcggcaa caccgccagc ctgacaatca gcggactgca ggccgaggac     660
gaggccgact actactgttg agcttcgcc ggcagctact acgtgttcgg caccggcacc     720
gatgtgaccg tgctggcggc cgcaatcgaa gtgatgtacc ccctccccta cctggacaac     780
gagaagtcca acggcaccat tatccacgtg aagggaaagc acctgtgccc cagccctctg     840
ttccctggcc ctagcaagcc tttctgggtg ctggtggtcg tgggcggagt gctggcctgt     900
```

| | |
|---|---:|
| tatagcctgc tcgtgaccgt ggccttcatc atctttttggg tgcgcagcaa gcggagccgg | 960 |
| ctgctgcaca gcgactacat gaacatgacc cccagacggc ccggacccac cagaaagcac | 1020 |
| taccagcctt acgcccctcc cagagacttc gccgcctaca gatctcgagt gaagttcagc | 1080 |
| agaagcgccg acgcccctgc ctatcagcag ggccagaacc agctgtacaa cgagctgaac | 1140 |
| ctgggcagac gggaagagta cgacgtgctg gacaagcgga gaggcaggga ccctgagatg | 1200 |
| ggcggcaagc ccagaagaaa gaaccccag gaaggcctgt ataacgaact gcagaaagac | 1260 |
| aagatggccg aggcctacag cgagatcggc atgaagggcg agcggagaag aggcaagggc | 1320 |
| cacgatggcc tgtaccaggg cctgagcacc gccaccaagg acacctatga cgccctgcac | 1380 |
| atgcaggccc tgccccccag a | 1401 |

<210> SEQ ID NO 139
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 139

| | |
|---|---:|
| gacatccaga tgacccagtc tccatctgcc atgtctgcat ctgtaggaga cagagtcacc | 60 |
| atcacttgcc gggcaagtca gagcattagc agctatttaa attggtatca gcagaaacca | 120 |
| gggaaagccc ctaagctcct gatctatgct gcatccagtt tgcaaagtgg ggtcccatca | 180 |
| aggttcagtg gcagtggatc tgggacagat ttcactctca ccatcagcag tctgcagcct | 240 |
| gaagattttg caacttacta ttgtcagcaa tattatagta ctcctcaaac tttcggccct | 300 |
| gggaccaaag tggatatcaa aggctctaca gcggctctg gcaagcctgg atctggcgag | 360 |
| ggaagcacca agggccaggt gcagctgcag gagtcgggcc caggactggt gaagccttcg | 420 |
| gataccctgt ccctcacctg tcttgtctct ggtggctcca tcagtagtaa ttactggagc | 480 |
| tggatccggc aggccccagg gaagggactg gagtggattg gacatgtctc ctacagtggg | 540 |
| agcaccaact acaacccctc cctcaagagt cgagttacca tatcagtaga cacgtctaag | 600 |
| aaccagttct ccctgaagct gagctctgtg actgccgcgg acacggccgt gtattactgt | 660 |
| gcgagagagt cctactacta ctacggtatg gacgtctggg gccaagggac cacggtcacc | 720 |
| gtctcctcag cggccgcaat cgaagtgatg taccccctc cctacctgga caacgagaag | 780 |
| tccaacggca ccattatcca cgtgaaggga aagcacctgt gccccagccc tctgttccct | 840 |
| ggccctagca gccttttctg ggtgctggtg gtcgtgggcg gagtgctggc ctgttatagc | 900 |
| ctgctcgtga ccgtggcctt catcatcttt tgggtgcgca gcaagcggag ccggctgctg | 960 |
| cacagcgact acatgaacat gaccccccaga cggcccggac ccaccagaaa gcactaccag | 1020 |
| ccttacgccc ctcccagaga cttcgccgcc tacagatctc gagtgaagtt cagcagaagc | 1080 |
| gccgacgccc ctgcctatca gcagggccag aaccagctgt acaacgagct gaacctgggc | 1140 |
| agacgggaag agtacgacgt gctggacaag cggagaggca gggaccctga gatgggcggc | 1200 |
| aagcccagaa gaaagaaccc ccaggaaggc ctgtataacg aactgcagaa agacaagatg | 1260 |
| gccgaggcct acagcgagat cggcatgaag ggcgagcgga agaggcaa gggccacgat | 1320 |
| ggcctgtacc agggcctgag caccgccacc aaggacacct atgacgccct gcacatgcag | 1380 |
| gccctgcccc ccaga | 1395 |

<210> SEQ ID NO 140
<211> LENGTH: 1395

```
<212> TYPE: DNA
<213> ORGANISM: Artificial Sequence
<220> FEATURE:
<223> OTHER INFORMATION: nucleotide of Chimeric antigen receptor

<400> SEQUENCE: 140
gacatccaga tgacccagtc tccatcctcc ctgtctgcat ctgtaggaga cagagtcacc      60
atcacttgcc gggcaagtca gagcattagc agctatttaa attggtatca gcagaaagca    120
gggaaagccc ctaagcttct gatctatgct gcatccagtt tgcaaagtgg ggtcccatca    180
aggttcagcg gcagtggatc tgggacagat ttcactctca ccatcagctg cctgcagtct    240
gaagatgttg caacctatta ctgccaacag tatgaaagtt atcgaaggtc gttcggccaa    300
gggaccaagg tggaaatcaa aggctctaca agcggctctg gcaagcctgg atctggcgag    360
ggaagcacca agggccaggt gcagctgcag gagtcgggcc caggactggt gaagccttcg    420
gataccctgt ccctcacctg tcttgtctct ggtggctcca tcagtagtaa ttactggagc    480
tggatccggc aggccccagg aagggactg gagtggattg acatgtctc ctacagtggg    540
agcaccaact acaacccctc cctcaagagt cgagttacca tatcagtaga cacgtctaag    600
aaccagttct ccctgaagct gagctctgtg actgccgcgg acacggccgt gtattactgt    660
gcgagagagt cctactacta ctacggtatg gacgtctggg gccaagggac cacggtcacc    720
gtctcctcag cggccgcaat cgaagtgatg taccccctc cctacctgga caacgagaag    780
tccaacggca ccattatcca cgtgaaggga agcacctgt gccccagccc tctgttccct    840
ggccctagca gccttttctg gtgctggtg gtcgtgggcg gagtgctggc ctgttatagc    900
ctgctcgtga ccgtggcctt catcatcttt tgggtgcgca gcaagcggag ccggctgctg    960
cacagcgact acatgaacat gaccccccaga cggcccggac ccaccagaaa gcactaccag   1020
ccttacgccc ctcccagaga cttcgccgcc tacagatctc gagtgaagtt cagcagaagc   1080
gccgacgccc ctgcctatca gcagggccag aaccagctgt acaacgagct gaacctgggc   1140
agacgggaag agtacgacgt gctggacaag cggagaggca gggaccctga gatgggcggc   1200
aagcccagaa gaaagaaccc ccaggaaggc ctgtataacg aactgcagaa agacaagatg   1260
gccgaggcct acagcgagat cggcatgaag ggcgagcgga agagggcaa gggccacgat   1320
ggcctgtacc agggcctgag caccgccacc aaggacacct atgacgccct gcacatgcag   1380
gccctgcccc ccaga                                                     1395

<210> SEQ ID NO 141
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 141
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagctg cctgcagtct    240
gaagattttg caacttatta ctgccaacag tataatagtt attcccggac gttcggccaa    300
gggaccaagg tggaaatcaa aggctctaca agcggctctg gcaagcctgg atctggcgag    360
ggaagcacca agggccaggt gcagctgcag gagtcgggcc caggactggt gaagccttcg    420
```

```
gataccctgt ccctcacctg tcttgtctct ggtggctcca tcagtagtaa ttactggagc      480
tggatccggc aggccccagg gaagggactg gagtggattg acatgtctc ctacagtggg       540 agcaccaact acaacccctc cctcaagagt cgagttacca tatcagtaga cacgtctaag      600
aaccagttct ccctgaagct gagctctgtg actgccgcgg acacggccgt gtattactgt      660
gcgagagagt cctactacta ctacggtatg gacgtctggg gccaagggac cacggtcacc      720
gtctcctcag cggccgcaat cgaagtgatg taccccccctc cctacctgga caacgagaag    780
tccaacggca ccattatcca cgtgaaggga aagcacctgt gccccagccc tctgttccct     840
ggccctagca agccttcctg gtgctggtg gtcgtgggcg gagtgctggc ctgttatagc      900
ctgctcgtga ccgtggcctt catcatcttt tgggtgcgca gcaagcggag ccggctgctg     960
cacagcgact acatgaacat gacccccaga cggcccggac ccaccagaaa gcactaccag    1020
ccttacgccc ctcccagaga cttcgccgcc tacagatctc gagtgaagtt cagcagaagc     1080
gccgacgccc ctgcctatca gcagggccag aaccagctgt acaacgagct gaacctgggc    1140
agacgggaag agtacgacgt gctggacaag cggagaggcc gggaccctga gatgggcggc    1200
aagcccagaa gaagaaccc caggaaggc ctgtataacg aactgcagaa agacaagatg      1260
gccgaggcct acagcgagat cggcatgaag ggcgagcgga agagggcaa gggccacgat    1320 ggcctgtacc agggcctgag caccgccacc aaggacacct atgacgccct gcacatgcag    1380
gccctgcccc ccaga                                                      1395

<210> SEQ ID NO 142
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 142
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagat tggaaagtgg ggtcccatca    180
aggttcagtg gcagtggatc tgggacagat ttcactctca ccatcagctg cctgcagtct    240
gaagattttg caacttatta ctgccaacag tataatagtt attcccggac gttcggccaa    300
gggaccaagg tggaaatcaa aggctctaca agcggctctg gcaagcctgg atctggcgag    360
ggaagcacca agggccaggt gcagctgcag gagtcgggcc caggactggt gaagccttcg    420
gataccctgt ccctcacctg tcttgtctct ggtggctcca tcagtagtaa ttactggagc     480
tggatccggc aggccccagg gaagggactg gagtggattg acatgtctc ctacagtggg      540 agcaccaact acaacccctc cctcaagagt cgagttacca tatcagtaga cacgtctaag     600
aaccagttct ccctgaagct gagctctgtg actgccgcgg acacggccgt gtattactgt     660
gcgagagagt cctactacta ctacggtatg gacgtctggg gccaagggac cacggtcacc     720
gtctcctcag cggccgcaat cgaagtgatg taccccccctc cctacctgga caacgagaag   780
tccaacggca ccattatcca cgtgaaggga aagcacctgt gccccagccc tctgttccct    840
ggccctagca agccttcctg gtgctggtg gtcgtgggcg gagtgctggc ctgttatagc     900
ctgctcgtga ccgtggcctt catcatcttt tgggtgcgca gcaagcggag ccggctgctg    960
cacagcgact acatgaacat gacccccaga cggcccggac ccaccagaaa gcactaccag   1020
ccttacgccc ctcccagaga cttcgccgcc tacagatctc gagtgaagtt cagcagaagc    1080
```

```
gccgacgccc ctgcctatca gcagggccag aaccagctgt acaacgagct gaacctgggc    1140
agacgggaag agtacgacgt gctggacaag cggagaggca gggaccctga gatgggcggc    1200
aagcccagaa gaaagaaccc ccaggaaggc ctgtataacg aactgcagaa agacaagatg    1260
gccgaggcct acagcgagat cggcatgaag ggcgagcgga agaggcaa gggccacgat    1320 ggcctgtacc agggcctgag caccgccacc aaggacacct atgacgccct gcacatgcag    1380
gccctgcccc ccaga    1395

<210> SEQ ID NO 143
<211> LENGTH: 1398
<212> TYPE: DNA
<213> ORGANISM: Artificial Sequence
<220> FEATURE:
<223> OTHER INFORMATION: nucleotide of Chimeric antigen receptor

<400> SEQUENCE: 143
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gctctatgct gcatccagat tggaaagtgg ggtcccatca    180
aggttcagcg gcagtggatc tgggacagaa ttcactctca ccatcagcag cctgcagcct    240
gatgattttg caacttatta ctgccaacag tataatagtt attctccgtg cactttcggc    300
cctgggacca agtggatat caaaggctct acaagcggct ctggcaagcc tggatctggc    360
gagggaagca ccaagggcca ggtgcagctg caggagtcgg gcccaggact ggtgaagcct    420
tcggatatcc tgtccctcac ctgtcttgtc tctggtggct ccatcagtag taattactgg    480
agctggatcc ggcaggcccc agggaaggga ctggagtgga ttggacatgt ctcctacagt    540
gggagcacca actacaaccc ctccctcaag agtcgagtta ccatatcagt agacacgtct    600
aagaaccagt tctccctgaa gctgagctct gtgactgccg cggacacggc cgtgtattac    660
tgtgcgagag agtcctacta ctactacggt atggacgtct ggggccaagg gaccacggtc    720
accgtctcct cagcggccgc aatcgaagtg atgtaccccc ctccctacct ggacaacgag    780
aagtccaacg gcaccattat ccacgtgaag ggaaagcacc tgtgccccag ccctctgttc    840
cctggcccta gcaagccttt ctgggtgctg gtggtcgtgg cggagtgct ggcctgttat    900 agcctgctcg tgaccgtggc cttcatcatc ttttgggtgc gcagcaagcg gagccggctg    960
ctgcacagcg actacatgaa catgacccccc agacggcccg acccaccag aaagcactac    1020 cagccttacg ccctcccag agacttcgcc gcctacagat ctcgagtgaa gttcagcaga    1080
agcgccgacg cccctgccta tcagcagggc cagaaccagc tgtacaacga gctgaacctg    1140
ggcagacggg aagagtacga cgtgctggac aagcggagag gcagggaccc tgagatgggc    1200
ggcaagccca gaagaaagaa ccccaggaa ggcctgtata cgaactgca gaaagacaag    1260 atggccgagg cctacagcga gatcggcatg aagggcgagc ggaagaggag caagggccac    1320
gatggcctgt accagggcct gagcaccgcc accaaggaca cctatgacgc cctgcacatg    1380
caggccctgc ccccaga    1398

<210> SEQ ID NO 144
<211> LENGTH: 1392
<212> TYPE: DNA
<213> ORGANISM: Artificial Sequence
<220> FEATURE:
<223> OTHER INFORMATION: nucleotide of Chimeric antigen receptor
```

<400> SEQUENCE: 144

```
gacatccaga tgacccagtc tccatcctcc ctgtctgcat ctgtagggga cagagtctcc    60
atcacttgcc gggcaagtca ggacattagc aggtatttaa attggtatca gcagaaacca   120
gggaaagccc ctaagctcct gctctatgct gcatccagat tggaaagtgg ggtcccatcc   180
aggttcagtg gcagtggatc tgggacagac ttcactctca ccatcaccag cctgcagcct   240
gatgactttg caacttatta ctgccaacag tatgataatc tgatcacctt cggccaaggg   300
acacgactgg agattaaagg ctctacaagc ggctctggca agcctggatc tggcgaggga   360
agcaccaagg ccaggtgca gctgcaggag tcgggcccag gactggtgaa gccttcggat   420
accctgtccc tcacctgtct tgtctctggt ggctccatca gtagtaatta ctggagctgg   480
atccggcagg ccccagggaa gggactggag tggattggac atgtctccta cagtgggagc   540
accaactaca accctccct caagagtcga gttaccatat cagtagacac gtctaagaac   600
cagttctccc tgaagctgag ctctgtgact gccgcggaca cggccgtgta ttactgtgcg   660
agagagtcct actactacta cggtatggac gtctggggcc aagggaccac ggtcaccgtc   720
tcctcagcgg ccgcaatcga agtgatgtac ccccctccct acctggacaa cgagaagtcc   780
aacggcacca ttatccacgt gaagggaaag cacctgtgcc ccagccctct gttccctggc   840
cctagcaagc ctttctgggt gctggtggtc gtgggcggag tgctggcctg ttatagcctg   900
ctcgtgaccg tggccttcat catcttttgg gtgcgcagca gcggagccg gctgctgcac   960
agcgactaca tgaacatgac ccccagacgg cccggaccca ccagaaagca ctaccagcct  1020
tacgcccctc ccagagactt cgccgcctac agatctcgag tgaagttcag cagaagcgcc  1080
gacgcccctg cctatcagca gggccagaac cagctgtaca acgagctgaa cctgggcaga  1140
cgggaagagt acgacgtgct ggacaagcgg agaggcaggg accctgagat gggcggcaag  1200
cccagaagaa agaaccccca ggaaggcctg tataacgaac tgcagaaaga caagatggcc  1260
gaggcctaca gcgagatcgg catgaagggc gagcggagaa gaggcaaggg ccacgatggc  1320
ctgtaccagg gcctgagcac cgccaccaag gacacctatg acgccctgca catgcaggcc  1380
ctgccccca ga                                                      1392
```

<210> SEQ ID NO 145
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 145

```
gacatccaga tgacccagtc tccatcctcc ctgtctgcat ctgtagggga cagagtctcc    60
atcacttgcc gggcaagtca ggacattagc aggtatttaa attggtatca gcagaaacca   120
gggaaagccc ctaagctcct gctctatgct gcatccagat tggaaagtgg ggtcccatcc   180
aggttcagtg gcagtggatc tgggacagac ttcactctca ccatcaccag cctgcagcct   240
gatgactttg caacttatta ctgccaacag tataatagtt attcccggac gttcggccaa   300
gggaccaagg tggaaatcaa aggctctaca agcggctctg gcaagcctgg atctggcgag   360
ggaagcacca agggccaggt gcagctgcag gagtcgggcc caggactggt gaagccttcg   420
gataccctgt ccctcacctg tcttgtctct ggtggctcca tcagtagtaa ttactggagc   480
tggatccggc aggccccagg gaagggactg gagtggattg acatgtctc ctacagtggg   540
agcaccaact acaacccctc cctcaagagt cgagttacca tatcagtaga cacgtctaag   600
```

```
aaccagttct ccctgaagct gagctctgtg actgccgcgg acacggccgt gtattactgt      660
gcgagagagt cctactacta ctacggtatg gacgtctggg gccaagggac cacggtcacc      720
gtctcctcag cggccgcaat cgaagtgatg tacccccctc cctacctgga caacgagaag      780
tccaacggca ccattatcca cgtgaaggga agcacctgt gccccagccc tctgttccct       840
ggccctagca agcctttctg ggtgctggtg gtcgtgggcg gagtgctggc ctgttatagc      900
ctgctcgtga ccgtggcctt catcatcttt tgggtgcgca gcaagcggag ccggctgctg      960
cacagcgact acatgaacat gacccccaga cggcccggac ccaccagaaa gcactaccag     1020
ccttacgccc tcccagaga cttcgccgcc tacagatctc gagtgaagtt cagcagaagc       1080
gccgacgccc ctgcctatca gcagggccag aaccagctgt acaacgagct gaacctgggc     1140
agacgggaag agtacgacgt gctggacaag cggagaggca gggaccctga gatgggcggc     1200
aagcccagaa gaaagaaccc ccaggaaggc ctgtataacg aactgcagaa agacaagatg     1260
gccgaggcct acagcgagat cggcatgaag ggcgagcgga agaggcaa gggccacgat       1320 ggcctgtacc agggcctgag caccgccacc aaggacacct atgacgccct gcacatgcag     1380
gccctgcccc ccaga                                                     1395

<210> SEQ ID NO 146
<211> LENGTH: 1392
<212> TYPE: DNA
<213> ORGANISM: Artificial Sequence
<220> FEATURE:
<223> OTHER INFORMATION: nucleotide of Chimeric antigen receptor

<400> SEQUENCE: 146
gacatccaga tgacccagtc tccatcctcc ctgtctgcat ctgtaggga cagagtcacc        60 atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagac ttcactctca ccatcaccag cctgcagcct     240
gatgactttg caacttatta ctgccaacag tatgataatc tgatcacctt cggccaaggg     300
acacgactgg agattaaagg ctctacaagc ggctctggca gcctggatc tggcgaggga     360 agcaccaagg gccaggtgca gctgcaggag tcgggcccag gactggtgaa gccttcggat     420
accctgtccc tcacctgtct tgtctctggt ggctccatca gtagtaatta ctggagctgg     480
atccggcagg ccccagggaa gggactggag tggattggac atgtctccta cagtgggagc     540
accaactaca acccctccct caagagtcga gttaccatat cagtagacac gtctaagaac     600
cagttctccc tgaagctgag ctctgtgact gccgcggaca cggccgtgta ttactgtgcg     660
agagagtcct actactacta cggtatggac gtctggggcc aagggaccac ggtcaccgtc     720
tcctcagcgg ccgcaatcga agtgatgtac ccccctccct acctggacaa cgagaagtcc     780
aacggcacca ttatccacgt gaagggaaag cacctgtgcc ccagccctct gttcctggc      840 cctagcaagc ctttctgggt gctggtggtc gtgggcggag tgctggcctg ttatagcctg     900
ctcgtgaccg tggccttcat catcttttgg gtgcgcagca agcggagccg gctgctgcac     960
agcgactaca tgaacatgac ccccagacgg cccggaccca gaaagca ctaccagcct       1020 tacgcccctc ccagagactt cgccgcctac agatctcgag tgaagttcag cagaagcgcc    1080
gacgcccctg cctatcagca gggccagaac cagctgtaca acgagctgaa cctgggcaga    1140
cgggaagagt acgacgtgct ggacaagcgg agaggcaggg accctgagat gggcggcaag    1200
```

| | |
|---|---|
| cccagaagaa agaaccccca ggaaggcctg tataacgaac tgcagaaaga caagatggcc | 1260 |
| gaggcctaca gcgagatcgg catgaagggc gagcggagaa gaggcaaggg ccacgatggc | 1320 |
| ctgtaccagg gcctgagcac cgccaccaag gacacctatg acgccctgca catgcaggcc | 1380 |
| ctgcccccca ga | 1392 |

<210> SEQ ID NO 147
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 147

| | |
|---|---|
| gaaattgtgt tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag actggagcct | 240 |
| gaagattttg caacctatta ctgccaacag tataatagtt attcccggac gttcggccaa | 300 |
| gggaccaagg tggaaatcaa aggctctaca gcggctctg gcaagcctgg atctggcgag | 360 |
| ggaagcacca agggccaggt gcagctgcag gagtcgggcc caggactggt gaagccttcg | 420 |
| gatacccctgt ccctcacctg tcttgtctct ggtggctcca tcagtagtaa ttactggagc | 480 |
| tggatccggc aggccccagg aagggactg gagtggattg acatgtctc ctacagtggg | 540 |
| agcaccaact acaaccctc cctcaagagt cgagttacca tatcagtaga cacgtctaag | 600 |
| aaccagttct ccctgaagct gagctctgtg actgccgcgg acacggccgt gtattactgt | 660 |
| gcgagagagt cctactacta ctacggtatg gacgtctggg gccaagggac cacggtcacc | 720 |
| gtctcctcag cggccgcaat cgaagtgatg tacccccctc cctacctgga caacgagaag | 780 |
| tccaacggca ccattatcca cgtgaaggga agcacctgt gccccagccc tctgttccct | 840 |
| ggccctagca agccttctg ggtgctggtg gtcgtgggcg gagtgctggc ctgttatagc | 900 |
| ctgctcgtga ccgtggcctt catcatcttt tgggtgcgca gcaagcggag ccggctgctg | 960 |
| cacagcgact acatgaacat gaccccagga cggcccggac ccaccagaaa gcactaccag | 1020 |
| ccttacgccc ctcccagaga cttcgccgcc tacagatctc gagtgaagtt cagcagaagc | 1080 |
| gccgacgccc ctgcctatca gcagggccag aaccagctgt acaacgagct gaacctgggc | 1140 |
| agacgggaag agtacgacgt gctggacaag cggagaggca gggaccctga tggggcggc | 1200 |
| aagcccagaa gaaagaaccc ccaggaaggc ctgtataacg aactgcagaa agacaagatg | 1260 |
| gccgaggcct acagcgagat cggcatgaag ggcgagcgga agaggcaa gggccacgat | 1320 |
| ggcctgtacc agggcctgag caccgccacc aaggacacct atgacgccct gcacatgcag | 1380 |
| gccctgcccc ccaga | 1395 |

<210> SEQ ID NO 148
<211> LENGTH: 1395
<212> TYPE: DNA
<213> ORGANISM: Artificial Sequence
<220> FEATURE:
<223> OTHER INFORMATION: nucleotide of Chimeric antigen receptor

<400> SEQUENCE: 148

| | |
|---|---|
| gacatccaga tgacccagtc tccatcctcc ctgtctgcat ctgtaggaga cagagtcacc | 60 |
| atcacttgcc gggcaagtca gagcattagc agctatttaa attggtatca gcagaaagca | 120 |

```
gggaaagccc ctaagcttct gatctatgct gcatccagtt tgcaaagtgg ggtcccatca      180
aggttcagcg gcagtggatc tgggacagat ttcactctca ccatcagctg cctgcagtct      240
gaagatgttg caacctatta ctgccaacag tatgaaagtt attcccggac gttcggccaa      300
gggaccaagg tggaaatcaa aggctctaca agcggctctg gcaagcctgg atctggcgag      360
ggaagcacca agggccaggt gcagctgcag gagtcgggcc caggactggt gaagccttcg      420
gatacgctgt ccctcacctg tcttgtctct ggtggctcca tcagtagtaa ttactggagc      480
tggatccggc aggccccagg aagggactg gagtggattg acatgtctc ctacagtggg       540 agcaccaact acaaccctc cctcaagagt cgagttacca tatcagtaga cacgtctaag      600
aaccagttct ccctgaagct gagctctgtg actgccgcgg acacggccgt gtattactgt      660
gcgagagagt cctactacta ctacggtatg acgtctggg gccaagggac cacggtcacc      720
gtctcctcag cggccgcaat cgaagtgatg taccccctc cctacctgga caacgagaag      780
tccaacggca ccattatcca cgtgaaggga aagcacctgt gccccagccc tctgttccct      840
ggccctagca agcctttctg ggtgctggtg gtcgtgggcg gagtgctggc ctgttatagc      900
ctgctcgtga ccgtggcctt catcatcttt ggggtgcgca gcaagcggag ccggctgctg      960
cacagcgact acatgaacat gacccccaga cggcccggac ccaccagaaa gcactaccag     1020
ccttacgccc ctccagaga cttcgccgcc tacagatctc gagtgaagtt cagcagaagc      1080
gccgacgccc ctgcctatca gcagggccag aaccagctgt acaacgagct gaacctgggc     1140
agacgggaag agtacgacgt gctggacaag cggagaggca gggacctga tgggcggc       1200 aagcccagaa gaaagaaccc ccaggaaggc ctgtataacg aactgcagaa agacaagatg     1260
gccgaggcct acagcgagat cggcatgaag ggcgagcgga agagcgcaa gggccacgat     1320 ggcctgtacc agggcctgag caccgccacc aaggacacct atgacgccct gcacatgcag     1380
gccctgcccc ccaga                                                      1395
```

<210> SEQ ID NO 149
<211> LENGTH: 1404
<212> TYPE: DNA
<213> ORGANISM: Artificial Sequence
<220> FEATURE:
<223> OTHER INFORMATION: nucleotide of Chimeric antigen receptor

<400> SEQUENCE: 149

```
cagtctgccc tgactcagcc tccctccgcg tccgggtctc ctggacagtc agtcaccatc       60
tcctgcactg gaaccagcag tgacgttggt ggttatgact ttgtctcctg gtaccaacag      120
cacccaggcg aagcccccaa actcctcgtt tatgatgtca ataaccggcc ctcaggggtt      180
tctaatcgct tctctggctc caagtctggc aacacggcct cctgaccat ctctgggctc       240 caggctgagg acgagggtga ctattactgc agctcatatg caggcagcaa cagcgtcttc     300
ggaactggga ccaaggtcac cgtcctaggc tctacaagcg gctctggcaa gcctggatct     360
ggcgagggaa gcaccaaggg cgaagtgcag ctgctggaat ctggcggcgg actggtgcag    420
cctggcggat ctctgagact gagctgtgcc gccagcggct tcaccttcag cacctaccag    480
atgagctggg tgcgccaggc ccctggcaaa ggactgaat gggtgtccgg catcgtgtcc     540
agcggcggct ctacagccta cgccgatagc gtgaagggcc ggttcaccat cagccgggac    600
aacagcaaga cacccctgta cctgcagatg aacagcctga gagccgagga caccgccgtg    660
tactattgtg ccggggagct gctgccctac acggcatgg atgtgtgggg ccagggcacc    720
```

| | |
|---|---:|
| accgtgacag tgtcctcagc ggccgcaatc gaagtgatgt accccctcc ctacctggac | 780 |
| aacgagaagt ccaacggcac cattatccac gtgaagggaa agcacctgtg ccccagccct | 840 |
| ctgttccctg gccctagcaa gccttctgg gtgctggtgg tcgtgggcgg agtgctggcc | 900 |
| tgttatagcc tgctcgtgac cgtggccttc atcatctttt gggtgcgcag caagcggagc | 960 |
| cggctgctgc acagcgacta catgaacatg accccccagac ggcccggacc caccagaaag | 1020 |
| cactaccagc cttacgcccc tcccagagac ttcgccgcct acagatctcg agtgaagttc | 1080 |
| agcagaagcg ccgacgcccc tgcctatcag cagggccaga accagctgta caacgagctg | 1140 |
| aacctgggca gacgggaaga gtacgacgtg ctggacaagc ggagaggcag ggaccctgag | 1200 |
| atgggcggca agcccagaag aaagaacccc caggaaggcc tgtataacga actgcagaaa | 1260 |
| gacaagatgg ccgaggccta cagcgagatc ggcatgaagg cgagcggag aagaggcaag | 1320 |
| ggccacgatg gcctgtacca gggcctgagc accgccacca aggacaccta tgacgccctg | 1380 |
| cacatgcagg ccctgccccc caga | 1404 |

<210> SEQ ID NO 150
<211> LENGTH: 1404
<212> TYPE: DNA
<213> ORGANISM: Artificial Sequence
<220> FEATURE:
<223> OTHER INFORMATION: nucleotide of chimeric antigen receptor

<400> SEQUENCE: 150

| | |
|---|---:|
| gaagtgcagc tgctggaatc tggcggcgga ctggtgcagc ctggcggatc tctgagactg | 60 |
| agctgtgccg ccagcggctt caccttcagc acctaccaga tgagctgggt cgcccaggcc | 120 |
| cctggcaaag gactggaatg ggtgtccggc atcgtgtcca gcggcggctc tacagcctac | 180 |
| gccgatagcg tgaagggccg gttcaccatc agccgggaca cagcaagaa caccctgtac | 240 |
| ctgcagatga acagcctgag agccgaggac accgccgtgt actattgtgc cggggagctg | 300 |
| ctgcccctact acggcatgga tgtgtggggc cagggcacca ccgtgacagt gtcctcaggc | 360 |
| tctacaagcg gctctggcaa gcctggatct ggcgagggaa gcaccaaggg ccagtctgcc | 420 |
| ctgactcagc ctccctccgc gtccgggtct cctggacagt cagtcaccat ctcctgcact | 480 |
| ggaaccagca gtgacgttgg tggttatgac tttgtctcct ggtaccaaca gcacccaggc | 540 |
| aaagccccca actcctcgt ttatgatgtc aataaccggc cctcagggt ttctaatcgc | 600 |
| ttctctggct ccaagtctgg caacacggcc tccctgacca tctctgggct ccaggctgag | 660 |
| gacgagggtg actattactg cagctcatat gcaggcagca cagcgtctt cggaactggg | 720 |
| accaaggtca ccgtcctagc ggccgcaatc gaagtgatgt accccctcc ctacctggac | 780 |
| aacgagaagt ccaacggcac cattatccac gtgaagggaa agcacctgtg ccccagccct | 840 |
| ctgttccctg gccctagcaa gccttctgg gtgctggtgg tcgtgggcgg agtgctggcc | 900 |
| tgttatagcc tgctcgtgac cgtggccttc atcatctttt gggtgcgcag caagcggagc | 960 |
| cggctgctgc acagcgacta catgaacatg accccccagac ggcccggacc caccagaaag | 1020 |
| cactaccagc cttacgcccc tcccagagac ttcgccgcct acagatctcg agtgaagttc | 1080 |
| agcagaagcg ccgacgcccc tgcctatcag cagggccaga accagctgta caacgagctg | 1140 |
| aacctgggca gacgggaaga gtacgacgtg ctggacaagc ggagaggcag ggaccctgag | 1200 |
| atgggcggca agcccagaag aaagaacccc caggaaggcc tgtataacga actgcagaaa | 1260 |
| gacaagatgg ccgaggccta cagcgagatc ggcatgaagg cgagcggag aagaggcaag | 1320 |
| ggccacgatg gcctgtacca gggcctgagc accgccacca aggacaccta tgacgccctg | 1380 |

-continued

| | |
|---|---|
| cacatgcagg ccctgccccc caga | 1404 |

<210> SEQ ID NO 151
<211> LENGTH: 1407
<212> TYPE: DNA
<213> ORGANISM: Artificial Sequence
<220> FEATURE:
<223> OTHER INFORMATION: nucleotide of Chimeric antigen receptor

<400> SEQUENCE: 151

| | |
|---|---|
| cagtctgccc tgactcagcc tgcctccgtg tctgggtctc ctggacagtc gatcaccatc | 60 |
| tcctgcactg ggaccagcag tgacgttggt ggttatgaat ttgtctcctg gtaccaacaa | 120 |
| cacccaggca gcgcccccaa actcattatt tatgacgtaa tagagcgtcc cttcggtgtc | 180 |
| tcctatcggt tctctgcctc caagtcaggc aacacggcct ccctgacgat ctctgggctc | 240 |
| cagggtgaag acgaggctga ttacttctgc agctcatata agcagcag cacttatgtc | 300 |
| ttcggaactg ggaccaaggt caccgtccta ggctctacaa gcggctctgg caagcctgga | 360 |
| tctggcgagg gaagcaccaa gggcgaagtg cagctgctgg aatctggcgg cggactggtg | 420 |
| cagcctggcg gatctctgag actgagctgt gccgccagcg gcttcacctt cagcacctac | 480 |
| cagatgagct gggtgcgcca ggcccctggc aaaggactgg aatgggtgtc cggcatcgtg | 540 |
| tccagcggcg gctctacagc ctacgccgat agcgtgaagg gccggttcac catcagccgg | 600 |
| gacaacagca agaacaccct gtacctgcag atgaacagcc tgagagccga ggacaccgcc | 660 |
| gtgtactatt gtgccgggga gctgctgccc tactacggca tggatgtgtg gggccagggc | 720 |
| accaccgtga cagtgtcctc agcggccgca atcgaagtga tgtacccccc tccctacctg | 780 |
| gacaacgaga agtccaacgg caccattatc cacgtgaagg gaaagcacct gtgccccagc | 840 |
| cctctgttcc ctggccctag caagcctttc tgggtgctgg tggtcgtggg cggagtgctg | 900 |
| gcctgttata gctgctcgt gaccgtggcc ttcatcatct tttgggtgcg cagcaagcgg | 960 |
| agccggctgc tgcacagcga ctacatgaac atgacccca gacggccgg acccaccaga | 1020 |
| aagcactacc agccttacgc ccctcccaga gacttcgccg cctacagatc tcgagtgaag | 1080 |
| ttcagcagaa gcgccgacgc ccctgcctat cagcagggcc agaaccagct gtacaacgag | 1140 |
| ctgaacctgg gcagacggga agagtacgac gtgctggaca gcggagagg cagggaccct | 1200 |
| gagatgggcg gcaagcccag aagaaagaac ccccaggaag gcctgtataa cgaactgcag | 1260 |
| aaagacaaga tggccgaggc ctacagcgag atcggcatga agggcgagcg agaagaggc | 1320 |
| aagggccacg atggcctgta ccagggcctg agcaccgcca ccaaggacac ctatgacgcc | 1380 |
| ctgcacatgc aggccctgcc ccccaga | 1407 |

<210> SEQ ID NO 152
<211> LENGTH: 1407
<212> TYPE: DNA
<213> ORGANISM: Artificial Sequence
<220> FEATURE:
<223> OTHER INFORMATION: nucleotide of Chimeric antigen receptor

<400> SEQUENCE: 152

| | |
|---|---|
| cagtctgccc tgactcagcc tgcctccgtg tctgggtctc ctggacagtc gatcaccatc | 60 |
| tcctgcactg gaaccggcag tgacgttggt gcttatgact atgtctcctg gtaccaacat | 120 |
| cacccaggca gagcccccag actcatcatt cgtgatgtca gtgtgcggcc ctcaggggtc | 180 |
| cctgatcgct tctctggctc caagtctggc aacacggcct ccctgaccat ctctgggctc | 240 |

| | |
|---|---|
| caggctgagg acgaggctga ttattactgc tcctcatatt caggcagcag cacttgggtg | 300 |
| ttcggcgggg ggaccaagct gaccgtccta ggctctacaa gcggctctgg caagcctgga | 360 |
| tctggcgagg gaagcaccaa gggcgaagtg cagctgctgg aatctggcgg cggactggtg | 420 |
| cagcctggcg gatctctgag actgagctgt gccgccagcg gcttcacctt cagcacctac | 480 |
| cagatgagct gggtgcgcca ggcccctggc aaaggactgg aatgggtgtc cggcatcgtg | 540 |
| tccagcggcg gctctacagc ctacgccgat agcgtgaagg gccggttcac catcagccgg | 600 |
| gacaacagca agaacaccct gtacctgcag atgaacagcc tgagagccga ggacaccgcc | 660 |
| gtgtactatt gtgccgggga gctgctgccc tactacggca tggatgtgtg gggccagggc | 720 |
| accaccgtga cagtgtcctc agcggccgca atcgaagtga tgtaccccc tccctacctg | 780 |
| gacaacgaga agtccaacgg caccattatc cacgtgaagg gaaagcacct gtgcccagc | 840 |
| cctctgttcc ctggccctag caagcctttc tgggtgctgg tggtcgtggg cggagtgctg | 900 |
| gcctgttata gcctgctcgt gaccgtggcc ttcatcatct tttgggtgcg cagcaagcgg | 960 |
| agccggctgc tgcacagcga ctacatgaac atgacccca gacggccgg acccaccaga | 1020 |
| aagcactacc agcccttacgc ccctcccaga gacttcgccg cctacagatc tcgagtgaag | 1080 |
| ttcagcagaa gcgccgacgc ccctgcctat cagcagggcc agaaccagct gtacaacgag | 1140 |
| ctgaacctgg gcagacggga agagtacgac gtgctggaca gcggagagg cagggaccct | 1200 |
| gagatgggcg gcaagcccag aagaaagaac ccccaggaag cctgtataa cgaactgcag | 1260 |
| aaagacaaga tggccgaggc ctacagcgag atcggcatga agggcgagcg gagaagaggc | 1320 |
| aagggccacg atggcctgta ccagggcctg agcaccgcca ccaaggacac ctatgacgcc | 1380 |
| ctgcacatgc aggccctgcc ccccaga | 1407 |

<210> SEQ ID NO 153
<211> LENGTH: 1410
<212> TYPE: DNA
<213> ORGANISM: Artificial Sequence
<220> FEATURE:
<223> OTHER INFORMATION: nucleotide of Chimeric antigen receptor

<400> SEQUENCE: 153

| | |
|---|---|
| cagtctgccc tgactcagcc tgcctccgtg tctgggtctc ctggacagtc gatcaccatc | 60 |
| tcctgcactg gaaccagcag tgatgttggg agttataacc ttgtctcctg gtaccaacaa | 120 |
| cacccaggca aagcccccaa actcatgatt tatgatgtca gtaatcggcc ctcagggtt | 180 |
| tcttatcgct tctctggctc caagtctggc aacacggcct ccctgaccat ctctgggctc | 240 |
| caggctgagg acgaggctga ttattactgc agctcatata caagcagcag cactttcgcg | 300 |
| gtgttcggcg gagggaccca gctgaccgtc ctcggctcta aagcggctc tgcaagcct | 360 |
| ggatctggcg agggaagcac caagggcgaa gtgcagctgc tggaatctgg cggcggactg | 420 |
| gtgcagcctg gcggatctct gagactgagc tgtgccgcca gcggcttcac cttcagcacc | 480 |
| taccagatga gctgggtgcg ccaggcccct ggcaaaggac tggaatgggt gtccggcatc | 540 |
| gtgtccagcg gcggctctac agcctacgcc gatagcgtga agggccggtt caccatcagc | 600 |
| cgggacaaca gcaagaacac cctgtacctg cagatgaaca gcctgagagc cgaggacacc | 660 |
| gccgtgtact attgtgccgg ggagctgctg ccctactacg gcatggatgt gtggggccag | 720 |
| ggcaccaccg tgacagtgtc ctcagcggcc gcaatcgaag tgatgtaccc ccctccctac | 780 |
| ctggacaacg agaagtccaa cggcaccatt atccacgtga aggaaagca cctgtgcccc | 840 |
| agccctctgt tccctggccc tagcaagcct ttctgggtgc tggtggtcgt gggcggagtg | 900 |

```
ctggcctgtt atagcctgct cgtgaccgtg gccttcatca tcttttgggt gcgcagcaag    960
cggagccggc tgctgcacag cgactacatg aacatgaccc ccagacgcc cggacccacc   1020 agaaagcact accagcctta cgcccctccc agagacttcg ccgcctacag atctcgagtg   1080
aagttcagca aagcgccga cgcccctgcc tatcagcagg ccagaaacca gctgtacaac   1140
gagctgaacc tgggcagacg ggaagagtac gacgtgctgg acaagcggag aggcagggac   1200
cctgagatgg gcggcaagcc cagaagaaag aaccccagg aaggcctgta taacgaactg   1260
cagaaagaca agatggccga ggcctacagc gagatcggca tgaagggcga gcggagaaga   1320
ggcaagggcc acgatggcct gtaccagggc ctgagcaccg ccaccaagga cacctatgac   1380
gccctgcaca tgcaggccct gccccccaga                                    1410

<210> SEQ ID NO 154
<211> LENGTH: 1404
<212> TYPE: DNA
<213> ORGANISM: Artificial Sequence
<220> FEATURE:
<223> OTHER INFORMATION: nucleotide of Chimeric antigen receptor

<400> SEQUENCE: 154
caatctgccc tgcctcagcc tgcctccgtg tctgggtctc ctggacagtc agtcaccatc     60
tcctgcactg gaaccagcag tgatgttggt ggttataact atgtctcctg gtaccaacag    120
cacccaggca agcccccaa actcatgatt tatgatgtca gtaagcggcc ctcaggggtc    180
cctgatcgct tctctggttc caagtctggc aacacggcct ccctgaccgt ctctgggctc    240
caggctgagg atgaggctga ttatttctgc tgttcgtatg caggcggcta ttatgtcttc    300
ggaactggga ccaagctgac cgtcctaggc tctacaagcg gctctggcaa gcctggatct    360
ggcgagggaa gcaccaaggg cgaagtgcag ctgctggaat ctggcggcgg actggtgcag    420
cctggcggat ctctgagact gagctgtgcc gccagcggct tcaccttcag cacctaccag    480
atgagctggg tgcgccaggc ccctggcaaa ggactggaat gggtgtccgg catcgtgtcc    540
agcggcggct ctacagccta cgccgatagc gtgaagggcc ggttcaccat cagccgggac    600
aacagcaaga cacccctgta cctgcagatg aacagcctga gaccgagga caccgccgtg    660 tactattgtg ccggggagct gctgcccctac acggcatgg atgtgtgggg ccagggcacc    720
accgtgacag tgtcctcagc ggccgcaatc gaagtgatgt accccccctcc ctacctggac    780 aacgagaagt ccaacggcac cattatccac gtgaagggaa agcacctgtg ccccagccct    840
ctgttccctg ccctagcaa gccttttctgg gtgctggtgg tcgtgggcgg agtgctggcc    900
tgttatagcc tgctcgtgac cgtggccttc atcatctttt gggtgcgcag caagcggagc    960
cggctgctgc acagcgacta catgaacatg acccccagac ggcccggacc caccagaaag   1020
cactaccagc cttacgcccc tcccagagac ttcgccgcct acagatctcg agtgaagttc   1080
agcagaagcg ccgacgcccc tgcctatcag caggccagaa accagctgta caacgagctg   1140
aacctgggca gacgggaaga gtacgacgtg ctggacaagc ggagaggcag ggaccctgag   1200
atgggcggca agcccagaag aaagaaccc caggaaggcc tgtataacga actgcagaaa   1260
gacaagatgg ccgaggccta cagcgagatc ggcatgaagg gcgagcggag aagaggcaag   1320
ggccacgatg gcctgtacca gggcctgagc accgccacca aggacaccta tgacgccctg   1380
cacatgcagg ccctgccccc caga                                          1404

<210> SEQ ID NO 155
```

<211> LENGTH: 1413
<212> TYPE: DNA
<213> ORGANISM: Artificial Sequence
<220> FEATURE:
<223> OTHER INFORMATION: nucleotide of Chimeric antigen receptor

<400> SEQUENCE: 155

| | | | | |
|---|---|---|---|---|
| cagtctgccc | tgactcagcc | tccctccgcg | tccgggtctc | ctggacagtc  agtcaccatc | 60 |
| tcctgcactg | gaaccagcag | tgacgttggt | ggttataact | atgtctcctg  gtaccaacag | 120 |
| cacccaggca | agccccccaa | actcatgatt | tatgatgtca | gtaagcggcc  ctcagggtc | 180 |
| cctgatcgct | tctctggctc | caagtctggc | aacacggcct | ccctgaccat  ctctgggctc | 240 |
| cagactgagg | acgaggctga | ttactattgc | agctcatatg | caggcagcgg  cagcacccc | 300 |
| tttgtcttcg | gaactgggac | caagctgacc | gtcctaggct | ctacaagcgg  ctctggcaag | 360 |
| cctggatctg | gcgagggaag | caccaagggc | gaagtgcagc | tgctggaatc  tggcggcgga | 420 |
| ctggtgcagc | ctggcggatc | tctgagactg | agctgtgccg | ccagcggctt  caccttcagc | 480 |
| acctaccaga | tgagctgggt | gcgccaggcc | cctggcaaag | gactgaatg   ggtgtccggc | 540 |
| atcgtgtcca | gcggcggctc | tacagcctac | gccgatagcg | tgaagggccg  gttcaccatc | 600 |
| agccgggaca | acagcaagaa | cacactgtac | ctgcagatga | acagcctgag  agccgaggac | 660 |
| accgccgtgt | actattgtgc | cggggagctg | ctgccctact | acggcatgga  tgtgtggggc | 720 |
| cagggcacca | ccgtgacagt | gtcctcagcg | gccgcaatcg | aagtgatgta  cccccctccc | 780 |
| tacctggaca | acgagaagtc | caacggcacc | attatccacg | tgaagggaaa  gcacctgtgc | 840 |
| cccagccctc | tgttccctgg | ccctagcaag | cctttctggg | tgctggtggt  cgtgggcgga | 900 |
| gtgctggcct | gttatagcct | gctcgtgacc | gtggccttca | tcatctttg   ggtgcgcagc | 960 |
| aagcggagcc | ggctgctgca | cagcgactac | atgaacatga | ccccagacg   gcccggaccc | 1020 |
| accagaaagc | actaccagcc | ttacgcccct | cccagagact | cgccgccta   cagatctcga | 1080 |
| gtgaagttca | gcagaagcgc | cgacgcccct | gcctatcagc | agggccagaa  ccagctgtac | 1140 |
| aacgagctga | acctgggcag | acgggaagag | tacgacgtgc | tggacaagcg  gagaggcagg | 1200 |
| gaccctgaga | tggcggcaa  | gcccagaaga | aagaaccccc | aggaaggcct  gtataacgaa | 1260 |
| ctgcagaaag | acaagatggc | cgaggcctac | agcgagatcg | gcatgaaggg  cgagcggaga | 1320 |
| agaggcaagg | gccacgatgg | cctgtaccag | ggcctgagca | ccgccaccaa  ggacacctat | 1380 |
| gacgccctgc | acatgcaggc | cctgccccc  | aga | | 1413 |

<210> SEQ ID NO 156
<211> LENGTH: 1404
<212> TYPE: DNA
<213> ORGANISM: Artificial Sequence
<220> FEATURE:
<223> OTHER INFORMATION: nucleotide of Chimeric antigen receptor

<400> SEQUENCE: 156

| | | | | |
|---|---|---|---|---|
| cagtctgccc | tgactcagcc | tgcctccgtg | tctgggtctc | ctggacagtc  gatcaccatc | 60 |
| tcctgcactg | gaaccagcag | tgacgttggt | ggttataact | atgtctcctg  gtaccaacaa | 120 |
| cacccaggca | agccccccaa | actcatgatt | tatgatgtca | gtaatcggcc  ctcaagggtc | 180 |
| cctgatcgct | tcgctggctc | caagtctggc | aacacggcct | ccctgaccat  ctctgggctc | 240 |
| caggctgaag | acgaggctga | ttattactgc | tgctcatatg | ccggcagacg  ttatgtgttc | 300 |
| ggaactggga | ccaagctgac | cgtcctaggc | tctacaagcg | gctctggcaa  gcctggatct | 360 |
| ggcgagggaa | gcaccaaggg | cgaagtgcag | ctgctggaat | ctggcggcgg  actggtgcag | 420 |

```
cctggcggat ctctgagact gagctgtgcc gccagcggct tcaccttcag cacctaccag      480
atgagctggg tgcgccaggc ccctggcaaa ggactggaat gggtgtccgg catcgtgtcc      540
agcggcggct ctacagccta cgccgatagc gtgaagggcc ggttcaccat cagccgggac      600
aacagcaaga cacccctgta cctgcagatg aacagcctga gagccgagga caccgccgtg      660
tactattgtg ccggggagct gctgccctac tacggcatgg atgtgtgggg ccagggcacc      720
accgtgacag tgtcctcagc ggccgcaatc gaagtgatgt accccctcc ctacctggac       780 aacgagaagt ccaacggcac cattatccac gtgaagggaa agcacctgtg ccccagccct      840
ctgttccctg ccctagcaa gccttttctgg gtgctggtgg tcgtgggcgg agtgctggcc      900
tgttatagcc tgctcgtgac cgtggccttc atcatctttt gggtgcgcag caagcggagc      960
cggctgctgc acagcgacta catgaacatg acccccagac ggcccggacc caccagaaag     1020
cactaccagc cttacgcccc tcccagagac ttcgccgcct acagatctcg agtgaagttc     1080
agcagaagcg ccgacgcccc tgcctatcag cagggccaga accagctgta caacgagctg     1140
aacctgggca gacgggaaga gtacgacgtg ctggacaagc ggagaggcag ggaccctgag     1200
atgggcggca gcccagaag aaagaacccc caggaaggcc tgtataacga actgcagaaa      1260
gacaagatgg ccgaggccta cagcgagatc ggcatgaagg gcgagcggag aagaggcaag     1320
ggccacgatg gcctgtacca gggcctgagc accgccacca ggacaccta tgacgccctg      1380 cacatgcagg ccctgccccc caga                                             1404

<210> SEQ ID NO 157
<211> LENGTH: 1401
<212> TYPE: DNA
<213> ORGANISM: Artificial Sequence
<220> FEATURE:
<223> OTHER INFORMATION: nucleotide of Chimeric antigen receptor

<400> SEQUENCE: 157
cagctgcagc tgcaggagtc gggcccagga ctggtgaagc cttcacagac cctgtccctc       60
acctgcactg tctctggtgg ctccatcagt agttactact ggagctggat ccggcagccc      120
ccagggaagg gactggagtg gattgggaa atcaatcata gtggaagcac caactacaac       180
ccgtccctca gagtcgagt caccatatca gtagacacgt ctaagaacca gttctccctg      240
aagctgagct ctgtgactgc cgcggacacg gccgtgtatt actgtgcgag gtgccctatc      300
tactactacg gtatggacgt ctggggccaa gggaccacgg tcaccgtctc ctcaggctct      360
acaagcggct ctggcaagcc tggatctggc gagggaagca ccaagggcca gagcgagctg      420
acacagccta atccgtgtc tggcagccct ggccagagcg tgaccatcag ctgtaccggc      480
accagcagag atgtgggcgg ctacaactac gtgtcctggt atcagcagca tcccggcaag      540
gcccccaagc tgatcatcca cgacgtgatc gagcggagca gcgcgtgcc cgatagattc       600 agcggcagca gagcggcaa caccgccagc ctgacaatca cgggactgca ggccgaggac      660
gaggccgact actactgttg agcttcgcc ggcagctact acgtgttcgg caccggcacc       720
gatgtgaccg tgctggcggc cgcaatcgaa gtgatgtacc ccctccccta cctggacaac      780
gagaagtcca acggcaccat tatccacgtg aagggaaagc cctgtgccc agccctctg       840 ttccctggcc ctagcaagcc tttctggggtg ctggtggtcg tgggcggagt gctggcctgt      900
tatagcctgc tcgtgaccgt ggccttcatc atctttggg tgcgcagcaa gcggagccgg      960
ctgctgcaca gcgactacat gaacatgacc cccagacggc ccggacccac cagaaagcac     1020
```

```
taccagcctt acgcccctcc cagagacttc gccgcctaca gatctcgagt gaagttcagc    1080
agaagcgccg acgcccctgc ctatcagcag ggccagaacc agctgtacaa cgagctgaac    1140
ctgggcagac gggaagagta cgacgtgctg acaagcgga gaggcaggga ccctgagatg    1200
ggcggcaagc ccagaagaaa gaaccccag gaaggcctgt ataacgaact gcagaaagac    1260
aagatggccg aggcctacag cgagatcggc atgaagggcg agcggagaag aggcaagggc    1320
cacgatggcc tgtaccaggg cctgagcacc gccaccaagg acacctatga cgccctgcac    1380
atgcaggccc tgcccccag a                                              1401
```

```
<210> SEQ ID NO 158
<211> LENGTH: 44
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid

<400> SEQUENCE: 158

Xaa Gly Ser Thr Ser Gly Ser Gly Lys Pro Gly Ser Gly Glu Gly Ser
1               5                   10                  15

Thr Lys Gly Xaa Ser Gly Ser Gly Xaa Gly Ser Thr Ser Gly Ser Gly
            20                  25                  30

Lys Pro Gly Ser Gly Glu Gly Ser Thr Lys Gly Xaa
        35                  40
```

```
<210> SEQ ID NO 159
<211> LENGTH: 124
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is any nucleotide
<220> FEATURE:
<221> NAME/KEY: misc_feature
<222> LOCATION: (56)..(56)
<223> OTHER INFORMATION: n is any nucleotide
<220> FEATURE:
<221> NAME/KEY: misc_feature
<222> LOCATION: (69)..(69)
<223> OTHER INFORMATION: n is any nucleotide
<220> FEATURE:
<221> NAME/KEY: misc_feature
<222> LOCATION: (124)..(124)
<223> OTHER INFORMATION: n is any nucleotide

<400> SEQUENCE: 159
nggctctaca agcggctctg gcaagcctgg atctggcgag ggaagcacca agggcnagcg    60
gatctggcng gctctacaag cggctctggc aagcctggat ctggcgaggg aagcaccaag   120 ggcn                                                                124
```

```
<210> SEQ ID NO 160
```

```
<211> LENGTH: 44
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid

<400> SEQUENCE: 160

Xaa Gly Ser Thr Ser Gly Ser Gly Lys Pro Gly Ser Gly Glu Gly Ser
1               5                   10                  15

Thr Lys Gly Xaa Ser Gly Ser Gly Xaa Gly Ser Thr Ser Gly Ser Gly
            20                  25                  30

Lys Pro Gly Ser Gly Glu Gly Ser Thr Lys Gly Xaa
        35                  40

<210> SEQ ID NO 161
<211> LENGTH: 124
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is any nucleotide
<220> FEATURE:
<221> NAME/KEY: misc_feature
<222> LOCATION: (12)..(124)
<223> OTHER INFORMATION: n is any nucleotide
<220> FEATURE:
<221> NAME/KEY: misc_feature
<222> LOCATION: (56)..(56)
<223> OTHER INFORMATION: n is any nucleotide
<220> FEATURE:
<221> NAME/KEY: misc_feature
<222> LOCATION: (69)..(69)
<223> OTHER INFORMATION: n is any nucleotide

<400> SEQUENCE: 161
nggctctaca agcggctctg gcaagcctgg atctggcgag gaagcacca agggcnagcg      60 gatctggcng gctctacaag cggctctggc aagcctggat ctggcgaggg aagcaccaag   120 ggcn                                                                124

<210> SEQ ID NO 162
<211> LENGTH: 357
<212> TYPE: DNA
<213> ORGANISM: Artificial Sequence
<220> FEATURE:
<223> OTHER INFORMATION: Nucleotide of 3M4E5 heavy chain

<400> SEQUENCE: 162
gaagtgcagc tgctggaatc tggcggcgga ctggtgcagc ctggcggatc tctgagactg     60
agctgtgccg ccagcggctt caccttcagc acctaccaga tgagctgggt gcgccaggcc   120
cctggcaaag gactggaatg ggtgtccggc atcgtgtcca gcggcggctc tacagcctac   180
gccgatagcg tgaagggccg gttcaccatc agccgggaca cagcaagaa caccctgtac    240
```

```
ctgcagatga acagcctgag agccgaggac accgccgtgt actattgtgc cggggagctg      300
ctgccctact acggcatgga tgtgtggggc cagggcacca ccgtgacagt gtcctca         357
```

<210> SEQ ID NO 163
<211> LENGTH: 327
<212> TYPE: DNA
<213> ORGANISM: Artificial Sequence
<220> FEATURE:
<223> OTHER INFORMATION: Nucleotide of 3M4E5 light chain

<400> SEQUENCE: 163

```
cagagcgagc tgacacagcc tagatccgtg tctggcagcc ctggccagag cgtgaccatc       60
agctgtaccg gcaccagcag agatgtgggc ggctacaact acgtgtcctg gtatcagcag      120
catcccggca aggcccccaa gctgatcatc cacgacgtga tcgagcggag cagcggcgtg      180
cccgatagat tcagcggcag caagagcggc aacaccgcca gcctgacaat cagcggactg      240
caggccgagg acgaggccga ctactactgt tggagcttcg ccggcagcta ctacgtgttc      300
ggcaccggca ccgatgtgac cgtgctg                                         327
```

<210> SEQ ID NO 164
<211> LENGTH: 246
<212> TYPE: PRT
<213> ORGANISM: Artificial Sequence
<220> FEATURE:
<223> OTHER INFORMATION: 3M4E5HL scFv

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Ser Trp Val Arg Gln Ala Pro Gly Lys Gly Leu Glu Trp Val
        35                  40                  45

Ser Gly Ile Val Ser Ser Gly Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Leu Leu Pro Tyr Tyr Gly Met Asp Val Trp Gly Gln Gly
            100                 105                 110

Thr Thr Val Thr Val Ser Ser Gly Ser Thr Ser Gly Ser Gly Lys Pro
        115                 120                 125

Gly Ser Gly Glu Gly Ser Thr Lys Gly Gln Ser Glu Leu Thr Gln Pro
    130                 135                 140

Arg Ser Val Ser Gly Ser Pro Gly Gln Ser Val Thr Ile Ser Cys Thr
145                 150                 155                 160

Gly Thr Ser Arg Asp Val Gly Gly Tyr Asn Tyr Val Ser Trp Tyr Gln
                165                 170                 175

Gln His Pro Gly Lys Ala Pro Lys Leu Ile Ile His Asp Val Ile Glu
            180                 185                 190

Arg Ser Gly Val Pro Asp Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

Tyr Tyr Cys Trp Ser Phe Ala Gly Ser Tyr Tyr Val Phe Gly Thr Gly

```
                225                 230                 235                 240

Thr Asp Val Thr Val Leu
                245

<210> SEQ ID NO 165
<211> LENGTH: 738
<212> TYPE: DNA
<213> ORGANISM: Artificial Sequence
<220> FEATURE:
<223> OTHER INFORMATION: Nucleotide of 3M4E5HL scFv

<400> SEQUENCE: 165
gaagtgcagc tgctggaatc tggcggcgga ctggtgcagc ctggcggatc tctgagactg      60
agctgtgccg ccagcggctt caccttcagc acctaccaga tgagctgggt gcgccaggcc     120
cctggcaaag actggaatg gtgtccggc atcgtgtcca gcggcggctc tacagcctac       180
gccgatagcg tgaagggccg gttcaccatc agccgggaca acagcaagaa caccctgtac     240
ctgcagatga acagcctgag agccgaggac accgccgtgt actattgtgc cggggagctg     300
ctgccctact acggcatgga tgtgtgggc agggcacca ccgtgacagt gtcctcaggc       360
tctacaagcg gctctggcaa gcctggatct ggcgagggaa gcaccaaggg ccagagcgag     420
ctgacacagc ctagatccgt gtctggcagc cctggccaga gcgtgaccat cagctgtacc     480
ggcaccagca gagatgtggg cggctacaac tacgtgtcct ggtatcagca gcatcccggc     540
aaggccccca agctgatcat ccacgacgtg atcgagcgga gcagcggcgt gcccgataga     600
ttcagcggca gcaagagcgg caacaccgcc agcctgacaa tcagcggact gcaggccgag     660
gacgaggccg actactactg ttggagcttc gccggcagct actacgtgtt cggcaccggc     720
accgatgtga ccgtgctg                                                    738

<210> SEQ ID NO 166
<211> LENGTH: 246
<212> TYPE: PRT
<213> ORGANISM: Artificial Sequence
<220> FEATURE:
<223> OTHER INFORMATION: 3M4E5LH scFv

<400> SEQUENCE: 166

Gln Ser Glu Leu Thr Gln Pro Arg Ser Val Ser Gly Ser Pro Gly Gln
1               5                   10                  15

Ser Val Thr Ile Ser Cys Thr Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Ile Ile His Asp Val Ile Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Trp Ser Phe Ala Gly Ser
                85                  90                  95

Tyr Tyr Val Phe Gly Thr Gly Thr Asp Val Thr Val Leu Gly Ser Thr
            100                 105                 110

Ser Gly Ser Gly Lys Pro Gly Ser Gly Glu Gly Ser Thr Lys Gly Glu
        115                 120                 125

Val Gln Leu Leu Glu Ser Gly Gly Gly Leu Val Gln Pro Gly Gly Ser
    130                 135                 140

Leu Arg Leu Ser Cys Ala Ala Ser Gly Phe Thr Phe Ser Thr Tyr Gln
```

```
                145                 150                 155                 160
Met Ser Trp Val Arg Gln Ala Pro Gly Lys Gly Leu Glu Trp Val Ser
                    165                 170                 175

Gly Ile Val Ser Ser Gly Gly Ser Thr Ala Tyr Ala Asp Ser Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
210                 215                 220

Gly Glu Leu Leu Pro Tyr Tyr Gly Met Asp Val Trp Gly Gln Gly Thr
225                 230                 235                 240

Thr Val Thr Val Ser Ser
                245

<210> SEQ ID NO 167
<211> LENGTH: 738
<212> TYPE: DNA
<213> ORGANISM: Artificial Sequence
<220> FEATURE:
<223> OTHER INFORMATION: Nucleotide of 3M4E5LH scFv

<400> SEQUENCE: 167
cagagcgagc tgacacagcc tagatccgtg tctggcagcc ctggccagag cgtgaccatc      60
agctgtaccg gcaccagcag agatgtgggc ggctacaact acgtgtcctg gtatcagcag     120
catcccggca aggcccccaa gctgatcatc cacgacgtga tcgagcggag cagcggcgtg     180
cccgatagat tcagcggcag caagagcggc aacaccgcca gcctgacaat cagcggactg     240
caggccgagg acgaggccga ctactactgt tggagcttcg ccggcagcta ctacgtgttc     300
ggcaccggca ccgatgtgac cgtgctgggc tctacaagcg ctctggcaa gcctggatct     360
ggcgagggaa gcaccaaggg cgaagtgcag ctgctggaat ctggcggcgg actggtgcag     420
cctggcggat ctctgagact gagctgtgcc gccagcggct tcaccttcag cacctaccag     480
atgagctggg tgcgccaggc ccctggcaaa ggactggaat gggtgtccgg catcgtgtcc     540
agcggcggct ctacagccta cgccgatagc gtgaagggcc ggttcaccat cagccgggac     600
aacagcaaga acaccctgta cctgcagatg aacagcctga gagccgagga caccgccgtg     660
tactattgtg ccggggagct gctgccctac tacggcatgg atgtgtgggg ccagggcacc     720
accgtgacag tgtcctca                                                    738

<210> SEQ ID NO 168
<211> LENGTH: 110
<212> TYPE: PRT
<213> ORGANISM: Homo sapiens

<400> SEQUENCE: 168

Ala Ala Ala Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
        50                  55                  60

Ile Ile Phe Trp Val Arg Ser Lys Arg Ser Arg Leu Leu His Ser Asp
65                  70                  75                  80
```

Tyr Met Asn Met Thr Pro Arg Arg Pro Gly Pro Thr Arg Lys His Tyr
            85                  90                  95

Gln Pro Tyr Ala Pro Pro Arg Asp Phe Ala Ala Tyr Arg Ser
        100                 105                 110

<210> SEQ ID NO 169
<211> LENGTH: 330
<212> TYPE: DNA
<213> ORGANISM: Homo sapiens

<400> SEQUENCE: 169
gcggccgcaa tcgaagtgat gtaccccct ccctacctgg acaacgagaa gtccaacggc        60
accattatcc acgtgaaggg aaagcacctg tgccccagcc ctctgttccc tggccctagc      120
aagcctttct gggtgctggt ggtcgtgggc ggagtgctgg cctgtttatag cctgctcgtg     180 accgtggcct tcatcatctt tgggtgcgc agcaagcgga gccggctgct gcacagcgac       240
tacatgaaca tgaccccag acggcccgga cccaccagaa agcactacca gccttacgcc       300
cctcccagag acttcgccgc ctacagatct                                        330

<210> SEQ ID NO 170
<211> LENGTH: 112
<212> TYPE: PRT
<213> ORGANISM: Homo sapiens

<400> SEQUENCE: 170

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 171
<211> LENGTH: 336
<212> TYPE: DNA
<213> ORGANISM: Homo sapiens

<400> SEQUENCE: 171
cgagtgaagt tcagcagaag cgccgacgcc cctgcctatc agcagggcca gaaccagctg        60
tacaacgagc tgaacctggg cagacgggaa gagtacgacg tgctggacaa gcggagaggc      120
agggaccctg agatgggcgg caagcccaga agaaagaacc cccaggaagg cctgtataac      180
gaactgcaga agacaagat ggccgaggcc tacagcgaga tcggcatgaa gggcgagcgg        240
agaagaggca agggccacga tggcctgtac caggggcctga gcaccgccac caaggacacc     300
tatgacgccc tgcacatgca ggccctgccc cccaga                                 336

<210> SEQ ID NO 172
<211> LENGTH: 4
<212> TYPE: PRT

```
<213> ORGANISM: Artificial Sequence
<220> FEATURE:
<223> OTHER INFORMATION: furin cleavage site

<400> SEQUENCE: 172

Arg Ala Lys Arg
1

<210> SEQ ID NO 173
<211> LENGTH: 4
<212> TYPE: PRT
<213> ORGANISM: Artificial Sequence
<220> FEATURE:
<223> OTHER INFORMATION: Spacer sequence

<400> SEQUENCE: 173

Ser Gly Ser Gly
1

<210> SEQ ID NO 174
<211> LENGTH: 19
<212> TYPE: PRT
<213> ORGANISM: Artificial Sequence
<220> FEATURE:
<223> OTHER INFORMATION: Codon-optimized P2A sequence

<400> SEQUENCE: 174

Ala Thr Asn Phe Ser Leu Leu Lys Gln Ala Gly Asp Val Glu Glu Asn
1               5                   10                  15

Pro Gly Pro

<210> SEQ ID NO 175
<211> LENGTH: 45
<212> TYPE: DNA
<213> ORGANISM: Artificial Sequence
<220> FEATURE:
<223> OTHER INFORMATION: 5'-RACE primer

<400> SEQUENCE: 175
ctaatacgac tcactatagg gcaagcagtg gtatcaacgc agagt           45

<210> SEQ ID NO 176
<211> LENGTH: 21
<212> TYPE: DNA
<213> ORGANISM: Artificial Sequence
<220> FEATURE:
<223> OTHER INFORMATION: 3'IGHC primer

<400> SEQUENCE: 176
tgagttccac gacaccgtca c                                     21

<210> SEQ ID NO 177
<211> LENGTH: 22
<212> TYPE: DNA
<213> ORGANISM: Artificial Sequence
<220> FEATURE:
<223> OTHER INFORMATION: 3'IGHM primer

<400> SEQUENCE: 177
tccaggacaa agtgatggag tc                                    22

<210> SEQ ID NO 178
<211> LENGTH: 43
<212> TYPE: DNA
<213> ORGANISM: Artificial Sequence
<220> FEATURE:
```

<223> OTHER INFORMATION: Modified 5'-RACE primer

<400> SEQUENCE: 178
gtgtggtggt acgggaattc aagcagtggt atcaacgcag agt                43

<210> SEQ ID NO 179
<211> LENGTH: 44
<212> TYPE: DNA
<213> ORGANISM: Artificial Sequence
<220> FEATURE:
<223> OTHER INFORMATION: 3'IGHJ1 primer

<400> SEQUENCE: 179
cttgccagag ccgcttgtag agcctgagga gacggtgacc aggg               44

<210> SEQ ID NO 180
<211> LENGTH: 46
<212> TYPE: DNA
<213> ORGANISM: Artificial Sequence
<220> FEATURE:
<223> OTHER INFORMATION: 3'IGHJ2 primer

<400> SEQUENCE: 180
cttgccagag ccgcttgtag agcctgaaga gacggtgacc attgtc             46

<210> SEQ ID NO 181
<211> LENGTH: 46
<212> TYPE: DNA
<213> ORGANISM: Artificial Sequence
<220> FEATURE:
<223> OTHER INFORMATION: 3'IGHJ3 primer

<400> SEQUENCE: 181
cttgccagag ccgcttgtag agcctgagga gacggtgacc gtggtc             46

<210> SEQ ID NO 182
<211> LENGTH: 22
<212> TYPE: DNA
<213> ORGANISM: Artificial Sequence
<220> FEATURE:
<223> OTHER INFORMATION: 3'IGKC primer

<400> SEQUENCE: 182
agggtcagag gccaaaggat gg                                       22

<210> SEQ ID NO 183
<211> LENGTH: 20
<212> TYPE: DNA
<213> ORGANISM: Artificial Sequence
<220> FEATURE:
<223> OTHER INFORMATION: 3'IGLC primer

<400> SEQUENCE: 183
cttggagctc ctcagaggag                                          20

<210> SEQ ID NO 184
<211> LENGTH: 45
<212> TYPE: DNA
<213> ORGANISM: Artificial Sequence
<220> FEATURE:
<223> OTHER INFORMATION: 3'IGKJ1 primer

<400> SEQUENCE: 184
cttgccagag ccgcttgtag agcctttgat ttccaccttg gtccc              45

<210> SEQ ID NO 185
<211> LENGTH: 45
<212> TYPE: DNA
<213> ORGANISM: Artificial Sequence
<220> FEATURE:
<223> OTHER INFORMATION: 3'IGKJ2 primer

<400> SEQUENCE: 185
cttgccagag ccgcttgtag agcctttgat ctccagcttg gtccc    45

<210> SEQ ID NO 186
<211> LENGTH: 45
<212> TYPE: DNA
<213> ORGANISM: Artificial Sequence
<220> FEATURE:
<223> OTHER INFORMATION: 3'IGKJ3 primer

<400> SEQUENCE: 186
cttgccagag ccgcttgtag agcctttgat atccactttg gtccc    45

<210> SEQ ID NO 187
<211> LENGTH: 45
<212> TYPE: DNA
<213> ORGANISM: Artificial Sequence
<220> FEATURE:
<223> OTHER INFORMATION: 3'IGKJ4 primer

<400> SEQUENCE: 187
cttgccagag ccgcttgtag agcctttaat ctccagtcgt gtccc    45

<210> SEQ ID NO 188
<211> LENGTH: 45
<212> TYPE: DNA
<213> ORGANISM: Artificial Sequence
<220> FEATURE:
<223> OTHER INFORMATION: 3'IGLJ1 primer

<400> SEQUENCE: 188
cttgccagag ccgcttgtag agcctaggac ggtgaccttg gtccc    45

<210> SEQ ID NO 189
<211> LENGTH: 45
<212> TYPE: DNA
<213> ORGANISM: Artificial Sequence
<220> FEATURE:
<223> OTHER INFORMATION: 3'IGLJ2 primer

<400> SEQUENCE: 189
cttgccagag ccgcttgtag agcctaggac ggtcagcttg gtccc    45

<210> SEQ ID NO 190
<211> LENGTH: 45
<212> TYPE: DNA
<213> ORGANISM: Artificial Sequence
<220> FEATURE:
<223> OTHER INFORMATION: 3'IGLJ4 primer

<400> SEQUENCE: 190
cttgccagag ccgcttgtag agcctaaaat gatcagctgg gttcc    45

<210> SEQ ID NO 191
<211> LENGTH: 45
<212> TYPE: DNA
<213> ORGANISM: Artificial Sequence
<220> FEATURE:
<223> OTHER INFORMATION: 3'IGLJ5 primer

```
<400> SEQUENCE: 191
cttgccagag ccgcttgtag agcctaggac ggtcagctcg gtccc          45

<210> SEQ ID NO 192
<211> LENGTH: 45
<212> TYPE: DNA
<213> ORGANISM: Artificial Sequence
<220> FEATURE:
<223> OTHER INFORMATION: 3'IGLJ7 primer

<400> SEQUENCE: 192
cttgccagag ccgcttgtag agccgaggac ggtcagctgg gtgcc          45

<210> SEQ ID NO 193
<211> LENGTH: 1095
<212> TYPE: DNA
<213> ORGANISM: Homo sapiens

<400> SEQUENCE: 193
atggccgtca tggcgccccg aaccctcgtc ctgctactct cgggggctct ggccctgacc    60
cagacctggg cgggctctca ctccatgagg tatttcttca catccgtgtc ccggcccggc   120 cgcgggagc cccgcttcat cgcagtgggc tacgtggacg acacgcagtt cgtgcggttc   180
gacagcgacg ccgcgagcca gaggatggag ccgcgggcgc cgtggataga gcaggagggt   240
ccggagtatt gggacgggga gacacggaaa gtgaaggccc actcacagac tcaccgagtg   300
gacctgggga ccctgcgcgg ctactacaac cagagcgagg ccggttctca caccgtccag   360
aggatgtatg gctgcgacgt ggggtcggac tggcgcttcc tccgcgggta ccaccagtac   420
gcctacgacg gcaaggatta tatcgccctg aaagaggacc tgcgctcttg gaccgcggcg   480
gacatggcag ctcagaccac caagcacaag tgggaggcgg cccatgtggc ggagcagttg   540
agagcctacc tggagggcac gtgcgtggag tggctccgca gatacctgga aacgggaag   600 gagacgctgc agcgcacgga cgcccccaaa acgcatatga ctcaccacgc tgtctctgac   660
catgaagcca ccctgaggtg ctgggccctg agcttctacc ctgcggagat cacactgacc   720
tggcagcggg atggggagga ccagacccag gacacggagc tcgtggagac caggcctgca   780
ggggatggaa ccttccagaa gtgggcggct gtggtggtgc cttctggaca ggagcagaga   840
tacacctgcc atgtgcagca tgagggtttg cccaagcccc tcaccctgag atgggagccg   900
tcttcccagc ccaccatccc catcgtgggc atcattgctg gcctggttct ctttggagct   960
gtgatcactg gagctgtggt cgctgctgtg atgtggagga ggaagagctc agatagaaaa  1020
ggagggagct actctcaggc tgcaagcagt gacagtgccc agggctctga tgtgtctctc  1080
acagcttgta aagtg                                                  1095

<210> SEQ ID NO 194
<211> LENGTH: 864
<212> TYPE: DNA
<213> ORGANISM: Homo sapiens

<400> SEQUENCE: 194
atgggccaca cacggaggca gggaacatca ccatccaagt gtccatacct caatttcttt    60
cagctcttgg tgctggctgg tctttctcac ttctgttcag gtgttatcca cgtgaccaag    120
gaagtgaaag aagtggcaac gctgtcctgt ggtcacaatg tttctgttga agagctggca   180
caaactcgct ctactggca aaaggagaag aaaatggtgc tgactatgat gtctggggac   240
atgaatatat ggcccgagta caagaaccgg accatctttg atatcactaa taacctctcc   300
```

```
attgtgatcc tggctctgcg cccatctgac gagggcacat acgagtgtgt tgttctgaag      360
tatgaaaaag acgctttcaa gcgggaacac ctggctgaag tgacgttatc agtcaaagct      420
gacttcccta cacctagtat atctgacttt gaaattccaa cttctaatat tagaaggata      480
atttgctcaa cctctggagg ttttccagag cctcacctct cctggttgga aaatggagaa      540
gaattaaatg ccatcaacac aacagtttcc caagatcctg aaactgagct ctatgctgtt      600
agcagcaaac tggatttcaa tatgacaacc aaccacagct tcatgtgtct catcaagtat      660
ggacatttaa gagtgaatca gaccttcaac tggaatacaa ccaagcaaga gcattttcct      720
gataacctgc tcccatcctg ggccattacc ttaatctcag taaatggaat ttttgtgata      780
tgctgcctga cctactgctt tgccccaaga tgcagagaga aaggaggaa tgagagattg      840 agaagggaaa gtgtacgccc tgta                                             864

<210> SEQ ID NO 195
<211> LENGTH: 615
<212> TYPE: DNA
<213> ORGANISM: Homo sapiens

<400> SEQUENCE: 195
atgtcgcgcg gcctccagct tctgctcctg agctgcgcct acagcctggc tcccgcgacg      60
ccggaggtga aggtggcttg ctccgaagat gtggacttgc cctgcaccgc ccctgggat      120 ccgcaggttc cctacacggt ctcctgggtc aagttattgg agggtggtga agagaggatg      180
gagacacccc aggaagacca cctcagggga cagcactatc atcagaaggg gcaaaatggt      240
tctttcgacg cccccaatga aaggccctat tccctgaaga tccgaaacac taccagctgc      300
aactcgggga catacaggtg cactctgcag gacccggatg ggcagagaaa cctaagtggc      360
aaggtgatct tgagagtgac aggatgccct gcacagcgta aagaagagac ttttaagaaa      420
tacagagcgg agattgtcct gctgctggct ctggttatt tctacttaac actcatcatt      480
ttcacttgta gtttgcacg gctacagagt atcttcccag attttctaa agctggcatg      540 gaacgagctt ttctcccagt tacctcccca aataagcatt tagggctagt gactcctcac      600
aagacagaac tggta                                                       615

<210> SEQ ID NO 196
<211> LENGTH: 831
<212> TYPE: DNA
<213> ORGANISM: Homo sapiens

<400> SEQUENCE: 196
atggttcgtc tgcctctgca gtgcgtcctc tggggctgct tgctgaccgc tgtccatcca      60
gaaccaccca ctgcatgcag agaaaaacag tacctaataa acagtcagtg ctgttctttg      120
tgccagccag gacagaaact ggtgagtgac tgcacagagt tcactgaaac ggaatgcctt      180
ccttgcggtg aaagcgaatt cctagacacc tggaacagag agacacactg ccaccagcac      240
aaatactgcg accccaacct agggcttcgg gtccagcaga agggcacctc agaaacagac      300
accatctgca cctgtgaaga aggctggcac tgtacgagtg aggcctgtga gagctgtgtc      360
ctgcaccgct catgctcgcc cggctttggg gtcaagcaga ttgctacagg gtttctgat      420 accatctgcg agccctgccc agtcggcttc ttctccaatg tgtcatctgc tttcgaaaaa      480
tgtcacccct tggacaagct gtgagaccaaa gacctggttg tgcaacggc aggcacaaac      540 aagactgatg ttgtctgtgg tccccaggat cggctgagag ccctggtggt gatccccatc      600
```

```
atcttcggga tcctgtttgc catcctcttg gtgctggtct ttatcaaaaa ggtggccaag        660
aagccaacca ataaggcccc ccaccccaag caggaacccc aggagatcaa ttttcccgac        720
gatcttcctg gctccaacac tgctgctcca gtgcaggaga ctttacatgg atgccaaccg        780
gtcacccagg aggatggcaa agagagtcgc atctcagtgc aggagagaca g                 831

<210> SEQ ID NO 197
<211> LENGTH: 762
<212> TYPE: DNA
<213> ORGANISM: Homo sapiens

<400> SEQUENCE: 197
atggaatacg cctctgacgc ttcactggac cccgaagccc gtggcctcc cgcgccccgc         60 gctcgcgcct gccgcgtact gccttgggcc ctggtcgcgg ggctgctgct gctgctgctg        120
ctcgctgccg cctgcgccgt cttcctcgcc tgccctggg ccgtgtccgg ggctcgcgcc         180
tcgcccggct ccgcggccag cccgagactc cgcgagggtc ccgagctttc gcccgacgat        240
cccgccggcc tcttggacct gcggcagggc atgtttgcgc agctggtggc ccaaaatgtt        300
ctgctgatcg atgggcccct gagctggtac agtgacccag gcctggcagg cgtgtccctg        360
acggggggcc tgagctacaa agaggacacg aaggagctgg tggtggccaa ggctggagtc        420
tactatgtct tctttcaact agagctgcgg cgcgtggtgg ccggcgaggg ctcaggctcc        480
gtttcacttg cgctgcacct gcagccactg cgctctgctg ctggggccgc cgccctggct        540
ttgaccgtgg acctgccacc cgcctcctcc gaggctcgga actcggcctt cggtttccag        600
ggccgcttgc tgcacctgag tgccggccag cgcctgggcg tccatcttca cactgaggcc        660
agggcacgcc atgcctggca gcttacccag ggcgccacag tcttgggact cttccgggtg        720 accccgaaa tccagccgg actcccttca ccgaggtcgg aa                             762

<210> SEQ ID NO 198
<211> LENGTH: 9
<212> TYPE: PRT
<213> ORGANISM: Homo sapiens

<400> SEQUENCE: 198

Ser Leu Tyr Asn Thr Val Ala Thr Leu
1               5

<210> SEQ ID NO 199
<211> LENGTH: 21
<212> TYPE: DNA
<213> ORGANISM: Artificial Sequence
<220> FEATURE:
<223> OTHER INFORMATION: F primer 1

<400> SEQUENCE: 199
atcccagtgt ggtggtacgg g                                                  21

<210> SEQ ID NO 200
<211> LENGTH: 20
<212> TYPE: DNA
<213> ORGANISM: Artificial Sequence
<220> FEATURE:
<223> OTHER INFORMATION: R primer 1

<400> SEQUENCE: 200
gggtacatca cttcgattgc                                                    20

<210> SEQ ID NO 201
```

```
<211> LENGTH: 245
<212> TYPE: PRT
<213> ORGANISM: Homo sapiens

<400> SEQUENCE: 201

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Ser Thr Ser Gly Ser Gly Lys
        115                 120                 125

Pro Gly Ser Gly Glu Gly Ser Thr Lys Gly Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Lys Tyr Leu Asn Trp Tyr Gln Gln
                165                 170                 175

Lys Pro Asp Gly Thr Val Lys Leu Leu Ile Tyr His Thr Ser Arg Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Ile Ala Thr Tyr
    210                 215                 220

Phe Cys Gln Gln Gly Asn Thr Leu Pro Tyr Thr Phe Gly Gly Gly Thr
225                 230                 235                 240

Lys Leu Glu Ile Thr
                245

<210> SEQ ID NO 202
<211> LENGTH: 735
<212> TYPE: DNA
<213> ORGANISM: Homo sapiens

<400> SEQUENCE: 202
gaagtgaaac tgcaagagtc tggccctgga ctggtggccc catctcagtc tctgagcgtg     60
acctgtacag tcagcggagt gtccctgcct gattacggcg tgtcctggat cagacagcct    120
cctcggaaag gcctggaatg gctgggagtg atctggggca gcgagacaac ctactacaac    180
agcgccctga gtcccggct gaccatcatc aaggacaact ccaagagcca ggtgttcctg    240
aagatgaaca gcctgcagac cgacgacacc gccatctact attgcgccaa gcactactac    300
tacggcggca gctacgctat ggactattgg ggccagggca ccagcgttac agtgtcctcg    360
ggctctacaa gcggctctgg caagcctgga tctggcgagg gaagcaccaa gggcgatatc    420
cagatgaccc agacaacaag cagcctgagc gccagcctgg gcgatagagt gaccatcagc    480
tgtagagcca gccaggacat cagcaagtac ctgaactggt atcagcagaa acccgacggc    540
```

```
accgtgaagc tgctgatcta ccacaccagc agactgcaca gcggcgtgcc aagcagattt    600
tctggcagcg gctctggcac cgactacagc ctgaccatct ccaacctgga acaagaggat    660
atcgctacct acttctgcca gcaaggcaac accctgcctt acacctttgg cggaggcacc    720
aagctggaaa tcaca                                                     735
```

<210> SEQ ID NO 203
<211> LENGTH: 245
<212> TYPE: PRT
<213> ORGANISM: Homo sapiens

<400> SEQUENCE: 203

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245
```

<210> SEQ ID NO 204
<211> LENGTH: 735
<212> TYPE: DNA
<213> ORGANISM: Homo sapiens

<400> SEQUENCE: 204

```
gatatccaga tgacccagac aacaagcagc ctgagcgcca gcctgggcga tagagtgacc    60
atcagctgta gagccagcca ggacatcagc aagtacctga actggtatca gcagaaaccc   120
gacggcaccg tgaagctgct gatctaccac accagcagac tgcacagcgg cgtgccaagc   180
```

| | |
|---|---|
| agatttctg gcagcggctc tggcaccgac tacagcctga ccatctccaa cctggaacaa | 240 |
| gaggatatcg ctacctactt ctgccagcaa ggcaacaccc tgccttacac ctttggcgga | 300 |
| ggcaccaagc tggaaatcac aggctctaca agcggctctg caagcctggg atctggcgag | 360 |
| ggaagcacca agggcgaagt gaaactgcaa gagtctggcc ctggactggt ggccccatct | 420 |
| cagtctctga gcgtgacctg tacagtcagc ggagtgtccc tgcctgatta cggcgtgtcc | 480 |
| tggatcagac agcctcctcg gaaaggcctg aatggctggg agtgatctg gggcagcgag | 540 |
| acaacctact acaacagcgc cctgaagtcc cggctgacca tcatcaagga caactccaag | 600 |
| agccaggtgt tcctgaagat gaacagcctg cagaccgacg acaccgccat ctactattgc | 660 |
| gccaagcact actactacgg cggcagctac gctatggact attggggcca gggcaccagc | 720 |
| gttacagtgt cctcg | 735 |

<210> SEQ ID NO 205  
<211> LENGTH: 1668  
<212> TYPE: DNA  
<213> ORGANISM: Homo sapiens

<400> SEQUENCE: 205

| | |
|---|---|
| atgccacctc ctcgcctcct cttcttcctc ctcttcctca cccccatgga agtcaggccc | 60 |
| gaggaacctc tagtggtgaa ggtggaagag ggagataacg ctgtgctgca gtgcctcaag | 120 |
| gggacctcag atggccccac tcagcagctg acctggtctc gggagtcccc gcttaaaccc | 180 |
| ttcttaaaac tcagcctggg gctgccaggc ctgggaatcc acatgaggcc cctggccatc | 240 |
| tggcttttca tcttcaacgt ctctcaacag atgggggggct tctacctgtg ccagccgggg | 300 |
| ccccctctg agaaggcctg gcagcctggc tggacagtca atgtggaggg cagcggggag | 360 |
| ctgttccggt ggaatgtttc ggacctaggt ggcctgggct gtggcctgaa gaacaggtcc | 420 |
| tcagagggcc ccagctcccc ttccgggaag ctcatgagcc ccaagctgta tgtgtgggcc | 480 |
| aaagaccgcc tgagatctg ggaggggag cctccgtgtc tcccaccgag ggacagcctg | 540 |
| aaccagagcc tcagccagga cctcaccatg gcccctggct ccacactctg gctgtcctgt | 600 |
| ggggtacccc ctgactctgt gtccaggggc ccctctcct ggacccatgt gcaccccaag | 660 |
| gggcctaagt cattgctgag cctagagctg aaggacgatc gcccggccag agatatgtgg | 720 |
| gtaatggaga cgggtctgtt gttgccccgg gccacagctc aagacgctgg aaagtattat | 780 |
| tgtcaccgtg gcaacctgac catgtcattc cacctggaga tcactgctcg gccagtacta | 840 |
| tggcactggc tgctgaggac tggtggctgg aaggtctcag ctgtgacttt ggcttatctg | 900 |
| atcttctgcc tgtgttccct tgtgggcatt cttcatcttc aaagagccct ggtcctgagg | 960 |
| aggaaaagaa agcgaatgac tgaccccacc aggagattct tcaaagtgac gcctccccca | 1020 |
| ggaagcgggc cccagaacca gtacgggaac gtgctgtctc tccccacacc cacctcaggc | 1080 |
| ctcggacgcg cccagcgttg ggccgcaggc ctgggggggca ctgccccgtc ttatggaaac | 1140 |
| ccgagcagcg acgtccaggc ggatggagcc ttgggtcccc ggagcccgcc gggagtgggc | 1200 |
| ccagaagaag aggaagggga gggctatgag gaacctgaca gtgaggagga ctccgagttc | 1260 |
| tatgagaacg actccaacct tgggcaggac cagctctccc aggatggcag cggctacgag | 1320 |
| aaccctgagg atgagcccct gggtcctgag gatgaagact ccttctccaa cgctgagtct | 1380 |
| tatgagaacg aggatgaaga gctgaccag ccggtcgcca ggacaatgga cttcctgagc | 1440 |
| cctcatgggt cagcctggga ccccagccgg gaagcaacct ccctgggtc ccagtcctat | 1500 |
| gaggatatga gaggaatcct gtatgcagcc ccccagctcc gctccattcg gggccagcct | 1560 |

```
ggacccaatc atgaggaaga tgcagactct tatgagaaca tggataatcc cgatgggcca      1620
gacccagcct ggggaggagg gggccgcatg ggcacctgga gcaccagg                  1668
```

<210> SEQ ID NO 206
<211> LENGTH: 9
<212> TYPE: PRT
<213> ORGANISM: Homo sapiens

<400> SEQUENCE: 206

```
Ser Leu Leu Met Trp Ile Thr Gln Cys
1               5
```

<210> SEQ ID NO 207
<211> LENGTH: 9
<212> TYPE: PRT
<213> ORGANISM: Artificial Sequence
<220> FEATURE:
<223> OTHER INFORMATION: Peptide

<400> SEQUENCE: 207

```
Gly Leu Arg Met Trp Ile Lys Gln Val
1               5
```

<210> SEQ ID NO 208
<211> LENGTH: 711
<212> TYPE: DNA
<213> ORGANISM: Artificial Sequence
<220> FEATURE:
<223> OTHER INFORMATION: synthesized oligonucleotides

<400> SEQUENCE: 208

```
atggcggctg catctggaag cgtgctgcag agatgtatcg tgtcccagc cggcagacat       60 agcgccagcc tgattttct gcacggcagc ggcgattctg gccagggact gagaatgtgg      120
atcaaacagg tgctgaacca ggacctgacc ttccagcaca tcaagatcat ctaccccacc     180
gctccacctc ggagctacac acctatgaag ggcggcatca gcaacgtttg gttcgaccgg     240
ttcaagatca ccaacgactg ccccgagcac ctggaatcca tcgacgtgat gtgtcaggtg     300
ctcaccgacc tgatcgacga ggaagtgaag tccggcatca agaagaacag aatcctgatc     360
ggcggcttca gcatgggcgg ctgtatggcc attcacctgg cctacagaaa ccaccaggat     420
gtggctggcg tgttcgccct gagcagcttt ctgaacaaag ccagcgccgt gtatcaggcc     480
ctgcagaaat ctaacggcgt gctgcctgag ctgttccagt gtcatggcac agccgatgag     540
ctggtgctgc actcttgggc cgaagagaca aatagcatgc tgaaaagcct gggcgtgacc     600
accaagttcc acagcttccc caacgtgtac cacgagctga gcaagaccga gctggacatc     660
ctgaaactgt ggattctgac caagctgccc ggcgagatgg aaaagcagaa g              711
```

<210> SEQ ID NO 209
<211> LENGTH: 540
<212> TYPE: DNA
<213> ORGANISM: Artificial Sequence
<220> FEATURE:
<223> OTHER INFORMATION: synthesized oligonucleotides

<400> SEQUENCE: 209

```
atgcaggccg aaggccgggg cacagggggt tcgacgggcg atgctgatgg cccaggaggc      60
cctggcattc ctgatggccc aggggggcaat gctggcggcc caggagaggc gggtgccacg    120
ggcggcagag gtccccgggg cgcaggggca gcaagggcct cggggccggg aggaggcgcc    180
```

-continued

```
ccgcggggtc cgcatggcgg cgcggcttca gggctgaatg gatgctgcag atgcggggcc        240 aggggccgg  agagccgcct gcttgagttc tacctcgcca tgcctttcgc gacacccatg        300
gaagcagagc tggcccgcag gagcctggcc caggatgccc accgcttcc  cgtgccaggg        360 gtgcttctga aggagttcac tgtgtccggc aacatactga ctatccgact gactgctgca        420
gaccaccgcc aactgcagct ctccatcagc tcctgtctcc agcagctttc cctgttgatg        480
tggatcacgc agtgctttct gcccgtgttt ttggctcagc ctccctcagg gcagaggcgc        540
```

<210> SEQ ID NO 210
<211> LENGTH: 470
<212> TYPE: PRT
<213> ORGANISM: Artificial Sequence
<220> FEATURE:
<223> OTHER INFORMATION: Chimeric antigen receptor

<400> SEQUENCE: 210

```
Gln Ser Val Leu Thr Gln Pro Pro Ser Val Gly Ala Pro Gly Gln
1               5                   10                  15

Arg Val Thr Ile Ser Cys Thr Gly Ser Ser Ser Asn Leu Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Ser Thr Thr Arg Pro Ser Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Gly Thr Trp Asp Ser Ser
                85                  90                  95

Leu Ser Ala Gly Val Phe Gly Gly Gly Thr Gln Leu Thr Val Leu Gly
            100                 105                 110

Ser Thr Ser Gly Ser Gly Lys Pro Gly Ser Gly Glu Gly Ser Thr Lys
        115                 120                 125

Gly Glu Val Gln Leu Leu Glu Ser Gly Gly Gly Leu Val Gln Pro Gly
    130                 135                 140

Gly Ser Leu Arg Leu Ser Cys Ala Ala Ser Gly Phe Thr Phe Ser Thr
145                 150                 155                 160

Tyr Gln Met Ser Trp Val Arg Gln Ala Pro Gly Lys Gly Leu Glu Trp
                165                 170                 175

Val Ser Gly Ile Val Ser Ser Gly Gly Ser Thr Ala Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Gly Glu Leu Leu Pro Tyr Tyr Gly Met Asp Val Trp Gly Gln
225                 230                 235                 240

Gly Thr Thr Val Thr Val Ser Ser Ala Ala Ile Glu Val Met Tyr
                245                 250                 255

Pro Pro Pro Tyr Leu Asp Asn Glu Lys Ser Asn Gly Thr Ile Ile His
            260                 265                 270

Val Lys Gly Lys His Leu Cys Pro Ser Pro Leu Phe Pro Gly Pro Ser
        275                 280                 285

Lys Pro Phe Trp Val Leu Val Val Val Gly Gly Val Leu Ala Cys Tyr
    290                 295                 300
```

```
Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
            325                 330                 335

Pro Gly Pro Thr Arg Lys His Tyr Gln Pro Tyr Ala Pro Pro Arg Asp
            340                 345                 350

Phe Ala Ala Tyr Arg Ser Arg Val Lys Phe Ser Arg Ser Ala Asp Ala
            355                 360                 365

Pro Ala Tyr Gln Gln Gly Gln Asn Gln Leu Tyr Asn Glu Leu Asn Leu
370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
            405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
450                 455                 460

Gln Ala Leu Pro Pro Arg
465                 470

<210> SEQ ID NO 211
<211> LENGTH: 1410
<212> TYPE: DNA
<213> ORGANISM: Artificial Sequence
<220> FEATURE:
<223> OTHER INFORMATION: synthesized oligonucleotides

<400> SEQUENCE: 211
cagtctgtgc tgacgcagcc gccctcagtg tctggggccc cagggcagag ggtcaccatc     60
tcctgcactg ggagcagctc caacctcggg gcaggttatg atgtacactg gtaccagcag    120
cttccaggaa cagcccccaa actcctcatc tatggtagca ccactcggcc ctcagggatt    180
cctgaccgat tctctggctc caagtctggc acgtcagcca ccctgggcat caccggactc    240
cagactgggg acgaggccga ttattactgc ggaacatggg atagcagcct gagtgctggg    300
gtgttcggcg gaggcaccca gctgaccgtc ctcggctcta caagcggctc tgcaagcct     360 ggatctggcg agggaagcac caagggcgaa gtgcagctgc tggaatctgg cggcggactg    420
gtgcagcctg gcggatctct gagactgagc tgtgccgcca gcggcttcac cttcagcacc    480
taccagatga gctgggtgcg ccaggcccct ggcaaaggac tggaatgggt gtccggcatc    540
gtgtccagcg gcggctctac agcctacgcc gatagcgtga agggccggtt caccatcagc    600
cgggacaaca gcaagaacac cctgtacctg cagatgaaca gcctgagagc cgaggacacc    660
gccgtgtact attgtgccgg ggagctgctg ccctactacg gcatggatgt gtggggccag    720
ggcaccaccg tgacagtgtc ctcagcggcc gcaatcgaag tgatgtaccc ccctccctac    780
ctggacaacg agaagtccaa cggcaccatt atccacgtga agggaaagca cctgtgcccc    840
agccctctgt tccctggccc tagcaagcct ttctgggtgc tggtggtcgt gggcggagtg    900
ctggcctgtt atagcctgct cgtgaccgtg gccttcatca tcttttgggt gcgcagcaag    960
cggagccggc tgctgcacag cgactacatg aacatgaccc ccagacggcc cggacccacc   1020
agaaagcact accagcctta cgcccctccc agagacttcg ccgcctacag atctcgagtg   1080
```

-continued

```
aagttcagca gaagcgccga cgcccctgcc tatcagcagg gccagaacca gctgtacaac    1140
gagctgaacc tgggcagacg ggaagagtac gacgtgctgg acaagcggag aggcagggac    1200
cctgagatgg gcggcaagcc cagaagaaag aaccccagg aaggcctgta taacgaactg     1260
cagaaagaca gatggccga ggcctacagc gagatcggca tgaagggcga gcggagaaga    1320
ggcaagggcc acgatggcct gtaccagggc ctgagcaccg ccaccaagga cacctatgac    1380
gccctgcaca tgcaggccct gccccccaga                                     1410
```

<210> SEQ ID NO 212
<211> LENGTH: 467
<212> TYPE: PRT
<213> ORGANISM: Artificial Sequence
<220> FEATURE:
<223> OTHER INFORMATION: Chimeric antigen receptor

<400> SEQUENCE: 212

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Pro
                85                  90                  95

Lys Phe Thr Phe Gly Pro Gly Thr Lys Val Asp Ile Arg Gly Ser Thr
            100                 105                 110

Ser Gly Ser Gly Lys Pro Gly Ser Gly Glu Gly Ser Thr Lys Gly Gln
        115                 120                 125

Val Gln Leu Gln Glu Ser Gly Pro Gly Leu Val Lys Pro Ser Asp Thr
    130                 135                 140

Leu Ser Leu Thr Cys Leu Val Ser Gly Gly Ser Ile Ser Ser Asn Tyr
145                 150                 155                 160

Trp Ser Trp Ile Arg Gln Ala Pro Gly Lys Gly Leu Glu Trp Ile Gly
                165                 170                 175

His Val Ser Tyr Ser Gly Ser Thr Asn Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Glu Ser Tyr Tyr Tyr Gly Met Asp Val Trp Gly Gln Gly Thr Thr
225                 230                 235                 240

Val Thr Val Ser Ser Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Gly Gly Val Leu Ala Cys Tyr Ser Leu Leu
    290                 295                 300
```

```
Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
            355                 360                 365

Gln Gln Gly Gln Asn Gln Leu Tyr Asn Glu Leu Asn Leu Gly Arg Arg
        370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
            405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
        450                 455                 460

Pro Pro Arg
465

<210> SEQ ID NO 213
<211> LENGTH: 1401
<212> TYPE: DNA
<213> ORGANISM: Artificial Sequence
<220> FEATURE:
<223> OTHER INFORMATION: synthesized oligonucleotides

<400> SEQUENCE: 213
gaaattgtgt tgacgcagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catctatggt gcatccacca gggccactgg tatcccagcc       180
aggttcagtg gcagtgggtc tgggacagag ttcactctca ccatcagcag actggagcct       240
gaagattttg cagtgtatta ctgtcagcag tataataact ggcctccgaa attcactttc       300
ggccctggga ccaaagtgga tatcagaggc tctacaagcg ctctggcaa gcctggatct       360 ggcgagggaa gcaccaaggg ccaggtgcag ctgcaggagt cgggcccagg actggtgaag       420
ccttcggata cctgtccct cacctgtctt gtctctggtg gctccatcag tagtaattac       480
tggagctgga tccggcaggc cccagggaag ggactggagt ggattggaca tgtctcctac       540
agtgggagca ccaactacaa ccctccctc aagagtcgag ttaccatatc agtagacacg       600
tctaagaacc agttctccct gaagctgagc tctgtgactg ccgcggacac ggccgtgtat       660
tactgtgcga gagagtccta ctactactac ggtatgacg tctggggcca agggaccacg       720
gtcaccgtct cctcagcggc cgcaatcgaa gtgatgtacc ccctccta cctggacaac       780 gagaagtcca acggcaccat tatccacgtg aagggaaagc acctgtgccc cagccctctg       840
ttccctggcc ctagcaagcc tttctgggtg ctggtggtcg tgggcggagt gctggcctgt       900
tatagcctgc tcgtgaccgt ggccttcatc atctttggg tgcgcagcaa gcggagccgg       960
ctgctgcaca gcgactacat gaacatgacc cccagacggc ccggacccac cagaaagcac      1020
taccagcctt acgcccctcc cagagacttc gccgcctaca tctcgagt gaagttcagc      1080
```

```
agaagcgccg acgcccctgc ctatcagcag ggccagaacc agctgtacaa cgagctgaac    1140
ctgggcagac gggaagagta cgacgtgctg acaagcgga gaggcaggga ccctgagatg      1200
ggcggcaagc ccagaagaaa gaaccccag gaaggcctgt ataacgaact gcagaaagac     1260
aagatggccg aggcctacag cgagatcggc atgaagggcg agcggagaag aggcaagggc    1320
cacgatggcc tgtaccaggg cctgagcacc gccaccaagg acacctatga cgccctgcac    1380
atgcaggccc tgccccccag a                                              1401
```

<210> SEQ ID NO 214
<211> LENGTH: 249
<212> TYPE: PRT
<213> ORGANISM: Artificial Sequence
<220> FEATURE:
<223> OTHER INFORMATION: single chain Fv

<400> SEQUENCE: 214

```
Gln Ser Ala Leu Thr Gln Pro Arg Ser Val Gly Phe Pro Gly Gln
1               5                   10                  15

Ser Val Thr Ile Ser Cys Thr Gly Thr Thr Ser Asp Asp Val Ser Trp
            20                  25                  30

Tyr Gln Gln His Pro Gly Lys Ala Pro Gln Leu Met Leu Tyr Asp Val
        35                  40                  45

Ser Lys Arg Pro Ser Gly Val Pro His Arg Phe Ser Gly Ser Arg Ser
50                  55                  60

Gly Arg Ala Ala Ser Leu Ile Ile Ser Gly Leu Gln Thr Glu Asp Glu
65                  70                  75                  80

Ala Asp Tyr Phe Cys Cys Ser Tyr Ala Gly Arg Tyr Asn Ser Val Leu
                85                  90                  95

Phe Gly Gly Gly Thr Lys Leu Thr Val Leu Gly Ser Thr Ser Gly Ser
            100                 105                 110

Gly Lys Pro Gly Ser Gly Glu Gly Ser Thr Lys Gly Glu Val Gln Leu
        115                 120                 125

Val Glu Ser Gly Gly Gly Leu Val Gln Pro Gly Arg Ser Leu Arg Leu
130                 135                 140

Ser Cys Ala Ala Ser Gly Phe Thr Phe Asp Asp Tyr Ala Met His Trp
145                 150                 155                 160

Val Arg Gln Ala Pro Gly Lys Gly Leu Glu Trp Val Ser Gly Ile Ser
                165                 170                 175

Trp Asn Ser Gly Arg Ile Gly Tyr Ala Asp Ser Val Lys Gly Arg Phe
            180                 185                 190

Thr Ile Ser Arg Asp Asn Ala Lys Asn Ser Leu Phe Leu Gln Met Asn
        195                 200                 205

Ser Leu Arg Ala Glu Asp Thr Ala Val Tyr Tyr Cys Ala Arg Asp Gln
    210                 215                 220

Gly Tyr His Tyr Tyr Asp Ser Ala Glu His Ala Phe Asp Ile Trp Gly
225                 230                 235                 240

Gln Gly Thr Val Val Thr Val Ser Ser
                245
```

<210> SEQ ID NO 215
<211> LENGTH: 747
<212> TYPE: DNA
<213> ORGANISM: Artificial Sequence
<220> FEATURE:
<223> OTHER INFORMATION: synthesized oligonucleotides

<400> SEQUENCE: 215

```
caatctgctc tgacacagcc tagaagcgtg tccggctttc ctggccagag cgtgaccatc    60
agctgtaccg gcaccacctc cgatgacgtg tcctggtatc agcagcatcc tggcaaagcc   120
cctcagctga tgctgtacga cgtgtccaaa agacctagcg gcgtgcccca cagattcagc   180
ggatctagaa gtggcagagc cgccagcctg atcatctctg gactgcagac agaggacgag   240
gccgactact tctgctgtag ctacgccggc agatacaaca gcgtgctgtt tggcggcgga   300
acaaagctga cagtgctggg ctctacaagc ggctctggca gcctggatc tggcgaggga   360 agcaccaagg gcgaagtgca gcttgtggaa tctggcggag gactggtgca gcctggaaga   420
agcctgagac tgtcttgtgc cgccagcggc ttcaccttcg acgattatgc catgcactgg   480
gtccgacagg cccctggaaa aggccttgaa tgggtgtccg gcatctcttg gaacagcggc   540
agaatcggct acgccgactc tgtgaagggc agattcacca tcagccggga caacgccaag   600
aacagcctgt cctgcagat gaactccctg agagccgagg acaccgccgt gtactactgt   660
gccagagatc agggctacca ctactacgac tctgccgagc acgccttcga tatctggggc   720
cagggaacag tggtcaccgt tagttct                                        747
```

<210> SEQ ID NO 216
<211> LENGTH: 8
<212> TYPE: PRT
<213> ORGANISM: Homo sapiens

<400> SEQUENCE: 216

Gly Phe Thr Phe Asp Asp Tyr Ala
1               5

<210> SEQ ID NO 217
<211> LENGTH: 8
<212> TYPE: PRT
<213> ORGANISM: Homo sapiens

<400> SEQUENCE: 217

Ile Ser Trp Asn Ser Gly Arg Ile
1               5

<210> SEQ ID NO 218
<211> LENGTH: 18
<212> TYPE: PRT
<213> ORGANISM: Homo sapiens

<400> SEQUENCE: 218

Ala Arg Asp Gln Gly Tyr His Tyr Tyr Asp Ser Ala Glu His Ala Phe
1               5                   10                  15

Asp Ile

<210> SEQ ID NO 219
<211> LENGTH: 125
<212> TYPE: PRT
<213> ORGANISM: Homo sapiens

<400> SEQUENCE: 219

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

```
Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser
            115                 120             125
```

<210> SEQ ID NO 220
<211> LENGTH: 6
<212> TYPE: PRT
<213> ORGANISM: Homo sapiens

<400> SEQUENCE: 220

```
Lys Leu Gly Asp Lys Tyr
1               5
```

<210> SEQ ID NO 221
<211> LENGTH: 3
<212> TYPE: PRT
<213> ORGANISM: Homo sapiens

<400> SEQUENCE: 221

```
Gln Asp Ser
1
```

<210> SEQ ID NO 222
<211> LENGTH: 10
<212> TYPE: PRT
<213> ORGANISM: Homo sapiens

<400> SEQUENCE: 222

```
Gln Ala Trp Asp Ser Ser Thr His Val Val
1               5                   10
```

<210> SEQ ID NO 223
<211> LENGTH: 107
<212> TYPE: PRT
<213> ORGANISM: Homo sapiens

<400> SEQUENCE: 223

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr His Val
                85                  90                  95

Val Phe Gly Gly Gly Thr Lys Leu Thr Val Leu
                100                 105
```

<210> SEQ ID NO 224

```
<211> LENGTH: 9
<212> TYPE: PRT
<213> ORGANISM: Homo sapiens

<400> SEQUENCE: 224

Ser Ser Asp Val Gly Gly Tyr Asn Tyr
1               5

<210> SEQ ID NO 225
<211> LENGTH: 3
<212> TYPE: PRT
<213> ORGANISM: Homo sapiens

<400> SEQUENCE: 225

Asp Val Ser
1

<210> SEQ ID NO 226
<211> LENGTH: 11
<212> TYPE: PRT
<213> ORGANISM: Homo sapiens

<400> SEQUENCE: 226

Gly Thr Trp Asp Thr Ser Leu Thr Ala Val Val
1               5                   10

<210> SEQ ID NO 227
<211> LENGTH: 111
<212> TYPE: PRT
<213> ORGANISM: Homo sapiens

<400> SEQUENCE: 227

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Thr Gly Asp Glu Ala Asp Tyr Tyr Cys Gly Thr Trp Asp Thr Ser
                85                  90                  95

Leu Thr Ala Val Val Phe Gly Gly Gly Thr Glu Leu Thr Val Leu
            100                 105                 110

<210> SEQ ID NO 228
<211> LENGTH: 8
<212> TYPE: PRT
<213> ORGANISM: Homo sapiens

<400> SEQUENCE: 228

Trp Ser Asn Ile Gly Asp Asp His
1               5

<210> SEQ ID NO 229
<211> LENGTH: 3
<212> TYPE: PRT
<213> ORGANISM: Homo sapiens

<400> SEQUENCE: 229
```

Asp Thr Ser
1

<210> SEQ ID NO 230
<211> LENGTH: 11
<212> TYPE: PRT
<213> ORGANISM: Homo sapiens

<400> SEQUENCE: 230

Gly Thr Trp Glu Ser Ser Leu Ser Gly Val Val
1               5                   10

<210> SEQ ID NO 231
<211> LENGTH: 110
<212> TYPE: PRT
<213> ORGANISM: Homo sapiens

<400> SEQUENCE: 231

Gln Ser Val Leu Thr Gln Pro Pro Ser Val Ser Ala Ala Pro Gly Gln
1               5                   10                  15

Lys Val Thr Ile Ser Cys Ser Gly Ser Trp Ser Asn Ile Gly Asp Asp
            20                  25                  30

His Val Ser Trp Tyr Gln Gln Phe Pro Gly Ala Ala Pro Lys Leu Leu
        35                  40                  45

Ile Tyr Asp Thr Ser Lys Arg Pro Ser Arg Val Ala Asp Arg Phe Ser
    50                  55                  60

Gly Ser Lys Ser Gly Ala Ser Ala Thr Leu Ala Ile Thr Gly Leu Gln
65                  70                  75                  80

Ala Gly Asp Glu Ala Asp Tyr Tyr Cys Gly Thr Trp Glu Ser Ser Leu
                85                  90                  95

Ser Gly Val Val Phe Gly Gly Gly Thr Glu Leu Thr Val Leu
            100                 105                 110

<210> SEQ ID NO 232
<211> LENGTH: 9
<212> TYPE: PRT
<213> ORGANISM: Homo sapiens

<400> SEQUENCE: 232

Ser Ser Asp Val Gly Gly Tyr Asp Tyr
1               5

<210> SEQ ID NO 233
<211> LENGTH: 3
<212> TYPE: PRT
<213> ORGANISM: Homo sapiens

<400> SEQUENCE: 233

Asp Val Thr
1

<210> SEQ ID NO 234
<211> LENGTH: 10
<212> TYPE: PRT
<213> ORGANISM: Homo sapiens

<400> SEQUENCE: 234

Ser Ser Tyr Thr Thr Ser Thr Thr Trp Val
1               5                   10

<210> SEQ ID NO 235
<211> LENGTH: 111

```
<212> TYPE: PRT
<213> ORGANISM: Homo sapiens

<400> SEQUENCE: 235

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Thr Gly Asp Glu Ala Asp Tyr Tyr Cys Gly Thr Trp Asp Thr Ser
                85                  90                  95

Leu Thr Ala Val Val Phe Gly Gly Gly Thr Glu Leu Thr Val Leu
            100                 105                 110

<210> SEQ ID NO 236
<211> LENGTH: 9
<212> TYPE: PRT
<213> ORGANISM: Homo sapiens

<400> SEQUENCE: 236

Thr Ser Asp Val Gly Thr Thr Asn Tyr
1               5

<210> SEQ ID NO 237
<211> LENGTH: 3
<212> TYPE: PRT
<213> ORGANISM: Homo sapiens

<400> SEQUENCE: 237

Asp Val Thr
1

<210> SEQ ID NO 238
<211> LENGTH: 10
<212> TYPE: PRT
<213> ORGANISM: Homo sapiens

<400> SEQUENCE: 238

Ser Tyr Ala Gly Ser Tyr Thr Phe Val Val
1               5                   10

<210> SEQ ID NO 239
<211> LENGTH: 111
<212> TYPE: PRT
<213> ORGANISM: Homo sapiens

<400> SEQUENCE: 239

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asp Val Gly Thr Thr
            20                  25                  30

Asn Tyr Val Ser Trp Tyr Gln Gln His Pro Gly Lys Ala Pro Lys Leu
            35                  40                  45

Leu Ile Tyr Asp Val Thr Asn Arg Pro Ser Gly Val Pro Asp Arg Phe
        50                  55                  60
```

-continued

```
Ser Gly Ser Lys Ser Ala Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Phe Val Val Phe Gly Gly Gly Thr Glu Leu Thr Val Leu
            100                 105                 110

<210> SEQ ID NO 240
<211> LENGTH: 9
<212> TYPE: PRT
<213> ORGANISM: Homo sapiens

<400> SEQUENCE: 240

Ser Ser Asp Val Gly Val Tyr Asn Tyr
1               5

<210> SEQ ID NO 241
<211> LENGTH: 3
<212> TYPE: PRT
<213> ORGANISM: Homo sapiens

<400> SEQUENCE: 241

Asp Val Ser
1

<210> SEQ ID NO 242
<211> LENGTH: 11
<212> TYPE: PRT
<213> ORGANISM: Homo sapiens

<400> SEQUENCE: 242

Ala Ala Trp Asp Asp Ser Leu Asn Gly Val Val
1               5                   10

<210> SEQ ID NO 243
<211> LENGTH: 111
<212> TYPE: PRT
<213> ORGANISM: Homo sapiens

<400> SEQUENCE: 243

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Val Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Pro Asp Arg Phe
 50                  55                  60

Ser Gly Ser Lys Ser Ala Asn Thr Ala Ser Leu Thr Ile Ser Gly Leu
 65                  70                  75                  80

Gln Ala Glu Asp Glu Ala Asp Tyr Tyr Cys Ala Ala Trp Asp Asp Ser
                 85                  90                  95

Leu Asn Gly Val Val Phe Gly Gly Gly Thr Gln Leu Thr Val Leu
            100                 105                 110

<210> SEQ ID NO 244
<211> LENGTH: 8
<212> TYPE: PRT
<213> ORGANISM: Homo sapiens

<400> SEQUENCE: 244
```

Ser Ser Asn Ile Gly Asn Asn Tyr
1               5

<210> SEQ ID NO 245
<211> LENGTH: 3
<212> TYPE: PRT
<213> ORGANISM: Homo sapiens

<400> SEQUENCE: 245

Asp Asn Val
1

<210> SEQ ID NO 246
<211> LENGTH: 10
<212> TYPE: PRT
<213> ORGANISM: Homo sapiens

<400> SEQUENCE: 246

Ala Ala Trp Asp Asp Ser Leu Ser Ala Ile
1               5                   10

<210> SEQ ID NO 247
<211> LENGTH: 109
<212> TYPE: PRT
<213> ORGANISM: Homo sapiens

<400> SEQUENCE: 247

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Cys Trp Tyr Gln His Leu Pro Gly Thr Ala Pro Lys Leu Leu
        35                  40                  45

Ile Tyr Asp Asn Val Lys Arg Pro Ser Gly Ile Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ile Phe Gly Gly Gly Thr Glu Leu Thr Val Leu
            100                 105

<210> SEQ ID NO 248
<211> LENGTH: 9
<212> TYPE: PRT
<213> ORGANISM: Homo sapiens

<400> SEQUENCE: 248

Ser Ser Asp Val Gly Gly Tyr Asn Tyr
1               5

<210> SEQ ID NO 249
<211> LENGTH: 3
<212> TYPE: PRT
<213> ORGANISM: Homo sapiens

<400> SEQUENCE: 249

Asp Val Ser
1

<210> SEQ ID NO 250
<211> LENGTH: 10

```
<212> TYPE: PRT
<213> ORGANISM: Homo sapiens

<400> SEQUENCE: 250

His Ser Tyr Asp Ser Ser Leu Ser His Val
1               5                   10

<210> SEQ ID NO 251
<211> LENGTH: 110
<212> TYPE: PRT
<213> ORGANISM: Homo sapiens

<400> SEQUENCE: 251

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys His Ser Tyr Asp Ser Ser
                85                  90                  95

Leu Ser His Val Phe Gly Thr Gly Thr Lys Val Thr Val Leu
            100                 105                 110

<210> SEQ ID NO 252
<211> LENGTH: 6
<212> TYPE: PRT
<213> ORGANISM: Homo sapiens

<400> SEQUENCE: 252

Gln Ser Val Ser Ser Asn
1               5

<210> SEQ ID NO 253
<211> LENGTH: 3
<212> TYPE: PRT
<213> ORGANISM: Homo sapiens

<400> SEQUENCE: 253

Gly Ala Ser
1

<210> SEQ ID NO 254
<211> LENGTH: 11
<212> TYPE: PRT
<213> ORGANISM: Homo sapiens

<400> SEQUENCE: 254

Gln Gln Tyr Asn Asn Trp Pro Pro Leu Tyr Thr
1               5                   10

<210> SEQ ID NO 255
<211> LENGTH: 109
<212> TYPE: PRT
<213> ORGANISM: Homo sapiens

<400> SEQUENCE: 255

Glu Ile Val Leu Thr Gln Ser Pro Gly Thr Leu Ser Leu Ser Pro Gly
```

-continued

```
                1               5                  10                 15
        Glu Arg Ala Thr Leu Ser Cys Arg Ala Ser Gln Ser Val Ser Ser Asn
                        20                  25                  30

Leu Ala Trp Tyr Gln Gln Lys Pro Gly Gln Ala Pro Arg Leu Leu Ile
                        35                  40                  45

Tyr Gly Ala Ser Thr Arg Ala Thr Gly Ile Pro Ala Arg Phe Ser Gly
                        50                  55                  60

Ser Gly Ser Gly Thr Glu Phe Thr Leu Thr Ile Ser Ser Leu Gln Ser
         65                 70                  75                  80

Glu Asp Phe Ala Val Tyr Tyr Cys Gln Gln Tyr Asn Asn Trp Pro Pro
                        85                  90                  95

Leu Tyr Thr Phe Gly Gln Gly Thr Lys Leu Glu Ile Lys
                        100                 105
```

<210> SEQ ID NO 256
<211> LENGTH: 6
<212> TYPE: PRT
<213> ORGANISM: Homo sapiens

<400> SEQUENCE: 256

```
        Gln Ser Val Ser Ser Tyr
        1               5
```

<210> SEQ ID NO 257
<211> LENGTH: 3
<212> TYPE: PRT
<213> ORGANISM: Homo sapiens

<400> SEQUENCE: 257

```
        Asp Ala Ser
        1
```

<210> SEQ ID NO 258
<211> LENGTH: 10
<212> TYPE: PRT
<213> ORGANISM: Homo sapiens

<400> SEQUENCE: 258

```
        Gln Gln Ser Tyr Ser Thr Leu Leu Tyr Thr
        1               5                  10
```

<210> SEQ ID NO 259
<211> LENGTH: 108
<212> TYPE: PRT
<213> ORGANISM: Homo sapiens

<400> SEQUENCE: 259

```
                1               5                  10                 15
        Glu Ile Val Leu Thr Gln Ser Pro Gly Thr Leu Ser Leu Ser Pro Gly

Glu Arg Ala Thr Leu Ser Cys Arg Ala Ser Gln Ser Val Ser Ser Tyr
                        20                  25                  30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                        50                  55                  60

Ser Gly Ser Gly Thr Asp Phe Thr Leu Thr Ile Ser Ser Leu Glu Pro
         65                 70                  75                  80

Glu Asp Phe Ala Thr Tyr Tyr Cys Gln Gln Ser Tyr Ser Thr Leu Leu
                        85                  90                  95
```

-continued

Tyr Thr Phe Gly Gln Gly Thr Lys Leu Glu Ile Lys
            100                 105

<210> SEQ ID NO 260
<211> LENGTH: 6
<212> TYPE: PRT
<213> ORGANISM: Homo sapiens

<400> SEQUENCE: 260

Gln Ser Val Ser Ser Tyr
1               5

<210> SEQ ID NO 261
<211> LENGTH: 3
<212> TYPE: PRT
<213> ORGANISM: Homo sapiens

<400> SEQUENCE: 261

Asp Ala Ser
1

<210> SEQ ID NO 262
<211> LENGTH: 9
<212> TYPE: PRT
<213> ORGANISM: Homo sapiens

<400> SEQUENCE: 262

Gln Gln Tyr Asp Ser Leu Pro Leu Thr
1               5

<210> SEQ ID NO 263
<211> LENGTH: 107
<212> TYPE: PRT
<213> ORGANISM: Homo sapiens

<400> SEQUENCE: 263

Glu Ile Val Leu Thr Arg Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Ser Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ile Ala Thr Tyr Tyr Cys Gln Gln Tyr Asp Ser Leu Pro Leu
                85                  90                  95

Thr Phe Gly Gly Gly Thr Lys Leu Glu Ile Lys
            100                 105

<210> SEQ ID NO 264
<211> LENGTH: 7
<212> TYPE: PRT
<213> ORGANISM: Homo sapiens

<400> SEQUENCE: 264

Gln Thr Ile Ser Ala Ser Ser
1               5

<210> SEQ ID NO 265
<211> LENGTH: 3

```
<212> TYPE: PRT
<213> ORGANISM: Homo sapiens

<400> SEQUENCE: 265

Gly Ala Ser
1

<210> SEQ ID NO 266
<211> LENGTH: 9
<212> TYPE: PRT
<213> ORGANISM: Homo sapiens

<400> SEQUENCE: 266

Gln Gln Phe Asn Glu Trp Pro Leu Thr
1               5

<210> SEQ ID NO 267
<211> LENGTH: 108
<212> TYPE: PRT
<213> ORGANISM: Homo sapiens

<400> SEQUENCE: 267

Glu Ile Val Leu Thr Gln Ser Pro Ala Thr Leu Ser Leu Ser Pro Gly
1               5                   10                  15

Glu Arg Ala Thr Val Ser Cys Arg Pro Ser Gln Thr Ile Ser Ala Ser
            20                  25                  30

Ser Val Ala Trp Tyr Gln Gln Lys Ala Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asn Glu Trp Pro
                85                  90                  95

Leu Thr Phe Gly Gly Gly Thr Lys Val Glu Ile Lys
            100                 105

<210> SEQ ID NO 268
<211> LENGTH: 6
<212> TYPE: PRT
<213> ORGANISM: Homo sapiens

<400> SEQUENCE: 268

Gln Ser Val Ser Ser Asn
1               5

<210> SEQ ID NO 269
<211> LENGTH: 3
<212> TYPE: PRT
<213> ORGANISM: Homo sapiens

<400> SEQUENCE: 269

Gly Ala Ser
1

<210> SEQ ID NO 270
<211> LENGTH: 11
<212> TYPE: PRT
<213> ORGANISM: Homo sapiens

<400> SEQUENCE: 270

Gln Gln Tyr Gly Ser Ser Pro Asp Ile Phe Thr
```

<210> SEQ ID NO 271
<211> LENGTH: 109
<212> TYPE: PRT
<213> ORGANISM: Homo sapiens

<400> SEQUENCE: 271

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Leu Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Asp
                85                  90                  95

Ile Phe Thr Phe Gly Pro Gly Thr Lys Val Asp Ile Lys
            100                 105

<210> SEQ ID NO 272
<211> LENGTH: 250
<212> TYPE: PRT
<213> ORGANISM: Artificial Sequence
<220> FEATURE:
<223> OTHER INFORMATION: Anitgen binding domain of L4-18H

<400> SEQUENCE: 272

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr His Val
                85                  90                  95

Val Phe Gly Gly Gly Thr Lys Leu Thr Val Leu Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Arg Ser Leu Arg
    130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Arg Ile Gly Tyr Ala Asp Ser Val Lys Gly Arg
            180                 185                 190

Phe Thr Ile Ser Arg Asp Asn Ala Lys Asn Ser Leu Phe Leu Gln Met
        195                 200                 205

```
Asn Ser Leu Arg Ala Glu Asp Thr Ala Val Tyr Tyr Cys Ala Arg Asp
    210                 215                 220

Gln Gly Tyr His Tyr Tyr Asp Ser Ala Glu His Ala Phe Asp Ile Trp
225                 230                 235                 240

Gly Gln Gly Thr Val Val Thr Val Ser Ser
                245                 250

<210> SEQ ID NO 273
<211> LENGTH: 254
<212> TYPE: PRT
<213> ORGANISM: Artificial Sequence
<220> FEATURE:
<223> OTHER INFORMATION: Anitgen binding domain of L7-18H

<400> SEQUENCE: 273

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Gly Asp Glu Ala Asp Tyr Tyr Cys Gly Thr Trp Asp Thr Ser
                85                  90                  95

Leu Thr Ala Val Val Phe Gly Gly Gly Thr Glu Leu Thr Val Leu Gly
            100                 105                 110

Ser Thr Ser Gly Ser Gly Lys Pro Gly Ser Gly Glu Gly Ser Thr Lys
        115                 120                 125

Gly Glu Val Gln Leu Val Glu Ser Gly Gly Gly Leu Val Gln Pro Gly
    130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Arg Ile Gly Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Ala Glu Asp Thr Ala Val Tyr Tyr
    210                 215                 220

Cys Ala Arg Asp Gln Gly Tyr His Tyr Tyr Asp Ser Ala Glu His Ala
225                 230                 235                 240

Phe Asp Ile Trp Gly Gln Gly Thr Val Val Thr Val Ser Ser
                245                 250

<210> SEQ ID NO 274
<211> LENGTH: 253
<212> TYPE: PRT
<213> ORGANISM: Artificial Sequence
<220> FEATURE:
<223> OTHER INFORMATION: Anitgen binding domain of L9-18H

<400> SEQUENCE: 274

Gln Ser Val Leu Thr Gln Pro Pro Ser Val Ser Ala Ala Pro Gly Gln
```

```
                1               5                      10                      15
            Lys Val Thr Ile Ser Cys Ser Gly Ser Trp Ser Asn Ile Gly Asp Asp
                            20                      25                      30

His Val Ser Trp Tyr Gln Gln Phe Pro Gly Ala Ala Pro Lys Leu Leu
                            35                      40                      45

Ile Tyr Asp Thr Ser Lys Arg Pro Ser Arg Val Ala Asp Arg Phe Ser
                    50                      55                      60

Gly Ser Lys Ser Gly Ala Ser Ala Thr Leu Ala Ile Thr Gly Leu Gln
            65                      70                      75                      80

Ala Gly Asp Glu Ala Asp Tyr Tyr Cys Gly Thr Trp Glu Ser Ser Leu
                            85                      90                      95

Ser Gly Val Val Phe Gly Gly Thr Glu Leu Thr Val Leu Gly Ser
                            100                     105                     110

Thr Ser Gly Ser Gly Lys Pro Gly Ser Gly Glu Gly Ser Thr Lys Gly
                            115                     120                     125

Glu Val Gln Leu Val Glu Ser Gly Gly Gly Leu Val Gln Pro Gly Arg
                    130                     135                     140

Ser Leu Arg Leu Ser Cys Ala Ala Ser Gly Phe Thr Phe Asp Asp Tyr
            145                     150                     155                     160

Ala Met His Trp Val Arg Gln Ala Pro Gly Lys Gly Leu Glu Trp Val
                            165                     170                     175

Ser Gly Ile Ser Trp Asn Ser Gly Arg Ile Gly Tyr Ala Asp Ser Val
                            180                     185                     190

Lys Gly Arg Phe Thr Ile Ser Arg Asp Asn Ala Lys Asn Ser Leu Phe
                    195                     200                     205

Leu Gln Met Asn Ser Leu Arg Ala Glu Asp Thr Ala Val Tyr Tyr Cys
                    210                     215                     220

Ala Arg Asp Gln Gly Tyr His Tyr Tyr Asp Ser Ala Glu His Ala Phe
            225                     230                     235                     240

Asp Ile Trp Gly Gln Gly Thr Val Val Thr Val Ser Ser
                            245                     250

<210> SEQ ID NO 275
<211> LENGTH: 253
<212> TYPE: PRT
<213> ORGANISM: Artificial Sequence
<220> FEATURE:
<223> OTHER INFORMATION: Anitgen binding domain of L13-18H

<400> SEQUENCE: 275

Gln Ser Ala Leu Thr Gln Pro Ala Ser Val Ser Gly Ser Pro Gly Gln
            1               5                       10                      15

Ser Ile Thr Ile Ser Cys Thr Gly Leu Ser Ser Asp Val Gly Gly Tyr
                            20                      25                      30

Asp Tyr Val Ser Trp Tyr Gln Gln His Pro Gly Ile Ala Pro Lys Leu
                            35                      40                      45

Met Ile Tyr Asp Val Thr Asn Arg Pro Ser Gly Val Ser Ser Arg Phe
                    50                      55                      60

Ser Gly Ser Lys Ser Gly Asn Thr Ala Ser Leu Thr Ile Ser Gly Leu
            65                      70                      75                      80

Gln Ala Glu Asp Glu Ala Asp Tyr Tyr Cys Ser Ser Tyr Thr Thr Ser
                            85                      90                      95

Thr Thr Trp Val Phe Gly Ala Gly Thr Lys Leu Thr Val Leu Gly Ser
                            100                     105                     110

Thr Ser Gly Ser Gly Lys Pro Gly Ser Gly Glu Gly Ser Thr Lys Gly
```

```
            115                 120                 125
Glu Val Gln Leu Val Glu Ser Gly Gly Gly Leu Val Gln Pro Gly Arg
    130                 135                 140

Ser Leu Arg Leu Ser Cys Ala Ala Ser Gly Phe Thr Phe Asp Asp Tyr
145                 150                 155                 160

Ala Met His Trp Val Arg Gln Ala Pro Gly Lys Gly Leu Glu Trp Val
                165                 170                 175

Ser Gly Ile Ser Trp Asn Ser Gly Arg Ile Gly Tyr Ala Asp Ser Val
            180                 185                 190

Lys Gly Arg Phe Thr Ile Ser Arg Asp Asn Ala Lys Asn Ser Leu Phe
        195                 200                 205

Leu Gln Met Asn Ser Leu Arg Ala Glu Asp Thr Ala Val Tyr Tyr Cys
    210                 215                 220

Ala Arg Asp Gln Gly Tyr His Tyr Tyr Asp Ser Ala Glu His Ala Phe
225                 230                 235                 240

Asp Ile Trp Gly Gln Gly Thr Val Val Thr Val Ser Ser
                245                 250

<210> SEQ ID NO 276
<211> LENGTH: 254
<212> TYPE: PRT
<213> ORGANISM: Artificial Sequence
<220> FEATURE:
<223> OTHER INFORMATION: Anitgen binding domain of L14-18H

<400> SEQUENCE: 276

Gln Ser Ala Leu Thr Gln Pro Ala Ser Val Ser Gly Ser Pro Gly Gln
1               5                   10                  15

Ser Ile Thr Ile Ser Cys Thr Gly Thr Thr Ser Asp Val Gly Thr Thr
            20                  25                  30

Asn Tyr Val Ser Trp Tyr Gln Gln His Pro Gly Lys Ala Pro Lys Leu
        35                  40                  45

Leu Ile Tyr Asp Val Thr Asn Arg Pro Ser Gly Val Pro Asp Arg Phe
    50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Val Val Phe Gly Gly Gly Thr Glu Leu Thr Val Leu Gly
            100                 105                 110

Ser Thr Ser Gly Ser Gly Lys Pro Gly Ser Gly Glu Gly Ser Thr Lys
        115                 120                 125

Gly Glu Val Gln Leu Val Glu Ser Gly Gly Gly Leu Val Gln Pro Gly
    130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Arg Ile Gly Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Ala Glu Asp Thr Ala Val Tyr Tyr
    210                 215                 220

Cys Ala Arg Asp Gln Gly Tyr His Tyr Tyr Asp Ser Ala Glu His Ala
```

```
                225                 230                 235                 240
Phe Asp Ile Trp Gly Gln Gly Thr Val Val Thr Val Ser Ser
                    245                 250

<210> SEQ ID NO 277
<211> LENGTH: 254
<212> TYPE: PRT
<213> ORGANISM: Artificial Sequence
<220> FEATURE:
<223> OTHER INFORMATION: Anitgen binding domain of L16-18H

<400> SEQUENCE: 277

Gln Ser Ala Leu Thr Gln Pro Pro Ser Ala Gly Ser Pro Gly Gln
1               5                   10                  15

Ser Val Thr Ile Ser Cys Thr Gly Thr Ser Ser Asp Val Gly Val Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
    50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Tyr Cys Ala Ala Trp Asp Asp Ser
                85                  90                  95

Leu Asn Gly Val Val Phe Gly Gly Gly Thr Gln Leu Thr Val Leu Gly
                100                 105                 110

Ser Thr Ser Gly Ser Gly Lys Pro Gly Ser Gly Glu Gly Ser Thr Lys
            115                 120                 125

Gly Glu Val Gln Leu Val Glu Ser Gly Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Arg Ile Gly Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Ala Glu Asp Thr Ala Val Tyr Tyr
    210                 215                 220

Cys Ala Arg Asp Gln Gly Tyr His Tyr Tyr Asp Ser Ala Glu His Ala
225                 230                 235                 240

Phe Asp Ile Trp Gly Gln Gly Thr Val Val Thr Val Ser Ser
                245                 250

<210> SEQ ID NO 278
<211> LENGTH: 252
<212> TYPE: PRT
<213> ORGANISM: Artificial Sequence
<220> FEATURE:
<223> OTHER INFORMATION: Anitgen binding domain of L17-18H

<400> SEQUENCE: 278

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30
```

```
Tyr Val Cys Trp Tyr Gln His Leu Pro Gly Thr Ala Pro Lys Leu Leu
             35                  40                  45

Ile Tyr Asp Asn Val Lys Arg Pro Ser Gly Ile Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Ala Ile Phe Gly Gly Gly Thr Glu Leu Thr Val Leu Gly Ser Thr
            100                 105                 110

Ser Gly Ser Gly Lys Pro Gly Ser Gly Glu Gly Ser Thr Lys Gly Glu
            115                 120                 125

Val Gln Leu Val Glu Ser Gly Gly Gly Leu Val Gln Pro Gly Arg Ser
130                 135                 140

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
                165                 170                 175

Gly Ile Ser Trp Asn Ser Gly Arg Ile Gly Tyr Ala Asp Ser Val Lys
            180                 185                 190

Gly Arg Phe Thr Ile Ser Arg Asp Asn Ala Lys Asn Ser Leu Phe Leu
            195                 200                 205

Gln Met Asn Ser Leu Arg Ala Glu Asp Thr Ala Val Tyr Tyr Cys Ala
210                 215                 220

Arg Asp Gln Gly Tyr His Tyr Tyr Asp Ser Ala Glu His Ala Phe Asp
225                 230                 235                 240

Ile Trp Gly Gln Gly Thr Val Val Thr Val Ser Ser
            245                 250

<210> SEQ ID NO 279
<211> LENGTH: 253
<212> TYPE: PRT
<213> ORGANISM: Artificial Sequence
<220> FEATURE:
<223> OTHER INFORMATION: Anitgen binding domain of L22-18H

<400> SEQUENCE: 279

Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Gln Ser Glu Asp Glu Ala Asp Tyr Tyr Cys His Ser Tyr Asp Ser Ser
                 85                  90                  95

Leu Ser His Val Phe Gly Thr Gly Thr Lys Val Thr Val Leu Gly Ser
            100                 105                 110

Thr Ser Gly Ser Gly Lys Pro Gly Ser Gly Glu Gly Ser Thr Lys Gly
            115                 120                 125

Glu Val Gln Leu Val Glu Ser Gly Gly Gly Leu Val Gln Pro Gly Arg
            130                 135                 140
```

```
Ser Leu Arg Leu Ser Cys Ala Ala Ser Gly Phe Thr Phe Asp Asp Tyr
145                 150                 155                 160

Ala Met His Trp Val Arg Gln Ala Pro Gly Lys Gly Leu Glu Trp Val
                165                 170                 175

Ser Gly Ile Ser Trp Asn Ser Gly Arg Ile Gly Tyr Ala Asp Ser Val
            180                 185                 190

Lys Gly Arg Phe Thr Ile Ser Arg Asp Asn Ala Lys Asn Ser Leu Phe
        195                 200                 205

Leu Gln Met Asn Ser Leu Arg Ala Glu Asp Thr Ala Val Tyr Tyr Cys
    210                 215                 220

Ala Arg Asp Gln Gly Tyr His Tyr Tyr Asp Ser Ala Glu His Ala Phe
225                 230                 235                 240

Asp Ile Trp Gly Gln Gly Thr Val Val Thr Val Ser Ser
                245                 250
```

<210> SEQ ID NO 280
<211> LENGTH: 252
<212> TYPE: PRT
<213> ORGANISM: Artificial Sequence
<220> FEATURE:
<223> OTHER INFORMATION: Anitgen binding domain of K4-18H

<400> SEQUENCE: 280

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Tyr Thr Phe Gly Gln Gly Thr Lys Leu Glu Ile Lys Gly Ser Thr
            100                 105                 110

Ser Gly Ser Gly Lys Pro Gly Ser Gly Glu Gly Ser Thr Lys Gly Glu
        115                 120                 125

Val Gln Leu Val Glu Ser Gly Gly Gly Leu Val Gln Pro Gly Arg Ser
    130                 135                 140

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
                165                 170                 175

Gly Ile Ser Trp Asn Ser Gly Arg Ile Gly Tyr Ala Asp Ser Val Lys
            180                 185                 190

Gly Arg Phe Thr Ile Ser Arg Asp Asn Ala Lys Asn Ser Leu Phe Leu
        195                 200                 205

Gln Met Asn Ser Leu Arg Ala Glu Asp Thr Ala Val Tyr Tyr Cys Ala
    210                 215                 220

Arg Asp Gln Gly Tyr His Tyr Tyr Asp Ser Ala Glu His Ala Phe Asp
225                 230                 235                 240

Ile Trp Gly Gln Gly Thr Val Val Thr Val Ser Ser
                245                 250
```

```
<210> SEQ ID NO 281
<211> LENGTH: 251
<212> TYPE: PRT
<213> ORGANISM: Artificial Sequence
<220> FEATURE:
<223> OTHER INFORMATION: Anitgen binding domain of K5-18H

<400> SEQUENCE: 281

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Tyr Ser Thr Leu Leu
                85                  90                  95

Tyr Thr Phe Gly Gln Gly Thr Lys Leu Glu Ile Lys Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Arg Ser Leu
130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Gly
                165                 170                 175

Ile Ser Trp Asn Ser Gly Arg Ile Gly Tyr Ala Asp Ser Val Lys Gly
            180                 185                 190

Arg Phe Thr Ile Ser Arg Asp Asn Ala Lys Asn Ser Leu Phe Leu Gln
        195                 200                 205

Met Asn Ser Leu Arg Ala Glu Asp Thr Ala Val Tyr Tyr Cys Ala Arg
    210                 215                 220

Asp Gln Gly Tyr His Tyr Tyr Asp Ser Ala Glu His Ala Phe Asp Ile
225                 230                 235                 240

Trp Gly Gln Gly Thr Val Val Thr Val Ser Ser
                245                 250

<210> SEQ ID NO 282
<211> LENGTH: 250
<212> TYPE: PRT
<213> ORGANISM: Artificial Sequence
<220> FEATURE:
<223> OTHER INFORMATION: Anitgen binding domain of K6-18H

<400> SEQUENCE: 282

Glu Ile Val Leu Thr Arg Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Ser Ala Arg Phe Ser Gly
50                  55                  60
```

```
Ser Gly Ser Gly Thr Glu Phe Thr Leu Thr Ile Ser Ser Leu Gln Ser
 65                  70                  75                  80

Glu Asp Ile Ala Thr Tyr Tyr Cys Gln Gln Tyr Asp Ser Leu Pro Leu
                 85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
            115                 120                 125

Leu Val Glu Ser Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Arg Ile Gly Tyr Ala Asp Ser Val Lys Gly Arg
                180                 185                 190

Phe Thr Ile Ser Arg Asp Asn Ala Lys Asn Ser Leu Phe Leu Gln Met
            195                 200                 205

Asn Ser Leu Arg Ala Glu Asp Thr Ala Val Tyr Tyr Cys Ala Arg Asp
210                 215                 220

Gln Gly Tyr His Tyr Tyr Asp Ser Ala Glu His Ala Phe Asp Ile Trp
225                 230                 235                 240

Gly Gln Gly Thr Val Val Thr Val Ser Ser
            245                 250

<210> SEQ ID NO 283
<211> LENGTH: 251
<212> TYPE: PRT
<213> ORGANISM: Artificial Sequence
<220> FEATURE:
<223> OTHER INFORMATION: Anitgen binding domain of K9-18H

<400> SEQUENCE: 283

Glu Ile Val Leu Thr Gln Ser Pro Ala Thr Leu Ser Leu Ser Pro Gly
1               5                   10                  15

Glu Arg Ala Thr Val Ser Cys Arg Pro Ser Gln Thr Ile Ser Ala Ser
                20                  25                  30

Ser Val Ala Trp Tyr Gln Gln Lys Ala Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Asn Glu Trp Pro
                 85                  90                  95

Leu Thr Phe Gly Gly Gly Thr Lys Val Glu Ile Lys Gly Ser Thr Ser
            100                 105                 110

Gly Ser Gly Lys Pro Gly Ser Gly Glu Gly Ser Thr Lys Gly Glu Val
            115                 120                 125

Gln Leu Val Glu Ser Gly Gly Leu Val Gln Pro Gly Arg Ser Leu
130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Gly
                165                 170                 175
```

```
Ile Ser Trp Asn Ser Gly Arg Ile Gly Tyr Ala Asp Ser Val Lys Gly
            180                 185                 190

Arg Phe Thr Ile Ser Arg Asp Asn Ala Lys Asn Ser Leu Phe Leu Gln
            195                 200                 205

Met Asn Ser Leu Arg Ala Glu Asp Thr Ala Val Tyr Tyr Cys Ala Arg
210                 215                 220

Asp Gln Gly Tyr His Tyr Tyr Asp Ser Ala Glu His Ala Phe Asp Ile
225                 230                 235                 240

Trp Gly Gln Gly Thr Val Val Thr Val Ser Ser
                245                 250

<210> SEQ ID NO 284
<211> LENGTH: 252
<212> TYPE: PRT
<213> ORGANISM: Artificial Sequence
<220> FEATURE:
<223> OTHER INFORMATION: Anitgen binding domain of K10-18H

<400> SEQUENCE: 284

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Leu Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Asp
                85                  90                  95

Ile Phe Thr Phe Gly Pro Gly Thr Lys Val Asp Ile Lys Gly Ser Thr
            100                 105                 110

Ser Gly Ser Gly Lys Pro Gly Ser Gly Glu Gly Ser Thr Lys Gly Glu
        115                 120                 125

Val Gln Leu Val Glu Ser Gly Gly Gly Leu Val Gln Pro Gly Arg Ser
    130                 135                 140

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
                165                 170                 175

Gly Ile Ser Trp Asn Ser Gly Arg Ile Gly Tyr Ala Asp Ser Val Lys
            180                 185                 190

Gly Arg Phe Thr Ile Ser Arg Asp Asn Ala Lys Asn Ser Leu Phe Leu
        195                 200                 205

Gln Met Asn Ser Leu Arg Ala Glu Asp Thr Ala Val Tyr Tyr Cys Ala
    210                 215                 220

Arg Asp Gln Gly Tyr His Tyr Tyr Asp Ser Ala Glu His Ala Phe Asp
225                 230                 235                 240

Ile Trp Gly Gln Gly Thr Val Val Thr Val Ser Ser
                245                 250

<210> SEQ ID NO 285
<211> LENGTH: 472
<212> TYPE: PRT
<213> ORGANISM: Artificial Sequence
```

```
<220> FEATURE:
<223> OTHER INFORMATION: L4-18H CAR

<400> SEQUENCE: 285

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr His Val
                85                  90                  95

Val Phe Gly Gly Gly Thr Lys Leu Thr Val Leu Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Arg Ile Gly Tyr Ala Asp Ser Val Lys Gly Arg
            180                 185                 190

Phe Thr Ile Ser Arg Asp Asn Ala Lys Asn Ser Leu Phe Leu Gln Met
        195                 200                 205

Asn Ser Leu Arg Ala Glu Asp Thr Ala Val Tyr Tyr Cys Ala Arg Asp
    210                 215                 220

Gln Gly Tyr His Tyr Tyr Asp Ser Ala Glu His Ala Phe Asp Ile Trp
225                 230                 235                 240

Gly Gln Gly Thr Val Val Thr Val Ser Ser Ala Ala Ala Ile Glu Val
                245                 250                 255

Met Tyr Pro Pro Pro Tyr Leu Asp Asn Glu Lys Ser Asn Gly Thr Ile
            260                 265                 270

Ile His Val Lys Gly Lys His Leu Cys Pro Ser Pro Leu Phe Pro Gly
        275                 280                 285

Pro Ser Lys Pro Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400
```

```
Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 286
<211> LENGTH: 476
<212> TYPE: PRT
<213> ORGANISM: Artificial Sequence
<220> FEATURE:
<223> OTHER INFORMATION: L7-18H CAR

<400> SEQUENCE: 286

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Gly Asp Glu Ala Asp Tyr Tyr Cys Gly Thr Trp Asp Thr Ser
                85                  90                  95

Leu Thr Ala Val Val Phe Gly Gly Gly Thr Glu Leu Thr Val Leu Gly
            100                 105                 110

Ser Thr Ser Gly Ser Gly Lys Pro Gly Ser Gly Glu Gly Ser Thr Lys
        115                 120                 125

Gly Glu Val Gln Leu Val Glu Ser Gly Gly Gly Leu Val Gln Pro Gly
    130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Arg Ile Gly Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Ala Glu Asp Thr Ala Val Tyr Tyr
    210                 215                 220

Cys Ala Arg Asp Gln Gly Tyr His Tyr Tyr Asp Ser Ala Glu His Ala
225                 230                 235                 240

Phe Asp Ile Trp Gly Gln Gly Thr Val Val Thr Val Ser Ser Ala Ala
                245                 250                 255

Ala Ile Glu Val Met Tyr Pro Pro Pro Tyr Leu Asp Asn Glu Lys Ser
            260                 265                 270

Asn Gly Thr Ile Ile His Val Lys Gly Lys His Leu Cys Pro Ser Pro
        275                 280                 285
```

-continued

```
Leu Phe Pro Gly Pro Ser Lys Pro Phe Trp Val Leu Val Val Gly
    290                 295                 300
Gly Val Leu Ala Cys Tyr Ser Leu Leu Val Thr Val Ala Phe Ile Ile
305                 310                 315                 320
Phe Trp Val Arg Ser Lys Arg Ser Arg Leu Leu His Ser Asp Tyr Met
                325                 330                 335
Asn Met Thr Pro Arg Arg Pro Gly Pro Thr Arg Lys His Tyr Gln Pro
            340                 345                 350
Tyr Ala Pro Pro Arg Asp Phe Ala Ala Tyr Arg Ser Arg Val Lys Phe
        355                 360                 365
Ser Arg Ser Ala Asp Ala Pro Ala Tyr Gln Gln Gly Gln Asn Gln Leu
    370                 375                 380
Tyr Asn Glu Leu Asn Leu Gly Arg Arg Glu Glu Tyr Asp Val Leu Asp
385                 390                 395                 400
Lys Arg Arg Gly Arg Asp Pro Glu Met Gly Gly Lys Pro Arg Arg Lys
                405                 410                 415
Asn Pro Gln Glu Gly Leu Tyr Asn Glu Leu Gln Lys Asp Lys Met Ala
            420                 425                 430
Glu Ala Tyr Ser Glu Ile Gly Met Lys Gly Glu Arg Arg Arg Gly Lys
        435                 440                 445
Gly His Asp Gly Leu Tyr Gln Gly Leu Ser Thr Ala Thr Lys Asp Thr
    450                 455                 460
Tyr Asp Ala Leu His Met Gln Ala Leu Pro Pro Arg
465                 470                 475

<210> SEQ ID NO 287
<211> LENGTH: 475
<212> TYPE: PRT
<213> ORGANISM: Artificial Sequence
<220> FEATURE:
<223> OTHER INFORMATION: L9-18H CAR

<400> SEQUENCE: 287

Gln Ser Val Leu Thr Gln Pro Pro Ser Val Ser Ala Ala Pro Gly Gln
1               5                   10                  15
Lys Val Thr Ile Ser Cys Ser Gly Ser Trp Ser Asn Ile Gly Asp Asp
            20                  25                  30
His Val Ser Trp Tyr Gln Gln Phe Pro Gly Ala Ala Pro Lys Leu Leu
        35                  40                  45
Ile Tyr Asp Thr Ser Lys Arg Pro Ser Arg Val Ala Asp Arg Phe Ser
    50                  55                  60
Gly Ser Lys Ser Gly Ala Ser Ala Thr Leu Ala Ile Thr Gly Leu Gln
65                  70                  75                  80
Ala Gly Asp Glu Ala Asp Tyr Tyr Cys Gly Thr Trp Glu Ser Ser Leu
                85                  90                  95
Ser Gly Val Val Phe Gly Gly Gly Thr Glu Leu Thr Val Leu Gly Ser
            100                 105                 110
Thr Ser Gly Ser Gly Lys Pro Gly Ser Gly Glu Gly Ser Thr Lys Gly
        115                 120                 125
Glu Val Gln Leu Val Glu Ser Gly Gly Gly Leu Val Gln Pro Gly Arg
    130                 135                 140
Ser Leu Arg Leu Ser Cys Ala Ala Ser Gly Phe Thr Phe Asp Asp Tyr
145                 150                 155                 160
Ala Met His Trp Val Arg Gln Ala Pro Gly Lys Gly Leu Glu Trp Val
                165                 170                 175
```

```
Ser Gly Ile Ser Trp Asn Ser Gly Arg Ile Gly Tyr Ala Asp Ser Val
            180                 185                 190

Lys Gly Arg Phe Thr Ile Ser Arg Asp Asn Ala Lys Asn Ser Leu Phe
        195                 200                 205

Leu Gln Met Asn Ser Leu Arg Ala Glu Asp Thr Ala Val Tyr Tyr Cys
    210                 215                 220

Ala Arg Asp Gln Gly Tyr His Tyr Tyr Asp Ser Ala Glu His Ala Phe
225                 230                 235                 240

Asp Ile Trp Gly Gln Gly Thr Val Val Thr Val Ser Ala Ala Ala
                245                 250                 255

Ile Glu Val Met Tyr Pro Pro Pro Tyr Leu Asp Asn Glu Lys Ser Asn
                260                 265                 270

Gly Thr Ile Ile His Val Lys Gly Lys His Leu Cys Pro Ser Pro Leu
            275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
                340                 345                 350

Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
                420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 288
<211> LENGTH: 475
<212> TYPE: PRT
<213> ORGANISM: Artificial Sequence
<220> FEATURE:
<223> OTHER INFORMATION: L13-18H CAR

<400> SEQUENCE: 288

Gln Ser Ala Leu Thr Gln Pro Ala Ser Val Ser Gly Ser Pro Gly Gln
1               5                   10                  15

Ser Ile Thr Ile Ser Cys Thr Gly Leu Ser Ser Asp Val Gly Gly Tyr
            20                  25                  30

Asp Tyr Val Ser Trp Tyr Gln Gln His Pro Gly Ile Ala Pro Lys Leu
        35                  40                  45

Met Ile Tyr Asp Val Thr Asn Arg Pro Ser Gly Val Ser Ser Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                 85                  90                  95

Thr Thr Trp Val Phe Gly Ala Gly Thr Lys Leu Thr Val Leu Gly Ser
            100                 105                 110

Thr Ser Gly Ser Gly Lys Pro Gly Ser Gly Glu Gly Ser Thr Lys Gly
        115                 120                 125

Glu Val Gln Leu Val Glu Ser Gly Gly Leu Val Gln Pro Gly Arg
    130                 135                 140

Ser Leu Arg Leu Ser Cys Ala Ala Ser Gly Phe Thr Phe Asp Asp Tyr
145                 150                 155                 160

Ala Met His Trp Val Arg Gln Ala Pro Gly Lys Gly Leu Glu Trp Val
                165                 170                 175

Ser Gly Ile Ser Trp Asn Ser Gly Arg Ile Gly Tyr Ala Asp Ser Val
            180                 185                 190

Lys Gly Arg Phe Thr Ile Ser Arg Asp Asn Ala Lys Asn Ser Leu Phe
        195                 200                 205

Leu Gln Met Asn Ser Leu Arg Ala Glu Asp Thr Ala Val Tyr Tyr Cys
210                 215                 220

Ala Arg Asp Gln Gly Tyr His Tyr Tyr Asp Ser Ala Glu His Ala Phe
225                 230                 235                 240

Asp Ile Trp Gly Gln Gly Thr Val Val Thr Val Ser Ser Ala Ala Ala
                245                 250                 255

Ile Glu Val Met Tyr Pro Pro Pro Tyr Leu Asp Asn Glu Lys Ser Asn
                260                 265                 270

Gly Thr Ile Ile His Val Lys Gly Lys His Leu Cys Pro Ser Pro Leu
            275                 280                 285

Phe Pro Gly Pro Ser Lys Pro Phe Trp Val Leu Val Val Val Gly Gly
        290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
                340                 345                 350

Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
        370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
        450                 455                 460

Asp Ala Leu His Met Gln Ala Leu Pro Pro Arg
465                 470                 475
```

```
<210> SEQ ID NO 289
<211> LENGTH: 476
<212> TYPE: PRT
<213> ORGANISM: Artificial Sequence
<220> FEATURE:
<223> OTHER INFORMATION: L14-18H CAR

<400> SEQUENCE: 289
```

| | | | | | | | | | | | | | | | |
|---|---|---|---|---|---|---|---|---|---|---|---|---|---|---|---|
| Gln | Ser | Ala | Leu | Thr | Gln | Pro | Ala | Ser | Val | Ser | Gly | Ser | Pro | Gly | Gln |
| 1 | | | | 5 | | | | | 10 | | | | | 15 | |
| Ser | Ile | Thr | Ile | Ser | Cys | Thr | Gly | Thr | Thr | Ser | Asp | Val | Gly | Thr | Thr |
| | | | 20 | | | | | 25 | | | | | 30 | | |
| Asn | Tyr | Val | Ser | Trp | Tyr | Gln | Gln | His | Pro | Gly | Lys | Ala | Pro | Lys | Leu |
| | | 35 | | | | | 40 | | | | | 45 | | | |
| Leu | Ile | Tyr | Asp | Val | Thr | Asn | Arg | Pro | Ser | Gly | Val | Pro | Asp | Arg | Phe |
| 50 | | | | | 55 | | | | | 60 | | | | | |
| Ser | Gly | Ser | Lys | Ser | Ala | Asn | Thr | Ala | Ser | Leu | Thr | Ile | Ser | Gly | Leu |
| 65 | | | | | 70 | | | | | 75 | | | | | 80 |
| Gln | Ala | Glu | Asp | Glu | Ala | Asp | Tyr | Tyr | Cys | Cys | Ser | Tyr | Ala | Gly | Ser |
| | | | | 85 | | | | | 90 | | | | | 95 | |
| Tyr | Thr | Phe | Val | Val | Phe | Gly | Gly | Gly | Thr | Glu | Leu | Thr | Val | Leu | Gly |
| | | | 100 | | | | | 105 | | | | | 110 | | |
| Ser | Thr | Ser | Gly | Ser | Gly | Lys | Pro | Gly | Ser | Gly | Glu | Gly | Ser | Thr | Lys |
| | | 115 | | | | | 120 | | | | | 125 | | | |
| Gly | Glu | Val | Gln | Leu | Val | Glu | Ser | Gly | Gly | Gly | Leu | Val | Gln | Pro | Gly |
| 130 | | | | | 135 | | | | | 140 | | | | | |
| Arg | Ser | Leu | Arg | Leu | Ser | Cys | Ala | Ala | Ser | Gly | Phe | Thr | Phe | Asp | Asp |
| 145 | | | | | 150 | | | | | 155 | | | | | 160 |
| Tyr | Ala | Met | His | Trp | Val | Arg | Gln | Ala | Pro | Gly | Lys | Gly | Leu | Glu | Trp |
| | | | | 165 | | | | | 170 | | | | | 175 | |
| Val | Ser | Gly | Ile | Ser | Trp | Asn | Ser | Gly | Arg | Ile | Gly | Tyr | Ala | Asp | Ser |
| | | | 180 | | | | | 185 | | | | | 190 | | |
| Val | Lys | Gly | Arg | Phe | Thr | Ile | Ser | Arg | Asp | Asn | Ala | Lys | Asn | Ser | Leu |
| | | 195 | | | | | 200 | | | | | 205 | | | |
| Phe | Leu | Gln | Met | Asn | Ser | Leu | Arg | Ala | Glu | Asp | Thr | Ala | Val | Tyr | Tyr |
| 210 | | | | | 215 | | | | | 220 | | | | | |
| Cys | Ala | Arg | Asp | Gln | Gly | Tyr | His | Tyr | Tyr | Asp | Ser | Ala | Glu | His | Ala |
| 225 | | | | | 230 | | | | | 235 | | | | | 240 |
| Phe | Asp | Ile | Trp | Gly | Gln | Gly | Thr | Val | Val | Thr | Val | Ser | Ser | Ala | Ala |
| | | | | 245 | | | | | 250 | | | | | 255 | |
| Ala | Ile | Glu | Val | Met | Tyr | Pro | Pro | Pro | Tyr | Leu | Asp | Asn | Glu | Lys | Ser |
| | | | 260 | | | | | 265 | | | | | 270 | | |
| Asn | Gly | Thr | Ile | Ile | His | Val | Lys | Gly | Lys | His | Leu | Cys | Pro | Ser | Pro |
| | | 275 | | | | | 280 | | | | | 285 | | | |
| Leu | Phe | Pro | Gly | Pro | Ser | Lys | Pro | Phe | Trp | Val | Leu | Val | Val | Val | Gly |
| 290 | | | | | 295 | | | | | 300 | | | | | |
| Gly | Val | Leu | Ala | Cys | Tyr | Ser | Leu | Leu | Val | Thr | Val | Ala | Phe | Ile | Ile |
| 305 | | | | | 310 | | | | | 315 | | | | | 320 |
| Phe | Trp | Val | Arg | Ser | Lys | Arg | Ser | Arg | Leu | Leu | His | Ser | Asp | Tyr | Met |
| | | | | 325 | | | | | 330 | | | | | 335 | |
| Asn | Met | Thr | Pro | Arg | Arg | Pro | Gly | Pro | Thr | Arg | Lys | His | Tyr | Gln | Pro |
| | | | 340 | | | | | 345 | | | | | 350 | | |
| Tyr | Ala | Pro | Pro | Arg | Asp | Phe | Ala | Ala | Tyr | Arg | Ser | Arg | Val | Lys | Phe |
| | | 355 | | | | | 360 | | | | | 365 | | | |

Ser Arg Ser Ala Asp Ala Pro Ala Tyr Gln Gln Gly Gln Asn Gln Leu
370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
                435                 440                 445

Gly His Asp Gly Leu Tyr Gln Gly Leu Ser Thr Ala Thr Lys Asp Thr
                450                 455                 460

Tyr Asp Ala Leu His Met Gln Ala Leu Pro Pro Arg
465                 470                 475

<210> SEQ ID NO 290
<211> LENGTH: 476
<212> TYPE: PRT
<213> ORGANISM: Artificial Sequence
<220> FEATURE:
<223> OTHER INFORMATION: L16-18H CAR

<400> SEQUENCE: 290

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Val Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Tyr Cys Ala Ala Trp Asp Asp Ser
                85                  90                  95

Leu Asn Gly Val Val Phe Gly Gly Gly Thr Gln Leu Thr Val Leu Gly
                100                 105                 110

Ser Thr Ser Gly Ser Gly Lys Pro Gly Ser Gly Glu Gly Ser Thr Lys
                115                 120                 125

Gly Glu Val Gln Leu Val Glu Ser Gly Gly Gly Leu Val Gln Pro Gly
130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Arg Ile Gly Tyr Ala Asp Ser
                180                 185                 190

Val Lys Gly Arg Phe Thr Ile Ser Arg Asp Asn Ala Lys Asn Ser Leu
                195                 200                 205

Phe Leu Gln Met Asn Ser Leu Arg Ala Glu Asp Thr Ala Val Tyr Tyr
210                 215                 220

Cys Ala Arg Asp Gln Gly Tyr His Tyr Tyr Asp Ser Ala Glu His Ala
225                 230                 235                 240

Phe Asp Ile Trp Gly Gln Gly Thr Val Val Thr Val Ser Ser Ala Ala
                245                 250                 255

```
Ala Ile Glu Val Met Tyr Pro Pro Tyr Leu Asp Asn Glu Lys Ser
                260                 265                 270

Asn Gly Thr Ile Ile His Val Lys Gly Lys His Leu Cys Pro Ser Pro
            275                 280                 285

Leu Phe Pro Gly Pro Ser Lys Pro Phe Trp Val Leu Val Val Gly
    290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
                325                 330                 335

Asn Met Thr Pro Arg Arg Pro Gly Pro Thr Arg Lys His Tyr Gln Pro
            340                 345                 350

Tyr Ala Pro Pro Arg Asp Phe Ala Ala Tyr Arg Ser Arg Val Lys Phe
            355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 291
<211> LENGTH: 474
<212> TYPE: PRT
<213> ORGANISM: Artificial Sequence
<220> FEATURE:
<223> OTHER INFORMATION: L17-18H CAR

<400> SEQUENCE: 291

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Cys Trp Tyr Gln His Leu Pro Gly Thr Ala Pro Lys Leu Leu
        35                  40                  45

Ile Tyr Asp Asn Val Lys Arg Pro Ser Gly Ile Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ile Phe Gly Gly Gly Thr Glu Leu Thr Val Leu Gly Ser Thr
            100                 105                 110

Ser Gly Ser Gly Lys Pro Gly Ser Gly Glu Gly Ser Thr Lys Gly Glu
        115                 120                 125

Val Gln Leu Val Glu Ser Gly Gly Gly Leu Val Gln Pro Gly Arg Ser
    130                 135                 140
```

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
            165                 170                 175

Gly Ile Ser Trp Asn Ser Gly Arg Ile Gly Tyr Ala Asp Ser Val Lys
        180                 185                 190

Gly Arg Phe Thr Ile Ser Arg Asp Asn Ala Lys Asn Ser Leu Phe Leu
    195                 200                 205

Gln Met Asn Ser Leu Arg Ala Glu Asp Thr Ala Val Tyr Tyr Cys Ala
210                 215                 220

Arg Asp Gln Gly Tyr His Tyr Tyr Asp Ser Ala Glu His Ala Phe Asp
225                 230                 235                 240

Ile Trp Gly Gln Gly Thr Val Thr Val Ser Ser Ala Ala Ala Ile
        245                 250                 255

Glu Val Met Tyr Pro Pro Pro Tyr Leu Asp Asn Glu Lys Ser Asn Gly
            260                 265                 270

Thr Ile Ile His Val Lys Gly Lys His Leu Cys Pro Ser Pro Leu Phe
        275                 280                 285

Pro Gly Pro Ser Lys Pro Phe Trp Val Leu Val Val Val Gly Gly Val
290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
            340                 345                 350

Pro Pro Arg Asp Phe Ala Ala Tyr Arg Ser Arg Val Lys Phe Ser Arg
        355                 360                 365

Ser Ala Asp Ala Pro Ala Tyr Gln Gln Gly Gln Asn Gln Leu Tyr Asn
370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
            405                 410                 415

Gln Glu Gly Leu Tyr Asn Glu Leu Gln Lys Asp Lys Met Ala Glu Ala
        420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
450                 455                 460

Ala Leu His Met Gln Ala Leu Pro Pro Arg
465                 470

<210> SEQ ID NO 292
<211> LENGTH: 475
<212> TYPE: PRT
<213> ORGANISM: Artificial Sequence
<220> FEATURE:
<223> OTHER INFORMATION: L22-18H CAR

<400> SEQUENCE: 292

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

```
Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Gln Ser Glu Asp Glu Ala Asp Tyr Tyr Cys His Ser Tyr Asp Ser Ser
                 85                  90                  95

Leu Ser His Val Phe Gly Thr Gly Thr Lys Val Thr Val Leu Gly Ser
                100                 105                 110

Thr Ser Gly Ser Gly Lys Pro Gly Ser Gly Glu Gly Ser Thr Lys Gly
                115                 120                 125

Glu Val Gln Leu Val Glu Ser Gly Gly Gly Leu Val Gln Pro Gly Arg
130                 135                 140

Ser Leu Arg Leu Ser Cys Ala Ala Ser Gly Phe Thr Phe Asp Asp Tyr
145                 150                 155                 160

Ala Met His Trp Val Arg Gln Ala Pro Gly Lys Gly Leu Glu Trp Val
                165                 170                 175

Ser Gly Ile Ser Trp Asn Ser Gly Arg Ile Gly Tyr Ala Asp Ser Val
                180                 185                 190

Lys Gly Arg Phe Thr Ile Ser Arg Asp Asn Ala Lys Asn Ser Leu Phe
                195                 200                 205

Leu Gln Met Asn Ser Leu Arg Ala Glu Asp Thr Ala Val Tyr Tyr Cys
                210                 215                 220

Ala Arg Asp Gln Gly Tyr His Tyr Tyr Asp Ser Ala Glu His Ala Phe
225                 230                 235                 240

Asp Ile Trp Gly Gln Gly Thr Val Val Thr Val Ser Ser Ala Ala Ala
                245                 250                 255

Ile Glu Val Met Tyr Pro Pro Pro Tyr Leu Asp Asn Glu Lys Ser Asn
                260                 265                 270

Gly Thr Ile Ile His Val Lys Gly Lys His Leu Cys Pro Ser Pro Leu
                275                 280                 285

Phe Pro Gly Pro Ser Lys Pro Phe Trp Val Leu Val Val Val Gly Gly
                290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
                340                 345                 350

Ala Pro Pro Arg Asp Phe Ala Ala Tyr Arg Ser Arg Val Lys Phe Ser
                355                 360                 365

Arg Ser Ala Asp Ala Pro Ala Tyr Gln Gln Gly Gln Asn Gln Leu Tyr
                370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
                420                 425                 430

Ala Tyr Ser Glu Ile Gly Met Lys Gly Glu Arg Arg Arg Gly Lys Gly
                435                 440                 445

His Asp Gly Leu Tyr Gln Gly Leu Ser Thr Ala Thr Lys Asp Thr Tyr
```

```
                    450                 455                 460
Asp Ala Leu His Met Gln Ala Leu Pro Pro Arg
465                 470                 475

<210> SEQ ID NO 293
<211> LENGTH: 474
<212> TYPE: PRT
<213> ORGANISM: Artificial Sequence
<220> FEATURE:
<223> OTHER INFORMATION: K4-18H CAR

<400> SEQUENCE: 293

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Tyr Thr Phe Gly Gln Gly Thr Lys Leu Glu Ile Lys Gly Ser Thr
            100                 105                 110

Ser Gly Ser Gly Lys Pro Gly Ser Gly Glu Gly Ser Thr Lys Gly Glu
        115                 120                 125

Val Gln Leu Val Glu Ser Gly Gly Gly Leu Val Gln Pro Gly Arg Ser
130                 135                 140

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
                165                 170                 175

Gly Ile Ser Trp Asn Ser Gly Arg Ile Gly Tyr Ala Asp Ser Val Lys
            180                 185                 190

Gly Arg Phe Thr Ile Ser Arg Asp Asn Ala Lys Asn Ser Leu Phe Leu
        195                 200                 205

Gln Met Asn Ser Leu Arg Ala Glu Asp Thr Ala Val Tyr Tyr Cys Ala
210                 215                 220

Arg Asp Gln Gly Tyr His Tyr Tyr Asp Ser Ala Glu His Ala Phe Asp
225                 230                 235                 240

Ile Trp Gly Gln Gly Thr Val Val Thr Val Ser Ser Ala Ala Ala Ile
                245                 250                 255

Glu Val Met Tyr Pro Pro Pro Tyr Leu Asp Asn Glu Lys Ser Asn Gly
            260                 265                 270

Thr Ile Ile His Val Lys Gly Lys His Leu Cys Pro Ser Pro Leu Phe
        275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
```

```
                        340                 345                 350
Pro Pro Arg Asp Phe Ala Ala Tyr Arg Ser Arg Val Lys Phe Ser Arg
                355                 360                 365

Ser Ala Asp Ala Pro Ala Tyr Gln Gln Gly Gln Asn Gln Leu Tyr Asn
            370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
                435                 440                 445

Asp Gly Leu Tyr Gln Gly Leu Ser Thr Ala Thr Lys Asp Thr Tyr Asp
            450                 455                 460

Ala Leu His Met Gln Ala Leu Pro Pro Arg
465                 470

<210> SEQ ID NO 294
<211> LENGTH: 473
<212> TYPE: PRT
<213> ORGANISM: Artificial Sequence
<220> FEATURE:
<223> OTHER INFORMATION: K5-18H CAR

<400> SEQUENCE: 294

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Tyr Ser Thr Leu Leu
                85                  90                  95

Tyr Thr Phe Gly Gln Gly Thr Lys Leu Glu Ile Lys Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Arg Ser Leu
    130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Gly
                165                 170                 175

Ile Ser Trp Asn Ser Gly Arg Ile Gly Tyr Ala Asp Ser Val Lys Gly
            180                 185                 190

Arg Phe Thr Ile Ser Arg Asp Asn Ala Lys Asn Ser Leu Phe Leu Gln
        195                 200                 205

Met Asn Ser Leu Arg Ala Glu Asp Thr Ala Val Tyr Tyr Cys Ala Arg
    210                 215                 220

Asp Gln Gly Tyr His Tyr Tyr Asp Ser Ala Glu His Ala Phe Asp Ile
```

```
                225                 230                 235                 240
Trp Gly Gln Gly Thr Val Val Thr Val Ser Ser Ala Ala Ala Ile Glu
                    245                 250                 255

Val Met Tyr Pro Pro Pro Tyr Leu Asp Asn Glu Lys Ser Asn Gly Thr
                260                 265                 270

Ile Ile His Val Lys Gly Lys His Leu Cys Pro Ser Pro Leu Phe Pro
            275                 280                 285

Gly Pro Ser Lys Pro Phe Trp Val Leu Val Val Val Gly Gly Val Leu
        290                 295                 300

Ala Cys Tyr Ser Leu Leu Val Thr Val Ala Phe Ile Ile Phe Trp Val
305                 310                 315                 320

Arg Ser Lys Arg Ser Arg Leu Leu His Ser Asp Tyr Met Asn Met Thr
                325                 330                 335

Pro Arg Arg Pro Gly Pro Thr Arg Lys His Tyr Gln Pro Tyr Ala Pro
                340                 345                 350

Pro Arg Asp Phe Ala Ala Tyr Arg Ser Arg Val Lys Phe Ser Arg Ser
            355                 360                 365

Ala Asp Ala Pro Ala Tyr Gln Gln Gly Gln Asn Gln Leu Tyr Asn Glu
        370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
                420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
        450                 455                 460

Leu His Met Gln Ala Leu Pro Pro Arg
465                 470

<210> SEQ ID NO 295
<211> LENGTH: 472
<212> TYPE: PRT
<213> ORGANISM: Artificial Sequence
<220> FEATURE:
<223> OTHER INFORMATION: K6-18H CAR

<400> SEQUENCE: 295

Glu Ile Val Leu Thr Arg Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Ser Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Ile Ala Thr Tyr Tyr Cys Gln Gln Tyr Asp Ser Leu Pro Leu
                85                  90                  95

Thr Phe Gly Gly Gly Thr Lys Leu Glu Ile Lys Gly Ser Thr Ser Gly
                100                 105                 110

Ser Gly Lys Pro Gly Ser Gly Glu Gly Ser Thr Lys Gly Glu Val Gln
```

```
                115                 120                 125
Leu Val Glu Ser Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Asn Ser Gly Arg Ile Gly Tyr Ala Asp Ser Val Lys Gly Arg
            180                 185                 190

Phe Thr Ile Ser Arg Asp Asn Ala Lys Asn Ser Leu Phe Leu Gln Met
        195                 200                 205

Asn Ser Leu Arg Ala Glu Asp Thr Ala Val Tyr Tyr Cys Ala Arg Asp
210                 215                 220

Gln Gly Tyr His Tyr Tyr Asp Ser Ala Glu His Ala Phe Asp Ile Trp
225                 230                 235                 240

Gly Gln Gly Thr Val Thr Val Ser Ser Ala Ala Ala Ile Glu Val
                245                 250                 255

Met Tyr Pro Pro Pro Tyr Leu Asp Asn Glu Lys Ser Asn Gly Thr Ile
            260                 265                 270

Ile His Val Lys Gly Lys His Leu Cys Pro Ser Pro Leu Phe Pro Gly
        275                 280                 285

Pro Ser Lys Pro Phe Trp Val Leu Val Val Val Gly Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 296
<211> LENGTH: 473
<212> TYPE: PRT
<213> ORGANISM: Artificial Sequence
<220> FEATURE:
<223> OTHER INFORMATION: K9-18H CAR

<400> SEQUENCE: 296

Glu Ile Val Leu Thr Gln Ser Pro Ala Thr Leu Ser Leu Ser Pro Gly
```

-continued

```
1               5                   10                  15
Glu Arg Ala Thr Val Ser Cys Arg Pro Ser Gln Thr Ile Ser Ala Ser
                20                  25                  30

Ser Val Ala Trp Tyr Gln Gln Lys Ala Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asn Glu Trp Pro
                85                  90                  95

Leu Thr Phe Gly Gly Gly Thr Lys Val Glu Ile Lys Gly Ser Thr Ser
                100                 105                 110

Gly Ser Gly Lys Pro Gly Ser Gly Glu Gly Ser Thr Lys Gly Glu Val
                115                 120                 125

Gln Leu Val Glu Ser Gly Gly Gly Leu Val Gln Pro Gly Arg Ser Leu
        130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Gly
                165                 170                 175

Ile Ser Trp Asn Ser Gly Arg Ile Gly Tyr Ala Asp Ser Val Lys Gly
                180                 185                 190

Arg Phe Thr Ile Ser Arg Asp Asn Ala Lys Asn Ser Leu Phe Leu Gln
                195                 200                 205

Met Asn Ser Leu Arg Ala Glu Asp Thr Ala Val Tyr Tyr Cys Ala Arg
        210                 215                 220

Asp Gln Gly Tyr His Tyr Asp Ser Ala Glu His Ala Phe Asp Ile
225                 230                 235                 240

Trp Gly Gln Gly Thr Val Val Thr Val Ser Ser Ala Ala Ile Glu
                245                 250                 255

Val Met Tyr Pro Pro Pro Tyr Leu Asp Asn Glu Lys Ser Asn Gly Thr
                260                 265                 270

Ile Ile His Val Lys Gly Lys His Leu Cys Pro Ser Pro Leu Phe Pro
        275                 280                 285

Gly Pro Ser Lys Pro Phe Trp Val Leu Val Val Gly Gly Val Leu
        290                 295                 300

Ala Cys Tyr Ser Leu Leu Val Thr Val Ala Phe Ile Ile Phe Trp Val
305                 310                 315                 320

Arg Ser Lys Arg Ser Arg Leu Leu His Ser Asp Tyr Met Asn Met Thr
                325                 330                 335

Pro Arg Arg Pro Gly Pro Thr Arg Lys His Tyr Gln Pro Tyr Ala Pro
                340                 345                 350

Pro Arg Asp Phe Ala Ala Tyr Arg Ser Arg Val Lys Phe Ser Arg Ser
                355                 360                 365

Ala Asp Ala Pro Ala Tyr Gln Gln Gly Gln Asn Gln Leu Tyr Asn Glu
        370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
                420                 425                 430
```

Ser Glu Ile Gly Met Lys Gly Glu Arg Arg Gly Lys Gly His Asp
            435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 297
<211> LENGTH: 474
<212> TYPE: PRT
<213> ORGANISM: Artificial Sequence
<220> FEATURE:
<223> OTHER INFORMATION: K10-18H CAR

<400> SEQUENCE: 297

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Leu Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Asp
                85                  90                  95

Ile Phe Thr Phe Gly Pro Gly Thr Lys Val Asp Ile Lys Gly Ser Thr
            100                 105                 110

Ser Gly Ser Gly Lys Pro Gly Ser Gly Glu Gly Ser Thr Lys Gly Glu
        115                 120                 125

Val Gln Leu Val Glu Ser Gly Gly Gly Leu Val Gln Pro Gly Arg Ser
    130                 135                 140

Leu Arg Leu Ser Cys Ala Ala Ser Gly Phe Thr Phe Asp Asp Tyr Ala
145                 150                 155                 160

Met His Trp Val Arg Gln Ala Pro Gly Lys Gly Leu Glu Trp Val Ser
                165                 170                 175

Gly Ile Ser Trp Asn Ser Gly Arg Ile Gly Tyr Ala Asp Ser Val Lys
            180                 185                 190

Gly Arg Phe Thr Ile Ser Arg Asp Asn Ala Lys Asn Ser Leu Phe Leu
        195                 200                 205

Gln Met Asn Ser Leu Arg Ala Glu Asp Thr Ala Val Tyr Tyr Cys Ala
    210                 215                 220

Arg Asp Gln Gly Tyr His Tyr Tyr Asp Ser Glu His Ala Phe Asp
225                 230                 235                 240

Ile Trp Gly Gln Gly Thr Val Val Thr Val Ser Ser Ala Ala Ala Ile
                245                 250                 255

Glu Val Met Tyr Pro Pro Pro Tyr Leu Asp Asn Glu Lys Ser Asn Gly
            260                 265                 270

Thr Ile Ile His Val Lys Gly Lys His Leu Cys Pro Ser Pro Leu Phe
        275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

```
Val Arg Ser Lys Arg Ser Arg Leu Leu His Ser Asp Tyr Met Asn Met
            325                 330                 335

Thr Pro Arg Arg Pro Gly Pro Thr Arg Lys His Tyr Gln Pro Tyr Ala
            340                 345                 350

Pro Pro Arg Asp Phe Ala Ala Tyr Arg Ser Arg Val Lys Phe Ser Arg
            355                 360                 365

Ser Ala Asp Ala Pro Ala Tyr Gln Gln Gly Gln Asn Gln Leu Tyr Asn
            370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
            405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
            450                 455                 460

Ala Leu His Met Gln Ala Leu Pro Pro Arg
465                 470
```

<210> SEQ ID NO 298
<211> LENGTH: 1416
<212> TYPE: DNA
<213> ORGANISM: Artificial Sequence
<220> FEATURE:
<223> OTHER INFORMATION: Polynucleotide coding L4-18H CAR

<400> SEQUENCE: 298

```
tcctatgagc tgactcagcc accctcagtg tccgtgtctc caggacagac agccagcatc      60
acctgctctg gagataaaatt gggggataaa tatgcttgct ggtatcagca gaagccaggc     120
cagtcccctg tgctggtcat ctatcaagat agcaagcggc cctcagggat ccctgagcga     180
ttctctggct ccaactctgg gaacacagca ctctgaccca tcagcgggac ccaggctatg     240
gatgaggctg actattactg tcaggcgtgg gacagcagca cacatgtggt attcggcgga     300
gggaccaagc tgaccgtcct aggctctaca agcggctctg gcaagcctgg atctggcgag     360
ggaagcacca agggcgaagt gcagcttgtg aatctggcg gaggactggt gcagcctgga     420
agaagcctga actgtcttg tgccgccagc ggcttcacct tcgacgatta tgccatgcac     480
tgggtccgac aggcccctgg aaaaggcctt gaatgggtgt ccggcatctc ttggaacagc     540
ggcagaatcg gctacgccga ctctgtgaag gcagattca ccatcagccg ggacaacgcc      600
aagaacagcc tgttcctgca gatgaactcc ctgagagccg aggacaccgc cgtgtactac     660
tgtgccagag atcagggcta ccactactac gactctgccg agcacgcctt cgatatctgg     720
ggccagggaa cagtggtcac cgttagttct gcggccgcaa tcgaagtgat gtaccccct      780
ccctacctgg acaacgagaa gtccaacggc accattatcc acgtgaaggg aaagcacctg     840
tgccccagcc ctctgttccc tggccctagc aagcctttct gggtgctggt ggtcgtgggc     900
ggagtgctgg cctgttatag cctgctcgtg accgtggcct catcatcttt tgggtgcgc     960
agcaagcgga gcggctgct gcacagcgac tacatgaaca tgacccccag acggcccgga    1020
cccaccagaa agcactacca gccttacgcc cctcccagag acttcgccgc ctacagatct    1080
cgagtgaagt tcagcagaag cgccgacgcc cctgcctatc agcagggcca gaaccagctg    1140
```

| | |
|---|---|
| tacaacgagc tgaacctggg cagacgggaa gagtacgacg tgctggacaa gcggagaggc | 1200 |
| agggaccctg agatgggcgg caagcccaga agaaagaacc cccaggaagg cctgtataac | 1260 |
| gaactgcaga agacaagat ggccgaggcc tacagcgaga tcggcatgaa gggcgagcgg | 1320 |
| agaagaggca agggccacga tggcctgtac cagggcctga gcaccgccac caaggacacc | 1380 |
| tatgacgccc tgcacatgca ggccctgccc cccaga | 1416 |

<210> SEQ ID NO 299
<211> LENGTH: 1428
<212> TYPE: DNA
<213> ORGANISM: Artificial Sequence
<220> FEATURE:
<223> OTHER INFORMATION: Polynucleotide coding L7-18H CAR

<400> SEQUENCE: 299

| | |
|---|---|
| cagtctgccc tgactcagcc tcgctcagtg tccgggtctc ctggacagtc agtcaccatc | 60 |
| tcctgcactg gaaccagcag tgatgttggt ggttataact atgtctcctg gtaccaacaa | 120 |
| cacccaggca aagcccccaa actcatgatt tatgatgtca gtaatcggcc ctcagggggtt | 180 |
| tctaatcgct tctctggctc caagtctggc aacacggcct ccctgaccat ctctgggctc | 240 |
| cagactgggg acgaggccga ttattactgc ggaacatggg ataccagcct gactgctgtg | 300 |
| gtattcggcg gagggaccga gctgaccgtc ctcggctcta caagcggctc tggcaagcct | 360 |
| ggatctggcg agggaagcac caagggcgaa gtgcagcttg tggaatctgg cggaggactg | 420 |
| gtgcagcctg gaagaagcct gagactgtct tgtgccgcca gcggcttcac cttcgacgat | 480 |
| tatgccatgc actgggtccg acaggcccct ggaaaaggcc ttgaatgggt gtccggcatc | 540 |
| tcttggaaca gcggcagaat cggctacgcc gactctgtga agggcagatt caccatcagc | 600 |
| cgggacaacg ccaagaacag cctgttcctg cagatgaact ccctgagagc cgaggacacc | 660 |
| gccgtgtact actgtgccag agatcagggc taccactact acgactctgc gagcacgcc | 720 |
| ttcgatatct ggggccaggg aacagtggtc accgttagtt ctgcggccgc aatcgaagtg | 780 |
| atgtaccccc ctccctacct ggacaacgag aagtccaacg gcaccattat ccacgtgaag | 840 |
| ggaaagcacc tgtgccccag ccctctgttc cctggcccta gcaagccttt ctgggtgctg | 900 |
| gtggtcgtgg gcggagtgct ggcctgttat agcctgctcg tgaccgtggc cttcatcatc | 960 |
| ttttgggtgc gcagcaagcg gagccggctg ctgcacagcg actacatgaa catgaccccc | 1020 |
| agacggcccg gacccaccag aaagcactac cagccttacg cccctcccag agacttcgcc | 1080 |
| gcctacagat ctcgagtgaa gttcagcaga agcgccgacg cccctgccta tcagcagggc | 1140 |
| cagaaccagc tgtacaacga gctgaacctg ggcagacggg aagagtacga cgtgctggac | 1200 |
| aagcggagag caggggaccc tgagatgggc ggcaagccca agaaagaa cccccaggaa | 1260 |
| ggcctgtata cgaactgca gaaagacaag atggccgagg cctacagcga gatcggcatg | 1320 |
| aagggcgagc ggagaagagg caagggccac gatggcctgt accagggcct gagcaccgcc | 1380 |
| accaaggaca cctatgacgc cctgcacatg caggccctgc cccccaga | 1428 |

<210> SEQ ID NO 300
<211> LENGTH: 1425
<212> TYPE: DNA
<213> ORGANISM: Artificial Sequence
<220> FEATURE:
<223> OTHER INFORMATION: Polynucleotide coding L9-18H CAR

<400> SEQUENCE: 300

| | |
|---|---|
| cagtctgtgt tgacgcagcc gccctcagtg tctgcggccc caggacagaa ggtcaccatc | 60 |

```
tcctgctctg gaagctggtc aacattgga gatgatcatg tctcctggta ccagcagttc     120
ccaggagcag ccccaaact cctcatttat gacacttcta gcgaccctc acgcgttgct      180 gaccgattct ctggctccaa gtctggcgcg tcagccaccc tggccatcac tggactccag    240
gctggggacg aggccgacta ttattgcgga acatgggaaa gcagcctgag tggtgtggtt    300
ttcggcggag ggaccgagct gaccgtccta ggctctacaa gcggctctgg caagcctgga    360
tctggcgagg aagcaccaa gggcgaagtg cagcttgtgg aatctggcgg aggactggtg     420
cagcctggaa aagcctgag actgtcttgt gccgccagcg gcttcacctt cgacgattat    480
gccatgcact gggtccgaca ggcccctgga aaaggccttg aatgggtgtc cggcatctct    540
tggaacagcg gcagaatcgg ctacgccgac tctgtgaagg gcagattcac catcagccgg   600
gacaacgcca agaacagcct gttcctgcag atgaactccc tgagagccga ggacaccgcc    660
gtgtactact gtgccagaga tcagggctac cactactacg actctgccga gcacgccttc   720
gatatctggg gccagggaac agtggtcacc gttagttctg cggccgcaat cgaagtgatg    780 taccccctc cctacctgga caacgagaag tccaacggca ccattatcca cgtgaaggga   840
aagcacctgt gccccagccc tctgttccct ggcctagca agccttttctg ggtgctggtg    900 gtcgtgggcg gagtgctggc ctgttatagc ctgctcgtga ccgtggcctt catcatcttt    960
tgggtgcgca gcaagcggag ccggctgctg cacagcgact acatgaacat gaccccccaga 1020 cggcccggac ccaccagaaa gcactaccag ccttacgccc ctcccagaga cttcgccgcc    1080
tacagatctc gagtgaagtt cagcagaagc gccgacgccc ctgcctatca gcagggccag   1140
aaccagctgt acaacgagct gaacctgggc agacgggaag agtacgacgt gctggacaag   1200
cggagaggca gggaccctga tgggcggc aagcccagaa gaaagaaccc ccaggaaggc     1260
ctgtataacg aactgcagaa agacaagatg gccgaggcct acagcgagat cggcatgaag    1320
ggcgagcgga aagaggcaa gggccacgat ggcctgtacc agggcctgag caccgccacc    1380
aaggacacct atgacgccct gcacatgcag gccctgcccc caga                    1425
```

<210> SEQ ID NO 301  
<211> LENGTH: 1425  
<212> TYPE: DNA  
<213> ORGANISM: Artificial Sequence  
<220> FEATURE:  
<223> OTHER INFORMATION: Polynucleotide coding L13-18H CAR

<400> SEQUENCE: 301

```
cagtctgccc tgactcagcc tgcctccgtg tctgggtctc ctggacagtc gatcaccatc     60
tcctgcactg gactcagcag tgacgttggt ggttatgact atgtctcctg gtaccaacaa    120
cacccaggca tagccccaa actcatgatt tatgatgtca ctaatcggcc ctcagggtt     180 tctagtcgct ctctctggctc caagtctggc aacacggcct ccctgaccat ctctgggctc    240
caggctgagg acgaggctga ttattactgc agctcatata caaccagcac gacttgggtc   300
ttcggagctg ggaccaagct gaccgtccta ggctctacaa gcggctctgg caagcctgga    360
tctggcgagg aagcaccaa gggcgaagtg cagcttgtgg aatctggcgg aggactggtg     420
cagcctggaa aagcctgag actgtcttgt gccgccagcg gcttcacctt cgacgattat    480
gccatgcact gggtccgaca ggcccctgga aaaggccttg aatgggtgtc cggcatctct    540
tggaacagcg gcagaatcgg ctacgccgac tctgtgaagg gcagattcac catcagccgg   600
gacaacgcca agaacagcct gttcctgcag atgaactccc tgagagccga ggacaccgcc    660
```

| | |
|---|---|
| gtgtactact gtgccagaga tcagggctac cactactacg actctgccga gcacgccttc | 720 |
| gatatctggg gccagggaac agtggtcacc gttagttctg cggccgcaat cgaagtgatg | 780 |
| taccccctc cctacctgga caacgagaag tccaacggca ccattatcca cgtgaaggga | 840 |
| aagcacctgt gccccagccc tctgttccct ggccctagca agccttcctg ggtgctggtg | 900 |
| gtcgtgggcg gagtgctggc ctgttatagc ctgctcgtga ccgtggcctt catcatcttt | 960 |
| tgggtgcgca gcaagcggag ccggctgctg cacagcgact acatgaacat gacccccaga | 1020 |
| cggcccggac ccaccagaaa gcactaccag ccttacgccc tcccagaga cttcgccgcc | 1080 |
| tacagatctc gagtgaagtt cagcagaagc gccgacgccc ctgcctatca gcagggccag | 1140 |
| aaccagctgt acaacgagct gaacctgggc agacgggaag agtacgacgt gctggacaag | 1200 |
| cggagaggca gggaccctga gatgggcggc aagcccagaa gaaagaaccc caggaaggc | 1260 |
| ctgtataacg aactgcagaa agacaagatg gccgaggcct acagcgagat cggcatgaag | 1320 |
| ggcgagcgga agagggcaa gggccacgat ggcctgtacc agggcctgag caccgccacc | 1380 |
| aaggacacct atgacgccct gcacatgcag gccctgcccc caga | 1425 |

<210> SEQ ID NO 302
<211> LENGTH: 1428
<212> TYPE: DNA
<213> ORGANISM: Artificial Sequence
<220> FEATURE:
<223> OTHER INFORMATION: Polynucleotide coding L14-18H CAR

<400> SEQUENCE: 302

| | |
|---|---|
| cagtctgccc tgactcagcc tgcctccgtg tctgggtctc ctggacagtc gatcaccatc | 60 |
| tcctgcactg gaaccaccag tgacgttggt actactaatt atgtctcctg gtaccagcaa | 120 |
| cacccaggca aagccccaa actcctaatt tatgatgtca ctaatcggcc ctcaggggtc | 180 |
| cctgatcgct tctctggctc caagtctgcc aacacggcct ccctgaccat ctctgggctc | 240 |
| caggctgagg acgaggctga ttattactgc tgctcatatg caggcagcta caccttcgtg | 300 |
| gtattcggcg gagggaccga gctgaccgtc ctaggctcta caagcggctc tggcaagcct | 360 |
| ggatctggca agggaagcac caagggcgaa gtgcagcttg tggaatctgg cggaggactg | 420 |
| gtgcagcctg gaagaagcct gagactgtct tgtgccgcca gcggcttcac cttcgacgat | 480 |
| tatgccatgc actgggtccg acaggcccct ggaaaaggcc ttgaatgggt gtccggcatc | 540 |
| tcttggaaca gcggcagaat cggctacgcc gactctgtga agggcagatt caccatcagc | 600 |
| cgggacaacg ccaagaacag cctgttcctg cagatgaact ccctgagagc cgaggacacc | 660 |
| gccgtgtact actgtgccag agatcagggc taccactact acgactctgc cgagcacgcc | 720 |
| ttcgatatct ggggccaggg aacagtggtc accgttagtt ctgcggccgc aatcgaagtg | 780 |
| atgtacccc ctccctacct ggacaacgag aagtccaacg gcaccattat ccacgtgaag | 840 |
| ggaaagcacc tgtgcccag ccctctgttc cctggcccta gcaagccttt ctgggtgctg | 900 |
| gtggtcgtgg gcggagtgct ggcctgttat agcctgctcg tgaccgtggc cttcatcatc | 960 |
| ttttgggtgc gcagcaagcg gagccggctg ctgcacagcg actacatgaa catgaccccc | 1020 |
| agacggcccg gacccaccag aaagcactac cagccttacg cccctcccag agacttcgcc | 1080 |
| gcctacagat ctcgagtgaa gttcagcaga agcgccgacg cccctgccta tcagcagggc | 1140 |
| cagaaccagc tgtacaacga gctgaacctg ggcagacggg aagagtacga cgtgctggac | 1200 |
| aagcggagag gcagggaccc tgagatgggc ggcaagccca gaagaaagaa ccccaggaa | 1260 |
| ggcctgtata cgaactgca gaaagacaag atggccgagg cctacagcga gatcggcatg | 1320 |

```
aagggcgagc ggagaagagg caagggccac gatggcctgt accagggcct gagcaccgcc    1380
accaaggaca cctatgacgc cctgcacatg caggccctgc cccccaga                 1428
```

<210> SEQ ID NO 303
<211> LENGTH: 1428
<212> TYPE: DNA
<213> ORGANISM: Artificial Sequence
<220> FEATURE:
<223> OTHER INFORMATION: Polynucleotide coding L16-18H CAR

<400> SEQUENCE: 303

```
cagtctgccc tgactcagcc tccctccgcg tccgggtctc ctggacagtc agtcaccatc     60
tcctgcactg gaaccagcag tgacgttggt gtttataact atgtctcctg gtaccaacaa    120
cacccaggca aagcccccaa actcatgatt tatgatgtca gtaagcggcc ctcaggggtc    180
cctgatcgct tctctggctc caagtctgcc aacacggcct ccctgaccat ctctgggctc    240
caggctgagg atgaggctga ttattactgt gcagcatggg atgacagcct gaatggtgtg    300
gtattcggcg gaggcaccca gctgaccgtc ctcggctcta caagcggctc tggcaagcct    360
ggatctggcg agggaagcac caagggcgaa gtgcagcttg tggaatctgg cggaggactg    420
gtgcagcctg gaagaagcct gagactgtct tgtgccgcca gcggcttcac cttcgacgat    480
tatgccatgc actgggtccg acaggcccct ggaaaaggcc ttgaatgggt gtccggcatc    540
tcttggaaca gcggcagaat cggctacgcc gactctgtga agggcagatt caccatcagc    600
cgggacaacg ccaagaacag cctgttcctg cagatgaact ccctgagagc cgaggacacc    660
gccgtgtact actgtgccag agatcagggc taccactact acgactctgc cgagcacgcc    720
ttcgatatct ggggccaggg aacagtggtc accgttagtt ctgcggccgc aatcgaagtg    780
atgtaccccc ctccctacct ggacaacgag aagtccaacg gcaccattat ccacgtgaag    840
ggaaagcacc tgtgcccag ccctctgttc cctggcccta gcaagccttt ctgggtgctg    900
gtggtcgtgg gcggagtgct ggcctgttat agcctgctcg tgaccgtggc cttcatcatc    960
ttttgggtgc gcagcaagcg gagccggctg ctgcacagcg actacatgaa catgaccccc   1020
agacggcccg gacccaccag aaagcactac cagccttacg cccctcccag agacttcgcc   1080
gcctacagat ctcgagtgaa gttcagcaga agcgccgacg cccctgccta tcagcagggc   1140
cagaaccagc tgtacaacga gctgaacctg gcagacgggg aagagtacga cgtgctggac   1200
aagcggagag caggacccc tgagatgggc ggcaagccca agaaagaa ccccaggaa      1260 ggcctgtata cgaactgca gaaagacaag atggccgagg cctacagcga gatcggcatg    1320
aagggcgagc ggagaagagg caagggccac gatggcctgt accagggcct gagcaccgcc   1380
accaaggaca cctatgacgc cctgcacatg caggccctgc cccccaga                1428
```

<210> SEQ ID NO 304
<211> LENGTH: 1422
<212> TYPE: DNA
<213> ORGANISM: Artificial Sequence
<220> FEATURE:
<223> OTHER INFORMATION: Polynucleotide coding L17-18H CAR

<400> SEQUENCE: 304

```
cagtctgtac tgactcaacc accctcagcg tctgggaccc ccgggcagag ggtcaccatc     60
tcttgctctg gcagcagctc caacatcgga aataattatg tatgctggta ccaacacctc    120
ccaggaacgg cccccaaact tctcatttat gacaatgtta agcgaccctc agggattcct    180
```

```
gaccgattct ctggctccaa gtctggcacg tcagcctccc tggccatcag tgggctccgg      240
tccgaggatg aggctgatta ttactgtgca gcatgggatg acagcctgag tgccatattc      300
ggcggaggga ccgagctgac cgtcctaggc tctacaagcg gctctggcaa gcctggatct      360
ggcgagggaa gcaccaaggg cgaagtgcag cttgtggaat ctggcggagg actggtgcag      420
cctggaagaa gcctgagact gtcttgtgcc gccagcggct tcaccttcga cgattatgcc      480
atgcactggg tccgacaggc ccctggaaaa ggccttgaat gggtgtccgg catctcttgg      540
aacagcggca gaatcggcta cgccgactct gtgaagggca gattcaccat cagccgggac      600
aacgccaaga cagcctgtt cctgcagatg aactccctga gagccgagga caccgccgtg       660
tactactgtg ccagagatca gggctaccac tactacgact ctgccgagca cgccttcgat      720
atctggggcc agggaacagt ggtcaccgtt agttctgcgg ccgcaatcga agtgatgtac      780
ccccctccct acctggacaa cgagaagtcc aacggcacca ttatccacgt gaagggaaag      840
cacctgtgcc ccagccctct gttccctggc cctagcaagc cttctgggt gctggtggtc       900 gtgggcggag tgctggcctg ttatagcctg ctcgtgaccg tggccttcat catcttttgg      960
gtgcgcagca gcggagccg gctgctgcac agcgactaca tgaacatgac ccccagacgg       1020 cccgaccca ccagaaagca ctaccagcct acgcccctc ccagagactt cgccgcctac        1080
agatctcgag tgaagttcag cagaagcgcc gacgcccctg cctatcagca gggccagaac      1140
cagctgtaca cgagctgaa cctgggcaga cgggaagagt acgacgtgct ggacaagcgg       1200
agaggcaggg accctgagat gggcggcaag cccagaagaa agaacccca ggaaggcctg       1260 tataacgaac tgcagaaaga caagatggcc gaggcctaca gcgagatcgg catgaagggc      1320
gagcggagaa gaggcaaggg ccacgatggc ctgtaccagg gcctgagcac cgccaccaag      1380
gacacctatg acgccctgca catgcaggcc ctgccccca ga                         1422

<210> SEQ ID NO 305
<211> LENGTH: 1425
<212> TYPE: DNA
<213> ORGANISM: Artificial Sequence
<220> FEATURE:
<223> OTHER INFORMATION: Polynucleotide coding L22-18H CAR

<400> SEQUENCE: 305
cagtctgccc tgactcagcc tgcctccgtg tctgggtctc ctggacagtc gatcaccatc       60
tcctgcactg gaaccagcag tgacgttggt ggttataact atgtctcctg gtaccaacaa      120
cacccaggca agcccccaa actcatgatt tatgatgtca gtaatcggcc ctcaggggtc       180
cctgatcgct tctctggctc caagtctggc acctcagcct ccctggccat cagtgggctc      240
cagtctgagg atgaggctga ttattactgc cactcctatg acagcagcct gagtcatgtc      300
ttcggaactg ggaccaaggt caccgtccta ggctctacaa gcggctctgg caagcctgga      360
tctggcgagg aagcaccaa gggcgaagtg cagcttgtgg aatctggcgg aggactggtg      420
cagcctggaa gaagcctgag actgtcttgt gccgccagcg gcttcacctt cgacgattat      480
gccatgcact gggtccgaca ggcccctgga aaaggccttg aatgggtgtc cggcatctct      540
tggaacagcg gcagaatcgg ctacgccgac tctgtgaagg gcagattcac catcagccgg      600
gacaacgcca agaacagcct gttcctgcag atgaactccc tgagagccga ggacaccgcc      660
gtgtactact gtgccagaga tcagggctac cactactacg actctgccga gcacgccttc      720
gatatctggg gccagggaac agtggtcacc gttagttctg cggccgcaat cgaagtgatg      780
tacccccctc cctacctgga caacgagaag tccaacggca ccattatcca cgtgaaggga      840
```

```
aagcacctgt gccccagccc tctgttccct ggccctagca agcctttctg ggtgctggtg        900
gtcgtgggcg gagtgctggc ctgttatagc ctgctcgtga ccgtggcctt catcatcttt        960
tgggtgcgca gcaagcggag ccggctgctg cacagcgact acatgaacat gaccccaga        1020
cggcccggac ccaccagaaa gcactaccag ccttacgccc ctcccagaga cttcgccgcc       1080
tacagatctc gagtgaagtt cagcagaagc gccgacgccc ctgcctatca gcagggccag       1140
aaccagctgt acaacgagct gaacctgggc agacgggaag agtacgacgt gctggacaag       1200
cggagaggca gggaccctga tgggcggc aagcccagaa gaaagaaccc ccaggaaggc         1260
ctgtataacg aactgcagaa agacaagatg gccgaggcct acagcgagat cggcatgaag       1320
ggcgagcgga gaagaggcaa gggccacgat ggcctgtacc agggcctgag caccgccacc      1380
aaggacacct atgacgccct gcacatgcag gccctgcccc caga                          1425
```

<210> SEQ ID NO 306
<211> LENGTH: 1422
<212> TYPE: DNA
<213> ORGANISM: Artificial Sequence
<220> FEATURE:
<223> OTHER INFORMATION: Polynucleotide coding K4-18H CAR

<400> SEQUENCE: 306

```
gaaattgtgt tgacgcagtc tccaggcacc ctgtctttgt ctccagggga aagagccacc         60
ctctcctgca gggccagtca gagtgttagc agcaacttag cctggtacca gcagaaacct       120
ggccaggctc ccaggctcct catctatggt gcatccacca gggccactgg tatcccagcc       180
aggttcagtg gcagtgggtc tgggacagag ttcactctca ccatcagcag cctgcagtct       240
gaagattttg cagtttatta ctgtcagcag tataataact ggcctccctt gtacactttt       300
ggccagggga ccaagctgga gatcaaaggc tctacaagcg gctctggcaa gcctggatct       360
ggcgagggaa gcaccaaggg cgaagtgcag cttgtggaat ctggcggagg actggtgcag       420
cctggaagaa gcctgagact gtcttgtgcc gccagcggct tcaccttcga cgattatgcc       480
atgcactggg tccgacaggc ccctggaaaa ggccttgaat gggtgtccgg catctcttgg       540
aacagcggca gaatcggcta cgccgactct gtgaagggca gattcaccat cagccgggac       600
aacgccaaga acagcctgtt cctgcagatg aactccctga gagccgagga caccgccgtg       660
tactactgtg ccagagatca gggctaccac tactacgact ctgccgagca cgccttcgat       720
atctggggcc agggaacagt ggtcaccgtt agttctgcgg ccgcaatcga agtgatgtac       780
ccccctccct acctggacaa cgagaagtcc aacggcacca ttatccacgt gaagggaaag      840
cacctgtgcc ccagccctct gttccctggc cctagcaagc ctttctgggt gctggtggtc       900
gtgggcggag tgctggcctg ttatagcctg ctcgtgaccg tggccttcat catcttttgg       960
gtgcgcagca gcggagcccg gctgctgcac agcgactaca tgaacatgac cccagacgg       1020
cccgacccca gaaagca ctaccagcct tacgcccctc cagagacttc gccgcctac         1080
agatctcgag tgaagttcag cagaagcgcc gacgccctg cctatcagca gggccagaac       1140
cagctgtaca acgagctgaa cctgggcaga cgggaagagt acgacgtgct ggacaagcgg      1200
agaggcaggg accctgagat gggcggcaag cccagaagaa gaaccccca ggaaggcctg       1260
tataacgaac tgcagaaaga caagatggcc gaggcctaca gcgagatcgg catgaagggc      1320
gagcggagaa gaggcaaggg ccacgatggc ctgtaccagg gcctgagcac cgccaccaag     1380
gacacctatg acgccctgca catgcaggcc ctgccccca ga                          1422
```

<210> SEQ ID NO 307
<211> LENGTH: 1419
<212> TYPE: DNA
<213> ORGANISM: Artificial Sequence
<220> FEATURE:
<223> OTHER INFORMATION: Polynucleotide coding K5-18H CAR

<400> SEQUENCE: 307

| | |
|---|---|
| gaaattgtgt tgacgcagtc tccaggcacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg caacttacta ctgtcaacag agttacagta cccttttgta cacttttggc | 300 |
| caggggacca agctggagat caaaggctct acaagcggct ctggcaagcc tggatctggc | 360 |
| gagggaagca ccaagggcga agtgcagctt gtggaatctg gcggaggact ggtgcagcct | 420 |
| ggaagaagcc tgagactgtc ttgtgccgcc agcggcttca ccttcgacga ttatgccatg | 480 |
| cactgggtcc acaggccccc tggaaaaggc cttgaatggg tgtccggcat ctcttggaac | 540 |
| agcggcagaa tcggctacgc cgactctgtg aagggcagat tcaccatcag ccgggacaac | 600 |
| gccaagaaca gcctgttcct gcagatgaac tccctgagag ccgaggacac cgccgtgtac | 660 |
| tactgtgcca gagatcaggg ctaccactac tacgactctg ccgagcacgc cttcgatatc | 720 |
| tggggccagg gaacagtggt caccgttagt tctgcggccg caatcgaagt gatgtacccc | 780 |
| cctccctacc tggacaacga aagtccaac ggcaccatta tccacgtgaa gggaaagcac | 840 |
| ctgtgcccca gccctctgtt ccctggccct agcaagcctt ctgggtgct ggtggtcgtg | 900 |
| ggcggagtgc tggcctgtta tagcctgctc gtgaccgtgg ccttcatcat cttttgggtg | 960 |
| cgcagcaagc ggagccggct gctgcacagc gactacatga acatgacccc cagacggccc | 1020 |
| ggacccacca aaagcactac cagccttac gccctccca gagacttcgc cgcctacaga | 1080 |
| tctcgagtga agttcagcag aagcgccgac gcccctgcct atcagcaggg ccagaaccag | 1140 |
| ctgtacaacg agctgaacct gggcagacgg gaagagtacg acgtgctgga caagcggaga | 1200 |
| ggcagggacc ctgagatggg cggcaagccc agaagaaaga ccccagga aggcctgtat | 1260 |
| aacgaactgc agaaagacaa gatggccgag gcctacagcg agatcggcat gaagggcgag | 1320 |
| cggagaagag gcaagggcca cgatggcctg taccagggcc tgagcaccgc caccaaggac | 1380 |
| acctatgacg ccctgcacat gcaggccctg ccccccaga | 1419 |

<210> SEQ ID NO 308
<211> LENGTH: 1416
<212> TYPE: DNA
<213> ORGANISM: Artificial Sequence
<220> FEATURE:
<223> OTHER INFORMATION: Polynucleotide coding K6-18H CAR

<400> SEQUENCE: 308

| | |
|---|---|
| gaaattgtgt tgacacggtc tccagccacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcctccaaca gggccactgg tatttcagcc | 180 |
| aggttcagtg gcagtgggtc tgggacagag ttcactctca ccatcagcag cctgcagtct | 240 |
| gaagatattg caacatatta ctgtcaacag tatgatagtc tcccactcac tttcggcgga | 300 |
| gggaccaagc tggagatcaa aggctctaca agcggctctg gcaagcctgg atctggcgag | 360 |

```
ggaagcacca agggcgaagt gcagcttgtg aatctggcg gaggactggt gcagcctgga      420
agaagcctga gactgtcttg tgccgccagc ggcttcacct tcgacgatta tgccatgcac      480
tgggtccgac aggcccctgg aaaaggcctt gaatgggtgt ccggcatctc ttggaacagc      540
ggcagaatcg gctacgccga ctctgtgaag ggcagattca ccatcagccg gacaacgcc       600 aagaacagcc tgttcctgca gatgaactcc ctgagagccg aggacaccgc cgtgtactac      660
tgtgccagag atcagggcta ccactactac gactctgccg agcacgcctt cgatatctgg      720
ggccagggaa cagtggtcac cgttagttct gcggccgcaa tcgaagtgat gtaccccct       780 ccctacctgg acaacgagaa gtccaacggc accattatcc acgtgaaggg aaagcacctg      840
tgccccagcc ctctgttccc tggccctagc aagcctttct gggtgctggt ggtcgtgggc      900
ggagtgctgg cctgttatag cctgctcgtg accgtggcct tcatcatctt tgggtgcgc       960 agcaagcgga gccggctgct gcacagcgac tacatgaaca tgacccccag acggcccgga     1020
cccaccagaa agcactacca gccttacgcc cctcccagag acttcgccgc ctacagatct     1080
cgagtgaagt tcagcagaag cgccgacgcc cctgcctatc agcagggcca gaaccagctg     1140
tacaacgagc tgaacctggg cagacgggaa gagtacgacg tgctggacaa gcggagaggc     1200
agggaccctg agatgggcgg caagcccaga agaaagaacc cccaggaagg cctgtataac     1260
gaactgcaga agacaagat ggccgaggcc tacagcgaga tcggcatgaa gggcgagcgg      1320
agaagaggca agggccacga tggcctgtac cagggcctga gcaccgccac caaggacacc     1380
tatgacgccc tgcacatgca ggccctgccc cccaga                               1416
```

<210> SEQ ID NO 309
<211> LENGTH: 1419
<212> TYPE: DNA
<213> ORGANISM: Artificial Sequence
<220> FEATURE:
<223> OTHER INFORMATION: Polynucleotide coding K9-18H CAR

<400> SEQUENCE: 309

```
gaaatagtgt tgacacagtc tccagccacc ctgtctttgt ctccagggga aagagccacc       60
gtctcctgta ggcccagtca gaccattagt gccagttccg tagcctggta tcagcagaaa      120
gctggccagg ctccacggct cctcatctat ggtgcatcca gcagggccac tggcatccca      180
gacaggttca gtggcagtgg gtctgggaca gacttcactc tcaccatcag cagactggag      240
cctgaagatt ttgcagttta ttactgtcag caatttaatg aatggcctct cactttcggc      300
ggagggacca aggtggaaat caaaggctct acaagcggct ctggcaagcc tggatctggc      360
gagggaagca ccaagggcga agtgcagctt gtggaatctg gcggaggact ggtgcagcct      420 ggaagaagc tgagactgtc ttgtgccgcc agcggcttca ccttcgacga ttatgccatg       480
cactgggtcc gacaggcccc tggaaaaggc cttgaatggg tgtccggcat ctcttggaac      540
agcggcagaa tcggctacgc cgactctgtg aagggcagat tcaccatcag ccgggacaac      600
gccaagaaca gcctgttcct gcagatgaac tccctgagag ccgaggacac cgccgtgtac      660
tactgtgcca gagatcaggg ctaccactac tacgactctg ccgagcacgc cttcgatatc      720
tggggccagg gaacagtggt caccgttagt tctgcggccg caatcgaagt gatgtacccc      780 cctcccctacc tggacaacga gaagtccaac ggcaccatta tccacgtgaa gggaaagcac      840
ctgtgcccca gccctctgtt ccctggccct agcaagcctt tctgggtgct ggtggtcgtg      900
ggcggagtgc tggcctgtta tagcctgctc gtgaccgtgg ccttcatcat cttttgggtg      960
```

| | |
|---|---|
| cgcagcaagc ggagccggct gctgcacagc gactacatga acatgacccc cagacggccc | 1020 |
| ggacccacca gaaagcacta ccagccttac gcccctccca gagacttcgc cgcctacaga | 1080 |
| tctcgagtga agttcagcag aagcgccgac gcccctgcct atcagcaggg ccagaaccag | 1140 |
| ctgtacaacg agctgaacct gggcagacgg aagagtacg acgtgctgga caagcggaga | 1200 |
| ggcagggacc ctgagatggg cggcaagccc agaagaaaga accccagga aggcctgtat | 1260 |
| aacgaactgc agaaagacaa gatggccgag gcctacagcg agatcggcat gaagggcgag | 1320 |
| cggagaagag gcaagggcca cgatggcctg taccagggcc tgagcaccgc caccaaggac | 1380 |
| acctatgacg ccctgcacat gcaggccctg ccccccaga | 1419 |

<210> SEQ ID NO 310
<211> LENGTH: 1422
<212> TYPE: DNA
<213> ORGANISM: Artificial Sequence
<220> FEATURE:
<223> OTHER INFORMATION: Polynucleotide coding K10-18H CAR

<400> SEQUENCE: 310

| | |
|---|---|
| gaaattgtgt tgacacagtc tccagccacc ctgtctttgt ctccagggga aagagccacc | 60 |
| ctctcctgca gggccagtca gagtgttagc agcaacttag cctggtacca gcaaaaactt | 120 |
| ggccaggctc ccaggctcct catctatggt gcatccagca gggccactgg catcccagac | 180 |
| aggttcagtg gcagtgggtc tgggacagac ttcactctca ccatcagcag actggagcct | 240 |
| gaagattttg cagtgtatta ctgtcagcag tatggtagct cacccgatat attcactttc | 300 |
| ggccctggga ccaaagtgga tatcaaaggc tctacaagcg gctctggcaa gcctggatct | 360 |
| ggcgagggaa gcaccaaggg cgaagtgcag cttgtggaat ctggcggagg actggtgcag | 420 |
| cctggaagaa gcctgagact gtcttgtgcc gccagcggct tcaccttcga cgattatgcc | 480 |
| atgcactggg tccgacaggc ccctggaaaa ggccttgaat gggtgtccgg catctcttgg | 540 |
| aacagcggca atcggcta cgccgactct gtgaagggca gattcaccat cagccgggac | 600 |
| aacgccaaga acagcctgtt cctgcagatg aactccctga gccgagga caccgccgtg | 660 |
| tactactgtg ccagagatca gggctaccac tactacgact gccgagca cgccttcgat | 720 |
| atctggggcc agggaacagt ggtcaccgtt agttctgcgg ccgcaatcga agtgatgtac | 780 |
| ccccctccct acctggacaa cgagaagtcc aacggcacca ttatccacgt gaagggaaag | 840 |
| cacctgtgcc ccagccctct gttccctggc cctagcaagc ctttctgggt gctggtggtc | 900 |
| gtgggcggag tgctggcctg ttatagcctg ctcgtgaccg tggccttcat catcttttgg | 960 |
| gtgcgcagca agcggagccg gctgctgcac agcgactaca tgaacatgac ccccagacgg | 1020 |
| cccgaccca ccagaaagca ctaccagcct tacgcccctc cagagactt cgccgcctac | 1080 |
| agatctcgag tgaagttcag cagaagcgcc gacgcccctg cctatcagca gggccagaac | 1140 |
| cagctgtaca cgagctgaa cctgggcaga cggaagagt acgacgtgct ggacaagcgg | 1200 |
| agaggcaggg accctgagat gggcggcaag cccagaagaa agaaccccca ggaaggcctg | 1260 |
| tataacgaac tgcagaaaga caagatggcc gaggcctaca gcgagatcgg catgaagggc | 1320 |
| gagcggagaa gaggcaaggg ccacgatggc ctgtaccagg gcctgagcac cgccaccaag | 1380 |
| gacacctatg acgccctgca catgcaggcc ctgcccccca ga | 1422 |

<210> SEQ ID NO 311
<211> LENGTH: 841
<212> TYPE: PRT
<213> ORGANISM: Artificial Sequence

```
<220> FEATURE:
<223> OTHER INFORMATION: SLR protein

<400> SEQUENCE: 311
```

| | | | | | | | | | | | | | | |
|---|---|---|---|---|---|---|---|---|---|---|---|---|---|---|
|Met|Glu|Glu|Glu|Asn|Ile|Val|Asn|Gly|Asp|Arg|Pro|Arg|Asp|Leu|Val|
|1| | | |5| | | | |10| | | | |15|
|Phe|Pro|Gly|Thr|Ala|Gly|Leu|Gln|Leu|Tyr|Gln|Ser|Leu|Tyr|Lys|Tyr|
| | | |20| | | | |25| | | | |30| | |
|Ser|Tyr|Ile|Thr|Asp|Gly|Ile|Ile|Asp|Ala|His|Thr|Asn|Glu|Val|Ile|
| | |35| | | | |40| | | | |45| | | |
|Ser|Tyr|Ala|Gln|Ile|Phe|Glu|Thr|Ser|Cys|Arg|Leu|Ala|Val|Ser|Leu|
| |50| | | | |55| | | | |60| | | | |
|Glu|Lys|Tyr|Gly|Leu|Asp|His|Asn|Asn|Val|Val|Ala|Ile|Cys|Ser|Glu|
|65| | | | |70| | | | |75| | | | |80|
|Asn|Asn|Ile|His|Phe|Phe|Gly|Pro|Leu|Ile|Ala|Ala|Leu|Tyr|Gln|Gly|
| | | | |85| | | | |90| | | | |95| |
|Ile|Pro|Met|Ala|Thr|Ser|Asn|Asp|Met|Tyr|Thr|Glu|Arg|Glu|Met|Ile|
| | | |100| | | | |105| | | | |110| | |
|Gly|His|Leu|Asn|Ile|Ser|Lys|Pro|Cys|Leu|Met|Phe|Cys|Ser|Lys|Lys|
| | |115| | | | |120| | | | |125| | | |
|Ser|Leu|Pro|Phe|Ile|Leu|Lys|Val|Gln|Lys|His|Leu|Asp|Phe|Leu|Lys|
| |130| | | | |135| | | | |140| | | | |
|Lys|Val|Ile|Val|Ile|Asp|Ser|Met|Tyr|Asp|Ile|Asn|Gly|Val|Glu|Cys|
|145| | | | |150| | | | |155| | | | |160|
|Val|Phe|Ser|Phe|Val|Ser|Arg|Tyr|Thr|Asp|His|Ala|Phe|Asp|Pro|Val|
| | | |165| | | | |170| | | | |175| | |
|Lys|Phe|Asn|Pro|Lys|Glu|Phe|Asp|Pro|Leu|Glu|Arg|Thr|Ala|Leu|Ile|
| | | |180| | | | |185| | | | |190| | |
|Met|Thr|Ser|Ser|Gly|Thr|Thr|Gly|Leu|Pro|Lys|Gly|Val|Val|Ile|Ser|
| | | |195| | | | |200| | | | |205| | |
|His|Arg|Ser|Ile|Thr|Ile|Arg|Phe|Val|His|Ser|Ser|Asp|Pro|Ile|Tyr|
| |210| | | | |215| | | | |220| | | | |
|Gly|Thr|Arg|Ile|Ala|Pro|Asp|Thr|Ser|Ile|Leu|Ala|Ile|Ala|Pro|Phe|
|225| | | | |230| | | | |235| | | | |240|
|His|His|Ala|Phe|Gly|Leu|Phe|Thr|Ala|Leu|Ala|Tyr|Phe|Pro|Val|Gly|
| | | |245| | | | |250| | | | |255| | |
|Leu|Lys|Ile|Val|Met|Val|Lys|Lys|Phe|Glu|Gly|Glu|Phe|Phe|Leu|Lys|
| | |260| | | | |265| | | | |270| | | |
|Thr|Ile|Gln|Asn|Tyr|Lys|Ile|Ala|Ser|Ile|Val|Val|Pro|Pro|Pro|Ile|
| |275| | | | |280| | | | |285| | | | |
|Met|Val|Tyr|Leu|Ala|Lys|Ser|Pro|Leu|Val|Asp|Glu|Tyr|Asn|Leu|Ser|
|290| | | | |295| | | | |300| | | | | |
|Ser|Leu|Thr|Glu|Ile|Ala|Cys|Gly|Gly|Ser|Pro|Leu|Gly|Arg|Asp|Ile|
|305| | | | |310| | | | |315| | | | |320|
|Ala|Asp|Lys|Val|Ala|Lys|Arg|Leu|Lys|Val|His|Gly|Ile|Leu|Gln|Gly|
| | | |325| | | | |330| | | | |335| | |
|Tyr|Gly|Leu|Thr|Glu|Thr|Cys|Ser|Ala|Leu|Ile|Leu|Ser|Pro|Asn|Asp|
| | | |340| | | | |345| | | | |350| | |
|Arg|Glu|Leu|Lys|Lys|Gly|Ala|Ile|Gly|Thr|Pro|Met|Pro|Tyr|Val|Gln|
| | |355| | | | |360| | | | |365| | | |
|Val|Lys|Val|Ile|Asp|Ile|Asn|Thr|Gly|Lys|Ala|Leu|Gly|Pro|Arg|Glu|
| |370| | | | |375| | | | |380| | | | |
|Lys|Gly|Glu|Ile|Cys|Phe|Lys|Ser|Gln|Met|Leu|Met|Lys|Gly|Tyr|His|
|385| | | | |390| | | | |395| | | | |400|

```
Asn Asn Pro Gln Ala Thr Arg Asp Ala Leu Asp Lys Asp Gly Trp Leu
                405                 410                 415
His Thr Gly Asp Leu Gly Tyr Tyr Asp Glu Asp Arg Phe Ile Tyr Val
            420                 425                 430
Val Asp Arg Leu Lys Glu Leu Ile Lys Tyr Lys Gly Tyr Gln Val Ala
        435                 440                 445
Pro Ala Glu Leu Glu Asn Leu Leu Gln His Pro Asn Ile Ser Asp
450                 455                 460
Ala Gly Val Ile Gly Ile Pro Asp Glu Phe Ala Gly Gln Leu Pro Ser
465                 470                 475                 480
Ala Cys Val Val Leu Glu Pro Gly Lys Thr Met Thr Glu Lys Glu Val
                485                 490                 495
Gln Asp Tyr Ile Ala Glu Leu Val Thr Thr Lys His Leu Arg Gly
            500                 505                 510
Gly Val Val Phe Ile Asp Ser Ile Pro Lys Gly Pro Thr Gly Lys Leu
        515                 520                 525
Met Arg Asn Glu Leu Arg Ala Ile Phe Ala Arg Glu Gln Ala Lys Ser
    530                 535                 540
Lys Leu Arg Ala Lys Arg Ser Gly Ser Gly Ala Thr Asn Phe Ser Leu
545                 550                 555                 560
Leu Lys Gln Ala Gly Asp Val Glu Glu Asn Pro Gly Pro Met Asp Gly
                565                 570                 575
Pro Arg Leu Leu Leu Leu Leu Leu Leu Gly Val Ser Leu Gly Gly Ala
            580                 585                 590
Lys Glu Ala Cys Pro Thr Gly Leu Tyr Thr His Ser Gly Glu Cys Cys
        595                 600                 605
Lys Ala Cys Asn Leu Gly Glu Gly Val Ala Gln Pro Cys Gly Ala Asn
    610                 615                 620
Gln Thr Val Cys Glu Pro Cys Leu Asp Ser Val Thr Phe Ser Asp Val
625                 630                 635                 640
Val Ser Ala Thr Glu Pro Cys Lys Pro Cys Thr Glu Cys Val Gly Leu
                645                 650                 655
Gln Ser Met Ser Ala Pro Cys Val Glu Ala Asp Asp Ala Val Cys Arg
            660                 665                 670
Cys Ala Tyr Gly Tyr Tyr Gln Asp Glu Thr Thr Gly Arg Cys Glu Ala
        675                 680                 685
Cys Arg Val Cys Glu Ala Gly Ser Gly Leu Val Phe Ser Cys Gln Asp
    690                 695                 700
Lys Gln Asn Thr Val Cys Glu Glu Cys Pro Asp Gly Thr Tyr Ser Asp
705                 710                 715                 720
Glu Ala Asn His Val Asp Pro Cys Leu Pro Cys Thr Val Cys Glu Asp
                725                 730                 735
Thr Glu Arg Gln Leu Arg Glu Cys Thr Arg Trp Ala Asp Ala Glu Cys
            740                 745                 750
Glu Glu Ile Pro Gly Arg Trp Ile Thr Arg Ser Thr Pro Glu Gly
        755                 760                 765
Ser Asp Ser Thr Ala Pro Ser Thr Gln Glu Pro Glu Ala Pro Pro Glu
    770                 775                 780
Gln Asp Leu Ile Ala Ser Thr Val Ala Gly Val Val Thr Thr Val Met
785                 790                 795                 800
Gly Ser Ser Gln Pro Val Val Thr Arg Gly Thr Thr Asp Asn Leu Ile
                805                 810                 815
```

```
                Pro Val Tyr Cys Ser Ile Leu Ala Ala Val Val Gly Leu Val Ala
                        820                 825                 830

Tyr Ile Ala Phe Lys Arg Trp Asn Ser
                        835                 840

<210> SEQ ID NO 312
<211> LENGTH: 2526
<212> TYPE: DNA
<213> ORGANISM: Artificial Sequence
<220> FEATURE:
<223> OTHER INFORMATION: Polynucleotide coding SLR protein

<400> SEQUENCE: 312
atggaagaag agaacatcgt gaatggcgat cgccctcggg atctggtgtt ccctggcaca      60
gccggcctgc agctgtatca gtccctgtat aaatactctt acatcaccga cggaatcatc     120
gacgcccaca ccaacgaggt gatctcctat gcccagattt tcgaaacaag ttgccgcctg     180
gccgtgagcc tggagaagta tggcctggat acaacaacg tggtggccat ttgcagcgag      240
aacaacatcc acttcttcgg ccctctgatc gctgccctat accaggggat tccaatggcc     300
acatccaacg atatgtacac cgagagggag atgatcggcc acctgaacat ctccaagcca     360
tgtctgatgt tctgttccaa gagtccctg ccattcatcc tgaaggtgca gaagcacctg      420
gactttctca agaaggtgat cgtgatcgac agcatgtacg acatcaacgg cgtggagtgc     480
gtgttcagtt tcgtgtcccg gtacaccgat catgcgttcg atccagtgaa gttcaaccct     540
aaagagtttg atcccctgga gagaaccgcg ctgatcatga catcctctgg aacaaccggc     600
ctgcctaagg gcgtggtgat cagccacagg agcatcacca tcagattcgt ccacagcagc     660
gatcccatct acggcacccg catcgcccca gatacatcca tcctggccat cgccccttc      720 caccacgcct tcggactgtt taccgccctg gcttactttc agtgggcct gaagatcgtg      780 atggtgaaaa agtttgaggg cgagttcttc ctgaagacca tccagaacta caagatcgct     840
tctatcgtgg tgcctcctcc aatcatggtg tatctggcca agagccctct ggtggatgag     900
tacaatctgt ccagcctgac agagatcgcc tgtgcggct cccctctggg cagagacatc      960
gccgacaagg tggccaagag actgaaggtc acggcatcc tgcagggcta tggcctgacc     1020
gagacctgta gcgccctgat cctgagcccc aacgatagag agctgaagaa gggcgccatc    1080 ggcacccta tgccctatgt ccaggtgaag gtgattgaca tcaacaccgg caaagccctg    1140
ggaccaagag agaagggcga gatttgcttc aagagccaga tgctgatgaa gggctaccac    1200
aacaacccac aggccaccag ggatgccctg acaaggacg gtggctgca caccggcgat     1260 ctgggctact acgacgagga cagattcatc tatgtggtgg atcggctgaa agaactcatc    1320
aagtacaagg gctaccaggt ggcccctgcc gagctggaga acttgcttct gcagcaccct    1380
aacatctctg atgccggcgt catcggcatc ccagacgagt ttgccggcca gctgccttcc    1440
gcctgtgtcg tgctggagcc tggcaagacc atgaccgaga aggaggtgca ggattatatc    1500
gccgagctgg tgaccaccac caagcacctg cggggcggcg tggtgttcat cgacagcatt    1560
ccgaaaggcc caacaggcaa gctgatgaga aacgagctga gggccatctt tgcccgcgag    1620
caggccaagt ccaagctgag ggccaagcgg tccggatccg gagccaccaa cttcagcctg    1680
ctgaagcagg ccggcgacgt ggaggagaac cccggcccca tggacgggcc cgcctgctg    1740 ctgttgctgc ttctgggggt gtcccttgga ggtgccaagg aggcatgccc cacaggcctg    1800
tacacacaca gcgtgagtg ctgcaaagcc tgcaacctgg gcgagggtgt ggcccagcct    1860
tgtggagcca accagaccgt gtgtgagccc tgcctggaca gcgtgacgtt ctccgacgtg    1920
```

-continued

```
gtgagcgcga ccgagccgtg caagccgtgc accgagtgcg tggggctcca gagcatgtcg    1980
gcgccatgcg tggaggccga cgacgccgtg tgccgctgcg cctacggcta ctaccaggat    2040
gagacgactg ggcgctgcga ggcgtgccgc gtgtgcgagg cgggctcggg cctcgtgttc    2100
tcctgccagg acaagcagaa caccgtgtgc gaggagtgcc ccgacggcac gtattccgac    2160
gaggccaacc acgtggaccc gtgcctgccc tgcaccgtgt gcgaggacac cgagcgccag    2220
ctccgcgagt gcacacgctg ggccgacgcc gagtgcgagg agatccctgg ccgttggatt    2280
acacggtcca cacccccaga gggctcggac agcacagccc ccagcaccca ggagcctgag    2340
gcacctccag aacaagacct catagccagc acggtggcag gtgtggtgac cacagtgatg    2400
ggcagctccc agcccgtggt gacccgaggc accaccgaca acctcatccc tgtctattgc    2460
tccatcctgg ctgctgtggt tgtgggtctt gtggcctaca tagccttcaa gaggtggaac    2520
agctga                                                                2526
```

```
<210> SEQ ID NO 313
<211> LENGTH: 6
<212> TYPE: PRT
<213> ORGANISM: Artificial Sequence
<220> FEATURE:
<223> OTHER INFORMATION: CDRL1 of anti-NY-ESO1 157-165 antibody
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 313

Gln Xaa Xaa Ser Xaa Xaa
1               5

<210> SEQ ID NO 314
<211> LENGTH: 10
<212> TYPE: PRT
<213> ORGANISM: Artificial Sequence
<220> FEATURE:
<223> OTHER INFORMATION: CDRL3 of anti-NY-ESO1 157-165 antibody
<220> FEATURE:
<221> NAME/KEY: misc_feature
<222> LOCATION: (4)..(10)
<223> OTHER INFORMATION: Xaa can be any naturally occurring amino acid

<400> SEQUENCE: 314

Gln Gln Tyr Xaa Xaa Xaa Xaa Xaa Xaa Xaa
1               5                   10

<210> SEQ ID NO 315
<211> LENGTH: 9
<212> TYPE: PRT
<213> ORGANISM: Artificial Sequence
<220> FEATURE:
<223> OTHER INFORMATION: CDRL1 of anti-NY-ESO1 157-165 antibody
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
```

```
<223> OTHER INFORMATION: Xaa can be any naturally occurring amino acid

<400> SEQUENCE: 315

Xaa Xaa Asp Val Gly Xaa Tyr Xaa Xaa
1               5

<210> SEQ ID NO 316
<211> LENGTH: 12
<212> TYPE: PRT
<213> ORGANISM: Artificial Sequence
<220> FEATURE:
<223> OTHER INFORMATION: CDRL3 of anti-NY-ESO1 157-165 antibody
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(11)
<223> OTHER INFORMATION: Xaa can be any naturally occurring amino acid

<400> SEQUENCE: 316

Xaa Ser Xaa Xaa Xaa Xaa Xaa Xaa Xaa Xaa Xaa Val
1               5                   10

<210> SEQ ID NO 317
<211> LENGTH: 9
<212> TYPE: PRT
<213> ORGANISM: Artificial Sequence
<220> FEATURE:
<223> OTHER INFORMATION: CDRL1 of anti-CD19 antibody
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 317

Xaa Ser Xaa Xaa Gly Xaa Xaa Asn Tyr
1               5

<210> SEQ ID NO 318
<211> LENGTH: 3
<212> TYPE: PRT
<213> ORGANISM: Artificial Sequence
<220> FEATURE:
<223> OTHER INFORMATION: CDRL2 of anti-CD19 antibody
<220> FEATURE:
<221> NAME/KEY: misc_feature
<222> LOCATION: (2)..(3)
<223> OTHER INFORMATION: Xaa can be any naturally occurring amino acid

<400> SEQUENCE: 318

Asp Xaa Xaa
1

<210> SEQ ID NO 319
<211> LENGTH: 11
<212> TYPE: PRT
<213> ORGANISM: Artificial Sequence
<220> FEATURE:
<223> OTHER INFORMATION: CDRL3 of anti-CD19 antibody
<220> FEATURE:
<221> NAME/KEY: misc_feature
```

```
<222> LOCATION: (1)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid

<400> SEQUENCE: 319

Xaa Xaa Xaa Xaa Xaa Ser Xaa Xaa Xaa Xaa Xaa
1               5                   10

<210> SEQ ID NO 320
<211> LENGTH: 7
<212> TYPE: PRT
<213> ORGANISM: Artificial Sequence
<220> FEATURE:
<223> OTHER INFORMATION: CDRL1 of anti-CD19 antibody
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 320

Gln Xaa Xaa Ser Xaa Ser Xaa
1               5

<210> SEQ ID NO 321
<211> LENGTH: 12
<212> TYPE: PRT
<213> ORGANISM: Artificial Sequence
<220> FEATURE:
<223> OTHER INFORMATION: CDRL3 of anti-CD19 antibody
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 321

Gln Gln Xaa Xaa Xaa Xaa Xaa Xaa Xaa Leu Xaa Thr
1               5                   10

<210> SEQ ID NO 322
<211> LENGTH: 8
<212> TYPE: PRT
<213> ORGANISM: Artificial Sequence
<220> FEATURE:
<223> OTHER INFORMATION: CDRH1 of anti-NY-ESO1 157-165 antibody
<220> FEATURE:
<221> NAME/KEY: MISC_FEATURE
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (6)..(8)
<223> OTHER INFORMATION: Xaa can be any naturally occurring amino acid

<400> SEQUENCE: 322

Gly Xaa Xaa Xaa Ser Xaa Xaa Xaa
1               5
```

```
<210> SEQ ID NO 323
<211> LENGTH: 9
<212> TYPE: PRT
<213> ORGANISM: Artificial Sequence
<220> FEATURE:
<223> OTHER INFORMATION: CDRH2 of anti-NY-ESO1 157-165 antibody
<220> FEATURE:
<221> NAME/KEY: MISC_FEATURE
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 323

Xaa Xaa Xaa Xaa Ser Xaa Gly Ser Thr
1               5

<210> SEQ ID NO 324
<211> LENGTH: 10
<212> TYPE: PRT
<213> ORGANISM: Artificial Sequence
<220> FEATURE:
<223> OTHER INFORMATION: CDRH3 of anti-NY-ESO1 157-165 antibody
<220> FEATURE:
<221> NAME/KEY: MISC_FEATURE
<222> LOCATION: (2)..(6)
<223> OTHER INFORMATION: Xaa can be any naturally occurring amino acid

<400> SEQUENCE: 324

Ala Xaa Xaa Xaa Xaa Xaa Gly Met Asp Val
1               5                   10
```